(12) United States Patent
Moore et al.

(10) Patent No.: US 6,727,348 B2
(45) Date of Patent: Apr. 27, 2004

(54) COMPOSITIONS AND METHODS FOR THE DIAGNOSIS AND TREATMENT OF BODY WEIGHT DISORDERS, INCLUDING OBESITY

(75) Inventors: Karen Moore, Maynard, MA (US); Deborah Lynn Nagle, Watertown, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 406 days.

(21) Appl. No.: 09/893,238

(22) Filed: Jun. 27, 2001

(65) Prior Publication Data

US 2002/0150973 A1 Oct. 17, 2002

Related U.S. Application Data

(62) Division of application No. 09/245,041, filed on Feb. 5, 1999, now Pat. No. 6,274,339.
(60) Provisional application No. 60/093,630, filed on Jul. 21, 1998, and provisional application No. 60/104,978, filed on Oct. 20, 1998.

(51) Int. Cl.$^7$ .................................................. C07K 1/00
(52) U.S. Cl. ....................... 530/350; 530/350; 530/300; 435/69.1; 536/23.1
(58) Field of Search ................................. 530/350, 300; 435/69.1; 536/23.1

Primary Examiner—Karen Cochrane Carlson
Assistant Examiner—Hope A. Robinson
(74) Attorney, Agent, or Firm—Millennium Pharmaceuticals Inc.

(57) ABSTRACT

The present invention relates to mammalian mahogany genes, including the human mahogany gene, which are novel genes involved in the control of mammalian body weight. The invention encompasses nucleotide sequences of the mahogany gene, host cell expression systems of the mahogany gene, and hosts which have been transformed by these expression systems, including transgenic animals. The invention also encompasses novel mahogany gene products, including mahogany proteins, polypeptides and peptides containing amino acid sequences mahogany proteins, fusion proteins of mahogany proteins polypeptides and peptides, and antibodies directed against such mahogany gene products. The present invention also relates to methods and compositions for the diagnosis and treatment of mammalian body weight disorders, including obesity, cachexia, and anorexia, and for the identification of subjects susceptible to such disorders. Further, the invention relates to methods of using the mahogany gene and gene products of the invention for the identification of compounds which modulate the expression of the mahogany gene and/or the activity of the mahogany gene product. Such compounds can be useful as therapeutic agents in the treatment of mammalian body weight disorders, including obesity, cachexia, and anorexia.

17 Claims, 173 Drawing Sheets

GAATTCCGGGCGAAGGGAGCCCGGCGTGCGGGGTGTGTATGTGTTCGCTGGGGCGCTCAGCCCCAGGAAGATGGTG

GCGGTGGCGGCGGGCGGCGGCGACTGAGGCGCGGCTGAGGGGAGCACGAGGACACAGCGCCTGCGGGCAGGAAGG

GCAGGCAGCACCGACCCTGCACCGCGACAGGGGCCTGGAGGCCGGACCGCGCGCCGGCTGTGTCTCCCGCGGGTGCT

GTCGCGGGCGCTGCCCCCGCCGCGCTGCCGCGCTCTTTTCGCTGCTGCCGCTGCCCCGGAGGCCGAG

GCCGCTGCGGTGGCGGCGGGTGTCCGGCTCGGCGCGCAGCCGAGGCCAAGGAATGTGACCGGCCGTGTGTCAACGGCG

GCCGCTGCAACCCTGGCACCGGCCAGTGCGTCTGCCCCACGGGCTGGGTGGGCGAGCAATGCCAGCACTGCGGGGGCCG

CTTCAGGACATCTGTCTCACGCCTATAATCACAGCTGTTCGGAAGGTGAGGCTGGAGGAACAGTTCGAGGCAAGCTTCG

GCTACAGAATAAGTTCAAGAGTAACCTGGGGCAACTTGGGCTTGTCTCCAAAACCAAAATGAGCGAAAAGGAGCAAGCT

AGAGTCTTTGGGAAAATTTAGCTGACTAATTTTTCACCGAGAACTAACTGGCTCTTCTGGATTTGTAACAGATGGAC

CTGGGAATTATAAATATAAGACGAAGTGCACATGCTCATTGAAGGACAGCCAAATAGAATAATGAGACTTCGCTTCAA

CCATTTTGCTACAGAATGTGTGGGACCATTTATATGTTTATGATGGGGACTCAATCTACGCACCTCTGATTGCTGCC

TTTAGTGGCCTCATTGTTCCTGAAAGAGATGGCAATGAGACGGCTCCTGAGGTCACTGTCACTTCAGGTTATGCACTGC

TGCATTTTTCAGTGATGCTGCTTATAATCTGACTGGATTTAATATCACTTACAATTTTGACATGTGTCCGAATAATTG

FIG.2A(1)

CTCAGGCCGAGGAGAGTGTAAGAGCAGTAACAGCAGCAGCGCTGTTGAGTGTGAATGTTCTGAAAACTGGAAAGGGGAG

TCGTGTGACATTCCTCACTGTACAGACAACTGTGGCTTTCCTCACCGAGGCATCTGTAATGCAAGCGATACCAGAGGGT

GCTCCTGCTTTCCTCACTGGCAGGGTCCTGATGTTCAATTCCTGTGCCAGCTAACCAGTCTTTTGGACTCTGAGAAGA

ATATTCTGATTTAAAGCTTCCCAGAGCCTCTCATAAAGCTGTGGTCAATGGAAATATAATGTGGGTTGTTGGCGGATAT

ATGTTCAACCATTCAGATTACAGCATGGTTTTAGCGTATGACCTGACTTCTAGGGAATGGCTTCCACTAAACCATTCTG

TGAACAGTGTGGTTGTAAGATATGGTCATTCTTTGGCATTACATAAGGATAAAATCTACATGTATGGAGGAAAAATTGA

Figure 1:
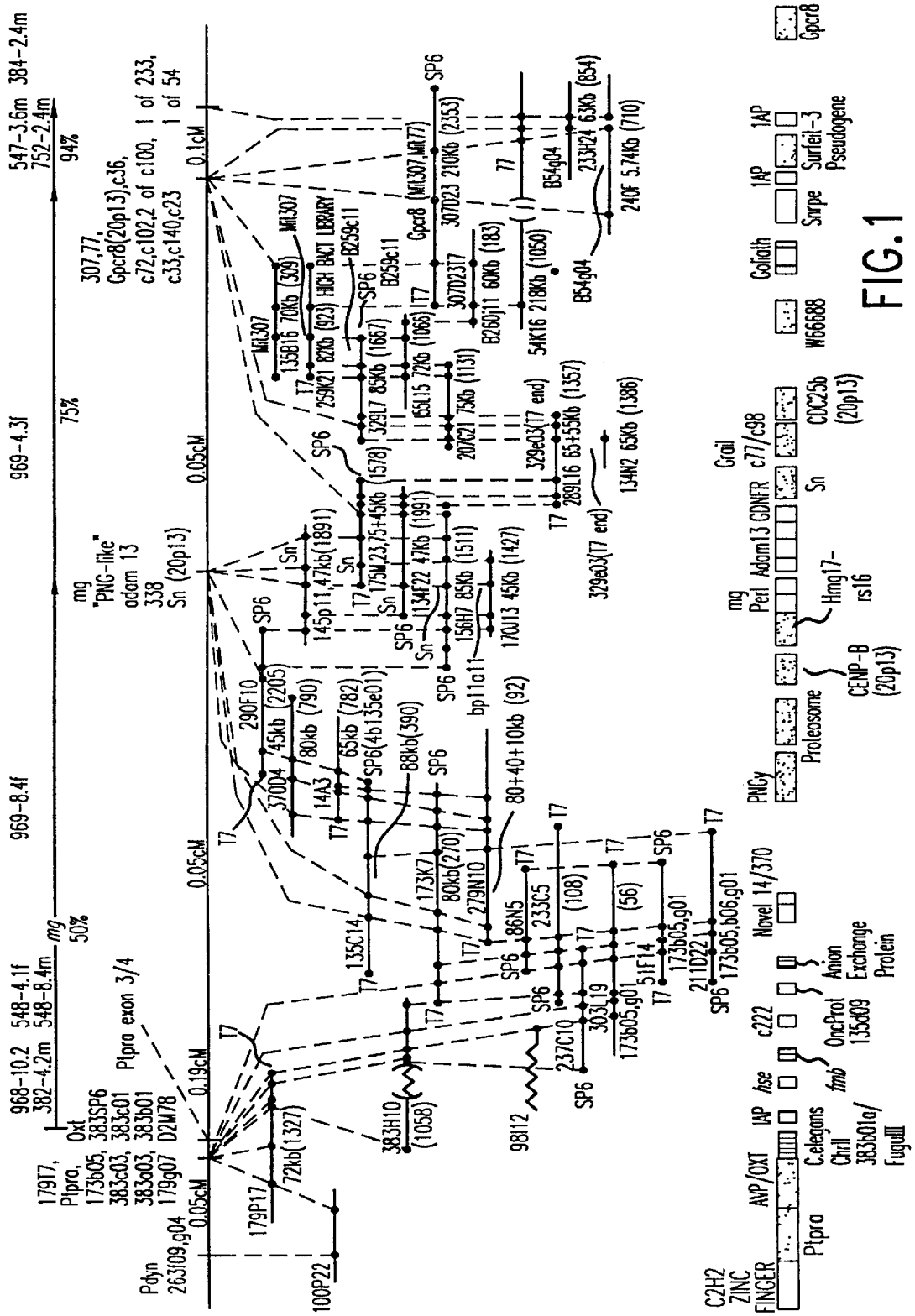

TTCAACAGGGAACGTGACCAATGAGCTGGACACTCAGCACACATTGTTACACTGGCATCTGGCCGTGTGGTCATGTTGGTCATCT

AAGGATCAGTATGCAGTGGTTGGACACTCTATGGATATATAAGCGTTGTGCAGGAATATGACTTGGAAAAGAACACATGGAGTATATTACA

TCGGTCATTGCCCACTCTATGGATATATAAGCGTTGTGCAGGAATATGACTTGGAAAAGAACACATGGAGTATATTACA

TACTCAGGGTGCTCTTGTGCAAGGGGTTATGGCCACAGTAGTGTTTATGATGACAGGACCAAGGCTCTGTACGTTCAT

GGTGGTACAAGGCTTTCAGGCGCCAACAAATACCGGCTTGCAGATGACCTCTACAGATACGATGTGGATACTCAGATGT

GGACCATTCTTAAGGACAGCCGATTTTTCCGTTACTTGCATACAGCTGTGATAGTGAGTGGAACCATGCTGGTGTTTGG

AGGGAACACACAATGACACTTCCATGAGCCACGGTGCCAAATGCTTCTCCTCGGACTTCATGGCTTATGACATTGCT

FIG.2A(2)

TGTGACCGATGGTCAGTGCTTCCCAGACCTGAGCTCCATCATGATGTCAACAGATTTGGCCATTCAGCAGTCTTGTACA

ACAGCACCATGTATGTTCGGCGGCTTCAACAGCCTCCTCCTCAGTGACGTCTTGGTCTTTACCTGGAGCAGTGCGA

TGCACACCGCAGTGAAGCTGCTTGTGTGGCAGGACCTGGTATCCGGTGTCTGTGGGACACACAGTCGTCTCGATGT

ACCTCCTGGGAGTTGGCAACTGAAGAACAAGCAGAAAAGTTAAAATCAGAGTGTTTTCTAAAAGAACCCTTGACCATG

ACAGATGTGACCAGCACACAGATTGTTACAGCTGCACAGCCAATACCAATGACTGCCACTGGTGCAATGATCACTGTGT

CCCTGTGAACCACAGCTGCACAGAAGGCCAGATCTCCATTGCCAAGTATGAGAGTTGCCCCAAGGATAACCCCATGTAC

TACTGCAATAAGAAAACCAGCTGCAGGAGCTGTGCCCTAGACCAGAACTGCCAGTGGGAGCCCCGGAATCAAGAGTGCA

TCGCCCTGCCGGAAAATATCTGTGGCAATTGGTTGGAAACTCGTGTCTGAAAATCACTACTGCTAAGGA

GAATTATGACAATGCTAAATTGTCCTGTAGGAACCACAATGCCTTTTGGCTTCCCTCACATCCCAGAAGAAGGTGGAG

TTTGTCCTTAAGCAGCTTCGATTAATGCAATCATCTCAAAGTATGTCCAAGCTCACTCTGACTCCATGGGTTGGTCTTC

GGAAGATCAATGTGTCTTACTGGTGCTGGGAGGATATGTCTCCATTCACAAATAGTTTGCTGCAGTGGATGCCATCTGA

GCCCAGTGATGCTGGCTTCTGTGGGATCTTGTCAGAGCCTAGTACTCGGGGATTAAAGGCTGCAACCTGCATCAACCCT

CTCAATGGCAGCGTCTGTGAAAGGCCTGCAAACCACAGTGCCAAGCAGTGCCGGACACCATGTGCCCTGCGGACAGCGT

FIG. 2A(3)

GTGGCGAGTGCACTAGCAGCTCGGAGTGCATGTGGTGCAGTAACATGAAGCAGTGTGTGGACTCCAATGCCTACGT

GGCCTCCTTCCCTTTTGGCCAGTGTATGGAATGGTATACGATGAGCAGCTGCCCACCTGAAAATTGCTCTGGCTACTGT

ACCTGCAGCCATTGCTTGGAGCAGCCAGGCTGTGGTTGGTGTACTGATCCTAGCAATACTGGGAAAGGAAAATGTATTG

AGGGCAGCTATAAAGGACCTGTGAAGATGCCGTCACAGGCCTCTGCAGGAAATGTGTATCCACAGCCCCTTCTGAACTC

CAGCATGTGTCTAGAGGACACAGCAGATACAACTGGTCTTTCATTCACTGTCCAGCTTGCCCAGTGCAACGGACACAGCAAA

TGCATCAACCAGAGTATCTGTGAGAAGTGTGAGGACCTGACCACGGCAAGCACTGCGAGACCTGCATATCTGGCTTCT

ATGGTGACCCGACTAATGGAGGCAAATGTCAGCCATGCAAGTGCAATGGGCACGCATCACTGTGCAACACCAACACCGG

CAAGTGCTTCTGTACCACCAAAGGTGTCAAGGGGGACGAGTGCCAGCTATGTGAGGTAGAAAATCGATACCAAGGAAAC

CCTCTCAAAGGAACATGCTACTATACCCTTCTCATTGACTATCAGTTCACCTTTAGCCTGTCCCAGGAAGACGACCGCT

ACTACACAGCCATCAACTTTGTGCGTACTCCTGATGAACAAAACAGGGATTGGACATGTTCATCAATGCCTCCAAAAA

CTTCAACCTCAACATCACCTGGGCCTGCACCAGCTTCCCAGCCGGAACCCAGACTGGAGAGAGGTGCCTGTTGTTCAAAA

ACCAACATCAAGGAATACAAAGATAGCTTCTCTAATGAGAAATTTGATTTTCGCAACGATCCAAACATCACTTTCTTTG

TTTATGTCAGTAATTTCACTTGGCCCATCAAAATTCAGATTGCCTTCTCCCAGCACAGCAACTTCATGGACCTGGTACA

FIG.2A(4)

```
GTTCTTCGTGACTTTCTTCCTCTCGCTGTTGTTCCTCTCGCTGCTTCTGGTGGCTGCAGTGGTCTGGAAGATCAAGCAGAGCTGT
TGGGCATCCAGGCGGAGAGAGCAACTTCTCGGGAGATGCAACAGATGGCCAGCCGCCCTTTGCTTCTGTAAACGTTG
CCTTGGAAACAGATGAGGAGCTCCTGATCTTATTGGGGGAGTATAAAGACTGTTCCCAAACCCATTGCACTGGAGCC
GTGTTTTGGCAACAAAGCCGTCTCCTCTCTGTGTTGTGAGGCTCCCTCGAGGCTCGGGTGGCATCCCTCCTCCTGGG
CAGTCAGGTCTTGCTGTGGCCAGCGCCCTGGTGCACGCCCTGCACAGCCTGGGACATTTCTCAGCAGATGCCGATAGTGTACAAGGAGAAGTCAGGAG
CCGTGAGAAACCGGAAGCAGCAGCCCCCTGCACAGCCTGGGACCTGCATCTGATGCTGGGGCCAGGGACTCTCCCACGC
ACGAGCTAGTGAGTGGCACACCAGAGCCATCTGCAGGGAAGGGCGTGGCGGGAAATGGCTGTGCGGTGCGGGACGGAA
GACTGGAAACCCTCAAAGCATCTGACTCACCTGCATGATCACACAGCTTTCTTTGACGGTTCTCCCCATCCGTGTTCCAG
CATCTAACCTTTTACTTTGCATAGGAAATACTTGATTTAATTACAGGTCCAGGGATGAGCTGATGGTTGCTGGAGGAG
GCCAGTGTAGAGCCAGTGAGAGAACTAGGAATGACACTCAGGTTCACTGTGGAAAACTGTTCTTGGGACTGTCTCAACT
GTGCAAAAAACAAAAGATGGAGTGTTACAAGTAGACATTCGTCATCTTTTAAAAGATGTGCTATTTATTCTTGCACGATTTAG
GTCAGATGAATTAACTGTTTCATCTGAAGCCTGCTATCTTTTTTCTAGTTGAGAATTAATAATGGTCCATCTCTTTTGATCATATCAAG
GCAATTATCTCTCTTCCAGGGAGTACCTTTTTTTCTAGTTGAGAATTAATAATGGTCCATCTCTTTTGATCATATCAAG
```

FIG. 2A(5)

```
CTAGGATAGAAGGGGGCTATTTAAATGTCAAGGTCAGCAGTGTTACTTTGAATGTAAACTGGTATAATAGGTAGTTT

TCTATAGTAACTTGATTAATTAGTCTTAATCCATTTGAAACTCTCTCTTCCTTCTCTCTGCCTGTCCCTCTCCTTCT

CCATCTCACCCTCCCTCTCTCACACATACACACAACACATACACACAACACTAAGTGCCTAGACTTAAATAGATC

TAGCAATTGGAAAGTTAGTAAGCCTAAGTTTTTACATAATTGCATTCCTACATTCTGTAAATTTAAATAGCTACCAT

TGGCAATCTGCTTTTTTCTAAAATCTGATTGCAGCCAGGAAAGAATTTCTCACCCAAGGAACATTTGATCTAGCAG

CAGGGATGAGAGGAAAGCAGAAATGAATGAACTGTGAAAGCTCCTGTTTTTATTATCAAAAGGACACTGTCAAGAAGG

CGCCCCCTGCCCACCCCGTGTCACCCTAGGCCTGATAAGGCTGATCAGAGGAAAGGACTCATTCATGTCACGCTTCCT

TGAGCAGAAAGAGCACTGAGAGCACTTGGGACCCCTGGATCAGGAGAGCATCTGTGTGTCCTGCAGCCTCCTCTGAACT

TGTGGTTCATTCTCAGGCTGGGGTGGACTCAGATGCCAGGAAAGGGACAGCCTCGACCCACCCCTCCCTCTCAGAAGCTGCCCAA

AGCCTGGAGAGGACTTGTTTGCCCTCTCTTTCCCCCAGGAGGGGCTCGACCCACCCCTCCCTCTCAGACCAAGGTGG

TGGCTGTGAGGAGGGCAGCAAATGCTGACAAGGATGAAAAAAATGACGAGGAGGGAAAACTCTGCC

AAATGGAAAATGACCAAATTTAAGAGGGTGGGACAGTCCCCTGCTCCTCTCCCAGAGGGCACTGCTTGGAAATTGTGTT

TTCCCCATTTATGGTGCTCTGTATTCTGGCATTATGCAGCAGCCTCCCAGAAGCTCTTCTTGCTTCAAAACCTGGGAT
```

FIG.2A(6)

CTCTGGCATTACCCTATTGGGATGGACCGCTGGACAGCAATGCTCGAGTTTGTGAATTTGGAGAGATACTCAAAAGAGC

TAAAACTGCAGCATTTTACCTTTAAATGCAGTGCCTAGAGAGAGAGTATTGTCTCTTCCCAACACTAACCCCACTCCC

ATGAAGAATTGCCTGGAAAGATGTTTCAAGGAATTTGAACCATAAAACACTATCTGATGCACAGAACACCTCTACTTT

GAGACTCACCTCTCATAAGCTTCTTTTTCACATTACTGTTAAAGACCAGACGTTCTAGAAAGACCCCTCTCTCATG

AGCTCCCCCATCCCTGCTACAGAACACAGCACCCATGGCGCCTGCAGTGGACTGGCCCCTTAATTCCCACAGGCCCCC

CAGCAAGGCCAAAGGGAGGCCCCTGGGTATTGTCCTCCTACAAGGAAGATCCTCTTTGTTTGTTCAAAGGACCAGTTTT

CCTAGGCCAAAGAAGAGTCTCTTCCCCATGTTAGTCCTATGCCTTGAAATATCATGCACCATGACCCACAGCCATCTGGTT

ATGTCTTATTTTTTCCTAAAAGATAATGTTTATTTTAAAAAGGAAGGAAGAAGCAAGTGAAGTTTCATTCTGCTCCA

GCGGTGGGGAAGCCGCTGAATCCACCTGCTTCTCCTTGCAACCGACAGCAAACAGCTTCTCCGGCCTCAGGGCAGAA

AAAGGGAATGCAGGGAGTAAGAGGCGCTGGGCTCGGAGCCTGTTTCCAAGAAGGAATTGGTTGTCATCTGGCAGTGTT

GCGCGTCACAGAGAGCCTGTATATAAATTAAAATAGTCAAGACAACACTGACCTTGCACTTGTACATAACTATACAGT

AGTGTCCAGAATGTTCAGACATTCGGAGTGTACATAAAACAGAAAAATCTTCATGTATTTTATTAAATATAACAATG

TCTGAGTTTCACCTAAGATGTTTTTGTGCCATATGCTGGATATCCAGGTTCTCGCCAGGCCCGATACATGAATAACAA

FIG.2A(7)

```
ACCCAAGAAACGCATCCCCATTGTGTGATGTGTTCAGATGCATCTGGCACCAATTAGGTATTTCTTAAAACAGGACTCA

TCTGTCAGAGTGCACATGAAAAATCAGGCAGGGAATCGAAACGACAGCGCTGGAGGAGACTCAGGAAGCAGAGGCGTCC

CTGCCGCTGCCCTTGGCCCTGCAAGCACATCATGACCCTTTCTGGCAGCCTCTCTGGTGTCTCTGGGTAGTGAGGGATGAC

CAGTCTTGTCTGAGAAATGTTTCTCTTAGTCTTAAGTTCAAAGACTAACCTGTAGCAATCAGACTTTCCAAAAGGGG

GTTCTCCATTTTTTGTAGTTTGTCTAAATTTTAATGACCATTTCCTGGAATCAGTTTATTATACTGAAAACTGGGGG

TGGGAGTAGGGAGCTAGTTTGTTGATAAATAGTTCCCATTTCCCCGTGGAGAATTTGACATACCCTGGACTCCTGTGTG

CCTCCTGCCATCCCTGCACACAGCCTGGGGAGAAGCCTGTGCCTCCCCGTGTGAGAGAAGGCAACCCCAGATCCCCTG

AGCTAACCCGGAGGAAACAGTCCTGGACAGAAGACTGTCAGCAGAAGGAAAGTACTGGACTACCCGTGGGTAAGTCC

TGCCATTCAAGACTGGAGACACCTGGGAATAAAAGAGCAGGGCACTGCTGGTGGGAAGAGGCATTTACCTTCCAGT

GCAAATCCTGCTCCTTTGATTTAATGGGGTGTACTGGGGCCAGGGGCTGATTCACTTCCTTGGGAGATGGTGGTGTTT

CATGAACATCTTTGATCCTTCCATTTCATTTATTCATCCATTCAACAAGTATTTGCTAAACACTAACTTAAGCTA

ATGCTAGGGTAGTGACTGAGATGTAAAAATAGATTTTAGAATTAAAACAAAATCCAAGTCCTCACACCCTGTCATCCC

AGGAGATCTTTCCTTGTGGTGGTTTCTGTGAGAATTGGCCATCCTGAGGACACAGCCAGGACGGCAGAGGCCTCCTGGC
```

FIG.2A(8)

CTCAGGGCATGCCCTGCCTACCTTCTGAAATGTTACCCCATTGACCAAACTTGGCTCCAGCCATTGCGGTGGTTTCTA

GATAGCCAGGCCCACCAAGAGATATTGCCCCTTGATGAGAGTCAAACACCCTGCCTACAAGGAGATGTTTGAAATGGA

GAGGAAAATTGGCACCTCATCTTTTAAAGGCAGTAATGGAATTCAGTAACTGATTTCGTAACTGAATTGTGCACAAAACATTCT

AAACACTAGTGAAGCCTGTTTCGTTGAACTAATTCTGGCTCTGGAAATGTTTTGTTTATAGTTATTACGATTTCGT

TTGTTTGGATTCAAGCTTAGTTGTTAATATGTATAATTTAGCATCTATTACACTCATGTAAATATGGAGTAAGTATTG

TAAACTATTTCATTGCGGGGATTGTGGGTGTTATACATACATTAGGACTGCAATTTTTGTATTTTTTGTATTGTAA

AATAACAGCTAATTTAAGCAGGAACAAGAGAACTAAGGGGAGGTCTGTGCATTTAAACACAAATGTGAAGAACTTGTAT

ATAAACAAAAGTAAATACTATAATACAAACTTCCTTCTGAAATAAAAGTAGATCTGGT

FIG.2A(9)

MRLRFNHFATECSWDHLYVYDGDSIYAPLIAAFSGLIVPERDGNETAPEVTVTSGYALLHFFSDAAYNLTGFNITYNFD

MCPNNCSGRGECKSSNSSSAVECECSENWKGESCDIPHCTDNCGFPHRGICNASDTRGCSCFPHWQGPGCSIPVPANQS

FWTREEYSDLKLPRASHKAVVNGNIMWVGGYMFNHSDYSMVLAYDLTSREWLPLNHSVNSVVVRYGHSLALHKDKIYM

YGGKIDSTGNVTNELRVFHIHNESWLLTPKAKDQYAVVGHSAHIVTLASGRVVMLVIFGHCPLYGYISVVQEYDLEKN

TWSILHTQGALVQGGYGHSSVYDDRTKALYVHGGYKAFSANKYRLADDLYRYDVDTQMMTILKDSRFFRYLHTAVIVSG

TMLVFGGNTHNDTSMSHGAKCFSSDFMAYDIACDRWSVLPRPELHHDVNRFGHSAVLYNSTMYVFGGFNSLLLSDVLVF

TSEQCDAHRSEAACVAAGPGIRCLWDTQSSRCTSWELATEEQAEKLKSECFSKRTLDHDRCDQHTDCYSCTANTNDCHW

CNDHCVPVNHSCTEGQISIAKYESCPKDNPMYYCNKKTSCRSCALDQNCQWEPRNQECIALPENICGNGWHLVGNSCLK

ITTAKENYDNAKLSCRNHNAFLASLTSQKKVEFVLKQLRLMQSSQSMSKLTLTPWVGLRKINVSYWCWEDMSPFTNSLL

QWMPSEPSDAGFCGILSEPSTRGLKAATCINPLNGSVCERPANHSAKQQCRTPCALRTACGECTSSSSECMWCSNMKQCV

DSNAYVASFPFGQCMEWYTMSSCPPENCSGYCTCSHCLEQPGCGWCTDPSNTGKGKCIEGSYKGPVKMPSQASAGNVYP

QPLLNSSMCLEDSRYNWSFIHCPACQCNGHSKCINQSICEKCEDLTTGKHCETCISGFYGDPTNGGKCQPCKCNGHASL

CNTNTGKCFCTTKGVKGDECQLCEVENRYQGNPLKGTCYTLLIDYQFTFSLSQEDDRYYTAINFVATPDEQNRDLDMF

INASKNFNLNITWATSFPAGTQTGEEVPVVSKTNIKEYKDSFSNEKFDFRNHPNITFFVYVSNFTWPIKIQIAFSQHSN

FMDLVQFFVTFFSCFLSLLLVAAVVWKIKQSCWASRRREQLLREMQQMASRPFASVNVALETDEEPPDLIGGSIKTVPK

PIALEPCFGNKAAVLSVFVRLPRGLGGIPPPGQSGLAVASALVDISQQMPIVYKEKSGAVRNRKQQPPAQPGTCI

FIG. 2B

AGATTTTATGCCTTCGTACACGCCTCCCATAAGATGGACAAGGTGTACTA

ATTACTGCCATTACTGTTGCTGACCCCAGAGGTCAATGTCCTCACATGGC

CTCTACTGGCACTGTCTGGGCAGAAACTGTATATCCAACTGGTGAACCTG

AAAGCCCTATGACTACTTGGTGTCTCTGGTGCTAACCCTAGTCGTTGGGG

CATCTTACTGTATCCTGGTAAGGAAAGACATCCAGGCTCCCCACTTAYMK

WWACYRGYWMRGMYCAKGSYMGRGCYAAWKTKCTGTRRMRTCTGGCTGGC

ATAGAGACATTACTATTGAAAGTTTTGTCTTTCTAAATCCTTGGACTAAA

GAGAGCACAAGATTTTCTGGAAGATCTTGCTTTAAATTTTTTTTTTATTC

TTTTGAGATGCTACATATAATTAGAGGCCCTGCACATGGAGGCGAGAACC

CCACCTCTGGGCTACATCCTACGTCTTTTCCTTAGGGTATTTTTTTTTCT

TTCTTGTACCTATCAGTATTACTAAGTTGCAAATGTGCTCAGCAGTAAAT

TTAACATACATAGGCAAAAAGAAAAGTCTCAGGACACCCTGCCTCACACT

GTTTACTGTGCTCAGGAGTACTGAGCCATACTGTTTTCTTGCTGCTGCTT

TTTTTCTCTTGGTTGTTTACACACAGTGTTCAAGGTGTGTTAATCATAGT

TAGTATTTCAATTTTTTTCTTAGGTCAGCAAGAAAGCTCACAGAGGAAGAG

TGCTTTGCTGCCAGCCTGATGACCTGGGTGACCCAAGTGATCTCACCTAC

AGGGTGGGAGCACAGCACAGCATTCCAAGTCTTTTTTCTGACCACACAGGC

ACTATGGCACACAAACACACAGGATACATAAATGTTAAAAAAAAAAAAAG

ACTTTTATATTTTTCTCCATATAATTTAAAAGATTCCTCTTTCAACATTC

CTTTTGCAAAGCAGTATCATTGTGTTTGTATATGTGTGTCCTTCCACATT

TTGTCTTCAATTCTAAATTTTTAGAATTGTTAGCCTGGTCCTCTCATTTC

FIG.3B(1)

TACTACTTTCTCTAGTAAACTGTCCTTTCATATTACACATCGCTCTCCTG

TCACCTGTTTTAGAGCTGTCATCCATTTTATAAGGTTACTTCACTGTTCT

ACACTACTTTGTGTCTTTTAATTACTATGCCTGGGGTGATTCAAAAACTG

TCTGTGATGGGTTGGTTGAGGATGGCTCCAATAGGTTCAACACTTGGTCC

TGATTGGTGGAACTGTTTTGGGAAGGATTAGGAGGTGTGACCTTGTGGGG

GAGTGTGTCACTGGGAGTGAGTGACCTTTGAGGTTTCAAAAGCCCATGCT

AGGCCCAGTGTCTGTCTGCCTGTCTGTCTGTCTCCTCCCTTTGCTCTTTC

TTCCCTCCCACTTGCTTGCAGATCAGATTCGAGCTCTTAGCTACTGCTCC

CGTGCTGTGCCTTGCTGCTACCATGCTTCTTGCCATGATGTTCATAGACT

TACTCTCTGAAACTGTAAATAAGCCCCCTAATAAAATGCTTTCTTTTAAA

ACTGCCTTGATCATGGTGTCTCTTCAAAGAAATAGAACATTAACAAAAAC

ACTATACCAAACTGCCTAATAGTCCTACTAATTTTATGATGAGTGCTAGT

GCTTTATAATCACTAGAAGAAAAAATTTCCAGGCCATAAAATTAACATGG

TTTTAAGTATGTATAAATCTTGTCTTGAAATCTGTTTTCTATAACTAACT

CTAATATGATAATGTATATTCTACCTTCAAAAAAGCACAAATAAGACTTC

AAACCCTGGGAATTGTTAGACAAAGGCCATTTAATACTAATAAGCTATAA

ACTGAAACCATCTGATATATGAAAACTATTAATAAAATCAAGATAAAATA

ACCCCTATTTATATAACTTACTATATACCTAAAGCAAAATATCAAAGAAA

GTACCTTAAAAAGATAAATTATTCTTATTTTGACAATGAATTCTTTGGGG

CGTTAAATTGTAGAATATCAACACATATCAAGAAAGTTTAGAAGAAAACT

ACCAAAGTTTAAACAGACTTTCCTCGGTAATTACTGGTGATTTCTTGGCT

FIG.3B(2)

TTTTTTTTTTTACACTGCAGTTTTTCAGGGTGGAAACTTAAGCTTTGTACA

GAAGCACTTACCACCACTCTCAGAGCTGGAAATGGCTCAAAGGGCAAAGC

ATTACAAGCCTGGCAACCTGAACCAAATACCCAAAACACTTGCAAAGGTG

AAAGGAGAAAACTAACTCCAGGAAGTTGTCCTTCGAGCTCCTCTTGCACA

CCACTGTATACACCCCCTTATATACACTCAGTTACCATAAATAAAATGTT

TCATTATAAAGACACTTACGCTAAAACCATGCTGTAATCTGAATGGTTGA

ACATATATCCGCCAACAACCCACATTATATTTCCATTGACCACAGCTTTA

TGAGAGGCTCTGGGAAGCTTTAAATCAGAATATTCTTCTCGAGTCCAAAA

AGACTGGTTAGCTGGCACAGGAATTGAGCATCCAGGACCTAATAAAAAAA

AAAAAAACAACAACAACAACAAATAGCTTCACAAAATGCAGCCTGAAAGT

TTATAGTATTCCAAGTTCCAATCTAAGTGCAAAGAATATTTAAAGACTTG

TGGGGCTAGAGAGATGGCTCAGTGGTTAAGAAAACTGACTGCTCTTCTTG

GAGGTCCTGAGTTCAAATCCCAGCAACTACATGGTGGCTCACAACCATAT

GTAATGGGGATCTGATGCCCTCTTCTGGTGTGTCTGAAGACAGCAACAAT

GTACTCACATGAAATAAATAAATTAATTTTTTAAAAAACAGACCAGAAAA

AAAAAAAAAAAAAGACTTGTGTTTCCTTTAGCACTTAAGCGCAAACATC

TTTAACTTGTGGGGTTTTAAAGGTTTTTACATGTACAGGTATTTTGTTTA

CATGTATGCCTATATACCACTTGCTTGCTTGGTACCCAATGATGTCAGGA

AAAGGCATTGAATCCCCTGGAACTAGAGTTACAGATCTTATGAGCTACTT

TGTGGATGCTAGGATCAAACCTGAGTCCTCTGGAAGAGCAACCAGTACTC

TTAACCAAGAAGCCATCTGCTTAGCACCTAACATGAGTTTTTAACTTACT

FIG.3B(3)

```
CAAGATACAGACCAAAACCAATCACTCCCTTATAAAATTTAATACTACAC

ACTTTCTGATAATTTGGCAATTTCTGATAATCAGGTTAAACTTTTTTAGA

GGTAAAAATCTTGCTGAAGCAACATTTAGTAGAAAGGGTAGACCAAGGGG

TTATTATATTAACTCATGTGGAAAAGGCATTAGGGTTGAAATATAATGAC

AGATCAAAATCGATCTTCTGGCAAGTCCAGGCGCTGAATAGATGAAAGAG

ACAAAGGGAGAATTGGACAAACTAAAAACATTTACATGAACACTTACTTT

CTGAGGACCTAAGCATAGAAGGAAAATCACTAAACCAACGATGACTGCTT

CCTCAATACCCCAGGGAATTCCCTACAGTACCTTAGTACCCGGTTGTGTT

GGGTAATGGCACTAGATGACAGCACTGAGACTCTAAGGAACGCTTGTCCT

CCTCTCAGCTTGAGTCTCTGCTTCTCTATCACCAGACCATGTTCCCTAAT

TCCCACGAATGAGTTGCAAAGGATTTGTCAAACCTTTCCACAATTCTAAG

CACATAGATAACAACCACATATATGTAAATTCAAAGAATCTGAATAAATG

GAGATGAATGCTTAAATGCCACCTGATACATGATTAACATAAGGCGTATG

GCTGCTAAAATAAACTCCCTACAGTTCACTAACTCAGAACTTTCTGTGAG

GGAAAGGACTTTGAAGGGCAGCTCCTACCCTGCCAGTGAGGAAAGCAGGA

GCACCCTCTGGTATCGCTTGCATTACAGATGCCTCGGTGAGGAAAGCCAC

AGTTGTCTGTACAGTGAGGAATGTCACACGACTCCCCTTTCCAGTTTTCA

GAACATTCACACTCAACAGCGCTGCTGCTGTTACTGCTCTTACACTCTCC

TCGGCCTGAGCAATTATTCGGACACATGTCAAAACTACAAAGACAGGAGA

AAACGAAGTCAACAATTTCAACTAAGCAACATTGCAACTAATGCAGACCT

TCCTCCTTCAGTTTAAGTTCAGTTCATTTGCAAGTGTGACTGCAGGACTT
```

FIG.3B(4)

```
ACCAGTTAGCCCAAGTGTGCTCACAGAGCTCTGTGTAGCTAGAGCCCCAG

GCTCAAGTAATGAAATCAAATCAACCTTGCTGCATTCACATATGAAGAAG

GAAGAATAAATAACTCACAAAGTTAGAGAAATTACAAAACAATAGACATT

TGTGCAAAATCACTTAGACTTAGCTCAAGACTGGCAACCAGGATCCTACT

CTTTCTGGTAGCTCATTAGTAAAGAGTTCTACAAAAGCAGCAAGGTCATG

CTAGGAAGTGGAGGAAGGAGAGGAAGCCAATGAGCTGCCAACATTCACGG

TATACATTTCTCTGTAAAGATTCTGAGAATTAACAGAATTTAAGATTATT

TTCCAGTGATGTAGTTAAAGGTCTTTAGTAACTTTTATCAGCTTAGAAGG

AGAAGAGCAGTTAACTTCATGTATGAGTTTAAGTGTCTCATGACTTAAGA

TAACAGTTTTGCTACAATTTGAAATGCCATACTTCAGACTTTTTAAAGGG

GTGCATTAGTGGACTATTACAATAGCTTAAAAATATAGATTTCTCCTACT

GATGATTATTACTGAGACACTACTAGTCTTTATTAAATTCACTTAGCAAA

ACTCCTGACATTTTCTTCCAGCAGCGGAAGAATGTCTCTCTCTTCTAGGA

GATCCTCAGTGACAAGATCTAGAAAGACCAAGAACTGTGGTCCCAACCAG

TGGGGCTGATATTTGTTTAACCTTTTAGCTCCTGTTTCTTCAATTATGAA

AAAAAAAAAAAGAAGAAGAAGAAAATCCATGTTAAAATTTAGCAAGGAG

CCTGACTAGCTAGAAGCCTCCCTCCAATATATTAGTGTTATTAAGTCATT

TGAGTAGTATCACAAATATTAAATCTAAATATCTTACTTGTAAGTGATAT

TAAATCCAGTCAGATTATAAGCAGCATCACTGAAAAAATGCAGCAGTGCA

TAACCTGAAGTGACAGTGACCTCAGGAGCCGTCTCATTGCCATCTCTTTC

AGGAACAATGAGGCCACTGAAATGTAAACACAGACCAGATTACAGCAACT
```

FIG.3B(5)

TCAACAGAAACTGTCTATATGTTACTATTTGATCCTGCTGCTCCTGTTCC

AACACACACTGTAAATGTGACTCTAGCTGGCCTCAAATTCACAGACCCAC

CTGCTTCCACCTCCTGGGTTATAGGCATGCGCTACTATGCCCAACATCTA

AAAGGATTTGAAATCTATGACTTTGATTGAATTTTTGGTTTTTTGTTTTT

GCTATAAACTTTTTATTATAATACTCTCAAGTCTCTACAATAACATTATT

AACAAACTTTATGAATTGACAACTGTCAAATATATACTGTTGAAAGAAAA

TACTTTACATATTTTTGTAATATGTATCATATAATCTTTTTAATGTATTT

TATAGATGTCTTATATAAGTAAAAATAGAAAAGTTTACTGATTTATAATC

CTTATACTATTAGCTTTCAGACGTATTTTTGTTGTTAAACTGGTAACACA

TTTTATGTTTATAATTCACAATAAGCACTGCCACTGAAGGTGCCAAAGGC

TCCCTAGAATCTCAGTAAGAACCTAGTGGGTAATATTTGAAGTTTTGGAT

GCCAGTAAATTCATGTGTAAAGATTTATTGAGTAAGTGACTACCAGCGGG

ACAGTGGTGGTGCACGCCTTTAGTCCCAGCACTTGGGAGGCAGAGGCAGG

CGAATTTCTGAGTTCGAGGCCAGCCTGGTCTACAGAGTGAGTTCCCAGGA

TAACCAGGGCTACACAGAGAAACCCTGTCACCCTGTCTCAAAAAAAAAAA

AAAAAAAAAAAAGAATATACCATTTTTAAGGCATTTGATCCACAAAATCA

TACCACCTTGTTTTACAAAAGATATATATTAACTTGAAGGCTGGAAATGG

TGGCACATGTCTTTAGTCCCAGTATTGGGAAGACAGACCCAGATGGATCT

CTGAGTTCAAGACCAGCATGGTCTACATAGTGAATTCCATGTAAGTTTGT

CCGTGTGTGTAACTTGAAACCTCATTATAGAATGGAAGTGTCTACCCCAC

CCCACTTACCAACAGTAAGGAATATTATGTTGGTCCCGCTCATTTAATAC

FIG.3B(6)

```
ATGGTGTACTCCCAAGGTAAATCATTTTCATGTTTAGTCGCTCCTATTAT

TTTTTCCATTATCAATTCACTACAACTACTACCACCAATCACATTTAGCC

ACTAGAAAAGCCATGTGATTTGCTCCACACATACAACTTCACTCAATAAA

TAAACATCTTATCAGTACTACTCTCTTTCACTCACTCAATCCCTAGTC

CCCTAAGTTTTTGGACGATTACACCAGGTAAATTCCTACTTCAGGGTTAT

GACCATCTTAAAAACTACGACCTAGCAATTCTCTTTGTATAAGAAATACT

TCCCCGTATATACACAGAAAAACAAAGAACACTACTACAGCACTATTCAG

ATGACAACTGACTAAAAGTCACCTAATTGCTTATTTATGGGAGTTGATTA

AATTAGTCATTACAAATCTGTAGGTCTGCAAGACTAACCAAGAGCTTCGT

GAGGACAATAGGTAGGGCTACCCAGAGAAACCCTGTCACCCTGTCTCGAA

AAAAAAAAAAAAAAAGGGAGGCACAGAGAAAAAACAACAGGCCCGGGGTA

CCTGTACATCTATGTAAGCGTAGGTACATGCACATAAAAGTGACTACAAG

AGAACATAAACAGAGAGCGCCGATGAGAAGAGGATGGGATTTTTCATTTA

ATTTGCGTGTATGAGAGCACCTATATGTGCATGTTATCCGCACCAAAGTG

TGTAGGGTACATTATGTGAGTGTGCCTGCAGACGTCACTGTCAGGTGTCT

TCAATCACTCCCCTCCTTTTTCTTCTGGAGATAAGAGTTTCATGAAGTAG

TACTGGCTGGACTAGAACTCACTATGCAAACCAGGCTGGCCTTGAATTCT

CAGAGAGCCTCTTGAGTGCTGGAATTATATGCATGTGCCGCAACACAGCC

CACCTCATTTTGGGGGGTAGGATCTTTCACTGAACCTGAGCTCACTGATT

GGTTAGACCGGACTGGCCAGTAAGTTCCAGGACCTCTCTTGTCTCCGCCT

CTTCAGCACTGTGATCACAGGCTCACAACCACACCTGGACTTTTACTTGA
```

FIG.3B(7)

GTCCTGGAGATCTAAACTCAGCTCTCCATGCCTGTGCAGAAGGAATTAAA

CTGAGCCAGCTGTCTCAGTATCAAGAGAGAACATAGGAACTGTAAGATTC

TGACAGTACTCTAGGGCTTACAGAACACCGACACATTTTCTACTATGTAT

TCAGTTAATAAAAGAATAAATACAAACAAAAAAACATGAGAAACATATAG

AGGCAGAGACAGACAGACACACACACACACACACACACACGCACACAC

ACACACACACACACGCACTTAGACGGGTGTGGGGGAAGAAAGAGCAAG

GCCACCTAGAAACAGGTACGTTCCATGCAAATGATCACAGGAAAGGATTG

GGGATTTTTAACCACTTGTGGGAAATGCTGTACTCTCCTATTCTAGCACA

GATTTGAGGAAAAAGTAGACCAGAGAGTCTGTCCTTCCACATATCCTGGA

AAGTCACTGACATGTCCAAGTTTTGATTTCTTCATAGGGACAATGAGAGA

AACCCAGACTATCTCACAGCAGCACAGCAAGGACCAACCAGCAGAGCAGG

AGAAGTGCTTACAGCAGTGTGCTGCTAGAAGGTGCAACAGTCTTCTTACA

GAGGGCATTTAAATATGCAGGATGGATAAGTTTGCCAACTACAACTACAG

AGGCTGGACAAGGTAGGACAGCTTCTTCACTGTCAAAGACGTTTGGGCAG

TTGCTTCTATTTACCTTAAAATCAAACTGTGACAGCTGTGGCATATATAG

ATTTCTCCCAGAATGAAAACACATTAACTCACTTATGTCAATAATATGGA

GTAAACACAAACATAGTCTATCTAGCTCAGCATGCAAGACATGTGAGGAA

GAGGAGCTACTGTGAGTCCCTATCCCTGTCCCTAAGGAAACCAATATATG

TAAATGTAGTCTAAGCTGCAGGCAGTTCTTCAACTGCCTACCCCAGGCTG

CTCACCACTTCACATTCTAAGCACAGACTAGAAAGTATGATCAACCTCTG

AACACTGTGCTATAATGTTACCATCAATCTCACACACAAATTTCATAACA

FIG.3B(8)

TTTTAAGTAAGTCTATGATGATTCTATGTTGTGTCCCAGTTATATAAGAT

CCATAGGTCACAGGGTAGACATTCAAGGACACCAACATTTGGAATTTTGG

GTTTTTTTGGTGTACTGTATATACTTGCTAGTGCAGGTACCCATGCTCAT

GTGTGTAGAAGTTGGGCGTCTTTCTTCTATCACTGTCTACTTTATATTTT

CTTTATTGTTTCATTTGATATGTATAGGTGTTTTGCCTGCATATATGTGT

ATGTTTGTTGCCAGAAGAGGGTATTGAATTCCCTGGGACTAGAGTTACAG

GTGGTTGTGAGGCACCATTATGGGTACTGGGACTCAATCCTGGGTTCTCT

GGAAGGGCAGCCAGTACTTTTAATCACTGAGCCATCTCTTTAGCTTCCTT

CGTTCATTCGTTCGTTCATTCCTTCATTCCTTCATTCCTTCATTCAGAGG

ATTGAGATACCTTCCTCAGTTAGGCTGGCTAGCCAATGGACTCTGGGAAT

CTATCTGTTCAGCTATTCTCTCCTTCCCCATCCAAGTGCTGGGGATACAG

GCAGGTCCTACTGGGTTCATTTTGAAAAATTACAGAACTATGTATTTTCT

TCATAAATCTGAAACTCAGCATAACTGTCTCAGGCTAACATGGAATCCCT

AAATATATATGAGGCACAACCTGACTTTACCAACTGTACTATGTAAATTT

GCTAGTATATTAGTCAACACTTAATGGAAAAACATCTGATAAAAACAACT

TACAGGCCAATAGGCAAGGAGACACTTGGGGAGGTGGATTCAAGGCAGTC

ACTGGATTCTTGAATTTAAGTCCAGCCTAGGCTACATGAGATTCTGCTTC

AAAAAATAAACAATTAAATTTATGGGGGAAAGAATGATGTATTTTGGTTT

CAGAAATTCCATCCTATCATCCAAGGGAGATATTGTATAACAGCGAAGTT

CCTCAGCTCACAGCAGTCAGTAGCATATAGACAATCCTGGCTCCAAGCCT

ATGAAAACACAGCCTGTACTAAAGGTGTGTTCCTGTGTTTTGAGTGAGAT

FIG.3B(9)

GTGCCCCCTAAGTCTTGTGTATTTGAATACTTGGCACTCACTTGGTGGCG

ATTTGGGAGGAATTAGGAGGTGTGGCCTTGGTGGAAAAGGAGCATCACTA

GGGTCAAGGTTTCAAAATCCTCCTGCCATCATCCCCAATATGTCCTCTCT

GCCTCCTGCTTGCAGTTCAAGCTATGAGCTCTTAGTTACTACTTCCACCA

CCTACCCCTGCTATCTCTGCTCCATCATCATGGACTCCTATTCTGGTGGA

ACTGTTAGTCCAAAAAAGTCCTTTCTTCTACAACTTGATTTGATGCCAGA

TCTAGCCCCCCAGCCTAGCTAGCAATATACCAAGGTATACCATCTTGAAC

TCTAGGTGTCTCTCAATCCAATCAAGCTACATAAGATTAACCATCATACC

TAGTCATCCCCAAATCAGTGTATCTCTCCTCCCAAGACTATAAGCTCC

TCAAGGGTCAAAATATGTAGAAAGGAAGAAAGATTCTCAAAGGTCAAGGA

TCAGACCTTGGTGAGGATTGAGCACTGTCTACACTTTGCCTGGTAAAGAA

GGGTCCACAATGTAAAAGAGAACTGACCTGAACAGTTTTCAATTAGGTGC

TAACAAATGTCTCATACGTATTGAGTTTCTTATAAATAAATAAATAAATA

AATAAATAAATAAGCAAGCAAGCAAGCAAGCACTTAAGAGCACTAGCTGC

TTTCTTCCTGAAGACCTGGTTTCAATTACCCAGCACTTATACAGAGGCTC

ATACCAATTGTAACTCCAGTTTGATGATATCCAACATCTTCTTCTAGCCT

TCAGACACCAAGCACCAAGCATGTAATGGTATAACACATGTATACCAAAC

ACCCATACAAACCAATTTTTAAAAAAATATTCGAGCCGGCGTGGTGGCGC

ACGCCTTTAATCCCAGCACTCGGGAGACAGAGGCAGGTGGATTTCTGAGT

TCGAGGCCAGCGTGGTCTACAGAGTGAGTTCCAGGACAGCCAGGGCTGCA

CAGAGAAACCCTGTCTCGAAAAACCAAAAAAAAAAAAAAAAAAAAAAAAT

FIG.3B(10)

AGTCATTTTAGGGCTGGAGAGATGGCTCAGGGGTTAAGAGCACTGACTGT

TCTTCCAGAGGTCCTTAGTTCAATATCCAGCAACCACATGGTGGCTCACA

GCCATTTGTAATGGGGATCCAATATCCCATTCTGGTGTGTCTGAAGACAG

CTATAGTGTAAATAAAATAAAGAAATCATATAAATAAAATAAATAAATCT

TTTTAAAAATATTAATTAACCCAGGCTGAACCTAAACTTACAAACTTCCC

ACATTAGGCTCTTTAATGCGGGTGTTATAGGTCTGAATACCAGCTTAAGA

ATAATATTCTTCTGAAGAATGTGCCCTGGTCAATCACCATGACCACACCT

GCCAACAGGTCCTTCATAAAATACTTGGTATATGTTGAATGTTCCATAAA

ATTATGGAGCTAGAAAAGGTAGTGAGCTAGAAGGATATTAAAGATATAAA

CCATTGCCCCAGTGGTCCTCACATTTGTCTAGTAATAGAACGTTGTTAAA

CTGTTTTTATTTAGAATTTCAATATATAAAAGACAAATATGAAATAGTCC

GGAAGCAAATTAAGCTACAGCTTGCAGCAAAGCCAGATAGAATGCAGATT

AAACTAACACAGTACCTTTGTCTTATGTTTTAGATGCTAAAGTCTAGTCT

ACAACCCCAGCTGCCCTTGAACTCTTAGCAGTCCTCTTGCTTCAGCCTCT

CATGCTGCTAGGGTTAAAAGTATGTGCGACCACACACAGTTTTGAAGTTT

AGAGCACTTAAATGATCTATTCAGCAACTCAGGCAGGATTTACACTGAAA

GTAAATTATCTTATGAATCCTTTTTGGTTTTCCTTTTATTCATTTCATTC

ATGCACCTTACATGAACTATCTATTGCTAGGCTGTCTCTATACTGGATGC

TCAGCACATCACCAACATGCCGATTCTTCTACTGGTACAATGGCAATGCT

GAGAAAACCACACAACCTAAGACAGTAGGGAGGTGGTGCTCTGATTGTTG

GTGTTGTTGTTGTTGTTGTTTTGGTTTTTCGAGACAGGGTTTCTCTGTGT

FIG.3B(11)

```
AGCCCTGGCTGTCCTAGAACTCACTCTGTAGACCGGGCTGGCCTCAAACT

CAGAAATCCGCCTGCCTCTGCCTCCCAAGTGCTGGGATTAAAGGCGTGTG

CCACCACGCCGGGCTCTGGTGCTCTGATTTTTAAATACAACAATTTTCAG

CTAGCAATGTAACTCAGTAGTAAAATGCCTGCCCAGCATGCACAAGGCTC

CAGACTGGACCCTGAGCACCACAACACTTTTTAAAAGATGTGTTTATTTT

ATTTTATGTGCATGAGTGTTTTGCTTACATGAATGTCTGCACTGTGTTTA

CCTGGTGCCTGTGAAGGTTAGAAGGCAATGGAGCTATGGAGAGTTGTAAA

CTACCATGTGGAAATGGAGCTATGGAGAGTTGTAAACTACCATGTGGGTA

CTAGGAATTGAATCAGGGCACTCCTCTGCAAGAACAACAAAGGCTCTTAA

CAGCTAAAATATTACTACAAACCCACACCACAAAATTTTAAATTGATAGA

CATTATCACCTTAGTTCTAGATAGAGAATGTGCTTGGCATTGTAAGTACT

AAAAAGGTTTTGGGGTGGATCTTTTATATTATCTCACTATAATTTTATAA

AATTAATACTCAAATATGTTATAAGTTAAGGTTTTTATTTTTGTTTTTCA

TTTCTGTATTTTGTCTATGTAGCTCTGCCTGGCCTGAAACTCATGGGAAC

TTGACTGGCCTCAAACTCAGAGAGACCTGAACGGCCCTGCCTCCAAAGAG

CTGGGACTAACCATGCCCAACAGTAGGTAGCTTTAATACCTAACCAGTGT

ATTAGTTCATGCTCTCAATTAACCAACATTCTCTACATACAGAAATTTTT

ATGCCTATTTAATCAAATACACAGTCTAAGTAAACTCTAAGTACAACTGC

TTGGCTCATATTCTTACAATGGCTATGGCTAGCTAATTCAAAGGCCAGTC

ACATAAAAGGGTCTCTATGAATTCTGATTAACAAATGCAGTTAAATAGAT

GAATTCCTAAAAAGTAGTATCATAATAATATCATATTTAGTTTTTGTGCT
```

FIG.3B(12)

```
TCCATTATAGTTTGAGGTGCCTCCTCCCATAATGCAAGGTATATTTCAAA

TAATAGATATATACATGGTTAACACATGGCAAATGCCATTTTAAATGCTT

AGCACAGCCTGCTCTTTGGCTCCATTAAGTGAAACTCTTAAGTTCTCAGT

TAAAATAATTGTTGGAGAGCTATAGGAGCAATGGGTGGAGAACTAGTCTT

CTAATTTGTCCTTTGCCTCCTTGCGTACTAAGTAGTCCCTCCCTCACTAT

GTGGCATTCCAGCAGACTACCACCAAGAGAAGAACAGAAAAGTGTTGATT

TCTTTCTAAAGTAAAGAAATAAGGGGCCAGTGAGATACCTCAGCAGGTCA

AAGCCATTTGCCTAGAAACCAAAGTTCAATCCTTGGAAGCCCTGTAAAGG

TGGAATTAGAAAACAGACTCCACAAAACTGTCCTCTAACCTCCACTCGGG

CACACATGTGCCAACCCCTCCATTCTCCCTCCCCCACATACAAAGTAACA

ATAAACTTTCAGAAAATTTAAGTTGCTACGCATGGTGATTGATGAATGTC

TTTAATTCTAGCTCTTGGGAAGCAGAAGTGGGTGGATCTCTGTCAGTTCA

AGACCAACCTGGTCTATATAGTGTGTTCCAGGCATCCAGGACTACACACA

CACACACAAAATTACGTGAAGGAAGTAGAATGTTTGAAGGAAAGAAGTCT

GGAAATGGGGATGGAGAGAGACCTCAGCAATTAAGAAAAGGTCTTGCACC

GGACGTGGTGGTGCATGCCTTTAATCCCAGCACTCGGGAGGCAGAGGCAG

GCGGATTTCTGAGTTCGAGGCCAGCCTGGTCTACAAAGTGAGTTCCAGGA

CAGCCAGGGCTACACAGAGAAACCCAGTCTCGAAAAAACCAAAACCAAAA

ACAGAAAACCAGTATGATAGGTCAGGCAATTGGATCGAGACAGGACACTC

AAGATAGCTAGCCTGTGCAATATAGAAAGAAGTCTCATGGAAGAGAGAGG

GAAGGGAAGGAGGGGGGAGAGAGAGAGAGAGAGAGAGAGAGAGAGAGAGA
```

FIG.3B(13)

```
GAGAGAGAGAGAGAATGAGAGCGAGAGAGCGAGCGCACCTCAGTTGATAC

AAGATTGGGGCCCTGAGTTCCATCCCCAGCATCCCATAAATTGGGTGTAG

CAGCACACACCTGTATCCCAGCAGAGAGGCAAAAGACAAGTTCAAAGTCC

TATATGGAAAAAGTGTGAGATCAGCCTGGAGACCTGGTGTGTGGCAGTGG

GGTGAGGGGTGTCATCAAGGAGAAGGCTTAGTAAGTAAAGGACCTGCGTT

GGTTCTTGAGTTCAAGTCTCCAGCAATCAGAGAAAGCCAGAACCATTGCA

CAAACTTGTAAGCCAAGTGTTGGACTGGACAGAGACAGGCAAATGTTTGA

GGTCCAGGTTCAGTAAGAGACCCTATCTCAAAAAATCTGATGGAGAGTAA

CACTGGAAGAACTCAGAGTGAGTCACACATGCACACACAGGTGAATGTGT

ATACAAAGGGGCAGGGAGGGAGAATGAGAGGAGACTGGGAGATATCTGT

AGTTCATGTCTGTAATTCTAGCACTTCAGAGGCAGCTGGAGCTACACAGC

AAGACCCCGTCTCAAAAACAAACCCAAGCCTGACAGTGGTGAGGTACACC

TTTAAGCCCAGAGGCAGGAGAATCTCTGAGTTCAAGGGCAGCCTGAGTGA

GTTCCAGGACAACCAGGGCTCCACAAAGAAACACTGTCTTGAAAAAAACC

AAAACCAACCAAACAAAAAAGAATCAAAAACAACCACCACCACTACAACA

AAGCAAACAAGGGAGAAGGTATAAAATGCTTAGGAGAGTCTTCCTTTAGT

CTCCATCCTTTGGGTACTCCTTCCCCACAGAAAGCCACTACTACCAATTT

CTTACATAAGCTGCTGTTTTAGACACAGGTTTTTTTTTTTTTTAAATATA

GTAACATATTCATGTGTAGCTCATTTTTTCTAGTGAGTGGTTGGTCCTTCT

TTTAACAGTTTAAAGGACCTCTATGTTTAAAGGCGATTGGCCCTTGTCTG

GAGTATGGGTTGTATTTTCCCAATTTGTGAGTTTTACCCAACCTATTGCC
```

FIG.3B(14)

TATTACCTATGGCCATTTATTCTTGTCGATAAGTAGTTTCCAATTGTATG

ACTATGGTCACAGTGTTCCATGGACTCTTCTGCCGCTAGACAGCCCCTGG

GTCTGAATTTGAGATGGTTACAAGGGTGATTGGCTCTGCTCCCTGGGTGC

TGGGATTAAAGGCGTGCACCTCCACACCCAATTTGTTCTGTTTTGTAAGA

AATGAGGTTTTATTGTGTTGCTCAGGCTGATCTCAGTCTCCTGGCCTCAA

GGTATCCTCCCATGTCGATACACAGCACAAGGCGTAGGAAAAGTGGCAGA

TTTTTTTAAATTAAGTTTTCTTTCCAAAATATAGATTCAGAAATGTGAGA

TTTTCACAAAGTGAACCTGCTCACTTCCCTGGCTCTMGAATCTCCATTGT

GGCTCCCGCCCATCCCTTTTGCCCACCAGTGGCTGTTGTATTGACTTCTA

TCCCATTCCTTAACTATACCTGTCCTTGGTCTTCGCTGTGAACTTGCTTG

GGCTGAGAATCACCTTGTTCCGGGCACATCAGGTCAGTGAGGGTGTTTCC

AGAGAGTTTTAACAGAGACCAGAAGACCCACTCCAAATGTGGGTGGCAAT

ACCTGATGTTCTGTCATCCTGGACTGGGTAGGAAGAGGAAAGTAAGAAGC

AAACGGCACCCCCACCTCTCTGTCTGCTTCCTCGCCGACACAAAGTGACC

AGGGCCTCCCACTCCTGCCCCCTCAGCTAGAGACACTTGCTGCCATCTTT

CCAACCACTCTGAGACTGTGCCTACTAACCGTGACCCAAAATAAATGTTT

CCTTCCTTAAGGTTGCCTTTGTTAGCTCCTTTAATAGAGCGGTAGGACAT

GTAACTGCCACAGGCAGCCATCGCTGCCAGCCCCTCCCACTGACCGTCTG

AGAACCACACTCAGCTGTAGGCACAGCTCTCATAGCTGTGTGGGCGTAGC

TCTGTCTACTCGGTCATTCCCCTGCTGCCGAGCATTTATTGTTTTCAGTT

CCTGGCTGATGGGTAGCACTGTTATGAACATCCTAGTACAAATCTCAGGG

FIG.3B(15)

```
TGACACGCGCCTTCATTTTTCCTGAGAAAATGCCCAAGGATAAAATGCTA

GGGCCAAGGGAAGAATATTTCACCATTAAGAGACACTGGTCAGGACTGGA

AAGATGGCCCAGTGGTTAAGAGCACTGACTACTCTTCCAGAGGTCCTGAG

TTCAATTCTCAGCAACCACATGGTGGCTCACAACCATCTGTAATGGGATC

CAATGTCCTCTTCTGGTGTGTCTGAAGACAGTGACAGTGTACCTACATAC

ATGAAATAAATAAATAAATATCTGAGAGAGACAGACAGACAGACACTGGC

TAGTCATCTCACAATGTTCTCATGTTTAAAATATGATACCATTTGTATAA

AGCAGAAACACAGGAAAAATAAAATCTGTGGTATTATATTTGATTTTTAA

ATTAACTTGATTAGTGAAGTTAGCAGCTACACTGGGCAGGGGTTGGGAGT

GGGGTACTCTGAAGTGCTGGTATTTCTGGTTTTGTTTTTTGTTTGTTTGT

TTTTTTATCTTATTTATATTACATAGAAAGCCATTTTGCTAATACACTTA

CCATGTGTATATATTGTGCTTGAATTACAGCTAAGTAATTATTTCTGAGG

GGCTTTAGACTACTGAAGATTGGGCCCAATGAGCCCCACCCCAAGTAGTC

TCCAACATCCCTCTTGGAAGTACTTGAGAGCAAAGATTCAAGTCACATGT

CCCCAAACCCTCAGCAGCCACCACCCTTTAGGTGTGGCTTTTGCTCTCGG

TCATCCTGGAACATCTTGCCATCTTTGGTTTGTTCTCTCCCTGTCTTGCC

TCTGGTAGAGCTGGGTTTCTGTGCTTCTATTCAACCATGTACAAGAACCA

TGTGCCACCTGCCATGTGCCAAGCCTGTGCCAGTCCCTGTGAGCGAGCAG

CCCACCCCGTGAGTTATCATGTGAGGAGCTATGAGGAGCAGGAAGGGGCC

CGGATGACTTCAGCAGACAGTATGAAGCAAGCACTGTGCGATTTATGCTC

CCTGGCCACATGCCCACAGATGGTGTCTGAGACACTAGCGTTTAATATTT
```

FIG.3B(16)

```
GAATTCTCCACATTCTAGCCTAGACATTTTGGTTGCAAGAAGAAAATTGA

CTCCAGTTGTATCCTGGAATGAAATTTATTGGAGGAAAATACTGGACAGG

CTCCCAGAGAAAATACGATATTCAGGCACAAAAAGAAATGGGGACTGAGG

ATCTGAAGTTCAAGGTCATCTGTAATGAGATTGAAGTCAGTTTGGGCTAC

ATGGGACCTGGTCTAGGGGGAATGGGGAAGAGAAGGGAAGGGATCGAGAT

AGGGAT
```

FIG.3B(17)

```
CAATGTGCTCTGACGATTAATGGGCTAGAAATGTGTGGCTGTTGATTAGT

GAAAAGATGTCATGGTTCAGGAGATTGGTAGTCTCTGTGGGAAGACAACT

CACTGAAAGGGAGGAAATAGCCTGGAAGAGATAAAGAGACAGTGATCAGC

TAGGAAGCTTAAAATTTAAATTTTGTTGGAAGTACTGTTAGGAATACTAG

CAGAGGCCAGATGAATGTATGGTTAAGTTATAGCAAAGGAAAAGATTGTT

AATGGTGAGGTTAGGAATGCAGGGTGACACCAACCTGTAATGTCAGCATT

AGCGAGATAGAAGCAGGTGTTTAAGGCCATTCTCTGCTACTTAGCAAGTT

GAGGCCAATCTGGACCACATGAGACCTTTTTTCAAAAATAAATCTCCTTA

AACAAAAGAGGCTGGGTTTTTTGATAGATTCTTCAAGATGTTAATGTAAA

TAAATGGAAGACCAAGGATGGCATGCTAATATCCTCAGTGTCTGAAGAAG

GACTATGTAGTGTTGGCTGCTGACTCTGAAGTAAGTGCTCATTACTGACA

GATAGTGTATCTTAGAGCCTGGCAGATGGGATGGAAGTGAGGAAGCAAGT

AGCACCTTTGTATATTATGTTCTAAGTAGCCAGAGATACTTGACACAAAA

CAAAGTTGAGAAAATGTATCTTCTAGAAAATACAGACATGGAAAGGTGTC

CTTTCTATAAAAGAGGTATTAAACATTAACCTGAAAAAAAAGTTAGCAAA

TTGGGCTTTGGCAAATGAATATAGTCAAGTTTCATTTTTATTTTGTTTTT

TGTATATGACTGTTTGGCTTGTTGTACCATGTGTGTTCCTGGTGCCTAGG

AAGTCAGCTGGAGTTACAGATGGTGTGAGTTGCCATGTGGGTGCTGAGAG

ATGAACCTAGGTCCTCTGGAAGAGCAGTTAGTGCTCTTAACCACTGAGCC

ATCTCTCTAGTTCCTTCTGTAGAATTTTCATTAATTTACAAAGGAGAAAG

TATAAATGATAAAACCATGAGAAGATAGACCGGCACTAGAATTAGTGGAG
```

FIG.3C(1)

```
TCAAAATGTTAATGATATGTCAGATACGCCTTATATGAGGAAGTTGCAAA

ATTATGAAAATCCAGGCACTCCACTGAGTTAGAAATCTAGGCTCTGATGC

ATACTGCTATGGTAAGGTAGCAAGTGGCCATTGAGTGCAGAAGTGAGTCT

GGATGGGTCTTCTGGTGTTGTGGAGCACACAGACTGCTGTCTTCTGCATT

GCAGTTTCACCTGTATTTCCTTGGAACTACTTAGCTTTGCAACTAGGCGT

TAAAAAAAACTTTATATTTATGGTTTTAAGTTATTTATTTGTTTTATTTT

ATTTTATGAGACATAGTCTCACTCTCTAACCTAGGCTGGCCTGGAACTGC

CTAGGTAACTTGAGCTGGTGATTCTCTTGCCATAGCCTTCTAAAATTTTA

GATTGCAGGCATAAGCCAGACCACTCCTGACTTTTGTAGCCATTTTTTCTG

ACATGAAGTGTAACTTTGCTTTCATAACTAAAATGATTTAGTTGTTTTGT

TATTGTTTAATCCCTTTTGCTTTGAATGTATCCTTTTGTGTGGGTGGCAG

ATATATAACCACAGACTTTTCCACAGGCATCCTACCCTAGGTCCAGAAAT

GACTCTGAGACGTCTTATATATGAATGAATGCCTAGGCCAATAGCTTTGG

CTGATTTCCACGGGTTCATAGCTCAGTTATCCCATTTAAACTAGTCTAAG

TCATGCCATGAGGCTACATACCCCTCCTTCAGTTTCAGGCGACTGTCTTC

TCAGTTGTGTAATGTCCTATCCTCTGTTGCTGCTCCCCAACCCCCATCCT

TGCGTCATAGTCCGTCTGTCCTCGTCTCCCCCCATTTACTTGCACAACGG

ACTCTACTCTAGAAGTCCTCTCTGTGCTGGAGCTTGCACCTCCGCTCTCC

CCGTCTAAGCTAATAGGCAACAGCATTGTACAGACAGGTGATGCTTCCAT

ACATCGCACAGGAGATTCTCCCTACACAGATACTTATTCATCCAGCGTGA

ATGCAACCGTCCAGGCGTGTTCTCCTAGTTGTAGTACATGCTGTTGTATC
```

FIG.3C(2)

```
AGTCTGATGAATTTCTTTGTCTTTACAACCAAGAAAGATAATACTGTAAG

AAATTTTGACTAACATTTTTTCTTTATTTAAATTACAGACTAACTGGCTC

TTCTGGATTTGTAACAGATGGACCTGGGAATTATAAATATAAGACGAAGT

GCACATGGCTCATTGAAGGACAGTAAGTTATAATGGCTGACTTTATTTTA

ATTTATTATAAGAGCACAGTATAGCACAAAATACTTCCATGTGTGTTATT

GCTATTTCTTGAGACAGGACCTTTCTGACTGAGTAACTCAGGCTGACCTT

GAATTTTGCTATGCTACCTCTGCTTCCCAAGTGCTAGGGTGGTAGGTGTG

GACCACCATGCCCTGCTGCTAAAATACCGTTCATTGATGCTTTTCATTTG

GATAGTGTTCTTGCTTTTTAAAATTTACTTTTTGGGGGACCAGAGAGATG

GCTCAGTGGGTAAAGTGCTTGCTGAACAAGTCTGGTTATGTGAGTTAATC

CCTGGCTCCCACAGTGGAAGAGTGACTCCTGAAAGTTGTCTTCTGACTCC

CACGCTTGTGCATGCACGCACACACACAAATAATAAAATAAAAAATTAAA

AGGAAATTTTCTTTTTTGGGTGATAGGGATTGAACCTATGACTTCACTAA

GCAAGTGCTCTATTGTTAAATAATTCCTTTAATTTGTGGGTTTTTTTTTT

TTAGGTTCCAAGTTGACTTAATGTTATAAATGAAAGATACATACCAGAAA

TTTGCATATTTCTAATAGTTTAAAAAACTTAGTTAAAATCTTTTTAATAG

TTTGCTTAAATCTTTATATAATAATGCTATTATATCATTTTTCTAAATAT

TGATTTTATTATCAGCAAAACAGTAAATGAGCCATCAGAATAACCACTGT

AGCCTGTTTCCCTGGCCCTCTGTCCTTCCATCTGTCTATCTTCTCTTTTT

TTTCCTTTTTTGTGCCTGTCATTTAGGGCAAAGCATTTTAGTCTCTGAAC

AAAACTTTGAAATTTCCAAGTAACTCTTGTTTATTTGTTGTGTCTCATAT
```

FIG.3C(3)

TCAACCCAAGAAATATTATTTACTAACTCATTTAAAAGCAACAATTATAA

CCCACTACATGTTAGCAGAAAAACCTATTTGTTTTTATTGAGACGGGATC

ACACTAGTAAGCACTACATGGCATGGCGTTCACTGTGTAGATCAGGCAGG

CTGGCTTCGTGCTCTTGACAGTCCTCCTGTGTTTGTCTCTCACTTCTGAG

TGCTGGGATTATAGACATTACCAACACACCGATTTGGGGGGTTGGGGTAC

TGGGATCAGTCCAGAGTTGCATGGATGCTAGGCAAGCACTCCACCAACTT

AGCTATATCCCTGGTCATAAATGTCATAAGGAAAAAAATTCCTTATATTT

AAAGAAATTTTAAGAATTGCATTGTTTAAGATTTCACAGATCTCTTTGCT

ATCTGGCAATCTTTTTTGATATTTTGTTTTGTTTTTAAAAATATGTGGTA

TGTAAACAAACTTAAATATGAATGGGACAGTTCCAGATGAGAGTGAAAAG

TTAAATATTTGGGAGAAAAATTGATAGGTTTATCTATTATGGAAAATTTC

AGAGATTTTAGTAAAATTTGAAAATGGAGCTGGGAGGTCTGAGGTAGTCA

TCTAAAGCTGCCAGTTGTAGAGCGTGTTGGAGTGTGGAGTCAGAGGGAGT

TACTGATACACTTGTTGAAATTGCCCAGGCTTCATGGGAAGTGATGAGGG

GCTGTTACTGTGACTCTGGGCAGGGCTTGTTAGTTTCCTTTGGATTTAGT

CTCAGTCAGAGTTGATACATAGTTTCCTGAGGACGTGGCTTTTTGGTACA

GTGCTGTGAAAAGGCAGAGAAGCAGGTAAACTTAGAAAATGTGTGTTTTT

AAAGTGATGTGTTATGAAATCTTACGTAAGATGAATAAAGAAAGAAGTGG

GGACACTGAGGGCTCCTGTTTCTAAATGTTAAAAGCAAGGCTGGAAACAT

TCTTTGAAGGCCCCTGAAGTCAGAGCCCGTGTCTCTTTTGGTTCCCAGGA

CATTTTTGATATTCCCTTACACATAGCAAATACTAACTAGATCTCTGACA

FIG.3C(4)

```
AATGCAGGAAAGCTGTTTATATTTATATATATTTATATTGTATATTTTTC

TCCTTATAAATTCTTTAAAAGTCTGTTTTAGTAGTTAATGTTATGATTAT

TATAAATTACTTAATTATTTTTCTAGGCCAAATAGAATAATGAGACTTCG

CTTCAACCATTTTGCTACAGAATGTAGCTGGGACCATTTATATGTTTATG

ATGGGGACTCAATCTACGCACCTCTGATTGCTGCCTTTAGGTAAGCCCTG

CTGCATTTCATCTCAGGAAGTAAGTGTGTCTCCAGGATGGAGTCCGTGCT

GCATTTACTTTATTCTGCAGTCACACTCATCTCATGGAATTAGTTCTGTT

CTGGTGAGCTACAGTTCACTTGGTTTTTATGTACTGGGTCGTTTTCCATG

TATACTAGTATGTAGCCACGGTTAGTCTTGAACTTCTGGTTCTCCTGCCT

CCACCTTCCAAGTGCTAGGAGTATAGGCTTGTGCCACTGTGCCTGACTCA

TTTCACATTCTTGAACTGTGAAGTTTTGATAACACTATTAAATTTACCTG

CTATTTGTGATTTTGTTAAAGTTTGCATTAAAAAGTTTTTGACTATATTG

ATAATATTTTTGTGACAAATTTAAATCAGAAACCATACCTTTCTTGTTCT

TGTATGTATTTCATTCCATAGGCCCTTAGGAATAACTTTTTTTCAATAGTA

TATAGTTCTCTCAGTTTGTATATATGTATTATTAGGGATAGGAGGAGCTT

TCTGGAAGACTATTTATAAATTGGACAATGGCTAGCTGTTGAGAGTGAGG

AATTTGCTAGTTTTGTTTTGTAAATCCCTCCCCAATGCATCTGTATTAGT

GATTTAATAAAATAATGCAATTTTGTCAGTTATATGGGTTGCACTGAATT

TTTGCTATTTTATTTTAAGAAAGATTTTTGTGTGTCTACAGTGTATATGA

GTGTATGATATGTGTGCGTGTGCATGTGTGTGTGTACTTCTATGCAGGTA

CTCACATGCTATGGTGTGCACGTAAGGTTGGAGTGCAGCCTCACATGTTG
```

FIG.3C(5)

```
ATCATTATATTCCACCTTGTTAGAGATAGGTTGTCTTTGTTGTTTGCTGC

GGCCTGGAGCTGGAGCTGGAGCTAACGAGTCTCAGCCACCTGACATGGGT

ACTGGGAACCAAGAGCAGCAAGACCTCTTCTTCTTCTTCTTCTTTTTTCA

TTTTCGGTTTTTTCAAGACAGGGTTTCTCTGTATAGCCCTGGCTGTCCTGG

AACTCACTCTGTAGACCAGGCTGGCCTCGAACTCAGAAATCTGCCTGCCT

CTGCCTCCCAAATGCTGGGATTAAAGGTGTGTGCCACCACCACCCAGCCT

AAAAGATTTTCTTACTAAAATATATTTCTAAATTAATTAGTTGGAATCTG

GTTCATACTTCTTTTTGAAACAAAACCAGCATTTTTTTTCATTCTACATA

CAGAGACATTGACACTAGACACTGGTTATGAGTAGTTACTATAAGAATGG

GAAATTATTCCACCCTTGTAAAACTTAATACAACTCCTTATCAGGCTCTG

AAGACTTTTTAAAAGCAAGAATTGTATATAACACACAGAAATGATTTAGA

CTATTTAGATCTTTATTGCATGGGATTTTAAAATTATTATTGTATTTCGT

GGGCATGTTTTGTCTATGTAGCATATGTGCCTGTAGAGGCAACCACCAAG

TAGGTCCTGGGAATCAAACCTGGTACCCCTGCTCTTAGGTGTTCTTAACT

GCTGAGCCATCTCTCCAGTCCTC
```

FIG.3C(6)

AGGCAAGAAAGAGCCAGCGAGCCTCCAGACAGACCATTAGAAATTCCACA

GTCAGCACAATAGGGAGAACAGTAAATCTTACATTAAAAGAAGGCCAGGG

CCTGGTAGCAAAAGGTTTTAATTTAAGCACTTGAGAGGGAGAGGAGGCAA

ATCTCTCTGATTGGGGGTTGGGGTTAATGGTGAATGCCATGACACCCTGC

TCAGAGTTAGCCTTCTCCCCTAAAAAAATTTTAAATTCATTTTCAATGCT

GACACAGTTAATCATAGACATTGTATCTCAGACACCTCAACATACTCCAG

ACTGCAGCACCAGCCCACTGCTGAGGCTGTCGTTCAGTTGGTAGAAGGCA

TGCTCAGCATTCGCGAAGCACCAGACTTCATCCTTAGCACTACATAAAAC

TGGGTGTGGTCATGCACACTTATAACTTCAGCACCATGGAGGCAGAGGCA

GGATGATGAGAACTTGAGGATCATTCTCAGTTACATAGGGAGTTTGAGGT

TAAGCAGGGGTACAGGAGGCCTGTCTCAAACAAACAGACAAACAGACAAA

CAAACAAACTTCAAAAAACTCTTGAAGTACTAGGCCTAGTACGTGCTGAG

ATTGTAGGTATATGTCATCATGCCTGTTGTAGAATGAGTGAGAGCGGACT

CCATAGGCTTATAGATTTGAATCTTGGTGTCTGTCTATGTCATGTCATCC

CTGCACAAAAGCCCACACTAGGCCCACACATTCTCTCTGTCTGCTGCATG

TGGGTTAGATGTGAGCTCTCAGCTGCTGCTCCAGTGCCATGCCTGCCTGC

TGCCAGGCTCCAGCCATGACGGTCAGGGACTAACTCTCTGAAACTGTAAC

CAAGTTCCCAATGAAATGCTTTCTTTCATAAGTTGCCTTGGTCATGGTGT

CTGCTTCACAGCAATAACACGGTGACTAAGATACCTGGCTCCTCCCCTCC

CCACCCCACCATTATTTACCATAAAGTAAACAATACACAGTTGGATAACA

TGATACTGAAGTTATTTTCCTGTTTCCTGATGTAACCCAATTTTGGACAA

FIG.3D(1)

```
GATTAAGCCTTAAATAGCAAGCTGTGAGGCAGGATAAAGAAAAAGCTCGC

AGGCCAATGTCTGCTTTACCAAATTCTGTTCAGCAGTCTAAAGCTGCCGT

CACCTCGACTCCTGTGATGGCATTTCCATCACTATCTTAGATATTCCCTG

GGTCACAACCTTTTAGTACACAGATTGCAACTCTGATGGAATGGCTGACT

GCTTGGCTAATTAAAGCAAGCTAGAGTTTGTCTGGCTTCCTTGTCTGAAT

GGGGAGGTGGTATTTACAAAATTTTGTAAATAAACTACTATATTTGCATG

ATGTATATAAATTTGATGTGGCTGCTTTTAAATCATTTAACCTAAACTGT

CCCACAGAATCATCTGTTTGATTGGAAAGATTGTAGCTTCAAGAGAATTT

CTGCTGAACCTGAAATGATTCATAATGATGTGTCTGAAGAATGTGTGCTA

TCACCTACGGTTTTTGTTTTAGTTGATATTTGTACTTTAAGATTTCCTTT

ATGTATGTGTGTGTGTGTATTTATGTGAATGTATACCTCATGTATGTG

GTGCTCAAGGACACCTGAAGAAGGGCTCTGGAGCTGGAGTTACAGGGAGT

TGTGAGTGCTAGGAAAGAAAGCTGGGTACACTGGGAAATCAAAAGGTGCT

TCTAACCACTGAGAAATCCTGCCAGCCCCTTGGTTTATTAAAAATATCAA

ACAAAACCAACACTAGTTACATAAGTATCTCTCTCTCTTTCTTTCTCTCT

TTCTTTCTCTCTCTCTTTCTCTCTCTCTCTCTCTGTCACACACACACA

CACACACACACACACACACACACAAAGGATCCATAATAGTTCTTCTGT

ATCCCGGTTAAATATAAGTTCTTAGGGGCTAGAGAGATGGCTCAGCAGTT

AAGAGTGCTTGTTGTTCTTCCAGAGGACCCAAGTTCAGATCCTAGTACAC

ACATCAGGCAGCTCACAGCTACCCATATCTCCAGCTCCAGGAAGAACCAA

TCAATGCCTATGGCCCATGCAAGCACCAGCACACATATGCTCCACAAACA
```

FIG.3D(2)

TCCATATATATAGCTAAAAGTAATAAAAATAAATCTTCAAAAAATTAATT

CTGGTTGAACTGAAAAAGATCACCTAACATTTAGAAAAAGCAGTTTACTA

GTGAATAGGACATAAATCATGGTATCAAATATTCTGTTGTTAAAGGAAGC

AACTAGAAAAAGCATGTGTTTGAAATAACCAATGGATACAAAACAAATGA

GGCAACCCCAACATCTGTCAGTACCTTGCAAACCAACACAATAAATTTGA

TTTTATTTAAATCGTAGTTATTTTTCATGCTAGTAGTTTTGAAACACAAT

AAATTTGATTTTATTTAAATCGTAGTTATTTTTCATGCTAGTAGTTTTGA

AACCAAGATCTAGATTTTGTATAGCCACATAAATACACATTAGAATTGCA

AACTGATACGAGCTTCATCTTCATCAGTCTCTCTTCATGAAAAGCAGTTA

CAGGGACTGAGACATGACTCAGCAGTTACGGCATGGGCTGTTCTTCCATA

CGACATGGATTCAATTCTCAGTGCCCAAATGTTGGCTCACAACCATTTGT

AACTCTGGTCCCAGGGGATCTGACACTCTTCTTGGCTTCTATGGCCACTG

TATTCATACGGTACACAGACACATATGCAGGCAAAACTCAACAAAAAAAA

TAAGGTTTAAAAAAAAGAATTAGAACTTAAAGGCACTTCATTCCGTCAGC

ACTAAATCAGCCTCTCTGGAGTCTTCCCACTTCATGAGAAAATCGTCAGC

TCTCCACTGCTGTCTGTGGCTGAGGAGCAGGACCTGGACAACGTTCAGAG

ATTGTCAGTGCATCTCTTTTCTTCTTTGGTTTGCTGTCATCAGGTTCACT

GTCACATTCCCTTTGTACCATCCTTCCTTTAACAGCCTTTTGAAAATGCA

GAAATGTTGGATGCTGCCTTCAGTTCACACAGGCTGTCTTTTTAGCTCCT

CATCTATCTATGCTTAATTTGTTAGTGGTGCTCACCCATGTATGTGTTTA

TGTCATGAAGCCACAAGATGAGCCTTGATTGAGTCTTGCTGTCAGTGTGG

FIG.3D(3)

```
ATCACAGAAATGACACCCTATCATCTTTGCTTCCTGCTTGTTAGAAGTCA

TTGATTCTGCTTATACTCAAGGCCCACAGTATTATACTTGGGTGTGAACC

CCAGGAAGCAGGGAGGTGGGGGGTGTCATGGATACTACTCAGATATCTGA

CTGTTGTGATATTTCATCAGTTCTCATTGGTCCTATCTTTAAAATCTGCC

CTACATCTAGAGCTGGCTGTGGTGGTGTGTGTGGTGGCATCAGTATCAGA

ACTTGGATTACAGAGGCAGGAAGATTGTGATTTTTGAGGCCAGAATAGGT

GCATACAAAGATCCTGTCTGCAAAAGAAACAAATGTGCAAATAATTATAA

CTACTTTACTAATAGCCTAACTAATAACCACTGCTAGTGCTGTGTCCACG

AAAAGGTGAAGTAAACTGTGAAAATGACTTCCCCTTCTGTGTGACACACG

CCGTCATGTGATTTTACTTGTGTCTCATCATTGTTTTTCCTTCTGTTTGC

ATGTGTGAATGTTCACATGTGGAAGCCAGAAGTCAGTGTTGAGTGTCTTC

ATAATTGATCTCTATTCTCTTTGTTTTGAGACAGGGTTTTGAGACTAAGC

CCAGTGCTCAGTGATTCATCCAGTAAACTGTAGGGAGCTTCCTGTCTCTG

CCTCCACAGTGTTGGGATTACAAGCATGATCCAAATTATGTGACAAGCGC

TTTACTAACTTAGCCATGTCCTCAGCTCCCCACTCCCCTTTTCTTTTCTT

CTTCTTTTTTTTAGACTTACTTGTTTATTTTTATGAATGTCTTGCCTGCA

TGCATACACACACACACACACACACACACACACACACCCCACATGC

AAGCAATTCCAGAAGAGGGCATTGAATCCCTGAAACTGGAGTTCCAGTTA

ACTGTGAGCCTGTCATGTGCGTACTGGGAGCTAAATCCGGGTTCTCTGGA

AGGTCAGCAAGGTCTTACCTGGGAGCCGTCTCTTTAGCTCATGTGTTTCT

CTCTTGAAGCAAGAAACCTAGGAATCATTTTGAAACTTCCTTCACAGCCT
```

FIG.3D(4)

```
TTATCATAACTTCACGTCAATTTTTACCTACTCTTTCAACAAATACATGT

TATATTTACTTATTTTTATGTTTAGCCTGCTATTGGTTTCTACTTAGCCT

CTTGCAGTAGAGTTCTGTCAGATTTATGTTTCTATTGCTTTTAATTTATT

TGTAAAGGTGAATGGGAAAATATTTAAAAATTACAGATCCCATCATTTAC

TATATTCTTAAAAGCCATGGCTAGCCAGGCTTGGTTGTGCATGCTTGTAC

TCCCAGGACTCTGACAACTCAGTAAGGAGGAGAGTGAATCAGAAAATAGC

GCCAGCCTGTGCTGCTTAGCAAGAAACAGAAACAAGTACAATCACACACA

TAGAAAATCCCCCATTAATACCATCCCATTAGATATAATGGTCCTGTATG

ACCATTCAACCACTGTTTGTCCTCTGTACTGCAGTAACAGTCTTCTGCCC

TTGCCCGTGAAGCACGTGCGCACCCCGCCTCCAAGTGCTTTTGCACTGGT

GTCCTCCGTCTAGATGTCCTGTTACTATATGTAAGGACTGGTTTCTCCTC

CTCTTTACAGTTCAATCTAATTGTCTCATGAAAAGATCTTTCCTGACCAT

CTGGTTCAGACAGGTTCTCCCTGTTGTTGTTTTGTTTTTTGTTTTATAGT

TCTAAATTCCTTTCAGGAACTTTTGCTTATTTTAAATTCCCTGAGTGCAT

ACGTGTGCTTGTTGTTGCTCATGCTCGTTGTTTGGGCTTACTTTACTATC

AGCTCTGGATGTGGTTCACAGAAGGTGCTCAGGGGAGCACTCTCAGCCAC

TCATCTCACACGGGTTATAGATATATGTATTGATGCTACGTTTGCTTGTG

AGCCATGTTTTAAAGATTAGAATATCTTTTCTATGTGTACTCTATCAAAA

CACATGTTAGGGCTTTATCTATTTTATACAGATATTGGTGTTCTTGCTTT

ACTAATTTTCATGGAATTTCGGTGAATATTAGTATTTTAGATAGGAAGAC

TTGTCTCAAAATGTAGCTCAGCTGGTTGAGTGCCTGCCTGCATGTAGAAA
```

FIG.3D(5)

```
GCCCTGTATTCACTCTCCAGCACCTCAGAAGTGGGCCATGGTGCATATGC

TGTCATCTCAGCACTCCGGAGGGAGAGAAAAGAGAATCTGGAGTTCAAGG

TTATCCTTGGCTATATAACAAGTCCAAGATCAGCCTGGGCTACATGGCAT

CCTGCCTCAAAATCAAACACCAAATCAAAAAGCTCACATCTTGATCCAAA

AGAAGGTAGAGAGAATACACTGGGAAAGTCTTTGAAACCTCAAAGCTAAC

TCCAAGTGACAGTGACACCTCCTTAGCAGGGCCATAAATTCTAATCCTTC

CCCAAAGCCCACCAACTGGAGACCAAGTATTCAAAGATAAGAATCTATGC

AGTCCATTCTCCTTCAAACTACCACAGTAGGTTTTCTTAAAAAAAGAAAA

AAGAATATTTTAATTGATTGTGATTATTCAGTATTATTCATGAATAATCA

TGAACTACATGGCAGGACTATAAACTATTATTTTTTTTAAAGATTTATTT

ATTTATTTTATGTATGTGAGTACACTGTAGCTGTCTTCAGACACACCAGA

AGAGAGCATCAAATCCCATTACAGATGGTTGTGAGCCACCAAGTGGTTGC

TGGGAATTGAACTCAGGACCTCTGGAAGAACAGTCAGTTCTCTTAACCAC

TAAGCCATCTCTCCAGCCCCTATAAACTATTATTATATTTATAAAATATA

AATCCGTGAGTCTGTGCACCCCTGTGTGCACATGGATGGGACATCTTTGA

ACTGGATTATATCATACTTAGAAGAATACAAGATACTCTGTTTTGTCATT

TGGGTGAAAATATGGTCTGTTTATTTTGCAGGTATGACCTGACTTCTAGG

GAATGGCTTCCACTAAACCATTCTGTGAACAGTGTGGTTGTAAGATATGG

TCATTCTTTGGCATTACATAAGGTAAACTATCTCAACTCTTCACCAAGCA

AGAAGTTCAACTCTTCCTGTTGCTTTATGTCATTGAATACTATCGAGCTT

TGGTTTTAGTTGGTATAAGCTTTGTTTTGATGTCATGGAGGTATATAATT
```

FIG.3D(6)

CACCAAGTTGTCACCAAGTTGTAATTGGAAATTGAAGTTAGAACGATTTT

AATCCATGGTGTCTTGCATTTGGATACTCTGATCACAGTTAACAATGAAG

ATTAAATAGTGTCAGCAAGCCTATGCCCATTATCAAGTCTAGCATACTGC

ATGCGTGTGACTGAGTAGCCATTGTTATCTCCTTGTTTTGAGCGTATATT

GTAGAATGAGGCAACTGTATTTTCCACACCATTTTCGTTCTGTAACACGT

TTCATGTAGAGAAGGTGATTTAGAGAGGGGAAGAATGTGATTGTATTGGT

TGGTTCTTTCTCTATGCTATTCCTAGCAAGTCACCGAAGAGCTCATGTTA

CTCACACTTCTTAAGCTGGGATCACAATGAGATTGTGAACCACTCATTGT

TGTTTTCCAATATAATTTTTAAAAAGATGTATTTATTTTTATTTTATGTG

TGTGGGTGTTTTGCCTGCATGTATGCCTGTGTATACTGTTCCTCCAGAGG

TCAGAAGAGGATGGCATCAGAACTGGTGGCTGTTAGCTGCCATGTGGGTA

CTAGGAACTAAACCCGGGTCCTCTGCAAGAGCAGCAAGTGTTCATAAACT

CTCTCTCCAGCCCTAGAGTTGATTTCTTAATGGTTTTAAAAATCCTGTTT

ACATCTTTCTTATAGGATAAAATCTACATGTATGGAGGAAAAATTGATTC

AACAGGGAACGTGACCAATGAGCTGAGAGTATTTCATATTCATAATGAAT

CATGGGTATTGTTAACTCCGAAAGCTAAGGATCAGTATGCAGTGGTTGGA

CACTCAGCACACATTGTTACACTGGCATCTGGCCGTGTGGTCATGTTGGT

CATCTTCGGTCATTGCCCACTCTATGGATATATAAGCGTTGTGCAGGAAT

ATGACTTGGGTATGTATTTTTTCCAGTGGAGGCATCTTGAATATCATACT

GAGAACCCCTGCCCTTATTATTAGGACACCGTAACAAAATTCAGCATGAT

CTTGATCCAGTACCTTGTCTTGAAATAGTATCAGTAGATAACTGGTGAGA

FIG.3D(7)

TTGAGGTTGTTGAAGTCCCTGTGCAACAGCTGTTTCTTACTTGTCAAGGT

CTAGTCTTGGCTTGGGAGGGGTTCTGAGGAAAGGGGTGTCAAAAAACCCA

AAAAGTCCAATTGTAGGTCCAAGCTGGCAGCTGTATATTGCATTAAGGAA

AGCTGAGGGAAATTTGGGATATTTATTTCATCTATTAGTCTACATCAAGC

AAGTCAAGCGCTCACAGTCAACGTTTGCACCCTCAAATTAGTAACAAAAG

AGGGGGAACTGAGGAGTCCAGCATGGTCCTGGTTGGGACAGAATGACATG

GTTCCAGCCCTGAGACAGGGGCAGCAGGTCCGGGCCTCCATGGATGTCAC

ACTATGGACATAAACCTGTTTGTATAATAATGTACATATTTCATGCTCCT

CTTCTGAGTAATGTCCTTCTGTTAATGTGAATGACTTCATGATAATCAGA

GCCAGTGTGAGTCTGGGAAGTAAATGGTGGGACCTTCAGGACAGCTCTTA

AGGCTGTGGAAAAGAACATGAGTTCAAAACCATATACTTCCTCAACTATA

CAAAAATAGAAGGATGCAATATGAATTGTATGAGGGGCTTCACAGATCTA

AAGGAACAAAAGCAGCTTCGCTGTGAGCCAACTTGTCAGAAAGATATTGA

GTAAGCAGTTAAAGAGATTTAGGGAGTGCTGATTGCTAGAGGAGGCCACC

CAGCTAAGTTTGTGCTTACAAAGGCAGACAAAGTCCTGAGTTCAGGGTGG

GCCTGGAACAGAGCAAGGTTAGTTAGACCTTGGTGTGGTAGAAATGGTAA

TTTCCAGACAGGATACCCAACTAGTTTTTGTGCTTAACAGAGGCAGGTAG

ATCTCTGAATTCTTTTGTAATGTTAAAAGGAAATGTGTGCTTGTTGTCTC

CCAAGGGGCCTGAGTCCCAGGATGCTGATTTATAGGAAACCTGGAGTAAC

TGGGTTTATGACCTGCAGGAGACGAGCTATCCAGAATGTTTTTTGCAATA

GCAAGAGAGAACTGCCTGGAGAACTGCCTTCAGCAAAGAATAGCAAGAGA

FIG.3D(8)

```
AAGCTGTCTAGAGAGAGAGCTGTCTGTAGAGAAAGCCGGTCAGAGAGAAA

GTAGACTGGAAAACTGTCTCCAGCTTGGACCCACAATTTGACTTTTTGTT

TTTGTTGACAAGTTGCCCTCCCCCAGAAACACCTTCCTCAGGACCCCTCC

CAAGCCAAGGCAGGGCCTTGGCCCTTCTTGTCAGCTTGCAAGGAGCCAAA

GATAGCATTAAATGCTTTGGATATCAAAATAAGCAAAATGCAAAACAGTA

AACACTCTAAAATAATTCTGGCTAGTCCTTTAAATATTAGGCCAGTGCAC

TGTTATTTTACCTTAATGTATAATCTTGTGTTACATTTTATTGTTTTTAT

TGTATAATAGGAATGTCAGAATTATAATTTTGTAACATTTGTTTGACATT

CCTGTGAAAATGCATCTAAAGATCATTAAAGTGCATCTGAAGATCATAAG

GACTCACTGAGGAGCACAGGGAATTAAGTGTCTGCTTAAGAGAACTTTGA

ATCTTTAATCTTTAGAATTTGTTTTAAAAATTTGAATCTTGCCAGTGTGG

TGGCGCATCCCTTTGGTCCCAGCACTCAAGGGGCAGAGGCAGGTGTATCT

CCATTAGTGTGAGGCCAGCCTGGTCTACAGAGCAAGTTCCAGGCCAGGCA

GGGTACACAGAGAAACCCTAGCTTAACAAAACAAAACAAAATATGAATCT

TTAAAAACTTGTTCTGTGAAAATTTCATACATGTATACAATATAGCTTGT

TCATATCCACCGCCATTCCTTCCAGCTCCTCTAGGCTTTCCCAGTGCATC

TCCTTCCTAGCCTTATGGCCTCCCTTTCAGGGTGAAGGTTAGCACACTGA

GTCCAGTTAGTGCTGATCCGATGCAGTCTTGTCTAGATGGTCTTCTTTAT

AATAAGGTGAAAGTATATCCTAAACTTCCGTCTTTTGCTCTAAGGTGTTT

AGACTTTAAACTAATGTTTAAATCGTTTAAATAATTTATTATTTCATAAG

AAGAGGAGCCTGCAACATTGACTTTAACTATTGTCTCTTATCCAGAAAAG
```

FIG.3D(9)

```
AACACATGGAGTATATTACATACTCAGGGTGCTCTTGTGCAAGGGGGTTA

TGGCCACAGTAGTGTTTATGATGACAGGACCAAGGCTCTGTACGTTCATG

GTGGCTACAAGGCTTTCAGCGCCAACAAATACCGGCTTGCAGATGACCTC

TACAGATACGATGTGGATACTCAGATGTGGTGGGTGTTTTCCTAGAGCTT

TCCCTTGGTAGTCTAGAATCTGCAGAGGCAATTGATTAAAAATACTGTGC

TATGGTTTGACTTTTGTTCAGCATTGTATGTAACAAAGTTAGGAGATCAA

TACAGTAATAGAGTTAAGGTACTAATGGTGCTGTTGCTGTCTGTTAGTGC

TTAGTGCTTTAGACCTGATTCACTGAACTCTAGCAAGGTTTCCTCTCTTC

AGAATTCTCAGCAATAAAAGCTGTGCTGATTTTATCCATACTTAAAAAGC

ATATCCTTCCTTTTCTCTTTTTGGTGTTGGGGATCAAACCTTGTACATGA

ATAGGCTATACCATCTTTATCCATTTACATCACCAAACAGGATGCTCTCG

TGCCTATTTGATAGGGTTTTCACTCACTTCGAACTGAAACTTGGGTTGTA

AGAGTATGGTACTTTTAGCAAATGGAAATAAATTTGAGTTATGATGCAAT

TATAAAGCACTGGTCTCTCTGTATTTCCCTCCTCCTTCTACTCCCTCCCT

CTTCCTTTCTGACCCCCTCTCTCAACATACATTAGAGACCATGCTTTGAC

TGTCAATTTATGCTGTGCTGAAGATCAGGTCTTTAGTGGCTGTGAACCAC

GGAGCCTATGCAGTGGAAGTTCTGGTCTCTGGCTTTTGCCTTACTAATAA

AACACTGAGCATAAATTTTGATTTGTATTTCACAATTCTTACCTGGAATT

CTTAAGTGGAATTATGGAGCCATAGAGAATGAACATTTTAGGGCTTTTAA

TATAGTTTCCCGAAATTTTAACAGATTTTCATGATTGTTAAAGGAAGTGG

CTTACGTATAGGGGGAAATCAAGTATTGCACATTTGAATCTAAAGTTATA
```

FIG.3D(10)

```
AAGTAATTACATTTAAATTGGCAAATAAGTATTCTTTTAAAACTAACCTT

ATATTTATTATTTCTAAATAAACTCAAAAGGACCATTCTTAAGGACAGCC

GATTTTTCCGTTACTTGCATACAGCTGTGATAGTGAGTGGAACCATGCTG

GTGTTTGGAGGGAACACACACAATGACACTTCCATGAGCCACGGTGCCAA

ATGCTTCTCCTCAGACTTCATGGCTTATGACATTGGTAAGCTTTCCAAAG

ATGTTTTAGCTTCAGGAATATTTTCTTTGCTGATGGAAAGATCACTATGT

TAAAATAATTGCACCATTTAAAAGAAGTCCAGGTGGTAGAATTTGCATTT

AATTTGAGTAGGGTTACACATCTATTGAAAAGCATTATTTTGGATTAAAC

TACATTAAATTCTTTGTGAAATCACTCTTCTTAATTGCTTTAATTCTTTT

TTTAGGTTGAGTTAATTGGTATCTTCTTTCTTATAAGTGCCTTACATAGT

AGTGGTGGTAGTTGTAACCACCAGTGTTATGTTAAGTTTGATGGGATATG

CTGTTTCCTAGAAACCTGGTTTTACACATGCTGTTGATGTCAATATACAT

GTGGCCAGAAGAGGGCAGTGTCTGTTTATTCCTGGAAAATAAACATCAGC

TGCTCTGTTGTGTAAATATCACCCATGTGATGTTCTTTCTGTTTATTTGT

CTTTGCATTTTGAGACAGCCTCACTATGTAGTCTAATTGGCTGAAGCTCA

GTATATAGATCAAGGTGACCTTGAACTTAGAGAAATCCTCCTGCCTCTTC

TGAGTGCTAAGATTAAAGATGTGTACTACGAATGAAAAAAAAAAATGTGT

ACTACCACACCTGACTAGAGATTCATTTTAAAAATTATTCTTATTGTGAT

AAAATGCTCAGAATAACACTCACCATCTTAATGTTTTAAGTAGTTTAGAT

TTAAATATATTCCTAGTGTTATTCATGTTATAATACCATCTGCTTGCCGA

CTTCTTGTAAAACTGAAACTCTGCCCTTAAACAATAGTTCCTCTCTTCAT
```

FIG.3D(11)

```
CCCTCACTCCAGCCTCTTGAAATCATTTTCTATATCTCTATGATTTTGAC

TAGTCTAAATTAGGCATTTTTTAAAAAAAATATTTTGTTTACTTGTATGT

GTATGAGTGTTTTGCATGCATGTATGTTAAGCACACCATGTATATTCAGT

GCCCATAGAAGCCAAAAGTAGGCATAGATTCCCCAGAGCTGGAATTACAG

ACTTTTGTGAGCCACCATGTGGGTGCTGGATACTGTGCCCAAATCCTTTG

GAGGAATAGTGAGTCTTCTTAGCTGTTGAGCCATCTTGTCAGCCCTAGAT

GTTTGTTTTTAACAAACGTGTTTTTGCCAGCCATTGAGTTTTTAAATTGA

GAATGGGGGGTACACTATAGTTAGTCCTTAGCTTCAAGCTTGTGGAAGCA

GAAATGAGAAGACAATATAATCTTAACTCAGGAGGATTCTTGCTGGCTGA

AACAAAGATGTGAAATTACCTCCGAGCACTCCTAAGCCACTGGGGTGAGC

AGGGTGGTCTGGAGAGGCCTTGAAGAGAAGCTGTCTGAGCTTGTTCCTGG

GGACACTGGGAGTCAAATAGACCTCCTGGGCAGGGGGATTTAGTGCAGAC

AAGAGGCAGGAAAGTACATGTCAAATATTTAGGACTTTTGAACCGCTACC

TTTCTTTTGTCATGGTAACACAGAAGGTAGCAGGTGACTGTTAGACTAGA

ATGTTCAGATCTGATTCAGAGTGCCAGGGATCGTTGGTTGGTCTTGTGTA

AAGTCTCACAAGTGATAGAATCATATGTGTGTCTTAGACTTTTTTTGTTG

TAGGTATTTTAGATTTTTCTTGTTTTTCCTTTTTTGTAAGTCTGGCCCTCA

CACTATGGTCCAGGCAGGCTTAAGACTTATGGTAACCATCCTACTCTGCC

TTTATGGGCCACCATGACCAATTTAAGAAGCTCTCTTGGGTGGCATTGTG

ATAAGTGATCTGGAAGGGGCATATTGACAGTTAGCAGGCTGCTACTGCAG

AAGTCCTAATTAGGTTTGTATCAAGGCCATGGAAGGAGCAGTGACTTCTA
```

FIG.3D(12)

```
GTACCTGGCTGTTGTGTGTCTTGACAAAAATATAACTGCCCTTTCTTCCC

AAGTGTCTACTATGGACCACCTTTGCCAAAACTAAAAGCAGATTCAGAGA

AAAACATATCATGATTGCACATGGCTATAATCCCTGAACTTAGGAGGATG

AGAAATATGGCAAGATTGAGACCAGTCTGAACTATCTAGTAAGACCGTGT

CTTTAATAAAAATAGTAAAAATTATAAAATCAGGGAGTAGGATCTGGGAA

GAAGAGAATGAAGTAAGTGTGGGGCATATCCAATTGGAGATGTCTTTAGG

ACAGAGCTGATTGCTGAGAGGTGGTTGTAGGAGAGGTGAGTTATTGTGGG

GCATAAAAGATGAGCAAGAGTCAGAGACAGTTGGAGAACAGAGTCTGAAC

AAGAGTAGAGACTAAAGAGAGTGTCAGAGAAGCAGGGAGAAAATAGGTGA

GATTGATGACCTGTGAGATATGTTAATGGCCAGAAGAGTGGCTAAAAATG

ACTGGAGAATCCTTCAGACTTGTCAACAAAGAAATCCTTTAGCCTAATTT

AGGGTGCAGGCGGCTGAGGAAGGACATAGGTGAAATATGTGCTCTGTGTG

TTCATTTTTATTAAAGCTTATCTGCAAAGGCCTCAGATTTGCTGTGTACT

TGTAGCTGAGGCTCTTTTTGAACTCCTGGTTCTCCTGGCTCCACCTTCCCA

AGTGCTAGGATTACAGATGTGTGCCCTAGTTAAAATAGCTGTATACCTAG

CATTAAAAATTTTAAGTTAGAAAATACTGTGGTGCTCCGGGGATGCATCT

CAGCAGTAGAGTGCTTGCCTGCTATACACAAGGCCCTGGGACTGATCCCT

AGCACCACAAATACTAAAGCAGACATTCTGGTAGGGAAAACTGGTAGACA

GCAGAGTGGTGACCATCAGGAGGGGGGTTGTGGGTGATGAATGACTACAT

TAATTAGAAGTTCTGTGCAGTATATTTATTTCATGCCCTGAAACATTGCT

GCTGCTGTTGCTGCTTTCCTTTACACATAATAACATAACTAAAAGACAGA
```

FIG.3D(13)

CAAGCATGTGGTATGAGGCTGTGGATGAGGCATTCTTTGTTTTCCTTTTT

TTTTTTTTTTTTGAGACAGGGTTTCTCTGACCTGGCTGTCTGAAACTCAGT

AGGTAGAACAGGCTGGCCTTGAATGCACAGAGACCCTCCTGCTTCTGCCT

TCTGAGTGCTGGGTTCAAAATTTATGTTTTTTTCTATAAAGACTGAGAGT

TCACATGGACTATATATGACAACCTACTCTGAAATGTGTTTTTCTCCCCC

TTAGCTTGTGACCGATGGTCAGTGCTTCCCAGACCTGAGCTCCATCATGA

TGTCAACAGATTTGGCCATTCAGCAGTCTTGTACAACAGGTAATTGGAAA

GCAAAGGCTCTATTACTGTCTTACATCTTATATTCATTTTTAATATCAAC

TTCCTAACAGTTGTATCTGAATGGTAAGAGGTTTGGGGAGAAAAAAGGAG

AGAAGGCAGTTCTAAGTGCACGATAAGGTAAGGGGAATAGGACTGGGAGG

TTATGGGGTCAAAGAGCAAGTCTGAAGTCTGCACTATATCCAGGTGTGTG

CTCAGGAATACTTTTCTGACCAGCAGAGCTCTTTTTCCATTTGCTCCAGG

AACCTTAGTCCTGTAAAGGACATGCAAAGGACTAGGGTTGTGGGCCAGCA

ATAGAGTGTTTATCTAGCTTGCACAAGATCCTGAGTTCTGACCTCAGCAT

TTTGCCTTCTGCAAACACAGCATTTGCCATAAGGGACATGCAGAATGGCC

ATTTTACCTAGTCACTTGAAAGTGTGCTTTAAGATTGAGAAACTTAACAG

CCTGCTGATGCTGACTTTTCTTATTTTGCTTCTGTTACTGCTTTCTGCTT

CTTTCTTTAATACTCTAATGCTTACATTATATAGTCCTACAGGTATTCAA

ATTTTCTGTTGGAGTTTCCTAATACAAGTAATTTAACTTGCATTAGGAAA

AGGATAAAAGTGCCATTCTGGAGTTGTGAAGAATGACCGTTTAGAAGCTA

GATAGTGGGGAAAGATGATATCTTTAATCATGTGATTATTTAGTGTTTTA

FIG.3D(14)

```
CAAGTATATAGGGGATTGTGGCAAGACCATTGTATGATTAGAGACTAAAG
TGGAAAGATTTTTTAAATATCTTGTTAACTTGAGTGTTATCTTAAATTAC
AATCTGATGCTTTCCTTCAGAAAAAGCCCTAAATGCCTCTTGAGGTTTTC
ATCTGGCAAGTATCATGTCACCTGGCCTTGCTGGTGGAATCTGCCCCAGC
TCATGTGTGTTCTTAGTGTTCTCCTAGCACAGAGTTAGGCACGTGTGGGC
ATTTGCATACTAATGTATAGTAATAGTAACAATTGAATGAATTGTCTATT
AAAACATTCTTAAGTTTTACCCAAACACAGAGAGGTCGACAATTTGTCAT
AAAATGTAGTTTATCCATGAATCAAAATCAGGAATGACTGTCTGAACAGT
GTTTTTATTTTTTATTTTATTTTATTTTGTGTAATTTCTGTGATGTGTTT
GAATATCTCAGTTTTAGGCAGGATTGGAAATGTTAGAGGTTGGTAAGAGG
TCATGGTTGCAGTTTGATCATGAGAGAAATCGATGGCTCTCCCTTCATTG
CAGTGTTGTCAGTCAGCAGTGTGGGATCACCTATGTCTAACAGTTGTTCT
AATTGAGAGAGGATTACAGGAGGGAAAGCAGTGAGATTGTGAGGTGCTAG
ATGAGGAGATGGCATTTACCTAGCAGCCTTCTCTCCCGCCCTCCCATCAT
GTGACCTGAGAGATTCACAATTTCTGAAGATATCAGCTGTGCTTAGTTTA
AGCAATAGTTTTATTAACTAAATCCAACTTGATTCATGTTATTCCCAGGG
AACCAGTGGTAGGATTAAAAATGAATCCTAGTGTTCTTTTTGGTTATTGG
AATGTCAAGTTTTCAGACACTGTAACGAATACAGAGCCATACAATCACTA
TATTTATTTGGTCCTTTGTTGACTTAGAAAAATTGAAGCCCAGTTTAGGT
GAGCTACCAAATTTCTCATTGTGGATTAGTATTAAACTTGCGTGGAGTTG
TGGGATCTTGGAAGTGGGGGCTAAGCATCCGTGTTTGTCACAGCCCAGAA
```

FIG.3D(15)

GGAACAGATGAGGTTCCTTTTGAGGAGTCTTATGTCTTTATGAACTTGGA

CTTAGAAATATTTGATGTGTTTAATTCTGCTGTAGTTTTTTAAACTCTAG

CTAGTGAGCATCTTTTCACAGGAGCGCTTGAGTCTGACCTACAGCCATTG

TCTGTCTCTGGTGTGCATATTACAAATGCACTGGGAGCGTTTCTTGACCC

AAACATATAATTAGATTTTTCTTCTAAAAAGGTCTAGTTTGGGAAGGAAT

GAAAGGGATTAGAGAAATGTTGTGGGTTTGGTATTTATTTATTTATTTAT

TTATTTATTTAATGTATATGAATGATCTATCTTCATGTATACCTGCATGC

CAAAAGAGGACATCAGACTCATGATGGTGATGAACCATCATGTGGTTGCT

GGGAATTGAACTCAAGACCTCTGGAAAAACAGCTGGTGATCTTAACTGCT

GAGGCATCTCTCCAGCCCAATTGTTCTGTTTTAGTTTGAGGATGAACATC

TAATTTAGAGATGCCCTGCTTTTCCAAAAGTGAGTTTTAAACACTAATTT

CCATTGTCAGTGGATTGGTCTTTTAAGAATATAGGTAGTGGTGGCACACG

CCTTTAATCCCAGCACTTGGGAGGCAGAGGCAGGTGGATTTCTGAGTTCG

AGACCAGCCTGGTTTACAGAGTGAGTTCCAGGACAGCCAGGGATACACAG

AGAAACCCTGTCTCGAAAAGCAAACAAACAAAAACAAAACAAACAAACAA

AAACAAACAAAAAGAATATAGGTTGGAATAGGTTGGAAGCAGCCAATGAT

AGTGCATACCTTTAATCCCAGCACTTGAGAAGCAGAGGCAGGTGGAACTC

TGAGTTTGAGGCCAGCCTAGTTAGTCTACAGAGTATTTTCCTGGAGAGCC

AAGGCTATATATAGAAACCCTATCTTGAAAGGCCAAAAAAGGAGGAAAAA

AAAAAAAAGAAAAGAAAAAAGAAAAAAAGAATGCAGGTTGGGCAGTCAG

GGTAAGTGTCTAAGGTAAGAGGAATTCTTCAAGGTGGAAAGTCATGAGTT

FIG.3D(16)

CTGCGCCAGCCTAGGCTACAGAGTACTGAAAGGGGAAGAGACTGTCCATG

TGTCAGACCCTCATTTCTCCAAAAGTCACATGACTATATTTTTTCTGTAT

TGCCCACTCTTCCATACATGCACCTAACAATAAATATTGAAGTTCACTCT

GTGGCACTATATCTATGTGATAGACTTCTAGAAAAGTGATTTAAAGTTCA

AAAGGTAAATACGTAGTTTTGTTTCAAGTTGCCAAAATCCCTTTAGTAGA

CTCCTACAATCTTACATGCCCAGTAGCAGTATAGAAGCTTGCTTGTTGCC

TTGAAGCCTCACCAATTCAAATATTAGGTAACATTTGTTACATTTTTCTT

TGTCAGCTGGATAGGTAATGAATGACACAACAATGTGTTCCCATTTTCTC

TGCATTACTAATTGAAGTCCTATCACCCACAGCAGACTGAAGAGTTCCTT

TAATATTTTATGGACTTTGACAAACCTAGGATTCATAGCTTCCATACAGA

GAGGAATTTCACAAATAGCAAAGTTGGGCTGTTAGAAGAATAAAAAGAGA

ATTCTGAGTACAGCTTCTCAAAGAAGAGTCCCACGTAGGTGTCCTCTGGG

ATGTGCCTAGATGCAGGGTTATTGTACAGGAGCTCTTCTGTCTGCTCTCT

GATACTTGAGATTATAGGGTTGCAGGGAAATGCATTAGATGGCATTACAA

ACTGATAAGATAAAGTTAGGAGCTATCAGAGATTTAGGACATGGTTTTTC

TCTGTAAATGGGGCTTCTGGTGAGATTCCTAGAAAATGCTGTTTATAGCT

AGGAATGGGGTTATAGCTAGGAATGGGGAAAGACCTTAAGCAGTTGTGAG

CTGTGGTGGAATGCATGTGTTTTCAGTTTGCTAAGGCTTCCGGGAATACT

TTTCCTGTCGATAATTTTCTTTCACTCTCTTTGTAGCCTTCTTTGTATTA

AAATCCTCTCTGCTTGCTTTTGTGTGTGAATGTGTGTATGTGTGTGTTTG

TGTATGTGTGTGTATGCATGTGCATGTAGGTCCCTACATAGGACAGAACA

FIG.3D(17)

```
TATTTCCTGGAGTTATAGGTGCTTGTGAGCAGCCTTTTAGGGAACCAAAC

TCTGTCCTCTGGAAGAGTAGCCCCTTTAACTGCTGAGTCATTTCAGCCTC

AAGAATCTTCTCTTTTCCCTATTAGTAGAAGATGTCATCTTAGCTCTAGG

AACTACACCACCTCTGGCCTCAGTGGACACCCATTTACATATGCACATAC

AGCAGACAGACATATAACTAAAGATAAAATAAATCTTTTTAAAATGTCAT

TTCCCTGTGTACTAATTTTCCATGTACACACTCACAGGTAGATTTTTAAA

CTATTCTGAGTGATCACAAAGCAGAGCAGAAGGTGAAATTTGAGAGAATA

GATGATATTAGTGGATTTTGAGACCTTGAAAATAATGTCTCAGAGCATTA

AATTAATCACTCATGTATGTATGTATGTATATAAGTATGTATGCATGTAT

TATGTGGATGGGGGTGCTGTAGCACATGTGTGGAAGTCAGAGGACAACTT

TGTGAAGTCATGTTTCTCCTTCCATCTTTATATGGTTCCAGTGATTGAGC

TCAGATTGTCTACCTGTGTAGCAAGTGCCTTACCTGCTGACCTGTCGCAC

TAGCCCTCTCAGAGGACTTTTAATATTTGGAATATTTCTAACGATTGACA

GTCAAAAGTTTATTGTGAGCCAGGCACTTAAAATCCTAGCACTTGTGAGA

CACAAGATGGAGGTCAGTCCAGTCTACTGAGTTCTAGACCAGCAAGGGCT

ACACAGTGAAACCTGTCTCAAAAATTTCAAAAGCGGAGCTAGAGAAATTA

CCCAAGGAGCTAAAGGGAACTGCAACCCTATAGGTGGAACAACAATATGA

ACTAACCAGTACCTGGGAGCTCTTGTCTTTAGCTGCATATGTATCAAAAG

ATGGCCTAGTCGGCCATCACTGCAAAGAGAGGCCCATTGGACTTGCAAAC

TTTATATGCCCCAGTACAGGGGAACGCCAGGGCCAAAAAGGGGGAGTGGG

TGGGTAGGGGATTGGGGGGGTGGGTATGGGGAACCTTTGGGATAGCATTG
```

FIG.3D(18)

```
AAAATGTAAACGAGGAAAATACCTAATAATAAAAAAAAGAAATGATATCA

GAAAAAAATAAAAAAATAAAAAATAAAATAAAATAAAATTTCAAAAGCAA

CAACTCAAACCAGCCCTACGTCGTGCCTCTGAGTTCTCAGTAAATTCCTT

CTCTCTCTCCTCTCAGCACCATGTATGTGTTCGGCGGCTTCAACAGCCTC

CTCCTCAGTGACGTCTTGGTCTTTACCTCGGAGCAGTGCGATGCACACCG

CAGTGAAGCTGCTTGTGTGGCAGCAGGACCTGGTATCCGGTGTCTGTGGG

ACACACAGTCGTCTCGATGTACCTCCTGGGAGTTGGCAACTGAAGAACAA

GCAGAAAAGTTAAAATCAGAGTGTTTTTCTAAAAGAAGTATGTTTTTTCT

CTACTTAGAATTTAAAAATCTAATTTTATCTGAATTGTGAAGGAACCTAG

TCTCTGTACTTTCCTGTTCACCTTACTCTCTAGTTATTTCTTAATAAAAA

AATACACAAGATCTTTGGATGGGAGGAAGCATGTGGCTCCTGGAAGCTGT

TAGCAGGTAATAAGTTGTCTTTGAATTACACAGGCTTTGTGTACCAACTC

CTGGTCTGGCTGCAGGTGATCTGAAGCCATAGCACAATGAAATTTGTTTT

CATTTTGGTTTTATGAGACAGGGTCTTGCTCTATAGCTCATACTGGTCAA

GCTCCTTGTCAGCCTCCTCCTTCAGCCTCTTGAATGCTGGGGTTATAGGC

ATGCATCACTGGCCCTACTTGGGAAATATTTTGATGACAGACATGCTATA

TATTTCTTTGTTCAGTTTAGTAGCCACTAGCAATCTGTTATTATTAGATA

TTTGAAATGTGGCTATGTAACTAAGGGGCTAACTGTTTTCTTTTCTTTAG

TGTATGTAGTGAGGCAGATGTAGTAGCACACGCCTGCAATCCAGACACTC

ACGAGGCTGAGGCAAGAGGCAGTTCTAGGCCAGCCTGGGCTGTGTAATGA

GACCTTGTCTCAAGAGCCAAAACATCAACAATAAAAGAACAGTATGTGGC
```

FIG.3D(19)

TATTGGCTGTTATGTTGATGATGAAGGTCTAGTGTTAAGGATAAGAGCCT

CTAATGGTATGATCACATATAGCAAATTGCTCTGGTAGACAGCAGAGAGC

TGCTGTTCTTGAAAAGTATTTCCAGCCCCCTTTAGCTGTATATAGCAAGC

AGTACAGCATAACAGACAAACTATGGTCCCTTCTTCTAGAGCCCCTGGCG

TGCTCTTGTTATTTTTCTCTCCTTTGCTACTTGCTTAGTGGTTGCTCTGA

GCACCACTTCACCAACTCAGCGAAGTAACGTGCAAAAATGTTTGGAAAAT

AAGAATGCCTCCAAGATATTTGTCCATATCAATCTTTAAAGTATGAAACT

ACTTCCTTATCTAGTTGTTGCAGTTACATGAGAGTTATATTAGGCAGAGA

CTACTTCTGTTTTTTCTGGTATGTGTTAAATAAAGTTGTGCAGGGACATAA

AGCTCCTGAGGCTGTGCTGTTGATTAGAATTTTGGTTCATTTATGGAAAA

CAGCTTACCAGAACCTGGTAGGATTCATAATTCTCCCGAAACAGTTAGAA

TTGGTAGAATAACCAAAATTTAAAGTTAAGCTTAAATATACAGTGCATTG

GAAATAATATTATCTTCTGAGGTTCAGTATGAGCCCATTAGTTTACCTCA

CTTTCTGGGTAGACCTAATCCTGTCAGAGTAAACTTGGCAAGAAAAGCAG

CCTACATGAAAACTGATCAGGCAGGGAAGTTTCTGTGGCCTCTCTTCCTG

CTTGTGTATGTCATATTCATGAAATGATTTATAGATGGCAACATGGCTTT

TAGCTTCTTGTTTGGGGATTTAATGAGAATTATGTTAGGTCTACAAAGAG

TGGAAGTTGTGAAATCCACAGGTTTGGAGTCACATGAGTATATAGAGTTC

GAGTTAGCAAGTGCCTCCTGTGGGGTTGTGGGTCACTGGGTATACCTGCA

CCCAGGTAGGCCTTGCATTTGTAACAAGGACAAATGTATTGGTCTCTCAT

ATTGCTTTCTTAGGCTTCTGCACAGCTTCTGGTGTTAATTCTGTTGCTAG

FIG.3D(20)

```
TTGATGTTTGTCGTGGGAAGAAAAGCATCCATTACTTCTTAGAAGCTATA

AAATTAACAGACCTTTGCTTTTCACTTTCTGGACACTATGGGAGGACAGT

TATAAAACAGTGTTTCTCGGATTGTCTGCTTATATCTGTTTTATTTTAAC

CTAAACATGGCACTGCTTTTTTCCTTTCAGTTTGACTATACACTTTGCTT

CCTGACTATTGTTAGGAGCTTTCCTACCTCAGATTATACATAAGAGAGGC

TGCCGCATAGTTGATGGGTTTGTCTTCTCTCTGTAGCCCTTGACCATGAC

AGATGTGACCAGCACACAGATTGTTACAGCTGCACAGCCAATACCAATGA

CTGCCACTGGTGCAATGATCACTGTGTCCCTGTGAACCACAGCTGCACAG

AAGGCCAGGTCAGATGCTGTTTTTCACGGATTTTAGGGAATAGAAAAATG

CTAGATGAGTGTGAGTGTAGGGCAAATAATGAGTAGAGTTCTTTTTAAAA

TGGGATATCGATTTGAATTCTACTGTTGCTCAGGTTTTCTCTTAGGAAGG

GATGCTATATACATCCTGATTCCAAGGATCGCTCCTGCTGCTGAGGTCTT

TGTGCAGTGTTTCCGAAAGCATGTTTTACAGAATGCCCTTGGCCCATATC

TGACTCAGCATGACATCTGGGCTAATCATGTATGATTTGTTATAGGTGAT

AATAGGCTATGAGTAAGGTGATCCAGCTTTTGCTGTCTTTGATGGCTTAT

GACATTTTTTTCTCAAAGTTTAATGCATTTCATAAGAAATAAGACTTGAG

ATTGCTATGGTGGGCACGGGCTGGGAGGAGCTCTGGAAAAGCAGCAGGTT

CAGCTTTCACGTTTTACAGATAAGCATTGGCTGAGGCTTGGTGGTGCCAG

TGGTTCCGTTGGGCTGCTAGCTTGCCAGCTAAAAGCATGTTAGTGAGAAT

ACACACTGTGGTATTCACATTGCAGTGCTGCTTCCTGTTCATTCTAATTC

TATCATTCATCCATCTACCTATCTCTATCTATCTATCTATCTATCTATCT
```

FIG.3D(21)

```
ATCTACCTACCTACCTACCTACCTACCTACCTACCTACCTACCTACCACT

TATCTAATTCTATCTGTCTGTCTGTCTGTCTTTCTGTCTATCTATCCTCC

ATCTAATTCTATCTATCTGTCCACCTATCTATCATCTAATTTTATACATC

CATCCATCTATCCATCTATCTGTCTGTCTATCATATATGTAATTCTAACC

ATTCATCTATCTATCCACTTATCTGTCTGTCATCTAATTCCATCCATTTA

TGTATCTATCTATATATCTAATTCTATCTATTCAATTCTTTTCTTTTTTT

CTATCTTTCTTTCTGCAGTTACCATTCTCAGTTAATTCTCACTGAGTTAT

TTGTGTGAATAACAAAACACTTCTCCCCTGTGTTCCAGATCTCCATTGCC

AAGTATGAGAGTTGCCCCAAGGATAACCCCATGTACTACTGCAATAAGAA

AACCAGCTGCAGGAGCTGTGCCCTAGACCAGAACTGCCAGTGGGAGCCCC

GGAATCAAGAGTGCATCGCCCTGCCGGGTAGGCCTTGCACAGGGATGTCC

TCTATAAGGTCCAAGCTTGGTCCTCCCTCCTCAGATCAAGGTGGACCTAG

GAACAAGATTGCTTATTCTGTCTATTTAGCCCTCTCACTATTGGGGGGGG

GGGGGGGCGATATTTTGTATGTTTTTAACTTAAATGTGGTTTTTATGTAT

GTATTTACTAGCCTTTGAAAGAAAGTGAAGTGTCAGCTCATGTTCTGGAG

AATTGGGGGGTAGCTTAGATCCATGTTACAAACTGTGTCCCACTGTCCTT

CCTTCTGCTGTGAAGGAGAACCTGGCACTAGAGCTCTGTGGTCTCAGCAG

CAGTCAGGAACCTGCAGGAAGCACTTACTGACAGTTGTGTGAGAAGAGAT

TTCTGTACCAGCATCATCTCCCATGTGACCTTCCTTCCCGACTATTTCAG

CAGAGGTTGTTCAGGGTATTAACTTAGGTCCTGAGGCCAGCTAGCCCTGA

CTAAATCTCTATGATGTATTTGCTTGATCAGGATATCCAGGAAGGGGAGC
```

FIG.3D(22)

```
TTCTGTGCTCTCCAACATCGAGGTTTGAGGGGAAGTTGGTCTGACTCTTT

TGAAAGCATTTTATTTAGTTTGCTGAATGGGCTTTAGTTTAGCCAGTGTT

CTATTGCTGTGAAGAGATACCATTTCCAACGTGTAACTTTTATGAAAGGA

AACATTTAAGTGGGGGCTTGCAGTCTCAGAAGCTATTATCATCATGACAG

GGAGCATAGAGGCACAAAGGCAGGCATTAGAGTGGTAGCTGAGAGCTACA

TCCTCATCTGTGAGCAGAGGCAGACAAGGTGTGAAAAAGACAGAACCTGG

CCTGGGCTTTTGAGACCTCAAAGTCTACCACCCCAGTGAGACACTTCCT

CCAACAGCTCCTGCAACAAAGCTCCATCCCCCGATCCTTCTCCAGTCCTG

CCACTCCCTGGTGAATGAGCACTCACATATATGAGCCTATGGGGGTCATT

CTTACTCAAGCCACTACAGGCTTTGTTTTGTGTCTCAGACTTTATGTCAA

TAGAATACCTAGACACCTTGTTACAAGACAGGCCTGGAAAGCCTGCAGTG

CTGACTCCCTGCCAGTAGCACATTCTGAGGAGCAAGTCCCTTAAGTCGCT

TACCTGCTCTTACATTACGCCTTTCCCTGACCATTTAGTGAGCACTGTTG

GTGTCCCCAACCTGAACCTGGTTCTGGGGAAACACTTGCTTATTCACTTC

CGTGCTAATGGCCAGGGAGCAAGCATGCTTTCATGCAACACTGTGAGTTC

AGTACAACCACAGGAGGAGATTGCAGACTTCCTTCGTGTACTGTATCACT

ATGAGGTTTTCCAAACCAGTCTCCCTTTCACCTCATTTTTTGGCATGCCT

TATGTACTTGCTTATACTTTCTATCTTATGACATGAAAACAGAGTGGCAT

TTGGAGGCTTAAATTTATCACATTCCCAATTCAATTCCATTTTCAGTTTA

CTCTTTCTGTATATACATCAGTGTGCAGATAAATATCTCTTTGTGTGAGC

ATTGGAGGCCAGAGGTTAACCTCTGGTATATTCTTCCTCTATCACTCTTC
```

FIG.3D(23)

```
ACAGGGTCCTTTGATGAATGTGGAGCTCACTGATTACATAGACTAGCTGA

CTCAACCCTCAGGCCTCATAACCCTGCCTCTAGCCCTCAGATGAGATTAC

AAGCAAGCAAAACTACGCCTGGCCTTTTATGTGGGTGCTTGGAATTTGAA

CTGGGTACTTATGCTTGACACAAGTATTTTATCCACTGAACCATCTCCCA

AGCCTCCATTTGCAGTTTTTTACCTCACCCTTCCAATATATATATTTATT

TGTATGCCCTTTGTTCAAGATTTTAGTCACCTTTTACATTTTTCTTCAAA

AATAATTGCACCAATTTCTTAATAATGGCACCCAAAAGTAGGAACATTAG

CCTAGAGTATACCCTGTGAGCCAGGAAATGTGACTGGTGAGACTTGTAAA

AGGGTCTTTTTATTCTGGCCCTCAGCGGAGGCTCAGCAGTGGAGCATGCA

TGCTGTTCCTCTGGAGGACCCGAGGTCCCCAGGGGCCAGGTCACAACCAC

TTGTAACTTTAACTCTGATCTAATGCCCTCTATGGCTTTTGTGCTATAGT

CTCTTGCACTAACCCACACTCAAGGCACACATACACACATTCTTTAAAAG

ATAAATTATTTTATTTTCAAAGGTTTTTTTCTGCATATAGAAGTTAATAA

TTTGTCTGTTATGCTCACCAGATCCTAACAAAGCACCTGAAATTCAAATC

AGGATGAGTTCAGATGTTCAGTATTTTGAACTAGTAAACCGAACTGCATA

ATTCCTAAAACTTTGTTTTCTTTCCTCTTCCCCTTTAAAAAAGAAAATAT

CTGTGGCAATGGCTGGCATTTGGTTGGAAACTCGTGTCTGAAAATCACTA

CTGCTAAGGAGAATTATGACAATGCTAAATTGTCCTGTAGGAACCACAAT

GCCTTTTTGGCTTCCCTCACATCCCAGAAGAAGGTGGAGTTTGTCCTTAA

GCAGCTTCGATTAATGCAATCATCTCAAAGTATGGTGAGTTAATGTGTTC

AGAACTTTGGTTTCTAGGGCACAACAGCAGCTCTTATGTAGAAGGCCACA
```

FIG.3D(24)

```
GTTGTATGTTATTTGCCTGGTAAGAGAAAGAATTACAATAAATGATTAAT

AATATACTGTGGGCCTCTATTTCAGAGGCTCTTCTTTTGATACCTTTCTT

CTTGTCTTAAAAAGTTCAGTACTTTGCATATTTTATTAGTTGTTATTATT

AAGTAAATTATAAGGTATGAACATATGGAATGAATGGTAATATGTGTACA

TATTCTGGTGACATCAGATTATTTTGTACTTGATTTATATCTAGATTCTG

CTTGGGAAAAGGGAGAGTAAAATGTTAGTTACCTAGGTGTCATTAAAGCC

ATCTACAGCCCCTGGAGGTATTATTATAGCACATAGTGTAATCGTCAGTA

AGAAATGTAAAATCTGCCCAGGTTTTATAGCCTTCTTCCTAAGGCTTCTG

AACTCAGAAAGTTCTCTTACTCTAGAGCCAAACTCTCAAATGGCTTGTAG

TTACTATATAGTCTCATTTGGTATTTTTCTTGGTAAGTCTAATTCTAAGA

CTTGTGATTTGACTGTGATGCTTCAGTCAATTAGATATTCACAGAGCAGC

TTTTCTGTCTATGCTGGCTGTGGTACAGAGAGATGTGAGGGACATGTTTT

TGTCTAGCCAGGAGAAGACAGAATGCAGCTCAGCATCTCTCATTTGGCAC

CACCTTCATGTGATGGGATGCCGGTATGGTGTGGGTCCTGGTTGTTAAAT

CTCAGGAAGTCCATATATCCAGAAATGACCTCAACTATAGGTGGATTTCT

GGCAATTAGGTAAAAGTCAGCATTCCTTGGGCACTTGGGAAACTGGTTAC

CATCTGCATAAAGGAGTCATTTCCCTTCTATCTGGCAGAAGGGACATATG

GCTATCTATTGTGCCTGTCAGCATGGAAGCACATGCTAGTCTCCAGGTCC

CCCCAATATCACAAGTACCTATAGCAGTGAATTAGTTAAACTGATTTGGC

TCCCAATGGGTCAAGTACAGCTGCACCTGCCCAAGAGCTCTTTGGGTTTG

CAAATGAGAGACACATAGTTAATTTTTATATGCTTTGACTAGTTCAGTTG
```

FIG.3D(25)

```
CTGGACATTTCTAATCCTCCCTGCAGTAGCATACATTAACCCCTCCAACT

TTCCTGAGTCAACTTACTAACTCAACATTTCATCTCTGACACCCCAGACC

TAATGGCAGAGTGGCCCTTAGAGCCACTTTCCCAATTTTTTTTTTATCAG

ATATTTTCTTTATTTTCATTTCCAATGTCCCCTTTCCTAGTTTCCCTGTC

CTCTCCCCCTGCTCCCCAACCCACCCACTCCCTCTTCCTGGCCTTGGCAT

TCCCCTATACTGGGGCATAGAGCCTTCACAGGACCAAGGACCTCTCCTCC

CATTGATGACCGACTAGGCCATCCTCTGCTGAATATACAGCTAGCACCAC

GAGTCCCACCATGTGTTTTCTTTGATTGGTGGTTTAGTCTCAGGGAGCTC

TGGGGTACTGGTTAGTTCATATTGGTGTTCACTTTCCCAAATTCTTACAT

GGCTGGTTTAGTTCTTTCCTGCAGCTCTTAGGTCTAATCCCTTTCCTTCC

TCTGTCATGGTGATTGCCTTCCTCTCCTATCTCAGTTCCTTGCCTGCTCA

ATCTAAAAGTCCCACCTCCATCTTTCTGCCCAGCCACTGGCTGTATGCAG

TTCTTTATTATCAGTTGAAGCCAGCTAGGGGCAGAGACCTTCAGGTCTGT

AAGTGCTTTGGGGAGCAGAATTAAGACAAAGCATTAGAACCAATTCCCAA

CAAGTACCTGCTATACATTTCAAAGTCCATATTAGTCTCCTGGGTCTTCC

CTTCCCCAGCTACTTGTCCTCCTTGTAATCCAAATGACAAGCTTTTTCAC

ACATCTCTTTATCTCACATTTCCCTAGCCCTGGCCATGTCCACTTGTTCT

TTTACTCTCTGCTCTGCTCTCTTTCCAATGCCTCTGGATATTTTCTCTCT

CTTATTCACAATAAAAACCAAACCAAACCAAACAAAAAACCTTACCCTAA

TAATGGAGTGGTCACGCCTGAGGTTTCCTTACTGCTCCCCCTTGCACACG

TCTTGTGTCTGACACACTGGCAGGCTTTTATTAGCAGCAGGCTCTAGGAG
```

FIG.3D(26)

CTGAGAGAAGCAGCAGGCACCTCTGAGGTGGTAGTTACTAGAGTGATTAG

AACAGACAGTGGAGACGTGGCTGGAAATATGGACTCTGGTGTTTGGAGCC

AAGTATGGTAGGCGGCAGAAGCCAGCAGAAGCATGATCCACACCTTCACC

AGGTTGCTTCCATTGGGAAAGGCTGGACCCCTTGGGAAGGGGTCCCTTTG

TGCCTTCCTAGGTGTTCGGAGCCAGGTGTGTGAGGGATACAGTAAAGGGA

CTGACTGCATGACTGCTCCATTAGGGTGAAGGGTTTTGTTGTGAATAGGA

GAAACAAAATGTGCAGAGGCATCTGGGAGAGAGCAGAGCAGAGTGAAAAG

GAAGCAGTGTAGGCATGGTCAGGGCTAGGGACAGCGGAGACAGCAAGATA

GCGAGTGGGTGATAAGGTGAGAGAGAGTGTGTGTGTGCGGTGCACACATC

ACGTGCATTATAAGGAGGCTGAGTAGCTAGCTGGGGGGAGGGAAGGGCCA

GAAAACTAGCATGCACTCTGAAACGGGTACTTGTGATGCTGAGGGAGCTT

GGGGGAGAAGGGCATGCCTCAAGACCAGAAGAGGGAGTTGGAGTTACAGT

TTGTAAGATGCCTAATTTGAATGCTGAGATCCAAACTCTGATCCTTTGGC

TGAACATCATATCTGCTGAGCCATCTCTCCAGCCCCTAGAAAGGTGGTGA

TGGTGGTTGTTCTTGTTTTGTTTTATTTTGTTTAAATGGGGAGCCAGGTA

CAGTACATCATGCCTTTAATCCCAGCAGGAGATTCAGGAGATAGAGACAG

GTAGATCTCTTTGAGTTCAAGGGCACCTTGGTGTGTATAGGAAATTCCAT

CCACCCAGGGCTACAGAAGGGTACCTTGTCTTTAAAAAAAAAAAAAAGAA

AGAAAGAAAGAAAAAGAAAAAAAAAAGAGAATGAAATTTCAGAGTTATGC

AAGATAGGAGCTCAGTGGTAGAGTGTGTGCCCAGGAAGTGCTGGGTTTGA

CTCCTCAGAACAACAGCAGGGGCAGAAACTAGTCTACAGGTTCATGAGTG

FIG.3D(27)

```
GTGTTTTGTTTTGTTTTACATAAAATGTGTTGAATTAGATAAGTAGATAA

AATGTGACTCATACACAGATAAATAGATAAAATGTGATACATGTACCTGT

ACATAGAAGATTATGATCTCACCTTTAAAAAGGAGGAAATAGAGAGTTTT

GGTAGTTACACCACAGGAAAACTGGAAAAGAAAATGTATATATGAGGCTG

TGCCCCATGGCTAAAGGAACATGTTTTTAAGTCATTTGAATTCACCAAAC

AGTTTTAGGTAATGATATATGGTTTTGCATACAACCAGTATTTTATAAAT

ATTAGCAAGGTCACATCATTTATGAACCAACATTTAAACTAAATTTGTAA

ATCATCATTTCTTTATAGCACTTGTCATAGAACATAAGTAGTTTAAAATG

TGATTATTGCTTTGCTCTTGATGTCTGAAAATCTTCATGTATTCTCTTCT

TTGAGCCATTTTTATGCTTTGCAGTACTGGATGCATATTGAAGTGATCAC

TTATTTTAATCTACCTTGCCTGAGTTTGGGGAATAGATGGTTTCCACATG

TCTGTGGGTTATGCCTAAGCTAGTGGTTTTTATGTTAGAGCTTGTTTTGG

GGAAGGCACTGGTTGCATTCATAGCTGTGTTTCTTTTGCCTGTAGTCCAA

GCTCACTCTGACTCCATGGGTTGGTCTTCGGAAGATCAATGTGTCTTACT

GGTGCTGGGAGGATATGTCTCCATTCACAAATAGTTTGCTGCAGTGGATG

CCATCTGAGCCCAGTGATGCTGGCTTCTGTGGGATCTTGTCAGAGCCTAG

TACTCGGGGATTAAAGGCTGCAACCTGCATCAACCCTCTCAATGGCAGCG

TCTGTGAAAGGCCTGGTAAGGACATGGGTGCATATAGTGCTCCAGGAGGA

GCCAAGACAGCAAAGGAGGCACAGCTGAATGAGCGCTGAGGTGATGAAGT

ACTTATGGCAGCAGGGAGAGGAGCACCAATTTAGGCATATGTATTTCAAA

CAGAACCCGATTCCAGATAGTCTTTCTTGGCCTCTGACTGCTTTAAGCCA
```

FIG.3D(28)

```
TACTGAAAACCAAAAATAAAATTGCTGAAAGAACCCAGTTTATATTGAGC

TGCACTGTTTCGTTGGTCTCAAAGTGTTGAGAATTGTTCTAGAAGATTAT

TTCCTTGGTGTTGGCAGAGAAGTGCTATGGAGGAAACAACAACCTGAAAC

CAAAGAAACATTTAGAAAAGCAGCAAGTCAGGACACTATTCAGACACTGC

TGGGGTGGGGGGAGAGGGGCATGGCCAAAGAAGCCGACAGAGCCAACACC

AGGCTGTGGCAATGTCCTGCGCTGAGGTTAAGGTTAGACTCCATGAGGCC

AGGCCCAGAACAGCCATACACAAATGAGGACTCCAAAACAAGAGGTGCAA

GTGTAGTGGAGACTCCATCCCTGCAGGTCCTGTTTCAGGAAATGATTGTA

CTTTGCCTGAGTAATACAGCCTAGGAGCTACTTTCTGATAGGGTTTTTTA

AATACTTACAAAGAATTATTTATCTTTAATCATGTGGTTTTGTATGTGTG

TGCTTGCACATGCAGTGCTTGTGAGAGAGAGTATGTGTGAGAGCATGCAT

GTATGAGAGTGTGAGAATATATGTGAGAGAGTGTGAGTGCATGTGTGCGT

GTGTGCATCTGTGTGTACAGGTGTGTGTACATGCATGTGTGTATAAGAGT

ATGTGAGAGTGTGGGTGTGTGTGTGAGAGTATGTGAGAATATATGTATGA

GTGTGTGTGAGTATGAGTGTATGTGCGTGCCTGCATGTGTGTGTGTGTGT

GTGTGTGTGTGTGTGTGTGTGTGTGTGTAGAAGTGGCCTTGGAAAACA

GAGTTGTCAGATCTCTTAGAGATATAGTTGCAGTTGGTTGTGAGCCATCT

CATATGAGCGCTGGAAGTTGAAATTGGGTTCTCTGGAATCCTCTGGGTTC

CTTGTTGAAGCCTGAATATTTTGATAAATATTTATGTCATTATCCCTCAA

AATTGTAAATGTAGAATTTAACAAACTCAGGTCTTGAGTCATCTTTGTCC

CAAGGTTTGTTTGTTTGGTTTTTTGTTCCCCCACCTTTTCTTCAGTGCTT
```

FIG.3D(29)

```
TTAAAAAAGAGAGTCCATTTTTTCCTAAATGTTTAAATACAGTTGAGGAA

TAGAACATCTGACTCCAATTTCCTGGGTTTCCCTCCATGTAGTGTAGTGC

TGACCTGATTTCAGTGTGCATTGAAAACTTTGATCACTTGGAAGGCAGCT

ATGCTCACCACTATACTACCAATGTCTGCAATCCTATAGGAGAAACAACA

ATATGAACTAACTAGTACCCCCCAGAGCTGTGTCTCTAGTTGCATATGTA

GCAGAGGATGGCCTAGTCAGCCATCATTGGGAGGAGAGGCCCTTGGTATT

GCGAAGATCATATGCCCCAGTACAGGGGAATGCCAGGACCAGGAAGCAAG

AGTGGGTGGGTTGGGGAGCAGTGCGGGGGGGGGGGGTATAGGGGGTTTTG

GGGATAGCATTTGAAATGTAAATGAAGAAAATAACTAATAAAAATTGCCT

TAAAAAAAAACAAAAAAGAAAAGTTTTTGATCTTAGCTGACCAGTGTCTC

TTTGGGTCTTAATTTCCAGCAAACCACAGTGCCAAGCAGTGCCGGACACC

ATGTGCCCTGCGGACAGCGTGTGGCGAGTGCACTAGCAGCAGCTCGGAGT

GCATGTGGTGCAGTAACATGAAGCAGTGTGTGGACTCCAATGCCTACGTG

GCCTCCTTCCCTTTTGGCCAGTGTATGGAATGGTATACGATGAGCAGCTG

CCCACGTAAGTGGAAGGAGCTTTTGAACATTTGCAGGCAAGTTGGGCTTG

ACTTTCTGCTCAAGTCCATGCAGAAGCTGGTCGGGCCGGCCCTTCCAGAT

TAACATGTATGTATAGAATGCAGCACAGTGTTCCATGCAGTAAATCAGTT

ACATCAAGGAGAAGGCACAGGGTACAGAAATACCTTTTCTTCTTCAGGGT

AATATTATAATTCAATCTGTATAATGTTTCTACATCTTAATCTACCAGTA

TGTAAAGTGCTTTCTAGTAGAGGCCTCCCCAGCTCCCTTTTTCATCCAAC

ATCCTGATATTAAAAGGTTGGAAAAGTCCCTGTTATATATTATGTAAAAT
```

FIG.3D(30)

GTGGGGCCCTTTAAATTATTTCAGTTCAATAATCACTATAGGGTACTATT

TTTAATTCATGGAAGTTAAATCATCTGTTAAAAGAAAAGGTAATAACAGT

AAATTCAAATCTTGTGATAGTGAATTACAAGTTGGATTGTTTTGCCTTGT

TTTTTAATAGCTGAAAATTGCTCTGGCTACTGTACCTGCAGCCATTGCTT

GGAGCAGCCAGGCTGTGGTTGGTGTACTGATCCTAGCAATACTGGGAAAG

GAAAATGTATTGAGGGCAGCTATAAAGGACCTGTGAAGATGCCGTCACAG

GCCTCTGCAGGAAATGTGTATCCACAGCCCCTTCTGAACTCCAGCATGTG

TCTAGAGGACAGCAGATACAACTGGTCTTTCATTCACTGTCCAGGTAAGA

TGCCTGTGTATCCTAGTTCAAATCTCGTACATAAACTAGACGCCCAGATC

CCTTGGCTCACTTGTTTTCTTGACTGTGTTTGAGTTCTTTCTGTGTTCTG

CATCACCTTGTTGGATCATAGCTGGCAAAGGTGCTCTCCTTTCTGTGGGC

TTTTTCTTTACTTGATTGATTGTTTCTTTGGTTGCACAGAAGCTTTTTAG

CTTTCTGAAGTCCCATTTGCCAGTTGTCCTTAATTCCTGGGCGAGTAGAA

GCCTCATAAAAAAAAGTTCCTTCCTACACATGTATCATGTAGGGCACTGC

CTATGTTTTATTCCAGAAGTTTCAGAGGTTCGGGTTATGTCTTTGATCCA

TTTAGGGTTACTTTTTGTGAAAGGTAATGGACACAGTTCTGTTTCATTCA

TTATTCTACATGTGGACATCTACTTTTCCCAGCACCAGTTTTGAAGATGT

TATCTTTTCTGCAGGTTGTTTGTTTGCTTGTTTTGTCTCTTCAGAAAATC

CCAGATGGCGGTAGCTGTGAGTGCTTAGGCTTGGCCTACCTGTTTCATTA

TGTTGGCTTGCATGTCTGTTTTGTGCAGTGCCACCATATTGTCTTAATTG

CTATAGCTCTGCAATCTATCTTGACATCTGTGTTGGCAATCCTGCAGTTT

FIG.3D(31)

```
CGACCCTTCTGCTCAGCAGTGCTTTGGCCATCTGGGGTCTTTTCTGGGTT

CATAATGAATTTTAGGATTTTTTTTTCTATTTCTGAGAAAGTATTGTTGA

TATTTTGATTGCGATTGAATTGAATCTGTAAATTGCTTTTGGTAGAATGG

TCATTTTCACAATATTAATTTTACTGATCCATGAACATAGGATGACTCCA

GTCTCTCATGTCTCCCTATAGCCCTGTCTTAAGAGATTTGGAGTCTTCAT

TGTAGAAGTCCTTCACCTCCTTGGTTAAGTTTATTTCTAGATATTGTATT

GTCTTTGGTATTATAAATGGTAGTATGTCCATGATCTTGTTCTCAGTGTT

TTTTTAGTTTAGTTTTTTTTAATTTATGTGTATGAGTGTTTGTTTTATAT

ATGTGTATATGTGCATTCATGTCCTCTGGGCATCAGATCCCCTGGGACTG

GATTTACAGACAGCTTTGAGCTGCCTGTAGGTGCTGAGAATTGAACCCAG

GTCCTCTGCAAGAACAGCCAGTGCTCCTACTCCCCAGCCCCAGAAGTACT

AATTTTTAAGAGCTGATTTTCTACCTTTGCTGACATTGTTGATTGTTTCT

AGAAGTTTAGTGATAGAGTTTTTGAGATTTCTTATATATCTTATGTTATC

TGTAAAAAGGGATAATTTGACTCCTTTTCCTATTTATATCCTTTTATTTC

TTTCATTTGCCATATTGTTCTAGCTAGTGCTTCCCGCTCAGTATTGAAAA

GAGTGGTGATTGTGAACAGCTTTTCTTATTTCTTATTTTAATGGGATTAT

TCACCCATTTAAGATAATGTTGGTTATGGGTTTGTCATACACAGCCCTTC

TTATATTGAGGTATGTTCCTTCCAGTCCTGTTCTCTCTAGGACTTTTTTT

TTTTTAATCAAGAAAGCATATTGGGTTTTTTGTTGTTGTTATTTTGTTTT

GTTTTTCTAGACAAGGTTTCTCTGTGCAGCCCTGGCTGTCCTGGAATTCA

CTCTGTAGACCAGGCTGGCCTTGAACTCAGAAATCCACCTGCCTCTGCCT
```

FIG.3D(32)

```
CCCGAGTGCTGGGATTAAAGGCGTGCACCACCACTGCCTGGCACATGTTG

GTTATTTTGCAAGCCCTTTCTACATCTACTAAGATGAGCATGTGGTTTCA

TCTTTGTCTGTTTATATTGTCTGTTGTATTTATTGACTTATGTGTGTTGA

GCCAACCTGAAGTTCTGGGATAAAACCCACATGCTTTGGATGATTTTTGT

GCTATGTGCTTATATTGTGTTTGTTAGTGCTTTATTGAGGACGTCTGCAT

CCGTGTTCATCTGGGGTACTGTCTGTAGTTTGCTTATTTTGTTGTCTTTA

CCTGCTCTGCATTTTAGAGTAATCCTGGATTTATAGAAAGCATTTGGGAG

TAGTCCTTCTGTTTATTAAAAAAAAAAAATTAAGAATGATTGGTTGTTGTG

TGGTGGAATTCTGCTGTGAACCCATCTGGTTCTGGACTCTATTCGGAAGG

CTTTTTATTACTGTTTCAGTCTCCTTGTTTGCAGTGATCTATTTAGGTTG

CTAATCTCCTTATGATTCATTTGGATGAATCAAGAAATTAATCCATCTCT

TTAGATTTCCAGCTTAATGGAATATGAGTGTTAAAGTATTTCTTTATAGC

ATTCTGTATTTTTTGGCATCTGTTGTAATATTTCCCTGTTCTTTCTGTTA

ATCTCTTTCTTTCTTGTGGTTAGTTGGGCTAAGAGGCTCTTGGTTTTTTT

TTTTTTTTTTTATCTTTTTAAAGGACCAGCTCTTAGATTCATTAATTCTT

TGTATTATTTTCCTTGTTTCTTTTTCACTGATTTCATTTTAGATTTTATT

ATTTCTTGCCATCTACTGCGTTTGGGTTGGTTTTAGTTATTTTTCCAAGA

TTTTCAGTTTCATCACTAAGTCATTCATTTGGGCTCTTTTGGGTTTCTTC

ACGAGAACCCACTTGGGACTGTTACCTTCCCTTTTAGACCTGCTTTTAAT

GTGCCCCAGAGATTTGTTACATTGTCTTTTCGATTTAACTTAGTTTCAGG

AATATTTTGATTTCTTCTTTGACCCATTCATCATTCGGTAATGAGTTGTT
```

FIG.3D(33)

```
TAATCTCTAGTGAGTTTATACATTTATTAGAATTTTGTTTACTGATGATT

TTAAGGTGTTTGGCTTTGTTTGTTTGTTTGTTTGTTTGTTTTTCGAGACA

GGGTTTCTCTGTTGTAGCTCTGGCTTTCTCTATGTAGAACAGTCTGACCT

CAAATTCACAGAGATCCACCTGCCTCTGCCACTGAAGTTCTGGGATTAAA

GGTGTGTGCCACCACTACCTGGCTGATTTTAAGTTTTATTACATAATAGA

CAGGTAGGGTACATAGATTTTCTACATTTGTGAAGGTTTGCGTTGTTTGT

CAGCATGTAATTCTGTGTGCTGCTGAGGGAATGTATGTTGTTTTGACAGT

TAGGTGGAAAAGTCTGTAGACATCTGTTAGATCCATTTTACATTTCAAGA

AGCCATTTAATTCTGAAGTTTCTCTGCTTATTTTTTCCCAGGTGACTTAC

CTATTGGAGAAAATAGGGTGCTAAAATCATTTACTATTATTGTTTTTTTT

AAGAAGAAAATAATTAATTTAAAAAACCCTGGAAAGAAAGATACCAAATG

TGAATCATGTTTCCTGGATAGTGGGGTTATATTTGATCATTTATTTTTCC

TCTCAAATACTGTGAGTTTTTACAATGAATAACAACATAAATATTTTTAT

GTTGCTGTGGACTTTAACTTTGCTTTGATAATATATTTGGTTTTTTTGAGA

CTAATTTCTTTTTGATATTTTATTTTCTCATACTAGTTTTTAGTAAACTT

TGGTTTTGTTTTGTTTGTATTTTTTAGACTGGCCACCAACTTGCTATGTT

GTCAAGGGTGGCCTTAAAATCCACACCCAATACTTTGTCCTCTCTTTCTT

TCTTTCTTTTTTTTTTTTTTATTGGAACAAAATTTCTAGGTGGGAATCTCAC

TATGTTACCCAGGCTGACCTGAAACTTCTGGGCTTAAGCAAGATGGGTGC

ACATGATCAGAGACGCTGCGCTGCCCGCCTCAGCCCCTGCTAGTTGGAAC

TATAGGCACAGACAGCTGTACTTCACTCATTTCAATGATTTAACATTTAG
```

FIG.3D(34)

```
ACTATATGCAAATAAATATGAAATGTATTCACCAAGTTCTCCTATGGGAG

AAACAGAGCCCTTAAGATTTTTTCCTTTCAGCTTGCCAGTGCAACGGACA

CAGCAAATGCATCAACCAGAGTATCTGTGAGAAGTGTGAGGACCTGACCA

CGGGCAAGCACTGCGAGACCTGCATATCTGGCTTCTATGGTGACCCGACT

AATGGAGGCAAATGTCAGCGTAAGTCACACAGGTCAAGTTAGTCACAAGT

CAGGTACAATAGTACAGTACCTGCAGTTGACTTAAATATCTTAAAGGGAA

AAGGCCTCTTGGTTTGGGATATTGCCTTTCTTAATTATGTTAAATTGTTA

AAAGTTTAACTGAGGGGCTAGAAATGTGGCTCAGTTGGCTAAGAACACTG

ACTGTTCTTCTAGAGGACCGAGGTTCAATTCCCAGCACCCACATGGCAGC

TCACAAGTGCTTGTAACACCTGGGATCCAACAACCTCATACAGACATACA

TGCATGCAAAACACTAATATACATAAAATAAATCCATTAAAAAGTGTTTG

ATGATGCTGGAAGAGGAAAAAAGGCTCAACTTGTGGGTTTGGGAGCAGTT

AGTTAAAGCAACAAACCGACAGTAAAGGAGCTAAGCTTTTATTTCTTCAG

CAGAGGCATAAACAAGGGGCCGAAGTCACTGAGGCACCAGCTGCCTTTAT

TCCATTTCCCTCCCATGGAAGCACATCAGCTCAAGTCAAGCAGAGCAGCC

TGGGATGGGAGGTCATCTCATTGGAGAAGGAGGCAGGAGGCATTGTGAGG

GGAGGGAGGACAAGGCTGGGAATGGGAAGTCCTGAGCTCAGAATCAGAAT

GAGGACAAGATCTTCAGTTTCCTTCTTAATATAAAGAGGTATCACAGAGG

TCTCTATAGAAGTCTACTGGAAGCCTCACACAGGCACAAGGGTACATTTG

AAAAACTGTGACAGCCAGGGAGAGTCCCCTTCTGAAGTGTCCTTCCTCAG

AGACTGCAGCACCTGACTGTGCCCCAGTCTGCAAGAGGTTTGGGGAGAGC
```

FIG.3D(35)

```
AACTGACCTCCTGAGGACCCCAGATGAATCTTTAAGATGGCCTGCTTTTG
GTTTTGGTTGGTTGGTTTTTAGACAGATCTAGGAGAGTTGGTGATGAGCT
TGAATTCTCTGTCCTCCTGCCTGACCTCCAAATGCCCAGCTTCACATGGG
CTCCCATTAAGTTGTGAGTTTCGGTGTCTGGCTCCTGCTCTCACAGCCAG
TGCAGTACATTGAGCTCCATAGAGATAGCGCCGGGGCAAATGAGAGCTGG
ACGGGCACTGGGTGACTCTGTGCCTTGTGCCGGAAAATCAACTAAACATG
GGCAAAGGAGATCCTAAGAAGCCGAGAGGCAAAATGTCCTCATATGCACT
CTTTGTGAAAACCTGCTGGGAGGAGCACAAGAAGAAGCACCCGGATGCTT
CTGTCAACTTCTCAGAGTTCTCCAAGAAGTGCTCAGAGAGGTGGAAGACC
ATGTCTGCTAAAGAAAAGGGGAAATTTGAAGATATGGCAAAGGCTGACAA
GGCTCGTTATGAAAGAGAAATGAAAACCTACATCCCCTGCCCCCAAACAG
GAGACCAAAACGAAGTACTAGGACCCCAATGCACCCAATGCCTTCTTCGG
CCTTCTTGTTCTGTTCTGAGTACCTCCCCAAAATCAAAGGTGAGCACCCA
GCTTATCCATTGGTGATGTTGCAAAGAAACTAGGAGAGATGTGAACAACG
CTGCAGCAGATGACAAGCAACCCTAGGAGAAGAAGGCTGCCAAGCTGAAG
GAAAAGTACGAGAAGGATATTGCTGCCTACAGAGCTAAAGGAAAACCTGA
TGCAGCAAAAAAAAAAAAAAAAGGGGGGTGGCCAAGGCTGAAAAGAGCAAGA
AAAAGAAGGAAGAGGAAGATGGGAGGAGTATGAGGAAGAGGAGGAAGAAG
AAAGATGAAGAAGAATATGATGATGATGAATAAGCTGGTTCTAGTTTTTT
TCTCATCTATAAAGCATTTAACCCCCCTGTATACAATTCACTCCTTTTAA
AGAAAAAAATTGAAATGTAAGCCTGTGTTAGATTTGTTTTTAAACTTTAC
```

FIG.3D(36)

AGTGTCTTTTTTTTGTATAATTAACATACTGCCGAATATGTCTTTAGATA

GCCCTGTTCTGGTGGTATTTTCAATAGCCAGTAACCTTGCCTGGTACAGT

CTGGGGGTTGTAAATTGGCATGGAAATTTAAAGCAGGTTCTTGTTGGTGC

ACAGCATAAATTAGTTATATATGGGGACAGTAGTTTGGTTTTGGTTTTAT

TTTTGGGTTTTTTTTTTTTCATCTTCAGTCGCCTCTGATGCAGCTTATATG

AATATGATTGTTGTTCTGTTAACTGAATACCACTCTGTAATTGAAAAAAA

AAAATCGTGGCTGTCTTGACATCCTGAATGTTTCTAAGTAAATACAGTTT

TGTTTTTATTAATATTGTCCTTTCGACAGGTCTGAAAGTTTTCTTCTTGA

GGGAAAGCAGTCTTTTGCTTTTGTCCCTTTTGGGTCACATGGGTTACTGC

AGTGTGTATCTTTTCATATAGTTAGCTGGAAGAAAGCTTTTGTCCACACA

CCCTGCATATTGTGGTAGGGGTAACACTTTCATCCATATTCAAAGAATCT

CCAAAATCGTGATCAGTTGGATAAGAAATATTATATAACCTACTTGGCAA

AGCAAGGTGTGATCAATTCTGTCACACCATGGGATCATTAGAATCAAGCA

ATCTGAAAATCTGTCCTTAAAGGACTGATAGAAAAGTATTTTCTAATCCT

TATACAAAGGCTCTCCTTTAACTGCCACTGCTATGTAATGACAGTTATGT

TTTGCAGTTTCCCTACTAAAGAAGACCTGAGAATGTATCCCCAAAAGCGT

GAGCCTAAACTACACAACTGCAGTACTATTTGTTGACCTTAGTCCCAGCG

AAGGCTATCACGAGAATGCTAGCTATAATATAATGCCTCTGCCCCTCTAT

CTAAATATGGATTGCTCAGGAAACTTGACTGCTTAAAGGTATTTTTTTCA

TATTGTTGTTCCTCCTATAGGGTTGCAGACCCCTTTAGCTCCTTGGGTAC

TCTCTCTATCTATCTATCTATCTATCTATCTATCTATCTATCTATCTATC

FIG.3D(37)

TATCTCTTGTCAGATTTCTTTTTTCTTTTCTCTTTCTTTCTTTCTTTTTT

TAAGATTTATTTATTATTATTTCTAAGTACACTGTAGCTGTCTTCAGATG

CACCAGAAGAGGGTGTCAGATCTCATTACGGATGGTTGTGAGCCACCATG

TGGTTGCTGGGCTTTGAACTCAGGACCTTAGGAAGAGCAGTCGGTGCTCT

TAACCACTGAGCCATCTCTACAACCCTTAAAGGTATTTTTAAGTAGTTGA

GTCAGCTTTTAAAATTATGCCAGAAGTGTCAAAAGTTCAAAAGTTTAGGA

CCATCCTCTATTGAAGTACAGGGTCATCCTGGGCTACATGAGACCCTGCC

TTAAAACCAAAATCAAACAAACAACAGGAAAAACAAGAGTTAAGAAAGAG

AAAAAGAAGCACTTGGAAACAAAGATCTGTGGAGTATGTATAGGCTTCTC

TACAACAGGTGTATGTAGGATCTTGATGGCTTTTGAGTCTATTACCCTCA

AAGAGGTACTGAGAAACCTAAATGTGATCACCGTGGTCTCTGAGGGGCAC

CTGGCAGGATTATGGGAGATAACTAAAGCTTGCTAATCACAGAGTTTAGG

GAGGGAGGACGTCTCTAAGGCAAGTTAACTGTCTGGTTTGAGATGCTTAG

GTGATGTCTGAGGAAGTAATAAGGCCTGTCCATTTTCATACACACTCAGG

CCTTAAGTCTGGGTAATGGCTACTTGAACATAAAATAGTCCTCTATGAAA

GGAATAATATCTCTGTGTCAGCAGCCTTCACGGCTAATGTTAATTGTGCA

GGAACCCTGCTTCTCAGTCAGACAGAAGCTCAATCAGGCAGGGGCAGGAC

TTCTTTGCCTTTCCCATGTCCTTGTAATTTCCCTGGCTTTTCATCTTGGT

TCAAACATACTTACCTGTTAGGTAATTATAAGAACACCAAATATTACTGA

ATAAAATGTGTTTATGACTTTGTGGTGACTGCCATTCAAGAATTAGATGC

CTTAGCCAGCAATGATGGCACACGCCTTTAATCCCAGCACTTGGGAGGCA

FIG.3D(38)

```
GAGATAGGCAGATTTCTGAGTTCCAGGACAGCCAGGGCTACACAGAGAAA

CCCTGTCTCGAAAAAACAAAACAAACAAACAAAAAGATTTCGATGTCTTT

ATCACCCAAATCAAGTAACTTTCCAAAGTCTCACAGTGAGATGTAGCCTA

GTTGGGAGCCACATCTAATATATGCTGATGATCTTAACAAGTAGCCTGCT

TGTGTCTTCAGGTGACCACCCCGGTGTCCTCAGCTACCTCTAGAAAGATC

ACACTTTCCTCTGTGGTCTCTGCAGGGTCCCTGTATGATTCTGGAACCTT

GCTGTACTTCTCAGAGTCCTGATTCATAAAGCACTGAGTTTTTGCTTGTT

TGTTTGTTTTGATACTATTGGTAAGAATATATATTGAACCTTGACATGCC

TTTTTAAAATAACATTATTTTTACAATAGTACTTTAGCCTTGATTATGTT

AACTGCTTACTGTTTCAGATGACATTCGTACATCTTTTAATCCTCAAACC

AGTCCTATGAGATGGCTAGCATCATTGTCACATCATTTAGGCAAGGAAAC

AGGTCTTGGGTTAAGCTTCATGCTCAGAGCTCCTTGGAACACAGTGGACT

CAAGTGCAAGCAGACTGACGCGACTGGGTTTTACTAATTCAGTAAGCCTG

TACTCTATGGAGGAAGAGTTTCTGACCACTGGATGCAGTCTGATGACCTC

TGACTGTTCTGTTTGAAAGGTTTCTTTCAGTGATTTTATTTTTCTCCATG

TGGACTTTTTTTTCCAGCTTTTAAAATATATATATATATCTTATTCGCTTC

ACATCCTGCTCACTGTCCTCCCTCCCCTGTCATCCCCTCCTACAATCCTT

CATATCCCCCCTTACCTTCTGAGCAGCTGGGAGCCCCTCTGGGTATCCCC

ACACTCGGGCACATCAAGTCTGTGAGGCTGGACGCATCTTCCCCCACTGT

GGCCAGACAAGGCAGCCCAACTAGAACATATCCCACAGACAGGCAACAGC

TTTTAGGATAGCCCCTGCTCCAGTTGTTCAGCACCCACATGAAGACCAAG
```

FIG.3D(39)

```
CTGCACATCTGCTACATATGTGCAGGGAGGCCTAAGTTCAGCCCATGTAT

GTTCTTTGGTTTGTGGTTCAGTCTCTGAGAACCCCAAGGATACAAGTTAT

CTGACTCTCTTAATCTTCCTATAGAGTTCCTATCTCCTCTGGGGCCCACG

ATTGGTGTCCCTATTGCTTCACTGGGATTCCTGCCTGGCTACACCCACTA

TGACCAAGGCAAGTCTTAGAAAAGACAACATTTAACTGGGGCTGGCTTAC

AGGTTCAGAGGTTCAGTTCAGTATCATCAAGGCAGGAACATGGCATCATC

CAAGCAGGCATAGTATAGAAAGAGCTGAGAGTTCTACAACTTATCTGAAG

GCTGCTAGCAGAATACCGACTTCCAGGCAGCTAGGATGGGGGTCTTCAGA

CCCACACCCACAGTTGGTGTCCCTATTGCTTCACTGGGGTTCCTGCCTGG

CTACAGGAGGTAGCCTCTTCAGGTTCCATATCCCCAATGCTGTGAGCCAC

AGTTAAGGTCACCCACTATTGATTCTAGGGTGTCTCCCTCATCCCAGGTC

TCTTTCATTGTGGAGATGCCCCCCACTTCCCCACCACTGTCAGTTGCAGA

TTTCCATTCTCGGGACCATCTGGCCATGCCTTCTGTTTCTCCTCACACCT

GATCCCGACACCCCCGCCCATTCCTTCTCCTACCTAGTTCCCTCCCTCCA

TATGCTTCCTATGACTATTTTATTCCCCCTTCTAAGTGAGATTCAAGCAT

CCTCACTTGGGCCGGCCTTCTTGTTTTGTTTCTTTGGGACTGTGGAGTGT

AGCTTGGGTATCCCATTTTTTTTATGGCTAATATCTGCTTATAAGTGAGTA

CATACCATTCGTGTCCTTTTGGGATTGAGTTACCTCACTCAGGATGGTAT

TCTTAAGTTCTATTCATTTGCCTGCAAAATTCATGATGTTTTTGTTTTTA

GTAACTGAATAGTAGTCCACTGTATAGATGTACCACAGTTTCTTTATCCA

TTCTTCAGTTGAGTGAAATCTAGGTTGTTTCCAGTTTCTGGCTATTACAA
```

FIG.3D(40)

ATAAAGCTGCTATGAACATAGTGGAGCATGTGTCCTTGTGGGATGGTAGA

GCATCTTTTGGGCATATGCCCAGGAGTGATGATATAGCTGAGTCTTGAAG

TAGAACTATTCTTAGTTTTCTAAAAAACCACGAAATTGATTTCCAAAGTA

GTTGTACAAATTTGCACTCCCTCTAACCAAGCAAGTGAAAGATCTGTATG

ACAAGAACTACAAGTCCCTGAAGAAATAAACTGAAGAAGATATCAAAAGA

TGGAAAGATCTCCCATGATCGTGAATAGGTAGGATTAACAAGGTGAAACT

GGACATCTTACCAAAAGCAATCTAGAGATTCAGTGCAATCCCCATCAAAA

TTCCAACACAATTTTTCTGTAGACCTTGAAAGAGCAATTCTCAGTTTCAT

ATAGGAAAACATAAAGCCCAGGAGAGCCAAAACAGTTCTGAGCCATAAAC

GAACTTGTGGAGGAATCACCATCCCTGACCTTAAAGCCGCACTACAGAGC

AGTCGTGATTAAAACAACAACAAAGGCTGCGCACTTTTGGTACAGAAACA

GACGTGCTGACCAATGGCATCCAATCCAAGATCCAGAAAGAAACCCACAC

ACTATAGTTTTTTTTTAAATATAAAGTTCTTCAGCTTAATGCTTCTCATT

ATTCATGAGAGAAGAAGACTCAACAGCAAAGAAGGTGAAACAAGGGTGAC

AAGTACCACAGGGCTCTCGAGTGTCTCTTGTGATGGACTAGGGAGCCCGT

CAGTTCTGAATGCTCAGGAATGTGGTTCACAGTGTGGCCACAGTACAGAA

GATCCCCGAGATAAGGCAGAAGACAGTCACCACAGGTCATCTCCACAGGG

CAAGGACTCAGTATATGGCATATTACTAATGCTCTTAAATATTTACTGAA

CAAAGGAACAAAATGCTGAGTCTGTCACAGAGATGAAAATAGCCGTTGCT

TCAGGGGACAGCAGAAGATAGCCTTTTTTTCTCCTTGAATGGTAGTTAAT

TTAATGTTGCCTCTATATTATTAGAAATAAATTACAAGCTGAAAAATAAT

FIG.3D(41)

```
GAGTCATACGCAGTGATTTCTCTTGCTTTAGGCTGTCTTTACTACAAACC

CATTTCAGGCTAAATGATTTTGTCTTAATCACAGTCTATGGTAATCTGTC

AAGCCAGTTGTGACCTGTCTTCCTTTCCTTCTTCCCAGCATGCAAGTGCA

ATGGGCACGCATCACTGTGCAACACCAACACCGGCAAGTGCTTCTGTACC

ACCAAAGGTGTCAAGGGGGACGAGTGCCAGCTGTGAGTACCACACACT

CTGTGTCTCCAGTGGGGGACTGGGCCTTGCAGCTGCCTGGGCCCTGTCGG

CCACCTGCTTGCCTGGGCATTGTTGCCCTTCACTCCCAGGGTCTTTGAGT

GGACTAGTGTGGAGGTTTACCTTTTTTCCTTCAGACAGGTTATCTCAGTT

ACTTTAATATTGCTCTGATAAAACATATGACCAAGGCAACTTACAAAATA

AAGCCTTTAATTGGGCTTATGACTTAAGAGCATTGGAGTCTACATTGAGT

TCCAGGGCAATAGAGCTACATAGTAAGACTGTATCAATCAATCAATAAAT

AGGACTACATAGTAAGACTGTATCAATCAATCAGTAGATGAAGAGAAAGA

AAGAAAGAAAGAAAGAAAGAAAGAAAGGAAGGAAGGAAGGAAGGAA

GGAAGGAAGGAAGGAAGGGGAAGAACAAAACAAGCTTAGATAGGAAGAAC

AGGATAGAATGAATGACAAATGCTTGAAAAATGTTTTAGCTGTACTTTTA

GAAGCATACTCAATCCACACAGAAGTAAAAATGTTGTTCCTTATGAGTAG

TACCTAGCATTATTACATATGTACTTGCCTGTGTCCTTGGGCAAGTATTT

GTTTATTTGTTGTTTTTATACTGTTGCTGGTGTAAATTACTGAGCAGTTA

GCAGAAACATTCCTGCAAATGGGATAGTCTCTCTGATCTGAATAATGATA

TAGTTTATGTAAAAGGATTTACTTGGTTTAAAAATAAATATAGAGTCTGT

GCTTTAAATGTCAATAGAAGATAATTTCTTTTTTCCCTAGATGTGAGGTA
```

FIG.3D(42)

```
GAAAATCGATACCAGGGAAACCCTCTCAAAGGAACATGCTACTGTAAGTT

TTTGTAATTGTTTCTAGAGAGTAATTGAACAAAACGACATTGCTTTTTTT

TTTTACCATTGTCTGAGAATGATAAATGCTTGGGGGATGAAGCAAATACT

CATAGCCATGCCCCTGACTTGGTGAACACTGTTCTAACTGAGGCATGGTC

TCTGCTGGTCATCCAGAGCAGTTAGCAGGGGTGCTGTCCTGCCTGTCCTT

GTTCAGCTCCCGCGGAGGCGTGCTCATTCACCATTGCCCAGTGTAGCTTA

TCATGTCCAATCTTCAGACAGCCAGGAAGGAGTTTCTAAGATAGAGGTGC

GTTCCACCATTCTCTCTGCAGCTGATTTGTGCTCACAAACAAGTAAATAA

AACACCAAATTAATACCTTGGTGTGAAAGTGAATCTGGTAAGCTTACAGC

TTTATCATAAATATATTTTTTGTCTATGAGAATCTACATAGTAGGTTCTA

GACTATAGAACAATAAAAAAAGGAATTAACATTTGGCATATGCAGCATAA

TGGTATATATAAATTGTAGAAGAAAATGGATGGTTCTAGACCTGAAAAGA

CAAGAAAATTGCTTGTGTGTAATCTGGGCAGGTCTTAAGTTGTGACCTTC

AACATCTGCTTCCCAAGCAGCTGGAACCACCAGGCCTACAGAATTCTTAG

CTATGATTCTAAAGGTCATTCATCAAATATAATGTTAATGTGTATTTTAT

TAAAGTTTCAAACTTCTATCTTTAATAATCTGCAAATGTAGCTCAGTAGA

GGAGAGCTCTCGCTGTAAGGTCCTGTGTTCTATCCCCAGCACAACAAAAC

AAGACATTTAAGAAAAAATTAAAACAAGTTGGCTGTATTGTCTCAGTATC

TCATCCTTGAGATAGTGAGGCAGGAGGACTTTTAGTTTGAGGCCTATGTG

GGTTATGTAGTGTGAAACCTTTCTCAAATAATATTTACACTTTTTTCTTT

AAAAAACAACTTTTTTTCTTAATTTATGTGTTTTGCAACATGTAAGTCTGT
```

FIG.3D(43)

GCAATGTGAACATATCTGTTGCCTTTGAATGCCAGAGAGGGTTTCAGTTT

TCCTGGATCTGGAGTTACCAAGGGTTGTGAGCTGCCATAGTGGGTGCTGG

TAATGAACTGAGTCCTCTGGAAGAGCAGCCAGTGCTCTTAACTGCTGAGC

CATCTCTGCTGCTAGGTACTCCCCCTTCCCCCCTTAAATTTAAGACAAAG

GTCTCACTGTGTAGCCTCAGATGGTCTAGAACTCAATTTGTAGAATGGTT

GACCTTTGAACTCACAAAACTCTGCCTGCTTCTGCCTCCTGAGTGTTGAG

ATTAAAGTTGTATGTCACCACACCTGCCCCTATGATTTCTATATTTAATA

AAGATCATGACTAGGATATAGAGAACACTTTTAGAACTGAAGAAGAAGAC

AGTTACAGTTAAAAGCAAAACAAAAACAAAAACAAAACAAAACCCAGAAA

AAAAAAGAATGAAAACTAGCACTGAAGAAAAAATAAATTTTAAAAATAGG

CAAAGAGTCACTATTATATTGTGATGGATGTGTTATATGTTTAAAACCAC

AAGTGAGATACAGGCCTGAAATGACTTTAATCGAAGCTACACCAGCCTGG

GGTGGTAGTTCAGTTGGTAAAGTTCTTGCTATGCAAGCACAAGAAGCTGG

GTTTGATGCCCAGGACCCATGCTGAAACCCAGGAGTGCTGCTGAGTGCTT

CAGCTCTGGGGTGGCAGGGCTCACTGGCAGGAAGCCTAGGCTAAGAGAGA

CTCTGTCTCGAAAAACAAGGCCGATGGCACCTGATGAACGGCATCTCAGC

ATGACCTTTGCTCGGCATATAATGTGTACACACAAATTCATAGTTTAGTA

GAAGACAAGTATGATCTGCTTTTTCATGAAGTCTGTTGTAATACGCCTTCT

TTAGTTAACCATAGTTGCTTAAAAAAAGAAAAAAATCGACCTCACTGGAC

AGAAAATGGATAGAGTGTTCTAATAGCCAATTCAATTCATCATCATTATC

AAAACCTATAACTTAGGGGGCTGGAGAGATGGCTCAGCGGGTAAGAGCAC

FIG.3D(44)

```
TGACTCCTCTTCTGAAGGTCCTGAGTTCAAATCCCAGCAACCAGATGGTG

GCTCACAACCATCCATAAAGAGATCTGATGCCCTCTTCTGGAGTGTCTGA

AGACAGCTACAGTGTACTTACATAAAATAAATAAATAAATCTTTAAAAAA

AAACACCTATAACTTAAACTTATCAATAACTTTAACTTTCCTACCCCATG

CTTCCTAGTTACCCATTCTGCTTTCTGTTTGTATGATCCTGGGTATGGCA

TCTTAATGGAACCACAGTGTTTGACTTTGTATCTACTTAATATTAGGCAT

GATGCCTCTGACTCTCATCCCTGATATAGCACAGTTCAAAATTGCCTTTC

TTTGGTGCTGTACATATAGCTGAGCGTTTGAGTGCTTCCCTGCATGCACA

GGTTTCTGAATTCAATCCCCAGCACAAAAAATGATAAAAAGAAAGCAAAA

AGGCTTATTTTTACAGCTGGACAGATCATCCTGCATTGTGCCTGTCATGT

TTTGCTTGTTTCTTCTGTCAGTGGACACTGTGTTACTTCTACCTTTTGGT

TGTTGTCAGGAATATTGTAAACATGAGTGAATATACACCCAGAAGTACAA

CTGGATGTGGTAATTCTATGAGTGTTTTGTTTTTTGAGGGATGGTTATTA

TTGTTTCCATACAATAAATTACATTTCCTTACAGTTCATTACATTTCCAA

AAGCCATGCATAGCATTTCTGTTGTTCTACATTCTTATTGACACCAGTTT

TCAATTTACATTTATTTTGTGAGTTTTTTAATTGGTAACCATCATAATGG

ACATAAAAAATAGCTCATTGTAGTTTTGGTATTTGTATTTCAGTAATGCT

TGGTGTGATTATCTTTTTATATTCTTATTAACCATTAGTGTGTATCTTTT

TTTGGAAAAACACCTCTTCAAGGGTTTTACTATGTAGCTCTGGCTGGCCT

GGAACTTGTGCAGACCAGGCTTGCCTCCGGTTCCCACTGTCTTAGGTAGG

TTTCCATTGCTGTGAAGAGGCACCATGACCAGAGCAACTCTTACGAAGGA
```

FIG.3D(45)

CATTTAATTGGGGCTGGCTTACAGTTTCAGAGGTTTAATCCATTATCATC

ATGGCAGGAAGCATGGCAGCATCCAGGCAGATGTGGTGCTGGAGGAGCCG

AGAGAGTTCTATATCTTGATTCAAAAATAGCCAGGAAAAGACTGTCTACA

GCAGGCAACCAGGAGGAGACTGTCTTCCATATTGGGCAGAACTTGAGCAC

TAGGAGTGTTCCAAAGCCACCTACACAGTGACACAGTACATCCAAAAAGG

CCACACCTATTCCAACAAGGCCACACCTCCTAATAGTTCTACTTCTCATG

GGCCAAGCATACTCAAACCACTACATCCACCTACTTCTGTCTCCCGAATG

CTGGGATTAAAGGCATATGTTGCCATTACCCAATTTTAAACCAGATTATT

ATTGTTTTTTTGTACAACAGACTTTTAAGGTTAAAGTTTGCAGCAATAGG

CATTCTTTGAAGCTGTATCACACTGATATATGTCTGTTGTTTTCTTCCTT

CCTAGATTAAAATAGTACAGTATATTCAAGTTTCAATTGTCCCTTTCCAT

AAGAAGTCCTGGTTTCTGTTCCATTATTAGTTTATATCTTAGTGTTCTTA

AGTAAAAATACTCAGTATTTATAGATGAGTTAGATTAGAGCCAAACCCCA

ATCAGGGTATTGGTAATGAAGGTTTGCTGGATAATTCAAAGGATACTGCA

AAGATCTGGTTTCTAATGGAAAGAACATGTAAGTTGGCCATTAGTGGACC

ACACATCTGTATTTCTTATTCTTTGGAACCTTGGGCAGGATAGACAGATG

AGCTAAGATTCCTTCATAGCTATTGAATTTGTGAGAAAAACAAATTGTGT

TTCCAGAAACCTGCTTTAGTTTGTATCAACACTTACTTTCTTTCTGTGTG

TGGTGTGTGTGATGTGCCTGTACCATTTTCAAGTTTTTCTTCCTTCTTTC

CATAGATACCCTTCTCATTGACTATCAGTTCACCTTTAGCCTGTCCCAGG

AAGACGACCGCTACTACACAGCCATCAACTTTGTGGCTACTCCTGATGAA

FIG.3D(46)

```
GTAAGCTTTTCTTTTAAGCTGTCTTATTTTGTGTTAAATTTTGTATAGGT

TTTTTTCTTGGTCATCCTGGACAAAAGTACTACATAGAAGCAGACAGTAT

CAGGGTGGGAATATAAAAGGCAACCAGTTTTTAAGTATTTTTTTATTTAC

TTGTTGACAGTTTTATATGATTATATAATGTGCTTGATGATATTCAACCT

GTGACCTTTTGTCTCCCTCATACTTAGTTCCTTCTCTCCCCACCAAGTCA

CCTTCACTCCCTCTCGTGTGTGTGTGTGTGTGTGTGTGTGTGTGTGTGTG

TGTGTGTGAGAGAGAGAGAGAGAGAGAGAGAGAGAGAGAGAGAGAGAGAA

AGACAGACAGACAGATAGACAGAGAGACAGAGATTGATTGATTGATTGAT

TGATTGATTGATTGATTGATTTACCTACCTAGTTTACCAGCTGACTGCAG

GAGCATGCTGGGTGGGAAGTTCTTACTGGAGCATAGACACATTACAGTGA

CTACACCACTGAAGAAAGTGACTCCCTCTCAGGTAGTCTTCACTGCCACT

AGGTCCTCAGGGATCAAGAGAATGTTTGGAGTCTACATTTTATCTTTTTT

CCACTCAGAAGGCAAACATTACTGAATGTTTTTAAGTAGTAGAATAATGT

TCATGATAGTCTGTTTAATATTAAATTAAGAATTTGTTCCTAATTATAAA

ATTTTTAGAAGATAGACAAGAAGACAAAATTTTTGAGTTAACAGTTTGAA

AGGTTTATTTTTATTTTATTTTATATGTATGAATATTTTAGCTTCTTGTA

TCCCTGTGCATCATGTGTGTGCAGTGCCTGTGGAGGCCAGAAATAGATAT

TGGATCCCTGGAACTAGAGTGATAGATCATTGTGAGCCATCATATGGGTG

CTAGAACCAACCCAGGGTCCTCTGCAAGAGCAGTGAGTGCTCTTAACTGC

TAGGCCATTTCTTTAGCCCCTAAATGTGAACAACTCTTTAAATAAATGTA

AGTGATCTTAAATACTCTGGAGAAAAATCTGTAGCTATACCTTACTTTTT
```

FIG.3D(47)

```
AAAAATTATTTTGTTTTATATTATGAGTGTTTTGCCTACATATATGTGTG

TCTGATGCCTGCAGAGGTCAGAAGAGGGTGTTGGATCCCCTAGAACTGGG

GTTACAGATGGCTGTGAGCAGCTATGTGGTGCCTGGGAGTTGAACCCTGG

TTCTCTGTTAGGGCAACAACTGCTTTTAACCATCAACCCATCTCTTTGGC

ACATGGGTGCATTGTTGGTTTGGCTGCTTGAGTTGTGTGTGAGGGGTGTG

TGTGCATACATATGTGGGTCCATGCTTATCCAGTGGAGGCCAGAGGTCAG

AGTCATGTATCTCTCTGTTACTTTCTACCTTATGTTTTGGAAGCAAGATT

AGATAGACCCCTGGGACCTTCCTGTCTTCTCCTCAGCACTAGGACTACAA

GTCCACACCTGACTTTTTACATGGGGCTTCAGATCTAACTCAGTCCCAAC

ACTTGTTTCATTTCCTTAGCACCTTGGCTAGATTCTTAGGATTTTAGAAG

GAGCTTATAGCAAAATACCACAAGTGAAATTTACTACTGCCTTAGTCATA

AGCAAATATTGAAGGCTCAGTCTTTAAGGGTATAATTGATAGTGTTCTTT

TTTTTTTTTAAGTAAACAAATAGCCTGTCATGGTAACTATCGCTGTAGTCC

CATTACTTGTGAGAGATGTCAGCTCAAGGCCAGCCTCCGCTACATAAGTA

AGGGAAGACCAGCCTGAGCTATATGGGACTCTATCAAAACAAATAAACAT

TGTAGAATTTTTGTAATACTTATTAGAAGGTAGCTGATGATCATGAGAGT

CTTTAGACATTTCTTCATTCCACTGTTTTGTGTGTGTGTGTTTCATGACA

GATTTCTTACTAGATTTATCTCTTTGTGTGTGTGTGTGTGTGTGTGTGTT

TTACAAAATGACAAAGATTTTAGTCCTTCTCGTGGAAAGTAGTTGCTAGT

GGTCAGCAGATACTTGCTAGTATAAATAAATGAGCATAGATCTGCGCTTG

CAAAGGAAGACAAAGGGAAAAAAGGTTTTCTTGAACATAATTCCTACTTT
```

FIG.3D(48)

```
GTGAAAGAAACTTCTCATTTGGAAATTACATTTTGAAAATAGGTATTGTG

AATGTTTCCATTGTGGTTTGTGGTATAACTATCAAATAACACTTTTTTAA

AAAGAAAAATCTTAATTTTCTAAGATTTTTAAATACCCTTTTAAAATGAG

CATTTCCAGCATGGTTTGATTAATTTGTAAAATGTAAGAATATAGTATCT

AAGGCTACAGAAATGACTCAGTGGTTAAGAGCACTGGCTGCTTTACAGAG

GACCCAGGTTCCATCCCCAGCACCCTCATGACAGTTCACAGCCATCTGTA

TTTCTAGTTCCAGGGCATCTGATGCCCTTCTCTGATTTTCTCCAGTACTA

GTGACACACAGCATACATTTGAACAAAACCACTGATACACATAAAATAAA

TTGTTTTCAAGAAACAATATAGCATCTAATTAGCTTACAAAACTAATTAT

TTGTTTCTGTACTAATTACGTTTCTATTGGCATGACTAAGGCAACTTATA

AGAGAAAGCATTTAATTTGGGGTTCACACTTCTAGTGCCTTAGATTCTAT

GAGCATCATGGTAGGGAGTGTGGCAGTAGGCAGGCAGGCATGGTGCTGGA

GCAGAGGCTGAGAGCTCACATTTGATTTTCTACTAGAAGACACAGAGAGA

GCTAACTGGAAAAGGCATGGGCTTTTCAAACCTCAAAGCCCCCCTCTAGG

AACACACACCTCCACCAAGGCCATACCTCCTAATCAAACAGTCCTACCAA

CTGAGGACTAACCATTCAGAGATAGATGAGTCTATGGAGGCCATTGTCAT

CCAAACCACCACAGGCCCCAAGAAAGATTTGTTAGTGAAATTTCAGTGAA

AACTAAAACAGCATTAGAATTTACCTGGCATAGCCAGCAATGATCTCTTC

TGTTCAGTGCCACAGATTTCTTTGAGTTAAAACTCAGTTGTTAAAACCAA

AAATCAAAATGTAATTGGCACTTTAAATTGCTATAAGGGGAAACAAGGTT

TTCAAAGCCATGAAACCATATTCAGAATAATTTTAGCGAGAGAAATATTT
```

FIG.3D(49)

```
TTTCTTTTTTTTGTCGTTTCTTTTTTTTCTTGGAGAGAAATATTTTTATT

ATTTTATATTATTTTAATTACATATTTAATTATTAACCATTTCTGACAGA

GGGCAAAAGGTGAGGATCTTCATGGAACTAATATCTGATAAAGCACCAAA

TTCTTCCCAACTCTGGGATGCAAATGACAGTTCAACTTCAGTTTATTGCT

TGTATTGAAGAAAATTGACAAGAAATGTCATGTCTTAACATAAGCATGGA

TTTCTTTTAAGATGTAGAATAGTCTATAATTAATGTTTTTGAGACTAGTA

AGACCTGATTATTGTTGTATCTTAAAATCTAGAAGGTACTAACAATTTTC

TAATGTGTATTTTTTTTTTTCATCAGCAAAACAGGGATTTGGACATGTTCA

TCAATGCCTCCAAAAACTTCAACCTCAACATCACCTGGGCCACCAGCTTC

CCAGGTACAGACACACCTAGAGAGATGGATTGGCAAGTTTAGTGTAGGAG

TTGGGGAAGGAGGCTCTGAAGGCTGGTGAGTGAGTTCAGAGCCCACCTCT

GCCTCTTAGTAGCCATGGCACCTTGAACAAGCCATGCTTGAACAAGCATG

TACAATTCCCTCTCTACCTTAGGCTACTCAGAGTGAGGAGTCACAGCTCT

TGCCTCCAGCGTTGCTGGTTCAGGTTGGTTGGATGGCTGCTCCCTGCTTT

GCCACCACCTTCCAGCACTATGACTATCTCTATGTTTGTGCTTCACAGGG

GAAAAACTAAAGTGACTCATAGTTTTAAGAAATGAAAACTCTTTAAGGGA

AGGGGGATAACTCTAATATGTAGAGGTATTCATACTTTGGGATAACTCCT

AAAAGTACAGCTTTTCCATTCTTGTTTATCTTATAGTGACTATAAAATTC

TGATGGCCCTAATGTAGCAGTTACTATAAATAACCACTCCATAACTTGAT

AGCCCTGAAGATAGACCTAGGTTTGAATTTACCTGCACGGTGTTGAACAA

GTTACTGAAGCTTTCTTTTCTTTGTTTTTTAAGTTTGTTTTATTTTATGT
```

FIG.3D(50)

```
GTGTGTTTGCCTTTGCCTGTATGTGTATAAGTGTACCATGTATGTGCAGT

GCTTGAGAAGGTCAGAAGAGGACATCAGCTCCCCACCCTCAACGAGTTAC

AGACAATTATGAACTACTATATCTGTGCTGGCAACAGAACCCAGGTCTTC

TGAAAGAGCAACCAGTGCTCTTAACTGCTGAGCCATCTCTCTCTAGCCCC

CAAGTTACCTAAACTTTCTGATCCAGTTTCCTTCTTTATAAAATGATACA

GTGAAAATAGCTTTGCTATGTACAGAGATATTCCAACTTTTTAATATTAC

AACATGACATCTACAAATATGTTAGCCCTCATTCATAATCTTGCCTGAAT

TGTAGAGTGTTGCAAGGAATAAATGAAATAAAGGAGGTACTTATTATAGA

GTTTGAGGTTTGCCTTCATGCATAAAGAGAAGCTTTTTTGAGTCTGTACT

ACTCATGTTCTTAGCCAATGGAGTATATAAAATATGGTAGAACCATTTAG

AAATGGAGTCTCACTGGGTACAGGCCTGAATGCAGTGGTAGCAGGTAGCA

GAAAGAAGGCCTGAGTGGCTGCTTGAGCACCTTCTCCATCAAGACTTGAG

GACCTTTCTGCTTAGGAAGTGATGAGCGAGTAAGTGTCCCTGAACAGGAG

CCTTGAGCATATTCTACAGTGTGAAGCAGAAATACAAAGGAGTTGAGGTA

TCATGTGCAAAATGAATGCAGTGTCTGTTTTATATGTATGATTGTTTTAC

ATACATGTATGTCTGTGCATCGCTTATATATCTGGAGCCTCTGAGACAGA

TTACTTAATCTATTGGGACTTGAGTTTTTCCAATCTGTAGATGGAGATAG

GAAGGTGTTGTGTGGGTTAGAGACTGAAGCTCATAAGGCTATATTCTTTT

GACACTGTAAGTGCTCAATAAACTTTTACCCTCATTACTAGTGCGCAAAG

ATTCTTTCTGATTGGCATACCCGCCTCCCAAGTCTTTATTTTTATTCTTG

CTTCTTTCTAGCCGGAACCCAGACTGGAGAAGAGGTGCCTGTTGTTTCAA
```

FIG.3D(51)

```
AAACCAACATCAAGGAATACAAAGATAGCTTCTCTAATGAGAAATTTGAT

TTTCGCAACCATCCAAACATCACTTTCTTTGTTTATGTCAGTAATTTCAC

TTGGCCCATCAAAATTCAGGTAAGAACTGCTTTTTAACTTCATTCCCGTA

AAGATGGTGACATCTCTTTAGTGGAGACTAACTTCACTCATTTGGAATCT

GTGGTGACTGAAAGATAGTGTTGCTTTGCCTTTGAGGGATCTTTGCCATA

GACTGAGTAGCAGGTGAGTGCTGTTCTTAGGTTGGAGAGATGTTCAGTGA

GTGGAGTGCTTGCTACACAAGCCTGAGGACATGCAGTTCATCTGCAGCCT

CTCATACAAAGCGGGACACGCAGGGTGTGCCTGTCACCTCAGCACTGGAC

ATGCAGTGTGTGCCTGTCACCCCAGCACAGGACACGCAGGGTGTGCCTGT

CACCTCAGCACTGGACATGCAGTGTGTGCCTGTCACCCCAGCACAGGACA

CGCAGTGTGTGCCTGTCACCCCAGCACTGGACACGCAGTGTGTGCCTGTC

ACCCCAGCACTGGGAAGCAGGGGACAGAAAGATCTTGCTTGCTGGCCAGC

CACTCAAAGCTGGATCTGTGAGTTCTAGATTCAGTTAGAGACCCTGTCTC

AAGTAAAATAAGGTAGAGAGGAATTGAGGAAGACACCTGATTACCTCTGG

CTTCTGTATGCATGTGCACATATATATACCTTCACACATATACACACTCA

GAGAAAAAATTCTGAGAGTGTCATATCACTTGTGAAGAAAGTTTTAAAGC

ACTTTTAAAAGCAAGATGAAAGCTATGCAAGGTATGCAAGGTAGTATACT

TTTGTAATCCCAGGATGTGGAAGACCAATGCAGGAGGATCACCCTGAGTT

TGAGGCCATAGGAAGACCCTGCCTCAAAAGGAGGGAAGGAGGGAGGGAGG

GAGAGAGAGAAAGAGAAAGAGAAAGAGAGAGAGAAAGAGAAAGAGAAAAA

GAAAGAAAGAAAGAAAGAAGGAAGGAAGGAGAAAGAAAATCAAATTGATT
```

FIG.3D(52)

```
GGCATATAGTTATGTGTTTATTTTTTGAGTAATTGCTATGTAAAAGCCTT

TAGAAATACACAGTTTTAATTATGGAATTGAGTATAAATAAAACAAGTAC

ATGTTTGTAACCAATAAAGTATAAAAATGACACATAAGATGTCAAAGTGG

TATGATGGCTATAATGTGGAGTCCATAGAGGAAGCAGTAGGCAGTATGAG

GTACTGTGTAAAAACACATAGCTTTACTATTGCACAGACAAGTGTGGATT

CTTGTTCTGTGTGTGGTTCATGGAGGCTCTCCAGTTTGCAGATTCTCTGT

GCATGTGTCCTGAAGGATTGGTCTTCCTGCTATGACCTCTGGTGTTATTA

GCCTGAACTGAGTCCTAAGGAGACAGGTAGTGGAAATGTTTGTATTGCAA

AGACAGTATGGGTAGTTGTTTTTAGAAACAGGAGTTCAACAGAATTGATA

GAACTTGTGATCAAGAAGCTAACAGCTGGACTGGGATGTAGCTCAGTTGA

AAGAACGCTTGTCTAACATTAAGAAGCCCTGGGTACCATCACTACCACAG

CATAAACTGAGAGTAGTGACAGACTCATGTGTCCCAGCACTGGGAAGGTA

GAGGTAGGAGGATCAGAGGCTGCCCAGGGAGGTTGAGAGTGACTTACGCT

AGGAGATAGATCTAAAAATGAAAAGGAAAAAGAACTTGGTAGCTGCTAGA

GCTACCATGAAGAGAGTGGAGCTTAAGGATTCAGCTGAAGAATGTAAACT

GCCTTCTGATGACAACTGAGAGTCGCTGAGTTATTTAAAGTCAGGAAGTG

AACAAAGATCAGTGTTTCAGAAAGACCTCTGTGGCAACAGTATTGACTAG

AAGTAGCCCCTCCTATGTCAGGTACTGGTTTAGACTGTATTTGGAAGTGT

CCTCTTTCTTGATGGCCCTCAGACACCTTTCATGGCCACTCCTCTGCATT

TGTACCCCATAGCCACACACTTGATGGTTCTTTATTACATAAATAGCTCC

TTATAGGCAATGATAGATTTTATATTTTTGATAATTTTAAGATAAACTCT
```

FIG.3D(53)

```
ATGTCATTGCATAGAATTTAGTAGTTGTAGGTACTCAGTAAATGTATATA

GGATGAATACAAAAGCTTTAGGGTAACAGTATTTTGTTCTTCTTCCCCCG

CATTTTTAACTATCTCATAGTAGCACAGACTAACCCATAACTGACCATGA

AGCCAAGGATGACCTTGAACTCCTGTACCTTCTACCTCTTCCCCGAAAGT

GCTGAAGTTACTGGCATGTGCTGCTCACCCAACTAATAGCAAGTTTTTCT

TATAAAGGTGCTGATGCCCTTTCCCTGTTTGTGTTAATTGCTGACACTTA

AAAGCTCTTTATCCCAACCCACAGTGTTAAAGAGTTTAGTTAAATTTTGT

GGAAATTTTGTCCCAAATGAAGTGGTTGATGGCAGGCCTGGTGGCTCCTT

CCTATAATTCCAACACTCAGGAGACAGAGTCAGGACGATGGCCAAGAATT

CAAGGCCTTGGGCCTACAGAGTAGAAGAGAGAAGAATGAGGATTCGAACA

CCTGATTAAATAGATACCATTTCCTGCTACCAACCTGTGCCTTAGCTACT

CTTCTATTGCCGTGACAAAACATCATACCCAAGGCAGCTTATAAAAGAAA

GCATTTATTAGGACTCACAGTTTCAAGGGTTATACTCCAAAACCATCATG

GCCGGGAGCAGGCAGCAGGCAGGAACATCTGCTGTGAGGAAGAGCTGAGA

GCTCACTTCTTTATCCACAAATAGGAGGCAGAGAGAAAGCTAACTAGGAA

TAGAATGAGCTTTGCAGACCTCAAAGCCCACCTCCTTCCCAAACATTTCC

ACCAATTGGGAACTAAGTATTCTAATCTGTGAGCCTCTGGAGGCCCATTC

TTATTTAAACTACCACACTTTATAAGTTAATACTACATGTGATGAGGAAA

CTGGTATGGGAATTCTGAAAAGTAGTTCACAGGAGTGGGAGGGGCTGAAC

GTGAGTAGATGCTAGCATGTGTGTCAGGAGTGAAGTGTTCAGAGCATTGC

CTGGTTTGACTTCTCTCCAGAGCTGAGGTGAACATGCTTTGTGCCAATAC
```

FIG.3D(54)

```
AAACCCGTATTAAAGCGGTGGTAGTTACTGAAAATCAGTGCAGGGCTGTG

GTCTCAACACAATGTTTGAAAAAGAAAACAGGGCATCCACATCAGGCAGT

GTACAGCTGCTTATAATTCCAGTCCTCTGGCCTCTGCTCACATGCACATA

CCCCCCCATACATACACACATGATTAAACATAATGAAAAATTAAAAATTA

ATGCTATAAAAATGGAAAGAGCCGGGCGTGGTGGTGCATGCCTTTAATCC

CAGCACTTGGGAGGCAGAGGCAGGCGGATTTCTGAGTTCGAGGCCAGCCT

GATCTACAGAGTGAGTTCCAGTACAGCTAGGGCTACACAGAGAAACCCTG

TCTCGAAAAACAAAAACAAAAACAAAAACAAAAAAAAAAGTGGAAAGAAA

GGTTCACTGTTTCACAGGAAAACTCTGAGAGGTGATAATCCAATCCCAGT

TTAAAATATACTCCATAGTGCACACAGCCTCTCCCATCCTTGGCAACTGA

GGCCTGTGAGAAGACTCAGTCCTCTCCTGGCTTCCAACCTTACAGTGTTC

AAAACTCTTCTGCAAGATCCACATGGTCCTACCAAGACCCTGAAGGTCAG

GCATGCTGATTAGGCTGTCTCTGGGCCTGAAGTGAAAGGTAAACACTTCC

GAGATCTCCAAAGCCTTGGGAAGATTCTGAAATGTATGGGTGTTGGTTCA

GGTAGACTCTCAGCCTTGGTGAAGCTGCCCCCGGAGCTGTAGGGTTATCT

GCAGAAAGTCAGCCAGGTGCACTTACCCTGGAATCCTCTCCCATTCACAG

ACACCTCCCTGAGGCTTTGTGGCTTCACCTCACTGTGCAGCTAGCTCCTG

TTTTACATGCTTATATAATGAATGGTCTTGGTAAAGAAGATGATAAAGGC

AAGCTAGAGGCCTTTTTTTTTCCCCTCTTCAAATTTTGATTGGCCTTTCCC

TACTGTTACACTGTCTACTCAAGGTTTTGAGCATTTACTTTGTGTACATA

GTAAAAGCAAAGTACATATTTTTAAGTAGAAAAGAAAGCATCTGTGGTCT
```

FIG.3D(55)

```
TTGATATAGGTGCTTTTCTTTATTTTAATAGTAATACTTATTCCATGCTT

GTTAAGAAATTCATTCACAGCGTGTTTTCATAGAGACTTTCTCTATAGAG

ATATATAGAAATCTAGACATGAGGACAGCCCACTAACCCACTCTTCAGAC

ACTAGCTGCTTCTCTTAGAGCCCTGGGCTCTCACCCTTTGGAGGACAGCC

ATCCTCACTCATATGTGACAAGCTTAGACACAGAATAATCACAGAGACTC

CAGCCTCCCCCACAAACCCACAATGCCAATATCCCATATTCCCAGGAACT

TTTAATAAGCCATCCACTCTAATACTCCATCTCTTATCTCAGGCATAGGC

CCTGGTTTTGGTTTGCTTCAGAGTACTGCCTTTTCTCTACCACGCCCTTC

CCACTCTTTGCTGACCCTCCAGAGATGTCATTTCCAAATGAAGGGGGTTT

TTGGTTCTGTGGGTGTTTTGTTTTTCAGTGCAGTTCCTTAACTGCTATTC

AGGGGACGGAGCAGGCAAACCAGATCTCTAACTTCTGAGGCCTGTGAAGA

GAAGCATCAGAACCTCCCAGGGGAGCTGTAGGAGCAGGAGTCAGGCCTAG

ATATGACTGTGAGAGAGTGGGGACCATTACCAGTGTCTTACAAATGAGGG

GAAGGACTACCGTGCTGGGCCCTGAAAGATAAGGAGGACCAGGCTTCAGG

AAGGTAGGACACATTCTGCTGACTGTCTGGGATTGAGGACAGTAACACAA

CTACTTAGACATACTTTGAATGAAGGACAGACTTAGTGCTTCAGAACTGT

AAATCCATTATATCTTTCCCAAGTCTTAGGCTAGCCAAGTTTCTCAACAT

TTATCTACCTCATCCCAAAGGGTTCCCAGGACAAATATTTCTTACTCAAA

CATTTGATGGGAGTTGGAATCAGGTTGAGGAAATGCAGGGGTGTAGATTT

TAGATTTCTGGGAATATGTATAGATAGCTACCTTCTGTTGGATAGAAAAT

GAGATTGTAAGTTTTTCAGTGTTTTTTTACACGAGTTTGTGTGCCCATGT
```

FIG.3D(56)

ATGCACATGTGGAGGCCACGGGTCTACCTTAGGTGTCTTCTTCAGGAACC

AGCCATCTTATTTTTAAGATGATCTCTCTCCAGACCTCAGGGCTATCAAC

ACACCTCAGGGATCCATCCTCCTGACTGTATGTCCCTAGCATTTGGGTTA

CTGTACCACCATGCTCAGGTCTTTGTGTAGGTCCTGGGGATCACAGTTAG

GTTCTCATACTGCAGGGCAAGCACTTTGTAAACAACTATCTCCCCTGCAT

ATGGAAGTATTACCACTAAATTACAACAAGATTTTCTTCTATTAAAATTA

TATTTTAGAAGCTGGATATAGTAATGCGTTGGGGCAAAAGGAGGGAGGGA

AATGAAGAGGATAGGAAGAGGGGGAGGGAGAAGGGAAAGAGTGGAGGCGG

GATCAGAAGTCCAATGTTATTCAAGGGCAGCCTGACCTAGATAAATCCCT

ATTAAAAAGTTTTCAGTATAGAAACTTCTCATCACCTTCATTATCAGAAA

AGCCCCTAAATTCAGAACACTTTTTAATCTTAATTAGTTGACAATTTCAT

AAATGTATTATTTATATATATGAATAACATTTTCCTCCTACCTTTTTTTC

CCTTCCCCTCTGATGATTCCCATCCTCCCAACCAAGCCCCCCTTCTGCAT

TTGTTTGTTGCTTTAATGACCCACTGAGTTCCATTGGGCTCACTTCCATG

AGTGTGACTAGAAGAGCTATTTATCAGAATGTGGGCAACTTACCAGTAGT

GACACTGATGAAGAAAGTGTTTCCCTCTTACCCAGTAACCATTAATGGCC

AGGAGCTCCTGGGAGGGGTGGGCGCCTTATGAGCCCCTTCTCCAAAATGC

TTTCAAACTGTGACCAGCTATATTTAATGTTTTTATTATGCCTGTGTATC

CATGTGGGACAAGAAAGCTTGAGAGTATCATAGCATGCATGTGGAGGTCA

AAGAACAACTGTGTAAAGTCAGATCTCACTTCCCACCTTCACATGGGCTC

TGGCACTGAACTCATGTCAGTGACCTGAGAGGCACTTTATCCTCTAACAC

FIG.3D(57)

```
GCACCCTGTGCCCAGCCTAAAATTTGACCTTTGCAAGGTTTAGTGTGTGT

TATCTGACTGTCTGAGTAAGGATGACAAAATGAAACCAAACTTATGGGAT

AAAGCTTGGTGGTTGTATCAGTACATTTTTATTGTTGTGATAAAACATTA

TGACCAAGACAGCTTATAGAAGAGTTTATTTGGGTGTATAGTTCCAGAGA

GGTAAGAGTCTGTCCTGACAAGGAAGCTGTGGCAGCAAGTGGCAGGTATG

GCTACAGGAGCAGGAAGCAGAAAGAGCAAACTAGAAACAGTTGAGGTTTT

TTAATAGGAAAGCCCACTCCCCTAATGATGTCCTTCCCCTAGCAGACCAC

AAGTCCTAACCCTCCCTACACAGCACCACCAGCTGGGGAGTTCAAATGTC

TGGGACTGCAGGGGACATCTCATTCAGACCACCTCAGTGGGAGAATGCTT

GCCTTCATAGTATGTGCAAGGCCCTAGGTTCAATTCTAGCCAAGAAAAGA

GAACATGAGGAAAGAAAAGAAGGTGGGAGAGAGTAGAGAAAGAAGAGAAG

AAGAGGAAAAAGGAAGGGAAGGGGGAGACAGAGGAAAGCAGGGAAGCAGA

GGAGAGGAGAAGAGAAAGAAAAGATTAACCAGCCTGGTTTTTAATAGCAC

CCCTCCCACTCTCAGTAGTTCCCAATTTGAGCATTAAGTTCAAGACTGAT

AGATATTTCTGGGTGGGTGACCAGTGTGGTCATAAACATGGTGACTTTTG

CTCTCCGTACAACTTGTGATTATGAACTTGTTAGATGATCAGCTTCAACA

GGAGAGGGCCTCCTTTAGTCTCAGGTGCCCCCTCCAGCCACCCTGGGACT

CGCAGCCTCTCTGTGATGAGACACAGGACATTAACTGGTATGGTTCTGCT

TTGCCAAAACGTCAGTCCATGGTTGAACTCTCCACAATGAGAAAGAAGCT

TTGAGAATCATTACATGGCATCAGGCAAGCCAGGACTGATGGAGCCTGAG

AAAGGGCCAGGAGCATCCGCAGGTTTTGGCACCCAGTACTAACTAGTAAA
```

FIG.3D(58)

```
AGCACCTCATAGGTTTCTTTAAAATGCAAACACTAAGGAAAATCTAACTT

TTTTTTATTTATTAAGGCCATTCATTTTATTTTATAAGTATTTTGCCTGT

ATACATATGTACCACATGCATACAAGGTCAAAAGATAGTATTGGGTCTTC

GAACTGGAGGTACAGATGATTGTGAGCTGCCATGTGGATCCTCGAAATTG

AACCTAGGTCGTCTACAAGAGCAGGAAGTGCTCTTAACTTCTGAGCCATC

TCTCCAGCTCCAGAAAAGCTACTCATAAAAGTCAAATCTAAGCCATGTGT

CTGGTGATGTACACCTTTAATTGTAGCACATGGAAGGCGGAAGTAGGCGG

ATTGTTATTCATCCAAGGCCAGTCTTCTCTTAACAGTGACAAAAACAAAA

CCAAACCCGAAACCTGTTACTTTGCACTTTAGAGTATAAGTGATAGAGAA

AAGACACAGAAATTTTAGAATCTATACCTTAAAATACCTTATGGCTTATA

TGATACTGTTGGGACCATATTTACTTATGGAATGCAAAAAAAAAAAAAAA

AAAAAAAGATGGGGGGGGAGCTGAAGGTCTCCTTTCTATTCTGTTGTAAA

TCTAGCTATAAAAAGAGTAAGAGGCATGAGTGTGTCTCAGTGGTAGAGCA

CCTGCTTAGCTTGTGTGGGATTGAATGATCCTCAGCACCACAGAAGAAGG

GTGGGGCAATAAATTTAGGAAAATAAGATGCTAATCATTGACTTTCTTGA

TTTTTTTAAAAAAAGTTATTATTTTATGTTTATTGTATATGTTTATATTT

TCTATGTGTGTTTTTTGATGTGTGCTGGAGGGATGGGGGCCACTTGCTGAA

CTTCCCAATTGTTATCATAACTACCATCTTTAGTGAAACAGTTACCATCT

ACTTAGTAATTGTTTCATTCGAATAGATACTGAACACTCTTAATCTGAAA

CTAATGCTCAGAAAGTTCCACTTTGCCAAGCAAGCAGGATAATGTAAGCC

TATAATTTTAGCACTGGGAGGGTGAGGCAGAATTGTGAGCTCAAGGGCAC
```

FIG.3D(59)

```
CCTGAGCTTTTGAGATCCTGTCTCAAATAAAATTAAATTATATAGATATC

AGATTTTCAGAATAGGTGTGTTCAGCTGCTGAATAAATCTAAGCAAATAT

CCCCAAAGAACCCTGAAATCTGAAACGTATTAGTTCTAAGCCCTATGTTG

TGTGTGTGTGTGTGTGTGTGTGTGTGTGTGTGTGTGTGTGTGTGTGTGTG

TAAGATAGATTCTCACTATGTAACCCTAGCTTGCCTGGATCTTGCTATAT

AGAGAGACCAGGCATATGCTATCGTGCCTGGGAGTCCCAAACGTTTTAGA

TGAAAGATTTCAGTTGTACCATTATCTTCCTAATGAGGGCTCTGGTCTAG

TGAGGCAGGTGACATTAGGCCAGTAGTAAGTATTAGGAATTGGTGATGAC

GGTCAATTCTGAGACACACAGTAGATACATCTAATCTACCAATACAACCA

ATGATTTAGAAAGAATTAGGCCATAGTTAAATTTGCAGTGTTTTTCTTCT

CCACAAAATAATGTTACTTCTTTCAGTTCTTAGTTCAAATACAGTAGGAA

TTTTTTATATTCTTGGTGCTAAACACTATTATTTTATAGTAAAGTTAGTA

AGATAGAAATGACGCCCTGTGGGTTGTCTGGTCGTAGTCTGTAGCTGAGG

CCATTTTGCTGAGAAGCAGCGTAGGCTGTCACTGGCTTTGTCACCCATAT

TTTCTGTATTTTTGCTGCAGATTGCCTTCTCCCAGCACAGCAACTTCATG

GACCTGGTACAGTTCTTCGTGACTTTCTTCAGGTAATTTCTCTATGCTAA

TTGTACACATTCCATCGAGACAGTCCCTTAACTGCAGCTTGCTTTGTATA

TCCCTACAAAGCTGCTTTTCACTCACAGTGATGTAAATTTAGTCTGATGT

GATAAAACTCTCCGTTTGTATGATTCGGCTCTTTGCATGGGGAGAGGTTT

GGGCTCAAGCAGTTATTAATAATATAGCTACTGCTGTGAGCTACATGTCT

TAATCTGTCTTAATCAAGATATGACTGTGATTTTCCATAGGGAAAGGTAA
```

FIG.3D(60)

```
GGTTTACTTGCAAACTCCTGGGGTTCTCCTTTTTTTATAGTTTTCTTATT

AGTAGGGTTTTTTTTTTTTTTTGAGAATACTATGCAGAAATGATTGAAAAG

AACAAATTAGTCATTGCATATTGGTAAGAGAAGCAGCAAGAGCCACCTCA

CCTCCCTCTGCTCTCCCCAAATAGAAACTGCTCTGCTGTGCTGCTTCTCT

ACCTTCACACCAATGCTCGGCCTGCCAACTCAGTTATCTTTCCTTTCCTT

TTAAGATAGGGTCTCTCCTTATAGTAGTTATGACTGTCCTGGAATTCTAA

ATAGAAGAGGTTGGCTTTCAAATCACAGATCCTCCTGCCTCTGCCTTCTG

AGTACTGGAAGTATGGTGTATGCCACCGTGCCACAGCTAACTCAGTTATT

TTTTGGTGTTCTATAACTGCCTTACATACATACAGACCAGGTACACACAA

AATTCCTTTCCATTAATTTAATAGTTATATCACAATGCATTGACCAACTA

AAAAATCCTAAATTGACTTATGATTCTACTTGCTCATGTTTTAAAGGAAA

GGTTACTCTTTGCTTATCTTAAATGTAATATTTTTCCTTTGCAGTTGCTG

TTTAAATTTTCCCTATAAGTCGACCCCAAATTTACATCTATAATCTGGCA

AAACAAAAGACCTCTAGTGATGGTTGTCTCTTAGCTTTAGTCTCTCTTG

GACTCCATTCCCTCCACCCATAATGTTCCATCCTCTGTCCTTAAGTGTAC

TAGTCTCCAAGGCCTGCTATGTGGTTGTCATTGTTGTAGTTACTTTTCTA

TGTTGTGACAAAGCACCCTGACAGTGGCAATTTAGAAAGCATATAATTTG

AGGATCACAGTTCCTGGTTAGAATCCATGACCATCTTAGCAAAGGCAGAC

AGGCAGGCCTGGCACTGAACAAGTAGCTGAGATCGTCCATCTGGTCCACA

AGCATAAGGCAGAGAAGCTAATTGGGAATGGCATGGGCTTTGGAAACCTC

AGAGTCCACTCTTAGTGATACCTCCTTATCCTTCCAAACAGTATTACACA
```

FIG.3D(61)

TTCAAACTTCAAATGTGTGAGCCTCTGGGGACCACTCTCATTTAAACCAC

CACAGTGATCTTGGCAACTTCTTTTGTGTTCGTCCCATGCCACAGTCTTT

CCATGTATTTCTCCTTTTGCTGGAACTTTTTCCCTCGAAGGTTCCTGAGG

AAAGAAACATAGATAACTTTTGTATGTACTTCTACAACTGAAAGTATCTT

AATTTTTGCCCTAACAAATTTTTGTTTGCTTACTTGCTTGCTTACTTGAT

TCTGCGTGCATGCATTTATTTGTTTGTTTGTTTGTTTGTTTGTTTGAGAC

AAGATCTCTCTTTGTAGTTCTGGCTGCCTCAAACTCAGAGAGATTCATCT

GCCTCTGCCTCCAGAATGCTGGGATAAAGGCATGCTCCACCATACCTAAT

CCAACCTCACAATTTTTTAAGTGTGTATTTATATGTGTGTGTGGTATATG

TAAAGGTGTGTGTGTTCATGCACACATGTGCAGAGATCAGAGGAGTCAGG

TTTTCTCATCTATCACTCTCTGCCTTATTATTTTGAGACAGGGTCTCTTG

TTCGATATTACATATACTAGGTGAGATAGCCCAGGAGCTTGTAGGAATTC

TCTCCCATTTCTACCTTCCAAATGTGTGCTACTGCATCTGGCTTTAAGCA

AGTTCTGGGAATCTGAGGTCAGGTCCTTACACCTATGTAGCAACTCTGCC

TACTGAGTCATCTTACTAGTATTCACAAGGTCAAAGGTTGGGACCAACAG

CCAAGGTTGTCCTCAGATCTCCACACAGATGTACCCACAATTATACAAAC

ACTCAACATAAACCTATTTACACACCCACATCACACGCACACACATACAT

GCACATACAAAAAAATGCTTTTTGAAAGAAGTAGAGAATGCTAGATATGG

TATTACACGTATATAATCCAAGCCACTCTGGAAGCTGAGGCAGGAGGATT

TCAAGTTTGAAACCAGCTTGACCACATAATTATACCATGCCTCAAAAATT

GTATAGAGAATAAGAATGAATATGAATGAGACTAAAGTCATATCTCAGTT

FIG.3D(62)

```
ACTTTTCTATTGCTGTGGCAAAACACCATGACAAAGGTAATTTACAGAAG

AGATTATTGGGGCATATAGTTTCAGAGGGTGAGTCCATGACAATTATGAT

ATGGCACTGAAGTAATAGCTGAGAGCTTAAATCTGGTCCACAACATTAGG

CAGACAGAGAGCTAACTGGAAATAGCCATGAGATTTTGAAACCTCAAGCC

CCACTCCTAGTGATGTCCCACACCTCCTAATCCTTCCCAAACAGTTCCAT

CAGCTGGGAACAAGATATTCAACATATAAGCCTATGGGGGTCATTCTCAT

TCAAACCACCAGTAGTAATTATTAGAGCCCAGCAAAGAAGGAAGGGATAG

AAAGAAATGATTGATGGGAACTGGGGTGAAGTCTGATACAGAGAGATCTT

TATGTACTGCAGCGTAGCTCAGGAAGATAACTATGGTTAAGGACAATTAG

CTAAGTGATTAGTAGAGAGGATTTTAATATTTCCAATACAAAGAAATGCT

GCAGGCCTGAAATAGGGTACGTTTCAGTGACCCAGATCTGATTATTACAA

CTCATACACTTGTACCAACCACATAAATATGTACAATAATTGTGTCAGTT

TTATATTAAATAAAAATGTGGAGCAAGTTAAAAAATGCCTGTTTTAAACT

GATCACAGTTATATGCCAGCTTTTCTTTGCTGTGACAAAATACCATAGGG

AGTAGTTTATAAGGAAAGAGATTTCCTCCAGCTCATAATTCCAGAATTTT

CAGTCTAGAGTCAGTTAGTTCTATCATATTGGGCCCACAGCTAGACCAAA

TACAATGATGGGGAGAATGTGGTAAAGAAAAGTATTTACCTCAGAGTGGT

CAGGAGGAACACAAGACAAAATATACATTTCAGTCCCATACCTCCAGTGA

CTTGCTTCATCCAAACAGACGCCACCATCCAATAGCCATTAAAATACAAG

TCAACCAGTTGATTGACATCCATTGATCTTAGTCATATCCCTAAATTCAA

CCTCTAAGCTCTGATGCTCTGGGGGCCAAGCCTCTATTGCATAAATCTCT
```

FIG.3D(63)

```
GGAGCATATTTCATAATATGAAATATTAAACAGGTCTCTCAGGAGCTGTT

TGGTAGACTTAGTTGTTTTTTTTTTTTTTTTGTTTAAGGTTTTTTTGGTT

GGGTTTTGTTTTGTTTTGTTTTGTTTTGTTTGTTTGTTTGTTTTTT

TTCGAGACCGGGTTTCTCTGTATAGCCCTGGCGGTCCTGGAACTCACTTG

TAGACCAGGCTGGCCTCGGACTCAGAAATTTACCTGCCTCCTCCTCCCAA

GTGCTGGGATTAAAGGTGTGCGACACCACTGCCTGGCCTAGACTTATTTT

TTTAATCAGATTTGAGTCTTTGCCTCTGGAATCACAGTAGCTTTTCCCAT

TCAACACCTAGTTTACAGAAGAAAGAAAACCCAATTTTTTTTTTTATAAT

CATTAGACAACTAGAAGTTTTCCCTCCTATTAAGAAAACATATTAACGGG

CTGGCGAGATGGCTCAGTGGGTAAGAGCACCCGACTGCTCTTCCCAAGGT

CCAGAGTTCAAATCCCAGCAACCACATGGTGGCTCACAACCATCCGTAAC

GAGATCTGACTCCCTCTTCTGGAGTGTCTGAAGACAGCTACAGTGTACTT

ACATATAATCAATAAATAAATCTTTTTAAAAAAAAAAAAAAAAGAAAAAGA

AAAAGAAAACATATTAACAGTATTGAGAAAACTGTTGGCTTAAATTTGAT

GATTTGAATTTTATTTTACTAATAAATGCATGTATTGCTGGGCATGGCAG

CACATCCCAGCACTCAGGATTCCGAGATAAGAGATCATAAGTCCACGCTA

GCTGGAATAGCAAAATAAAATCTTTTTTTAAAAAATATACATACATACAT

ACATACATACATACATACATACACACACACACACTTTTCTCAGT

AGTACGGCCAATTAGTTGACTTGTCTAACGGAGGGAGGAAGAGGAGGCAG

AGAGCATGCTGTTCAGATCACGTTCTCTTTTGCATTCAGTCTGGGACCCC

AGCCCATAGTGTGGTGCTGCCCACATTGATTATTGGTATTCAGTTAACCC
```

FIG.3D(64)

```
AGTGTAGAAACTCTCTCAGAGACATGCCCAGATGCTTGCCTCATAACCAC

TGTGTATGTATATATGCTTACAGAAAATATACTCATCATTACACATAAAT

TTCATCCACTTACCTCTTATGAAAAGTTGATTATTTACTGAGATTTTTCT

CATTCTGAAAATCCATAAAGTCTACCACATTGATTAAATTACTTGTTTTT

TACCTGTTATTGCTCATGTTAGAATTGCTTTCCTTATTTGGGGTAAGCTG

TCGTTGGCCACTGTGAGGGGCTTATCAAGAAGTCAGAAATGGGAACACCT

TCTAGGAAGTCAGGACTGGAAGCTTAGCTGAGCCAGCAAGTGTTTCTCAC

ACTGCACTTCCTGTGAGCCTACCTGTGCGGCATCAGGAACTGGAGTTGGG

ACCTTGAGGATTGTTCCCTGGAGGCAGGGGTGGAGTCAGGCAGGGGTGAA

GCTGACTCACAAGATGGTCTTGCCTTTCAGTTGTTTCCTCTCGCTGCTTC

TGGTGGCTGCAGTGGTCTGGAAGATCAAGCAGAGCTGTTGGGCATCCAGG

CGGAGAGAGGTAAGCCCAAGTAGACAAACTCCACATAAAACTCATTTTTT

TCCTTCTTTCTAGGCAGATCACTTTTACCTGTTGAGTGATGACTAATATT

CATATGAGAAGCATGCTGTTTAACCTGCATTCTGTGGTTCCACTATGTGC

CATCAGTAGATTTTAATTATTCTTGCATAAAGTGTCATTAGTTTTGCCAC

TGCTTGATTCAAGTCTTCCTAAGAGTCTTTCCTAAGAATATGAGTGTAGA

GACAAGTTCAGCTCAGTGACAGAGCACTTGCCTGGCATAAACTGAGTCCC

TGGATTCTAGTCTCAGCACCCTCTAATAGCACAACACTAGAGACAAAGCT

TCTAACCTGTGGGTCTTGGGCAGCAGGTAGGGGAGGGGGATTTAAAAAAC

AAAAACAAACCTCTAGCTGTAGCCTGTGTCATTTGTTATGACTAAGCACT

AGAGTGGGTACTAGTAGACATGCCATGTGGACATTGAGCACCTCTCCATC
```

FIG.3D(65)

```
CCAGGCACTGATCCAGGTGGTTCTGCTTTATCTTCATCTCCACCCTAGGA

TATAAGGGAGGCTACGTAACTACCCATCACCACACAGATGCTGAGGTACA

GAACTGAGGGGTAACTAGTGCCTCTGCCTTCACAGCACAGGTTCCTAAAC

ACGTTTTCTACAAACACTTCATTTGTTCTAGTCTGTTCATTTAAGAATCT

CATGTTCTGACTGAATGAGCTAGACAACTCACCCTAGACTATACATTCTA

AAGAAGGGCAACAAGGCAGTTTTGTTACTGTTGAGAAGAAAACAAAGTTA

TTTCCGTATGAGTTATTGAGATAGAATAGTAGAGATTTGTCTGAATACAA

AATAGAAAGTATATAAAAGTATATAAGTGGATCATAAAGAAAGCAACAAT

CAACTGGAAAATATTTGCAGTATCATGAGAGAGAGAAAACTAGAAGATGA

ACCCCCTCAAAAAAGGATTTTTAAAATATGCTTAGACTGTATTCAGTCAG

CTAATAAACTTTTTTTACCTTTATTTGGAATTTACGAATAGCACTGAACC

TGACCATTGTAAATGCACGAGGTCAGGCATGACTTGTTCCCAGTAGGAAG

TTGTTTTTAGTTCTTGCTGTGGCCTGGGTCCTGATGGAAGTTCTTTACCC

ACCTTATCTCCTGTCCTCTTGGCAGAGGTTCTAGAATAGTGCTGTGATGG

GGTAGCAACTGTCTTCCTGTGACCCTGCACCTAGATTATTACAGAACCCA

GACTGGGTTTGCTGAGTTAATGGAAATTCTTTCTAGGTTCAGTAGAGAGA

TGTGCTGACACATACTAGGCCATCTAGTTTTTCAGTAATGCTCAGAGACC

GCAATAGGATATGTAACAGCAACAAAATTTTTAACATAAAATTTCCCTTC

TAAAACAGAGTGATGATTTATGTAGCTTCAGGATCCTGCCTCCTAGAAGA

TGGTTTGAAGCAAGGCCAGTTTGTCTTCCCTAGCATAACCTCAGAAGACC

TCTCATATTATTGATGGTATAGGAATGAATGCCCACATTCTGTATTTGAG
```

FIG.3D(66)

```
ATGTGTGCTATAGTATCTCATCTGACCCAACATGAAAACATTTCAAGCCA

TGTGTGCTTGGGTAAGGTAGGAGTTCAAAGTCATCCAGTGAGTTCAAGGC

CAGCCTGGGCTGCATGAGACACTGTCTCATAAACAGACACTTGAATCTCA

TTTAAAGAAGACATTGAAGACTTGATACTTTGAACACCTATCCTAACGTA

TCCACCCCCAAATCCAGAGTCCTTCATGTTCTTGTCCTCTGCAGTTCCAC

TTTCATTGTGTTCTCAGCAGCAGCTCTCTCCGAGGAGAGTTGTCTCCCAT

CCTATCAGCCATCTTTTTTATTGTTGTTGCTCTGACAATGTCTGGTTCAG

GTTTTAACACAAAGCAAGCTAGAGTGATTTTAATCTAGCAACAAAAATAT

AAAAAGGTAAGTTTTTGCCCTTTTATATATTCAATCAACAGATATCATAG

CATTATATCCTCCACTTTAACTTTTATTTCTTACTGGTAAGGGCTTTTTA

TAAAAATATAATAGTGTTACCACATGTAACAAAATTTGATACCTTGTGCT

ACCTAGCACCTTGTCATGTCCAGTTTTCCTCAGCTGTCACAGAAGCGACA

CTGCATCTGATCAGTTTGAATCAGAGAGAGTGTAGCATGTCTAATATCTA

GTATTCACTAATAAAATCTCAGTACTAAGCATATTAATAATACTATATTA

TTCATTAGCAACTTCTTCGGGAGATGCAACAGATGGCCAGCCGCCCCTTT

GCTTCTGTAAACGTTGCCTTGGAAACAGATGAAGAACCTCCTGATCTCAT

TGGGGGAAGTATAAAGGTGAGAAGTGGCTCAAAGGTCCATATAGCTTTTC

AGAACTCAGGCCTCAGTTTGCTAGGCTACAGACAGCAAGCGCTCTGTGTG

TCACTCCTGTCTCCTCTCTAACAGTTAGTCAGCAGAAGCAACCCCGAGCG

ACCGTAAGGGGCTCTGTGTGTGGCTTTACTTTTCGAGTTGTTGCATGTCA

GATTTTAACATGCAAATTAAGCTTGTTATTCTTACTTTGTGGCATAATAC
```

FIG.3D(67)

```
TTTATAGTTTTTATTTGGAAATATCTAATCTGGGCTAGGTGTGATGGTGC

ACATCTTTAATCTCAGTTCAGAGGAGGCAGAGACAGAGGCAGGCAGGATC

TCCTTGAGTTCTAGAACAGCTGGTCTACATAATGAGACCCTATATGTTAG

AAAAAAAGAAAGAGGGGGTGGGGGAAGGCAGCTAACTTTAACCATTAATT

GAACCAACACACACATTTTGTTCAGAGCCCCAGTACTCAATTAAAAGC

CAGGCAGGCATGGTAACAGTACTTAGGGAGTCAGAAACAGGATTCCCAGA

GTAAGCAGTCTGACTAGGCTAGCAGGAAATGGTGAGTTTCAGGTTCAGCA

AGAGGCCCTGCCTCAGTAAGTAAATTGAAGAACAACTGAGGGAGACTTGC

ATGTGCACTTGTGCATGCACCCACACATGCACTTGCACACATACCATATG

TCACCATGCTTAGACTATAAAATGTAGTCACTACTGGCAGCACATGCCTA

CAATACAGATGCAGGAGAATCACTGCAAATTTGAGATCAGCCTGGGCTAC

TGGACAAGATTTTGTCTCAAGAAAACTAAAACAATACAAAAGTGTACTGG

GGGGGTTATTCTAATGCCAGTGTTTATGACAGCACATTCAGAACTGACAG

TAAAGGCAATCAAGGACTGTCAGTGGTGGGTATATACATAGGCAGAGGAG

CAACTGCTACTAGAAACTGTTTATCCTTTAAAAGACTAATGTATGCTGCA

GCATAGACAAACGTTAAGTTGTGTTAAGTAAAAGATGCTGTATCATTCCA

CTTACCCATCGAGAATAATCAAATACAAGACAGAGTAAAATAGTGACTGC

TAGAGGCTTAAAAGAAAAGACCAGGGGGTGGGGAAAGGGAGGGAAGGAAG

TGGGAGAGGGAGGAAGGGAGAGAGGGAGGGAGGGAGCCAGACTTTGTGGC

TTACAGCATCAAGAGGCTGAGGCAGAAGGGTTACAAATTCAAGGCCCTAC

TGGGCTACATAGTGAGAAGTAGGATTTCCTTGAGCTGTCTTTCTAGGTCA
```

FIG.3D(68)

```
TAATCTCTCATTGGGGGAAGTCAGGGCAGGGACTTGAGGCAGAAACCATG

GGGAATGCTATTTGCTGGCTCCTTCCCAGGCTCCTCTCTAGCTTTGTTTT

CTCATTTTGTTTTTACTGTCTATGGGTGTTTTACCTGCTTGTTTTTCTGT

GTACCATATACATGCCTGCTACCCACAGAGGCACTGATGCCTGGAACTGG

AGTTACAGATGGTTGCAGGCTGCCCTGTGAGTGCTGGGAACTAAACTCGG

GTCCTCTACATGAGCAAGTGTTCTTAACCATTGAGCCATCTCTCCAGCCT

ATAAAATTCTTTTTTAAAAATAAAGTCTGCAACAGAAAATGAATATTTTC

TAGAGCTGAAGCATTCAATGAGTGGATAAAGAATCCATTTGATGAGCTAT

CTACCTTTCACAAGCTCTTAACCCCTACAGACTCAGGACTTAGTGGCTGG

AAGATGAATGTAAAACAGGTAGCTCTCTCCATAATATCTGGTCTGTTTGT

GCCAGGTGTGCAGAACTGTGCAACAGGTCACCATACAAACCGGCGTGGGC

CTTTCCTGACACTCACACAGCTCTCGGGACAGTGCCCGTGGGGACCTCTT

ATTGACCTTATAAGCACCTGACTGTGCAGTGTAGCAGGGAGTTAAGGTGC

TTCTGTTTTCTTCCTCCAGACCGTTCCTAAGCCCATTGCCCTGGAGCCCT

GCTTTGGTAACAAAGCCGCAGTCCTCTCTGTATTCGTGAGGCTCCCTCGA

GGACTGGGAGGAATCCCTCCTCCTGGTCAGTCAGGTGAGTAGACAGGAGA

CAATGACAGATATTGGTCTGTGAAGGACTGAGTCTTAGACACTTCTTCTG

GTATAGAACCTGGGTCTGGGCACAGTGCTTAGTGGTACAGAGCTTTGGTG

GAACAATTCTATAGTCCCCAAACTGTGTTCTGAGCACTGACATTCCTGTC

CTGGGGTGGAAGTTCAGGACCTTCCTCACGGTGCACAGCGTCCTCAGACA

TTCATGCTCTGGTCCCCTTGACTCTATTGATCCCTGCTTTCTTTTTTTTT
```

FIG.3D(69)

```
TTAACCCCTTGTTCTTATCTCAAATTTAGGCTTTTTCTTCCTTGATACAA

GCTCCTATTCATCTCCATGCCTCTGGCTTCCAGCCATGTCCTCAAAGCTT

GTGTTGCCAAGTACAGAGTTCTAGTCATGCTCCACATCTTCTTAAGGTCT

TGCTATGCAGCCTTAGCTGGACGAGTGCTCGTTATAGGCCAGGCAGTGGT

GGTACACGCCTTATGTCCTAGCACTGAGGAGGCAGAGGCAGGCAGATCTC

TGAGTTCAAGACCACCCTGGTCTACAGAGTAAATTCCAGGACAACCAGAG

CTACATAGGGAAACCCTGTCTCAAAAAAATAAAAACAACAACAGGAACAA

CCCCAAAAACTCATTATATTGCCCAGGCTGGCTTCAAACTCATAGTTATC

CTCCTACTTCAGCCTCCAAAGTGCTGGGATTATGGGTGTGACCCTTCATG

CCCAGATTGTCTTAAATATGAGGCATGAAGAAGTATTATGAAAACATAAA

GGATATTTTGAAAATTATAATTCTACTGGGTTAATGCAGATCCATTTTCA

TTTCATTGAAATAATGATACAGCCTTTGGAGGTTAGGGGAGCCTCTCCTG

TTTTCAAACTGACTTTGAACTTCTGATCATCCCGCCACCACCGCCACCTC

CTCCTCCTCCTCCTCCCCAGTGCTGAGATACATCACTACTCCTGGTT

TATGTGGCACAGAGGCTCAAACCCAGGGCCTCATGCATGCTAGGCAGACA

CTCTACCAGCCAACCTACCCACAGCTCCTAGATGTGCACCGTATTACAAA

CATTTATTCTTCAGCATGTTTTTTTTTTTTTTCCTAAAAATCATCTCTA

CAGGAAACAAGTACCAGTGGTGTTTTAGGGCAGGAATAGGAAGAAAATAT

TTTTACTATATACTCTTTTTTTTTTAATCATTTTTTAGATTTTATTTATTT

TAAAATTTATTTACTATTATTAATAAGTACACTGTAGCTGTCTTCAGACA

ACCCAGCAGAGGGCATCAGATCTCATTACGGATGGTTGTGAGCCACCACG
```

FIG.3D(70)

```
TAGTTGCTGGGATTTGAACTCAGGACCTTTGGAAGAGCAGTCAGTGCTCT

TAACTGGTGAGCCATCTCTCCAGCCCCTACTATATACTCTTTTAAATGAC

TTATTTGCTTTTATTTTTATGTGCATTGGTAATCTGCCTGCATGTATGTC

TCTGAGAGAGGATCAGATTCCTTGGAATTTGAGTTACCTTGTGGGTGCTG

GGAATTGAACCCAGGTCCTCTGGAAGAACAGCCAGTGCTCATAACTGCTG

AGCCGTCTCTGCAGCCCCTACTATATACTTTTTTTATAGTTTTGAATTTT

TTTTTCTTTTTGGGTATTGCTAAGGATCAAATATAGATCTACTATTTATT

TTTTATAACATCCATTAGTATTTTTATAACTTACTACATAGTTTGCCAAT

TCTTTTATACATGTCCATCAAACATGTAAGTCATAATTTATATAAACCTT

GTGTTAAAGCTGGAGGCACAGAAGGAAGATTGCTACAGAGTGAAGTCTAG

ACTAGCCAGGGCTATATAGTGGGACCCTGTTGCAAAGAAAAAGTTCTCTC

TTTAAACACAAAGGCAGTATGAAAAGACATACCTTGATTCTGAAGCTGTG

CATAGGAATGCCTCACACAGTGTTCTGCTCAGGACTATACTCAGATGCAG

TGGTCTGAGGGACTTGGTGGTGTCTCAGCCAAAATAACCTGGAGTTTAGT

AGGAAAGTCTCCTTTATCCGTGTCCAGTCCTGAAGGGAAGCCTTATTTAT

GTATGATGAGTCAGGACCCATTGTCTTCATCTTACTTGGCATCCCCCCAG

CACTGAGTCTCTGAGTTAGCCTTACTTGGACAGAGTGACTCTCTGGGCAC

TCTGGACAGCATCTCCTGCTTCAAAAGGGCAAGATCTTTAGAAGACACAG

AGATGGAGCAGGTCTTACATGGAGATATAGCAGCTTTTCCTTCCTGACCC

TTGACCCAATGCTTCTTTGGAAATCCTCATGAAACCCTGCTCCTTTCTGG

AGACCCACCCCACAGCAGGGTTATCCATGCCAAGCTTCCTGTACTTTCTC
```

FIG.3D(71)

TTTTTGAGGAAGCACATACACACAAAGTTTTAGTAGCTCGCACATCTCAC

TGTGAAGTAGTGATACTTTCATTGCTATCTTCTGGAAACAGGCAGGAGTA

GGCACACGCTCAGAGCATAGCTGCACTCTCATTCACTTGCCACCCTGAGG

CAGAGCACACGACTTTGTGATCTGCTATGGAGGAGAGAGAAATGAGTAGT

TAGGTGTGTATAAATAAGCTAACACCATCACCCCTTTATCTTTCACTAGG

GAAATGTAAAAGAAATCTGAAATTATTTTGTAAAAAAGTAAGCTGCTTC

ATGACACATGTCCCCTCTTGTGGGTTCTTCCAAGGTCTCGCTGTGGCCAG

TGCCCTGGTGGACATTTCTCAGCAGATGCCAATAGTGTACAAGGAGAAGT

CAGGAGCTGTAAGAAACCGGAAGCAGCAGCCGCCTGCACAGCCTGGAACC

TGCATTTGATACTGGGGCAGGAATTCGCCCTCACAGAGGGCGTGTGGTCC

ACGAAGCTGTCTACAGGGGAGGCTGCAGGCAGGAAGCAGGCGTGGGGCAG

AAGACTGGGGACCCTTGAAGCGTCCAACTCATGTGCATGATCATGCAAGC

TGTTTTCATGGCTCACCCCTCTGTGTCCAGCATCTAACCTTTTACTTCTG

TGTAGGAAATAATTTAATTACAAGTCCAGGAATGGTCTGCTCTACTCATG

GGTGGAGGAGACCAGTGCCGACCCCGTGAGAGCTGAAGGTGATGCTGAGG

TCCCTTGTGGAAGCCTCTCTTGGGAATCTCAACTGCAGAGGAGCTGCCCT

CTGTCAGCAGCTCTCCAGCATGGTCCTCTGACACTCCTCAGATGAACTGT

TCTCATCGGAAGCTTGCTGTCTTTTTACAAGATGAGCTTTTACTCTCTTC

CAGGAAGTAGCTTTTTTTTCTAGCTGAGAATTAATAATGGTCTTTCTCTTT

GGAAGTCATATCAAAGTATAATTGATGGGGGCCTTGTTTTGTTTTGTTTT

GGTTTTTGGAGACAGGGTCTCACTGTGTAGTCCTAGCTGGCCTGGAACTC

FIG.3D(72)

ACTATGTAGATCAGGCTGGACTGAACTCACAAAGATCCACCTGCCTCTGC

CTCACAAATGCTGGGATAAAAAGCATGAACCACCAGGCCCAGCAAAGAGG

GCTATTCTAAATGTCAAGGTCAATGGAGTTAGAATATATATAAAAAAATG

CAATTGATAATTCTCTATAGAAACTTGATTAATTTTAATCCATTCTTTCC

TTCTCTTTCTCTCACTCTGTCTTACACACATGCACACATACACACACACT

AAGTGCCTAGACTTTGAATAGATCTAGCAATTGGACATTAGTAAGCCTAA

GTTTTTACATGATTGCATTCCTACATTCTTGTAAACTTTAAGTAACTACC

ATTGCAGTTTGTTCTTTTTTTAAAGTCTAATTTGCAGCCAAGAACGAGTA

ATTCTCACCCCAAGCAACATCTAATAGGGACTGAGTGACCCCAGCCCAGC

CTAGTGTCACTTTAGGCCTGACGTTTGAGCAACCCTCGGCTCTTGCCAAG

GCACCACAGAATGCACTTGCTCATGCCCTGTGCCTCTTGAGCAGAAAAGA

GCACTGACAACTGGGACACCTGGCTCTGTCTTCCTACAGCTGCTCGCACT

GACCTGTGGGAACCTGTGGGTCATCCCCAGGCTGAATGGAGTACACACTA

GAAGAGGGATGATGCCTAGCATTGGGGCAGCATCTGCTCAGCACATGGAA

AGGGACCTGGTTCCATCTCCCCTGGGCAGGAGTTGGTCCAGCCTCCTCCC

AGACCCAGCTGGTGGCTGTGAGGAGGTGGGGAATGCTAATGAGAATGAAA

AGCACATGGGTTGATGGGAAGGGACAAGATTACCACGTTAGGAGGGTGAG

CAGCCCTCTGCTATGTGCCCAGGACCCTGCCTGGACATTGCATTTCCCCA

TTTATGGTGCTCCGTATTCTGGCATTATGCAGCAGCCTCACACACCTGTC

CTCTCCTTCTTCATGTCCTACAGTTCTGCTATCACCTGACTAGAATAGCC

CTCTAGGCAACAGTGCTCAAATGTATGAGTTTGGAGAAGTTAACAATCAG

FIG.3D(73)

```
AAGAACAAAAACTGTAGTGTTTCACCTTTAAATGCAGTGTTGAAGAGGGA

GCCTTTCTCTAAGCCCTGCACTAACCCACTCCTCCCAAGACTCTTGTGGA

GTGACAGTTCCAAGCTGAACCATAAATCACTGATGCACAAAACACTGCTA

GAAGGCTCACCTCTCAAAACACGACTCTTTGCATCACTATTAAAGAGCAG

AAAGTTCTAGAAATGATCCCAGCCTCATCCCCTATACAGTTAGGAGCTCC

CCACATCTCTACCAAAACCCAGCACATAAGTATCTGCGTGGTCTAGCCTT

TCATCTCCGTAACAAGCCAGGGGACTCTTGGCCAAAAGAAAGAAAGGGAA

GTTGCACTAGGGCTTGTCCGTCCATAAGGAATTCCCCTCTGCTTTGCTCA

AAGGACCAAATTTCTTTGGCCAAAGAAGTTGCTTCTATGTTAGTCCCATA

CCCTGAAGTAATATGTACCATGGCTCCCACCTACCTGTTTATGCTCTCCC

TGCCCCCAGGGAAACTGTTTATTCTTTCAAAAGAAGCAAACAGCGTTCAT

TTCTGCTCCTGTAATGGAGAAACAGCCAGCTCCCCTGCATCCCTTACAGC

CAACAGCTCCCTTCAGGCTTAGAGCAGGGGGAATGGCAGGGATTAAGAGC

TCAGCTCAGAGCCAGTTACCAAGATGGAATGGAGTTGTGACCCAGTAACT

GTGTCACGAGAGACCATGTATATAAAATAGTCATGACGACACTGACCTCT

TGCACTTGTACATAACTATACTGTAGTGTCCAGAATGTTCAGACATTCAG

GGTGTACATAAACAGAAGAGTATCATAATGTATTTTTATTAAACACTAAC

ATCTGAGTTTCACCTAATCTGTTTCTGTGCCATATACTGGGTATCCAAGC

TCTGGGAAGTTATCCTACCAGGCCCTGATCTGTTGATAAGGCACTATACA

CCATGCTGGTGTGTTCTGTAGCCTTGTGCCCATTAGGTAACTGAACAATG

ATTCAGCTCTTAGAATACCTAGGAAGACAGCAAGCAGGGTGACACACGGC
```

FIG.3D(74)

TGTGATCTAAGCATTCAGAAGACAGAGGCAGGAAGAAAATTCAAAAATGG

GGCTGGAGAGATGGCTCAGTGGTTAAAAGCACTGGCTGCTCTTGGTCAGG

ACACTAGTTCAGTTCCCAGTACCCACATGGTGGCTCACAACCTTCTGTGA

CTACAGTTCCAGATAACCTGACACCCTCCTCTGGCCTCCTCGGGTGCCTG

TGGTGGTCCACCTGGTGCACAGACAAACACCCAATACACACAAAACAAAA

GTAACTCAAGAATAGCCTGGGCTACATAGCAAGAGCCTGTCTCAAAACAA

ACGAACCTATGAAGAGCCAGGCAGTCTATCTATTTACATGGCAGTATACT

AGAGAAACTCAGGAAGCAAGAGTGTTCATCACTGTTGTAATTTCAAATGC

TCCTTGTGATTTCTGGCATCTCTGTGGGGTGAGGTGTTCTGTTACTCTTC

ACATTCAAAGACTGTCACCCATGAACGTCAGACTTTGCAAAGGGGCTCTC

TAAGCTGCACTGTTGTGGCTTTGTCTAAAATTTTAATGACGTTTCTGAGA

ACCATGTTCTTTTTATACTAAAATCTGGGGATGGGAGGGCTCATTTGTTG

ATAAATAGCACTATTTTCCCACACCTCAGCCTCCTGTCCCCGTCCTGGTC

TTCCCTACACAGTCTGGAGAGGGCTCTGAAAGGTCCACAGAGTTTGACAG

ACACGAAAGCAACCCATTGCCCCGTTGACCTGACCTGGAAGAAGACTGTC

AGCAAAAGGAAAATACCAGAATATCTGGAAAGCTTGAAGTGTAAGATGGG

ATCTCGTTGGGGAATTGGATGAAGAAAAGCAGAGCGCCTCTGGTAGGTGA

CTCTGCAGCCTGCCAGCGCCCGCCCTCTTTCTACACAGCAGAGTGTGCAT

GGCAAGGAAATGAGTCACCTCCTTGGGGGATGGTGCTGTTTTTATGAAAA

CCTCTGATCCTTGGTGTCCTTTAATTGATCTGTTCAACAAATATTTACTA

AACACTTCTAAGCTAACATTAGGGCAGTGACTGAGGTGGAAACCCAGCTC

FIG.3D(75)

```
TTTAGACAGCTGTCATCCTAGGATAGCTTCCTGGAAGCAGAACCAAGAAG

CCAGAAGGTTCTTCCTAGGGTGGCCTTGGCTCCCTGAAGGAATCTGAAAT

GCTGACCCTGTCACAACCTCCCAGCACAGCTTTGGAATGAGACATCAGCC

TGGCCTCCAGCAGAGCAGAGGCTCTGGAGCTCCACATCCTGCCTGCAGGG

AGCCCTCAGGGTGCCCTCCAGAGTACAGGGAGAAACTAAAGGCAATAACA

GAAGCTGCTCTCAGAGCCTGACTGTGCACAAAACACTAGTGAAGCCTGCT

GAACTAATTCTGCCTCTGGAAATCTTTTCTGGTTCTTTACAGTTTGTTGT

TTTGTTTTGATCCAAGCTTAGTTTGTTACTATGTGTGATTTAGCATCTGT

CGCACTTGTGTAAATATGGAGTAAGTATTGTAAACTATTTAATTGCTGCG

ATTGTTGGGTTATACATACATTTAGGACTGCAATTTTTTGGTATTTTTTG

TATTGTAAAATAACAGCTAATTTCATCAGGAACAAGAGAATTAAGGGGGT

CTGCATTTTAAATGCAGATGTGAAGCACTTGTATATAAATAAAAGTAAAT

ACTATAATACAAAGTTCCTTCTGAAATAAAAGTAGATCTGGTAAAAATGT

GCGTGCGTTTCGTTCTGAATGTTCAATGCTAATTTTGTTTTATTTTATAT

TTACATTTTAGTCCTTATTTTAGCAGTGAGGAGACAGGCACAGCAGTGCA

TTCTCACCTTGGCAGCTGAGGAATCCCCTAGAGTAGACTGCAACTCAAGA

CTCTTGGCTTCCACACTGAAAAGAGTTTCAGTTTATGAAGCAGAGTTTAG

GAAGTTTAGTGAGGAATTTAAGGACTTCTTTTAATGTTTGTGTCTACATA

TGTGGGTACATATATGACACAGCATGCATGTGGAAGGCAAACAACACCTT

AATGGAAGTGGCCTGAAGAACAAACTCAGGACTTCAATCTTGGCAGCATA

AACCTTTACCTAATGAGTCATCTCCAGTCTATACGGGGTGTGTGTGTGAA
```

FIG.3D(76)

```
CACATGTGCAACAGCACACAGTGGAGGTCAGCACAACTCTTGCGAGTCAA

TTCTCCCTTACCTTGTAAGACCTAGAATTCCACATTGCCCAGGCTCTGAA

AGTTAGGTTGGGTCCACACTGGGCCATGGCTGATGAAATGTTGGAAAAGT

GATAACACCAAACTTTTGCACAGAAAATATTTTCATCTGGGGCCTTCCCT

GGAGTTCACAGGCTAAAGTGTTGGAAGGAACATGGGTCCCTGAGCCACCA

CTTTCACAAAAACTACCTGATCAAGAAGAACTATTCTGGGTTTCTGTTGC

TAAAATTCCTTCCCAGAGAGAAATGTAAGCAATGTCTGCCCCTTCAAGGG

TCCCAGCAAGAAACCAAGGCACAATTCCACCAAAGTTCACTAGAAAACCA

GTGAGTTTATTGGGCTTCCGTGCAGAACATACATGAGGGGTTACTTAGAG

AAGTGTGGATACTCCTCCCCCTAACAATCCACACCCTGAAAAAGCCTTAC

CCAGCAGGGATGAGGGCTTCCCCAGACCCACATTGATGGTGCTCCCATTC

CATTTTTCCCTGGCATGCAAAGAGATAGACAGAAAAATAGATTATATATA

ATATACACATAAATTAGAAAAATAGATTATATAATATACACATAAATTAT

ATATTATATATATAATATATAATACACAGATAGATTATATATGATATATA

AAACACACAGAAATAGGGTATATATAATATATAATACACAAACTACTCAG

CTATTAAAAACAGTGGATTCATGAAATTCTTAGGCAAATGGATGGAACTA

GAAAATATTCTGAGTGAGGTAACCCAATCACAAAAGAACACACATGGTAT

GCACTCACTGATAAGTGGATATTAGCCCAGAAGCTTGGAATACCCAAGAT

ACCATTCACAGACCACATGAAGCTCAAGAAAGGAAGATCAACGTGTGGGT

GCTTCTGTTCTTCTTAGAGGAACACCCTCATAAAGTAGTGGTGGGGGGTG

GGGGGAGACAGAATAGGTGGTTTCCAGGAGAGGAGGAAAACAGGAAAGGG
```

FIG.3D(77)

```
AATAAATAACATTTGAAATGTAAATAAAGAAAATACCCAATAATAAAAGA

AAAAGAATTTTGAAACAGAGGGTAAAAAATAATACACAAACCAGGTAGAT

AGATTATATATAATATATATAACACAGAGATAGATAGATAGATAGATAGA

TAGATAGATAGATAGATAGATAGATAGATAGATAGATAGGTCAACTGCTC

GCCCCTCCACTAGGTAACATGCAGTTAAGGCAGAGCTGCATACAACAGAT

GTTAGGGATACTCAGGTGAGAATCTCAGGCTTTGCTCCATCCATCTATGC

TGGGGTGTAAGCTGTCAACAAGTTTAGCTGGGATGATGCTTTGCAAGAGG

GCACAGCTGAATGCCCTAAGATGGTAGATGCTTGGCTCAAAGGAGACACT

ACAGCTCTGCATCAAGGCAAACTAACTGAGATGAGGGCCTTTATTTTCCA

GATCTGTATCCTGGAGCATCATTCACCTGTTACTACACTGAAAACATTTG

GTGTTGGTTTCATGGCAGATGACAGGCAGTGAGAGAAGTACAGCAGCGGA

CTGCTAGAGGTGGGGGTTCTGTCAGGACGTGGGAGGCTGTTTGGTTAGTA

ACTTGGAAAGCAACAAGTTTTTAGCTAGAGGGAGAAAAGCTGGAGATAAC

TGTACTTGCTTGATTTCTTAAATATCAAATTTTATTTTATGCATATGGGT

ATTTTGCTTGCATGTATGGCTATACACTACATGCTTGTGGTGCCCACAGA

GACCAGAGGAAGTAGTGTGAGCCTCTGAAACTGAAGTTACAGACATTACG

ACTTGAGTGCCTGAAACTGAACCTTGGTCCTCTGGAAGAACAGCCAGGGC

TCCTAACCACTGAGCTATCTCTCCAGCCCTGACAGAACATCATGTACTCC

AGGCTGGTCTCAAATTTGCTTTATAGCCAAGAACGGTCTTAAATTCTGAT

CCTCCTGTTCTCTCAAGTAGTGGGGTTACAGGTCTACACTGCCGTTTTCT

TGAGCAAATCATTACAAATTGAGTTCTAAGCCAGGTGTAATAGTTCATGT
```

FIG.3D(78)

```
AGTAACAATCTGGAATTTTGGTCTCTTAAAAAAACAAATATTATAAGAAT

GTATTTTCATTTTAATCCCAGGTGTATGGCATATATCGAACTGCTTTGGA

CTGACTACAGCAGCTATGATTTTTTCTTGTTCTAGCAGAGGTATGGTTTT

GCCAGCTACAGATAGTTTCTGTGATTGTGTGACATTTGGAATTCTGGAAA

CTTTTCAGATGGTATATAAATATTAGAGCCCCAATAGGCAGAGTTGATGA

TTGTTGGTCATTCAGGGGTATTGGTTGTGGTTAGTAGTCTTGCTTGAAGA

AGAAACAAGAACAAATTAGATTCAGAGATCTCTATATCTCTCTCTATCTT

CCTTTCTGTCCTATCTAGTAATAGGGGGTAAAACCAGGATGATAAAGGGT

TGGGGGAACCCACAAAGTAACAAAGACTGGCTACAAGTGGCACCCAACTT

GGAACTCAAAATTGCCATAGAGGAAGCAGCAGGGGATGAAGGAATGGATT

GTGGCTGTTGTTGCTGGGATATTCCTCACTTTGCTCCCAGAGGGGATTTT

TCTGAGGTTTTGTTGTTTTGCTTTGCTTTGCTTTGGTTTTCTTCTACATA

TTCTGTTTTTTAAGTAAGTTGAAATAATAGCCGAGAAGCTGGAAAAGTTT

GGTGTGGAAATGGAGCAGCCTGAGAAACAAACAATGTATGAAATGGGAAA

ACTAAAGGGGCCACTCTTCTCTCTTTTCTGAAAGGCTTGCAGACTTGGTG

GTGCACCTGGAGAGTTTATGGATGGAGATGGAAGCTCTTAGGAGACAAGA

AGCATGGAAAAAGAGAACAAAGGCTCAGTCCCAGTGACTGAAGAGAGCAG

GAGTTTTCCAAAGAAGGTGCATGGGAGGGCCACTGGTCAGAAAAAAAAGG

CTGAAAAATACCAAAGGACAATGTGCTGAAATAGCCCATTTCAAGAGAAA

GGGTTCATCTCAAACCAGCATTCTGACAGAGTGGAAGGAGGGGTGGCTCA

GGGTTATGAGATCACCATCAGCTTTTCCAGTTTTCCCATATAGCATATGC
```

FIG.3D(79)

```
CTGCTAATGGTATGGAACAAGAGTAAGGCAAAATAGGATGGTGTCCTATA

GAAATGATAGCTCTAAGGTGTTTTTAAAAGGCCTTGATTTCATATGGAAT

GCACTCTCCTTATGTGGAACGGATATTAAATAACCGGGGTACACAAACTA

GAATCCCTTCCCAAGATTGGAAGGGATTGGTAACAGCTGTACTAGAGACT

GTCAGCCGTTGCAATGGTTAACATGCTGGAGGAAAGAAGCTGTGAACATT

GAACAGTAAAACAGAGCAAGGGGTATTAATATAGTGAACGAACAGCTGCT

AGGTGAAGGGCGGTACTCTAGTGTACAAGCACAGACTCGGTGTCATGAAA

CTACTATAGAACAAGGTTGCCTCAGTGGCTATAACACCTTGGGACAAAGG

AGGAGCCAGGAAAAAGTCCAGTTCATTTACAAAGATTATATAAGGCTCTG

GAGAAGCCTTCACTGATTTTTTTTTTTACAAAGATTAGTCTCAGCTATGA

ACAAAGCCATATCAGACCCTGACACAAGGCAGGTGTTGATAGAGACCTTG

GTGTATGACAATGCAAATACCAAATATAAAAATGTCATTAGACTTTTAAA

GGCACAAGTAATGCCTATGGATGAGTGGATAAGGGATAAGACCAATATTA

GTTCTAATGTGTACTGTGCTAATATCATTGATCAAGCTATAGCTAGAGAT

CTCTGATGTCAAAATGCCTTGTGCTTCAGTTGCAGCAAATACAGTAATTT

GCAAGGAGTCATTGTGGCCAAAACTAAAGGTCTCAGATCTCAAAATGCCT

GATGCTTTGTGGGAAATAGGGTCATTTGCAACAAAAATGTGAACAAGACA

TCTTTAAGGGCAATGGTTTTTTCTAAATATAAACCAGAAAGACGGCCTAGG

CTTCCAAGGTTGTGCTGGCGATGTGGCCAGGGTTGCCACTGGACCAATGA

GTGTAGGTCCAAAAGAGATATTCAAGGTAACGTATTACCATCATGAAATG

GTCTTGGGGGCCTATCTTGAGGCCCTGCAGCAAAGAGTATGAGCCATTCC
```

FIG.3D(80)

```
AACCAGAGAGTGGCATGGAGACTCAAAACCTTCACTGGGCACTGGAGATT

TAATGCACACTAGCTATTGCAGGCAGCATGGCTCTAGACTTGGCCACAGA

TAAACATCTTGCTCTATCCCCCAAAATTCAAAGTTATAACATAGCTACTG

GAGTGTATGGTCTTTTTCCCTCAGGGACAGTAAGGATAATCTTGGGAAGG

AGTGGATTGACTTCCTAAGAATTCACTGTGCATCAGGAAGTATAGATGAA

TATTTCAAAGGAGAAATTAAAATTGTGGCATATGTAAAGGTAGAGCTGCA

ACTTAACACAGGCGATAGGGTTGCTCAGCTGCTGCTGTTTCCCTATATCA

AAGGCAAAGCAACTGCAGCAGAAAGAGGAGAGGCCTGAAAACCTTGGGCA

CTGACACAAAAATTGCTTATTTCATTGAAAATGTCTGTTTATAACTTCCC

ACTATACAGCACAACAGGAGGGGGCTTAAAACATAATGGGGAAAATGTCA

CAATTCTGCAATTTTTGTTTCCTTAAAAAAAACACACACACAGAATTTTA

ATAATGTGTTCTCATCTTAATCCCGGGTGTGGGAATTAGGGCTGCTTTGG

ACCATTCCCAGCAGCTGACTATGATTTGCCTCATGCTCTAGCAGAAGTAT

GATTTTTGCCACCTGCAGATAGTTTCTGGGATTGTGTGACATTTGGAATT

TTGGGAACTTTTCTGAAGGTATATAAATGCTAAGGCCCTGGTGGGGAGGG

TTGGTGGTTGGTGGTCATTCAGGGGGGTGGTTGTGGTTAGTGGTCTTGCT

CAAAGAACAAACAAGAAAGTCATTTGATTCAGATGTATCTTTCTTCCTTC

CCCCACTCTTTCTCTCCTCCCCCCGGCACCCTGCCCCCTGCCCCGACCTC

TACCCTTCTTTTTCTATCTAGTGACAAGGATGAAACCAGGGGGATAAAGG

GTGGGAAAAAGAAGAGCCCACAAAGTAACTCAGGTTGGCTACAAGTTCAT

GCCAAGAATCCTAGGACCTTGTTGTTTAAAGGCTTGTTTTATTTTGTGAA
```

FIG.3D(81)

```
CATGAATGTTAAATGTACATACATGTTAAGTGTATGTATGTACACCATAT

GCATGCATACAGAATCCAGAAGAAAGTACATTATACCCTGGAATGGAACT

TAGAGTTGTGAGACAGCATGAGGATGCTGGGAACTGAACCCAGTTTCTCC

ACAAGAGGAGTAGTTGCTCTTCACTGCTTAACCTTTCCTCCAGCCCCAAT

CCTAGCATTTTGGAGGCTGATGTAGGAAGATTATCCCAAGTGTGAGGTCA

TCTTGGGCTCCATAATAAGTTTAAGACCAATCTCAGCTCCAGAGTAGGAC

CCTGCCTCAAAAACACACAGGTGGAAAGATGGGTCGGCAATGAAGAGCAC

ACACTGTGCCTCCAGGGGACCCAAGCTTGGGTCCAAGCACCCTTGTTGGG

CAGCTCACAACTGCCTGTAACTCCACCTCCAGAGGATCCTAAGCCACCTT

CTGGCTTGGCTTCATGGAGGGAACAGGTATGTGGGTATCTGAGTGTGACG

AATGAGCAGCAAGTGAGTCTCGCTGTGGCTAGCACAAAGTATGGGCTGAA

GAGCAGGAGGACAGCTGAAAAGTGGCCTTTCCTGGTGACTAAGTTGGTCT

GAGCAGCTGAGTCAGTTTCTTCCTGGCTGCTTGGCTGGTCTCAGTGCTTA

TAAGCTGCTCACTTGTAAGTCTTTTCCTAGGAGCCCAGCTTGTCTAGGGG

TTGTCTTTGCAACTGGCCTTGTCTGACAGTGACTTTCAGCAGTCTTAGCT

GCTTATATACACAGTCTTAGGAAAGAAGGCTGGTGAATCTGATCCATTTC

AGGAACTTTCTGAAGCTATTCTGAATTTACTTTACAAGCTTACCTGCAGG

ATAGAGGATCTCAGCTCTTTATAAACATCCTGTCCTAAAACACCCTGTTG

TTCCTCTTCTCTTTTACATCCTGTGTCTTGAGAAGTTTGCCTCCAGGATG

GAAGTTGTTCAATTCAGAGGACACTGTTGCACAAGCTCCCAGCACCCACA

TGTGAGCTCAGTGCTCTCCTTGGCTCTAGCTCTGCCCTATGAGGTTTTTT
```

FIG.3D(82)

```
ATTTTGTCATCATAATCTTTTCCTATATCCTTCCTTGTTCTGGGAACTCA

TCTGGTTCATTTTTTTGGCATTTTGAGAAAAGCTCTCACTATACAAATCA

GGCTGCCTCCAAATCATCTTTTTGCCTTAACCTCCTCAGTACCAAGATCA

CGAGTGGATCTTAACACTTGACTGACTCGTTTAAGTGTGAGGAAATGTGG

ACCAATAAGAGAGCCCAGGAAAGCCCAGGAGAATCTGTAGCCCCATGGCT

GTTGTGTCAGAACCCAGAGTTTTGTCAACAGAATTTGGTTCCTAATTTCT

CCACTTTATAAAAACGAGTGAGAGAAACAGGAACCTATTCAGATCTGGCG

TCTGAGCAATCAGTGGGTGAACATCTAGAGATCTGTTCTGCATCTCCTCG

CCAGCTGGCAGAGCATGCGTAAGGCGGGAGGGAACAAGGGCAATCACTCA

CTCTGGGGCTCAGGCTTGCCCCTTGGGTCAGGTGTTTCTGAGAGACGTGA

TGTCTGCTTCTCTTGTTACCATCCCTCATCCTCTCCCCTCCTTCTGTCCC

CTACTTACCAATTTCACTGGCCAGTGTCCATATTTCCTGCAAAAGCGATT

TGGTTTAATGAGCTTGACTATGCCCGACTCCTTTAGGGAGGGTGGGGAAA

GGGCAACGAGGGCAGTAAGTGGTTTCCACAACCACTTTGCACCCGGCTGC

TGGGCCCCAAGCCAGAGGAACGTGCATGAGCCATGAAGTTTCCACTGATA

AATCCACAGATGCTTCTAGCACCTGCCTTTCTGACTCAGCCTCACCGTGC

CGCCTGCCAGCTGTGAAATCAGTGCCAACAACAGGTAACCGAGACCCAGG

CGCAGGGCCAGGACAGCTGTCTGACACTTCCAGACAGGATGTGGAGGCTG

ACAGTTGTGATGGAGAGGAGATGGGGAGGACAGAGACGGGCTCAGCTTTA

AGACACCGAGCCACAGAGCACCAAACAAAAGCCAGGGCCTTCTGAGGTAG

AAGTAACAGAAACCAAACAGGCAATTCTACTAGTTTCCTGGGACTGTTTG
```

FIG.3D(83)

CTGCATTTGCCAATCTTGGTAGTTTTAAAAAACAAAAACAGTTTGTTCTC

AGCACTGGCAGAGCTTTCCTCCTCTGGAGGCTCCAGGGGTCCAGACTCTC

CTCTGTGGTACACTGGCTTCAGACATATCTCTTGCCTATGGCTGCCTCAC

TCTAAACTCTGCCTGTCCTTGAATTACCTCTCTCTGCACTGGCTTTATAA

AGGAAACATGAGATTGTGTTTAGGGCCTGTTTGGGTGACCTCCTCAGGAT

CTATAACATAATCACATCTCTACCGTATGAAGTGACGCTTCCGTCCCAGT

GTGTAATACATTTGCCGGCGCCTGTCCTTAGGACAGTGACCACCACCAAC

TGTGGAACTTGACTATGTCCACGTCATCTTCCTACTAGCTTTAGAAGGCT

TATACCCACACTTTCTATCCAGAATTGTATTTTTATTTAGAATCATTCCT

ACTTTTAAAAAAGTCTCTGTGGTTAAAAGCATTGCAGAGGGCTTGGGTTT

TGGTCCCCAGGACCCACATCAAGTGGCTCACAGTGTCCTGGAACTCTTGT

TCCAATACCCTCTTCTGGTCTCCATAGGCACTACATACATATGGCACATA

TATGTATACTCAGGCACACGTGTAAATTTTAATGTCTACTTTTTATGCTA

AATATCAAAGTCACTCGAGCAGTGGAGTTGAGCACACTCACATAAGGAAA

TCATCAGACAGACACTTCATCCTGTGTTGGAGCCACTTTGTGGCTGGAGT

AAGCAGGGCAGAGTGATGTTTTCATTACTCTCTGGCCCCAGCACCCCCTG

CCTCTCCCCACCCATTCGTCCATGCAGGTGGGGAAGAGAATTCTCTTTGT

GAAATTGGAAGTTTGGACCCAGCTTCACTCTTACTCTGCCCAGTACCTCC

TGTGAGAAACCCTCCTATCCCAGGTGACCTGCTGGCTGTGACTCTCCTCA

GCAAAAGGCCCGTGACCCACACTGCGCCACTAATGTATCATCCCCAAATG

CTGAAAAGGAAGCGTGTCTTCCTCTCTCTCTCTTTTTTCTTTTGGTCTTTT

FIG.3D(84)

```
TGAGACAGAGTTTCTCTGTATAGCCCTGGCTGTCCTGGAACTCACTTTGT

AGACCAGGCTGGCCTCGAACTCAGAACTCCGCCTGCCTCTGCCTCCCGAG

TGCTGGGATTAAAGGCGTGCATCACCACTGCCCGGCTGCGTGTCTTTCTC

TTAGCGGTCTCTGTGGAGATGCTGAGTATGAAGCTCATCCTACCCACCCT

TCAGTGGGGCCTTTTCTAGCTACTGAGCAGCTGTGTGAGGACTCGTGATC

ACAAGGTCCTTTGAACCCTTGAGACAGATGTGCCTGAGCCCAGTTTGACC

TGACAAAAGCCTAGAGCTCACTGATAATGCCAGCAAACACCATCTTTGAG

TTTGCAAAGGAATCGCAACACATGCATTCAGTTTCCGTTGCTGGCTGCTG

CTCCAGAGATGGCTATATTCATTCTCAGGTACTCAGACTCAAGAGTAGTT

CTGGCCACACAGGTCTCCACATTTCGAGGTCAAATGACAGAAAACCAGGT

TGGTCTCAGTGCACATGGGTTTATTGAGCCACTGCAGGTGCTGGGGAAAC

CATGGCAGGGAGATCCTGGGAAGCCAGTGGGGTGCTGAGCAGGAGGGACC

TCAGTCTCTCCTTAATGTCTACACACTGTGTCATAGGTGACAAGCCACGT

CAGTGCTGTGACACGGGTAAGCTTAATGGTGAGTAATGGCTAACTGGGAG

GGTATTTAGGCAGCCTTGTCTGTCAGCCTGTTCATATGATCTCCTTAGTG

CCTTGTCATCTTGGAAAAGGACAGTTCCAAATTCTAGGAGCGGGGGCTAG

TCTCTGTCCTGCTCTGTAAGCCCAGGGGACCCAATGAGGCCTCATCTATG

GGTGCTCAGCTCTAGGATGGGGAAGAAAATGGACAAGATGCCTACTGACG

GGAACACAGGCTTTTCAGTCAGACCCTAGCCTCCAGCCCCCAATCCAGAG

GACAGCCACACAGGGGTCCAGGCCTGCAAAGGGCAGCAGACCTGAGGGCA

AGGGAGTTTCAGCTCAGTGAGCAGTCATCGGGAGACATGGCAGTCAGCTG
```

FIG.3D(85)

TGTCGTCCACGGTTCATGTTCCTAATCAGAGCAGGGCCTGGAGAGCCAGG

GCAGTGAGTGCATACAGCCAGGACACCTTGGGCGTTAGGACAAAACAAGG

ACTGTTTCTGCCTCCAGCTCTTCTCAGGCCACTCGTGCCTTGCCTAGGAA

GGGTAAGAGAGCACAGATGGGAAGGATTCGGAAACTGTCAACTCCCTGTC

CTCTCCCCATACCTACCCGCGGGAAACAGCACCCAGCAGTCTGGTCCTGC

AGAACTGATGGCTGCAAGCTGTCAAAGGCTTGTATGGCACCATCTGCGGA

GTGCAGAGATCCAGAGAAGGCTTGGCCAGGAAACCCTAGAAACTACCCCA

CTCCCTTGGGACAAAAAATAAGACACCCTGGAACCTGCAAGGCATGGCCT

GAGATGGAAGGTCACTGTGCTAAGAATGACCCACAAACTGCTAGTGAGGT

TGACAAGGGCTGCCCCCTCTCCCTTTACAGGTGAACACAATCGGGATTAA

TAAGAGTTTAACTCTCAGCTACTAAGTGGCAGAGACAGGCTTCAAACAGA

CCCCCAGAAATCTGGAACTGAGCCATTCCACCCAGAGGCAAGAACAGCAG

AGGTAAGTTGGGCACACATGGAAGAAAGGGCCACCCCATTAGTGTCAAAA

GGGAGGCCAACTTCAGGCCATTGGACACGTTTTAACGCTGACTTCCACCC

ATGTACCATGGCATGTGCACACTGTCCATCGCCCACACCAAACATGATGC

GACGTAAATAAGACCCACGGGCCAGGCAGCTTGGATTGGGCCACAGACAT

FIG.3D(86)

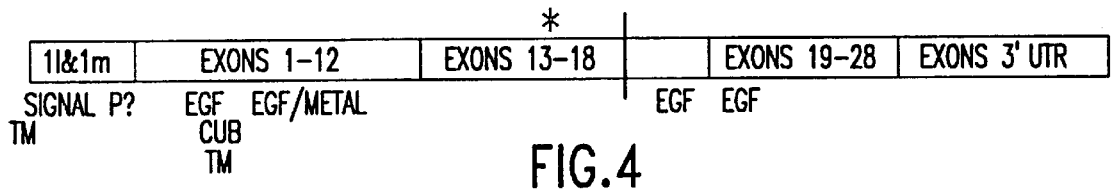

FIG.4

| | | |
|---|---|---|
| Exon 1 | CelegE106 | TCTCCTAGTTGTAGTACATGCTGTTG |
| | CelegE108 | AGGTCCTGTCTCAAGAAATAGCAATAAC |
| Exon2 | CelegE33 | TTTGAAGGCCCCTGAAGTCAGAG |
| | CelegE36 | TTGAGTCCCCATCATAAACATATAAATGG |
| | CelegE37 | TTCTAGGCCAAATAGAATAATGAGACTTC |
| | CelegE40 | AGAACTAATTCCATGAGATGAGTGTG |
| Exon 3 | CelegE41 | TGAAGTTGCTGTAATCTGGTCTGTG |
| | CelegE44 | AAGGAGCCTGACTAGAAGCCTC |
| Exon4 | CelegE69 | TAAACTCCCTACAGTTCACTAACTCAG |
| | CelegE72 | AGCGCTGTTGAGTGTGAATGTTCTG |
| | CelegE73 | AAAGCCACAGTTGTCTGTACAGTGAG |
| | CelegE76 | AGGTCTGCATTAGTTGCAATGTTGC |
| Exon5 | CelegE77 | TATACACCCCCTTATATACACTCAG |
| | CelegE80 | AGAGCCTCTCATAAAGCTGTGGTC |
| | CelegE81 | TTGAACATATATCCGCCAACAACCC |
| | CelegE84 | CTTGGAATACTATAAACTTTCAGGCTGC |
| Exon6 | CelegE101 | TAAAGCAACAGGAAGAGTTGAACTTCTTG |
| | CelegE104 | TGCACCCTGTGTGCACATGG |
| Exon7 | CelegE109 | TTACGGTGTCCTAATAATAAGGGCAG |
| | CelegE111 | AATCATGGGTATTGTTAACTCCGAAAGC |
| | CelegE114 | TGTAACAATGTGTGCCGAGTGTCC |
| | CelegE116 | TCTCTCTCCAGCCCTAGAGTTG |
| Exon8 | CelegE86 | AGAAGAGGAGCCTGCAACATTGAC |
| | CelegE88 | TTTGTTGGCGCTGAAAGCCTTG |
| | CelegE89 | TGGCCACAGTAGTGTTTATGATGAC |
| | CelegE91 | TTAATCAATTGCCTCTGCAGATTCTAG |

FIG.5(1)

| | | |
|---|---|---|
| Exon9 | CelegE93 | TGGCTTACGTATAGGGGGAAATCAAG |
| | CelegE95 | TTGTGTGTGTTCCCTCCAAACACC |
| | CelegE98 | GGACCATTCTTAAGGACAGCCGAT |
| | CelegE100 | ACATAGTGATCTTTCCATCAGCAAAG |
| Exon10 | CelegE117 | TGAATGCACAGAGACCCTCCTG |
| | CelegE120 | CCTCTTACCATTCAGATACTGTTAGG |
| Exon11 | CelegE121 | AGCAACAACTCAAACCAGCCCTAC |
| | CelegE124 | TTCTTCAGTTGCCAACTCCCAGG |
| | CelegE125 | AAGCTGCTTGTGTGGCAGCAG |
| | CelegE128 | AGTAAGGTGAACAGGAAAGTACAGAG |
| Exon12 | CelegE130 | TACATAAGAGAGGCTGCCGCATAG |
| | CelegE132 | CCCTACACTCACACTCATCTAGC |
| Exon13 | CelegE30 | CCCTGTGTTCCAGATCTCCATTG |
| | CelegE32 | TTCCTAGGTCCACCTTGATCTGAG |
| Exon14 | CelegE14 | AGCACCTGAATTCAAATCAGGATGAG |
| | CelegE15 | AAACCAAAGTTCTGAACACATTAACTCAC |
| Exon15 | CelegE17 | CTGGTTGCATTCATAGCTGTGTTTC |
| | CelegE20 | ACAGAAGCCAGCATCACTGGG |
| | CelegE21 | TTACTGGTGCTGGGAGGATATGTC |
| | CelegE24 | ATAAGTACTTCATCACCTCAGCGCTC |
| Exon16 | CelegE1 | TTGATCTTAGCTGACCAGTGTCTC |
| | CelegE4 | TCTGCATGGACTTGAGCAGAAAGTC |
| Exon17 | CelegE6 | CAAATCTTGTGATAGTGAATTACAAGTTGG |
| | CelegE8 | TTTATAGCTGCCCTCAATACATTTTCC |
| | CelegE9 | TGTACCTGCAGCCATTGCTTGG |
| | CelegE12 | GGATCTGGGCTCTAGTTTATGTACG |

FIG.5(2)

| | | |
|---|---|---|
| Exon18 | CelegE25 | TTGAACTATAGGCACAGACAGCTG |
| | CelegE27 | AACTTGACCTGTGTGACTTACGC |
| Exon19 | CelegE193 | TCACAGTCTATGGTAATCTGTCAAGC |
| | CelegE194 | AAGGGCAACAATGCCCTGGCAA |
| Exon20 | CelegE195 | TTCCTGCAAATGGGATAGTCTCTCTG |
| | CelegE196 | ATCCCCCAAGCATTTATCATTCTCAG |
| Exon21 | CelegE197 | TGTGTTTCCAGAAACCTGCTTTAGTTTG |
| | CelegE198 | TAGTACTTTTGTCCAGGATGACCAAG |
| Exon22 | CelegE199 | TGACAAGAAATGTCATGTCTTAACATAAGC |
| | CelegE200 | TTCAGAGCCTCCTTCCCCAACT |
| Exon23 | | |
| Exon24 | CelegE203 | TAGTCTGTAGCTGAGGCCATTTTGC |
| | CelegE204 | AAGCAAGCTGCAGTTAAGGGACTGT |
| Exon25 | CelegE205 | TTGGGACCTTGAGGATTGTTCCC |
| | CelegE206 | CACTCAACAGGTAAAAGTGATCTGCC |
| Exon26 | CelegE207 | TGCATCTGATCAGTTTGAATCAGAGAG |
| | CelegE208 | AAACTGAGGCCTGAGTTCTGAAAAGC |
| Exon27 | CelegE181 | CACCAAAGCTCTGTACCACTAAGC |
| | CelegE182 | TGACTGTGCAGTGATGCAGGG |
| Exon28 ÕUTR? | CelegE171 | TTGACCTTGACATTTAGAATAGCCCTC |
| | CelegE172 | GCTGAGAATTAATAATGGTCTTTCTCTTTG |
| | CelegE173 | TACACAGTGAGACCCTGTCTCC |
| | CelegE174 | TAGCTGAGGTCCCTTGTGGAAG |
| | CelegE175 | AGTGTCAGAGGACCATGCTGG |
| | C.elegE176 | CTTGAAGCGTCCAACTCATGTGC |

FIG.5(3)

| | |
|---|---|
| CelegE161 | AACTCATACATTTGAGCACTGTTGCC |
| CelegE162 | TGAGGAGGTGGGGAATGCTAATG |
| | |
| CelegE163 | ACATAGCAGAGGGCTGCTCAC |
| CelegE164 | ACTGACCTGTGGGAACCTGTG |
| | |
| CelegE165 | AATGCTAGGCATCATCCCTCTTCTAG |
| CelegE166 | AACATCTAATAGGGACTGAGTGACCC |
| | |
| CelegE167 | TTCTGTGGTGCCTTGGCAAGAG |
| CelegE168 | CACACATACACACACACTAAGTGCC |
| | |
| CelegE169 | TGGTAGTTACTTAAAGTTTACAAGAATGTAGG |
| CelegE170 | AAATGCTGGGATAAAAAGCATGAACCAC |
| | |
| C.elegE145 | TTCAGTTACCTAATGGGCACAAGGC |
| CelegE148 | ACGACACTGACCTCTTGCACTTG |
| | |
| CelegE150 | TGTACACCCTGAATGTCTGAACATTC |
| CelegE152 | GCGTTCATTTCTGCTCCTGTAATGG |
| | |
| CelegE153 | TGAGCTCTTAATCCCTGCCATTCC |
| CelegE154 | TAGGGCTTGTCCGTCCATAAGG |
| | |
| CelegE157 | TGTTACGGAGATGAAAGGCTAGACC |
| CelegE158 | TAAGCCCTGCACTAACCCACTC |
| | |
| CelegE159 | TGTTTTGAGAGGTGAGCCTTCTAGC |
| CelegE160 | CATGTCCTACAGTTCTGCTATCACC |
| | |
| CelegE141 | CTTTTCTTCATCCAATTCCCCACGAG |
| CelegE144 | TCTCTAAGCTGCACTGTTGTGGCT |
| | |
| C.elegE129 | TGGAAGCCAAGAGTCTTGAGTTGC |
| CelegE132 | GTCTGCATTTTAAATGCAGATGTGAAGC |
| | |
| CelegE134 | CGAAACGCACGCACATTTTTACCAG |
| CelegE136 | GTGTGATTTAGCATCTGTCGCACTTG |
| | |
| CelegE137 | TGTATGTATAACCCAACAATCGCTGC |
| CelegE140 | TCCAGAGTACAGGGAGAAACTAAAGG |

FIG.5(4)

AGCGCTATTCAGCTGTGCCTCCTTTGCTGTCTTGGCTCCTCCTGGAGCACTAT
ATGCACCCATGTCCTTACCAGGCCTTTCACAGACGCTGCCATTGAGAGGGT
TGATGCAGGTTGCAGCCTTTAATCCCCGAGTACTAGGCTCTGACAAGATCCCA
CAGAAGCCAGCATCACTGGGCTCAGATGGCATCCACTGCAGCAAACTATTTG
TGAATGGAGACATATCC

FIG.6

```
GAATTCCGGGCGAAGGGGAGCCGGCGTGCGGGGTGTGTATGTGTTCGCTGGGCGCCGGCTCAGCCCCAGGAAGATGGTG

GCGGTGGCGGCGGCGGCGACTGAGGCGCGGCTGAGGGGGAGCACGAGGACGACAGCAGCGCCTGCGGGCAGGAAGG

GCAGGCAGCACCGACCCTGCACCGCGCGACAGGGGCCTGGAGGCCGGGACCGCGCGCGGCTGTGTCTCCCGCGGGTGCT

GTCGCGGGGCGCTGCCCCCGCCGCGCTGCCGCGCTGCTCTTTTCGCTGCTGCTGCCGCTGCCCCGGGAGGCCGAG

GCCGCTGCGGTGGCGGCGGGTGTCCGGCTCGGGCGCCAGCCGAGGCCAAGGAATGTGACGGCCGTGTGTCAACGGCG

GCCGCTGCAACCCTGGCACCGGCCAGTGCGTCTGCCCCACGGGCTGGGTGGGCGAGCAATGCCAGCACTGCGGGGCCG

CTTCAGGACATCTGTCTCACGCTATAATCACAGCTGTTCGGAAGGTGAGGCTGGAGGAACAGTTCGAGGCAAGCTTCG

GCTACAGAATAAGTTCAAGAGTAACCTGGGCAACTTGGGCTTGTCTCCAAAACCAAAATGAGCGAAAAGGAGCAAGCT

AGAGTCTTTTGGGAAAATTTTAGCTGACTAATTTTTCACCGAGAACTAACTGGCTCTTCTCTGGATTTGTAACAGATGGAC

CTGGGAATTATAAATATAAGACGAAGTGCACATGGCTCATTGAAGGACAGCCAAATAGAATAATGAGACTTCGCTTCAA

CCATTTTGCTACAGAATGTAGCTGGGACCATTTATATGTTTATGATGGGGACTCAATCTACGCACCTCTGATTGCTGCC

TTTAGTGGCCTCATTGTTCCTGAAAGAGATGGCAATGAGACGGCTCCTGAGGTCACTGTCACTTCAGGTTATGCACTGC

TGCATTTTTCAGTGATGCTGCTTATAATCTGACTGGATTTAATATCACTTACAATTTTGACATGTGTCCGAATAATTG
```

FIG.8A

```
CTCAGGCCGAGGAGAGTGTAAGAGCAGTAACAGCAGCAGCGCTGTTGAGTGTGAATGTTCTGAAAACTGGAAAGGGGAG
TCGTGTGACATTCCTCACTGTACAGACAACTGTGGCTTTCCTCACCGAGGCATCTGTAATGCAAGCGATACCAGAGGGT
GCTCCTGCTTTCCTCACTGGCAGGGTCCTGGATGTTCAATTCCTGTGCCAGCTAACCAGTCTTTTGGACTCGAGAAGA
ATATTCTGATTTAAAGCTTCCCAGAGCCTCTCATAAAGCTGTGGTCAATGGAAATATAATGTGGGTTGTTGGCGGATAT
ATGTTCAACCATTCAGATTACAGCATGGTTTAGCGTATGACCTGACTTCTAGGGAATGGCTTCCACTAAACCATTCTG
TGAACAGTGTGGTTGTAAGATATGGTCATTCTTTGGCATTACATAAGGATAAAATCTACATGTATGGAGAAAAATTGA
TTCAACAGGGAACGTGACCAATGAGCTGAGAGTATTTCATATTCATAATGAATCATGGGTATTGTTAACTCCGAAAGCT
AAGGATCAGTATGCAGTGGTTGGACACTCAGCACACACATTGTTACACTGGCCGTGTGGTCATGTTGGTCATCT
TCGGTCATTGCCCACTCTATGGATATATAAGCGTTGTGCAGGAATATGACTTGGAAAAGAACACATGGAGTATATTACA
TACTCAGGGTGCTCTTGTGCAAGGGGGTTATGGCCACAGTAGTGTTTATGATGACAGGACCAAGGCTCTGTACGTTCAT
GGTGGCTACAAGGCTTTCAGCGCCAACAAATACCGGCTTGCAGATGACCTCTACAGATACGATGTGGATACTCAGATGT
GGACCATTCTTAAGGACAGCCGATTTTTCCGTTACTTGCATACAGCTGTGATAGTGAGTGGAACCATGCTGGTGTTGG
AGGGAACACACACAATGACACTTCCATGAGCCACGGTGCCAAATGCTTCCTCCTGGACTTCATGGCTTATGACATTGCT
```

FIG.8B

TGTGACCGATGGTCAGTGCTTCCCAGACCTGAGCTCCATCATGATGTCAACAGATTTGGCCATTCAGCAGTCTTGTACA

ACAGCACCATGTATGTGTTCGGCGGCTTCAACAGCCTCCTCCTCAGTGACGTCTTGGTCTTTACCTCGGAGCAGTGCGA

TGCACACCGCAGTGAAGCTGCTTGTGTGTGGCAGCAGGACCTGGTATCCGGTGTCTGTGTGGGACACAGTCGTCTCGATGT

ACCTCCTGGGAGTTGGCAACTGAAGAACAAGCAGAAAAGTTAAAATCAGAGTGTTTTCTAAAAGAACCCTTGACCATG

ACAGATGTGACCAGCAGCACACAGATTGTTACAGCTGCAACAGCCAATACCAA

FIG.8C

MRLRFNHFATECSWDHLYVYDGDSIYAPLIAAFSGLIVPERDGNETAPEVTVTSGYALLHFFSDAAYNLTGFNITYNFD

MCPNNCSGRGECKSSNSSSAVECECSENWKGESCDIPHCTDNCGFPHRGICNASDTRGCSCFPHWQGPGCSIPVPANQS

FWTREEYSDLKLPRASHKAVVNGNIMWVGGYMFNHSDYSMVLAYDLTSREWLPLNHSVNSVVVRYGHSLALHKDKIYM

YGGKIDSTGNVTNELRVFHIHNESWVLLTPKAKDQYAVVGHSAHIVTLASGRVVMLVIFGHCPLYGYISVVQEYDLEKN

TWSILHTQGALVQGGYGHSSVYDDRTKALYVHGGYKAFSANKYRLADDLYRYDVDTQMWTILKDSRFFRYLHTAVIVSG

TMLVFGGNTHNDTSMSHGAKCFSSDFMAYDIACDRWSVLPRPELHHDVNRFGHSAVLYNSTMYVFGGFNSLLLSDVLVF

TSEQCDAHRSEAACVAAGPGIRCLWDTQSSRCTSWELATEEQAEKLKSECFSKRTLDHDRCDQHTDCYSCTANTX

FIG. 8D

```
GAATTCCGGAAAAAAAAAAAAAAAAAAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAGGAGGGCGAAGGGGAGCCGG
CGTGCGGGGTGTGTATGTGTTCGCTGGGCGCCGGCTCAGCCCCAGGAGATGGTGGCGGTGGGCGGCGGCGGGGACT
GAGGCGCGGCTGAGGGGGAGCACGACGACAGCAGCGCCTGCGGGCAGGAAGGGCAGGCAGCACCGACCCTGCACCG
CGACAGGGGCCTGGAGGCCGGACCGCGCGCCCGGCTGTGTCTCCCGGGGTGCTGTCGCGGGCGCTGCCCCCGCCC
GCTGCTGCCGCTGCTCTTTTCGCTGCTGCTGCCCCGGGAGGCCGCTGCGGTGGCGGCGGTG
TCCGGCTCGGCCCGCAGCCGAGGCCAAGGAATGTGACCGGCCGTGTGTCAACGGCCGCTGCAACCCTGGCACCGGCC
AGTGCGTCTGCCCCACGGGCTGGGTGGGCGAGCAATGCCAGCACTGCGGGGCCGCTTCAGACTAACTGGCTCTTCTGG
ATTTGTAACAGATGGACCTGGGAATTATAAATATAAGACGAAGTGCACATGGCTCATTGAAGGACAGCCAAATAGAATA
ATGAGACTTCGCTTCAACCATTTGCTACAGAATGTAGCTGGGACCATTTATATGTTTATGATGGGACTCAATCTACG
CACCTCTGATTGCTGCCTTTAGTGCCCTCATTGTTCCTGAAAGAGATGGCAATGAGACGGCTCCTGAGGTCACTGTCAC
TTCAGGTTATGCACTGCTGCATTTTTCAGTGATGCTGCTTATAATCTGGATTTAATATCACTTACAATTTTGAC
ATGTGTCCGAATAATTGCTCAGGCCGAGGAGAGTGTAAGACAGTAACACAGCAGCGCTGTTGAGTGTGAATGTTCTG
AAAACTGGAAAGGGGCCGGAATTC
```

FIG. 9A

EFRKKKKKKKKKKKKKKKKKKKKKKKKKKGGRRGAGVRGVYVFAGRRLSPRKMVAVAAAAT

EARLRGSTTTTAAPAGRKGRQHRPCTATGAWRPGPRARLCLPRVLSRALPPPPLLPLLFSLLLLPLPREAEAAAVAAAV

SGSAAAEAKECDRPCVNGGRCNPGTGQCVCPTGWVGEQCQHCGGRFRLTGSSGFVTDGPGNYKYKTKCTWLIEGQPNRI

MRLRFNHFATECSWDHLYVYDGDSIYAPLIAAFSGLIVPERDGNETAPEVTVTSGYALLHFFSDAAYNLTGFNITYNFD

MCPNNCSGRGECKSSNSSSAVECECSENWKGAGIX

FIG.9B

SIGNAL PEPTIDE PREDICTIONS

| METHOD | PREDICT | SCORE | Mat@ |
|---|---|---|---|
| SignalP (eukaryote) | MAYBE | | 127 |

TRANSMEMBRANE SEGMENTS PREDICTED BY MEMSAT

| START | END | ORIENT | SCORE |
|---|---|---|---|
| 102 | 120 | INS-->OUT | 2.1 |
| 234 | 250 | OUT-->INS | 1.7 |
| 262 | 279 | INS-->OUT | 0.5 |

ATGTACTACTGTAACAAGAAGACCAGCTGCAGGAGCTGTGCCCTGGACCAGAACTGCCAGTGGGAGCCCGGAATCAGG

AGTGCATTGCCCTGCCCGAAAATATCTGTGGCATTGGCTGGCATTGGTTGGAAACTCATGTTTGAAAATTACTACTGC

CAAGGAGAATTATGACAATGCTAAATTGTTCTGTAGGAACCACAATGCCCTTTGGCTTCTCTTACAACCCAGAAGAAG

GTAGAATTTGTCCTTAAGCAGCTGCGAATAAATGCAGTCATCTCAGAGCATGTCCAAGCTCACCTTAACCCCATGGGTCG

GGCCCTTCGGGAAGGTYCAATGTGTCCTACTKGGTGCTGGGGAAGGATATGKTCCCCATTTTACAAATAGTTTTACTACA

GTGGGATGSCCGTCTTGAGGCCCAGTGTTGCTTGGRATTCTGTGGGAATTTT:ATTCAGGAACCCAGTTACTTCGGGGA

CTGAAGGGCTGCAACCTGCATTCAACCCACTYMAATGGTAGTGTCTGTGAAAGGCCTGCAAACCACAGTGCTAAGGCAGT

GCCGGACACCATGTGCCTTGAGGACAGCATGTGGAGATTGCACCAGCGGCAGCTCTGAGTG::CATGTGGTGCAGCAACA

TGAAG::CAGTGTGTGGACTCCAATGCCTATGTGGCCTCCTTCCCTTTTGG::CCAGTGTATGGAATGGTATACGATGAGC

ACCTGCCCCCTGAAAATTGTTCAGGCTACTGTACCTGTAGTCATTGCTTGGAGCAACCAGGCTGTGGCTGGTGTACTG

ATCCCAGCAATACTGGCAAAGGGAAATGCATAGAGGGGTTCCTATAAAGGACCAGTGAAGATGCCTTCGCAAGCCCTAC

AGGAAATTTCTATCCACAGCCCCTGCTCAATTCCAGCATGTGTCTAGAGGACAGCAGATACAACTGGTCTTTCATTCAC

TGTCCAGCTTGCCAATGCAAACGGCCACAGTAAATGCATCAATCAGAGCATCTGTGAGAAGTGTGAGAACCTGACCACAG

FIG.10A(1)

GCAAGCACTGCGAGACCTGCATATCTGGCTTCTACGGTGATCCCACCAATGGAGGGAAATGTCAGCCATGCAAGTGCAA

TGGGCACGCGTCTCTGTGCAACACCAACACGGGCAAGTGCTTCTGCACACCAAGGGCGTCAAGGGGACGAGTGCCAG

CTATGTGAGGTAGAAATCGATACCAAGGAAACCCTCTCAGAGGAACATGTTATTATACTCTTCTTATTGACTATCAGT

TCACCTTTAGTCTATCCCAGGAAGATGATCGCTATTACACAGCTATCAATTTTGTGGCTACTCCTGACGAACAAAACAG

GGATTTGGACATGTTCATCAATGCCTCCAAGAATTTCAACCTCAACATCACCTGGGCTGCCAGTTTCTCAGCTGGAACC

CAGGCTGGAGAAGAGATGCCTGTTGTTCAAAAACCAACATTAAGGAGTACAAAGATAGTTTCTAATGAAGAAGTTTG

ATTTTCGCAACCACCCAAATATCACTTCTTTGTTATGTCAGTAATTTCACCTGGCCCATCAAAATTCAGATTGCCTT

CTCTCAGCACAGCAATTTTATGGACCTGGTACAGTTCTTCGTGACTTTCTTCAGTTGTTCCTCTCTTGCTCCTGGTG

GCTGCTGTGGTTTGGAAGATCAAACAAAGTTGTTGGGCCTCCAGACGTAGAGAGCAACTTCTTCGAGAGATGCAACAGA

TGGCCAGCCGTCCCTTGCCTCTGTAAATGTCGCCTTGGAAACAGATGAGGAGCCTCCTGATCTTATTGGGGGAGTAT

AAAGACTGTTCCCAAACCCATTGCACTGGAGCCGTGTTTTGGCAACAAAGCCGTCGTCCTCTGTGTTTGTGAGGCTC

CCTCGAGGCCTGGGTGGCATCCCTCCTCCTGGGCCAGTCAGGTCTTGCTGTGGCCAGCCCCTGGTGGACATTTCTCAGC

AGATGCCGATAGTGTACAAGGAGAAGTCAGGAGCCGTGAGAAACCGGAAGCAGCCCCCTGCACAGCCTGGGACCTG

FIG.10A(2)

CATCTGATGCTGGGGCCAGGACTCTCCCACGCACGAGCTAGTGAGTGGCACACCAGAGCCATCTGCAGGGAAGGGCGT

GGCGGGGAAATGGCTGTGCGGTGCGGGACGGAAGACTGGAAACCCTCAAGACATCTGACTCACCTGCATGATCACAAGC

TTTCTTTGACGGTTTCTCCCATCCGTGTTCCAGCATCTAACCTTTTACTTTTGCATAGGAAATACTTGATTTAATTACA

GGTCCAGGGATGAGCTGATGGTTGCTGGAGGAGGCCAGTGTAGAGCCAGTGAGAGAACTAGGAATGACACTCAGGTTCA

CTGTGGAAAACTGTTCTTGGGACTGTCTCAACTGTGCAAAAAACAAAGATGGAGTGTTTACAAGTAGACATTCGTCAT

CAGTTGTTCTTGAACATGGTCTTTAAAAACTAGTCAGATGAATTAACTTGTTTTCATCTGAAGCCTGCTATCTTTTT

AAAAGATGTGCTATTTATTCTTGCACGATTTAGGCAATTATCTCTCTTCCAGGAGTACCTTTTTTTCTAGTGAGAAT

TAATAATGGTCCATCTCTTTTGATCATATCAAGCTAGGATAGAAGGGGGCTATTTAAATGTCAAGGTCAGCAGTGTT

ACTTTGAATGTAAACTGGTATAATAGGTAGTTTTCTATAGTAACTTGATTAATTTAGTCTTAATCCATTGAAACTCTC

TCTTCCTTTCTCTGCCTGTCCCTCTCCTTCTCCATCTCACCCTCCCTCTCACACATACACACACAAACACATACA

CACAACACTAGTGCCTAGACTTTAAATAGCTAGCAATTGGAAAGTTAGTAAGCCTAAGTTTTACATAATTGCATT

CCTACATTCTTGTAAATTTAAATAGCTACCATTGGCAATCTGCTTTTTCTAAAATCTGATTTGCAGCCAGGAAAGA

ATTTTCTCACCCAAGGAACATTTGATCTAGCAGCAGGGATGAGCAGGATGAGAGGAAAGCAGAAATGAATGAACTGTGAAAGCTCCTG

FIG.10A(3)

TTTTTATTATTCAAAAAGGACACTGTCAAGAAGGGCGCCCCTGCCCCACCCCGTGTCACCCTAGGCCTGATAAGCGAT

CAGAGGAAAGGACTCATTCATGTCACGCTTCCTTGAGCAGAAAGAGCACTGAGAGCACTTGGGACCCCTGGATCAGAG

AGCATCTGTGTGTCCTGCAGCCTCCTCTGAACTTGTGGTTCATTCTCAGGCTGGGGTGGACTCAGATGCCAGGAAAGGG

ACAGCCTCCCATTGTCAGGCAGAAGCTGCCAAAGCTGGAGAAGGACTTGTTGCCCTCTTTCCCCAGGAGGGGCTC

GACCCACCCACCCTCCCTCTCAGACCAAGGTGGTGGCTGTGAGGAGGGCAGCAAATGCTGACAAGGATGAAAAGCACAT

GGAAAAAAATGACGAGGAGGGAAAACTCTGCCAAATGGAAAATGACCAAATTTAAGAGGGTGGGACAGTCCCCTGCTC

CTCTCCCAGAGGGCACTGCTTGGAAATTGTGTTTCCCCATTTATGGTGCTCTGTATTCTGGCATTATGCAGCAGCCTC

CCAGAAGCTCTCTTCTGCTTCAAAACCTGGGATCTCTGGCATTACCCTATTGGGATGGACCGCTGGACAGCAATGCTCG

AGTTTGTGAATTTGGAGAGATACTCAAAAGAGCTAAAACTGCAGCATTTACCTTTAAATGCAGTGCCTAGAGAGAGAG

TATTGTCTCTTCCCAACACTAACCCCACTCCCATGAAGAATTGCCTGGAAAGATGTTTCAAGGAATTTGAACCATAA

AACACTATCTGATGCACAGAACACCTCTACTTTGAGACTCACCTCTCATAAAGCTTCTTTTCACATTACTGTTAAAGA

CCAGACGTTCTAGAAAAGACCCCTCCTCTCATGAGCTCCCCATCCCTGCTACAGAACACAGCACCCATGGCGCCTGCA

GTGGACTGGCCCCTTAATTCCCACAGGCCCCCCCAGCAAGGCCAAAGGGAGCCCCTGGGTATTGTCCTCCTACAAGGA

FIG.10A(4)

```
AGATCCTCTCTTTGTTTGTTCAAAGGACCAGTTTTCCTAGGCCAAAGAAGTCTCTTCCCCATGTTAGTCCTATGCCTTGAA
ATATCATGACCCACAGCCATCTGGTTATGTCTTATTTTTTCCTAAAAGATAATGTTTATTTTTAAAAAGGA
AGGAAGAAGCAAGTGAAGTTTCATTCTGCTCAGCGGTGGGGAAGCGCTGAATCCACCTGCTTCTCCTTTGCAACCGA
CAGCAAACAGCTTTCTCCGGCCTCAGGGCAGAAAAAAGGGAATGGCAGGAGTAAGAGGGCGTGGGCTCGGAGCCTGTTT
CCAAGAAGGAATTGGTTGTCATCTGGCAGTGTTGCGCGTCACAAGAGAGCCTGTATATAAATTAAAATAGTCAAGACAA
CACTGACCTTGCACTTGTACATAACTATACAGTAGTGTCCAGATGTTCAGATCATTCGGAGTGTACATAAAACAGAAAA
AATCTTCATGTATTTTTATTAAATATAACAATGTCTGAGTTTCACCTAAGATGTTTTGTGCCATATGCTGGATATCCA
GGTTCTCGCCAGGCCCCGATACATGAATAACAAACCCAAGAAAACGCATCCCCATTGTGTGATGTGTTCAGATGCATCTG
GCACCAATTAGGTATTTCTTAAAAACAGGACTCATCTGTCAGAGTGCACATGAAAAATCAGGCAGGAATCGAAACGACA
GCGCTGGAGGAGACTCAGGAAGCAGAGGGCGTCCCTGCCGCTCCCTTGGCCCTGCAAGCACATCATGACCCTTTCTGGC
AGCCTCTTGGTGCTCTGGGTAGTGAGGGATGACCAGTCTTGTCCTGAGAAATGTTCTCTTAGTCTTTAAGTTCAAAGA
CTAACCTGTAGCAATCAGACTTTCCAAAAGGGGTTCTCCATTTTTTGTAGTTTGTCTAAATTTTAATGACCATTTC
CTGGAATCAGTTTATTATTACTGAAAACTGGGGGTGGGAGTAGGAGCTAGTTGTTGATAAATAGTTCCCATTTCCCCG
```

FIG.10A(5)

TGGAGAATTTGACATACCCTGGACTCCTGTGTGCCTCCTGCCATCCCTGCACACAGCCTGGGGAGAAGCCTGTGCCTCC

CCGTGTGGAGAGAAGGCAACCCCAGATCCCCTGAGCTAACCCGGAGGAAAGGCAGTCCTGGACAGAGACTGTCAGCAG

AAGGAAAGTACTGGACTACCCGTGGGTAAGTCCTGCCATTCAAGACTGGAGAGACACCTGGGAAATAAAAGAGCAGGGCA

CTGCTGGTGGGAAGAGGCATTTACCTTCCAGTGCAAATCCTGCTCCTTTGATTTAATGGGGTGTACTGGGGCCAGGGG

CTGATTCACTTCCTTGGGAGATGGTGGTGTTTTCATGAACATCTTTGATCCTTCCATTCATTTATTCATCCATCCATT

CAACAAGTATTTGCTAAACACTAACTTAAGCTAATGTAGGGTAGTGACTGAGACTGAAAAATAGATTTTAGAATTAAA

ACAAAAATCCAAGTCCTCACACCCCTGTCATCCCAGGAGATCTTTCCTTGTGGTGGTTTCTGTGAGAATTGGCCATCCTG

AGGACACAGCCAGGACGGGCAGAGGCCCTCCTGGCCTGGGTTTCTAGATAGCCAGGCCCACCAAGAGATATTGCCCCTTGATGAGAGTCAAA

CAAACTTGGCTCCAGCCATTGCGGGTGGTTTCTAGATAGCCAGGCCCACCAAGAGATATTGCCCCTTGATGAGAGTCAAA

CACCCTGCCTACAAGGAGATGTTTGAAATGGAGAGGAAAATTGGCACCTCATCTTTAAAGGCAGTAATGGAATTGAT

TTTCAGTAACTGAATTTGTGCACAAAACATTCTAAACACTAGTGAAGCCTGTTTCGTTGAACTTAGTTTGTTAATATGTATAATTTAGCATC

ATGTTTTGTTTTATAGTTATTTACGATTTCGTTTGTTTGGATTCAAGCTTAGTTTGTTAATATGTATAATTTAGCATC

TATTACACTCATGTAAATATGGAGTAAGTATTGTAAACTATTTCATTGCGGGGATTGTGGGTGTTATACATACATTTAG

FIG.10A(6)

GACTGCAATTTTTTGGTATTTTTGTATTGTAAAATAACAGCTAATTTAAGCAGGAACAAGAGAACTAAGGGAGGTCTG

TGCATTTTAAACACACAAATGTGAAGAACTTGTATATAAACAAAGTAAATACTATATACAAACTTCCTTCTGAAATAAA

AGTAGATCTGGTAAAAAAAAAAAAAAGAAAAAAAAAAAAAAAAAAGGGCGGCCGC

FIG. 10A(7)

MYYCNKKTSCRSCALDQNCQWEPRNQECIALPENICGIGWHLVGNSCLKITTAKENYDNAKLFCRNHNALLASLTTQKK

VEFVLKQLRIMQSSQSMSKLTLTPWVGPSGRXNVSYXVLGKDMXPILQIVLLQWDXRLEAQCCLXFCGNFXSGTQLLRG

LKAATCIQPTXMVVSVKGLQTTVLRQCRTPCALRTACGDCTSGSSEXHVVQQHEXSVWTPMPMWPPSLLXQCMEWYTMS

TCPPENCSGYCTCSHCLEQPGCGWCTDPSNTGKGKCIEGSYKGPVKMPSQAPTGNFYPQPLLNSSMCLEDSRYNWSFIH

CPACQCNGHSKCINQSICEKCENLTTGKHCETCISGFYGDPTNGGKCQPCKCNGHASLCNTNTGKCFCTTKGVKGDECQ

LCEVENRYQGNPLRGTCYYTLLIDYQFTFSLSQEDDRYYTAINFVATPDEQNRDLDMFINASKNFNLNITWAASFSAGT

QAGEEMPVVSKTNIKEYKDSFSNEKFDFRNHPNITFFVYVSNFTWPIKIQIAFSQHSNFMDLVQFFVTFFSCFLSLLLV

AAVVWKIKQSCWASRRREQLLREMQQMASRPFASVNVALETDEEPPDLIGGSIKTVPKPIALEPCFGNKAAVLSVFVRL

PRGLGGIPPPGQSGLAVASALVDISQQMPIVYKEKSGAVRNRKQQPPAQPGTCI

```
                                                                    Transmembrane
obe2       FRNHPNITFFVYVSNFTWP------IKIQIAFSQHSNFMDLVQFFVTFFSCFLSLLLVA
KIAA0534   FRSNPNITFYVYVSNFSWP------IKIQIAFSQHNTIMDLVQFFVTFFSCFLSLLLVA
YC81_CAEEL FGPDSNITFFVRVYNFNTP------VQIVVSFAQSPPIN-WVLFFVIFAACFIVLLVVA
MEGF8      LKSSRFYLLLLLGVGDPSGPGANGSADSQGLLFFRQDQAHIDLFVFFSVFFSCFLFLSLC
                                          Site obe2       AVVWKIKQSCWASRRREQLLREMQQMASRPFASVETLPWNR-------------------
KIAA0534   AVVWKIKQTCWASRRREQLLRERQQMASRPFASVDVALEVGAEQTEFLRGPLEGAPKPIA
YC81_CAEEL GLLWMIKVRIEAYRRNQRRIDEIEHMASRPFASTKMELSMLSQFSSAG------------
MEGF8      VLLWKAKQALDQRQEQRRHLQEMTKMASRPFAKVTVCFPPDPTAPASAWKP-AGLPPP-A
```

FIG. 16A

```
           10        20        30        40        50        60
inputs  MVAVAAAAATEARLRGSTTTTAAPAGRKGRQHRPCTATGAWRPGPRARLCLPRVLSRALP
        :::  ::::::::::::  :::::  :::  :                  :::
        MVA- AAAATEARLRRRTAATAALAGRSG--------------GPH--------------
          10        20      [    EGF           30
                                                             EGF1
           70        80        90       100       110       120
inputs  PPPLLPLLFSLLLLPLPREAEAAAVAAAVSGSAAAEAKECDRPCVNGGRCNPGTGQCVCP
                                                    ::::::::::::::
        ------------------------------------------- CVNGGRCNPGTGQCVCP
                                                            40

130   CUB 140       150  CUB 160       170       180
inputs  TGWVGEQCQHCGGRFRLTGSSGFVTDGPGNYKYKTKCTWLIEGQPNXIMRLRFNHFATEC
         :::::::::::::::::::::::::::::::::::::::::::::: :::::::::::
        AGWVGEQCQHCGGRFRLTGSSGFVTDGPGNYKYKTKCTWLIEGQPNRIMRLRFNHFATEC
         50   J L 60        70        80   CUB 90       100

190       200       210       220       230       240
inputs  SWDHLYVYDGDSIYAPLIAAFSGLIVPERDGNETAPEVTVTSGYALLHFFSDAAYNLTGF
        ::::::::::::::::: :::::::::::::::: ::: :::::::::::::::::::::
        SWDHLYVYDGDSIYAPLVAAFSGLIVPERDGNETVPEVVATSGYALLHFFSDAAYNLTGF
         110       120       130       140       150       160
              EGF2                                          EGF3
          250       260       270       280       290       300
inputs  NITYNFDMCPNNCSGRGECKSSNSSSXVECECSENWKGXACDIPHCTDNCGFPHRGICNX
        :::: ::::::::::::::::: :::: :::::::::::: :::::::::::::::::::
        NITYSFDMCPNNCSGRGECKISNSSDTVECECSENWKGEACDIPHCTDNCGFPHRGICNS
        170  J L    180 EGF2 190       200       J 210       220
                                                Kelch1        Kelch2
          310       320       330       340       350       360
inputs  SDXRGCSCFSDWQGPGCSVPVPANQSFWTREEYSNLKLPRASHKAVVNGNIMWVVGGYMF
         ::::::::::::::::::::::::::::::::::::::::::::::::::::::::::
        SDVRGCSCFSDWQGPGCSVPVPANQSFWTREEYSNLKLPRASHKAVVNGNIMWVVGGYMF
         230       240       250       260       270       280
                                                 Kelch3
          370       380       390       400       410       420
inputs  NHSDYNMVLAYDLASREWLPLNRSVNNVVVRYGHSLALYKDKIYMYGGKIDSTGNVTNEL
        ::::::::::::::::::::::::::::::::::::::::::::::::::::::::::::
        NHSDYNMVLAYDLASREWLPLNRSVNNVVVRYGHSLALYKDKIYMYGGKIDSTGNVTNEL
         290       300       310       320       330       340
```

FIG.17A

```
                                    kelch4
              430       440       450       460       470       480
inputs  RVFHIHNESWVLLTPKAKEQYAVVGHSAHIVTLKNGRVVMLVIFGHCPLYGYISNVQEYD
        ::::::::::::::::::::::::::::::::::::::::::::::::::::::::::::
        RVFHIHNESWVLLTPKAKEQYAVVGHSAHIVTLKNGRVVMLVIFGHCPLYGYISNVQEYD
              350       360       370       380       390       400
                                    Kelch5
              490       500       510       520       530       540
inputs  LDKNTWSILHTQGALVQGGYGHSSVYDHRTRALYVHGGYKAFSANKYRLADDLYRYDVDT
        ::::::::::::::::::::::::::::::::::::::::::::::::::::::::::::
        LDKNTWSILHTQGALVQGGYGHSSVYDHRTRALYVHGGYKAFSANKYRLADDLYRYDVDT
              410       420       430       440       450       460
                                   Kelch 6nt
              550       560       570       580       590       600
inputs  QMWTILKDSRFFRYLHTAVIVSGTMLVFGGNTHNDTSMSHGAKCFSSDFMAYDIACDRWS
        ::::::::::::::::::::::::::::::::::::::::::::::::::::::::::::
        QMWTILKDSRFFRYLHTAVIVSGTMLVFGGNTHNDTSMSHGAKCFSSDFMAYDIACDRWS
              470       480       490       500       510       520
                                   kelch 1ct
              610       620       630       640       650       660
inputs  VLPRPDLHHDVNRFGHSAVLHNSTMYVFGGFNSLLLSDILVFTSEQCDAHRSEAACLAAG
        :::::::::          :::::::::::::::::::::::::::::::::::::::::
        VLPRPDSTMMSTDLAIPAVLHNSTMYVFGGFNSLLLSDILVFTSEQCDAHRSEAACLAAG
              530       540       550       560       570       580
                                    plexin 1
              670       680       690       700       710       720
inputs  PGIRCVWNTGSSQCISWALATDEQEEKLKSECFSKRTLDHDRCDQHTDCYSCTANTNDCH
        ::::::::::::::::::::::::::::::::::::::::::::::::::::::::::::
        PGIRCVWNTGSSQCISWALATDEQEEKLKSECFSKRTLDHDRCDQHTDCYSCTANTNDCH
              590       600       610       620       630      [640
                                                ligand-binding γcytokine chain
              730       740       750       760       770       780
inputs  WCNDHCVPRNHSCSEGQISIFRYENCPKDNPMYYCNKKTSCRSCALDQNCQWEPRNQECI
        ::::::::::::::::::::::::::::::::::::::::::::::::::::::::::::
        WCNDHCVPRNHSCSEGQISIFRYENCPKDNPMYYCNKKTSCRSCALDQNCQWEPRNQECI
              650       660       670       680       690       700
                                  c-type lectin
              790       800       810       820       830       840
inputs  ALPENICGIGWHLVGNSCLKITTAKENYDNAKLFCRNHNALLASLTTQKKVEFVLKQLRI
        ::::::::::::::::::::::::::::::::::::::::::::::::::::::::::::
        ALPENICGIGWHLVGNSCLKITTAKENYDNAKLFCRNHNALLASLTTQKKVEFVLKQLRI
              710 [     720       730       740       750       760
```

FIG.17B

```
              850       860       870       880       890       900
inputs  MQSSQSMSKLTLTPWVGLRKINVSYWCWEDMSPFTNSLLQWMPSEPSDAGFCGILSEPST
        ::::::::::::::::::::::::::::::::::::::::::::::::::::::::::::
        MQSSQSMSKLTLTPWVGLRKINVSYWCWEDMSPFTNSLLQWMPSEPSDAGFCGILSEPST
         770       780       790       800       810       820
                                                    plexin repeat 2
              910       920       930       940       950       960
inputs  RGLKAATCINPLNGSVCERPANHSAKQCRTPCALRTACGDCTSGSSECMWCSNMKQCVDS
        ::::::::::::::::::::::::::::::::::::::::::::::::::::::::::::
        RGLKAATCINPLNGSVCERPANHSAKQCRTPCALRTACGDCTSGSSECMWCSNMKQCVDS
         830       840       850       860       870       880

970       980       990       1000      1010      1020
inputs  NAYVASFPFGQCMEWYTMSTCPPENCSGYCTCSHCLEQPGCGWCTDPSNTGKGKCIEGSY
        ::::::::::::::::::::::::::::::::::::::::::::::::::::::::::::
        NAYVASFPFGQCMEWYTMSTCPPENCSGYCTCSHCLEQPGCGWCTDPSNTGKGKCIEGSY
         890       900       910       920       930       940
                                                      lamin-like EGF-1
              1030      1040      1050      1060      1070      1080
inputs  KGPVKMPSQAPTGNFYPQPLLNSSMCLEDSRYNWSFIHCPACQCNGHSKCINQSICEKCE
        ::::::::::::::::::::::::::::::::::::::::::::::::::::::::::::
        KGPVKMPSQAPTGNFYPQPLLNSSMCLEDSRYNWSFIHCPACQCNGHSKCINQSICEKCE
         950       960       970       980       990       1000
                                                      lamin-like EGF-2
              1090      1100      1110      1120      1130      1140
inputs  NLTTGKHCETCISGFYGDPTNGGKCQPCKCNGHASLCNTNTGKCFCTTKGVKGDECQLCE
        ::::::::::::::::::::::::::::::::::::::::::::::::::::::::::::
        NLTTGKHCETCISGFYGDPTNGGKCQPCKCNGHASLCNTNTGKCFCTTKGVKGDECQLCE
         1010      1020      1030      1040      1050      1060

1150      1160      1170      1180      1190      1200
inputs  VENRYQGNPLRGTCYYTLLIDYQFTFSLSQEDDRYYTAINFVATPDEQNRDLDMFINASK
        ::::::::::::::::::::::::::::::::::::::::::::::::::::::::::::
        VENRYQGNPLRGTCYYTLLIDYQFTFSLSQEDDRYYTAINFVATPDEQNRDLDMFINASK
         1070      1080      1090      1100      1110      1120

1210      1220      1230      1240      1250      1260
inputs  NFNLNITWAASFSAGTQAGEEMPVVSKTNIKEYKDSFSNEKFDFRNHPNITFFVYVSNFT
        ::::::::::::::::::::::::::::::::::::::::::::::::::::::::::::
        NFNLNITWAASFSAGTQAGEEMPVVSKTNIKEYKDSFSNEKFDFRNHPNITFFVYVSNFT
         1130      1140      1150      1160      1170      1180
```

FIG.17C

```
                                         TM
              1270      1280      1290      1300      1310      1320
inputs   WPIKIQIAFSQHSNFMD[LVQFFVTFFSCFLSLLLVAAVVWKI]KQSCWASRRREQLLREMQ
         :::::::.                                      :.         ::
         WPIKIQV-------------------------------------QT       EQ-----
         1190

1330      1340      1350      1360      1370      1380
inputs   QMASRPFASVNVALETDEEPPDLIGGSIKTVPKPIALEPCFGNKAAVLSVFVRLPRGLGG

------------------------------------------------------------

1390      1400      1410      1420
inputs   IPPPCQSGLAVASALVDISQQMPIVYKEKSGAVRNRKQQPPAQPGTCIN

------------------------------------------------
```

FIG.17D

ATGGTGGCGGTGGCCGCAGCGGCGGCGGCAACTGAGGCAAGGCTGAGGAGGAGGACGGGCGGGCAGGAGCGGGGGCC

GCACCGACCCTGCACCGCGACAGGGGCCTGGAGGCCTGGAGGCGGGACCCGCGCCCGGCTGTGTCTCCCCGGGTGCTGTCGCGGGGCTGCCCCGC

CGCCGCTGCTGCCGCTGCTCTTTTCGCTGCTGCTGCTGCGCTGCCCCGGGAGGCCGAGGCCGCTGCCGGGTGGCGGCGGCGGTGTCCGGCTCG

GCCGCAGCCGAGGCCAAGGAATGTGACCGGCGTCGCTGCAACCCTGGCACCGGCCAGTGCGTCTGCCCCGCCGGCTG

GGTGGGCGAGCAATGCCAGCACTGCGGGGGCCGCTTCAGAGACTAACTGGATCTTCTCGGGTTTGTGACAGATGGACCTGGAAATTATAAATACA

AAACGAAGTGCACGTGGCTCATTGAAGGACTCAATTTATGCACCGCTAGTTGCTGCATTTTTTAGTGATGCTGCTTATAATTTGACTGGATTTAATATTACTTACAGTT

CCCTGAGGTTGTTGCCACATCAGGTTATGCCTTGCTGAGGAGAGTGTAAGATCAGTAATAGCAGCGATACTGTTGAATGTGAAAACTGG

TTGATATGTGTCCAAATAACTGCTCAGGCCGAGGAGGAGAGTGTAAGATCAGTAATAGCAGCGATACTGTTGAATGTGAATGTTCTGAAAACTGG

AAAGGTGAAGCATGTGACATTCCTCACTGTACAGACAACTGTGGTTTTCCTCATCGAGGCATCTGCAATTCAAGTGATGTCAGAGAGGATGCTC

CTGCTTCTCAGACTGGCAGGGTCCTGGATGTTCAGTTCCTGTACCAGTCATTTGGACTCGAGAGGAATATTCTAACTTAAAGC

TCCCCAGAGCATCTCATAAAGCTGTGTCAATGGAAACATTATGTGGTTGTTGGAGGATATATGTTCAACCACTCAGATTAACATGGTT

CTAGCGTATGACCTTGCTTCTAGGGAGTGGCTTCCACTAAACCGTTCTGTGAACAATGTGGTTGTTAGATATGGTCATTCTTTGGCATTATA

FIG.18A(1)

```
CAAGGATAAAATTACATGTATGGAGGAAAAATTGATTCAACTGGGAATGTGACCAATGAGTTGAGAGTTTTTCACATTCATAATGAGTCAT
GGGTGTTGTTGACCCCTAAGGCAAAGGAGCAGTATGCAGTGGTTGGGCACTCTGCACACATTGTTACACTGAAGAATGGCCGAGTGGTCATG
CTGGTCATCTTTGGTCACTGCCCTCTCTATGGATATATAAGCAATGTGCAGGAATATGATTTGGATAAGAACACATGGAGTATATTACACAC
CCAGGGTGCCCTTGTGCAAGGGGTTACGGCCATAGCAGTGTTTACGACCATAGGACCAGGGCCCTATACGTTCATGGTGGCTACAAGGCTT
TCAGTGCCAATAAGTACCGGCTTGCAGATGATCTCTACCGATATGATGAGTGGATACCCAGATGTGGACCATTCTTAAGGACAGCCGATTTTC
CGTTACTTGCACACAGCTGTGATAGTGAGTGGAACCATGCTGGTGTTTGGGGGAAACACACACAATGACACATCTATGAGCCATGCGCCAA
ATGCTTCTCTTCAGATTTCATGGCCTATGACATTGCCTGTGACCGCTGGTCAGTGCTTCCCAGACCTGATCTCCACCATGATGTCAACAGAT
TTGGCCATTCAGCAGTCTTACACAACAGCACCATGTATGTGTTCGGTGGTTTCAATAGTCTCCTCCTCAGCGACATCCTGGTATTCACCTCG
GAACAGTGTGATGCGCATCGGAGTGAAGCCGCTTGTTTAGCAGCAGGACCTGGTATTCGGTGTGTGTGGAACAGGGTGTCTCAGTGTAT
CTCGTGGGCGCTGGCAACTGATGAACAAGAGAAAAAGTTAAAATCAGAATGTTTTCCAAAAGAACTCTTGACCATGACAGATGTGACCAGC
ACACAGATTGTTACAGCTGCACAGCCAACACCAATGACTGCCACTGTACTGTAACCCTATGTACTGTAACAAGAAGACCAGCTGCAGGAGCTGTGCCCTGGA
CAGATCTCCATTTTTAGGTATGAGAATTGCCCCAAGGATAACCCTATGTACTGTGCCCGAAAATATCTGTGGCATTGGCTGGCATTTGGAAACTCAT
CCAGAACTGCCAGTGGGAGCCCCGGAATCAGGAGTGCATTGCCCTGCCCTGCCCGAAAATATCTGTGGCATT
```

FIG. 18A(2)

```
GTTTGAAAATTACTACTGCCAAGGAGAATTATGACAATGCTAAATTGTTCTGTAGGAACCACAATGCCCTTTGGCTTCTCTTACAACCCAG
AAGAAGGTAGAATTTGTCCTTAAGCAGCTGCGAATAATGCAGTCATCTCAGAGCATGTCCAAGCTCACCTTAACCCATGGGTCGGCCTTCG
GAAGATCAATGTGTCTCCTGGTGCTGGGAAGATATGTCCCCATTTACAAATAGTTTACTACAGTGGATGCCGTCGAGCCCAGTGATGCTG
GATTCTGTGGAATTTTATCAGAACCCAGTACTCGGGGACTGAAGGCTGCAACCTGCATCAACCCACTCAATGGTAGTGTCTGTGAAAGGCCT
GCAAACCACAGTGCTAAGCAGTGCCGGACACCATGTGCCTTGAGGACAGCATGTGGAGATTGCACCAGCGGCAGCTCTGAGTGCATGTGGTG
CAGCAACATGAAGCAGTGTGTGGACTCCAATGCCTATGTGGCCTCCTTCCCTTTGGCCAGTGTATGGAATGGTATACGATGAGCACCTGCC
CCCCTGAAAATTGTTCAGGCTACTGTACCTGTAGTCATTGCTTGGAGCAACCAGGCTGTGGCTGGTACTGATCCCAGCAATACTGGCAAA
GGGAAATGCATAGAGGGTTCCTATAAAGGACCAGTGAAGATGCCTTCGCCAAGCCCCTACAGGAAATTTCTATCCACAGCCCTGCTCAATTC
CAGCATGTGTCTAGAGGACAGAGATACAACTGGTCTCTTTCATTCACTGTGTCCAGCTTGCCAATGCAACGGCCACAGTAAATGCATCAATCAGA
GCATCTGTGAGAAGTGTGTGAACCTGACCACCAGCAAGCACTGCGAGACCTGCATATCTGGCTTCTACGGTGATCCACCAATGGAGGGAAA
TGTCAGCCATGCAAGTGCAATGGGCACGCGTCTCTGTGCAACACCAAGGGCAAGTGCTTCTGCACCACCAAGGGGCGTCAAGGGGACGA
GTGCCAGCTATGTGAGGTAGAAAATCGATACCAAGGAAACCCTCAGAGGAACATGTTATTATACTCTTCTTATTGACTATCAGTTCACCT
TTAGTCTATCCCAGGAAGATGATCGCTATTACACAGCTATCAATTTGTGGCTACCTCCTGACGAACAAAACAGGGATTTGGACATGTTCATC
```

FIG.18A(3)

```
AATGCCTCCAAGAATTTCAACCTCACACATCACCTGGGCTGCCAGTTTCTCAGCTGGAACCCAGGCTGGAGAAGAGATGCCTGTTGTTTCAAA
AACCAACATTAAGGAGTACAAAGATAGTTTCTCTAATGAGAAGTTTGATTTTCGCAACCACCCAAATATCACTTTCTTTGTTTATGTCAGTA
ATTTCACCTGGCCCATCAAAATTCAGATTGCCTTCTCTCAGCACAGCAATTTATGGACCTGTACAGTTCTTCCTGTACTTCTTCAGTTGT
TTCCTCTCTTTGCTCCTCTGGTGGCTGCTGTGGTTTGGAAGATCAAACAAAGTGTTGGGCCTCCAGACGTAGAGAGCAACTTCTTCGAGAGAT
GCAACAGATGGCCAGCCGTCCCTTTGCCTCTGTAAATGTGCCTTGGAAACAGATGAGGAGCCTCCTGATCTTATTGGGGGAGTATAAAGA
CTGTTCCCAAACCATTGCACTGGAGCCGTGTTTGGCAACAAAGCCGTCTCCTCTCTGTGTTGTGAGGCTCCCTCGAGGCCTGGGTGGC
ATCCCTCCTCCTGGGCAGTCAGGTCTTGCTGTGTGGCCAGCCCTGGTGACCTGCATCTGATGCTGGGGGCCAGGGACTCTCCCACGCACGAGCTAGTG
AGCCGTGAGAAACCGAAGCAGCCATCTGCAGGGAAGGGCGTGGCGGGGAAATGGCTGTGTGCGGTGCGGGACGGAAGACTGAAACCCTCAAAGCATCTG
AGTGGCACACCAGAGCCATCTGCAGGGAAGCTTTCTTTGACGGTTCTCTGCTGAGGAGGCCAGTGTGAGAGCCAGTAGAATGACACTCAGGTTCACTGT
ACTCACCTGCATGATCACACAAGCTTTCTTTGACGGTTCTCTGCTGAGGAGGCCAGTGTGAGAGCCAGTAGAATGACACTCAGGTTCACTGT
TTAATTACAGGTCCAGGATGAGCTGATGTTGCTCAACTGTGCAAAAACAAAAGATGGAGTGTTACAAGTAGACATTCGTCATCAGTTGTTCTTGAACAT
GGAAAACTGTTCTTGGGACTGTCTCAACTGTGCAAAAACAAAAGATGGAGTGTTACAAGTAGACATTCGTCATCAGTTGTTCTTGAACAT
GGTCTTTTAAAAACTAGTCAGATGAATTAACTTGTTTCATCTGAAGCCTGCTATCTTTTAAAAGATGTGCTATTATTCTGCACGATT
```

FIG.18A(4)

```
TAGGCAATTATCTCTCTTCCAGGGAGTACCTTTTTTTCTAGTTGAGAATTAATAATGGTCCATCTCTTTGATCATATCAAGCTAGGATAGA

AGGGGGGCTATTTAAATGTCAAGGTCAGCAGTGTTACTTTGAATGTAAACTGGTATAATAGGTAGTTTTCTATAGTAACTTGATTAATTTA

GTCTTAATCCATTTGAAACTCTCTCTTCCTTCTCTCTGCCTGTCCCTCTCCTTCTCCACATACACACACA

AACACATACACACAAACACTAAGTGCCTAGACTTTAAATAGATCTAGCAATTGGAAAGTTAGTAAGCCTAAGTTTTACATAATTGCATTCCT

ACATTCTTGTAAAATTTAAATAGCTACCATTGGCAATCTGCTTTTTTCTAAAATCTGATTTGCAGCCAGGAAAGAATTTTCTCACCCAAGG

AACATTTGATCTAGCAGCAGGGATGAGAGGAAAGCAGAAATGAATGAACTGTGAAAGCTCCTGTTTTATTATCAAAAGGACACTGTCAAG

AAGGCGCCCCTGCCCCACCCCGTGTCACCCTAGGCCTGATAAGGCATCAGAGAGCATCTGTGTCCTGCAGCCTCCTCTGAACTTGTGGTTCATTCTCAGGCTGGG

AAGAGCACTGAGAGCACTTGGGACCCCTGGACCCTCCCATTGTCAGGCAGAAGCTGCCCAAAGCCTGGAGAGGCAGCAAATGCTGACAAGGATGAAAAGCACATGG

GTGGACTCAGATGCCAGGAAAGGGACAGCCTCCCATTGTCAGGCAGAAGCTGCCCAAAGCCTGGAGAGGCAGCAAATGCTGACAAGGATGAAAAGCACATGG

AGGAGGGGCTCGACCCACCCCACCCTCTCAGACCAAGGTGTGGCTGTGTGAGGAGGGCAGCAAATGCTGACAGTCCCCTGCTCCTCTCCCAGAGGGCA

AAAAAAATGGACGAGGAGGAAAACTCTGCCAAATGGAAAATGACCAAATTTAAGAGGGTGGGACAGTCCCCTGCTCCTCTCCCAGAGGGCA

CTGCTTGGAAATTGTGTTTCCCCATTTATGGTGCTCTGTATTCTGGCATTATGCAGCAGCCTCCCAGAAGCTCTCTTCTGCTTCAAAACCT

GGGATCTCTGGCATTACCCTATTGGGATGGACCGCTGGACAGCAATGCTCGAGTTTGTGAATTTGGAGAGATACTCAAAAGAGCTAAAACTG
```

FIG.18A(5)

CAGCATTTTACCTTTAAATGCAGTGCCTAGAGAGAGAGTATTGTCTCTTCCCAACACTAACCCCACTCCCATGAAGAATTGCCTGGAAAGA

TGTTTCAAGGAATTTGAACCATAAAAACACTATCTGATGCACAGAAACACCTCTACTTTGAGACTCACCTCTCATAAAGCTTCTTTTCACAT

TACTGTTAAAGACCAGACGTTCTAGAAAAGACCCCTCCTCTCATGAGCTCCCCATCCCTGCTACAGAACACAGCACCCATGGGCGCTGCAG

TGGACTGGCCCCTTAATTCCCACAGGCCAAGGAGGCCCCTGGGTATTGTCCTCCTACAAGGAAGATCTCTTTGTT

TGTTCAAAGGACCAGTTTTCCTAGGCCAAAGAAGTCTCTTCCCCATGTAGTCCTATGCCTTGAAATATCATGCACCATGACCCACAGCCAT

CTGGTTATGTCTCTTATTTTTTCCTAAAGATAATGTTTATTTTAAAAAGGAAGAAGCAAGTGAAGTTTCATTCTGCTCCAGCGGTGG

GGAAGCCGCTGAATCCACTGCTTCTCCTTTGCAACCGACAGCAAACAGCTTTCTCCGGCCTCAGGGCAGAAAAAAGGGAATGGCAGGGAGTA

AGAGGGCGCTGGGCTCGGAGCCTGTTCCAAGGAATTGGTTGTCATCTGGCAGTGTTGCGCGTCACAAGAGAGCCTGTATATAAATTAAA

ATAGTCAAGACAACACTGACCTTGCACTGTGTACATAACTATACAGTAGTGTCCAGAATGTTCAGACATTCGGAGTGTACATAAACAGAAAA

AATCTTCATGTATTTTTATTAAATATAACAATGTCTGAGTTTCACCTAAGATGTTTTTGTGCCATATGCTGGATATCCAGGTTCTCGCCAGG

CCCGATACATGAATAACAAACCCAAGAAACGCATCCCCATTGTGATGTTCAGATGCATCTGGCACCAATTAGGTATTTCTTAAAACA

GGACTCATCTGTCAGAGTGCACATGAAAAATCAGGCAGGAATCGAAACGACAGGCTGGAGGAGACTCAGGAAGCAGAAGGCGTCCCTGCCG

CTGCCCTTGGCCCTGCAAGCACACATGACCCTTTCTGGTCCTCTTGGTGCTCTGGGTAGTGAGGGATGACCAGTCTTGTCCTGAGAAAT

FIG.18A(6)

```
GTTCTCTTAGTCTTTAAGTTCAAAGACTAACCTGTAGCAATCAGACTTTCCAAAAGGGGGTTCTCCATTTTTTGTAGTTTTGTCTAAATTT

TTAATGACCATTTCCTGGAATCAGTTTATTATACTGAAAACTGGGGGTGGGAGTAGGGAGCTAGTTTGTTGATAAATAGTTCCCATTTCCCC

GTGGAGAATTTGACATACCCTGGACTCCTGTGTGCCTCCTGCACACAGCCTGGGGAGAAGCCTGTGCCTCCCGTGTGGAGAG

AAGGCAACCCCAGATCCCCTGAGCTAACCCGGAGAAAGGCAGTCCTGGACAGAAGACTGTCAGCAGAAGGAAAGTACTGGACTACCCGTGG

GTAAGTCCTGCCATTCAAGACTGGAGACACCTGGGAAATAAAAAGAGCAGGGCACTGCTGGTGGGAAGAGGCATTTACCTTCCAGTGCAAA

TCCTGCTCCTTTGATTAATGGGGTGTACTGGGGCCAGGGCTGATTCACTTCCTGGGAGATGGTGGTGTTTTCATGAACATCTTTGATCC

TTCCATTTCATTTATTCATCCATTCAACAAGTATTGCTAAACACTAACTTAAGCTAATGCTAGGGTAGTGACTGAGATGTAAAAATA

GATTTTAGAATTAAAACAAAATCCAAGTCCTCCACACCCCTGTCATCCCAGGAGATCTTTCCTTGGTGTTCTGTGAGAATTGGCCATCC

TGAGGACACAGCCAGGAGGGCAGAGGCCTCCTGGCCTCAGGGCATGCCCTGCCTACCTTCTGAAATGTTACCCCATTGACCAAACTTGGCT

CCAGCCATTGCGGTGGTTTCTAGATAGCCAGGCCCACCAGGAGATATTGCCCTTGATGAGAGTCAAACACCCTGCCTACAAGGAGATGTTT

TGAAATGGAGAGGAAAATTGGCACCTCATCTTTTAAAGGCAGTAATGAATTGATTTTCAGTAACTGAATTTGTCACAAAACATTCTAAAC

ACTAGTGAAGCCTGTTTCGTTGAACTAATTCTGGCTCTGGAAATGTTTTTGTTTATAGTTATTTACGATTTCGTTTGTTTGGATTCAAGCT

TAGTTTGTTAATATGTATAATTTAGCATCTATTACACTCATGTAAATATGGAGTAAGTATTGTAAACTATTTCATTGCGGGGATTGTGGGTG
```

FIG.18A(7)

TTATACATACATTTAGGACTGCAATTTTTTGGTATTTTTTGTATTGTAAAATAACAGCTAATTTAAGCAGGAACAAGAGAACTAAGGGAGGT

CTGTGCATTTTAAACACAAATGTGAAGAACTTGTATATAAAACAAAGTAAATACTATAATACAAACTTCCTTCTGAAATAAAAGTAGATCTG

GTAAAAAAAAAAAGAAAAAAAAAAAAAAA

FIG.18A(8)

MVAVAAAATEARLRRRTAATAALAGRSGGPHRPCTATGAWRPGPRARLCLPRVLSRALPPPPLLPLLFSLLLLPLPREAEAAAVAAAVSGS

AAAEAKECCDRPCVNGGRCNPGTGQCVCPAGWVGEQCQHCGGRFRLTGSSGFVTDGPGNYKYKTKCTWLIEGQPNRIMRLRFNHFATECSWDH

LYVYDGDSIYAPLVAAFSGLIVPERDGNETVPEVVATSGYALLHFFSDAAYNLTGFNITYSFDMCPNNCSGRGECKISNSSDTVECECSENW

KGEACDIPHCTDNCGFPHRGICNSSDVRGCSCFSDWQGPGCSVPVPANQSFWTREEYSNLKLPRASHKAVVNGNIMWVGGYMFNHSDYNMV

LAYDLASREWLPLNRSVNNVVVRYGHSLALYKDKIYMYGGKIDSTGNVTNELRVFHIHNESWVLLTPKAKEQYAVVGHSAHIVTLKNGRVVM

LVIFGHCPLYGYISNVQEYDLDKNTWSILHTQGALVQGGYGHSSVYDHRTRALYVHGGYKAFSANKYRLADDLYRYDVDTQMWTILKDSRFF

RYLHTAVIVSGTMLVFGGNTHNDTSMSHGAKCFSSDFMAYDIACDRWSVLPRPDLHHDVNRFGHSAVLHNSTMYVFGGFNSLLLSDILVFTS

EQCDAHRSEAACLAAGPGIPCVWNTGSSQCISWALATDEQEEKLKSECFSKRTLDHDRCDQHTDCYSCTANTNDCHWCNDHCVPRNHSCSEG

QISIFRYENCPKDNPMYYCNKKTSCCRSCALDQNCQWEPRNQECIALPENICGIGWHLVGNSCLKITTAKENTDNAKLFCRNHNALLASLTTQ

KKVEFVLKQLRIMQSSQSMSKLTLTPWVGLRKINVSYWCWEDMSPFTNSLLQWMPSEPSDAGFCGILSEPSTRGLKAATCINPLNGSVCERP

ANHSAKQCRTPCALRTACGDCTSGSSECMWCSNMKQCVDSNAYVASFPFGQCMEWYTMSTCPPENCSGYCTCSHCLEQPGCGWCTDPSNTGK

GKCIEGSYKGPVKMPSQAPTGNFYPQPLLNSSMCLEDSRYNWSFIHCPACQCNGHSKCINQSICEKCENLTTGKHCETCISGFYGDPTNGGK

CQPCKCNGHASLCNTNTGKCFCTTKGVKGDECQLCEVENRYQGNPLRGTCYYTLLIDYQFTFSLSQEDDRYYTAINFVATPDEQNRDLDMFI

FIG. 18B

NASKNFNLNITWAASFSAGTQAGEEMPVVSKTNIKEYKDSFSNEKFDFRNHPNITFFVYVSNFTWPIKIQIAFSQHSNFMDLVQFFVTFFSC

FLSLLLVAAVWKIKQSCWASRRREQLLREMQQMASRPFASVNVALETDEEPPDLIGGSIKTVPKPIALEPCFGNKAAVLSVFVRLPRGLGG

IPPPGQSGLAVASALVDISQQMPIVYKEKSGAVRNRKQQPPAQPGTCICWGQGLSHARASEWHTRAICREGRGGEMAVRCGTEDWKPSKHLT

HLHDHKLSLTVSPIRVPASNLLLLHRKYLILQVQGADGCWRRPVSQENEHSGSLWKTVLGTVSTVQKTKDGVFTSRHSSSVVLEHGLLKTSQ

MNLVFISLLSFLKDVLFILARFRQLSLFQGVPFFLVENWSISFDHIKLGKGGYFKCQGQQCYFECKLVVVFYSNLINLVLIHLKLSLPFSLP

VPLLLHLTLPLSHIHTQTHTHNTKCLDFKIQLESAVFTLHSYILVKFKLPLAICFFSKIFAARKEFSHPRNISSSRDERKAEMNELKLLFLL

SKRTLSRRRPLPPPCHPRPDKRSEERTHSCHASLSRKEHEHLGPLDQRASVCPAASSELVVHSQAGVDSDARKGTASHCQAEAAQSLEKDL

FALFPPGGARPTHPPSQTKVVAVRRAANADKDEKHMEKNGRGGKTLPNGKPNLRGWDSPLLLSQRALLGNCVFPIYGALYSGIMQQPPRSSL

LLQNLGSLALPYWDGPLDSNARVCEFGEILKRAKTAAFYLMQCLEREYCLFPNTNPTPMKNCLERCFQGITIKHYLMHRTPLLDSPLIKLLF

HITVKDQTFKRPLLSAPPSLLQNTAPMAPAVDWPLNSHRPPQQGQREAPGYCPPTRKILFVCSKDQFSAKEVSSPCSYALKYHAPPTAIWLC

LIFFLKDNVYFKGRKKQVKFHSAPAVGKPLNPPASPLQPTANSFLRPQGRKREMQGVRGAGLGACFQEGIGCHLAVLRVTREPVYKLKSRQH

PCTCTLYSSVQNVQTFGVYIKQKKSSCIFIKYNNVVSPKMFLCHMLDIQVLARPRYMNNKPKKRIPIVCVQMHLAPIRYFLKQDSSVRVHMK

NQAGNRNDSAGGDSGSRGVPAAALGPASTSPFLAASWCSGGMTSLVLRNVSLSLVQRLTCSNQTFQKGVLHFLFCLNPFPGISLLYKLGVG

FIG. 18C

VGSFVDKFPFPRGEFDIPWTPVCLLPSLHTAWGEACASPCGEKATPDPLSPGGKAVLDRRLSAEGKYWTTRGVLPFKTGDTWEIKRAGHCWW

EEAFYLPVQILLLFNGVYWGQGLIHFLGRWWCFHEHLSFHFIYSSIHSTSICTLTANARVVTEMKILELKQNPSPHTPVIPGDLSLWWFLEL

AILRTQPGRQRPPGLRACPAYLLKCLPHPNLAPAIAVVSRPGPPRDIAPESNTLPTRRCFEMERKIGTSSFKGSNGIDFQLNLCTKHSKHSL

FRTNSGSGNVFVLLFTISFVWIQAFVNMYNLASITLMIWSKYCKLFHCGDCGCYTYIDCNFLVFFVLNNSFKQEQENGRSVHFKHKCEELVY

KQKILYKLPSEIKVDLVKKKEKKKKK

FIG. 18D

ATGGTGGGCGGTGGCCAGCGGCGGGCAACTGAGGCAAGGCTGAGGAGGAGACGGCGGCGACGCAGCGCTCGCGGGCAGGAGGCGGCGGGCCGCACCGACCCTGCACC

GCGACAGGGGCCTGGAGGGCCGGGACCGCGCGGCCCGGCTGTGTCTCCCCGGGTGCTGTGTCGCGGGCGCTGCCCGCGCTGCTGCCGCTGCTCTTTTCGCTGCTG

CTGCTGCCGCTGCCCCCGGGAGGCCGAGGCCGCTGCGGTGGCGGCGGCGGTGTCCGGCTCGGCCGCAGCCGAGGCCAAGGAATGTGACCGGCGTGTGTCAACGGCGGT

CGCTGCAACCCTGGCACCGGCCAGTGCGTCTGCGCCCCGGCTGGGTGGGCGAGCAATGCCAGCACTGCGGGGGGCCGCTTCAGACTAACTGGATCTTCTGGGTTTGTG

ACAGATGGACCTGGAAATTATAAATACAAACGAAGTGCACGTGGCTCATTGAAGGACAGCCAAATAGAATAATGAGACTTCGTTTCAATCATTTTGCTACAGAGTGT

AGTTGGGACCATTTATATGTTTATGGGGACTCAATTTATGCACCGCTAGTTGCTGCATTAGTGGCCTCATTGTTCCTGAGAGAGATGGCAATGAGACTGTCCCT

GAGGTTGTTGCCACATCAGGTTATGCCTTGCTGCATTTTTTAGTGATGCTGCTTATAATTGACTGGATTAATATTACTACAGTTTGATATGTGTCCAAATAAC

TGCTCAGGCCGAGGAGAGTGTAAGATCAGTAATAGCAGCGATACTGTTGAATGTTCTGAAAACTGGAAAGGTGAAGCATGTGACATTCCTCACTGTACAGAC

AACTGTGGTTTTCCTCATCGAGGCATCTGCAATTCAAGTGATGTCAGAGGATGTCCTCTGCTTCTCAGACTGGCAGTGTCCTGGATGTTCAGTTCCTGTACCAGCTAAC

CAGTCATTTTGGACTCGAGAGGAATATTCTAACTTAAAGCTCCCCAGAGCATCTCATAAAGCTGTGGTCAATGAAACATTATGTGGGTTGTTGGAGGATATATGTTC

AACCACTCAGATTATAACATGGTTCTAGCCGTATGACCTTGCTTCTAGGAGTGGCTTCCACTAAACCGTTCTGTGAACAATGTTCTGTGAACAATGTGGTTGTTAGATATGGTCATTCTTG

GCATTATACAAGGATAAAATTTACATGTATGGAGGAAAAATTGATTCAACTGGGAATGTGACCAATGAGTTGAGAGTTTTCACATTCATAATGAGTCATGGGTGTTG

TTGACCCCTAAGGCAAGGAGCAGTGGTTGGGCACTCTGCACACATTGTTACACTGAAGAATGGCCGAGTGGTCATGCTGGTCATCTTTGGTCACTGCCCT

FIG. 19A

```
CTCTATGGATATATAAGCAATGTGCAGGAATATGATTTGGATAAGAACACATGGAGTATATTACACACCCAGGGTGCCCTTGTGCAAGGGGTTACGGCCATAGCAGT

GTTTACGACCATAGGACCAGGGCCCTATACGTTCATGGTGGCTACAAGGCTTTCAGTGCCAATAAGTACCGGCTTGCAGATGATCTCTACGATATGATGTGGATACC

CAGATGTGGACCATTCTTAAGGACAGCCGATTTTTCCGTTACTTGCACACAGCTGTGATAGTGAGTGGAACCATGCTGGTGTTTGGGGGAAACACACACAATGACACA

TCTATGAGCCATGGGCCAAATGCTTCTCTTCAGATTTCATGGCCTATGACATTGCCTGTGACCGCTGGTCAGTGCTTCCCAGACCTGATCTCCACCATGATGTCAAC

AGATTGGCCATTCAGCAGTCTTACACAACAGCACCATGTATGTGTTCGGTGGTTCAATAGTCTCTCCTCAGCGACATCCTGGTATTCACCTGGAACAGTGTGAT

GCGGCATCGGAGTGAAGCGCTTGTTTAGCAGCAGGACCTGGTATTCGGTGTGTGGAACACAGGGTCGTCTCAGTGTATCTCGTGGGCGCTGGCAACTGATGAACAA

GAAGAAAAGTTAAAATCAGAATGTTTTCCAAAAGAACTCTTGACCATGACAGATGTGACCAGCACAGCCAACACCAATGACTGCCAC

TGGTGCAATGACCATTGTGTCCCCAGGAACCACAGCTGCTCAGAAGGCCAGATCTCCATTTTAGGTATGAGAATTGCCCCAAGGATAACCCTATGTACTACTGTAAC

AAGAAGAGACCAGCTGCAGGAGCTGTGCCCTGGACAGAACTGCCAGTGGGAGCCCCGGAATCAGGAGTGCATTGCCCTGCCCGAAAATATCTGTGCCATTGGCTGGCAT

TTGGTTGGAAACTCATGTTTGAAAATTCCTTAAGCAGCTGCGAATAATGCAGTCATCTCAGAGCATGTCCAAGCTCACCTTAACCCATGGGTCGGCCTTCGGAAGATCAATGTGTCC

AAGAAGGTAGAATTTGTCCTTAAGCAGCTGCGAATATGTCCCCATTTACAAATAGTTTACTACAGTGGATGCGTCTGAGCCCAGTGATGCTGGAATTCTGTGGAATTTATCAGAACCCAGTACT

TACTGGTGCTGGGAAGATATGTCCCCATTTACAAATAGTTTACTACAGTGGATGCGTCTGAGCCCAGTGATGCTGGATTCTGTGGAATTTATCAGAACCCAGTACT

CGGGGACTGAAGGCTGCAACCTGCATCAACCTCAATGGTAGTGTCTGTGAAAGGCCTGCAAACCACAGTGCTAAGCAGTGCCGGACACCATGTGCCTTGAGGACA
```

FIG.19B

GCATGTGGAGATTGCACCAGGCGGCAGCTCTGAGTGTCATGTGGTGCAGCAACATGAAGCAGTGTGTGGACTCCAATGCCTCCTTCCCTTTTGGCCAGTGT

ATGGAATGGTATACGATGAGCACCTGCCCCCCTGAAAATTGTTCAGGCTACTGTACCTGTAGTCATTGCTTGGAGCAACCAGGCTGTGGCTGGTGTACTGATCCCAGC

AATACTGGCAAAGGGAAATGCATAGAGGGTTCCTATAAAGGACCAGTGAAAGATGCCTTCGCAAGCCCTACAGGAAATTTCTATCCACAGCCCTGCTCAATTCCAGC

ATGTGTCTAGAGGACAGCAGATACAACTGGTCTTTTCATTCACTGTCCAGCTTGCCAATGCAACGGCCACAGTAAATGCATCAATCAGAGCATCTGTGAGAAGTGTGAG

AACCTGACCACAGGCAAGCACTGCGAGACCTGCATATCTGGCTTCTACGGTGATCCCACCAATGGAGGGACGAGTGCCAGCTATGTGAGGTAGAAAATGCGATACCAAGGAAACCCTCTCAGAGGA

TGCAACACACCAACACGGGCAAGTGCTTCTGCACCACCAAGGGCGTCAAGGGGGACGAGTGCCAGCTATGTGAGGTAGAAAATGCGATACCAAGGAAACCCTCTCAGAGGA

ACATGTTATTATACTCTTCTTATTGACTATCAGTTCACCTTTAGTCTATCCCAGGAAGATGATCGCTATTACACAGCTATCAATTTGTGGCTACTCCTGACGAACAA

AACAGGGATTTGGACATGTTCATCAATGCCTCCCAAGAATTTCAACCTCAACATCACCTGGGCTGCCAGTTTCTCAGCTGGAACCCAGGCTGGAGAAGAGATGCCTGTT

GTTTCAAAAACCAACATTAAGGAGTACAAAGATAGTTTCTCTAATGAGAAGTTTGATTTTCGCAACCACCCAAATATCACTTTCTTTGTTTATGTCAGTAATTTCACC

TGGCCCATCAAAATTCAGGTGCAAACTGAACAATGAGGACGCATGGACACAGGAAGGGAACATCACACACCAGGCCTGTTGTGGGGTGGGGGAAGGGGAAGGGAT

AGCATTAGGGGATATACCTAATGTTAAATGACGAGTTAATGGGTGCAGCACACCAACATGGCATATGTATACATATGTAACAAACCTGCATGTTGTGCACATGTACCC

TAAAACTTAAAGTATAATTAAAAAAAAAAAAAAGAAAAAAAAAAAAAAAAAAAAAAAAAAAAAAAAA

FIG. 19C

MVAVAAAATEARLRRRTAATAALAGRSGGPHRPCTATGAWRPGPRARLCLPRVLSRALPPPPLLPLLFSLLLLPLPREAEAAAVAAVSGSAAAEAKECDRPCVNGG

RCNPGTGQCVCPAGWVGEQCQHCGGRFRLTGSSGFVTDGPGNYKYTKCTWLIEGQPNRIMRLRFNHFATECSWDHLYVYDGDSIYAPLVAAFSGLIVPERDGNETVP

EVVATSGYALLHFFSDAAYNLTGFNITYSFDMCPNNCSGRGECKISNSSDTVECECSENWKGEACDIPHCTDNCGFPHRGICNSSDVRGCSCFSDWQGPGCSVPVPAN

QSFWTREEYSNLKLPRASHKAVVNGNIMWVGGYMFNHSDYNMVLAYDLASREWLPLNRSVNNVVVRYGHSLALYKDKIYMYGGKIDSTGNVTNELRVFHIHNESWVL

LTPKAKEQYAVVGHSAHIVTLKNGRVVMLVIFGHCPLYGYISNVQEYDLDKNTWSILHTQGALVQGGYGHSSVYDHRTRALYVHGGYKAFSANKYRLADDLYRYDVDT

QMWTILKDSRFFRYLHTAVIVSGTMLVFGGNTHNDTSMSHGAKCFSSDFMAYDIACDRWSVLPRPDLHHDVNRFGHSAVLHNSTMYVFGGFNSLLLSDILVFTSEQCD

AHRSEAACLAAGPGIRCVWNTGSSQCISWALATDEQEEKLKSECFSKRTLDHDRCDQHTDCYSCTANTNDCHWCNDHCVPRNHSCSEGQISIFRYENCPKDNPMYYCN

KKTSCRSCALDQNCQWEPRNQECIALPENICGIGWHLVGNSCLKITTAKENYDNAKLFCRNHNALLASLTTQKKVEFVLKQLRIMQSSQSMSKLTLTPWVGLRKINVS

YWCWEDMSPFTNSLLQWMPSEPSDAGFCGILSEPSTRGLKAATCINPLNGSVCERPANHSAKQCRTPCALRTACGDCTSGSSECMWCSNMKQCVDSNAYVASFPFGQC

MEWYTMSTCPPENCSGYCTCSHCLEQPGCGWCTDPSNTGKGKCIEGSYKGPVKMPSQAPTGNFYPQPLLNSSMCLEDSRYNWSFIHCPACQCNGHSKCINQSICEKCE

NLTTGKHCETCISGFYGDPTNGGKCQPCKCNGHASLCNTNTGKCFCTTKGVKGDECQLCEVENRYQGNPLRGTCYTLLIDYQFTFSLSQEDDRYYTAINFVATPDEQ

NRDLDMFINASKNFNLNITWAASFSAGTQAGEEMPVVSKTNIKEYKDSFSNEKFDFRNHPNITFFVYVSNFTWPIKIQVQTEQGRMDTGRGTSHTRACCGVGGRGRDS

IRGYTCMTSWVQHTNMAYVYICNKPACCAHVPNLKYNKKKKKKKKKKKKKKKK

FIG. 19D

ATGGTGGCGGTGGCCGCAGCGGCGGCAACTGAGGCTGAGGAGGAGGACGGCGGCGGACAGCGCTCGCGGGCAGGAGGCGGCGGGGCCGCACCGACCCTGCACC
GCGACAGGGGCCTGGAGGCCGGGGACCGCGCGGAGGCCGGGCCTGTGTCTCCCCGGGCTGTGTCGCGGGGCGTGCTGCCCCCCGCCGCTGCCGCTGCTCTTTCGCTGCTG
CTGCTGCCGCTGCCCCGGGAGGCCGCTGCGGTGGCGGCGGCCGCTGGGGTGTCCGGCCAAGGAATGTGACCGGCGTGTGTCAACGGCGGT
CGCTGCAACCCTGGCACGGCCAGTGCGTCTGCCCCGCGGCTGGGTGGGCGAGCAATGCCAGCACTGCGGGGGCCGCTTCAGACTAACTGGATCTTCTGGGTTTGTG
ACAGATGGACCTGGAAATTATAAATACAAAACGAAGTGCACGTGGCTCATTGAAGGACAGCCAAATAGAATAATGAGACTTCGTTTCAATCATTTTGCTACAGAGTGT
AGTTGGGACCATTTATATGTTTATGATGGGACTCAATTTATGCACCGCTAGTTGCTGCATTTTTTAGTGATGCTGCTTATAATTTGACTGGATTAATATTACAGTTTGATATGTGTCCAAATAAC
GAGGTTGTTGCCACATCAGGTTATGCCTTGCTGCATTTTTTAGTGATGCTGCTTATAATTTGACTGGATTAATATTACAGTTTGATATGTGTCCAAATAAC
TGCTCAGGCCGAGGAGTGTAAGATCAGTAATAGCAGGATACTGTTGAATGTGTTCTGAAAACTGGAAGGTGAAGCATGTGACATTCCTCACTGTACAGAC
AACTGTGGTTTTCCTCATCGAGGCATCTGCAATTCAAGTGATGTCAGAGGATGCTCCTGCTTCTCAGACTGGCCAGGGTCCTGGATGTTCAGTTCCTGTACCAGCTAAC
CAGTCATTTTGGACTCGAGAGAATATTCTAACTTAAAGCTCCCCAGAGCATCTCATAAAGCTGTGGTCAATGGAAACATTATGTGGGTTGTTGGAGGATATATGTTC
AACCACTCAGATTATAACATGGTTCTAGCGTATGACCTTGCTTCTCAGGAGTGGCTTCCACTAAACCGTTCTGTGAACAATGTGGTTGTTAGATATGGTCATTCTTG
GCATTATACAAGGATAAAATTACATGTATGGAGGAAAAATTGATTCAACTGGGAAATGTGACCAATGAGTTGAGAGTTTTTCACATTCATAATGAGTCATGGGTGTTG
TTGACCCCTAAGGCAAAGGAGCAGTATGCAGTGGTTGGGCACTCTGCACACATTGTTACACTGAAGAATGGCCGAGTGGTCATGCTGGTCATCTTGGTCACTGCCCT

FIG.20A

```
CTCTATGGATATATAAGCAATGTGCAGGAATATGATTTGGATAAGAACACATGGAGTATATTACACACCCAGGGTGCCCTTGTGCAAGGGGTTACGGCCATAGCAGT

GTTTACGGACCATAGGACCAGGGCCCTATACGTTCATGGTGGCTACAAGGCTTTCAGTGCCAATAAGTACCGGCTTGCAGATGATCTCTACGATATGATGTGGATACC

CAGATGTGGACCATTCTTAAGGACAGCCGATTTTTCCGTTACTTGCACACAGCTGTGATAGTGAGTGGAACCATGTGGTGTTTGGGGGAAACACACAATGACACA

TCTATGAGCCATGGGCCCAAATGCTTCTCTCTTCAGATTTCATGGCCTATGACATTGCCTGTGACCGCTGGTCAGTGCTTCCCAGACCTGATCTTCCACCATGATGTCAAC

AGATTTGGCCATTCAGCAGTCTTACACAACAGCACCATGTATGTGTTCGGTGGTTTCAATAGTCTCCTCCTCAGCGACATCCTGGTATTCACCTCGGAACAGTGTGAT

GCGCATCGGAGTGAAGCCGCTTGTTAGCAGCAGGACCTGGTATTCGGTGTGTGTGGAACAGGGTCGTCTCAGTGTATCTCGTGGGCGCTGGCAACTGATGAACAA

GAAGAAAGTTAAAATCAGAATGTTTTCCAAAAGAACTCTTGACCATGACAGATGTGACGCACACAGATTGTTACAGCTGCACCAACACCAATGACTGCCAC

TGGTGCAATGACCATTGTGTCCCAGGAACCACAGCTGCTCAGAGGCCAGATCTCCATTTTAGGTATGAGAATTGCCCCAAGGATAACCCTATGTACTACTGTAAC

AAGAAGAGACCAGCTGCAGGAGCTGTGCCCTGGACCAGAGAACTGCCAGTGGGAGCCCCGGAATCAGGAGTGCATTGCCCTGCCCGGTAGGCCTTGCAGGGTCATCTTGGTG

TGTGTGGGTCCATTACTTCAGCCTGCTTCCCCCAACACTGTGCAGCCTAAGTTGAACCTAGCAGAGGGGAAGAGCTAATTCTGTCCATTCATCCCCACGAGTATT

ATGGGCTTTTTTGTTTTAACTAAAATACAGTTCTTAAGTATTTGTTCCTACTGTCCTTTGAAATAAAGTGAAACATCCTTTGCTGCTCTGTAAAAAAAAAAAAA

AAAAAAAAAAAAAAAAAAAAAAAAAAAAA
```

FIG.20B

MVAVAAAAATEARLRRRTAATAALAGRSGGPHRPCTATGAWRPGPRARLCLPRVLSRALPPPPLLPLLFSLLLLPLPREAEAAAVAAVSGSAAAEAKECDRPCVNGG

RCNPGTGQCVCPAGWVGEQCQHCGGRFRLTGSSGFVTDGPGNYKYKTKCTWLIEGQPNRIMRLRFNHFATECSWDHLYVYDGDSIYAPLVAAFSGLIVPERDGNETVP

EVVATSGYALLHFFSDAAYNLTGFNITYSFDMCPNNCSGRGECKISNSSDTVECECSENWKGEACDIPHCTDNCGFPHRGICNSSDVRGCSCFSDWQGPGCSVPVPAN

QSFWTREEYSNLKLPRASHKAVVNGNIMWVGGYMFNHSDYNMVLAYDLASREWLPLNRSVNNVVVRYGHSLALYKDKIYMYGGKIDSTGNVTNELRVFHIHNESWVL

LTPKAKEQYAVVGHSAHIVTLKNGRVVMLVIFGHCPLYGYISNVQEYDLDKNTWSILHTQGALVQGGYGHSSVYDHRTRALYVHGGYKAFSANKYRLADDLYRYDVDT

QMWTILKDSRFFRYLHTAVIVSGTMLVFGGNTHNDTSMSHGAKCFSSDFMAYDIACDRWSVLPRPDLHHDVNRFGHSAVLHNSTMYVFGGFNSLLLSDILVFTSEQCD

AHRSEAACLAAGPGIRCVWNTGSSQCISWALATDEQEEKLKSECFSKRTLDHDRCDQHTDCYSCTANTNDCHWCNDHCVPRNHSCSEGQISIFRYENCPKDNPMYYCN

KKTSCRSCALDQNCQWEPRNQECIALPGRPCRVILVCVGPLLQPASPNTVQPKLNLAEGKSFCPFIPHTSIMGFFVFNNTVLKYLFLLSFEIKNILCCSVKKKKKKK

KKKKKKK

FIG.20C

SEQUENCE LISTING

<160> NUMBER OF SEQ ID NOS: 129

<210> SEQ ID NO 1
<211> LENGTH: 8827
<212> TYPE: DNA
<213> ORGANISM: Mus musculus

<400> SEQUENCE: 1

| | | | | | |
|---|---|---|---|---|---|
| gaattccggg | cgaaggggag | ccggcgtgcg | gggtgtgtat | gtgttcgctg | ggcgccggct | 60 |
| cagccccagg | aagatggtgg | cggtggcggc | ggcggcggcg | actgaggcgc | ggctgagggg | 120 |
| gagcacgagg | acgacagcag | cgcctgcggg | caggaagggc | aggcagcacc | gaccctgcac | 180 |
| cgcgacaggg | gcctggaggc | cgggaccgcg | cgcccggctg | tgtctcccgc | gggtgctgtc | 240 |
| gcgggcgctg | ccccgccgc | cgctgctgcc | gctgctcttt | tcgctgctgc | tgctgccgct | 300 |
| gccccgggag | gccgaggccg | ctgcggtggc | ggcggcggtg | tccggctcgg | ccgcagccga | 360 |
| ggccaaggaa | tgtgaccggc | cgtgtgtcaa | cggcggccgc | tgcaaccctg | gcaccggcca | 420 |
| gtgcgtctgc | cccacgggct | gggtgggcga | gcaatgccag | cactgcgggg | gccgcttcag | 480 |
| gacatctgtc | tcacgcctat | aatcacagct | gttcggaagg | tgaggctgga | ggaacagttc | 540 |
| gaggcaagct | tcggctacag | aataagttca | agagtaacct | ggggcaactt | gggcttgtct | 600 |
| ccaaaaccaa | aatgagcgaa | aaggagcaag | ctagagtctt | tgggaaaat | tttagctgac | 660 |
| taatttttca | ccgagaacta | actggctctt | ctggatttgt | aacagatgga | cctgggaatt | 720 |
| ataaatataa | gacgaagtgc | acatggctca | ttgaaggaca | gccaaataga | ataatgagac | 780 |
| ttcgcttcaa | ccattttgct | acagaatgta | gctgggacca | tttatatgtt | tatgatgggg | 840 |
| actcaatcta | cgcacctctg | attgctgcct | ttagtggcct | cattgttcct | gaaagagatg | 900 |
| gcaatgagac | ggctcctgag | gtcactgtca | cttcaggtta | tgcactgctg | cattttttca | 960 |
| gtgatgctgc | ttataatctg | actggattta | atatcactta | caattttgac | atgtgtccga | 1020 |
| ataattgctc | aggccgagga | gagtgtaaga | gcagtaacag | cagcagcgct | gttgagtgtg | 1080 |
| aatgttctga | aaactggaaa | ggggagtcgt | gtgacattcc | tcactgtaca | gacaactgtg | 1140 |
| gctttcctca | ccgaggcatc | tgtaatgcaa | gcgataccag | agggtgctcc | tgctttcctc | 1200 |
| actggcaggg | tcctggatgt | tcaattcctg | tgccagctaa | ccagtctttt | tggactcgag | 1260 |
| aagaatattc | tgatttaaag | cttcccagag | cctctcataa | agctgtggtc | aatggaaata | 1320 |
| taatgtgggt | tgttggcgga | tatatgttca | accattcaga | ttacagcatg | gttttagcgt | 1380 |
| atgacctgac | ttctagggaa | tggcttccac | taaaccattc | tgtgaacagt | gtggttgtaa | 1440 |
| gatatggtca | ttctttggca | ttacataagg | ataaaatcta | catgtatgga | ggaaaaattg | 1500 |
| attcaacagg | gaacgtgacc | aatgagctga | gagtatttca | tattcataat | gaatcatggg | 1560 |
| tattgttaac | tccgaaagct | aaggatcagt | atgcagtggt | tggacactca | gcacacattg | 1620 |
| ttacactggc | atctggccgt | gtggtcatgt | tggtcatctt | cggtcattgc | ccactctatg | 1680 |

```
gatatataag cgttgtgcag gaatatgact tggaaaagaa cacatggagt atattacata   1740
ctcagggtgc tcttgtgcaa gggggttatg gccacagtag tgtttatgat gacaggacca   1800
aggctctgta cgttcatggt ggctacaagg ctttcagcgc caacaaatac cggcttgcag   1860
atgacctcta cagatacgat gtggatactc agatgtggac cattcttaag gacagccgat   1920
ttttccgtta cttgcataca gctgtgatag tgagtggaac catgctggtg tttggaggga   1980
acacacacaa tgacacttcc atgagccacg gtgccaaatg cttctcctcg gacttcatgg   2040
cttatgacat tgcttgtgac cgatggtcag tgcttcccag acctgagctc catcatgatg   2100
tcaacagatt tggccattca gcagtcttgt acaacagcac catgtatgtg ttcggcggct   2160
tcaacagcct cctcctcagt gacgtcttgg tctttacctc ggagcagtgc gatgcacacc   2220
gcagtgaagc tgcttgtgtg gcagcaggac ctggtatccg tgtctgtgg gacacacagt    2280
cgtctcgatg tacctcctgg gagttggcaa ctgaagaaca agcagaaaag ttaaaatcag   2340
agtgtttttc taaaagaacc cttgaccatg acagatgtga ccagcacaca gattgttaca   2400
gctgcacagc caataccaat gactgccact ggtgcaatga tcactgtgtc cctgtgaacc   2460
acagctgcac agaaggccag atctccattg ccaagtatga gagttgcccc aaggataacc   2520
ccatgtacta ctgcaataag aaaaccagct gcaggagctg tgccctagac cagaactgcc   2580
agtgggagcc ccggaatcaa gagtgcatcg ccctgccgga aaatatctgt ggcaatggct   2640
ggcatttggt tggaaactcg tgtctgaaaa tcactactgc taaggagaat tatgacaatg   2700
ctaaattgtc ctgtaggaac cacaatgcct ttttggcttc cctcacatcc agaagaagg    2760
tggagtttgt ccttaagcag cttcgattaa tgcaatcatc tcaaagtatg tccaagctca   2820
ctctgactcc atgggttggt cttcggaaga tcaatgtgtc ttactggtgc tgggaggata   2880
tgtctccatt cacaaatagt ttgctgcagt ggatgccatc tgagcccagt gatgctggct   2940
tctgtgggat cttgtcagag cctagtactc ggggattaaa ggctgcaacc tgcatcaacc   3000
ctctcaatgg cagcgtctgt gaaaggcctg caaaccacag tgccaagcag tgccggacac   3060
catgtgccct gcggacagcg tgtggcgagt gcactagcag cagctcggag tgcatgtggt   3120
gcagtaacat gaagcagtgt gtggactcca atgcctacgt ggcctccttc ccttttggcc   3180
agtgtatgga atggtatacg atgagcagct gcccacctga aaattgctct ggctactgta   3240
cctgcagcca ttgcttggag cagccaggct gtggttggtg tactgatcct agcaatactg   3300
ggaaaggaaa atgtattgag ggcagctata aggacctgt gaagatgccg tcacaggcct    3360
ctgcaggaaa tgtgtatcca cagccccttc tgaactccag catgtgtcta gaggacagca   3420
gatacaactg gtcttcatt cactgtccag cttgccagtg caacggacac agcaaatgca   3480
tcaaccagag tatctgtgag aagtgtgagg acctgaccac gggcaagcac tgcgagacct   3540
gcatatctgg cttctatggt gacccgacta atggaggcaa atgtcagcca tgcaagtgca   3600
atgggcacgc atcactgtgc aacaccaaca ccggcaagtg cttctgtacc accaaaggtg   3660
tcaagggggga cgagtgccag ctatgtgagg tagaaaatcg ataccaagga aaccctctca   3720
aaggaacatg ctactatacc cttctcattg actatcagtt caccttagc ctgtcccagg    3780
aagacgaccg ctactacaca gccatcaact tgtggctac tcctgatgaa caaaacaggg   3840
atttggacat gttcatcaat gcctccaaaa acttcaacct caacatcacc tgggccacca   3900
gcttccagc cggaacccag actggagaag aggtgcctgt tgtttcaaaa accaacatca   3960
aggaatacaa agatagcttc tctaatgaga aatttgattt tcgcaaccat ccaaacatca   4020
ctttctttgt ttatgtcagt aatttcactt ggcccatcaa aattcagatt gccttctccc   4080
```

-continued

| | |
|---|---|
| agcacagcaa cttcatggac ctggtacagt tcttcgtgac tttcttcagt tgttcctct | 4140 |
| cgctgcttct ggtggctgca gtggtctgga agatcaagca gagctgttgg gcatccaggc | 4200 |
| ggagagagca acttcttcgg gagatgcaac agatggccag ccgccccttt gcttctgtaa | 4260 |
| acgttgcctt ggaaacagat gaggagcctc ctgatcttat tgggggagt ataaagactg | 4320 |
| ttcccaaacc cattgcactg gagccgtgtt ttggcaacaa agccgctgtc ctctctgtgt | 4380 |
| ttgtgaggct ccctcgaggc ctgggtggca tccctcctcc tgggcagtca ggtcttgctg | 4440 |
| tggccagcgc cctggtggac atttctcagc agatgccgat agtgtacaag agaagtcag | 4500 |
| gagccgtgag aaaccggaag cagcagcccc ctgcacagcc tgggacctgc atctgatgct | 4560 |
| ggggccaggg actctcccac gcacgagcta gtgagtggca caccagagcc atctgcaggg | 4620 |
| aagggcgtgg cggggaaatg gctgtgcggt gcgggacgga agactggaaa ccctcaaagc | 4680 |
| atctgactca cctgcatgat cacaagcttt ctttgacggt ttctcccatc cgtgttccag | 4740 |
| catctaacct tttactttg cataggaaat acttgattta attacaggtc cagggatgag | 4800 |
| ctgatggttg ctggaggagg ccagtgtaga gccagtgaga aactaggaa tgacactcag | 4860 |
| gttcactgtg gaaaactgtt cttgggactg tctcaactgt gcaaaaaaca aaagatggag | 4920 |
| tgtttacaag tagacattcg tcatcagttg tccttgaaca tggtctttta aaaactagtc | 4980 |
| agatgaatta acttgttttc atctgaagcc tgctatcttt tttaaaagat gtgctatta | 5040 |
| ttcttgcacg atttaggcaa ttatctctct tccagggagt accttttttt ctagttgaga | 5100 |
| attaataatg gtccatctct tttgatcata tcaagctagg atagaaggg ggctatttta | 5160 |
| aatgtcaagg tcagcagtgt tactttgaat gtaaactggt ataataggta gttttctata | 5220 |
| gtaacttgat taatttagtc ttaatccatt tgaaactctc tcttcctttc tctctgcctg | 5280 |
| tccctctcct tctccatctc accctccctc tctcacacat acacacaa acacatacac | 5340 |
| acaacactaa gtgcctagac tttaaataga tctagcaatt ggaaagttag taagcctaag | 5400 |
| ttttacata attgcattcc tacattcttg taaaatttaa atagctacca ttggcaatct | 5460 |
| gcttttttc taaaatctga tttgcagcca ggaaagaatt ttctcaccca aggaacattt | 5520 |
| gatctagcag cagggatgag aggaaagcag aaatgaatga actgtgaaag ctcctgttt | 5580 |
| tattatcaaa aaggacactg tcaagaaggc gccccctgcc cccaccccg tgtcacccta | 5640 |
| ggcctgataa gcgatcagag gaaaggactc attcatgtca cgcttccttg agcagaaaag | 5700 |
| agcactgaga gcacttggga cccctggatc agagagcatc tgtgtgtcct gcagcctcct | 5760 |
| ctgaacttgt ggttcattct caggctgggg tggactcaga tgccaggaaa gggacagcct | 5820 |
| cccattgtca ggcagaagct gcccaaagcc tggagaagga cttgtttgcc ctctttcccc | 5880 |
| caggaggggc tcgacccacc caccctccct ctcagaccaa ggtggtggct gtgaggaggg | 5940 |
| cagcaaatgc tgacaaggat gaaaagcaca tggaaaaaaa tggacgagga gggaaaactc | 6000 |
| tgccaaatgg aaaatgacca aatttaagag ggtgggacag tcccctgctc ctctcccaga | 6060 |
| gggcactgct tggaaattgt gttttcccca tttatggtgc tctgtattct ggcattatgc | 6120 |
| agcagcctcc cagaagctct cttctgcttc aaaacctggg atctctggca ttaccctatt | 6180 |
| gggatggacc gctggacagc aatgctcgag tttgtgaatt tggagagata ctcaaaagag | 6240 |
| ctaaaactgc agcattttac cttttaaatgc agtgcctaga gagagagtat tgtctcttcc | 6300 |
| ccaacactaa ccccactccc atgaagaatt gcctggaaag atgttttcaa ggaatttgaa | 6360 |
| ccataaaaca ctatctgatg cacagaacac ctctactttg agactcacct ctcataaagc | 6420 |
| ttctttttca cattactgtt aaagaccaga cgttctagaa aagaccctc ctctcatgag | 6480 |

```
ctcccccatc cctgctacag aacacagcac ccatggcgcc tgcagtggac tggcccctta      6540
attcccacag gccccccag caaggccaaa gggaggcccc tgggtattgt cctcctacaa       6600
ggaagatcct ctttgtttgt tcaaggacc agttttccta ggccaaagaa gtctcttccc       6660
catgttagtc ctatgccttg aaatatcatg caccatgacc cacagccatc tggttatgtc     6720 ttatttttt cctaaaagat aatgtttatt tttaaaagg aaggaagaag caagtgaagt       6780
ttcattctgc tccagcggtg gggaagccgc tgaatccacc tgcttctcct ttgcaaccga     6840
cagcaaacac ctttctccgg cctcagggca gaaaaggga atggcaggga gtaagaggcg      6900
ctgggctcgg agcctgtttc caagaaggaa ttggttgtca tctggcagtg ttgcgcgtca     6960
caagagagcc tgtatataaa ttaaaatagt caagacaaca ctgaccttgc acttgtacat     7020
aactatacag tagtgtccag aatgttcaga cattcggagt gtacataaaa cagaaaaaat    7080
cttcatgtat ttttattaaa tataacaatg tctgagtttc acctaagatg ttttgtgcc     7140 atatgctgga tatccaggtt ctcgccaggc cccgatacat gaataacaaa cccaagaaac    7200
gcatccccat tgtgtgatgt gttcagatgc atctggcacc aattaggtat ttcttaaaac   7260
aggactcatc tgtcagagtg cacatgaaaa atcaggcagg gaatcgaaac gacagcgctg   7320
gaggagactc aggaagcaga ggcgtccctg ccgctgccct tggccctgca agcacatcat    7380 gacccttct ggcagcctct tggtgctctg ggtagtgagg gatgaccagt cttgtcctga    7440
gaaatgtttc tcttagtctt taagttcaaa gactaacctg tagcaatcag actttccaaa   7500
agggggttct ccattttttg tagttttgtc taaatttta atgaccattt cctggaatca   7560
gtttattata ctgaaaactg ggggtgggag tagggagcta gtttgttgat aaatagttcc   7620
catttccccg tggagaattt gacatacccct ggactcctgt gtgcctcctg ccatccctgc  7680
acacagcctg gggagaagcc tgtgcctccc cgtgtggaga aaggcaacc ccagatcccc    7740 tgagctaacc cggaggaaag gcagtcctgg acagaagact gtcagcagaa ggaaagtact   7800
ggactacccg tgggtaagtc ctgccattca agactggaga cacctgggaa ataaaaagag   7860
cagggcactg ctggtgggaa gaggcatttt accttccagt gcaaatcctg ctcctttgat   7920
ttaatggggt gtactggggc cagggctga ttcacttcct tgggagatgg tggtgttttc    7980
atgaacatct ttgatccttc catttcattt attcatccat ccattcaaca agtatttgct   8040
aaacactaac ttaagctaat gctagggtag tgactgagat gtaaaaatag attttagaat  8100
taaaacaaaa tccaagtcct cacacccctg tcatcccagg agatctttcc ttgtggtggt   8160
ttctgtgaga attggccatc ctgaggacac agccaggacg gcagaggcct cctggcctca   8220
gggcatgccc tgcctacctt ctgaaatgtt taccccattg accaaacttg gctccagcca  8280
ttgcggtggt ttctagatag ccaggcccac caagagatat tgccccttga tgagagtcaa   8340
acaccctgcc tacaaggaga tgttttgaaa tggagaggaa aattggcacc tcatcttta    8400 aaggcagtaa tggaattgat tttcagtaac tgaatttgtg cacaaaacat tctaaacact    8460
agtgaagcct gtttcgttga actaattctg gctctgaaa tgttttttgtt ttatagttat   8520 ttacgatttc gtttgtttgg attcaagctt agtttgttaa tatgtataat ttagcatcta   8580
ttacactcat gtaaatatgg agtaagtatt gtaaactatt tcattgcggg gattgtgggt   8640
gttatacata catttaggac tgcaatttt tggtatttt tgtattgtaa aataacagct     8700
aatttaagca ggaacaagag aactaaggga ggtctgtgca ttttaaacac aaatgtgaag  8760
aacttgtata taaacaaaag taaatactat aatacaaact tccttctgaa ataaaagtag   8820
atctggt                                                            8827
```

```
<210> SEQ ID NO 2
<211> LENGTH: 1260
<212> TYPE: PRT
<213> ORGANISM: Mus musculus

<400> SEQUENCE: 2

Met Arg Leu Arg Phe Asn His Phe Ala Thr Glu Cys Ser Trp Asp His
 1               5                  10                  15

Leu Tyr Val Tyr Asp Gly Asp Ser Ile Tyr Ala Pro Leu Ile Ala Ala
                20                  25                  30

Phe Ser Gly Leu Ile Val Pro Glu Arg Asp Gly Asn Glu Thr Ala Pro
             35                  40                  45

Glu Val Thr Val Thr Ser Gly Tyr Ala Leu Leu His Phe Phe Ser Asp
 50                  55                  60

Ala Ala Tyr Asn Leu Thr Gly Phe Asn Ile Thr Tyr Asn Phe Asp Met
 65                  70                  75                  80

Cys Pro Asn Asn Cys Ser Gly Arg Gly Glu Cys Lys Ser Ser Asn Ser
                 85                  90                  95

Ser Ser Ala Val Glu Cys Glu Cys Ser Glu Asn Trp Lys Gly Glu Ser
            100                 105                 110

Cys Asp Ile Pro His Cys Thr Asp Asn Cys Gly Phe Pro His Arg Gly
        115                 120                 125

Ile Cys Asn Ala Ser Asp Thr Arg Gly Cys Ser Cys Phe Pro His Trp
130                 135                 140

Gln Gly Pro Gly Cys Ser Ile Pro Val Pro Ala Asn Gln Ser Phe Trp
145                 150                 155                 160

Thr Arg Glu Glu Tyr Ser Asp Leu Lys Leu Pro Arg Ala Ser His Lys
                165                 170                 175

Ala Val Val Asn Gly Asn Ile Met Trp Val Val Gly Gly Tyr Met Phe
            180                 185                 190

Asn His Ser Asp Tyr Ser Met Val Leu Ala Tyr Asp Leu Thr Ser Arg
        195                 200                 205

Glu Trp Leu Pro Leu Asn His Ser Val Asn Ser Val Val Arg Tyr
    210                 215                 220

Gly His Ser Leu Ala Leu His Lys Asp Lys Ile Tyr Met Tyr Gly Gly
225                 230                 235                 240

Lys Ile Asp Ser Thr Gly Asn Val Thr Asn Glu Leu Arg Val Phe His
                245                 250                 255

Ile His Asn Glu Ser Trp Val Leu Leu Thr Pro Lys Ala Lys Asp Gln
            260                 265                 270

Tyr Ala Val Val Gly His Ser Ala His Ile Val Thr Leu Ala Ser Gly
        275                 280                 285

Arg Val Val Met Leu Val Ile Phe Gly His Cys Pro Leu Tyr Gly Tyr
    290                 295                 300

Ile Ser Val Val Gln Glu Tyr Asp Leu Glu Lys Asn Thr Trp Ser Ile
305                 310                 315                 320

Leu His Thr Gln Gly Ala Leu Val Gln Gly Tyr Gly His Ser Ser
                325                 330                 335

Val Tyr Asp Asp Arg Thr Lys Ala Leu Tyr Val His Gly Gly Tyr Lys
            340                 345                 350

Ala Phe Ser Ala Asn Lys Tyr Arg Leu Ala Asp Asp Leu Tyr Arg Tyr
        355                 360                 365

Asp Val Asp Thr Gln Met Trp Thr Ile Leu Lys Asp Ser Arg Phe Phe
    370                 375                 380
```

```
Arg Tyr Leu His Thr Ala Val Ile Val Ser Gly Thr Met Leu Val Phe
385                 390                 395                 400

Gly Gly Asn Thr His Asn Asp Thr Ser Met Ser His Gly Ala Lys Cys
            405                 410                 415

Phe Ser Ser Asp Phe Met Ala Tyr Asp Ile Ala Cys Asp Arg Trp Ser
            420                 425                 430

Val Leu Pro Arg Pro Glu Leu His His Asp Val Asn Arg Phe Gly His
            435                 440                 445

Ser Ala Val Leu Tyr Asn Ser Thr Met Tyr Val Phe Gly Gly Phe Asn
450                 455                 460

Ser Leu Leu Ser Asp Val Leu Val Phe Thr Ser Glu Gln Cys Asp
465                 470                 475                 480

Ala His Arg Ser Glu Ala Ala Cys Val Ala Gly Pro Gly Ile Arg
            485                 490                 495

Cys Leu Trp Asp Thr Gln Ser Ser Arg Cys Thr Ser Trp Glu Leu Ala
            500                 505                 510

Thr Glu Glu Gln Ala Glu Lys Leu Lys Ser Glu Cys Phe Ser Lys Arg
            515                 520                 525

Thr Leu Asp His Asp Arg Cys Asp Gln His Thr Asp Cys Tyr Ser Cys
            530                 535                 540

Thr Ala Asn Thr Asn Asp Cys His Trp Cys Asn Asp His Cys Val Pro
545                 550                 555                 560

Val Asn His Ser Cys Thr Glu Gly Gln Ile Ser Ile Ala Lys Tyr Glu
            565                 570                 575

Ser Cys Pro Lys Asp Asn Pro Met Tyr Tyr Cys Asn Lys Lys Thr Ser
            580                 585                 590

Cys Arg Ser Cys Ala Leu Asp Gln Asn Cys Gln Trp Glu Pro Arg Asn
            595                 600                 605

Gln Glu Cys Ile Ala Leu Pro Glu Asn Ile Cys Gly Asn Gly Trp His
            610                 615                 620

Leu Val Gly Asn Ser Cys Leu Lys Ile Thr Thr Ala Lys Glu Asn Tyr
625                 630                 635                 640

Asp Asn Ala Lys Leu Ser Cys Arg Asn His Asn Ala Phe Leu Ala Ser
            645                 650                 655

Leu Thr Ser Gln Lys Lys Val Glu Phe Val Leu Lys Gln Leu Arg Leu
            660                 665                 670

Met Gln Ser Ser Gln Ser Met Ser Lys Leu Thr Leu Thr Pro Trp Val
            675                 680                 685

Gly Leu Arg Lys Ile Asn Val Ser Tyr Trp Cys Trp Glu Asp Met Ser
            690                 695                 700

Pro Phe Thr Asn Ser Leu Leu Gln Trp Met Pro Ser Glu Pro Ser Asp
705                 710                 715                 720

Ala Gly Phe Cys Gly Ile Leu Ser Glu Pro Ser Thr Arg Gly Leu Lys
            725                 730                 735

Ala Ala Thr Cys Ile Asn Pro Leu Asn Gly Ser Val Cys Glu Arg Pro
            740                 745                 750

Ala Asn His Ser Ala Lys Gln Cys Arg Thr Pro Cys Ala Leu Arg Thr
            755                 760                 765

Ala Cys Gly Glu Cys Thr Ser Ser Ser Glu Cys Met Trp Cys Ser
            770                 775                 780

Asn Met Lys Gln Cys Val Asp Ser Asn Ala Tyr Val Ala Ser Phe Pro
785                 790                 795                 800
```

-continued

Phe Gly Gln Cys Met Glu Trp Tyr Thr Met Ser Ser Cys Pro Pro Glu
             805                 810                 815

Asn Cys Ser Gly Tyr Cys Thr Cys Ser His Cys Leu Glu Gln Pro Gly
             820                 825                 830

Cys Gly Trp Cys Thr Asp Pro Ser Asn Thr Gly Lys Gly Lys Cys Ile
             835                 840                 845

Glu Gly Ser Tyr Lys Gly Pro Val Lys Met Pro Ser Gln Ala Ser Ala
850                 855                 860

Gly Asn Val Tyr Pro Gln Pro Leu Leu Asn Ser Ser Met Cys Leu Glu
865                 870                 875                 880

Asp Ser Arg Tyr Asn Trp Ser Phe Ile His Cys Pro Ala Cys Gln Cys
             885                 890                 895

Asn Gly His Ser Lys Cys Ile Asn Gln Ser Ile Cys Glu Lys Cys Glu
             900                 905                 910

Asp Leu Thr Thr Gly Lys His Cys Glu Thr Cys Ile Ser Gly Phe Tyr
             915                 920                 925

Gly Asp Pro Thr Asn Gly Gly Lys Cys Gln Pro Cys Lys Cys Asn Gly
930                 935                 940

His Ala Ser Leu Cys Asn Thr Asn Thr Gly Lys Cys Phe Cys Thr Thr
945                 950                 955                 960

Lys Gly Val Lys Gly Asp Glu Cys Gln Leu Cys Glu Val Glu Asn Arg
             965                 970                 975

Tyr Gln Gly Asn Pro Leu Lys Gly Thr Cys Tyr Tyr Thr Leu Leu Ile
             980                 985                 990

Asp Tyr Gln Phe Thr Phe Ser Leu Ser Gln Glu Asp Asp Arg Tyr Tyr
             995                 1000                1005

Thr Ala Ile Asn Phe Val Ala Thr Pro Asp Glu Gln Asn Arg Asp Leu
       1010                1015                1020

Asp Met Phe Ile Asn Ala Ser Lys Asn Phe Asn Leu Asn Ile Thr Trp
1025                1030                1035                1040

Ala Thr Ser Phe Pro Ala Gly Thr Gln Thr Gly Glu Glu Val Pro Val
             1045                1050                1055

Val Ser Lys Thr Asn Ile Lys Glu Tyr Lys Asp Ser Phe Ser Asn Glu
       1060                1065                1070

Lys Phe Asp Phe Arg Asn His Pro Asn Ile Thr Phe Phe Val Tyr Val
       1075                1080                1085

Ser Asn Phe Thr Trp Pro Ile Lys Ile Gln Ile Ala Phe Ser Gln His
       1090                1095                1100

Ser Asn Phe Met Asp Leu Val Gln Phe Val Thr Phe Phe Ser Cys
1105                1110                1115                1120

Phe Leu Ser Leu Leu Leu Val Ala Ala Val Val Trp Lys Ile Lys Gln
             1125                1130                1135

Ser Cys Trp Ala Ser Arg Arg Arg Glu Gln Leu Leu Arg Glu Met Gln
             1140                1145                1150

Gln Met Ala Ser Arg Pro Phe Ala Ser Val Asn Val Ala Leu Glu Thr
             1155                1160                1165

Asp Glu Glu Pro Pro Asp Leu Ile Gly Gly Ser Ile Lys Thr Val Pro
       1170                1175                1180

Lys Pro Ile Ala Leu Glu Pro Cys Phe Gly Asn Lys Ala Ala Val Leu
1185                1190                1195                1200

Ser Val Phe Val Arg Leu Pro Arg Gly Leu Gly Gly Ile Pro Pro Pro
             1205                1210                1215

```
Gly Gln Ser Gly Leu Ala Val Ala Ser Ala Leu Val Asp Ile Ser Gln
        1220                1225                1230

Gln Met Pro Ile Val Tyr Lys Glu Lys Ser Gly Ala Val Arg Asn Arg
        1235                1240            1245

Lys Gln Gln Pro Pro Ala Gln Pro Gly Thr Cys Ile
    1250                1255                1260

<210> SEQ ID NO 3
<211> LENGTH: 17056
<212> TYPE: DNA
<213> ORGANISM: Mus musculus

<400> SEQUENCE: 3
agattttatg ccttcgtaca cgcctcccat aagatggaca aggtgtacta attactgcca        60
ttactgttgc tgacccccaga ggtcaatgtc ctcacatggc ctctactggc actgtctggg      120
cagaaactgt atatccaact ggtgaacctg aaagccctat gactacttgg tgtctctggt      180 gctaaccctca gtcgttgggg catcttactg tatcctggta aggaaagaca tccaggctcc      240
ccacttaymk wwacyrgywm rgmycakgsy mgrgcyaawk tkctgtrrmr tctggctggc      300
atagagacat tactattgaa agttttgtct ttctaaatcc ttggactaaa gagagcacaa      360
gattttctgg aagatcttgc tttaaatttt tttttattc ttttgagatg ctacatataa      420
ttagaggccc tgcacatgga ggcgagaacc ccacctctgg gctacatcct acgtctttc      480 cttagggtat tttttttct tcttgtacc tatcagtatt actaagttgc aaatgtgctc      540
agcagtaaat ttaacataca taggcaaaaa gaaaagtctc aggacaccct gcctcacact      600
gtttactgtg ctcaggagta ctgagccata ctgttttctt gctgctgctt tttttctctt      660
ggttgtttac acacagtgtt caaggtgtgt taatcatagt tagtatttca atttttctt      720 aggtcagcaa gaaagctcac agaggaagag tgctttgctg ccagcctgat gacctgggtg      780
acccaagtga tctcacctac agggtgggag cacagcacag cattccaagt cttttctga      840 ccacacaggc actatggcac acaaacacac aggatacata aatgttaaaa aaaaaaaaag      900
acttttatat ttttctccat ataatttaaa agattcctct ttcaacattc cttttgcaaa      960
gcagtatcat tgtgtttgta tatgtgtgtc cttccacatt ttgtcttcaa ttctaaattt     1020
ttagaattgt tagcctggtc ctctcatttc tactactttc tctagtaaac tgtcctttca     1080
tattacacat cgctctcctg tcacctgttt tagagctgtc atccatttta taaggttact     1140
tcactgttct acactacttt gtgtctttta attactatgc ctggggtgat tcaaaaactg     1200
tctgtgatgg gttggttgag gatggctcca ataggttcaa cacttggtcc tgattggtgg     1260
aactgttttg ggaaggatta ggaggtgtga ccttgtgggg gagtgtgtca ctgggagtga     1320
gtgacctttg aggtttcaaa agcccatgct aggcccagtg tctgtctgcc tgtctgtctg     1380
tctcctccct ttgctctttc ttccctccca cttgcttgca gatcagattc gagctcttag     1440
ctactgctcc cgtgctgtgc cttgctgcta ccatgcttct tgccatgatg ttcatagact     1500
tactctctga aactgtaaat aagccccta ataaatgct ttcttttaaa actgccttga     1560
tcatggtgtc tcttcaaaga aatagaacat taacaaaaac actataccaa actgcctaat     1620
agtcctacta attttatgat gagtgctagt gcttataat cactagaaga aaaatttcc     1680 aggccataaa attaacatgg ttttaagtat gtataaatct tgtcttgaaa tctgttttct     1740
ataactaact ctaatatgat aatgtatatt ctaccttcaa aaaagcacaa ataagacttc     1800
aaaccctggg aattgttaga caaaggccat ttaatactaa taagctataa actgaaacca     1860
```

-continued

```
tctgatatat gaaaactatt aataaaatca agataaaata accccctattt atataactta    1920 ctatataccct aaagcaaaat atcaaagaaa gtaccttaaa aagataaatt attcttattt    1980
tgacaatgaa ttctttgggg cgttaaattg tagaatatca acacatatca agaaagttta    2040
gaagaaaact accaaagttt aaacagactt tcctcggtaa ttactggtga tttcttggct    2100
tttttttttt acactgcagt ttttcagggt ggaaacttaa gctttgtaca gaagcactta    2160
ccaccactct cagagctgga aatggctcaa agggcaaagc attacaagcc tggcaacctg    2220
aaccaaatac ccaaaacact tgcaaaggtg aaaggagaaa actaactcca ggaagttgtc    2280
cttcgagctc ctcttgcaca ccactgtata caccccctta tatacactca gttaccataa    2340
ataaaatgtt tcattataaa gacacttacg ctaaaaccat gctgtaatct gaatggttga    2400
acatatatcc gccaacaacc cacattatat ttccattgac cacagctttta tgagaggctc    2460 tgggaagctt taaatcagaa tattcttctc gagtccaaaa agactggtta gctggcacag    2520
gaattgagca tccaggacct aataaaaaaa aaaaaaacaa caacaacaac aaatagcttc    2580
acaaaatgca gcctgaaagt ttatagtatt ccaagttcca atctaagtgc aaagaatatt    2640
taaagacttg tggggctaga gagatggctc agtggttaag aaaactgact gctcttcttg    2700
gaggtcctga gttcaaatcc cagcaactac atggtggctc acaaccatat gtaatgggga    2760
tctgatgccc tcttctggtg tgtctgaaga cagcaacaat gtactcacat gaaataaata    2820
aattaatttt ttaaaaaaca gaccagaaaa aaaaaaaaaa aaaagacttg tgtttccttt    2880
agcacttaag cgcaaacatc tttaacttgt ggggttttaa aggtttttac atgtacaggt    2940
attttgttta catgtatgcc tatataccac ttgcttgctt ggtacccaat gatgtcagga    3000
aaaggcattg aatcccctgg aactagagtt acagatctta tgagctactt tgtggatgct    3060
aggatcaaac ctgagtcctc tggaagagca accagtactc ttaaccaaga agccatctgc    3120
ttagcaccta acatgagttt ttaacttact caagatacag accaaaacca atcactccct    3180
tataaaattt aatactacac actttctgat aatttggcaa tttctgataa tcaggttaaa    3240
cttttttaga ggtaaaaatc ttgctgaagc aacatttagt agaaagggta gaccaagggg    3300
ttattatatt aactcatgtg gaaaaggcat tagggttgaa atataatgac agatcaaaat    3360
cgatcttctg gcaagtccag gcgctgaata gatgaaagag acaaagggag aattggacaa    3420
actaaaaaca tttacatgaa cacttacttt ctgaggacct aagcatagaa ggaaaatcac    3480
taaaccaacg atgactgctt cctcaatacc ccagggaatt ccctacagta ccttagtacc    3540
cggttgtgtt gggtaatggc actagatgac agcactgaga ctctaaggaa cgcttgtcct    3600
cctctcagct tgagtctctg cttctctatc accagaccat gttccctaat tcccacgaat    3660
gagttgcaaa ggatttgtca aacctttcca caattctaag cacatagata acaaccacat    3720
atatgtaaat tcaaagaatc tgaataaatg gagatgaatg cttaaatgcc acctgataca    3780
tgattaacat aaggcgtatg gctgctaaaa taaactccct acagttcact aactcagaac    3840
tttctgtgag ggaaaggact ttgaagggca gctcctaccc tgccagtgag gaaagcagga    3900
gcaccctctg gtatcgcttg cattacagat gcctcggtga ggaaagccac agttgtctgt    3960
acagtgagga atgtcacacg actccccttt ccagttttca gaacattcac actcaacagc    4020
gctgctgctg ttactgctct tacactctcc tcggcctgag caattattcg gacacatgtc    4080
aaaactacaa agacaggaga aaacgaagtc aacaatttca actaagcaac attgcaacta    4140
atgcagacct tcctccttca gtttaagttc agttcatttg caagtgtgac tgcaggactt    4200
accagttagc ccaagtgtgc tcacagagct ctgtgtagct agagccccag gctcaagtaa    4260
```

```
tgaaatcaaa tcaaccttgc tgcattcaca tatgaagaag gaagaataaa taactcacaa    4320
agttagagaa attacaaaac aatagacatt tgtgcaaaat cacttagact tagctcaaga    4380
ctggcaacca ggatcctact ctttctggta gctcattagt aaagagttct acaaaagcag    4440
caaggtcatg ctaggaagtg gaggaaggag aggaagccaa tgagctgcca acattcacgg    4500
tatacatttc tctgtaaaga ttctgagaat taacagaatt taagattatt ttccagtgat    4560
gtagttaaag gtctttagta acttttatca gcttagaagg agaagagcag ttaacttcat    4620
gtatgagttt aagtgtctca tgacttaaga taacagtttt gctacaattt gaatgccat     4680 acttcagact ttttaaaggg gtgcattagt ggactattac aatagcttaa aaatatagat    4740
ttctcctact gatgattatt actgagacac tactagtctt tattaaattc acttagcaaa    4800
actcctgaca ttttcttcca gcagcggaag aatgtctctc tcttctagga gatcctcagt    4860
gacaagatct agaagaccca agaactgtgg tcccaaccag tggggctgat atttgtttaa    4920
ccttttagct cctgtttctt caattatgaa aaaaaaaaa aagaagaaga agaaaatcca    4980
tgttaaaatt tagcaaggag cctgactagc tagaagcctc cctccaatat attagtgtta    5040
ttaagtcatt tgagtagtat cacaaatatt aaatctaaat atcttacttg taagtgatat    5100
taaatccagt cagattataa gcagcatcac tgaaaaaatg cagcagtgca taacctgaag    5160
tgacagtgac ctcaggagcc gtctcattgc catctctttc aggaacaatg aggccactga    5220
aatgtaaaca cagaccagat tacagcaact tcaacagaaa ctgtctatat gttactattt    5280
gatcctgctg ctcctgttcc aacacacact gtaaatgtga ctctagctgg cctcaaattc    5340
acagacccac ctgcttccac ctcctgggtt ataggcatgc gctactatgc ccaacatcta    5400
aaaggatttg aaatctatga ctttgattga attttttggtt ttttgttttt gctataaact    5460
ttttattata atactctcaa gtctctacaa taacattatt aacaaacttt atgaattgac    5520
aactgtcaaa tatatactgt tgaaagaaaa tactttacat attttttgtaa tatgtatcat    5580 ataatctttt taatgtattt tatagatgtc ttatataagt aaaaatagaa aagtttactg    5640
atttataatc cttatactat tagctttcag acgtattttt gttgttaaac tggtaacaca    5700
ttttatgttt ataattcaca ataagcactg ccactgaagg tgccaaaggc tccctagaat    5760
ctcagtaaga acctagtggg taatatttga agttttggat gccagtaaat tcatgtgtaa    5820
agatttattg agtaagtgac taccagcggg acagtggtgg tgcacgcctt tagtcccagc    5880
acttgggagg cagaggcagg cgaatttctg agttcgaggc cagcctggtc tacagagtga    5940
gttcccagga taaccagggc tacacagaga aaccctgtca ccctgtctca aaaaaaaaa    6000 aaaaaaaaaa aagaatatac cattttttaag gcatttgatc cacaaaatca taccaccttg    6060
ttttacaaaa gatatatatt aacttgaagg ctggaaatgg tggcacatgt ctttagtccc    6120
agtattggga agacagaccc agatggatct ctgagttcaa gaccagcatg gtctacatag    6180
tgaattccat gtaagtttgt ccgtgtgtgt aacttgaaac ctcattatag aatggaagtg    6240
tctaccccac cccacttacc aacagtaagg aatatattgt tggtcccgct catttaatac    6300
atggtgtact cccaaggtaa atcattttca tgtttagtcg ctcctattat ttttccatt     6360 atcaattcac tacaactact accaccaatc acatttagcc actagaaaag ccatgtgatt    6420
tgctccacac atacaacttc actcaataaa taaacatctt atcagtacta ctctctcttt    6480
cactcactca atccctagtc ccctaagttt ttggacgatt acaccaggta aattcctact    6540
tcagggttat gaccatctta aaaactacga cctagcaatt ctctttgtat aagaaatact    6600
tccccgtata tacacagaaa aacaaagaac actactacag cactattcag atgacaactg    6660
```

-continued

```
actaaaagtc acctaattgc ttatttatgg gagttgatta aattagtcat tacaaatctg   6720
taggtctgca agactaacca agagcttcgt gaggacaata ggtagggcta cccagagaaa   6780
ccctgtcacc ctgtctcgaa aaaaaaaaaa aaaaagggag gcacagagaa aaaacaacag   6840
gcccggggta cctgtacatc tatgtaagcg taggtacatg cacataaaag tgactacaag   6900
agaacataaa cagagagcgc cgatgagaag aggatgggga ttttcattta atttgcgtgt   6960
atgagagcac ctatatgtgc atgttatccg caccaaagtg tgtagggtac attatgtgag   7020
tgtgcctgca gacgtcactg tcaggtgtct tcaatcactc ccctccttt  tcttctggag    7080
ataagagttt catgaagtag tactggctgg actagaactc actatgcaaa ccaggctggc   7140
cttgaattct cagagagcct cttgagtgct ggaattatat gcatgtgccg caacacagcc   7200
cacctcattt tgggggtag  gatctttcac tgaacctgag ctcactgatt ggttagaccg    7260
gactggccag taagttccag gacctctctt gtctccgcct cttcagcact gtgatcacag   7320
gctcacaacc acacctggac ttttacttga gtcctggaga tctaaactca gctctccatg   7380
cctgtgcaga aggaattaaa ctgagccagc tgtctcagta tcaagagaga acataggaac   7440
tgtaagattc tgacagtact ctagggctta cagaacaccg acacattttc tactatgtat   7500
tcagttaata aaagaataaa tacaaacaaa aaaacatgag aaacatatag aggcagagac   7560
agacagacac acacacacac acacacacac acgcacacac acacacacac acacgcac    7620
ttagacgggt gtgggggaag aaagagcaag gccacctaga aacaggtacg ttccatgcaa   7680
atgatcacag gaaaggattg gggattttta accacttgtg ggaaatgctg tactctccta   7740
ttctagcaca gatttgagga aaaagtagac cagagagtct gtccttccac atatcctgga   7800
aagtcactga catgtccaag ttttgatttc ttcataggga caatgagaga aacccagact   7860
atctcacagc agcacagcaa ggaccaacca gcagagcagg agaagtgctt acagcagtgt   7920
gctgctagaa ggtgcaacag tcttcttaca gagggcattt aaatatgcag gatggataag   7980
tttgccaact acaactacag aggctggaca aggtaggaca gcttcttcac tgtcaaagac   8040
gtttgggcag ttgcttctat ttaccttaaa atcaaactgt gacagctgtg gcatatatag   8100
atttctccca gaatgaaaac acattaactc acttatgtca ataatatgga gtaaacacaa   8160
acatagtcta tctagctcag catgcaagac atgtgaggaa gaggagctac tgtgagtccc   8220
tatccctgtc cctaaggaaa ccaatatatg taaatgtagt ctaagctgca ggcagttctt   8280
caactgccta ccccaggctg ctcaccactt cacattctaa gcacagacta gaaagtatga   8340
tcaacctctg aacactgtgc tataatgtta ccatcaatct cacacacaaa tttcataaca   8400
ttttaagtaa gtctatgatg attctatgtt gtgtcccagt tatataagat ccataggtca   8460
cagggtagac attcaaggac accaacattt ggaattttgg gttttttt gg tgtactgtat   8520
atacttgcta gtgcaggtac ccatgctcat gtgtgtagaa gttgggcgtc tttcttctat   8580
cactgtctac tttatatttt ctttattgtt tcatttgata tgtataggtg ttttgcctgc   8640
atatatgtgt atgtttgttg ccagaagagg gtattgaatt ccctgggact agagttacag   8700
gtggttgtga ggcaccatta tgggtactgg gactcaatcc tgggttctct ggaagggcag   8760
ccagtacttt taatcactga gccatctctt tagcttcctt cgttcattcg ttcgttcatt   8820
ccttcattcc ttcattcctt cattcagagg attgagatac cttcctcagt taggctggct   8880
agccaatgga ctctgggaat ctatctgttc agctattctc tccttcccca tccaagtgct   8940
ggggatacag gcaggtccta ctgggttcat tttgaaaaat tacagaacta tgtatttct   9000
tcataaatct gaaactcagc ataactgtct caggctaaca tggaatccct aaatatatat   9060
```

-continued

```
gaggcacaac ctgactttac caactgtact atgtaaattt gctagtatat tagtcaacac      9120
ttaatggaaa aacatctgat aaaaacaact tacaggccaa taggcaagga gacacttggg      9180
gaggtggatt caaggcagtc actggattct tgaatttaag tccagcctag gctacatgag      9240
attctgcttc aaaaaataaa caattaaatt tatgggggaa agaatgatgt attttggttt      9300
cagaaattcc atcctatcat ccaagggaga tattgtataa cagcgaagtt cctcagctca      9360
cagcagtcag tagcatatag acaatcctgg ctccaagcct atgaaaacac agcctgtact      9420
aaaggtgtgt tcctgtgttt tgagtgagat gtgcccccta agtcttgtgt atttgaatac      9480
ttggcactca cttggtggcg atttgggagg aattaggagg tgtggccttg gtggaaaagg      9540
agcatcacta gggtcaaggt ttcaaaatcc tcctgccatc atccccaata tgtcctctct      9600
gcctcctgct tgcagttcaa gctatgagct cttagttact acttccacca cctacccctg      9660
ctatctctgc tccatcatca tggactccta ttctggtgga actgttagtc caaaaaagtc      9720
cttccttcta caacttgatt tgatgccaga tctagccccc cagcctagct agcaatatac      9780
caaggtatac catcttgaac tctaggtgtc tctcaatcca atcaagctac ataagattaa      9840
ccatcatacc tagtcatccc caaatcagtg tatctctctc ctcccaagac tataagctcc      9900
tcaagggtca aaatatgtag aaaggaagaa agattctcaa aggtcaagga tcagaccttg      9960
gtgaggattg agcactgtct acactttgcc tggtaaagaa gggtccacaa tgtaaaagag     10020
aactgacctg aacagttttc aattaggtgc taacaaatgt ctcatacgta ttgagtttct     10080
tataaataaa taaataaata aataaataaa taagcaagca agcaagcaag cacttaagag     10140
cactagctgc tttcttcctg aagacctggt ttcaattacc cagcacttat acagaggctc     10200
ataccaattg taactccagt ttgatgatat ccaacatctt cttctagcct tcagacacca     10260
agcaccaagc atgtaatggt ataacacatg tataccaaac acccatacaa accaattttt     10320
aaaaaaatat tcgagccggc gtggtggcgc acgcctttaa tcccagcact cgggagacag     10380
aggcaggtgg atttctgagt tcgaggccag cgtggtctac agagtgagtt ccaggacagc     10440
cagggctgca cagagaaacc ctgtctcgaa aaaccaaaaa aaaaaaaaaa aaaaaaaat     10500 agtcatttta gggctggaga gatggctcag gggttaagag cactgactgt tcttccagag     10560
gtccttagtt caatatccag caaccacatg gtggctcaca gccatttgta atggggatcc     10620
aatatcccat tctggtgtgt ctgaagacag ctatagtgta aataaaataa agaaatcata     10680
taaataaaat aaataaatct ttttaaaaat attaattaac ccaggctgaa cctaaactta     10740
caaacttccc acattaggct ctttaatgcg ggtgttatag gtctgaatac cagcttaaga     10800
ataatattct tctgaagaat gtgccctggt caatcaccat gaccacacct gccaacaggt     10860
ccttcataaa atacttggta tatgttgaat gttccataaa attatggagc tagaaaaggt     10920
agtgagctag aaggatatta aagatataaa ccattgcccc agtggtcctc acatttgtct     10980
agtaatagaa cgttgttaaa ctgttttat ttagaatttc aatatataaa agacaaatat     11040
gaaatagtcc ggaagcaaat taagctacag cttgcagcaa agccagatag aatgcagatt     11100
aaactaacac agtacctttg tcttatgttt tagatgctaa agtctagtct acaaccccag     11160
ctgcccttga actcttagca gtcctcttgc ttcagcctct catgctgcta gggttaaaag     11220
tatgtgcgac cacacacagt tttgaagttt agagcactta aatgatctat tcagcaactc     11280
aggcaggatt tacactgaaa gtaaattatc ttatgaatcc tttttggttt tccttttatt     11340
catttcattc atgcaccta catgaactat ctattgctag gctgtctcta tactggatgc     11400
tcagcacatc accaacatgc cgattcttct actggtacaa tggcaatgct gagaaaacca     11460
```

```
cacaacctaa gacagtaggg aggtggtgct ctgattgttg gtgttgttgt tgttgttgtt   11520
ttggtttttc gagacagggt ttctctgtgt agccctggct gtcctagaac tcactctgta   11580
gaccgggctg gcctcaaact cagaaatccg cctgcctctg cctcccaagt gctgggatta   11640
aaggcgtgtg ccaccacgcc gggctctggt gctctgattt ttaaatacaa caattttcag   11700
ctagcaatgt aactcagtag taaaatgcct gcccagcatg cacaaggctc cagactggac   11760
cctgagcacc acaacacttt ttaaaagatg tgtttatttt attttatgtg catgagtgtt   11820
ttgcttacat gaatgtctgc actgtgttta cctggtgcct gtgaaggtta gaaggcaatg   11880
gagctatgga gagttgtaaa ctaccatgtg gaaatggagc tatggagagt tgtaaactac   11940
catgtgggta ctaggaattg aatcagggca ctcctctgca agaacaacaa aggctcttaa   12000
cagctaaaat attactacaa acccacacca caaaatttta aattgataga cattatcacc   12060
ttagttctag atagagaatg tgcttggcat tgtaagtact aaaaaggttt tggggtggat   12120
cttttatatt atctcactat aattttataa aattaatact caaatatgtt ataagttaag   12180 gttttttattt ttgttttca tttctgtatt ttgtctatgt agctctgcct ggcctgaaac   12240
tcatgggaac ttgactggcc tcaaactcag agagacctga acggcccctgc ctccaaagag   12300 ctggactaa ccatgcccaa cagtaggtag ctttaatacc taaccagtgt attagttcat   12360
gctctcaatt aaccaacatt ctctacatac agaaattttt atgcctattt aatcaaatac   12420
acagtctaag taaactctaa gtacaactgc ttggctcata ttcttacaat ggctatggct   12480
agctaattca aaggccagtc acataaaagg gtctctatga attctgatta acaaatgcag   12540
ttaaatagat gaattcctaa aaagtagtat cataataata tcatatttag ttttttgtgct   12600 tccattatag tttgaggtgc ctcctcccat aatgcaaggt atatttcaaa taatagatat   12660
atacatggtt aacacatggc aaatgccatt ttaaatgctt agcacagcct gctctttggc   12720
tccattaagt gaaactctta agttctcagt taaaataatt gttggagagc tataggagca   12780
atgggtggag aactagtctt ctaatttgtc ctttgcctcc ttgcgtacta agtagtccct   12840
ccctcactat gtggcattcc agcagactac caccaagaga agaacagaaa agtgttgatt   12900 tcttttctaaa gtaaagaaat aaggggccag tgagatacct cagcaggtca agccatttg   12960 cctagaaacc aaagttcaat ccttggaagc cctgtaaagg tggaattaga aaacagactc   13020
cacaaaactg tcctctaacc tccactcggg cacacatgtg ccaacccctc cattctccct   13080
cccccacata caaagtaaca ataaactttc agaaaattta agttgctacg catggtgatt   13140
gatgaatgtc tttaattcta gctcttggga agcagaagtg ggtggatctc tgtcagttca   13200
agaccaacct ggtctatata gtgtgttcca ggcatccagg actacacaca cacacacaaa   13260
attacgtgaa ggaagtagaa tgtttgaagg aaagaagtct ggaaatgggg atggagagag   13320
acctcagcaa ttaagaaaag gtcttgcacc ggacgtggtg gtgcatgcct ttaatcccag   13380
cactcgggag gcagaggcag gcggatttct gagttcgagg ccagcctggt ctacaaagtg   13440
agttccagga cagccagggc tacacagaga acccagtct cgaaaaaacc aaaaccaaaa   13500
acagaaaacc agtatgatag gtcaggcaat tggatcgaga caggacactc aagatagcta   13560
gcctgtgcaa tatagaaaga agtctcatgg aagagagagg gaagggaagg aggggggaga   13620
gagagagaga gagagagaga gagagagaga gagagagaga gagaatgaga gcgagagagc   13680
gagcgcacct cagttgatac aagattgggg ccctgagttc catccccagc atcccataaa   13740
ttgggtgtag cagcacacac ctgtatccca gcagagaggc aaaagacaag ttcaaagtcc   13800
tatatggaaa aagtgtgaga tcagcctgga gacctggtgt gtggcagtgg ggtgagggt   13860
```

-continued

```
gtcatcaagg agaaggctta gtaagtaaag gacctgcgtt ggttcttgag ttcaagtctc    13920
cagcaatcag agaaagccag aaccattgca caaacttgta agccaagtgt tggactggac    13980
agagacaggc aaatgtttga ggtccaggtt cagtaagaga ccctatctca aaaaatctga    14040
tggagagtaa cactggaaga actcagagtg agtcacacat gcacacacag gtgaatgtgt    14100
atacaaaggg ggcagggagg gagaatgaga ggagactggg agatatctgt agttcatgtc    14160
tgtaattcta gcacttcaga ggcagctgga gctacacagc aagacccgt ctcaaaaaca     14220 aacccaagcc tgacagtggt gaggtacacc tttaagccca gaggcaggag aatctctgag    14280
ttcaagggca gcctgagtga gttccaggac aaccagggct ccacaaagaa acactgtctt    14340
gaaaaaaacc aaaccaacc aaacaaaaaa gaatcaaaaa caaccaccac cactacaaca     14400
aagcaaacaa gggagaaggt ataaaatgct taggagagtc ttcctttagt ctccatcctt    14460
tgggtactcc ttccccacag aaagccacta ctaccaattt cttacataag ctgctgtttt    14520
agacacaggt tttttttttt tttaaatata gtaacatatt catgtgtagc tcattttct    14580 agtgagtggt tggtccttct tttaacagtt taaaggacct ctatgtttaa aggcgattgg    14640
cccttgtctg gagtatgggt tgtattttcc caatttgtga gttttaccca acctattgcc    14700
tattacctat ggccatttat tcttgtcgat aagtagtttc caattgtatg actatggtca    14760
cagtgttcca tggactcttc tgccgctaga cagcccctgg gtctgaattt gagatggtta    14820
caagggtgat tggctctgct ccctgggtgc tgggattaaa ggcgtgcacc tccacaccca    14880
atttgttctg ttttgtaaga aatgaggttt tattgtgttg ctcaggctga tctcagtctc    14940
ctggcctcaa ggtatcctcc catgtcgata cacagcacaa ggcgtaggaa aagtggcaga    15000 ttttttttaaa ttaagttttc tttccaaaat atagattcag aaatgtgaga ttttcacaaa   15060
gtgaacctgc tcacttccct ggctctgmaa tctccattgt ggctcccgcc catcccttt    15120 gcccaccagt ggctgttgta ttgacttcta tcccattcct taactatacc tgtccttggt    15180
cttcgctgtg aacttgcttg ggctgagaat caccttgttc cgggcacatc aggtcagtga    15240 gggtgttttcc agagagtttt aacagagacc agaagaccca ctccaaatgt gggtggcaat    15300
acctgatgtt ctgtcatcct ggactgggta ggaagaggaa agtaagaagc aaacggcacc    15360
cccacctctc tgtctgcttc ctcgccgaca caaagtgacc agggcctccc actcctgccc    15420
cctcagctag agacacttgc tgccatcttt ccaaccactc tgagactgtg cctactaacc    15480
gtgacccaaa ataaatgttt ccttccttaa ggttgccttt gttagctcct ttaatagagc    15540
ggtaggacat gtaactgcca caggcagcca tcgctgccag cccctcccac tgaccgtctg    15600
agaaccacac tcagctgtag gcacagctct catagctgtg tgggcgtagc tctgtctact    15660
cggtcattcc cctgctgccg agcatttatt gttttcagtt cctggctgat gggtagcact    15720
gttatgaaca tcctagtaca aatctcaggg tgacacgcgc cttcattttt cctgagaaaa    15780
tgcccaagga taaaatgcta gggccaaggg aagaatattt caccattaag agacactggt    15840
caggactgga aagatggccc agtggttaag agcactgact actcttccag aggtcctgag    15900
ttcaattctc agcaaccaca tggtggctca caaccatctg taatgggatc caatgtcctc    15960
ttctggtgtg tctgaagaca gtgacagtgt acctacatac atgaaataaa taataaata    16020 tctgagagag acagacagac agacactggc tagtcatctc acaatgttct catgtttaaa    16080
atatgatacc atttgtataa agcagaaaca caggaaaaat aaaatctgtg gtattatatt    16140 tgattttaa attaacttga ttagtgaagt tagcagctac actgggcagg ggttgggagt    16200
ggggtactct gaagtgctgg tatttctggt tttgttttt gtttgttttgt tttttatct    16260
```

-continued

| | |
|---|---|
| tatttatatt acatagaaag ccattttgct aatacactta ccatgtgtat atattgtgct | 16320 |
| tgaattacag ctaagtaatt atttctgagg ggctttagac tactgaagat tgggcccaat | 16380 |
| gagccccacc ccaagtagtc tccaacatcc ctcttggaag tacttgagag caaagattca | 16440 |
| agtcacatgt ccccaaaccc tcagcagcca ccacccttta ggtgtggctt ttgctctcgg | 16500 |
| tcatcctgga acatcttgcc atctttggtt tgttctctcc ctgtcttgcc tctggtagag | 16560 |
| ctgggtttct gtgcttctat tcaaccatgt acaagaacca tgtgccacct gccatgtgcc | 16620 |
| aagcctgtgc cagtccctgt gagcgagcag cccaccccgt gagttatcat gtgaggagct | 16680 |
| atgaggagca ggaaggggcc cggatgactt cagcagacag tatgaagcaa gcactgtgcg | 16740 |
| atttatgctc cctggccaca tgcccacaga tggtgtctga cactagcg tttaatatttt | 16800 |
| gaattctcca cattctagcc tagacatttt ggttgcaaga agaaaattga ctccagttgt | 16860 |
| atcctggaat gaaatttatt ggaggaaaat actggacagg ctcccagaga aaatacgata | 16920 |
| ttcaggcaca aaagaaatg gggactgagg atctgaagtt caaggtcatc tgtaatgaga | 16980 |
| ttgaagtcag tttgggctac atgggacctg gtctagggg aatggggaag agaagggaag | 17040 |
| ggatcgagat agggat | 17056 |

<210> SEQ ID NO 4
<211> LENGTH: 5973
<212> TYPE: DNA
<213> ORGANISM: Mus musculus

<400> SEQUENCE: 4

| | |
|---|---|
| caatgtgctc tgacgattaa tgggctagaa atgtgtggct gttgattagt gaaaagatgt | 60 |
| catggttcag gagattggta gtctctgtgg gaagacaact cactgaaagg gaggaaatag | 120 |
| cctggaagag ataaagagac agtgatcagc taggaagctt aaaatttaaa ttttgttgga | 180 |
| agtactgtta ggaatactag cagaggccag atgaatgtat ggttaagtta tagcaaagga | 240 |
| aaagattgtt aatggtgagg ttaggaatgc agggtgacac caacctgtaa tgtcagcatt | 300 |
| agcgagatag aagcaggtgt ttaaggccat tctctgctac ttagcaagtt gaggccaatc | 360 |
| tggaccacat gagaccttttt ttcaaaaata aatctcctta aacaaagag ctgggtttt | 420 |
| ttgatagatt cttcaagatg ttaatgtaaa taaatggaag accaaggatg gcatgctaat | 480 |
| atcctcagtg tctgaagaag gactatgtag tgttggctgc tgactctgaa gtaagtgctc | 540 |
| attactgaca gatagtgtat cttagagcct ggcagatggg atggaagtga ggaagcaagt | 600 |
| agcacctttg tatattatgt tctaagtagc cagagatact tgacacaaaa caaagttgag | 660 |
| aaaatgtatc ttctagaaaa tacagacatg gaaaggtgtc ctttctataa aagaggtatt | 720 |
| aaacattaac ctgaaaaaaa agttagcaaa ttgggctttg gcaaatgaat atagtcaagt | 780 |
| ttcattttta ttttgttttt tgtatatgac tgtttggctt gttgtaccat gtgtgttcct | 840 |
| ggtgcctagg aagtcagctg gagttacaga tggtgtgagt tgccatgtgg gtgctgagag | 900 |
| atgaacctag gtcctctgga agagcagtta gtgctcttaa ccactgagcc atctctctag | 960 |
| ttccttctgt agaattttca ttaatttaca aggagaaag tataaatgat aaaccatga | 1020 |
| gaagatagac cggcactaga attagtggag tcaaatgtt aatgatatgt cagatacgcc | 1080 |
| ttatatgagg aagttgcaaa attatgaaaa tccaggcact ccactgagtt agaaatctag | 1140 |
| gctctgatgc atactgctat ggtaaggtag caagtggcca ttgagtgcag aagtgagtct | 1200 |
| ggatgggtct tctggtgttg tggagcacac agactgctgt cttctgcatt gcagtttcac | 1260 |
| ctgtatttcc ttggaactac ttagctttgc aactaggcgt taaaaaaaac tttatattta | 1320 |

-continued

```
tggttttaag ttatttattt gttttatttt attttatgag acatagtctc actctctaac       1380
ctaggctggc ctggaactgc ctaggtaact tgagctggtg attctcttgc catagccttc       1440
taaaatttta gattgcaggc ataagccaga ccactcctga cttttgtagc catttttctg       1500
acatgaagtg taactttgct ttcataacta aaatgattta gttgttttgt tattgtttaa       1560 tccctttgc tttgaatgta tccttttgtg tgggtggcag atatataacc acagactttt        1620
ccacaggcat cctaccctag gtccagaaat gactctgaga cgtcttatat atgaatgaat       1680
gcctaggcca atagctttgg ctgatttcca cgggttcata gctcagttat cccatttaaa       1740
ctagtctaag tcatgccatg aggctacata cccctccttc agtttcaggc gactgtcttc       1800
tcagttgtgt aatgtcctat cctctgttgc tgctccccaa cccccatcct tgcgtcatag       1860
tccgtctgtc ctcgtctccc cccatttact tgcacaacgg actctactct agaagtcctc       1920
tctgtgctgg agcttgcacc tccgctctcc ccgtctaagc taataggcaa cagcattgta       1980
cagacaggtg atgcttccat acatcgcaca ggagattctc cctacacaga tacttattca       2040
tccagcgtga atgcaaccgt ccaggcgtgt tctcctagtt gtagtacatg ctgttgtatc       2100
agtctgatga atttctttgt ctttacaacc aagaaagata atactgtaag aaattttgac       2160
taacattttt tctttatttta aattacagac taactggctc ttctggattt gtaacagatg       2220
gacctgggaa ttataaatat aagacgaagt gcacatggct cattgaagga cagtaagtta       2280
taatggctga ctttatttta atttattata agagcacagt atagcacaaa atacttccat       2340
gtgtgttatt gctatttctt gagacaggac ctttctgact gagtaactca ggctgacctt       2400 gaatttgct atgctacctc tgcttcccaa gtgctagggt ggtaggtgtg gaccaccatg        2460
ccctgctgct aaaataccgt tcattgatgc ttttcatttg gatagtgttc ttgctttta        2520 aaatttactt tttggggac cagagagatg gctcagtggg taaagtgctt gctgaacaag        2580
tctggttatg tgagttaatc cctggctccc acagtggaag agtgactcct gaagttgtc        2640 ttctgactcc cacgcttgtg catgcacgca cacacacaaa taataaaata aaaaattaaa       2700
aggaaatttt ctttttgg tgatagggat tgaacctatg acttcactaa gcaagtgctc        2760
tattgttaaa taattccttt aatttgtggg ttttttttt ttaggttcca agttgactta        2820
atgttataaa tgaaagatac ataccagaaa tttgcatatt tctaatagtt taaaaaactt       2880
agttaaaatc tttttaatag tttgcttaaa tctttatata ataatgctat tatatcattt       2940
ttctaaatat tgatttatt atcagcaaaa cagtaaatga gccatcagaa taaccactgt        3000
agcctgtttc cctggccctc tgtccttcca tctgtctatc ttctcttttt tttccttttt       3060
tgtgcctgtc atttagggca aagcatttta gtctctgaac aaaactttga aatttccaag       3120
taactcttgt ttatttgttg tgtctcatat tcaacccaag aaatattatt tactaactca       3180
tttaaaagca acaattataa cccactacat gttagcagaa aaacctatt gttttttattg        3240 agacgggatc acactagtaa gcactacatg gcatggcgtt cactgtgtag atcaggcagg       3300
ctggcttcgt gctcttgaca gtcctcctgt gtttgtctct cacttctgag tgctgggatt       3360
atagacatta ccaacacacc gatttggggg gttggggtac tgggatcagt ccagagttgc       3420
atggatgcta ggcaagcact ccaccaactt agctatatcc ctggtcataa atgtcataag       3480
gaaaaaaatt ccttatattt aaagaaattt taagaattgc attgtttaag atttcacaga       3540 tctcttgct atctgcaat cttttttgat attttgtttt gttttaaaa atatgtggta          3600 tgtaaacaaa cttaaatatg aatgggacag ttccagatga gagtgaaaag ttaaatattt       3660
gggagaaaaa ttgataggtt tatctattat ggaaaatttc agagatttta gtaaaatttg       3720
```

-continued

```
aaaatggagc tgggaggtct gaggtagtca tctaaagctg ccagttgtag agcgtgttgg   3780
agtgtggagt cagagggagt tactgataca cttgttgaaa ttgcccaggc ttcatgggaa   3840
gtgatgaggg gctgttactg tgactctggg cagggcttgt tagtttcctt tggatttagt   3900
ctcagtcaga gttgatacat agtttcctga ggacgtggct ttttggtaca gtgctgtgaa   3960
aaggcagaga agcaggtaaa cttagaaaat gtgtgttttt aaagtgatgt gttatgaaat   4020
cttacgtaag atgaataaag aaagaagtgg ggacactgag ggctcctgtt tctaaatgtt   4080
aaaagcaagg ctggaaacat tctttgaagg cccctgaagt cagagcccgt gtctcttttg   4140
gttcccagga cattttgat attcccttac acatagcaaa tactaactag atctctgaca    4200
aatgcaggaa agctgtttat atttatatat atttatattg tatattttc tccttataaa    4260
ttctttaaaa gtctgtttta gtagttaatg ttatgattat tataaattac ttaattattt   4320
ttctaggcca aatagaataa tgagacttcg cttcaaccat tttgctacag aatgtagctg   4380
ggaccattta tatgtttatg atggggactc aatctacgca cctctgattg ctgcctttag   4440
gtaagccctg ctgcatttca tctcaggaag taagtgtgtc tccaggatgg agtccgtgct   4500
gcatttactt tattctgcag tcacactcat ctcatggaat tagttctgtt ctggtgagct   4560
acagttcact tggttttat gtactgggtc gttttccatg tatactagta tgtagccacg    4620
gttagtcttg aacttctggt tctcctgcct ccaccttcca agtgctagga gtataggctt   4680
gtgccactgt gcctgactca tttcacattc ttgaactgtg aagttttgat aacactatta   4740
aatttacctg ctatttgtga ttttgttaaa gtttgcatta aaaagttttt gactatattg   4800
ataatatttt tgtgacaaat ttaaatcaga aaccatacct ttcttgttct tgtatgtatt   4860
tcattccata ggcccttagg aataactttt ttcaatagta tatagttctc tcagtttgta   4920
tatatgtatt attagggata ggaggagctt tctggaagac tatttataaa ttggacaatg   4980
gctagctgtt gagagtgagg aatttgctag tttttgtttg taaatccctc cccaatgcat   5040
ctgtattagt gatttaataa aataatgcaa ttttgtcagt tatatggggtt gcactgaatt   5100
tttgctattt tattttaaga aagattttg tgtgtctaca gtgtatatga gtgtatgata    5160
tgtgtgcgtg tgcatgtgtg tgtgtacttc tatgcaggta ctcacatgct atggtgtgca   5220
cgtaaggttg gagtgcagcc tcacatgttg atcattatat tccaccttgt tagagatagg   5280
ttgtctttgt tgtttgctgc ggcctggagc tggagctgga gctaacgagt ctcagccacc   5340
tgacatgggt actgggaacc aagagcagca agacctcttc ttcttcttct tcttttttca   5400
ttttcggttt ttcaagacag ggtttctctg tatagccctg gctgtcctgg aactcactct   5460
gtagaccagg ctggcctcga actcagaaat ctgcctgcct ctgcctccca aatgctggga   5520
ttaaaggtgt gtgccaccac cacccagcct aaaagatttt cttactaaaa tatatttcta   5580
aattaattag ttggaatctg gttcatactt cttttgaaa caaaaccagc attttttttc    5640
attctacata cagagacatt gacactagac actggttatg agtagttact ataagaatgg   5700
gaaattattc caccccttgta aaacttaata caactcctta tcaggctctg aagacttttt   5760
aaaagcaaga attgtatata acacacagaa atgatttaga ctatttagat ctttattgca   5820
tgggatttta aaattattat tgtatttcgt gggcatgttt tgtctatgta gcatatgtgc   5880
ctgtagaggc aaccaccaag taggtcctgg gaatcaaacc tggtacccct gctcttaggt   5940
gttcttaact gctgagccat ctctccagtc ctc                                5973
```

<210> SEQ ID NO 5
<211> LENGTH: 90050

<212> TYPE: DNA
<213> ORGANISM: Mus musculus

<400> SEQUENCE: 5

```
aggcaagaaa gagccagcga gcctccagac agaccattag aaattccaca gtcagcacaa      60
tagggagaac agtaaatctt acattaaaag aaggccaggg cctggtagca aaaggttttta    120
atttaagcac ttgagaggga gaggaggcaa atctctctga ttgggggttg gggttaatgg    180
tgaatgccat gacaccctgc tcagagttag ccttctcccc taaaaaaatt ttaaattcat    240
tttcaatgct gacacagtta atcatagaca ttgtatctca gacacctcaa catactccag    300
actgcagcac cagcccactg ctgaggctgt cgttcagttg gtagaaggca tgctcagcat    360
tcgcgaagca ccagacttca tccttagcac tacataaaac tgggtgtggt catgcacact    420
tataacttca gcaccatgga ggcagaggca ggatgatgag aacttgagga tcattctcag    480
ttacataggg agtttgaggt taagcagggg tacaggaggc ctgtctcaaa caaacagaca    540
aacagacaaa caaacaaact tcaaaaaact cttgaagtac taggcctagt acgtgctgag    600
attgtaggta tatgtcatca tgcctgttgt agaatgagtg agagcggact ccataggctt    660
atagatttga atcttggtgt ctgtctatgt catgtcatcc ctgcacaaaa gcccacacta    720
ggcccacaca ttctctctgt ctgctgcatg tgggttagat gtgagctctc agctgctgct    780
ccagtgccat gcctgcctgc tgccaggctc cagccatgac ggtcagggac taactctctg    840
aaactgtaac caagttccca atgaaatgct ttctttcata agttgccttg gtcatggtgt    900
ctgcttcaca gcaataacac ggtgactaag atacctggct cctcccctcc ccaccccacc    960
attatttacc ataaagtaaa caatacacag ttggataaca tgatactgaa gttattttcc   1020
tgtttcctga tgtaacccaa ttttggacaa gattaagcct taaatagcaa gctgtgaggc   1080
aggataaaga aaaagctcgc aggccaatgt ctgctttacc aaattctgtt cagcagtcta   1140
aagctgccgt cacctcgact cctgtgatgg catttccatc actatcttag atattccctg   1200
ggtcacaacc ttttagtaca cagattgcaa ctctgatgga atggctgact gcttggctaa   1260
ttaaagcaag ctagagtttg tctggcttcc ttgtctgaat ggggaggtgg tatttacaaa   1320
attttgtaaa taaactacta tatttgcatg atgtatataa atttgatgtg gctgcttttta   1380
aatcatttaa cctaaactgt cccacagaat catctgtttg attggaaaga ttgtagcttc   1440
aagagaattt ctgctgaacc tgaaatgatt cataatgatg tgtctgaaga atgtgtgcta   1500
tcacctacgg ttttttgtttt agttgatatt tgtactttaa gatttccttt atgtatgtgt   1560
gtgtgtgtgt atttatgtga atgtatacct catgtatgtg gtgctcaagg acacctgaag   1620
aagggctctg gagctggagt tacagggagt tgtgagtgct aggaaagaaa gctgggtaca   1680
ctgggaaatc aaaaggtgct tctaaccact gagaaatcct gccagcccct tggtttatta   1740
aaaatatcaa acaaaaccaa cactagttac ataagtatct ctctctcttt ctttctctct   1800
ttctttctct ctctcttttct ctctctctct ctctgtcaca cacacacaca cacacacaca   1860
cacacacaca cacacaaagg atccataata gttcttctgt atcccggtta aatataagtt   1920
cttaggggct agagagatgg ctcagcagtt aagagtgctt gttgttcttc cagaggaccc   1980
aagttcagat cctagtacac acatcaggca gctcacagct acccatatct ccagctccag   2040
gaagaaccaa tcaatgccta tggcccatgc aagcaccagc acacatatgc tccacaaaca   2100
tccatatata tagctaaaag taataaaaat aaatcttcaa aaaattaatt ctggttgaac   2160
tgaaaaagat cacctaacat ttagaaaaag cagtttacta gtgaatagga cataaatcat   2220
```

```
ggtatcaaat attctgttgt taaaggaagc aactagaaaa agcatgtgtt tgaaataacc     2280
aatggataca aaacaaatga ggcaacccca acatctgtca gtaccttgca aaccaacaca     2340
ataaatttga ttttatttaa atcgtagtta tttttcatgc tagtagtttt gaaacacaat     2400
aaatttgatt ttatttaaat cgtagttatt tttcatgcta gtagttttga aaccaagatc     2460
tagattttgt atagccacat aaatacacat tagaattgca aactgatacg agcttcatct     2520
tcatcagtct ctcttcatga aaagcagtta cagggactga gacatgactc agcagttacg     2580
gcatgggctg ttcttccata cgacatggat tcaattctca gtgcccaaat gttggctcac     2640
aaccatttgt aactctggtc ccaggggatc tgacactctt cttggcttct atggccactg     2700
tattcatacg gtacacagac acatatgcag gcaaaactaa acaaaaaaaa taaggtttaa     2760
aaaaaagaat tagaacttaa aggcacttca ttccgtcagc actaaatcag cctctctgga     2820
gtcttcccac ttcatgagaa aatcgtcagc tctccactgc tgtctgtggc tgaggagcag     2880
gacctggaca acgttcagag attgtcagtg catctctttt cttctttggt ttgctgtcat     2940
caggttcact gtcacattcc ctttgtacca tccttccttt aacagccttt tgaaaatgca     3000
gaaatgttgg atgctgcctt cagttcacac aggctgtctt tttagctcct catctatcta     3060
tgcttaattt gttagtggtg ctcacccatg tatgtgttta tgtcatgaag ccacaagatg     3120
agccttgatt gagtcttgct gtcagtgtgg atcacagaaa tgcaccccta tcatctttgc     3180
ttcctgcttg ttagaagtca ttgattctgc ttatactcaa ggcccacagt attatacttg     3240
ggtgtgaacc ccaggaagca gggaggtggg gggtgtcatg gatactactc agatatctga     3300
ctgttgtgat atttcatcag ttctcattgg tcctatcttt aaaatctgcc ctacatctag     3360
agctggctgt ggtggtgtgt gtggtggcat cagtatcaga acttggatta cagaggcagg     3420
aagattgtga ttttgaggc cagaataggt gcatacaaag atcctgtctg caaaagaaac     3480
aaatgtgcaa ataattataa ctactttact aatagcctaa ctaataacca ctgctagtgc     3540
tgtgtccacg aaaaggtgaa gtaaactgtg aaaatgactt cccccttctgt gtgacacacg     3600 ccgtcatgtg attttacttg tgtctcatca ttgtttttcc ttctgtttgc atgtgtgaat     3660
gttcacatgt ggaagccaga agtcagtgtt gagtgtcttc ataattgatc tctattctct     3720
ttgttttgag acagggtttt gagactaagc ccagtgctca gtgattcatc cagtaaactg     3780
tagggagctt cctgtctctg cctccacagt gttgggatta caagcatgat ccaaattatg     3840
tgacaagcgc tttactaact tagccatgtc ctcagctccc cactcccctt ttcttttctt     3900 cttcttttt ttagacttac ttgtttattt ttatgaatgt cttgcctgca tgcatacaca     3960
cacacacaca cacacacaca cacacacaca ccccacatgc aagcaattcc agaagagggc     4020
attgaatccc tgaaactgga gttccagtta actgtgagcc tgtcatgtgc gtactgggag     4080
ctaaatccgg gttctctgga aggtcagcaa ggtcttacct gggagccgtc tctttagctc     4140
atgtgtttct ctcttgaagc aagaaaccta ggaatcattt tgaaacttcc ttcacagcct     4200
ttatcataac ttcacgtcaa ttttttaccta ctctttcaac aaatacatgt tatatttact     4260 tattttatg tttagcctgc tattggtttc tacttagcct cttgcagtag agttctgtca     4320
gatttatgtt tctattgctt ttaatttatt tgtaaaggtg aatgggaaaa tatttaaaaa     4380
ttacagatcc catcatttac tatattctta aaagccatgg ctagccaggc ttggttgtgc     4440
atgcttgtac tcccaggact ctgacaactc agtaaggagg agagtgaatc agaaaatagc     4500
gccagcctgt gctgcttagc aagaaacaga aacaagtaca atcacacaca tagaaaatcc     4560
cccattaata ccatcccatt agatataatg gtcctgtatg accattcaac cactgtttgt     4620
```

```
cctctgtact gcagtaacag tcttctgccc ttgcccgtga agcacgtgcg caccccgcct      4680
ccaagtgctt ttgcactggt gtcctccgtc tagatgtcct gttactatat gtaaggactg      4740
gtttctcctc ctcttttacag ttcaatctaa ttgtctcatg aaaagatctt tcctgaccat      4800
ctggttcaga caggttctcc ctgttgttgt tttgtttttt gttttatagt tctaaattcc      4860
tttcaggaac ttttgcttat tttaaattcc ctgagtgcat acgtgtgctt gttgttgctc      4920
atgctcgttg tttgggctta ctttactatc agctctggat gtggttcaca gaaggtgctc      4980
aggggagcac tctcagccac tcatctcaca cgggttatag atatatgtat tgatgctacg      5040
tttgcttgtg agccatgttt taaagattag aatatctttt ctatgtgtac tctatcaaaa      5100
cacatgttag ggctttatct attttataca gatattggtg ttcttgcttt actaattttc      5160
atggaatttc ggtgaatatt agtattttag ataggaagac ttgtctcaaa atgtagctca      5220
gctggttgag tgcctgcctg catgtagaaa gccctgtatt cactctccag cacctcagaa      5280
gtgggccatg gtgcatatgc tgtcatctca gcactccgga gggagagaaa agagaatctg      5340
gagttcaagg ttatccttgg ctatataaca agtccaagat cagcctgggc tacatggcat      5400
cctgcctcaa aatcaaacac caaatcaaaa agctcacatc ttgatccaaa agaaggtaga      5460
gagaatacac tgggaaagtc tttgaaacct caaagctaac tccaagtgac agtgacacct      5520
ccttagcagg gccataaatt ctaatccttc cccaaagccc accaactgga gaccaagtat      5580
tcaaagataa gaatctatgc agtccattct ccttcaaact accacagtag gttttcttaa      5640
aaaaagaaaa aagaatattt taattgattg tgattattca gtattattca tgaataatca      5700
tgaactacat ggcaggacta taaactatta tttttttaa agatttattt atttatttta      5760
tgtatgtgag tacactgtag ctgtcttcag acacaccaga agagagcatc aaatcccatt      5820
acagatggtt gtgagccacc aagtggttgc tgggaattga actcaggacc tctggaagaa      5880
cagtcagttc tcttaaccac taagccatct ctccagcccc tataaactat tattatattt      5940
ataaaatata aatccgtgag tctgtgcacc cctgtgtgca catggatggg acatctttga      6000
actggattat atcatactta gaagaataca agatactctg ttttgtcatt tgggtgaaaa      6060
tatggtctgt ttattttgca ggtatgacct gacttctagg gaatggcttc cactaaacca      6120
ttctgtgaac agtgtggttg taagatatgg tcattctttg gcattacata aggtaaacta      6180
tctcaactct tcaccaagca agaagttcaa ctcttcctgt tgctttatgt cattgaatac      6240
tatcgagctt tggttttagt tggtataagc tttgttttga tgtcatggag gtatataatt      6300
caccaagttg tcaccaagtt gtaattggaa attgaagtta gaacgatttt aatccatggt      6360
gtcttgcatt tggatactct gatcacagtt aacaatgaag attaaatagt gtcagcaagc      6420
ctatgcccat tatcaagtct agcatactgc atgcgtgtga ctgagtagcc attgttatct      6480
ccttgttttg agcgtatatt gtagaatgag gcaactgtat tttccacacc attttcgttc      6540
tgtaacacgt ttcatgtaga aaggtgatt tagagagggg aagaatgtga ttgtattggt      6600
tggttctttc tctatgctat tcctagcaag tcaccgaaga gctcatgtta ctcacacttc      6660
ttaagctggg atcacaatga gattgtgaac cactcattgt tgttttccaa tataattttt      6720
aaaaagatgt atttattttt attttatgtg tgtgggtgtt ttgcctgcat gtatgcctgt      6780
gtatactgtt cctccagagg tcagaagagg atggcatcag aactggtggc tgttagctgc      6840
catgtgggta ctaggaacta aacccgggtc tctgcaagga gcagcaagtg ttcataaact      6900
ctctctccag ccctagagtt gatttcttaa tggttttaaa aatcctgttt acatctttct      6960
tataggataa aatctacatg tatggaggaa aaattgattc aacagggaac gtgaccaatg      7020
```

-continued

```
agctgagagt atttcatatt cataatgaat catgggtatt gttaactccg aaagctaagg    7080
atcagtatgc agtggttgga cactcagcac acattgttac actggcatct ggccgtgtgg    7140
tcatgttggt catcttcggt cattgcccac tctatggata tataagcgtt gtgcaggaat    7200
atgacttggg tatgtatttt ttccagtgga ggcatcttga atatcatact gagaacccct    7260
gcccttatta ttaggacacc gtaacaaaat tcagcatgat cttgatccag taccttgtct    7320
tgaaatagta tcagtagata actggtgaga ttgaggttgt tgaagtccct gtgcaacagc    7380
tgtttcttac ttgtcaaggt ctagtcttgg cttgggaggg gttctgagga aaggggtgtc    7440
aaaaaaccca aaaagtccaa ttgtaggtcc aagctggcag ctgtatattg cattaaggaa    7500
agctgaggga aatttgggat atttatttca tctattagtc tacatcaagc aagtcaagcg    7560
ctcacagtca acgtttgcac cctcaaatta gtaacaaaag agggggaact gaggagtcca    7620
gcatggtcct ggttgggaca gaatgacatg gttccagccc tgagacaggg gcagcaggtc    7680
cgggcctcca tggatgtcac actatggaca taaacctgtt tgtataataa tgtacatatt    7740
tcatgctcct cttctgagta atgtccttct gttaatgtga atgacttcat gataatcaga    7800
gccagtgtga gtctgggaag taaatggtgg gaccttcagg acagctctta aggctgtgga    7860
aaagaacatg agttcaaaac catatacttc ctcaactata caaaaataga aggatgcaat    7920
atgaattgta tgagggctt cacagatcta aggaacaaa agcagcttcg ctgtgagcca    7980
acttgtcaga aagatattga gtaagcagtt aaagagattt agggagtgct gattgctaga    8040
ggaggccacc cagctaagtt tgtgcttaca aaggcagaca aagtcctgag ttcagggtgg    8100
gcctggaaca gagcaaggtt agttagacct tggtgtggta gaaatggtaa tttccagaca    8160
ggatacccaa ctagtttttg tgcttaacag aggcaggtag atctctgaat tctttttgtaa   8220 tgttaaaagg aaatgtgtgc ttgttgtctc ccaaggggcc tgagtcccag gatgctgatt    8280
tataggaaac ctggagtaac tgggtttatg acctgcagga gacgagctat ccagaatgtt    8340
ttttgcaata gcaagagaga actgcctgga gaactgcctt cagcaaagaa tagcaagaga    8400
aagctgtcta gagagagagc tgtctgtaga gaaagccggt cagagagaaa gtagactgga    8460
aaactgtctc cagcttggac ccacaatttg acttttgtt tttgttgaca agttgccctc     8520
ccccagaaac accttcctca ggaccccctcc caagccaagg cagggccttg gcccttcttg    8580
tcagcttgca aggagccaaa gatagcatta aatgctttgg atatcaaaat aagcaaaatg    8640
caaaacagta aacactctaa aataattctg gctagtcctt taaatattag gccagtgcac    8700
tgttatttta ccttaatgta taatcttgtg ttacatttta ttgtttttat tgtataatag    8760
gaatgtcaga attataattt tgtaacattt gtttgacatt cctgtgaaaa tgcatctaaa    8820
gatcattaaa gtgcatctga agatcataag gactcactga ggagcacagg gaattaagtg    8880
tctgcttaag agaactttga atctttaatc tttagaattt gttttaaaaa tttgaatctt    8940
gccagtgtgg tggcgcatcc ctttggtccc agcactcaag gggcagaggc aggtgtatct    9000
ccattagtgt gaggccagcc tggtctacag agcaagttcc aggccaggca gggtacacag    9060
agaaacccta gcttaacaaa acaaaacaaa atatgaatct ttaaaaactt gttctgtgaa    9120
aatttcatac atgtatacaa tatagcttgt tcatatccac cgccattcct tccagctcct    9180
ctaggctttc ccagtgcatc tccttcctag ccttatggcc tccctttcag ggtgaaggtt    9240
agcacactga gtccagttag tgctgatccg atgcagtctt gtctagatgg tcttctttat    9300
aataaggtga agtatatcc taaacttccg tcttttgctc taaggtgttt agactttaaa     9360 ctaatgtta aatcgtttaa ataatttatt atttcataag aagaggagcc tgcaacattg     9420
```

```
actttaacta ttgtctctta tccagaaaag aacacatgga gtatattaca tactcagggt    9480
gctcttgtgc aagggggtta tggccacagt agtgtttatg atgacaggac caaggctctg    9540
tacgttcatg gtggctacaa ggctttcagc gccaacaaat accggcttgc agatgacctc    9600
tacagatacg atgtggatac tcagatgtgg tgggtgtttt cctagagctt tcccttggta    9660
gtctagaatc tgcagaggca attgattaaa aatactgtgc tatggtttga cttttgttca    9720
gcattgtatg taacaaagtt aggagatcaa tacagtaata gagttaaggt actaatggtg    9780
ctgttgctgt ctgttagtgc ttagtgcttt agacctgatt cactgaactc tagcaaggtt    9840
tcctctcttc agaattctca gcaataaaag ctgtgctgat tttatccata cttaaaaagc    9900
atatccttcc ttttctcttt tggtgttggg ggatcaaacc ttgtacatga ataggctata    9960
ccatctttat ccatttacat caccaaacag gatgctctcg tgcctatttg ataggttttt   10020
cactcacttc gaactgaaac ttgggttgta agagtatggt acttttagca aatggaaata   10080
aatttgagtt atgatgcaat tataaagcac tggtctctct gtatttccct cctccttcta   10140
ctccctccct cttcctttct gacccctct ctcaacatac attagagacc atgctttgac   10200
tgtcaattta tgctgtgctg aagatcaggt ctttagtggc tgtgaaccac ggagcctatg   10260
cagtggaagt tctggtctct ggcttttgcc ttactaataa aacactgagc ataaattttg   10320
atttgtattt cacaattctt acctggaatt cttaagtgga attatggagc catagagaat   10380
gaacatttta gggcttttaa tatagtttcc cgaaatttta acagattttc atgattgtta   10440
aaggaagtgg cttacgtata gggggaaatc aagtattgca catttgaatc taagttata   10500 aagtaattac atttaaattg gcaaataagt attcttttaa aactaacctt atatttatta   10560
tttctaaata aactcaaaag gaccattctt aaggacagcc gattttccg ttacttgcat   10620 acagctgtga tagtgagtgg aaccatgctg gtgtttggag ggaacacaca caatgacact   10680
tccatgagcc acggtgccaa atgcttctcc tcagacttca tggcttatga cattggtaag   10740 cttttccaaag atgttttagc ttcaggaata ttttctttgc tgatggaaag atcactatgt   10800
taaaataatt gcaccattta aaagaagtcc aggtggtaga atttgcattt aatttgagta   10860
gggttacaca tctattgaaa agcattattt tggattaaac tacattaaat tctttgtgaa   10920
atcactcttc ttaattgctt taattctttt tttaggttga gttaattggt atcttctttc   10980
ttataagtgc cttacatagt agtggtggta gttgtaacca ccagtgttat gttaagtttg   11040
atgggatatg ctgtttccta gaaacctggt tttacacatg ctgttgatgt caatatacat   11100
gtggccagaa gagggcagtg tctgtttatt cctggaaaat aaacatcagc tgctctgttg   11160
tgtaaatatc acccatgtga tgttctttct gtttatttgt ctttgcattt tgagacagcc   11220
tcactatgta gtctaattgg ctgaagctca gtatatagat caaggtgacc ttgaacttag   11280
agaaatcctc ctgcctcttc tgagtgctaa gattaaagat gtgtactacg aatgaaaaaa   11340
aaaaatgtgt actaccacac ctgactagag attcatttta aaaattattc ttattgtgat   11400
aaaatgctca gaataacact caccatctta atgtttaag tagtttagat ttaaatatat   11460
tcctagtgtt attcatgtta taataccatc tgcttgccga cttcttgtaa aactgaaact   11520
ctgcccttaa acaatagttc ctctcttcat ccctcactcc agcctcttga atcatttc     11580 tatatctcta tgattttgac tagtctaaat taggcatttt ttaaaaaaaa tattttgttt   11640
acttgtatgt gtatgagtgt tttgcatgca tgtatgttaa gcacaccatg tatattcagt   11700
gcccatagaa gccaaaagta ggcatagatt ccccagagct ggaattacag acttttgtga   11760
gccaccatgt gggtgctgga tactgtgccc aaatcctttg gaggaatagt gagtcttctt   11820
```

```
agctgttgag ccatcttgtc agccctagat gtttgttttt aacaaacgtg ttttttgccag    11880 ccattgagtt tttaaattga gaatgggggg tacactatag ttagtcctta gcttcaagct    11940
tgtggaagca gaaatgagaa gacaatataa tcttaactca ggaggattct tgctggctga    12000
aacaaagatg tgaaattacc tccgagcact cctaagccac tggggtgagc agggtggtct    12060
ggagaggcct tgaagagaag ctgtctgagc ttgttcctgg ggacactggg agtcaaatag    12120
acctcctggg caggggggatt tagtgcagac aagaggcagg aaagtacatg tcaaatattt    12180 aggactttg aaccgctacc tttcttttgt catggtaaca cagaaggtag caggtgactg    12240
ttagactaga atgttcagat ctgattcaga gtgccaggga tcgttggttg gtcttgtgta    12300
aagtctcaca agtgatagaa tcatatgtgt gtcttagact ttttttgttg taggtatttt    12360 agattttct tgttttttcct ttttgtaagt ctggccctca cactatggtc caggcaggct    12420
taagacttat ggtaaccatc ctactctgcc tttatgggcc accatgacca atttaagaag    12480
ctctcttggg tggcattgtg ataagtgatc tggaaggggc atattgacag ttagcaggct    12540
gctactgcag aagtcctaat taggtttgta tcaaggccat ggaaggagca gtgacttcta    12600
gtacctggct gttgtgtgtc ttgacaaaaa tataactgcc ctttcttccc aagtgtctac    12660
tatggaccac ctttgccaaa actaaaagca gattcagaga aaacatatc atgattgcac    12720 atggctataa tccctgaact taggaggatg agaaatatgg caagattgag accagtctga    12780
actatctagt aagaccgtgt ctttaataaa aatagtaaaa attataaaat cagggagtag    12840
gatctgggaa gaagagaatg aagtaagtgt ggggcatatc caattggaga tgtctttagg    12900
acagagctga ttgctgagag gtggttgtag gagaggtgag ttattgtggg gcataaaaga    12960
tgagcaagag tcagagacag ttggagaaca gagtctgaac aagagtagag actaaagaga    13020
gtgtcagaga agcagggaga aaataggtga gattgatgac ctgtgagata tgttaatggc    13080
cagaagagtg gctaaaaatg actggagaat ccttcagact tgtcaacaaa gaaatccttt    13140
agcctaattt agggtgcagg cggctgagga aggacatagg tgaaatatgt gctctgtgtg    13200
ttcattttta ttaaagctta tctgcaaagg cctcagattt gctgtgtact tgtagctgag    13260
gctcttttga actcctggtt ctcctggctc caccttccca agtgctagga ttacagatgt    13320
gtgccctagt taaaatagct gtataccctag cattaaaaat tttaagttag aaaatactgt    13380
ggtgctccgg ggatgcatct cagcagtaga gtgcttgcct gctatacaca aggccctggg    13440 actgatcccct agcaccacaa atactaaagc agacattctg gtagggaaaa ctggtagaca    13500
gcagagtggt gaccatcagg agggggggttg tgggtgatga atgactacat taattagaag    13560
ttctgtgcag tatatttatt tcatgccctg aaacattgct gctgctgttg ctgctttcct    13620
ttacacataa taacataact aaaagacaga caagcatgtg gtatgaggct gtggatgagg    13680
cattctttgt tttcctttt ttttttttttt tgagacaggg tttctctgac ctggctgtct    13740
gaaactcagt aggtagaaca ggctggcctt gaatgcacag agaccctcct gcttctgcct    13800
tctgagtgct gggttcaaaa tttatgtttt tttctataaa gactgagagt tcacatggac    13860
tatatatgac aacctactct gaaatgtgtt tttctccccc ttagcttgtg accgatggtc    13920
agtgcttccc agacctgagc tccatcatga tgtcaacaga tttggccatt cagcagtctt    13980
gtacaacagg taattggaaa gcaaaggctc tattactgtc ttacatctta tattcatttt    14040
taatatcaac ttcctaacag ttgtatctga atggtaagag gtttggggag aaaaaaggag    14100
agaaggcagt tctaagtgca cgataaggta agggggaatag gactgggagg ttatgggggtc    14160 aaagagcaag tctgaagtct gcactatatc caggtgtgtg ctcaggaata cttttctgac    14220
```

```
cagcagagct cttttttccat ttgctccagg aaccttagtc ctgtaaagga catgcaaagg   14280
actagggttg tgggccagca atagagtgtt tatctagctt gcacaagatc ctgagttctg   14340
acctcagcat tttgccttct gcaaacacag catttgccat aagggacatg cagaatggcc   14400
attttaccta gtcacttgaa agtgtgcttt aagattgaga aacttaacag cctgctgatg   14460
ctgacttttc ttattttgct tctgttactg ctttctgctt ctttctttaa tactctaatg   14520
cttacattat atagtcctac aggtattcaa attttctgtt ggagtttcct aatacaagta   14580
atttaacttg cattaggaaa aggataaaag tgccattctg gagttgtgaa gaatgaccgt   14640
ttagaagcta gatagtgggg aaagatgata tctttaatca tgtgattatt tagtgtttta   14700
caagtatata ggggattgtg gcaagaccat tgtatgatta gagactaaag tggaaagatt   14760 tttaaatat cttgttaact tgagtgttat cttaaattac aatctgatgc tttccttcag   14820
aaaaagccct aaatgcctct tgaggttttc atctggcaag tatcatgtca cctggccttg   14880
ctggtggaat ctgccccagc tcatgtgtgt tcttagtgtt ctcctagcac agagttaggc   14940
acgtgtgggc atttgcatac taatgtatag taatagtaac aattgaatga attgtctatt   15000 aaacattct taagttttac ccaaacacag agaggtcgac aatttgtcat aaaatgtagt   15060
ttatccatga atcaaaatca ggaatgactg tctgaacagt gttttttattt tttatttat   15120 tttatttttgt gtaatttctg tgatgtgttt gaatatctca gttttaggca ggattggaaa   15180
tgttagaggt tggtaagagg tcatggttgc agtttgatca tgagagaaat cgatggctct   15240
cccttcattg cagtgttgtc agtcagcagt gtgggatcac ctatgtctaa cagttgttct   15300
aattgagaga ggattacagg agggaaagca gtgagattgt gaggtgctag atgaggagat   15360
ggcatttacc tagcagcctt ctctcccgcc ctcccatcat gtgacctgag agattcacaa   15420
tttctgaaga tatcagctgt gcttagttta agcaatagtt ttattaacta aatccaactt   15480
gattcatgtt attcccaggg aaccagtggt aggattaaaa atgaatccta gtgttctttt   15540
tggttattgg aatgtcaagt tttcagacac tgtaacgaat acagagccat acaatcacta   15600
tatttatttg gtccttttgtt gacttagaaa aattgaagcc cagtttaggt gagctaccaa   15660
atttctcatt gtggattagt attaaacttg cgtggagttg tgggatcttg aagtgggggg   15720
ctaagcatcc gtgtttgtca cagcccagaa ggaacagatg aggttccttt tgaggagtct   15780 tatgtctta tgaacttgga cttagaaata tttgatgtgt ttaattctgc tgtagttttt   15840
taaactctag ctagtgagca tcttttcaca ggagcgcttg agtctgacct acagccattg   15900
tctgtctctg gtgtgcatat tacaaatgca ctgggagcgt ttcttgaccc aaacatataa   15960
ttagattttt cttctaaaaa ggtctagttt gggaaggaat gaaagggatt agagaaatgt   16020
tgtgggtttg gtatttatttt atttatttat ttatttattt aatgtatatg aatgatctat   16080
cttcatgtat acctgcatgc caaaagagga catcagactc atgatggtga tgaaccatca   16140
tgtggttgct gggaattgaa ctcaagacct ctggaaaaac agctggtgat cttaactgct   16200
gaggcatctc tccagcccaa ttgttctgtt ttagtttgag gatgaacatc taatttagag   16260
atgccctgct tttccaaaag tgagttttaa acactaattt ccattgtcag tggattggtc   16320
ttttaagaat ataggtagtg gtggcacacg cctttaatcc cagcacttgg gaggcagagg   16380
caggtggatt tctgagttcg agaccagcct ggtttacaga gtgagttcca ggacagccag   16440
ggatacacag agaaaccctg tctcgaaaag caaacaaaca aaaacaaaac aaacaaacaa   16500
aacaaaacaa aaagaatata ggttggaata ggttggaagc agccaatgat agtgcatacc   16560
tttaatccca gcacttgaga agcagaggca ggtggaactc tgagtttgag gccagcctag   16620
```

```
ttagtctaca gagtattttc ctggagagcc aaggctatat atagaaaccc tatcttgaaa   16680
ggccaaaaaa ggaggaaaaa aaaaaaaaag aaagaaaaa agaaaaaaag aatgcaggtt   16740
gggcagtcag ggtaagtgtc taaggtaaga ggaattcttc aaggtggaaa gtcatgagtt   16800
ctgcgccagc ctaggctaca gagtactgaa aggggaagag actgtccatg tgtcagaccc   16860
tcatttctcc aaaagtcaca tgactatatt ttttctgtat tgcccactct tccatacatg   16920
cacctaacaa taaatattga agttcactct gtggcactat atctatgtga tagacttcta   16980
gaaaagtgat ttaaagttca aaaggtaaat acgtagtttt gtttcaagtt gccaaaatcc   17040
ctttagtaga ctcctacaat cttacatgcc cagtagcagt atagaagctt gcttgttgcc   17100
ttgaagcctc accaattcaa atattaggta acatttgtta catttttctt tgtcagctgg   17160
ataggtaatg aatgacacaa caatgtgttc ccattttctc tgcattacta attgaagtcc   17220
tatcacccac agcagactga agagttcctt taatatttta tggactttga caacctagg    17280 attcatagct tccatacaga gaggaatttc acaaatagca aagttgggct gttagaagaa   17340
taaaaagaga attctgagta cagcttctca aagaagagtc ccacgtaggt gtcctctggg   17400
atgtgcctag atgcagggtt attgtacagg agctcttctg tctgctctct gatacttgag   17460 attataggt tgcagggaaa tgcattagat ggcattacaa actgataaga taaagttagg    17520
agctatcaga gatttaggac atggttttc tctgtaaatg gggcttctgg tgagattcct    17580
agaaaatgct gtttatagct aggaatgggg ttatagctag gaatggggaa agaccttaag   17640
cagttgtgag ctgtggtgga atgcatgtgt tttcagtttg ctaaggcttc cgggaatact   17700
tttcctgtcg ataattttct ttcactctct ttgtagcctt ctttgtatta aaatcctctc   17760
tgcttgcttt tgtgtgtgaa tgtgtgtatg tgtgtgtttg tgtatgtgtg tgtatgcatg   17820
tgcatgtagg tccctacata ggacagaaca tatttcctgg agttataggt gcttgtgagc   17880
agccttttag ggaaccaaac tctgtcctct ggaagagtag ccccttaac tgctgagtca    17940 tttcagcctc aagaatcttc tcttttccct attagtagaa gatgtcatct tagctctagg   18000
aactacacca cctctggcct cagtggacac ccatttacat atgcacatac agcagacaga   18060
catataacta aagataaaat aaatcttttt aaaatgtcat ttccctgtgt actaattttc   18120
catgtacaca ctcacaggta gattttaaa ctattctgag tgatcacaaa gcagagcaga    18180
aggtgaaatt tgagagaata gatgatatta gtggattttg agaccttgaa ataatgtct    18240 cagagcatta aattaatcac tcatgtatgt atgtatgtat ataagtatgt atgcatgtat   18300
tatgtggatg ggggtgctgt agcacatgtg tggaagtcag aggacaactt tgtgaagtca   18360
tgtttctcct tccatctta tatggttcca gtgattgagc tcagattgtc tacctgtgta    18420
gcaagtgcct tacctgctga cctgtcgcac tagccctctc agaggacttt taatatttgg   18480
aatatttcta acgattgaca gtcaaaagtt tattgtgagc caggcactta aaatcctagc   18540
acttgtgaga cacaagatgg aggtcagtcc agtctactga gttctagacc agcaagggct   18600
acacagtgaa acctgtctca aaatttcaa agcggagct agagaaatta cccaaggagc     18660 taagggaac tgcaaccta aggtggaac aacaatatga actaaccagt acctgggagc       18720
tcttgtcttt agctgcatat gtatcaaaag atggcctagt cggccatcac tgcaaagaga   18780
ggcccattgg acttgcaaac tttatatgcc ccagtacagg ggaacgccag ggccaaaaag   18840
ggggagtggg tgggtagggg attggggggg tgggtatggg gaacctttgg gatagcattg   18900
aaaatgtaaa cgaggaaaat acctaataat aaaaaaaaga aatgatatca gaaaaaaata   18960 aaaaataaa aaataaaata aaataaaatt tcaaaagcaa caactcaaac cagccctacg   19020
```

-continued

```
tcgtgcctct gagttctcag taaattcctt ctctctctcc tctcagcacc atgtatgtgt   19080
tcggcggctt caacagcctc ctcctcagtg acgtcttggt ctttacctcg gagcagtgcg   19140
atgcacaccg cagtgaagct gcttgtgtgg cagcaggacc tggtatccgg tgtctgtggg   19200
acacacagtc gtctcgatgt acctcctggg agttggcaac tgaagaacaa gcagaaaagt   19260
taaaatcaga gtgttttcct aaaagaagta tgttttttct ctacttagaa tttaaaaatc   19320
taattttatc tgaattgtga aggaacctag tctctgtact ttcctgttca ccttactctc   19380
tagttatttc ttaataaaaa aatacacaag atctttggat gggaggaagc atgtggctcc   19440
tggaagctgt tagcaggtaa taagttgtct ttgaattaca caggctttgt gtaccaactc   19500
ctggtctggc tgcaggtgat ctgaagccat agcacaatga aatttgtttt cattttggtt   19560
ttatgagaca gggtcttgct ctatagctca tactggtcaa gctccttgtc agcctcctcc   19620
ttcagcctct tgaatgctgg ggttataggc atgcatcact ggccctactt gggaaatatt   19680
ttgatgacag acatgctata tatttctttg ttcagtttag tagccactag caatctgtta   19740
ttattagata tttgaaatgt ggctatgtaa ctaaggggct aactgttttc ttttctttag   19800
tgtatgtagt gaggcagatg tagtagcaca cgcctgcaat ccagacactc acgaggctga   19860
ggcaagaggc agttctaggc cagcctgggc tgtgtaatga accttgtct caagagccaa    19920 aacatcaaca ataaaagaac agtatgtggc tattggctgt tatgttgatg atgaaggtct   19980
agtgttaagg ataagagcct ctaatggtat gatcacatat agcaaattgc tctggtagac   20040
agcagagagc tgctgttctt gaaaagtatt tccagccccc tttagctgta tatagcaagc   20100
agtacagcat aacagacaaa ctatggtccc ttcttctaga gccctggcg tgctcttgtt    20160 attttctct cctttgctac ttgcttagtg gttgctctga gcaccactc accaactcag     20220 cgaagtaacg tgcaaaaatg tttggaaaat aagaatgcct ccaagatatt tgtccatatc   20280
aatctttaaa gtatgaaact acttccttat ctagttgttg cagttacatg agagttatat   20340
taggcagaga ctacttctgt ttttctggta tgtgttaaat aaagttgtgc agggacataa   20400
agctcctgag gctgtgctgt tgattagaat tttggttcat ttatgaaaaa cagcttacca   20460
gaacctggta ggattcataa ttctcccgaa acagttagaa ttggtagaat aaccaaaatt   20520
taaagttaag cttaaatata cagtgcattg gaaataatat tatcttctga ggttcagtat   20580
gagcccatta gtttacctca ctttctgggt agacctaatc ctgtcagagt aaacttggca   20640
agaaaagcag cctacatgaa aactgatcag gcagggaagt ttctgtggcc tctcttcctg   20700
cttgtgtatg tcatattcat gaaatgattt atagatggca acatggcttt agcttcttg    20760 tttgggattt taatgagaat tatgttaggt ctacaaagag tggaagttgt gaaatccaca   20820
ggtttggagt cacatgagta tatagagttc gagttagcaa gtgcctcctg tggggttgtg   20880
ggtcactggg tatacctgca cccaggtagg ccttgcattt gtaacaagga caaatgtatt   20940
ggtctctcat attgctttct taggcttctg cacagcttct ggtgttaatt ctgttgctag   21000
ttgatgtttg tcgtgggaag aaaagcatcc attacttctt agaagctata aaattaacag   21060
acctttgctt ttcactttct ggacactatg ggaggacagt tataaaacag tgtttctcgg   21120
attgtctgct tatatctgtt ttattttaac ctaaacatgg cactgctttt ttcctttcag   21180
tttgactata cactttgctt cctgactatt gttaggagct ttcctacctc agattataca   21240
taagagaggc tgccgcatag ttgatgggtt tgtcttctct ctgtagccct tgaccatgac   21300
agatgtgacc agcacacaga ttgttacagc tgcacagcca ataccaatga ctgccactgg   21360
tgcaatgatc actgtgtccc tgtgaaccac agctgcacag aaggccaggt cagatgctgt   21420
```

-continued

```
ttttcacgga ttttagggaa tagaaaaatg ctagatgagt gtgagtgtag ggcaaataat    21480
gagtagagtt cttttttaaaa tgggatatcg atttgaattc tactgttgct caggttttct    21540
cttaggaagg gatgctatat acatcctgat tccaaggatc gctcctgctg ctgaggtctt    21600
tgtgcagtgt ttccgaaagc atgttttaca gaatgcccctt ggcccatatc tgactcagca    21660
tgacatctgg gctaatcatg tatgatttgt tataggtgat aataggctat gagtaaggtg    21720
atccagcttt tgctgtcttt gatggcttat gacattttt tctcaaagtt taatgcattt    21780
cataagaaat aagacttgag attgctatgg tgggcacggg ctgggaggag ctctggaaaa    21840
gcagcaggtt cagctttcac gttttacaga taagcattgg ctgaggcttg gtggtgccag    21900
tggttccgtt gggctgctag cttgccagct aaaagcatgt tagtgagaat acacactgtg    21960
gtattcacat tgcagtgctg cttcctgttc attctaattc tatcattcat ccatctacct    22020
atctctatct atctatctat ctatctatct atctacctac ctacctacct acctacctac    22080
ctacctacct acctaccact tatctaattc tatctgtctg tctgtctgtc tttctgtcta    22140
tctatcctcc atctaattct atctatctgt ccacctatct atcatctaat tttatacatc    22200
catccatcta tccatctatc tgtctgtcta tcatatatgt aattctaacc attcatctat    22260
ctatccactt atctgtctgt catctaattc catccattta tgtatctatc tatatatcta    22320
attctatcta ttcaattctt ttctttttt ctatctttct ttctgcagtt accattctca    22380
gttaattctc actgagttat ttgtgtgaat aacaaaacac ttctcccctg tgttccagat    22440
ctccattgcc aagtatgaga gttgccccaa ggataacccc atgtactact gcaataagaa    22500
aaccagctgc aggagctgtg ccctagacca gaactgccag tgggagcccc ggaatcaaga    22560
gtgcatcgcc ctgccgggta ggccttgcac agggatgtcc tctataaggt ccaagcttgg    22620
tcctccctcc tcagatcaag gtggacctag gaacaagatt gcttattctg tctatttagc    22680
cctctcacta ttgggggggg ggggggggcga tattttgtat gtttttaact taaatgtggt    22740
ttttatgtat gtatttacta gcctttgaaa gaaagtgaag tgtcagctca tgttctggag    22800
aattgggggg tagcttagat ccatgttaca aactgtgtcc cactgtcctt ccttctgctg    22860
tgaaggagaa cctggcacta gagctctgtg gtctcagcag cagtcaggaa cctgcaggaa    22920
gcacttactg acagttgtgt gagaagagat ttctgtacca gcatcatctc ccatgtgacc    22980
ttccttcccg actatttcag cagaggttgt tcagggtatt aacttaggtc ctgaggccag    23040
ctagccctga ctaaatctct atgatgtatt tgcttgatca ggatatccag gaaggggagc    23100
ttctgtgctc tccaacatcg aggtttgagg ggaagttggt ctgactcttt tgaaagcatt    23160
ttatttagtt tgctgaatgg gctttagttt agccagtgtt ctattgctgt gaagagatac    23220
catttccaac gtgtaacttt tatgaaagga acatttaag tggggcttg cagtctcaga    23280 agctattatc atcatgacag ggagcataga ggcacaaagg caggcattag agtggtagct    23340
gagagctaca tcctcatctg tgagcagagg cagacaaggt gtgaaaaaga cagaacctgg    23400
cctgggcttt tgagacctca aagtctacca ccccagtga gacacttcct ccaacagctc    23460
ctgcaacaaa gctccatccc ccgatccttc tccagtcctg ccactccctg tgaatgagc    23520 actcacatat atgagcctat gggggtcatt cttactcaag ccactacagg ctttgttttg    23580
tgtctcagac tttatgtcaa tagaatacct agacaccttg ttacaagaca ggcctggaaa    23640
gcctgcagtg ctgactccct gccagtagca cattctgagg agcaagtccc ttaagtcgct    23700
tacctgctct tacattacgc ctttccctga ccatttagtg agcactgttg gtgtccccaa    23760
cctgaacctg gttctgggga aacacttgct tattcacttc cgtgctaatg gccagggagc    23820
```

```
aagcatgctt tcatgcaaca ctgtgagttc agtacaacca caggaggaga ttgcagactt   23880
ccttcgtgta ctgtatcact atgaggtttt ccaaaccagt ctcccttca cctcattttt    23940 tggcatgcct tatgtacttg cttatacttt ctatcttatg acatgaaaac agagtggcat   24000
ttggaggctt aaatttatca cattcccaat tcaattccat tttcagttta ctctttctgt   24060
atatacatca gtgtgcagat aaatatctct ttgtgtgagc attggaggcc agaggttaac   24120
ctctggtata ttcttcctct atcactcttc acagggtcct ttgatgaatg tggagctcac   24180
tgattacata gactagctga ctcaaccctc aggcctcata accctgcctc tagccctcag   24240
atgagattac aagcaagcaa aactacgcct ggccttttat gtgggtgctt ggaatttgaa   24300
ctgggtactt atgcttgaca caagtatttt atccactgaa ccatctccca agcctccatt   24360
tgcagttttt tacctcaccc ttccaatata tatatttatt tgtatgccct ttgttcaaga   24420
ttttagtcac cttttacatt tttcttcaaa ataattgca ccaatttctt aataatggca    24480
cccaaaagta ggaacattag cctagagtat accctgtgag ccaggaaatg tgactggtga   24540
gacttgtaaa agggtctttt tattctggcc ctcagcggag gctcagcagt ggagcatgca   24600
tgctgttcct ctggaggacc cgaggtcccc aggggccagg tcacaaccac ttgtaacttt   24660
aactctgatc taatgccctc tatggctttt gtgctatagt ctcttgcact aacccacact   24720
caaggcacac atacacacat tctttaaaag ataaattatt ttattttcaa aggttttttt   24780
ctgcatatag aagttaataa tttgtctgtt atgctcacca gatcctaaca aagcacctga   24840
aattcaaatc aggatgagtt cagatgttca gtattttgaa ctagtaaacc gaactgcata   24900
attcctaaaa ctttgttttc tttcctcttc ccctttaaaa aagaaaatat ctgtggcaat   24960
ggctggcatt tggttggaaa ctcgtgtctg aaaatcacta ctgctaagga gaattatgac   25020
aatgctaaat tgtcctgtag gaaccacaat gcctttttgg cttccctcac atcccagaag   25080
aaggtggagt ttgtccttaa gcagcttcga ttaatgcaat catctcaaag tatggtgagt   25140
taatgtgttc agaactttgg tttctagggc acaacagcag ctcttatgta gaaggccaca   25200
gttgtatgtt atttgcctgg taagagaaag aattacaata aatgattaat aatatactgt   25260
gggcctctat ttcagaggct cttcttttga tacctttctt cttgtcttaa aaagttcagt   25320
actttgcata ttttattagt tgttattatt aagtaaatta taaggtatga acatatggaa   25380
tgaatggtaa tatgtgtaca tattctggtg acatcagatt attttgtact tgatttatat   25440
ctagattctg cttgggaaaa gggagagtaa aatgttagtt acctaggtgt cattaaagcc   25500
atctacagcc cctggaggta ttattatagc acatagtgta atcgtcagta agaaatgtaa   25560
aatctgccca ggttttatag ccttcttcct aaggcttctg aactcagaaa gttctcttac   25620
tctagagcca aactctcaaa tggcttgtag ttactatata gtctcatttg gtattttct    25680 tggtaagtct aattctaaga cttgtgattt gactgtgatg cttcagtcaa ttagatattc   25740
acagagcagc ttttctgtct atgctggctg tggtacagag agatgtgagg gacatgtttt   25800
tgtctagcca ggagaagaca gaatgcagct cagcatctct catttggcac caccttcatg   25860
tgatgggatg ccggtatggt gtgggtcctg gttgttaaat ctcaggaagt ccatatatcc   25920
agaaatgacc tcaactatag gtggatttct ggcaattagg taaaagtcag cattccttgg   25980
gcacttggga aactggttac catctgcata aaggagtcat ttcccttcta tctggcagaa   26040
gggacatatg gctatctatt gtgcctgtca gcatggaagc acatgctagt ctccaggtcc   26100
ccccaatatc acaagtacct atagcagtga attagttaaa ctgatttggc tcccaatggg   26160
tcaagtacag ctgcacctgc ccaagagctc tttgggtttg caaatgagag acacatagtt   26220
```

```
aatttttata tgctttgact agttcagttg ctggacattt ctaatcctcc ctgcagtagc   26280
atacattaac ccctccaact ttcctgagtc aacttactaa ctcaacattt catctctgac   26340
accccagacc taatggcaga gtggcccttta gagccacttt cccaattttt tttttatcag   26400
atattttctt tattttcatt tccaatgtcc cctttcctag tttccctgtc ctctcccct    26460 gctcccaac ccacccactc cctcttcctg gccttggcat tccctatac tggggcatag     26520 agccttcaca ggaccaagga cctctcctcc cattgatgac cgactaggcc atcctctgct   26580
gaatatacag ctagcaccac gagtcccacc atgtgttttc tttgattggt ggtttagtct   26640
cagggagctc tggggtactg gttagttcat attggtgttc actttcccaa attcttacat   26700 ggctggtttta gttctttcct gcagctctta ggtctaatcc ctttccttcc tctgtcatgg  26760
tgattgcctt cctctcctat ctcagttcct tgcctgctca atctaaaagt cccacctcca   26820
tctttctgcc cagccactgg ctgtatgcag ttctttatta tcagttgaag ccagctaggg   26880
gcagagacct tcaggtctgt aagtgctttg gggagcagaa ttaagacaaa gcattagaac   26940
caattcccaa caagtacctg ctatacattt caaagtccat attagtctcc tgggtcttcc   27000
cttccccagc tacttgtcct ccttgtaatc caaatgacaa gcttttcac acatctcttt    27060 atctcacatt tccctagccc tggccatgtc cacttgttct tttactctct gctctgctct   27120
ctttccaatg cctctggata ttttctctct cttattcaca ataaaaacca aaccaaacca   27180
aacaaaaaac cttaccctaa taatggagtg gtcacgcctg aggtttcctt actgctcccc   27240
cttgcacacg tcttgtgtct gacacactgg caggctttta ttagcagcag gctctaggag   27300
ctgagagaag cagcaggcac ctctgaggtg gtagttacta gagtgattag aacagacagt   27360
ggagacgtgg ctgaaaatat ggactctggt gtttggagcc aagtatggta ggcggcagaa   27420
gccagcagaa gcatgatcca caccttcacc aggttgcttc cattgggaaa ggctggaccc   27480
cttgggaagg ggtcccttttg tgccttccta ggtgttcgga gccaggtgtg tgagggatac   27540
agtaaaggga ctgactgcat gactgctcca ttagggtgaa gggttttgtt gtgaatagga   27600
gaaacaaaat gtgcagaggc atctgggaga gagcagagca gagtgaaaag gaagcagtgt   27660
aggcatggtc agggctaggg acagcggaga cagcaagata gcgagtgggt gataaggtga   27720
gagagagtgt gtgtgtgcgg tgcacacatc acgtgcatta taaggaggct gagtagctag   27780
ctggggggag ggaagggcca gaaaactagc atgcactctg aaacgggtac ttgtgatgct   27840
gagggagctt gggggagaag ggcatgcctc aagaccagaa gagggagttg gagttacagt   27900
ttgtaagatg cctaatttga atgctgagat ccaaactctg atcctttggc tgaacatcat   27960
atctgctgag ccatctctcc agcccctaga aaggtggtga tggtggttgt tcttgttttg   28020
ttttattttg tttaaatggg gagccaggta cagtacatca tgcctttaat cccagcagga   28080
gattcaggag atagagacag gtagatctct ttgagttcaa gggcaccttg gtgtgtatag   28140
gaaattccat ccacccaggg ctacagaagg gtaccttgtc tttaaaaaa aaaaaagaa    28200 agaaagaaag aaaaagaaaa aaaaagaga atgaaatttc agagttatgc aagataggag   28260
ctcagtggta gagtgtgtgc ccaggaagtg ctgggtttga ctcctcagaa caacagcagg   28320
ggcagaaact agtctacagg ttcatgagtg gtgttttgtt ttgttttaca taaaatgtgt   28380
tgaattagat aagtagataa aatgtgactc atacacagat aaatagataa aatgtgatac   28440
atgtacctgt acatagaaga ttatgatctc acctttaaaa aggaggaaat agagagtttt   28500
ggtagttaca ccacaggaaa actggaaaag aaaatgtata tatgaggctg tgccccatgg   28560
ctaaaggaac atgttttttaa gtcatttgaa ttcaccaaac agttttaggt aatgatatat   28620
```

```
ggttttgcat acaaccagta ttttataaat attagcaagg tcacatcatt tatgaaccaa   28680
catttaaact aaatttgtaa atcatcattt ctttatagca cttgtcatag aacataagta   28740
gtttaaaatg tgattattgc tttgctcttg atgtctgaaa atcttcatgt attctcttct   28800
ttgagccatt tttatgcttt gcagtactgg atgcatattg aagtgatcac ttattttaat   28860
ctaccttgcc tgagtttggg aatagatgg tttccacatg tctgtgggtt atgcctaagc    28920
tagtggtttt tatgttagag cttgttttgg ggaaggcact ggttgcattc atagctgtgt   28980
ttcttttgcc tgtagtccaa gctcactctg actccatggg ttggtcttcg aagatcaat    29040 gtgtcttact ggtgctggga ggatatgtct ccattcacaa atagtttgct gcagtggatg   29100
ccatctgagc ccagtgatgc tggcttctgt gggatcttgt cagagcctag tactcgggga   29160
ttaaaggctg caacctgcat caaccctctc aatggcagcg tctgtgaaag gcctggtaag   29220
gacatgggtg catatagtgc tccaggagga gccaagacag caaggaggc acagctgaat    29280 gagcgctgag gtgatgaagt acttatggca gcagggagag gagcaccaat ttaggcatat   29340
gtatttcaaa cagaacccga ttccagatag tctttcttgg cctctgactg ctttaagcca   29400
tactgaaaac caaaaataaa attgctgaaa gaacccagtt tatattgagc tgcactgttt   29460
cgttggtctc aaagtgttga gaattgttct agaagattat ttccttggtg ttggcagaga   29520
agtgctatgg aggaaacaac aacctgaaac caaagaaaca tttagaaaag cagcaagtca   29580
ggacactatt cagacactgc tggggtgggg ggagaggggc atggccaaag aagccgacag   29640
agccaacacc aggctgtggc aatgtcctgc gctgaggtta aggttagact ccatgaggcc   29700
aggcccagaa cagccataca caatgagga ctccaaaaca agaggtgcaa gtgtagtgga    29760
gactccatcc ctgcaggtcc tgtttcagga aatgattgta ctttgcctga gtaatacagc   29820
ctaggagcta ctttctgata gggttttta aatacttaca aagaattatt tatctttaat    29880
catgtggttt tgtatgtgtg tgcttgcaca tgcagtgctt gtgagagaga gtatgtgtga   29940
gagcatgcat gtatgagagt gtgagaatat atgtgagaga gtgtgagtgc atgtgtgcgt   30000
gtgtgcatct gtgtgtacag gtgtgtgtac atgcatgtgt gtataagagt atgtgagagt   30060
gtgggtgtgt gtgtgagagt atgtgagaat atatgtatga gtgtgtgtga gtatgagtgt   30120
atgtgcgtgc ctgcatgtgt gtgtgtgtgt gtgtgtgtgt gtgtgtgtgt gtgtgtgtgt   30180
agaagtggcc ttggaaaaca gagttgtcag atctcttaga gatatagttg cagttggttg   30240
tgagccatct catatgagcg ctggaagttg aaattgggtt ctctggaatc ctctgggttc   30300
cttgttgaag cctgaatatt ttgataaata tttatgtcat tatccctcaa aattgtaaat   30360
gtagaattta acaaactcag gtcttgagtc atctttgtcc caaggtttgt ttgtttggtt   30420
ttttgttccc ccaccttttc ttcagtgctt ttaaaaaga gagtccattt tttcctaaat    30480
gtttaaatac agttgaggaa tagaacatct gactccaatt tcctgggttt ccctccatgt   30540
agtgtagtgc tgacctgatt tcagtgtgca ttgaaaactt tgatcacttg gaaggcagct   30600
atgctcacca ctatactacc aatgtctgca atcctatagg agaaacaaca atatgaacta   30660
actagtaccc cccagagctg tgtctctagt tgcatatgta gcagaggatg gcctagtcag   30720
ccatcattgg gaggagaggc ccttggtatt gcgaagatca tatgcccag tacagggaa    30780 tgccaggacc aggaagcaag agtgggtggg ttggggagca gtgcgggggg gggggtata    30840 gggggttttg gggatagcat ttgaaatgta aatgaagaaa ataactaata aaaattgcct   30900
taaaaaaaaa caaaaagaa aagttttga tcttagctga ccagtgtctc tttgggtctt     30960
aatttccagc aaaccacagt gccaagcagt gccggacacc atgtgccctg cggacagcgt   31020
```

```
gtggcgagtg cactagcagc agctcggagt gcatgtggtg cagtaacatg aagcagtgtg    31080
tggactccaa tgcctacgtg gcctccttcc cttttggcca gtgtatggaa tggtatacga    31140
tgagcagctg cccacgtaag tggaaggagc ttttgaacat ttgcaggcaa gttgggcttg    31200
actttctgct caagtccatg cagaagctgg tcgggccggc ccttccagat taacatgtat    31260
gtatagaatg cagcacagtg ttccatgcag taaatcagtt acatcaagga gaaggcacag    31320
ggtacagaaa tacctttttct tcttcagggt aatattataa ttcaatctgt ataatgtttc    31380
tacatcttaa tctaccagta tgtaaagtgc tttctagtag aggcctcccc agctcccttt    31440
ttcatccaac atcctgatat taaaaggttg gaaaagtccc tgttatatat tatgtaaaat    31500
gtggggccct ttaaattatt tcagttcaat aatcactata gggtactatt tttaattcat    31560
ggaagttaaa tcatctgtta aaagaaaagg taataacagt aaattcaaat cttgtgatag    31620
tgaattacaa gttggattgt tttgccttgt tttttaatag ctgaaaattg ctctggctac    31680
tgtacctgca gccattgctt ggagcagcca ggctgtggtt ggtgtactga tcctagcaat    31740
actgggaaag gaaatgtgtat tgagggcagc tataaaggac ctgtgaagat gccgtcacag    31800
gcctctgcag gaaatgtgta tccacagccc cttctgaact ccagcatgtg tctagaggac    31860
agcagataca actggtcttt cattcactgt ccaggtaaga tgcctgtgta tcctagttca    31920
aatctcgtac ataaactaga cgcccagatc ccttggctca cttgttttct tgactgtgtt    31980
tgagttcttt ctgtgttctg catcaccttg ttggatcata gctggcaaag gtgctctcct    32040
ttctgtgggc ttttttcttta cttgattgat tgtttctttg gttgcacaga agcttttag    32100 ctttctgaag tcccatttgc cagttgtcct taattcctgg gcgagtagaa gcctcataaa    32160
aaaaagttcc ttcctacaca tgtatcatgt agggcactgc ctatgtttta ttccagaagt    32220
ttcagaggtt cgggttatgt ctttgatcca tttagggtta cttttttgtga aaggtaatgg    32280 acacagttct gtttcattca ttattctaca tgtggacatc tactttttccc agcaccagtt    32340 ttgaagatgt tatcttttct gcaggttgtt tgtttgcttg ttttgtctct tcagaaaatc    32400
ccagatggcg gtagctgtga gtgcttaggc ttggcctacc tgtttcatta tgttggcttg    32460
catgtctgtt ttgtgcagtg ccaccatatt gtcttaattg ctatagctct gcaatctatc    32520
ttgacatctg tgttggcaat cctgcagttt cgacccttct gctcagcagt gctttggcca    32580
tctggggtct tttctgggtt cataatgaat tttaggattt ttttttctat ttctgagaaa    32640
gtattgttga tattttgatt gcgattgaat tgaatctgta aattgctttt ggtagaatgg    32700
tcattttcac aatattaatt ttactgatcc atgaacatag gatgactcca gtctctcatg    32760
tctccctata gccctgtctt aagagatttg gagtcttcat tgtagaagtc cttcacctcc    32820
ttggttaagt ttatttctag atattgtatt gtctttggta ttataaatgg tagtatgtcc    32880
atgatcttgt tctcagtgtt tttttagttt agttttttttt aatttatgtg tatgagtgtt    32940
tgttttatat atgtgtatat gtgcattcat gtcctctggg catcagatcc cctgggactg    33000
gatttacaga cagctttgag ctgcctgtag gtgctgagaa ttgaacccag gtcctctgca    33060
agaacagcca gtgctcctac tccccagccc cagaagtact aattttttaag agctgatttt    33120 ctacctttgc tgacattgtt gattgtttct agaagtttag tgatagagtt tttgagatttt    33180 cttatatatc ttatgttatc tgtaaaaagg gataatttga ctccttttcc tattttatatc    33240 cttttatttc tttcatttgc catattgttc tagctagtgc ttcccgctca gtattgaaaa    33300
gagtggtgat tgtgaacagc ttttcttatt tcttatttta atgggattat tcacccattt    33360
aagataatgt tggttatggg tttgtcatac acagcccttc ttatattgag gtatgttcct    33420
```

```
tccagtcctg ttctctctag gactttttt ttttaatca agaaagcata ttgggttttt      33480
tgttgttgtt attttgtttt gtttttctag acaaggtttc tctgtgcagc cctggctgtc      33540
ctggaattca ctctgtagac caggctggcc ttgaactcag aaatccacct gcctctgcct      33600
cccgagtgct gggattaaag gcgtgcacca ccactgcctg gcacatgttg gttattttgc      33660
aagccctttc tacatctact aagatgagca tgtggtttca tctttgtctg tttatattgt      33720
ctgttgtatt tattgactta tgtgtgttga gccaacctga agttctggga taaacccac      33780 atgctttgga tgattttgt gctatgtgct tatattgtgt ttgttagtgc tttattgagg      33840
acgtctgcat ccgtgttcat ctggggtact gtctgtagtt tgcttatttt gttgtctta      33900 cctgctctgc attttagagt aatcctggat ttatagaaag catttgggag tagtccttct      33960
gtttattaaa aaaaaaatt aagaatgatt ggttgttgtg tggtggaatt ctgctgtgaa      34020
cccatctggt tctggactct attcggaagg cttttatta ctgtttcagt ctccttgttt      34080
gcagtgatct atttaggttg ctaatctcct tatgattcat ttggatgaat caagaaatta      34140
atccatctct ttagatttcc agcttaatgg aaatatgagtg ttaaagtatt tctttatagc      34200
attctgtatt ttttggcatc tgttgtaata tttccctgtt ctttctgtta atctctttct      34260
ttcttgtggt tagttgggct aagaggctct tggttttttt tttttttt tatcttttta      34320 aaggaccagc tcttagattc attaattctt tgtattattt tccttgtttc tttttcactg      34380
atttcatttt agattttatt atttcttgcc atctactgcg tttgggttgg ttttagttat      34440
ttttccaaga ttttcagttt catcactaag tcattcattt gggctctttt gggtttcttc      34500
acgagaaccc acttgggact gttaccttcc cttttagacc tgcttttaat gtgccccaga      34560
gatttgttac attgtctttt cgatttaact tagtttcagg aatatttga tttcttcttt      34620 gacccattca tcattcggta atgagttgtt taatctctag tgagtttata catttattag      34680
aattttgttt actgatgatt ttaaggtgtt tggcttgtt tgtttgtttg tttgtttgtt      34740
tttcgagaca gggtttctct gttgtagctc tggctttctc tatgtagaac agtctgacct      34800
caaattcaca gagatccacc tgcctctgcc actgaagttc tgggattaaa ggtgtgtgcc      34860
accactacct ggctgatttt aagttttatt acataataga caggtagggt acatagattt      34920
tctacatttg tgaaggtttg cgttgtttgt cagcatgtaa ttctgtgtgc tgctgaggga      34980
atgtatgttg ttttgacagt taggtggaaa agtctgtaga catctgttag atccatttta      35040
catttcaaga agccatttaa ttctgaagtt tctctgctta tttttcccca ggtgacttac      35100
ctattggaga aaataggtg ctaaaatcat ttactattat tgttttttt aagaagaaaa      35160 taattaattt aaaaaaccct ggaaagaaag ataccaaatg tgaatcatgt ttcctggata      35220
gtggggttat atttgatcat ttatttttcc tctcaaatac tgtgagtttt tacaatgaat      35280
aacaacataa atatttttat gttgctgtgg actttaactt tgctttgata atatatttgg      35340 tttttgaga ctaatttctt tttgatattt tatttctca tactagttt tagtaaactt      35400 tggttttgtt ttgtttgtat tttttagact ggccaccaac ttgctatgtt gtcaagggtg      35460
gccttaaaat ccacacccaa tactttgtcc tctctttctt tctttctttt tttttttat      35520 tggaacaaaa tttctaggtg ggaatctcac tatgttaccc aggctgacct gaaacttctg      35580
ggcttaagca agatgggtgc acatgatcag agacgctgcg ctgcccgcct cagcccctgc      35640
tagttggaac tataggcaca gacagctgta cttcactcat ttcaatgatt taacatttag      35700
actatatgca aataaatatg aaatgtattc accaagttct cctatgggag aaacagagcc      35760
cttaagattt tttccttttca gcttgccagt gcaacggaca cagcaaatgc atcaaccaga      35820
```

-continued

```
gtatctgtga gaagtgtgag gacctgacca cgggcaagca ctgcgagacc tgcatatctg    35880
gcttctatgg tgacccgact aatggaggca aatgtcagcg taagtcacac aggtcaagtt    35940
agtcacaagt caggtacaat agtacagtac ctgcagttga cttaaatatc ttaaagggaa    36000
aaggcctctt ggtttgggat attgcctttc ttaattatgt taaattgtta aaagtttaac    36060 tgagggcta  gaaatgtggc tcagttggct aagaacactg actgttcttc tagaggaccg    36120
aggttcaatt cccagcaccc acatggcagc tcacaagtgc ttgtaacacc tgggatccaa    36180
caacctcata cagacataca tgcatgcaaa acactaatat acataaaata aatccattaa    36240
aaagtgtttg atgatgctgg aagaggaaaa aaggctcaac ttgtgggttt gggagcagtt    36300
agttaaagca acaaaccgac agtaaaggag ctaagctttt atttcttcag cagaggcata    36360 aacaagggc  cgaagtcact gaggcaccag ctgcctttat tccatttccc tcccatggaa    36420
gcacatcagc tcaagtcaag cagagcagcc tgggatggga ggtcatctca ttggagaagg    36480
aggcaggagg cattgtgagg ggagggagga caaggctggg aatgggaagt cctgagctca    36540
gaatcagaat gaggacaaga tcttcagttt ccttcttaat ataaagaggt atcacagagg    36600
tctctataga agtctactgg aagcctcaca caggcacaag ggtacatttg aaaaactgtg    36660
acagccaggg agagtcccct tctgaagtgt ccttcctcag agactgcagc acctgactgt    36720
gccccagtct gcaagaggtt tggggagagc aactgacctc ctgaggaccc cagatgaatc    36780
tttaagatgg cctgcttttg gttttggttg gttggttttt agacagatct aggagagttg    36840
gtgatgagct tgaattctct gtcctcctgc ctgacctcca aatgcccagc ttcacatggg    36900
ctcccattaa gttgtgagtt tcggtgtctg gctcctgctc tcacagccag tgcagtacat    36960
tgagctccat agagatagcg ccggggcaaa tgagagctgg acgggcactg ggtgactctg    37020
tgccttgtgc cggaaaatca actaaacatg ggcaaaggag atcctaagaa gccgagaggc    37080
aaaatgtcct catatgcact ctttgtgaaa acctgctggg aggagcacaa gaagaagcac    37140
ccggatgctt ctgtcaactt ctcagagttc tccaagaagt gctcagagag gtggaagacc    37200
atgtctgcta aagaaaaggg gaaatttgaa gatatggcaa aggctgacaa ggctcgttat    37260
gaaagagaaa tgaaaaccta catcccctgc ccccaaacag gagaccaaaa cgaagtacta    37320 ggacccccaat gcacccaatg ccttcttcgg ccttcttgtt ctgttctgag tacctcccca    37380
aaatcaaagg tgagcaccca gcttatccat tggtgatgtt gcaaagaaac taggagagat    37440
gtgaacaacg ctgcagcaga tgacaagcaa ccctaggaga agaaggctgc caagctgaag    37500
gaaaagtacg agaaggatat tgctgcctac agagctaaag gaaaacctga tgcagcaaaa    37560
aaaaaaaaaa gggggggtggc caaggctgaa aagagcaaga aaaagaagga agaggaagat    37620
gggaggagta tgaggaagag gaggaagaag aaagatgaag aagaatatga tgatgatgaa    37680
taagctggtt ctagtttttt tctcatctat aaagcattta accccctgt  atacaattca    37740 ctcctttaa  agaaaaaaat tgaaatgtaa gcctgtgtta gatttgtttt taaactttac    37800
agtgtctttt ttttgtataa ttaacatact gccgaatatg tctttagata gcccgttct    37860 ggtggtattt tcaatagcca gtaaccttgc ctggtacagt ctgggggttg taaattggca    37920
tggaaattta aagcaggttc ttgttggtgc acagcataaa ttagttatat atggggacag    37980
tagtttggtt ttggttttat ttttgggttt ttttttttca tcttcagtcg cctctgatgc    38040
agcttatatg aatatgattg ttgttctgtt aactgaatac cactctgtaa ttgaaaaaaa    38100
aaaatcgtgg ctgtcttgac atcctgaatg tttctaagta aatacagttt tgttttttatt    38160 aatattgtcc tttcgacagg tctgaaagtt ttcttcttga gggaaagcag tcttttgctt    38220
```

```
ttgtcccttt tgggtcacat gggttactgc agtgtgtatc ttttcatata gttagctgga   38280
agaaagcttt tgtccacaca ccctgcatat tgtggtaggg gtaacactttt catccatatt   38340 caaagaatct ccaaaatcgt gatcagttgg ataagaaata ttatataacc tacttggcaa   38400
agcaaggtgt gatcaattct gtcacaccat gggatcatta gaatcaagca atctgaaaat   38460
ctgtccttaa aggactgata gaaaagtatt ttctaatcct tatacaaagg ctctccttta   38520
actgccactg ctatgtaatg acagttatgt tttgcagttt ccctactaaa gaagacctga   38580
gaatgtatcc ccaaaagcgt gagcctaaac tacacaactg cagtactatt tgttgaccttt  38640 agtcccagcg aaggctatca cgagaatgct agctataata taatgcctct gcccctctat   38700
ctaaatatgg attgctcagg aaacttgact gcttaaaggt atttttttca tattgttgtt   38760
cctcctatag ggttgcagac ccctttagct ccttgggtac tctctctatc tatctatcta   38820
tctatctatc tatctatcta tctatctatc tatctcttgt cagatttctt ttttcttttc   38880
tctttctttc tttctttttt taagatttat ttattattat ttctaagtac actgtagctg   38940
tcttcagatg caccagaaga gggtgtcaga tctcattacg gatggttgtg agccaccatg   39000
tggttgctgg gctttgaact caggacctta ggaagagcag tcggtgctct taaccactga   39060
gccatctcta caaccettaa aggtattttt aagtagttga gtcagctttt aaaattatgc   39120
cagaagtgtc aaaagttcaa aagtttagga ccatcctcta ttgaagtaca gggtcatcct   39180
gggctacatg agaccctgcc ttaaaaccaa aatcaaacaa acaacaggaa aaacaagagt   39240
taagaaagag aaaagaagc acttggaaac aaagatctgt ggagtatgta taggcttctc   39300
tacaacaggt gtatgtagga tcttgatggc ttttgagtct attaccctca aagaggtact   39360
gagaaaccta aatgtgatca ccgtggtctc tgaggggcac ctggcaggat tatgggagat   39420
aactaaagct tgctaatcac agagtttagg gagggaggac gtctctaagg caagttaact   39480
gtctggtttg agatgcttag gtgatgtctg aggaagtaat aaggcctgtc cattttcata   39540
cacactcagg ccttaagtct gggtaatggc tacttgaaca taaaatagtc ctctatgaaa   39600
ggaataatat ctctgtgtca gcagccttca cggctaatgt taattgtgca ggaaccctgc   39660
ttctcagtca gacagaagct caatcaggca ggggcaggac ttcttttgcct ttcccatgtc  39720 cttgtaattt ccctggcttt tcatcttggt tcaaacatac ttacctgtta ggtaattata   39780
agaacaccaa atattactga ataaaatgtg tttatgactt tgtggtgact gccattcaag   39840
aattagatgc cttagccagc aatgatggca cacgccttta atcccagcac ttgggaggca   39900
gagataggca gatttctgag ttccaggaca gccagggcta cacagagaaa ccctgtctcg   39960
aaaaaacaaa acaaacaaac aaaaagattt cgatgtcttt atcacccaaa tcaagtaact   40020
ttccaaagtc tcacagtgag atgtagccta gttgggagcc acatctaata tatgctgatg   40080
atcttaacaa gtagcctgct tgtgtcttca ggtgaccacc ccggtgtcct cagctacctc   40140
tagaaagatc acactttcct ctgtggtctc tgcagggtcc ctgtatgatt ctggaacctt   40200
gctgtacttc tcagagtcct gattcataaa gcactgagtt tttgcttgtt tgtttgtttt   40260
gatactattg gtaagaatat atattgaacc ttgacatgcc ttttttaaaat aacattattt   40320 ttacaatagt actttagcct tgattatgtt aactgcttac tgtttcagat gacattcgta   40380
catcttttaa tcctcaaacc agtcctatga gatggctagc atcattgtca catcatttag   40440
gcaaggaaac aggtcttggg ttaagcttca tgctcagagc tccttggaac acagtggact   40500
caagtgcaag cagactgacg cgactgggtt ttactaattc agtaagcctg tactctatgg   40560
aggaagagtt tctgaccact ggatgcagtc tgatgacctc tgactgttct gtttgaaagg   40620
```

```
tttctttcag tgattttatt tttctccatg tggactttt ttccagcttt taaaatatat    40680
atatatatct tattcgcttc acatcctgct cactgtcctc cctccctgt catccctcc     40740
tacaatcctt catatccccc cttaccttct gagcagctgg gagcccctct gggtatcccc   40800
acactcgggc acatcaagtc tgtgaggctg gacgcatctt ccccactgt ggccagacaa    40860
ggcagcccaa ctagaacata tcccacagac aggcaacagc ttttaggata gcccctgctc   40920
cagttgttca gcacccacat gaagaccaag ctgcacatct gctacatatg tgcagggagg   40980
cctaagttca gcccatgtat gttctttggt ttgtggttca gtctctgaga ccccaagga    41040
tacaagttat ctgactctct taatcttcct atagagttcc tatctcctct ggggcccacg   41100
attggtgtcc ctattgcttc actgggattc ctgcctggct acacccacta tgaccaaggc   41160
aagtcttaga aaagacaaca tttaactggg gctggcttac aggttcagag gttcagttca   41220
gtatcatcaa ggcaggaaca tggcatcatc caagcaggca tagtatagaa agagctgaga   41280
gttctacaac ttatctgaag gctgctagca gaataccgac ttccaggcag ctaggatggg   41340
ggtcttcaga cccacaccca cagttggtgt ccctattgct tcactgggt tcctgcctgg    41400
ctacaggagg tagcctcttc aggttccata tccccaatgc tgtgagccac agttaaggtc   41460
acccactatt gattctaggg tgtctccctc atcccaggtc tctttcattg tggagatgcc   41520
ccccacttcc ccaccactgt cagttgcaga tttccattct cgggaccatc tggccatgcc   41580
ttctgtttct cctcacacct gatcccgaca ccccgccca ttccttctcc tacctagttc    41640
cctccctcca tatgcttcct atgactattt tattcccct tctaagtgag attcaagcat    41700
cctcacttgg gccggccttc ttgttttgtt tctttgggac tgtggagtgt agcttggta    41760
tcccattttt ttatggctaa tatctgctta taagtgagta cataccattc gtgtccttt    41820
gggattgagt tacctcactc aggatggtat tcttaagttc tattcatttg cctgcaaaat   41880
tcatgatgtt tttgttttta gtaactgaat agtagtccac tgtatagatg taccacagtt   41940
tctttatcca ttcttcagtt gagtgaaatc taggttgttt ccagtttctg gctattacaa   42000
ataaagctgc tatgaacata gtggagcatg tgtccttgtg ggatggtaga gcatcttttg   42060
ggcatatgcc caggagtgat gatatagctg agtcttgaag tagaactatt cttagttttc   42120
taaaaaacca cgaaattgat ttccaaagta gttgtacaaa tttgcactcc ctctaaccaa   42180
gcaagtgaaa gatctgtatg acaagaacta caagtccctg aagaaataaa ctgaagaaga   42240
tatcaaagaa tggaaagatc tcccatgatc gtgaataggt aggattaaca aggtgaaact   42300
ggacatctta ccaaaagcaa tctagagatt cagtgcaatc cccatcaaaa ttccaacaca   42360
attttctgt agaccttgaa agagcaattc tcagtttcat ataggaaaac ataaagccca    42420
ggagagccaa aacagttctg agccataaac gaacttgtgg aggaatcacc atccctgacc   42480
ttaaagccgc actacagagc agtcgtgatt aaaacaacaa caaggctgc gcacttttgg    42540
tacagaaaca gacgtgctga ccaatggcat ccaatccaag atccagaaag aaacccacac   42600
actatagttt ttttttaaat ataaagttct tcagcttaat gcttctcatt attcatgaga   42660
gaagaagact caacagcaaa gaaggtgaaa caagggtgac aagtaccaca gggctctcga   42720
gtgtctcttg tgatggacta gggagcccgt cagttctgaa tgctcaggaa tgtggttcac   42780
agtgtggcca cagtacagaa gatccccgag ataaggcaga agacagtcac cacaggtcat   42840
ctccacaggg caaggactca gtatatggca tattactaat gctcttaaat atttactgaa   42900
caaaggaaca aaatgctgag tctgtcacag agatgaaaat agccgttgct tcaggggaca   42960
gcagaagata gcctttttt ctccttgaat ggtagttaat ttaatgttgc ctctatatta    43020
```

```
ttagaaataa attacaagct gaaaaataat gagtcatacg cagtgatttc tcttgcttta    43080
ggctgtcttt actacaaacc catttcaggc taaatgattt tgtcttaatc acagtctatg    43140
gtaatctgtc aagccagttg tgacctgtct tcctttcctt cttcccagca tgcaagtgca    43200
atgggcacgc atcactgtgc aacaccaaca ccggcaagtg cttctgtacc accaaaggtg    43260
tcaaggggga cgagtgccag ctgtgagtac cacacacact ctgtgtctcc agtgggggac    43320
tgggccttgc agctgcctgg gccctgtcgg ccacctgctt gcctgggcat tgttgccctt    43380
cactcccagg gtctttgagt ggactagtgt ggaggtttac cttttttcct tcagacaggt    43440
tatctcagtt actttaatat tgctctgata aaacatatga ccaaggcaac ttacaaaata    43500
aagcctttaa ttgggcttat gacttaagag cattggagtc tacattgagt tccagggcaa    43560
tagagctaca tagtaagact gtatcaatca atcaataaat aggactacat agtaagactg    43620
tatcaatcaa tcagtagatg aagagaaaga aagaaagaaa gaaagaaaga aagaaagaaa    43680
ggaaggaagg aaggaaggaa ggaaggaagg aaggaagggg aagaacaaaa caagcttaga    43740
taggaagaac aggatagaat gaatgacaaa tgcttgaaaa atgttttagc tgtacttttta   43800 gaagcatact caatccacac agaagtaaaa atgttgttcc ttatgagtag tacctagcat    43860
tattacatat gtacttgcct gtgtccttgg gcaagtattt gtttatttgt tgtttttata    43920
ctgttgctgg tgtaaattac tgagcagtta gcagaaacat tcctgcaaat gggatagtct    43980
ctctgatctg aataatgata tagttttatgt aaaaggattt acttggttta aaataaata    44040 tagagtctgt gctttaaatg tcaatagaag ataatttctt ttttccctag atgtgaggta    44100
gaaaatcgat accagggaaa ccctctcaaa ggaacatgct actgtaagtt tttgtaattg    44160
tttctagaga gtaattgaac aaaacgacat tgctttttt ttttaccatt gtctgagaat    44220
gataaatgct tgggggatga agcaaatact catagccatg cccctgactt ggtgaacact    44280
gttctaactg aggcatggtc tctgctggtc atccagagca gttagcaggg gtgctgtcct    44340
gcctgtcctt gttcagctcc cgcggaggcg tgctcattca ccattgccca gtgtagctta    44400
tcatgtccaa tcttcagaca gccaggaagg agtttctaag atagaggtgc gttccaccat    44460
tctctctgca gctgatttgt gctcacaaac aagtaaataa aacaccaaat taataccttg    44520
gtgtgaaagt gaatctggta agcttacagc tttatcataa atatatttttt tgtctatgag    44580 aatctacata gtaggttcta gactatagaa caataaaaaa aggaattaac atttggcata    44640
tgcagcataa tggtatatat aaattgtaga agaaaatgga tggttctaga cctgaaaaga    44700
caagaaaatt gcttgtgtgt aatctgggca ggtcttaagt tgtgaccttc aacatctgct    44760
tcccaagcag ctggaaccac caggcctaca gaattcttag ctatgattct aaaggtcatt    44820
catcaaatat aatgttaatg tgtattttat taaagtttca aacttctatc tttaataatc    44880
tgcaaatgta gctcagtaga ggagagctct cgctgtaagg tcctgtgttc tatccccagc    44940
acaacaaaac aagacattta agaaaaaatt aaaacaagtt ggctgtattg tctcagtatc    45000
tcatccttga gatagtgagg caggaggact tttagtttga ggcctatgtg ggttatgtag    45060
tgtgaaacct ttctcaaata atatttacac tttttctttt aaaaacaac ttttttctta    45120 atttatgtgt tttgcaacat gtaagtctgt gcaatgtgaa catatctgtt gcctttgaat    45180
gccagagagg gtttcagttt tcctggatct ggagttacca agggttgtga gctgccatag    45240
tgggtgctgg taatgaactg agtccctctgg aagagcagcc agtgctctta actgctgagc    45300
catctctgct gctaggtact cccccttccc cccttaaatt taagacaaag gtctcactgt    45360
gtagcctcag atggtctaga actcaatttg tagaatggtt gacctttgaa ctcacaaaac    45420
```

-continued

```
tctgcctgct tctgcctcct gagtgttgag attaaagttg tatgtcacca cacctgcccc   45480
tatgatttct atatttaata aagatcatga ctaggatata gagaacactt ttagaactga   45540
agaagaagac agttacagtt aaaagcaaaa caaaaacaaa aacaaaacaa aacccagaaa   45600
aaaaaagaat gaaaactagc actgaagaaa aaataaattt taaaaatagg caaagagtca   45660
ctattatatt gtgatggatg tgttatatgt ttaaaaccac aagtgagata caggcctgaa   45720
atgactttaa tcgaagctac accagcctgg ggtggtagtt cagttggtaa agttcttgct   45780
atgcaagcac aagaagctgg gtttgatgcc caggacccat gctgaaaccc aggagtgctg   45840
ctgagtgctt cagctctggg gtggcagggc tcactggcag gaagcctagg ctaagagaga   45900
ctctgtctcg aaaaacaagg ccgatggcac ctgatgaacg gcatctcagc atgacctttg   45960
ctcggcatat aatgtgtaca cacaaattca tagtttagta gaagacaagt atgatctgct   46020
tttcatgaag tctgttgtaa tacgccttct ttagttaacc atagttgctt aaaaaaagaa   46080
aaaaatcgac ctcactggac agaaaatgga tagagtgttc taatagccaa ttcaattcat   46140
catcattatc aaaacctata acttaggggg ctggagagat ggctcagcgg gtaagagcac   46200
tgactcctct tctgaaggtc ctgagttcaa atcccagcaa ccagatggtg gctcacaacc   46260
atccataaag agatctgatg ccctcttctg gagtgtctga agacagctac agtgtactta   46320
cataaaataa ataaataaat ctttaaaaaa aaacaccctat aacttaaact tatcaataac   46380
tttaactttc ctaccccatg cttcctagtt acccattctg ctttctgttt gtatgatcct   46440
gggtatggca tcttaatgga accacagtgt ttgactttgt atctacttaa tattaggcat   46500
gatgcctctg actctcatcc ctgatatagc acagttcaaa attgcctttc tttggtgctg   46560
tacatatagc tgagcgtttg agtgcttccc tgcatgcaca ggtttctgaa ttcaatcccc   46620
agcacaaaaa atgataaaaa gaaagcaaaa aggcttattt ttacagctgg acagatcatc   46680
ctgcattgtg cctgtcatgt tttgcttgtt tcttctgtca gtggacactg tgttacttct   46740 acctttttggt tgttgtcagg aatattgtaa acatgagtga atatacaccc agaagtacaa   46800
ctggatgtgg taattctatg agtgttttgt tttttgaggg atggttatta ttgtttccat   46860
acaataaatt acatttcctt acagttcatt acatttccaa aagccatgca tagcatttct   46920
gttgttctac attcttattg acaccagttt tcaatttaca tttatttttgt gagttttta   46980 attggtaacc atcataatgg acataaaaaa tagctcattg tagttttggt atttgtattt   47040
cagtaatgct tggtgtgatt atcttttttat attcttatta accattagtg tgtatctttt   47100
tttggaaaaa cacctcttca agggttttac tatgtagctc tggctggcct ggaacttgtg   47160
cagaccaggc ttgcctccgg ttcccactgt cttaggtagg tttccattgc tgtgaagagg   47220
caccatgacc agagcaactc ttacgaagga catttaattg gggctggctt acagtttcag   47280
aggtttaatc cattatcatc atggcaggaa gcatggcagc atccaggcag atgtggtgct   47340
ggaggagccg agagagttct atatcttgat tcaaaaatag ccaggaaaag actgtctaca   47400
gcaggcaacc aggaggagac tgtcttccat attgggcaga acttgagcac taggagtgtt   47460
ccaaagccac ctacacagtg acacagtaca tccaaaaagg ccacacctat tccaacaagg   47520
ccacacctcc taatagttct acttctcatg ggccaagcat actcaaacca ctacatccac   47580
ctacttctgt ctcccgaatg ctgggattaa aggcatatgt tgccattacc caattttaaa   47640
ccagattatt attgttttt tgtacaacag acttttaagg ttaaagtttg cagcaatagg   47700
cattctttga agctgtatca cactgatata tgtctgttgt tttcttcctt cctagattaa   47760
aatagtacag tatattcaag tttcaattgt cccttttccat aagaagtcct ggtttctgtt   47820
```

-continued

```
ccattattag tttatatctt agtgttctta agtaaaaata ctcagtattt atagatgagt    47880
tagattagag ccaaacccca atcagggtat tggtaatgaa ggtttgctgg ataattcaaa    47940
ggatactgca aagatctggt ttctaatgga agaacatgt aagttggcca ttagtggacc     48000
acacatctgt atttcttatt ctttggaacc ttgggcagga tagacagatg agctaagatt    48060
ccttcatagc tattgaattt gtgagaaaaa caaattgtgt ttccagaaac ctgctttagt    48120
ttgtatcaac acttactttc tttctgtgtg tggtgtgtgt gatgtgcctg taccattttc    48180 aagttttttct tccttctttc catagatacc cttctcattg actatcagtt cacctttagc   48240
ctgtcccagg aagacgaccg ctactacaca gccatcaact tgtggctac tcctgatgaa    48300 gtaagctttt cttttaagct gtcttatttt gtgttaaatt ttgtataggt ttttttcttg    48360
gtcatcctgg acaaaagtac tacatagaag cagacagtat cagggtggga atataaaagg    48420
caaccagttt ttaagtattt ttttatttac ttgttgacag ttttatatga ttatataatg    48480
tgcttgatga tattcaacct gtgaccttttt gtctccctca tacttagttc cttctctccc   48540
caccaagtca ccttcactcc ctctcgtgtg tgtgtgtgtg tgtgtgtgtg tgtgtgtgtg    48600
tgtgtgtgag agagagagag agagagagag agagagagag agagagagaa agacagacag    48660
acagatagac agagagacag agattgattg attgattgat tgattgattg attgattgat    48720
ttacctacct agtttaccag ctgactgcag gagcatgctg ggtgggaagt tcttactgga    48780
gcatagacac attacagtga ctacaccact gaagaaagtg actccctctc aggtagtctt    48840
cactgccact aggtcctcag ggatcaagag aatgtttgga gtctacattt tatcttttttt   48900 ccactcagaa ggcaaacatt actgaatgtt tttaagtagt agaataatgt tcatgatagt    48960
ctgtttaata ttaaattaag aatttgttcc taattataaa attttttagaa gatagacaag   49020 aagacaaaat ttttgagtta acagtttgaa aggtttattt ttattttatt ttatatgtat    49080
gaatatttta gcttcttgta tccctgtgca tcatgtgtgt gcagtgcctg tggaggccag    49140
aaatagatat tggatccctg gaactagagt gatagatcat tgtgagccat catatgggtg    49200
ctagaaccaa cccagggtcc tctgcaagag cagtgagtgc tcttaactgc taggccattt    49260
ctttagcccc taaatgtgaa caactcttta aataaatgta agtgatctta aatactctgg    49320
agaaaaatct gtagctatac cttactttt aaaaattatt ttgttttata ttatgagtgt     49380
tttgcctaca tatatgtgtg tctgatgcct gcagaggtca gaagagggtg ttggatcccc    49440
tagaactggg gttacagatg gctgtgagca gctatgtggt gcctgggagt tgaaccctgg    49500
ttctctgtta gggcaacaac tgcttttaac catcaaccca tctctttggc acatgggtgc    49560
attgttggtt tggctgcttg agttgtgtgt gaggggtgtg tgtgcataca tatgtgggtc    49620
catgcttatc cagtggaggc cagaggtcag agtcatgtat ctctctgtta cttttctacct  49680 tatgttttgg aagcaagatt agatagaccc ctgggacctt cctgtcttct cctcagcact    49740
aggactacaa gtccacacct gactttttac atggggcttc agatctaact cagtcccaac    49800
acttgtttca tttccttagc accttggcta gattcttagg atttttagaag gagcttatag   49860 caaaatacca caagtgaaat ttactactgc cttagtcata agcaaatatt gaaggctcag    49920
tctttaaggg tataattgat agtgttcttt tttttttaa gtaaacaaat agcctgtcat     49980
ggtaactatc gctgtagtcc cattacttgt gagagatgtc agctcaaggc cagcctccgc    50040
tacataagta agggaagacc agcctgagct atatgggact ctatcaaaac aaataaacat    50100
tgtagaattt ttgtaatact tattagaagg tagctgatga tcatgagagt ctttagacat    50160
ttcttcattc cactgttttg tgtgtgtgtg tttcatgaca gatttcttac tagatttatc    50220
```

```
tctttgtgtg tgtgtgtgtg tgtgtgtgtt ttacaaaatg acaaagattt tagtccttct    50280
cgtggaaagt agttgctagt ggtcagcaga tacttgctag tataaataaa tgagcataga    50340
tctgcgcttg caaaggaaga caaagggaaa aaaggttttc ttgaacataa ttcctacttt    50400
gtgaaagaaa cttctcattt ggaaattaca ttttgaaaat aggtattgtg aatgtttcca    50460
ttgtggtttg tggtataact atcaaataac acttttttaa aaagaaaaat cttaattttc    50520
taagattttt aaatacccct ttaaaatgag catttccagc atggtttgat taatttgtaa    50580
aatgtaagaa tatagtatct aaggctacag aaatgactca gtggttaaga gcactggctg    50640
ctttacagag gacccaggtt ccatccccag caccctcatg acagttcaca gccatctgta    50700
tttctagttc cagggcatct gatgcccttc tctgattttc tccagtacta gtgacacaca    50760
gcatacattt gaacaaaacc actgatacac ataaaataaa ttgttttcaa gaaacaatat    50820
agcatctaat tagcttacaa aactaattat ttgtttctgt actaattacg tttctattgg    50880
catgactaag gcaacttata agagaaagca tttaatttgg ggttcacact tctagtgcct    50940
tagattctat gagcatcatg gtagggagtg tggcagtagg caggcaggca tggtgctgga    51000
gcagaggctg agagctcaca tttgattttc tactagaaga cacagagaga gctaactgga    51060
aaaggcatgg gcttttcaaa cctcaaagcc cccctctagg aacacacacc tccaccaagg    51120
ccatacctcc taatcaaaca gtcctaccaa ctgaggacta accattcaga gatagatgag    51180
tctatggagg ccattgtcat ccaaaccacc acaggcccca agaaagattt gttagtgaaa    51240
tttcagtgaa aactaaaaca gcattagaat ttacctggca tagccagcaa tgatctcttc    51300
tgttcagtgc cacagatttc tttgagttaa aactcagttg ttaaaaccaa aaatcaaaat    51360
gtaattggca ctttaaattg ctataagggg aaacaaggtt ttcaaagcca tgaaaccata    51420
ttcagaataa ttttagcgag agaaatattt tttcttttt ttgtcgtttc ttttttttct    51480
tggagagaaa tattttatt atttatatt attttaatta catatttaat tattaaccat    51540
ttctgacaga gggcaaaagg tgaggatctt catggaacta atatctgata aagcaccaaa    51600
ttcttcccaa ctctgggatg caaatgacag ttcaacttca gtttattgct tgtattgaag    51660
aaaattgaca agaaatgtca tgtcttaaca taagcatgga tttcttttaa gatgtagaat    51720
agtctataat taatgttttt gagactagta agacctgatt attgttgtat cttaaaatct    51780
agaaggtact aacaattttc taatgtgtat tttttttttc atcagcaaaa cagggatttg    51840
gacatgttca tcaatgcctc caaaaacttc aacctcaaca tcacctgggc caccagcttc    51900
ccaggtacag acacacctag agagatggat tggcaagttt agtgtaggag ttggggaagg    51960
aggctctgaa ggctggtgag tgagttcaga gcccacctct gcctcttagt agccatggca    52020
ccttgaacaa gccatgcttg aacaagcatg tacaattccc tctctacctt aggctactca    52080
gagtgaggag tcacagctct tgcctccagc gttgctggtt caggttggtt ggatggctgc    52140 tccctgctttt gccaccacct tccagcacta tgactatctc tatgtttgtg cttcacaggg    52200
gaaaaactaa agtgactcat agttttaaga aatgaaaact cttaaggga aggggataa    52260 ctctaatatg tagaggtatt catactttgg gataactcct aaaagtacag cttttccatt    52320
cttgtttatc ttatagtgac tataaaattc tgatggccct aatgtagcag ttactataaa    52380
taaccactcc ataacttgat agccctgaag atagacctag gtttgaattt acctgcacgg    52440
tgttgaacaa gttactgaag ctttcttttc tttgttttt aagtttgttt tattttatgt    52500
gtgtgtttgc ctttgcctgt atgtgtataa gtgtaccatg tatgtgcagt gcttgagaag    52560
gtcagaagag gacatcagct cccccacccctc aacgagttac agacaattat gaactactat    52620
```

```
atctgtgctg gcaacagaac ccaggtcttc tgaaagagca accagtgctc ttaactgctg    52680
agccatctct ctctagcccc caagttacct aaactttctg atccagtttc cttctttata    52740
aaatgataca gtgaaaatag ctttgctatg tacagagata ttccaacttt ttaatattac    52800
aacatgacat ctacaaatat gttagccctc attcataatc ttgcctgaat tgtagagtgt    52860
tgcaaggaat aaatgaaata aaggaggtac ttattataga gtttgaggtt tgccttcatg    52920
cataaagaga agctttttg agtctgtact actcatgttc ttagccaatg gagtatataa     52980
aatatggtag aaccatttag aaatggagtc tcactgggta caggcctgaa tgcagtggta    53040
gcaggtagca gaaagaaggc ctgagtggct gcttgagcac cttctccatc aagacttgag    53100
gacctttctg cttaggaagt gatgagcgag taagtgtccc tgaacaggag ccttgagcat    53160
attctacagt gtgaagcaga atacaaagg agttgaggta tcatgtgcaa aatgaatgca    53220
gtgtctgttt tatatgtatg attgttttac atacatgtat gtctgtgcat cgcttatata    53280
tctggagcct ctgagacaga ttacttaatc tattgggact tgagttttc caatctgtag     53340 atggagatag gaaggtgttg tgtgggttag agactgaagc tcataaggct atattctttt    53400
gacactgtaa gtgctcaata aacttttacc ctcattacta gtgcgcaaag attctttctg    53460
attggcatac ccgcctccca gtctttatt tttattcttg cttctttcta gccggaaccc      53520
agactggaga agaggtgcct gttgtttcaa aaaccaacat caaggaatac aaagatagct    53580
tctctaatga gaaatttgat tttcgcaacc atccaaacat cactttcttt gtttatgtca    53640
gtaatttcac ttggcccatc aaaattcagg taagaactgc ttttaacttt cattcccgta    53700
aagatggtga catctcttta gtggagacta acttcactca tttggaatct gtggtgactg    53760
aaagatagtg ttgctttgcc tttgagggat ctttgccata gactgagtag caggtgagtg    53820
ctgttcttag gttggagaga tgttcagtga gtggagtgct tgctacacaa gcctgaggac    53880
atgcagttca tctgcagcct ctcatacaaa gcgggacacg caggtgtgc ctgtcacctc      53940 agcactggac atgcagtgtg tgcctgtcac cccagcacag gacacgcagg gtgtgcctgt    54000
cacctcagca ctgacatgc agtgtgtgcc tgtcaccca gcacaggaca cgcagtgtgt       54060
gcctgtcacc ccagcactgg acacgcagtg tgtgcctgtc accccagcac tgggaagcag    54120
gggacagaaa gatcttgctt gctggccagc cactcaaagc tggatctgtg agttctagat    54180
tcagttagag accctgtctc aagtaaaata aggtagagag gaattgagga agacacctga    54240
ttacctctgg cttctgtatg catgtgcaca tatatatacc ttcacacata tacacactca    54300
gagaaaaaat tctgagagtg tcatatcact tgtgaagaaa gttttaaagc acttttaaaa    54360
gcaagatgaa agctatgcaa ggtatgcaag gtagtatact tttgtaatcc caggatgtgg    54420
aagaccaatg caggaggatc accctgagtt tgaggccata ggaagaccct gcctcaaaag    54480
gagggaagga gggaggggagg gagagagaga aagagaaaga gaaagagaga gagaaagaga    54540
aagagaaaaa gaaagaaaga aagaaagaag gaaggaagga gaaagaaaat caaattgatt    54600
ggcatatagt tatgtgttta ttttttgagt aattgctatg taaagccttt tagaaataca    54660 cagtttaat tatggaattg agtataaata aaacaagtac atgtttgtaa ccaataaagt      54720
ataaaaatga cacataagat gtcaaagtgg tatgatggct ataatgtgga gtccatagag    54780
gaagcagtag gcagtatgag gtactgtgta aaaacacata gctttactat tgcacagaca    54840
agtgtggatt cttgttctgt gtgtggttca tggaggctct ccagtttgca gattctctgt    54900
gcatgtgtcc tgaaggattg gtcttcctgc tatgacctct ggtgttatta gcctgaactg    54960
agtcctaagg agacaggtag tggaaatgtt tgtattgcaa agacagtatg ggtagttgtt    55020
```

-continued

```
tttagaaaca ggagttcaac agaattgata gaacttgtga tcaagaagct aacagctgga    55080
ctgggatgta gctcagttga agaacgctt gtctaacatt aagaagccct gggtaccatc    55140
actaccacag cataaactga gagtagtgac agactcatgt gtcccagcac tgggaaggta    55200
gaggtaggag gatcagaggc tgcccaggga ggttgagagt gacttacgct aggagataga    55260
tctaaaaatg aaaaggaaaa agaacttggt agctgctaga gctaccatga agagagtgga    55320
gcttaaggat tcagctgaag aatgtaaact gccttctgat gacaactgag agtcgctgag    55380
ttatttaaag tcaggaagtg aacaaagatc agtgtttcag aaagacctct gtggcaacag    55440
tattgactag aagtagcccc tcctatgtca ggtactggtt tagactgtat ttggaagtgt    55500
cctctttctt gatggccctc agacaccttt catggccact cctctgcatt tgtaccccat    55560
agccacacac ttgatggttc tttattacat aaatagctcc ttataggcaa tgatagattt    55620 tatattttg ataattttaa gataaactct atgtcattgc atagaattta gtagttgtag    55680
gtactcagta aatgtatata ggatgaatac aaaagcttta gggtaacagt attttgttct    55740
tcttcccccg cattttaac tatctcatag tagcacagac taacccataa ctgaccatga    55800
agccaaggat gaccttgaac tcctgtacct tctacctctt ccccgaaagt gctgaagtta    55860
ctggcatgtg ctgctcaccc aactaatagc aagttttct tataaaggtg ctgatgccct    55920
ttccctgttt gtgttaattg ctgacactta aaagctcttt atcccaaccc acagtgttaa    55980
agagtttagt taaattttgt ggaaattttg tcccaaatga agtggttgat ggcaggcctg    56040
gtggctcctt cctataattc caacactcag gagacagagt caggacgatg gccaagaatt    56100
caaggccttg ggcctacaga gtagaagaga gaagaatgag gattcgaaca cctgattaaa    56160
tagataccat ttcctgctac caacctgtgc cttagctact cttctattgc cgtgacaaaa    56220
catcataccc aaggcagctt ataaaagaaa gcatttatta ggactcacag tttcaagggt    56280
tatactccaa aaccatcatg gccgggagca ggcagcaggc aggaacatct gctgtgagga    56340
agagctgaga gctcacttct ttatccacaa ataggaggca gagagaaagc taactaggaa    56400
tagaatgagc tttgcagacc tcaaagccca cctccttccc aaacatttcc accaattggg    56460
aactaagtat tctaatctgt gagcctctgg aggcccattc ttatttaaac taccacactt    56520
tataagttaa tactacatgt gatgaggaaa ctggtatggg aattctgaaa agtagttcac    56580
aggagtggga ggggctgaac gtgagtagat gctagcatgt gtgtcaggag tgaagtgttc    56640
agagcattgc ctggtttgac ttctctccag agctgaggtg aacatgcttt gtgccaatac    56700
aaacccgtat taaagcggtg gtagttactg aaaatcagtg cagggctgtg gtctcaacac    56760
aatgtttgaa aaagaaaaca gggcatccac atcaggcagt gtacagctgc ttataattcc    56820
agtcctctgg cctctgctca catgcacata cccccccata catacacaca tgattaaaca    56880
taatgaaaaa ttaaaaatta atgctataaa aatggaaaga gccgggcgtg gtggtgcatg    56940
cctttaatcc cagcacttgg gaggcagagg caggcggatt tctgagttcg aggccagcct    57000
gatctacaga gtgagttcca gtacagctag ggctacacag agaaaccctg tctcgaaaaa    57060 caaaacaaa aacaaaaaca aaaaaaaag tggaaagaaa ggttcactgt ttcacaggaa    57120
aactctgaga ggtgataatc caatcccagt ttaaaatata ctccatagtg cacacagcct    57180
ctcccatcct tggcaactga ggcctgtgag aagactcagt cctctcctgg cttccaacct    57240
tacagtgttc aaaactcttc tgcaagatcc acatggtcct accaagaccc tgaaggtcag    57300
gcatgctgat taggctgtct ctgggcctga agtgaaaggt aaacacttcc gagatctcca    57360
aagccttggg aagattctga aatgtatggg tgttggttca ggtagactct cagccttggt    57420
```

```
gaagctgccc ccggagctgt agggttatct gcagaaagtc agccaggtgc acttaccctg    57480
gaatcctctc ccattcacag acacctccct gaggctttgt ggcttcacct cactgtgcag    57540
ctagctcctg ttttacatgc ttatataatg aatggtcttg gtaaagaaga tgataaaggc    57600
aagctagagg cctttttttt cccctcttca aattttgatt ggcctttccc tactgttaca    57660
ctgtctactc aaggttttga gcatttactt tgtgtacata gtaaaagcaa agtacatatt    57720
tttaagtaga aaagaaagca tctgtggtct ttgatatagg tgcttttctt tattttaata    57780
gtaatactta ttccatgctt gttaagaaat tcattcacag cgtgttttca tagagacttt    57840
ctctatagag atatatagaa atctagacat gaggacagcc cactaaccca ctcttcagac    57900
actagctgct tctcttagag ccctgggctc tcaccctttg gaggacagcc atcctcactc    57960
atatgtgaca agcttagaca cagaataatc acagagactc cagcctcccc cacaaaccca    58020
caatgccaat atcccatatt cccaggaact tttaataagc catccactct aatactccat    58080
ctcttatctc aggcataggc cctggttttg gtttgcttca gagtactgcc ttttctctac    58140
cacgcccttc ccactctttg ctgaccctcc agagatgtca tttccaaatg aaggggggttt    58200 ttggttctgt gggtgttttg ttttttcagtg cagttcctta actgctattc aggggacgga    58260
gcaggcaaac cagatctcta acttctgagg cctgtgaaga aagcatcag aacctcccag    58320 gggagctgta ggagcaggag tcaggcctag atatgactgt gagagagtgg ggaccattac    58380
cagtgtctta caaatgaggg gaaggactac cgtgctgggc cctgaaagat aaggaggacc    58440
aggcttcagg aaggtaggac acattctgct gactgtctgg gattgaggac agtaacacaa    58500
ctacttagac atactttgaa tgaaggacag acttagtgct tcagaactgt aaatccatta    58560
tatctttccc aagtcttagg ctagccaagt ttctcaacat ttatctacct catcccaaag    58620
ggttcccagg acaaatattt cttactcaaa catttgatgg gagttggaat caggttgagg    58680
aaatgcaggg gtgtagattt tagatttctg ggaatatgta tagatagcta ccttctgttg    58740
gatagaaaat gagattgtaa gttttttcagt gtttttttac acgagtttgt gtgcccatgt    58800
atgcacatgt ggaggccacg ggtctacctt aggtgtcttc ttcaggaacc agccatctta    58860
tttttaagat gatctctctc cagacctcag ggctatcaac acacctcagg gatccatcct    58920
cctgactgta tgtccctagc atttgggtta ctgtaccacc atgctcaggt ctttgtgtag    58980
gtcctgggga tcacagttag gttctcatac tgcagggcaa gcactttgta aacaactatc    59040
tcccctgcat atggaagtat taccactaaa ttacaacaag attttcttct attaaaatta    59100
tattttagaa gctggatata gtaatgcgtt ggggcaaaag gagggaggga aatgaagagg    59160
ataggaagag ggggagggag aagggaaaga gtggaggcgg gatcagaagt ccaatgttat    59220
tcaagggcag cctgacctag ataaatccct attaaaaagt tttcagtata gaaacttctc    59280
atcaccttca ttatcagaaa agcccctaaa ttcagaacac ttttttaatct taattagttg    59340 acaatttcat aaatgtatta tttatatata tgaataacat tttcctccta ccttttttc    59400 ccttcccctc tgatgattcc catcctccca accaagcccc ccttctgcat tgtttgttg    59460 ctttaatgac ccactgagtt ccattgggct cacttccatg agtgtgacta aaagagctat    59520
ttatcagaat gtgggcaact taccagtagt gacactgatg aagaaagtgt ttccctctta    59580
cccagtaacc attaatggcc aggagctcct gggaggggtg ggcgccttat gagccccttc    59640
tccaaaatgc tttcaaactg tgaccagcta tatttaatgt ttttattatg cctgtgtatc    59700
catgtgggac aagaaagctt gagagtatca tagcatgcat gtggaggtca aagaacaact    59760
gtgtaaagtc agatctcact tcccaccttc acatgggctc tggcactgaa ctcatgtcag    59820
```

-continued

```
tgacctgaga ggcactttat cctctaacac gcaccctgtg cccagcctaa aatttgacct    59880
ttgcaaggtt tagtgtgtgt tatctgactg tctgagtaag gatgacaaaa tgaaaccaaa    59940
cttatgggat aaagcttggt ggttgtatca gtacatttt attgttgtga taaaacatta    60000
tgaccaagac agcttataga agagtttatt tgggtgtata gttccagaga ggtaagagtc    60060
tgtcctgaca aggaagctgt ggcagcaagt ggcaggtatg gctacaggag caggaagcag    60120
aaagagcaaa ctagaaacag ttgaggtttt ttaataggaa agcccactcc cctaatgatg    60180
tccttcccct agcagaccac aagtcctaac cctccctaca cagcaccacc agctggggag    60240
ttcaaatgtc tgggactgca ggggacatct cattcagacc acctcagtgg gagaatgctt    60300
gccttcatag tatgtgcaag gccctaggtt caattctagc caagaaaaga gaacatgagg    60360
aaagaaaaga aggtgggaga gagtagagaa agaagagaag aagaggaaaa aggaagggaa    60420
gggggagaca gaggaaagca gggaagcaga ggagaggaga agagaaagaa aagattaacc    60480
agcctggttt ttaatagcac ccctcccact ctcagtagtt cccaatttga gcattaagtt    60540
caagactgat agatatttct gggtgggtga ccagtgtggt cataaacatg gtgacttttg    60600
ctctccgtac aacttgtgat tatgaacttg ttagatgatc agcttcaaca ggagagggcc    60660
tcctttagtc tcaggtgccc cctccagcca ccctgggact cgcagcctct ctgtgatgag    60720
acacaggaca ttaactggta tggttctgct ttgccaaaac gtcagtccat ggttgaactc    60780
tccacaatga gaaagaagct ttgagaatca ttacatggca tcaggcaagc caggactgat    60840
ggagcctgag aaagggccag gagcatccgc aggttttggc acccagtact aactagtaaa    60900
agcacctcat aggtttcttt aaaatgcaaa cactaaggaa aatctaactt tttttttattt    60960 attaaggcca ttcattttat tttataagta ttttgcctgt atacatatgt accacatgca    61020
tacaaggtca aaagatagta ttgggtcttc gaactggagg tacagatgat tgtgagctgc    61080
catgtggatc ctcgaaattg aacctaggtc gtctacaaga gcaggaagtg ctcttaactt    61140
ctgagccatc tctccagctc cagaaaagct actcataaaa gtcaaatcta agccatgtgt    61200
ctggtgatgt acacctttaa ttgtagcaca tggaaggcgg aagtaggcgg attgttattc    61260
atccaaggcc agtcttctct taacagtgac aaaaacaaaa ccaaacccga aacctgttac    61320
tttgcacttt agagtataag tgatagagaa aagacacaga aattttagaa tctatacctt    61380
aaaatacctt atggcttata tgatactgtt gggaccatat ttacttatgg aatgcaaaaa    61440
aaaaaaaaaa aaaaaaagat ggggggggag ctgaaggtct cctttctatt ctgttgtaaa    61500
tctagctata aaaagagtaa gaggcatgag tgtgtctcag tggtagagca cctgcttagc    61560
ttgtgtggga ttgaatgatc ctcagcacca cagaagaagg gtggggcaat aaatttagga    61620
aaataagatg ctaatcattg actttcttga ttttttttaaa aaagttatt attttatgtt    61680 tattgtatat gtttatattt tctatgtgtg ttttgatgt gtgctggagg gatggggcc    61740 acttgctgaa cttcccaatt gttatcataa ctaccatctt tagtgaaaca gttaccatct    61800
acttagtaat tgtttcattc gaatagatac tgaacactct taatctgaaa ctaatgctca    61860
gaaagttcca ctttgccaag caagcaggat aatgtaagcc tataatttta gcactgggag    61920
ggtgaggcag aattgtgagc tcaagggcac cctgagcttt tgagatcctg tctcaaataa    61980
aattaaatta tatagatatc agattttcag aataggtgtg ttcagctgct gaataaatct    62040
aagcaaatat ccccaaagaa ccctgaaatc tgaaacgtat tagttctaag ccctatgttg    62100
tgtgtgtgtg tgtgtgtgtg tgtgtgtgtg tgtgtgtgtg tgtgtgtgtg taagatagat    62160
tctcactatg taaccctagc ttgcctggat cttgctatat agagagacca ggcatatgct    62220
```

-continued

```
atcgtgcctg ggagtcccaa acgtttaga tgaaagattt cagttgtacc attatcttcc    62280
taatgagggc tctggtctag tgaggcaggt gacattaggc cagtagtaag tattaggaat    62340
tggtgatgac ggtcaattct gagacacaca gtagatacat ctaatctacc aatacaacca    62400
atgatttaga aagaattagg ccatagttaa atttgcagtg ttttcttct ccacaaaata     62460 atgttacttc tttcagttct tagttcaaat acagtaggaa tttttatat tcttggtgct     62520 aaacactatt attttatagt aaagttagta agatagaaat gacgccctgt gggttgtctg    62580
gtcgtagtct gtagctgagg ccattttgct gagaagcagc gtaggctgtc actggctttg    62640
tcacccatat tttctgtatt tttgctgcag attgccttct cccagcacag caacttcatg    62700
gacctggtac agttcttcgt gactttcttc aggtaatttc tctatgctaa ttgtacacat    62760
tccatcgaga cagtccctta actgcagctt gctttgtata tccctacaaa gctgcttttc    62820
actcacagtg atgtaaattt agtctgatgt gataaaactc tccgtttgta tgattcggct    62880
ctttgcatgg ggagaggttt gggctcaagc agttattaat aatatagcta ctgctgtgag    62940
ctacatgtct taatctgtct taatcaagat atgactgtga ttttccatag ggaaaggtaa    63000
ggtttacttg caaactcctg gggttctcct ttttttatag ttttcttatt agtagggttt    63060
tttttttttt tgagaatact atgcagaaat gattgaaaag aacaaattag tcattgcata    63120
ttggtaagag aagcagcaag agccacctca cctccctctg ctctccccaa atagaaactg    63180
ctctgctgtg ctgcttctct accttcacac caatgctcgg cctgccaact cagttatctt    63240
tcctttcctt ttaagatagg gtctctcctt atagtagtta tgactgtcct ggaattctaa    63300
atagaagagg ttggctttca aatcacagat cctcctgcct ctgccttctg agtactggaa    63360
gtatggtgta tgccaccgtg ccacagctaa ctcagttatt ttttggtgtt ctataactgc    63420
cttacataca tacagaccag gtacacacaa aattcctttc cattaattta atagttatat    63480
cacaatgcat tgaccaacta aaaaatccta aattgactta tgattctact tgctcatgtt    63540
ttaaaggaaa ggttactctt tgcttatctt aaatgtaata ttttcctttt gcagttgctg    63600
tttaaatttt ccctataagt cgaccccaaa tttacatcta taatctggca aaacaaaaag    63660
acctctagtg atggttgtct cttagcttta gtctctcttg gactccattc cctccaccca    63720
taatgttcca tcctctgtcc ttaagtgtac tagtctccaa ggcctgctat gtggttgtca    63780
ttgttgtagt tacttttcta tgttgtgaca agcacccctg acagtggcaa tttagaaagc    63840
atataatttg aggatcacag ttcctggtta gaatccatga ccatcttagc aaaggcagac    63900
aggcaggcct ggcactgaac aagtagctga gatcgtccat ctggtccaca agcataaggc    63960
agagaagcta attgggaatg gcatgggctt tggaaacctc agagtccact cttagtgata    64020
cctccttatc cttccaaaca gtattacaca ttcaaacttc aaatgtgtga gcctctgggg    64080
accactctca ttaaaccac cacagtgatc ttggcaactt cttttgtgtt cgtcccatgc     64140
cacagtcttt ccatgtattt ctccttttgc tggaacttt tccctcgaag gttcctgagg     64200
aaagaaacat agataacttt tgtatgtact tctacaactg aaagtatctt aatttttgcc    64260
ctaacaaatt tttgtttgct tacttgcttg cttacttgat tctgcgtgca tgcatttatt    64320
tgtttgtttg tttgtttgtt tgtttgagac aagatctctc tttgtagttc tggctgcctc    64380
aaactcagag agattcatct gcctctgcct ccagaatgct gggataaagg catgctccac    64440
catacctaat ccaacctcac aattttttaa gtgtgtattt atatgtgtgt gtggtatatg    64500
taaaggtgtg tgtgttcatg cacacatgtg cagagatcag aggagtcagg ttttctcatc    64560
tatcactctc tgccttatta ttttgagaca gggtctcttg ttcgatatta catatactag    64620
```

-continued

```
gtgagatagc ccaggagctt gtaggaattc tctcccattt ctaccttcca aatgtgtgct    64680
actgcatctg gctttaagca agttctggga atctgaggtc aggtccttac acctatgtag    64740
caactctgcc tactgagtca tcttactagt attcacaagg tcaaggttg ggaccaacag     64800 ccaaggttgt cctcagatct ccacacagat gtacccacaa ttatacaaac actcaacata    64860
aacctattta cacacccaca tcacacgcac acacatacat gcatacacaa aaaaatgctt    64920
tttgaaagaa gtagagaatg ctagatatgg tattacacgt atataatcca agccactctg    64980
gaagctgagg caggaggatt tcaagtttga accagcttg accacataat tataccatgc     65040
ctcaaaaatt gtatagagaa taagaatgaa tatgaatgag actaaagtca tatctcagtt    65100
acttttctat tgctgtggca aaacaccatg acaaaggtaa tttacagaag agattattgg    65160
ggcatatagt ttcagagggt gagtccatga caattatgat atggcactga agtaatagct    65220
gagagcttaa atctggtcca caacattagg cagacagaga gctaactgga aatagccatg    65280 agatttgaa acctcaagcc ccactcctag tgatgtccca cacctcctaa tccttcccaa      65340
acagttccat cagctgggaa caagatattc aacatataag cctatggggg tcattctcat    65400
tcaaaccacc agtagtaatt attagagccc agcaaagaag gaagggatag aaagaaatga    65460
ttgatgggaa ctgggtgaa gtctgataca gagagatctt tatgtactgc agcgtagctc      65520
aggaagataa ctatggttaa ggacaattag ctaagtgatt agtagagagg attttaatat    65580
ttccaataca aagaaatgct gcaggcctga aatagggtac gtttcagtga cccagatctg    65640
attattacaa ctcatacact tgtaccaacc acataaatat gtacaataat tgtgtcagtt    65700
ttatattaaa taaaaatgtg gagcaagtta aaaaatgcct gttttaaact gatcacagtt    65760
atatgccagc ttttctttgc tgtgacaaaa taccataggg agtagtttat aaggaaagag    65820
atttcctcca gctcataatt ccagaatttt cagtctagag tcagttagtt ctatcatatt    65880
gggcccacag ctagaccaaa tacaatgatg gggagaatgt ggtaaagaaa agtatttacc    65940
tcagagtggt caggaggaac acaagacaaa atatacattt cagtcccata cctccagtga    66000
cttgcttcat ccaaacagac gccaccatcc aatagccatt aaaatacaag tcaaccagtt    66060
gattgacatc cattgatctt agtcatatcc ctaaattcaa cctctaagct ctgatgctct    66120
gggggccaag cctctattgc ataaatctct ggagcatatt tcataatatg aaatattaaa    66180
caggtctctc aggagctgtt tggtagactt agttgttttt ttttttttttt tgtttaaggt    66240 tttttttggtt gggttttgtt ttgttttgtt ttgttttgtt tgtttgtttg tttgtttttt    66300
ttcgagaccg ggtttctctg tatagccctg gcggtcctgg aactcacttg tagaccaggc    66360
tggcctcgga ctcagaaatt tacctgcctc ctcctcccaa gtgctgggat taaaggtgtg    66420
cgacaccact gcctggccta gacttatttt tttaatcaga tttgagtctt tgcctctgga    66480
atcacagtag cttttcccat tcaacaccta gtttacagaa gaaagaaaac ccaatttttt    66540
tttttataat cattagacaa ctagaagttt tccctcctat taagaaaaca tattaacggg    66600
ctggcgagat ggctcagtgg gtaagagcac ccgactgctc ttcccaaggt ccagagttca    66660
aatcccagca accacatggt ggctcacaac catccgtaac gagatctgac tccctcttct    66720
ggagtgtctg aagacagcta cagtgtactt acatataatc aataaataaa tcttttttaaa    66780 aaaaaaaaaaa aagaaaaaga aaagaaaac atattaacag tattgagaaa actgttggct    66840
taaatttgat gatttgaatt ttattttact aataaatgca tgtattgctg ggcatggcag    66900
cacatcccag cactcaggat tccgagataa gagatcataa gtccacgcta gctggaatag    66960
caaaataaaa tctttttttta aaaaatatac atacatacat acatacatac atacatacat    67020
```

-continued

```
acatacacac acacacacac tttctctcagt agtacggcca attagttgac ttgtctaacg   67080
gagggaggaa gaggaggcag agagcatgct gttcagatca cgttctcttt tgcattcagt   67140
ctgggacccc agcccatagt gtggtgctgc ccacattgat tattggtatt cagttaaccc   67200
agtgtagaaa ctctctcaga gacatgccca gatgcttgcc tcataaccac tgtgtatgta   67260
tatatgctta cagaaaatat actcatcatt acacataaat ttcatccact tacctcttat   67320
gaaaagttga ttatttactg agatttttct cattctgaaa atccataaag tctaccacat   67380
tgattaaatt acttgttttt tacctgttat tgctcatgtt agaattgctt tccttatttg   67440
gggtaagctg tcgttggcca ctgtgagggg cttatcaaga agtcagaaat gggaacacct   67500
tctaggaagt caggactgga agcttagctg agccagcaag tgtttctcac actgcacttc   67560
ctgtgagcct acctgtgcgg catcaggaac tggagttggg accttgagga ttgttccctg   67620
gaggcagggg tggagtcagg cagggtgaa gctgactcac aagatggtct tgcctttcag   67680
ttgtttcctc tcgctgcttc tggtggctgc agtggtctgg aagatcaagc agagctgttg   67740
ggcatccagg cggagagagg taagcccaag tagacaaact ccacataaaa ctcattttt   67800 tccttctttc taggcagatc acttttacct gttgagtgat gactaatatt catatgagaa   67860
gcatgctgtt taacctgcat tctgtggttc cactatgtgc catcagtaga ttttaattat   67920
tcttgcataa agtgtcatta gttttgccac tgcttgattc aagtcttcct aagagtcttt   67980
cctaagaata tgagtgtaga gacaagttca gctcagtgac agagcacttg cctggcataa   68040
actgagtccc tggattctag tctcagcacc ctctaatagc acaacactag agacaaagct   68100
tctaacctgt gggtcttggg cagcaggtag gggagggga tttaaaaaac aaaaacaaac   68160
ctctagctgt agcctgtgtc atttgttatg actaagcact agagtgggta ctagtagaca   68220
tgccatgtgg acattgagca cctctccatc ccaggcactg atccaggtgg ttctgcttta   68280
tcttcatctc caccctagga tataaggag gctacgtaac tacccatcac cacacagatg   68340
ctgaggtaca gaactgaggg gtaactagtg cctctgcctt cacagcacag gttcctaaac   68400
acgttttcta caaacacttc atttgttcta gtctgttcat ttaagaatct catgttctga   68460
ctgaatgagc tagacaactc accctagact atacattcta agaagggca acaaggcagt   68520 tttgttactg ttgagaagaa aacaaagtta tttccgtatg agttattgag atagaatagt   68580
agagatttgt ctgaatacaa aatagaaagt atataaaagt atataagtgg atcataaaga   68640
aagcaacaat caactggaaa atatttgcag tatcatgaga gagagaaaac tagaagatga   68700 acccccctcaa aaaaggattt ttaaaatatg cttagactgt attcagtcag ctaataaact   68760
ttttttacct ttatttggaa tttacgaata gcactgaacc tgaccattgt aaatgcacga   68820
ggtcaggcat gacttgttcc cagtaggaag ttgtttttag ttcttgctgt ggcctgggtc   68880
ctgatggaag ttcttaccc accttatctc ctgtcctctt ggcagaggtt ctagaatagt   68940
gctgtgatgg ggtagcaact gtcttcctgt gaccctgcac ctagattatt acagaaccca   69000
gactgggttt gctgagttaa tggaaattct ttctaggttc agtagagaga tgtgctgaca   69060
catactaggc catctagttt ttcagtaatg ctcagagacc gcaataggat atgtaacagc   69120
aacaaaattt ttaacataaa atttcccttc taaaacagag tgatgattta tgtagcttca   69180
ggatcctgcc tcctagaaga tggtttgaag caaggccagt ttgtcttccc tagcataacc   69240
tcagaagacc tctcatatta ttgatggtat aggaatgaat gcccacattc tgtatttgag   69300
atgtgtgcta tagtatctca tctgacccaa catgaaaaca tttcaagcca tgtgtgcttg   69360
ggtaaggtag gagttcaaag tcatccagtg agttcaaggc cagcctgggc tgcatgagac   69420
```

```
actgtctcat aaacagacac ttgaatctca tttaaagaag acattgaaga cttgatactt    69480
tgaacaccta tcctaacgta tccaccccca aatccagagt ccttcatgtt cttgtcctct    69540
gcagttccac tttcattgtg ttctcagcag cagctctctc cgaggagagt tgtctcccat    69600
cctatcagcc atcttttta ttgttgttgc tctgacaatg tctggttcag gttttaacac    69660
aaagcaagct agagtgattt taatctagca acaaaaatat aaaaaggtaa gttttttgccc    69720 ttttatatat tcaatcaaca gatatcatag cattatatcc tccactttaa cttttatttc    69780
ttactggtaa gggcttttta taaaaatata atagtgttac cacatgtaac aaaatttgat    69840
accttgtgct acctagcacc ttgtcatgtc cagttttcct cagctgtcac agaagcgaca    69900
ctgcatctga tcagtttgaa tcagagagag tgtagcatgt ctaatatcta gtattcacta    69960
ataaaatctc agtactaagc atattaataa tactatatta ttcattagca acttcttcgg    70020
gagatgcaac agatggccag ccgcccctt gcttctgtaa acgttgcctt ggaaacagat    70080
gaagaacctc ctgatctcat tgggggaagt ataaaggtga gaagtggctc aaaggtccat    70140
atagcttttc agaactcagg cctcagtttg ctaggctaca gacagcaagc gctctgtgtg    70200
tcactcctgt ctcctctcta acagttagtc agcagaagca accccgagcg accgtaaggg    70260
gctctgtgtg tggctttact tttcgagttg ttgcatgtca gatttttaaca tgcaaattaa    70320 gcttgttatt cttactttgt ggcataatac tttatagttt ttatttggaa atatctaatc    70380
tgggctaggt gtgatggtgc acatctttaa tctcagttca gaggaggcag agacagaggc    70440
aggcaggatc tccttgagtt ctagaacagc tggtctacat aatgagaccc tatatgttag    70500
aaaaaaagaa agaggggtg ggggaaggca gctaacttta accattaatt gaaccaacac    70560
acacacattt tgttcagagc cccagtactc aattaaaagc caggcaggca tggtaacagt    70620
acttagggag tcagaaacag gattcccaga gtaagcagtc tgactaggct agcaggaaat    70680
ggtgagtttc aggttcagca agaggccctg cctcagtaag taaattgaag aacaactgag    70740
ggagacttgc atgtgcactt gtgcatgcac ccacacatgc acttgcacac ataccatatg    70800
tcaccatgct tagactataa aatgtagtca ctactggcag cacatgccta caatacagat    70860
gcaggagaat cactgcaaat ttgagatcag cctgggctac tggacaagat tttgtctcaa    70920
gaaaactaaa acaatacaaa agtgtactgg gggggttatt ctaatgccag tgtttatgac    70980
agcacattca gaactgacag taaaggcaat caaggactgt cagtggtggg tatatacata    71040
ggcagaggag caactgctac tagaaactgt ttatcccttta aaagactaat gtatgctgca    71100
gcatagacaa acgttaagtt gtgttaagta aaagatgctg tatcattcca cttacccatc    71160
gagaataatc aaatacaaga cagagtaaaa tagtgactgc tagaggctta aaagaaaaga    71220 ccaggggggtg gggaaaggga gggaaggaag tgggagaggg aggaagggag agagggaggg    71280 agggagccaga actttgtggc ttacagcatc aagaggctga ggcagaaggg ttacaaattc    71340
aaggccctac tgggctacat agtgagaagt aggatttcct tgagctgtct ttctaggtca    71400
taatctctca ttgggggaag tcagggcagg gacttgaggc agaaaccatg gggaatgcta    71460
tttgctggct ccttcccagg ctcctctcta gctttgtttt ctcatttttgt ttttactgtc    71520 tatgggtgtt ttacctgctt gttttttctgt gtaccatata catgcctgct acccacagag    71580
gcactgatgc ctggaactgg agttacagat ggttgcaggc tgccctgtga gtgctgggaa    71640
ctaaactcgg gtcctctaca tgagcaagtg ttcttaacca ttgagccatc tctccagcct    71700
ataaaattct ttttaaaaa taaagtctgc aacagaaaat gaatattttc tagagctgaa    71760
gcattcaatg agtggataaa gaatccattt gatgagctat ctaccttca caagctctta    71820
```

-continued

```
acccctacag actcaggact tagtggctgg aagatgaatg taaaacaggt agctctctcc    71880
ataatatctg gtctgtttgt gccaggtgtg cagaactgtg caacaggtca ccatacaaac    71940
cggcgtgggc ctttcctgac actcacacag ctctcgggac agtgcccgtg gggacctctt    72000
attgacctta taagcacctg actgtgcagt gtagcaggga gttaaggtgc ttctgttttc    72060
ttcctccaga ccgttcctaa gcccattgcc ctggagccct gctttggtaa caaagccgca    72120
gtcctctctg tattcgtgag gctccctcga ggactgggag gaatccctcc tcctggtcag    72180
tcaggtgagt agacaggaga caatgacaga tattggtctg tgaaggactg agtcttagac    72240
acttcttctg gtatagaacc tgggtctggg cacagtgctt agtggtacag agctttggtg    72300
gaacaattct atagtcccca aactgtgttc tgagcactga cattcctgtc ctggggtgga    72360
agttcaggac cttcctcacg gtgcacagcg tcctcagaca ttcatgctct ggtccccttg    72420
actctattga tccctgcttt cttttttttt ttaaccccctt gttcttatct caaatttagg    72480 cttttttcttc cttgatacaa gctcctattc atctccatgc ctctggcttc cagccatgtc    72540
ctcaaagctt gtgttgccaa gtacagagtt ctagtcatgc tccacatctt cttaaggtct    72600
tgctatgcag ccttagctgg acgagtgctc gttataggcc aggcagtggt ggtacacgcc    72660
ttatgtccta gcactgagga ggcagaggca ggcagatctc tgagttcaag accaccctgg    72720
tctacagagt aaattccagg acaaccagag ctacataggg aaaccctgtc tcaaaaaaat    72780
aaaaacaaca acaggaacaa ccccaaaaac tcattatatt gcccaggctg gcttcaaact    72840
catagttatc ctcctacttc agcctccaaa gtgctgggat tatgggtgtg acccttcatg    72900
cccagattgt cttaaatatg aggcatgaag aagtattatg aaaacataaa ggatattttg    72960
aaaattataa ttctactggg ttaatgcaga tccattttca tttcattgaa ataatgatac    73020
agcctttgga ggttagggga gcctctcctg ttttcaaact gactttgaac ttctgatcat    73080
cccgccacca ccgccacctc ctcctcctcc tcctcctccc cagtgctgag atacatcact    73140
actcctggtt tatgtggcac agaggctcaa acccagggcc tcatgcatgc taggcagaca    73200
ctctaccagc caacctaccc acagctccta gatgtgcacc gtattacaaa catttattct    73260
tcagcatgtt ttttttttttt tttcctaaaa atcatctcta caggaaacaa gtaccagtgg    73320
tgttttaggg caggaatagg aagaaaatat ttttactata tactctttttt ttttaatcat    73380 tttttagatt ttatttattt taaaatttat ttactattat taataagtac actgtagctg    73440
tcttcagaca acccagcaga gggcatcaga tctcattacg gatggttgtg agccaccacg    73500
tagttgctgg gatttgaact caggaccttt ggaagagcag tcagtgctct taactggtga    73560
gccatctctc cagcccctac tatatactct tttaaatgac ttatttgctt ttatttttat    73620
gtgcattggt aatctgcctg catgtatgtc tctgagagag gatcagattc cttggaattt    73680
gagttacctt gtgggtgctg ggaattgaac ccaggtcctc tggaagaaca gccagtgctc    73740
ataactgctg agccgtctct gcagccccta ctatatactt tttttatagt tttgaatttt    73800 ttttttcttttt tgggtattgc taaggatcaa atatagatct actatttatt ttttataaca    73860
tccattagta tttttataac ttactacata gtttgccaat tcttttatac atgtccatca    73920
aacatgtaag tcataattta tataaaccctt gtgttaaagc tggaggcaca gaaggaagat    73980
tgctacagag tgaagtctag actagccagg gctatatagt gggaccctgt tgcaaagaaa    74040
aagttctctc tttaaacaca aaggcagtat gaaaagacat accttgattc tgaagctgtg    74100
cataggaatg cctcacacag tgttctgctc aggactatac tcagatgcag tggtctgagg    74160
gacttggtgg tgtctcagcc aaaataacct ggagtttagt aggaaagtct cctttatccg    74220
```

```
tgtccagtcc tgaagggaag ccttatttat gtatgatgag tcaggaccca ttgtcttcat   74280
cttacttggc atccccccag cactgagtct ctgagttagc cttacttgga cagagtgact   74340
ctctgggcac tctggacagc atctcctgct tcaaaagggc aagatcttta gaagacacag   74400
agatggagca ggtcttacat ggagatatag cagcttttcc ttcctgaccc ttgacccaat   74460
gcttcttTgg aaatcctcat gaaaccctgc tcctttctgg agaccaccc cacagcaggg    74520 ttatccatgc caagcttcct gtactttctc tttttgagga agcacataca cacaaagttt   74580
tagtagctcg cacatctcac tgtgaagtag tgatactttc attgctatct tctgaaaaca   74640
ggcaggagta ggcacacgct cagagcatag ctgcactctc attcacttgc caccctgagg   74700
cagagcacac gactttgtga tctgctatgg aggagagaga aatgagtagt taggtgtgta   74760
taaataagct aacaccatca cccctttatc tttcactagg gaaatgtaaa aagaaatctg   74820
aaattatttt gtaaaaaagt aagctgcttc atgacacatg tcccctcttg tgggttcttc   74880
caaggtctcg ctgtggccag tgccctggtg gacatttctc agcagatgcc aatagtgtac   74940
aaggagaagt caggagctgt aagaaaccgg aagcagcagc cgcctgcaca gcctggaacc   75000
tgcatttgat actgggcag gaattcgccc tcacagaggg cgtgtggtcc acgaagctgt    75060
ctacagggga ggctgcaggc aggaagcagg cgtggggcag aagactgggg acccttgaag   75120
cgtccaactc atgtgcatga tcatgcaagc tgttttcatg gctcacccct ctgtgtccag   75180
catctaacct tttacttctg tgtaggaaat aatttaatta caagtccagg aatggtctgc   75240
tctactcatg ggtggaggag accagtgccg accccgtgag agctgaaggt gatgctgagg   75300
tcccttgtgg aagcctctct tgggaatctc aactgcagag gagctgccct ctgtcagcag   75360
ctctccagca tggtcctctg acactcctca gatgaactgt tctcatcgga agcttgctgt   75420 cttttttacaa gatgagcttt tactctcttc caggaagtag ctttttttct agctgagaat   75480
taataatggt ctttctcttt ggaagtcata tcaaagtata attgatgggg gccttgtttt   75540
gttttgtttt ggttttttgga gacagggtct cactgtgtag tcctagctgg cctggaactc   75600
actatgtaga tcaggctgga ctgaactcac aaagatccac ctgcctctgc ctcacaaatg   75660
ctgggataaa aagcatgaac caccaggccc agcaaagagg gctattctaa atgtcaaggt   75720
caatggagtt agaatatata taaaaaaatg caattgataa ttctctatag aaacttgatt   75780
aattttaatc cattctttcc ttctctttct ctcactctgt cttacacaca tgcacacata   75840
cacacacact aagtgcctag actttgaata gatctagcaa ttggacatta gtaagcctaa   75900 gttttttacat gattgcattc ctacattctt gtaaacttta agtaactacc attgcagttt   75960
gttctttttt taaagtctaa tttgcagcca agaacgagta attctcaccc caagcaacat   76020
ctaataggga ctgagtgacc ccagcccagc ctagtgtcac tttaggcctg acgtttgagc   76080
aaccctcggc tcttgccaag gcaccacaga atgcacttgc tcatgccctg tgcctcttga   76140
gcagaaaaga gcactgacaa ctgggacacc tggctctgtc ttcctacagc tgctcgcact   76200
gacctgtggg aacctgtggg tcatccccag gctgaatgga gtacacacta gaagagggat   76260
gatgcctagc attgggcag catctgctca gcacatgaa agggacctgg ttccatctcc     76320
cctgggcagg agttggtcca gcctcctccc agacccagct ggtggctgtg aggaggtggg   76380
gaatgctaat gagaatgaaa agcacatggg ttgatggaa gggacaagat taccacgtta    76440
ggagggtgag cagccctctg ctatgtgccc aggaccctgc ctggacattg catttcccca   76500
tttatggtgc tccgtattct ggcattatgc agcagcctca cacacctgtc ctctccttct   76560
tcatgtccta cagttctgct atcacctgac tagaatagcc ctctaggcaa cagtgctcaa   76620
```

```
atgtatgagt tggagaagt taacaatcag aagaacaaaa actgtagtgt ttcacctta      76680
aatgcagtgt tgaagaggga gcctttctct aagccctgca ctaacccact cctcccaaga    76740
ctcttgtgga gtgacagttc caagctgaac cataaatcac tgatgcacaa aacactgcta   76800
gaaggctcac ctctcaaaac acgactcttt gcatcactat taaagagcag aaagttctag   76860
aaatgatccc agcctcatcc cctatacagt taggagctcc ccacatctct accaaaaccc   76920
agcacataag tatctgcgtg gtctagcctt tcatctccgt aacaagccag gggactcttg   76980
gccaaaagaa agaaagggaa gttgcactag ggcttgtccg tccataagga attcccctct   77040
gctttgctca aaggaccaaa tttctttggc caaagaagtt gcttctatgt tagtcccata   77100
ccctgaagta atatgtacca tggctcccac ctacctgttt atgctctccc tgccccccagg  77160
gaaactgttt attctttcaa aagaagcaaa cagcgttcat ttctgctcct gtaatggaga   77220
aacagccagc tcccctgcat cccttacagc caacagctcc cttcaggctt agagcagggg   77280
gaatggcagg gattaagagc tcagctcaga gccagttacc aagatggaat ggagttgtga   77340
cccagtaact gtgtcacgag agaccatgta tataaaatag tcatgacgac actgacctct   77400
tgcacttgta cataactata ctgtagtgtc cagaatgttc agacattcag ggtgtacata   77460
aacagaagag tatcataatg tatttttatt aaacactaac atctgagttt cacctaatct   77520
gtttctgtgc catatactgg gtatccaagc tctgggaagt tatcctacca ggccctgatc   77580
tgttgataag gcactataca ccatgctggt gtgttctgta gccttgtgcc cattaggtaa   77640
ctgaacaatg attcagctct tagaatacct aggaagacag caagcagggt gacacacggc   77700
tgtgatctaa gcattcagaa gacagaggca ggaagaaaat tcaaaaatgg ggctggagag   77760
atggctcagt ggttaaaagc actggctgct cttggtcagg acactagttc agttcccagt   77820
acccacatgg tggctcacaa ccttctgtga ctacagttcc agataacctg cacccctcct   77880
ctggcctcct cgggtgcctg tggtggtcca cctggtgcac agcaaacac ccaatacaca    77940
caaaacaaaa gtaactcaag aatagcctgg gctacatagc aagagcctgt ctcaaaacaa   78000
acgaacctat gaagagccag gcagtctatc tatttacatg gcagtatact agagaaactc   78060
aggaagcaag agtgttcatc actgttgtaa tttcaaatgc tccttgtgat ttctggcatc   78120
tctgtggggt gaggtgttct gttactcttc acattcaaag actgtcaccc atgaacgtca   78180
gactttgcaa aggggctctc taagctgcac tgttgtggct ttgtctaaaa ttttaatgac   78240
gtttctgaga accatgttct ttttatacta aaatctgggg atgggagggc tcatttgttg   78300
ataaatagca ctattttccc acacctcagc ctcctgtccc cgtcctggtc ttccctacac   78360
agtctggaga gggctctgaa aggtccacag agtttgacag acacgaaagc aacccattgc   78420
cccgttgacc tgacctggaa gaagactgtc agcaaaagga aaataccaga atatctggaa   78480
agcttgaagt gtaagatggg atctcgttgg ggaattggat gaagaaaagc agagcgcctc   78540
tggtaggtga ctctgcagcc tgccagcgcc cgccctcttt ctacacagca gagtgtgcat   78600
ggcaaggaaa tgagtcacct ccttggggga tggtgctgtt tttatgaaaa cctctgatcc   78660
ttggtgtcct ttaattgatc tgttcaacaa atatttacta aacacttcta agctaacatt   78720
agggcagtga ctgaggtgga aacccagctc tttagacagc tgtcatccta ggatagcttc   78780
ctggaagcag aaccaagaag ccagaaggtt cttcctaggg tggccttggc tccctgaagg   78840
aatctgaaat gctgaccctg tcacaacctc ccagcacagc tttggaatga gacatcagcc   78900
tggcctccag cagagcagag gctctggagc tccacatcct gcctgcaggg agccctcagg   78960
gtgccctcca gagtacaggg agaaactaaa ggcaataaca gaagctgctc tcagagcctg   79020
```

-continued

```
actgtgcaca aaacactagt gaagcctgct gaactaattc tgcctctgga aatcttttct    79080
ggttctttac agtttgttgt tttgttttga tccaagctta gtttgttact atgtgtgatt    79140
tagcatctgt cgcacttgtg taaatatgga gtaagtattg taaactattt aattgctgcg    79200
attgttgggt tatacataca tttaggactg caatttttg gtatttttg tattgtaaaa     79260
taacagctaa tttcatcagg aacaagagaa ttaaggggt ctgcatttta aatgcagatg    79320
tgaagcactt gtatataaat aaaagtaaat actataatac aaagttcctt ctgaaataaa    79380
agtagatctg gtaaaaatgt gcgtgcgttt cgttctgaat gttcaatgct aattttgttt    79440
tattttatat ttacatttta gtccttattt tagcagtgag gagacaggca cagcagtgca    79500
ttctcacctt ggcagctgag gaatcccta gagtagactg caactcaaga ctcttggctt     79560
ccacactgaa aagagtttca gtttatgaag cagagtttag gaagtttagt gaggaattta    79620
aggacttctt ttaatgtttg tgtctacata tgtgggtaca tatatgacac agcatgcatg    79680
tggaaggcaa acaacacctt aatggaagtg gcctgaagaa caaactcagg acttcaatct    79740
tggcagcata aacctttacc taatgagtca tctccagtct atacggggtg tgtgtgtgaa    79800
cacatgtgca acagcacaca gtggaggtca gcacaactct tgcgagtcaa ttctcccta    79860
ccttgtaaga cctagaattc cacattgccc aggctctgaa agttaggttg ggtccacact    79920
gggccatggc tgatgaaatg ttggaaaagt gataacacca aacttttgca cagaaaatat    79980
tttcatctgg ggccttccct ggagttcaca ggctaaagtg ttggaaggaa catgggtccc    80040
tgagccacca ctttcacaaa aactacctga tcaagaagaa ctattctggg tttctgttgc    80100
taaaattcct tcccagagag aaatgtaagc aatgtctgcc ccttcaaggg tcccagcaag    80160
aaaccaaggc acaattccac caaagttcac tagaaaacca gtgagtttat tgggcttccg    80220
tgcagaacat acatgagggg ttacttagag aagtgtggat actcctcccc ctaacaatcc    80280
acacctgaa aaagccttac ccagcaggga tgagggcttc cccagaccca cattgatggt     80340
gctcccattc cattttcccc tggcatgcaa agagatagac agaaaaatag attatatata    80400
atatacacat aaattagaaa aatagattat ataaatataca cataaattat atattatata   80460
tataatatat aatacacaga tagattatat atgatatata aaacacacag aaataggta    80520
tatataatat ataatacaca aactactcag ctattaaaaa cagtggattc atgaaattct    80580
taggcaaatg gatggaacta gaaaatattc tgagtgaggt aacccaatca caaagaaca    80640
cacatggtat gcactcactg ataagtggat attagcccag aagcttggaa tacccaagat    80700
accattcaca gaccacatga agctcaagaa aggaagatca acgtgtgggt gcttctgttc    80760
ttcttagagg aacaccctca taaagtagtg gtgggggtg gggggagaca gaataggtgg     80820
tttccaggag aggaggaaaa caggaaaggg aataaataac atttgaaatg taaataaaga    80880
aaatacccaa taataaaaga aaagaatttt tgaaacagag ggtaaaaaat aatacacaaa    80940
ccaggtagat agattatata taatatatat aacacagaga tagatagata gatagataga    81000
tagatagata gatagataga tagatagata gatgatagg tcaactgctc gccctccac     81060
taggtaacat gcagttaagg cagagctgca tacaacagat gttagggata ctcaggtgag    81120
aatctcaggc tttgctccat ccatctatgc tgggtgtaa gctgtcaaca gtttagctg      81180
ggatgatgct ttgcaagagg gcacagctga atgccctaag atggtagatg cttggctcaa    81240
aggagacact acagctctgc atcaaggcaa actaactgag atgagggcct ttattttcca    81300
gatctgtatc ctggagcatc attcacctgt tactacactg aaaacatttg gtgttggttt    81360
catggcagat gacaggcagt gagagaagta cagcagcgga ctgctagagg tgggggttct    81420
```

```
gtcaggacgt gggaggctgt ttggttagta acttggaaag caacaagttt ttagctagag   81480
ggagaaaagc tggagataac tgtacttgct tgatttctta aatatcaaat tttattttat   81540
gcatatgggt attttgcttg catgtatggc tatacactac atgcttgtgg tgcccacaga   81600
gaccagagga agtagtgtga gcctctgaaa ctgaagttac agacattacg acttgagtgc   81660
ctgaaactga accttggtcc tctggaagaa cagccaggc tcctaaccac tgagctatct    81720
ctccagccct gacagaacat catgtactcc aggctggtct caaatttgct ttatagccaa   81780
gaacggtctt aaattctgat cctcctgttc tctcaagtag tggggttaca ggtctacact   81840
gccgttttct tgagcaaatc attacaaatt gagttctaag ccaggtgtaa tagttcatgt   81900
agtaacaatc tggaattttg gtctcttaaa aaaacaaata ttataagaat gtattttcat   81960
tttaatccca ggtgtatggc atatatcgaa ctgctttgga ctgactacag cagctatgat   82020
tttttcttgt tctagcagag gtatggtttt gccagctaca gatagtttct gtgattgtgt   82080
gacatttgga attctggaaa cttttcagat ggtatataaa tattagagcc ccaataggca   82140
gagttgatga ttgttggtca ttcaggggta ttggttgtgg ttagtagtct tgcttgaaga   82200
agaaacaaga acaaattaga ttcagagatc tctatatctc tctctatctt cctttctgtc   82260
ctatctagta ataggggta aaaccaggat gataaagggt tggggaacc cacaaagtaa     82320 caaagactgg ctacaagtgg cacccaactt ggaactcaaa attgccatag aggaagcagc   82380 agggatgaa ggaatggatt gtggctgttg ttgctgggat attcctcact ttgctcccag    82440
agggattttt tctgaggttt tgttgttttg ctttgctttg ctttggtttt cttctacata   82500
ttctgttttt taagtaagtt gaaataatag ccgagaagct ggaaaagttt ggtgtggaaa   82560
tggagcagcc tgagaaacaa acaatgtatg aaatgggaaa actaaggggg ccactcttct   82620
ctcttttctg aaaggcttgc agacttggtg gtgcacctgg agagtttatg gatggagatg   82680
gaagctctta ggagacaaga agcatggaaa agagaacaa aggctcagtc ccagtgactg    82740
aagagagcag gagttttcca aagaaggtgc atgggagggc cactggtcag aaaaaaaagg   82800
ctgaaaaata ccaaaggaca atgtgctgaa atagcccatt tcaagagaaa gggttcatct   82860
caaaccagca ttctgacaga gtggaaggag gggtggctca gggttatgag atcaccatca   82920
gcttttccag ttttcccata tagcatatgc ctgctaatgg tatgaacaa gagtaaggca    82980 aaataggatg gtgtcctata gaaatgatag ctctaaggtg tttttaaaag gccttgattt   83040
catatggaat gcactctcct tatgtggaac ggatattaaa taaccggggt acacaaacta   83100 gaatccttc ccaagattgg aagggattgg taacagctgt actagagact gtcagccgtt    83160
gcaatggtta acatgctgga ggaaagaagc tgtgaacatt gaacagtaaa acagagcaag   83220
gggtattaat atagtgaacg aacagctgct aggtgaaggg cggtactcta gtgtacaagc   83280
acagactcgg tgtcatgaaa ctactataga acaaggttgc ctcagtggct ataacacctt   83340
gggacaaagg aggagccagg aaaaagtcca gttcatttac aaagattata taaggctctg   83400
gagaagcctt cactgatttt tttttttaca aagattagtc tcagctatga acaaagccat   83460
atcagaccct gacacaaggc aggtgttgat agagaccttg gtgtatgaca atgcaaatac   83520
caaatataaa aatgtcatta gacttttaaa ggcacaagta atgcctatgg atgagtggat   83580
aagggataag accaatatta gttctaatgt gtactgtgct aatatcattg atcaagctat   83640
agctagagat ctctgatgtc aaaatgcctt gtgcttcagt tgcagcaaat acagtaattt   83700
gcaaggagtc attgtggcca aaactaaagg tctcagatcc caaaatgcct gatgctttgt   83760
gggaaatagg gtcatttgca acaaaaatgt gaacaagaca tctttaaggg caatggtttt   83820
```

-continued

```
tctaaatata aaccagaaag acggcctagg cttccaaggt tgtgctggcg atgtggccag    83880
ggttgccact ggaccaatga gtgtaggtcc aaaagagata ttcaaggtaa cgtattacca    83940
tcatgaaatg gtcttggggg cctatcttga ggccctgcag caaagagtat gagccattcc    84000
aaccagagag tggcatggag actcaaaacc ttcactgggc actggagatt taatgcacac    84060
tagctattgc aggcagcatg gctctagact tggccacaga taaacatctt gctctatccc    84120
ccaaaattca aagttataac atagctactg gagtgtatgg tcttttccc tcagggacag     84180 taaggataat cttgggaagg agtggattga cttcctaaga attcactgtg catcaggaag    84240
tatagatgaa tatttcaaag gagaaattaa aattgtggca tatgtaaagg tagagctgca    84300
acttaacaca ggcgataggg ttgctcagct gctgctgttt ccctatatca aaggcaaagc    84360
aactgcagca gaaagaggag aggcctgaaa accttgggca ctgacacaaa aattgcttat    84420
ttcattgaaa atgtctgttt taacttccc actatacagc acaacaggag ggggcttaaa    84480
acataatggg gaaaatgtca caattctgca attttttgttt ccttaaaaaa aacacacaca    84540 cagaattttta ataatgtgtt ctcatcttaa tcccgggtgt gggaattagg gctgctttgg    84600
accattccca gcagctgact atgatttgcc tcatgctcta gcagaagtat gattttttgcc    84660 acctgcagat agtttctggg attgtgtgac atttggaatt ttgggaactt ttctgaaggt    84720
atataaatgc taaggccctg gtggggaggg ttggtggttg gtggtcattc agggggggtgg    84780 ttgtggttag tggtcttgct caaagaacaa acaagaaagt catttgattc agatgtatct    84840
ttcttccttc ccccactctt tctctcctcc ccccggcacc ctgccccctg ccccgacctc    84900 taccccttctt tttctatcta gtgacaagga tgaaaccagg gggataaagg gtgggaaaaa    84960
gaagagccca caaagtaact caggttggct acaagttcat gccaagaatc ctaggaccttt    85020 gttgtttaaa ggcttgtttt atttgtgaa catgaatgtt aaatgtacat acatgttaag     85080
tgtatgtatg tacaccatat gcatgcatac agaatccaga agaaagtaca ttatacccctg    85140 gaatggaact tagagttgtg agacagcatg aggatgctgg gaactgaacc cagtttctcc    85200
acaagaggag tagttgctct tcactgctta acctttcctc cagccccaat cctagcattt    85260
tggaggctga tgtaggaaga ttatcccaag tgtgaggtca tcttgggctc cataataagt    85320
ttaagaccaa tctcagctcc agagtaggac cctgcctcaa aaacacacag gtggaaagat    85380
gggtcggcaa tgaagagcac acactgtgcc tccaggggac ccaagcttgg gtccaagcac    85440
ccttgttggg cagctcacaa ctgcctgtaa ctccacctcc agaggatcct aagccaccttt    85500 ctggcttggc ttcatggagg gaacaggtat gtgggtatct gagtgtgacg aatgagcagc    85560
aagtgagtct cgctgtggct agcacaaagt atgggctgaa gagcaggagg acagctgaaa    85620
agtggccttt cctggtgact aagttggtct gagcagctga gtcagtttct tcctggctgc    85680
ttggctggtc tcagtgctta taagctgctc acttgtaagt cttttcctag agcccagct    85740 tgtctagggg ttgtctttgc aactggcctt gtctgacagt gactttcagc agtcttagct    85800
gcttatatac acagtcttag gaaagaaggc tggtgaatct gatccatttc aggaactttc    85860
tgaagctatt ctgaatttac tttacaagct tacctgcagg atagaggatc tcagctcttt    85920
ataaacatcc tgtcctaaaa cacctgttg ttcctcttct cttttacatc ctgtgtcttg     85980
agaagtttgc ctccaggatg gaagttgttc aattcagagg acactgttgc acaagctccc    86040
agcacccaca tgtgagctca gtgctctcct tggctctagc tctgcccctat gaggttttt    86100 attttgtcat cataatcttt tcctatatcc ttccttgttc tgggaactca tctggttcat    86160 tttttttggca ttttgagaaa agctctcact atacaaatca ggctgcctcc aaatcatctt    86220
```

-continued

```
tttgccttaa cctcctcagt accaagatca cgagtggatc ttaacacttg actgactcgt   86280
ttaagtgtga ggaaatgtgg accaataaga gagcccagga aagcccagga gaatctgtag   86340
ccccatggct gttgtgtcag aacccagagt tttgtcaaca gaatttggtt cctaatttct   86400
ccactttata aaacgagtg agagaaacag gaacctattc agatctggcg tctgagcaat    86460
cagtgggtga acatctagag atctgttctg catctcctcg ccagctggca gagcatgcgt   86520
aaggcgggag ggaacaaggg caatcactca ctctgggct caggcttgcc ccttgggtca    86580
ggtgtttctg agagacgtga tgtctgcttc tcttgttacc atccctcatc ctctcccctc   86640
cttctgtccc ctacttacca atttcactgg ccagtgtcca tatttcctgc aaaagcgatt   86700
tggtttaatg agcttgacta tgcccgactc ctttagggag ggtggggaaa gggcaacgag   86760
ggcagtaagt ggtttccaca accactttgc acccggctgc tgggccccaa gccagaggaa   86820
cgtgcatgag ccatgaagtt tccactgata aatccacaga tgcttctagc acctgccttt   86880
ctgactcagc ctcaccgtgc cgcctgccag ctgtgaaatc agtgccaaca acaggtaacc   86940
gagacccagg cgcagggcca ggacagctgt ctgacacttc cagacaggat gtggaggctg   87000
acagttgtga tggagaggag atggggagga cagagacggg ctcagcttta agacaccgag   87060
ccacagagca ccaaacaaaa gccagggcct tctgaggtag aagtaacaga aaccaaacag   87120
gcaattctac tagtttcctg ggactgtttg ctgcatttgc caatcttggt agttttaaaa   87180
aacaaaaaca gtttgttctc agcactggca gagctttcct cctctggagg ctccaggggt   87240
ccagactctc ctctgtggta cactggcttc agacatatct cttgcctatg gctgcctcac   87300
tctaaactct gcctgtcctt gaattacctc tctctgcact ggctttataa aggaaacatg   87360
agattgtgtt tagggcctgt ttgggtgacc tcctcaggat ctataacata atcacatctc   87420
taccgtatga agtgacgctt ccgtcccagt gtgtaataca tttgccggcg cctgtcctta   87480
ggacagtgac caccaccaac tgtggaactt gactatgtcc acgtcatctt cctactagct   87540
ttagaaggct tatcccaca ctttctatcc agaattgtat ttttatttag aatcattcct    87600 actttaaaa aagtctctgt ggttaaaagc attgcagagg gcttgggttt tggtcccag     87660 gacccacatc aagtggctca cagtgtcctg gaactcttgt tccaatacccc tcttctggtc  87720 tccataggca ctacatacat atggcacata tatgtatact caggcacacg tgtaaatttt   87780
aatgtctact ttttatgcta aatatcaaag tcactcgagc agtggagttg agcacactca   87840
cataaggaaa tcatcagaca gacacttcat cctgtgttgg agccactttg tggctggagt   87900
aagcagggca gagtgatgtt ttcattactc tctggcccca gcacccctg cctctcccca    87960 cccattcgtc catgcaggtg gggaagagaa ttctctttgt gaaattggaa gtttggaccc   88020
agcttcactc ttactctgcc cagtacctcc tgtgagaaac cctcctatcc caggtgacct   88080
gctggctgtg actctcctca gcaaaaggcc cgtgacccac actgcgccac taatgtatca   88140
tccccaaatg ctgaaaagga agcgtgtctt cctctctctc tcttttttctt ttggtctttt  88200 tgagacagag tttctctgta tagccctggc tgtcctggaa ctcactttgt agaccaggct   88260
ggcctcgaac tcagaactcc gcctgcctct gcctcccgag tgctgggatt aaaggcgtgc   88320
atcaccactg cccggctgcg tgtctttctc ttagcggtct ctgtggagat gctgagtatg   88380
aagctcatcc tacccaccct tcagtgggc cttttctagc tactgagcag ctgtgtgagg    88440
actcgtgatc acaaggtcct ttgaacccctt gagacagatg tgcctgagcc cagtttgacc  88500
tgacaaaagc ctagagctca ctgataatgc cagcaaacac catctttgag tttgcaaagg   88560
aatcgcaaca catgcattca gtttccgttg ctggctgctg ctccagagat ggctatattc   88620
```

```
attctcaggt actcagactc aagagtagtt ctggccacac aggtctccac atttcgaggt    88680
caaatgacag aaaaccaggt tggtctcagt gcacatgggt ttattgagcc actgcaggtg    88740
ctggggaaac catggcaggg agatcctggg aagccagtgg ggtgctgagc aggagggacc    88800
tcagtctctc cttaatgtct acacactgtg tcataggtga caagccacgt cagtgctgtg    88860
acacgggtaa gcttaatggt gagtaatggc taactgggag ggtatttagg cagccttgtc    88920
tgtcagcctg ttcatatgat ctccttagtg ccttgtcatc ttggaaaagg acagttccaa    88980
attctaggag cggggctag tctctgtcct gctctgtaag cccaggggac ccaatgaggc    89040
ctcatctatg ggtgctcagc tctaggatgg ggaagaaaat ggacaagatg cctactgacg    89100
ggaacacagg cttttcagtc agaccctagc ctccagcccc caatccagag acagccaca     89160 caggggtcca ggcctgcaaa gggcagcaga cctgagggca agggagtttc agctcagtga    89220
gcagtcatcg ggagacatgg cagtcagctg tgtcgtccac ggttcatgtt cctaatcaga    89280
gcagggcctg gagagccagg gcagtgagtg catacagcca ggacaccttg ggcgttagga    89340
caaaacaagg actgtttctg cctccagctc ttctcaggcc actcgtgcct tgcctaggaa    89400
gggtaagaga gcacagatgg gaaggattcg gaaactgtca actccctgtc ctctccccat    89460
acctacccgc gggaaacagc acccagcagt ctggtcctgc agaactgatg gctgcaagct    89520
gtcaaaggct tgtatggcac catctgcgga gtgcagagat ccagagaagg cttggccagg    89580
aaaccctaga aactacccca ctcccttggg acaaaaaata agacccctg gaacctgcaa     89640 ggcatggcct gagatggaag gtcactgtgc taagaatgac ccacaaactg ctagtgaggt    89700
tgacaagggc tgcccctct cccttttacag gtgaacacaa tcggattaa taagagttta      89760 actctcagct actaagtggc agagacaggc ttcaaacaga cccccagaaa tctggaactg    89820
agccattcca cccagaggca agaacagcag aggtaagttg ggcacacatg gaagaaaggg    89880
ccaccccatt agtgtcaaaa gggaggccaa cttcaggcca ttggacacgt tttaacgctg    89940
acttccaccc atgtaccatg gcatgtgcac actgtccatc gcccacacca aacatgatgc    90000
gacgtaaata agacccacgg gccaggcagc ttggattggg ccacagacat              90050

<210> SEQ ID NO 6
<211> LENGTH: 226
<212> TYPE: DNA
<213> ORGANISM: Mus musculus

<400> SEQUENCE: 6
agcgctattc agctgtgcct cctttgctgt cttggctcct cctggagcac tatatgcacc      60
catgtcctta ccaggccttt cacagacgct gccattgaga gggttgatgc aggttgcagc     120
ctttaatccc cgagtactag gctctgacaa gatcccacag aagccagcat cactgggctc    180
agatggcatc cactgcagca aactatttgt gaatggagac atatcc                    226

<210> SEQ ID NO 7
<211> LENGTH: 221
<212> TYPE: DNA
<213> ORGANISM: Mus musculus

<400> SEQUENCE: 7
agcgctattc agctgtgcct cctttgctgt cttggctcct cctggagcac tatatgcacc      60
catgtcctta ccaggccttt cacagaccat tgagagggtt gatgcaggtt gcagccttta    120
atccccgagt actaggctct gacaagatcc cacagaagca gcatcactg ggctcagatg     180 gcatccactg cagcaaacta tttgtgaatg gagacatatc c                         221
```

-continued

<210> SEQ ID NO 8
<211> LENGTH: 2419
<212> TYPE: DNA
<213> ORGANISM: Mus musculus

<400> SEQUENCE: 8

| | | | | | |
|---|---|---|---|---|---|
| gaattccggg | cgaaggggag | ccggcgtgcg | gggtgtgtat | gtgttcgctg | ggcgccggct | 60 |
| cagccccagg | aagatggtgg | cggtggcggc | ggcggcggcg | actgaggcgc | ggctgagggg | 120 |
| gagcacgagg | acgacagcag | cgcctgcggg | caggaagggc | aggcagcacc | gaccctgcac | 180 |
| cgcgacaggg | gcctggaggc | cgggaccgcg | cgcccggctg | tgtctcccgc | gggtgctgtc | 240 |
| gcgggcgctg | ccccgccgc | cgctgctgcc | gctgctcttt | tcgctgctgc | tgctgccgct | 300 |
| gccccgggag | gccgaggccg | ctgcggtggc | ggcggcggtg | tccggctcgg | ccgcagccga | 360 |
| ggccaaggaa | tgtgaccggc | cgtgtgtcaa | cggcggccgc | tgcaaccctg | caccggcca | 420 |
| gtgcgtctgc | cccacgggct | gggtgggcga | gcaatgccag | cactgcgggg | gccgcttcag | 480 |
| gacatctgtc | tcacgcctat | aatcacagct | gttcggaagg | tgaggctgga | ggaacagttc | 540 |
| gaggcaagct | tcggctacag | aataagttca | agagtaacct | ggggcaactt | gggcttgtct | 600 |
| ccaaaaccaa | aatgagcgaa | aaggagcaag | ctagagtctt | tgggaaaat | tttagctgac | 660 |
| taatttttca | ccgagaacta | actggctctt | ctggatttgt | aacagatgga | cctgggaatt | 720 |
| ataaatataa | gacgaagtgc | acatggctca | ttgaaggaca | gccaaataga | ataatgagac | 780 |
| ttcgcttcaa | ccatttttgct | acagaatgta | gctgggacca | tttatatgtt | tatgatgggg | 840 |
| actcaatcta | cgcacctctg | attgctgcct | ttagtggcct | cattgttcct | gaaagagatg | 900 |
| gcaatgagac | ggctcctgag | gtcactgtca | cttcaggtta | tgcactgctg | catttttca | 960 |
| gtgatgctgc | ttataatctg | actggattta | atatcactta | caattttgac | atgtgtccga | 1020 |
| ataattgctc | aggccgagga | gagtgtaaga | gcagtaacag | cagcagcgct | gttgagtgtg | 1080 |
| aatgttctga | aaactggaaa | ggggagtcgt | gtgacattcc | tcactgtaca | gacaactgtg | 1140 |
| gctttcctca | ccgaggcatc | tgtaatgcaa | gcgataccag | agggtgctcc | tgctttcctc | 1200 |
| actggcaggg | tcctggatgt | tcaattcctg | tgccagctaa | ccagtctttt | tggactcgag | 1260 |
| aagaatattc | tgatttaaag | cttcccagag | cctctcataa | agctgtggtc | aatgaaaata | 1320 |
| taatgtgggt | tgttggcgga | tatatgttca | accattcaga | ttacagcatg | gttttagcgt | 1380 |
| atgacctgac | ttctagggaa | tggcttccac | taaaccattc | tgtgaacagt | gtggttgtaa | 1440 |
| gatatggtca | ttcttttggca | ttacataagg | ataaaatcta | catgtatgga | ggaaaaattg | 1500 |
| attcaacagg | gaacgtgacc | aatgagctga | gagtatttca | tattcataat | gaatcatggg | 1560 |
| tattgttaac | tccgaaagct | aaggatcagt | atgcagtggt | tggacactca | gcacacattg | 1620 |
| ttacactggc | atctggccgt | gtggtcatgt | tggtcatctt | cggtcattgc | ccactctatg | 1680 |
| gatatataag | cgttgtgcag | gaatatgact | tggaaaagaa | cacatggagt | atattacata | 1740 |
| ctcagggtgc | tcttgtgcaa | gggggttatg | ccacagtag | tgtttatgat | gacaggacca | 1800 |
| aggctctgta | cgttcatggt | ggctacaagg | ctttcagcgc | caacaaatac | cggcttgcag | 1860 |
| atgacctcta | cagatacgat | gtggatactc | agatgtggac | cattcttaag | gacagccgat | 1920 |
| ttttccgtta | cttgcataca | gctgtgatag | tgagtggaac | catgctggtg | tttggaggga | 1980 |
| acacacacaa | tgacacttcc | atgagccacg | gtgccaaatg | cttctcctcg | gacttcatgg | 2040 |
| cttatgacat | tgcttgtgac | cgatggtcag | tgcttcccag | acctgagctc | catcatgatg | 2100 |
| tcaacagatt | tggccattca | gcagtcttgt | acaacagcac | catgtatgtg | ttcggcggct | 2160 |

```
tcaacagcct cctcctcagt gacgtcttgg tctttacctc ggagcagtgc gatgcacacc    2220
gcagtgaagc tgcttgtgtg cagcaggac  ctggtatccg gtgtctgtgg gacacacagt    2280
cgtctcgatg tacctcctgg gagttggcaa ctgaagaaca agcagaaaag ttaaaatcag    2340 agtgttttc  taaaagaacc cttgaccatg acagatgtga ccagcacaca gattgttaca    2400
gctgcacagc caataccaa                                                 2419
```

<210> SEQ ID NO 9
<211> LENGTH: 549
<212> TYPE: PRT
<213> ORGANISM: Mus musculus
<220> FEATURE:
<221> NAME/KEY: SITE
<222> LOCATION: (549)...(549)
<223> OTHER INFORMATION: Xaa=unknown amino acid

<400> SEQUENCE: 9

```
Met Arg Leu Arg Phe Asn His Phe Ala Thr Glu Cys Ser Trp Asp His
 1               5                  10                  15

Leu Tyr Val Tyr Asp Gly Asp Ser Ile Tyr Ala Pro Leu Ile Ala Ala
            20                  25                  30

Phe Ser Gly Leu Ile Val Pro Glu Arg Asp Gly Asn Glu Thr Ala Pro
        35                  40                  45

Glu Val Thr Val Thr Ser Gly Tyr Ala Leu Leu His Phe Phe Ser Asp
    50                  55                  60

Ala Ala Tyr Asn Leu Thr Gly Phe Asn Ile Thr Tyr Asn Phe Asp Met
65                  70                  75                  80

Cys Pro Asn Asn Cys Ser Gly Arg Gly Glu Cys Lys Ser Ser Asn Ser
                85                  90                  95

Ser Ser Ala Val Glu Cys Glu Cys Ser Glu Asn Trp Lys Gly Glu Ser
            100                 105                 110

Cys Asp Ile Pro His Cys Thr Asp Asn Cys Gly Phe Pro His Arg Gly
        115                 120                 125

Ile Cys Asn Ala Ser Asp Thr Arg Gly Cys Ser Cys Phe Pro His Trp
    130                 135                 140

Gln Gly Pro Gly Cys Ser Ile Pro Val Pro Ala Asn Gln Ser Phe Trp
145                 150                 155                 160

Thr Arg Glu Glu Tyr Ser Asp Leu Lys Leu Pro Arg Ala Ser His Lys
                165                 170                 175

Ala Val Val Asn Gly Asn Ile Met Trp Val Gly Gly Tyr Met Phe
            180                 185                 190

Asn His Ser Asp Tyr Ser Met Val Leu Ala Tyr Asp Leu Thr Ser Arg
        195                 200                 205

Glu Trp Leu Pro Leu Asn His Ser Val Asn Ser Val Val Arg Tyr
    210                 215                 220

Gly His Ser Leu Ala Leu His Lys Asp Lys Ile Tyr Met Tyr Gly Gly
225                 230                 235                 240

Lys Ile Asp Ser Thr Gly Asn Val Thr Asn Glu Leu Arg Val Phe His
                245                 250                 255

Ile His Asn Glu Ser Trp Val Leu Leu Thr Pro Lys Ala Lys Asp Gln
            260                 265                 270

Tyr Ala Val Val Gly His Ser Ala His Ile Val Thr Leu Ala Ser Gly
        275                 280                 285

Arg Val Val Met Leu Val Ile Phe Gly His Cys Pro Leu Tyr Gly Tyr
    290                 295                 300
```

```
Ile Ser Val Val Gln Glu Tyr Asp Leu Glu Lys Asn Thr Trp Ser Ile
305                 310                 315                 320

Leu His Thr Gln Gly Ala Leu Val Gln Gly Gly Tyr Gly His Ser Ser
            325                 330                 335

Val Tyr Asp Asp Arg Thr Lys Ala Leu Tyr Val His Gly Gly Tyr Lys
        340                 345                 350

Ala Phe Ser Ala Asn Lys Tyr Arg Leu Ala Asp Asp Leu Tyr Arg Tyr
            355                 360                 365

Asp Val Asp Thr Gln Met Trp Thr Ile Leu Lys Asp Ser Arg Phe Phe
        370                 375                 380

Arg Tyr Leu His Thr Ala Val Ile Val Ser Gly Thr Met Leu Val Phe
385                 390                 395                 400

Gly Gly Asn Thr His Asn Asp Thr Ser Met Ser His Gly Ala Lys Cys
            405                 410                 415

Phe Ser Ser Asp Phe Met Ala Tyr Asp Ile Ala Cys Asp Arg Trp Ser
            420                 425                 430

Val Leu Pro Arg Pro Glu Leu His His Asp Val Asn Arg Phe Gly His
        435                 440                 445

Ser Ala Val Leu Tyr Asn Ser Thr Met Tyr Val Phe Gly Gly Phe Asn
    450                 455                 460

Ser Leu Leu Leu Ser Asp Val Leu Val Phe Thr Ser Glu Gln Cys Asp
465                 470                 475                 480

Ala His Arg Ser Glu Ala Ala Cys Val Ala Ala Gly Pro Gly Ile Arg
            485                 490                 495

Cys Leu Trp Asp Thr Gln Ser Ser Arg Cys Thr Ser Trp Glu Leu Ala
        500                 505                 510

Thr Glu Glu Gln Ala Glu Lys Leu Lys Ser Glu Cys Phe Ser Lys Arg
    515                 520                 525

Thr Leu Asp His Asp Arg Cys Asp Gln His Thr Asp Cys Tyr Ser Cys
        530                 535                 540

Thr Ala Asn Thr Xaa
545

<210> SEQ ID NO 10
<211> LENGTH: 1051
<212> TYPE: DNA
<213> ORGANISM: Mus musculus

<400> SEQUENCE: 10
gaattccgga aaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa    120
aaaaaaaaaa aaaaaaaagg agggcgaagg ggagccggcg tgcgggtgt gtatgtgttc     180 gctgggcgcc ggctcagccc caggaagatg gtggcggtgg cggcggcggc ggcgactgag    240
gcgcggctga gggggagcac gacgacgaca gcagcgcctg cgggcaggaa gggcaggcag    300
caccgaccct gcaccgcgac agggcctggg aggccgggac cgcgcgcccg gctgtgtctc    360
ccgcgggtgc tgtcgcgggc gctgcccccg ccgccgctgc tgccgctgct cttttcgctg    420
ctgctgctgc cgctgccccg ggaggccgag gccgctgcgg tggcggcggc ggtgtccggc    480
tcggccgcag ccgaggccaa ggaatgtgac cggccgtgtg tcaacggcgg ccgctgcaac    540
cctggcaccg gccagtgcgt ctgccccacg ggctgggtgg gcgagcaatg ccagcactgc    600
gggggccgct tcagactaac tggctcttct ggatttgtaa cagatggacc tggaattat     660 aaatataaga cgaagtgcac atggctcatt gaaggacagc caaatagaat aatgagactt    720
```

```
cgcttcaacc attttgctac agaatgtagc tgggaccatt tatatgttta tgatggggac    780
tcaatctacg cacctctgat tgctgccttt agtggcctca ttgttcctga agagatggc     840 aatgagacgg ctcctgaggt cactgtcact tcaggttatg cactgctgca ttttttcagt    900
gatgctgctt ataatctgac tggatttaat atcacttaca attttgacat gtgtccgaat    960
aattgctcag gccgaggaga gtgtaagagc agtaacagca gcagcgctgt tgagtgtgaa   1020
tgttctgaaa actggaaagg ggccggaatt c                                  1051
```

<210> SEQ ID NO 11
<211> LENGTH: 351
<212> TYPE: PRT
<213> ORGANISM: Mus musculus
<220> FEATURE:
<221> NAME/KEY: SITE
<222> LOCATION: (351)...(351)
<223> OTHER INFORMATION: Xaa=unknown amino acid

<400> SEQUENCE: 11

```
Glu Phe Arg Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys Lys
             20                  25                  30

Lys Lys Lys Lys Lys Lys Lys Lys Lys Lys Lys Lys Lys Gly Gly
         35                  40                  45

Arg Arg Gly Ala Gly Val Arg Gly Val Tyr Val Phe Ala Gly Arg Arg
     50                  55                  60

Leu Ser Pro Arg Lys Met Val Ala Val Ala Ala Ala Ala Thr Glu
 65                  70                  75                  80

Ala Arg Leu Arg Gly Ser Thr Thr Thr Ala Ala Pro Ala Gly Arg
                 85                  90                  95

Lys Gly Arg Gln His Arg Pro Cys Thr Ala Thr Gly Ala Trp Arg Pro
                100                 105                 110

Gly Pro Arg Ala Arg Leu Cys Leu Pro Arg Val Leu Ser Arg Ala Leu
            115                 120                 125

Pro Pro Pro Leu Leu Pro Leu Leu Phe Ser Leu Leu Leu Pro
        130                 135                 140

Leu Pro Arg Glu Ala Glu Ala Ala Ala Val Ala Ala Ala Val Ser Gly
145                 150                 155                 160

Ser Ala Ala Ala Glu Ala Lys Glu Cys Asp Arg Pro Cys Val Asn Gly
                165                 170                 175

Gly Arg Cys Asn Pro Gly Thr Gly Gln Cys Val Cys Pro Thr Gly Trp
            180                 185                 190

Val Gly Glu Gln Cys Gln His Cys Gly Gly Arg Phe Arg Leu Thr Gly
        195                 200                 205

Ser Ser Gly Phe Val Thr Asp Gly Pro Gly Asn Tyr Lys Tyr Lys Thr
    210                 215                 220

Lys Cys Thr Trp Leu Ile Glu Gly Gln Pro Asn Arg Ile Met Arg Leu
225                 230                 235                 240

Arg Phe Asn His Phe Ala Thr Glu Cys Ser Trp Asp His Leu Tyr Val
                245                 250                 255

Tyr Asp Gly Asp Ser Ile Tyr Ala Pro Leu Ile Ala Ala Phe Ser Gly
            260                 265                 270

Leu Ile Val Pro Glu Arg Asp Gly Asn Glu Thr Ala Pro Glu Val Thr
        275                 280                 285
```

```
Val Thr Ser Gly Tyr Ala Leu Leu His Phe Phe Ser Asp Ala Ala Tyr
    290                 295                 300

Asn Leu Thr Gly Phe Asn Ile Thr Tyr Asn Phe Asp Met Cys Pro Asn
305                 310                 315                 320

Asn Cys Ser Gly Arg Gly Glu Cys Lys Ser Ser Asn Ser Ser Ser Ala
                325                 330                 335

Val Glu Cys Glu Cys Ser Glu Asn Trp Lys Gly Ala Gly Ile Xaa
                340                 345                 350

<210> SEQ ID NO 12
<211> LENGTH: 6370
<212> TYPE: DNA
<213> ORGANISM: Homo sapiens

<400> SEQUENCE: 12
atgtactact gtaacaagaa gaccagctgc aggagctgtg ccctggacca gaactgccag      60
tgggagcccc ggaatcagga gtgcattgcc ctgcccgaaa atatctgtgg cattggctgg     120
catttggttg gaaactcatg tttgaaaatt actactgcca aggagaatta tgacaatgct     180
aaattgttct gtaggaacca caatgccctt ttggcttctc ttacaaccca gaagaaggta     240
gaatttgtcc ttaagcagct gcgaataatg cagtcatctc agagcatgtc caagctcacc     300
ttaaccccat gggtcgggcc ttcgggaagg tycaatgtgt cctactkggt gctggggaag     360
gatatgktcc cattttaca aatagttta ctacagtggg atgsccgtct tgaggcccag     420
tgttgcttgg rattctgtgg gaattttatt caggaaccca gttacttcgg ggactgaagg     480
ctgcaacctg cattcaaccc actymaatgg tagtgtctgt gaaaggcctg caaaccacag     540
tgctaaggca gtgccggaca ccatgtgcct gaggacagca atgtggagat tgcaccagcg     600
gcagctctga gtgcatgtgg tgcagcaaca tgaagcagtg tgtggactcc aatgcctatg     660
tggcctcctt ccctttttggc cagtgtatgg aatggtatac gatgagcacc tgccccctg     720
aaaattgttc aggctactgt acctgtagtc attgcttgga gcaaccaggc tgtggctggt     780
gtactgatcc cagcaatact ggcaaaggga atgcataga gggttcctat aaaggaccag     840
tgaagatgcc ttcgcaagcc cctacaggaa atttctatcc acagccctg ctcaattcca     900
gcatgtgtct agaggacagc agatacaact ggtctttcat tcactgtcca gcttgccaat     960
gcaacggcca cagtaaatgc atcaatcaga gcatctgtga aagtgtgag aacctgacca    1020
caggcaagca ctgcgagacc tgcatatctg gcttctacgg tgatcccacc aatggaggga    1080
aatgtcagcc atgcaagtgc aatgggcacg cgtctctgtg caacaccaac acgggcaagt    1140
gcttctgcac caccaaggcc gtcaaggggg acgagtgcca gctatgtgag gtagaaaatc    1200
gataccaagg aaaccctctc agaggaacat gttattatac tcttcttatt gactatcagt    1260
tcaccttag tctatcccag gaagatgatc gctattacac agctatcaat tttgtggcta    1320
ctcctgacga acaaaacagg gatttggaca tgttcatcaa tgcctccaag aatttcaacc    1380
tcaacatcac ctgggctgcc agtttctcag ctggaaccca ggctggagaa gagatgcctg    1440
ttgtttcaaa aaccaacatt aaggagtaca agatagttt ctctaatgag aagtttgatt    1500
ttcgcaacca cccaaatatc actttcttg tttatgtcag taatttcacc tggcccatca    1560
aaattcagat tgccttctct cagcacagca attttatgga cctggtacag ttcttcgtga    1620
ctttcttcag ttgttttcctc tctttgctcc tggtggctgc tgtggtttgg aagatcaaac    1680
aaagttgttg ggccctccaga cgtagagagc aacttcttcg agagatgcaa cagatggcca    1740
gccgtcccttt tgcctctgta aatgtcgcct tggaaacaga tgaggagcct cctgatctta    1800
```

```
ttgggggag tataaagact gttcccaaac ccattgcact ggagccgtgt tttggcaaca    1860
aagccgctgt cctctctgtg tttgtgaggc tccctcgagg cctggtggc atccctcctc    1920 ctgggcagtc aggtcttgct gtggccagcg ccctggtgga catttctcag cagatgccga    1980
tagtgtacaa ggagaagtca ggagccgtga gaaaccggaa gcagcagccc cctgcacagc    2040
ctgggacctg catctgatgc tggggccagg gactctccca cgcacgagct agtgagtggc    2100
acaccagagc catctgcagg gaagggcgtg gcggggaaat ggctgtgcgg tgcgggacgg    2160
aagactggaa accctcaaag catctgactc acctgcatga tcacaagctt tctttgacgg    2220
tttctcccat ccgtgttcca gcatctaacc ttttacttt gcataggaaa tacttgattt    2280
aattacaggt ccagggatga gctgatggtt gctggaggag gccagtgtag agccagtgag    2340
agaactagga atgacactca ggttcactgt ggaaaactgt tcttgggact gtctcaactg    2400
tgcaaaaaac aaaagatgga gtgtttacaa gtagacattc gtcatcagtt gttcttgaac    2460
atggtctttt aaaaactagt cagatgaatt aacttgtttt catctgaagc ctgctatctt    2520
ttttaaaaga tgtgctattt attcttgcac gatttaggca attatctctc ttccagggag    2580
tacctttttt tctagttgag aattaataat ggtccatctc ttttgatcat atcaagctag    2640
gatagaaggg gggctatttt aaatgtcaag gtcagcagtg ttactttgaa tgtaaactgg    2700
tataataggt agttttctat agtaacttga ttaatttagt cttaatccat ttgaaactct    2760
ctcttccttt ctctctgcct gtccctctcc ttctccatct caccctccct ctctcacaca    2820
tacacacaca aacacataca cacaaacacta agtgcctaga ctttaaatag atctagcaat    2880
tggaaagtta gtaagcctaa gttttacat aattgcattc ctacattctt gtaaaattta    2940
aatagctacc attggcaatc tgctttttt ctaaaatctg atttgcagcc aggaaagaat    3000
tttctcaccc aaggaacatt tgatctagca gcagggatga gaggaaagca gaaatgaatg    3060
aactgtgaaa gctcctgttt ttattatcaa aaaggcacact gtcaagaagg cgcccctgc    3120 ccccaccccc gtgtcaccct aggcctgata gcgatcaga ggaaaggact cattcatgtc    3180
acgcttcctt gagcagaaaa gagcactgag agcacttggg acccctggat cagagagcat    3240
ctgtgtgtcc tgcagcctcc tctgaacttg tggttcattc tcaggctggg gtggactcag    3300
atgccaggaa agggacagcc tcccattgtc agcagaagc tgcccaaagc ctggagaagg    3360
acttgtttgc cctctttccc ccaggagggg ctcgacccac ccaccctccc tctcagacca    3420
aggtggtggc tgtgaggagg gcagcaaatg ctgacaagga tgaaaagcac atggaaaaaa    3480
atggacgagg agggaaaact ctgccaaatg gaaaatgacc aaatttaaga gggtgggaca    3540
gtcccctgct cctctcccag agggcactgc ttggaaattg tgttttcccc atttatggtg    3600
ctctgtattc tggcattatg cagcagcctc ccagaagctc tcttctgctt caaaacctgg    3660
gatctctggc attaccctat tgggatggac cgctggacag caatgctcga gtttgtgaat    3720
ttggagagat actcaaaaga gctaaaactg cagcatttta cctttaaatg cagtgcctag    3780
agagagagta ttgtctcttc cccaacacta accccactcc catgaagaat tgcctggaaa    3840
gatgttttca aggaatttga accataaaac actatctgat gcacagaaca cctctacttt    3900
gagactcacc tctcataaag cttctttttc acattactgt taaagaccag acgttctaga    3960
aaagacccct cctctcatga gctcccccat ccctgctaca gaacacagca cccatggcgc    4020
ctgcagtgga ctggccccctt aattcccaca ggccccccca gcaaggccaa agggaggccc    4080
ctgggtattg tcctcctaca aggaagatcc tctttgtttg ttcaaaggac cagttttcct    4140
aggccaaaga agtctcttcc ccatgttagt cctatgcctt gaaatatcat gcaccatgac    4200
```

```
ccacagccat ctggttatgt cttatttttt tcctaaaaga taatgtttat ttttaaaaag    4260
gaaggaagaa gcaagtgaag tttcattctg ctccagcggt ggggaagccg ctgaatccac    4320
ctgcttctcc tttgcaaccg acagcaaaca gctttctccg gcctcagggc agaaaaaggg    4380
aatggcaggg agtaagaggc gctgggctcg agcctgtttt ccaagaagga attggttgtc    4440
atctggcagt gttgcgcgtc acaagagagc ctgtatataa attaaaatag tcaagacaac    4500
actgaccttg cacttgtaca taactataca gtagtgtcca gaatgttcag acattcggag    4560
tgtacataaa acagaaaaaa tcttcatgta tttttattaa atataacaat gtctgagttt    4620
cacctaagat gtttttgtgc catatgctgg atatccaggt tctcgccagg ccccgataca    4680
tgaataacaa acccaagaaa cgcatcccca ttgtgtgatg tgttcagatg catctggcac    4740
caattaggta tttcttaaaa caggactcat ctgtcagagt gcacatgaaa atcaggcag    4800 ggaatcgaaa cgacagcgct ggaggagact caggaagcag aggcgtccct gccgctgccc    4860
ttggccctgc aagcacatca tgacccttc tggcagcctc ttggtgctct gggtagtgag    4920
ggatgaccag tcttgtcctg agaaatgttt ctcttagtct ttaagttcaa agactaacct    4980
gtagcaatca gactttccaa aaggggttc tccatttttt gtagttttgt ctaaattttt    5040
aatgaccatt tcctggaatc agtttattat actgaaaact gggggtggga gtagggagct    5100
agtttgttga taaatagttc ccatttcccc gtggagaatt tgacataccc tggactcctg    5160
tgtgcctcct gccatccctg cacacagcct ggggagaagc ctgtgcctcc ccgtgtggag    5220
agaaggcaac cccagatccc ctgagctaac ccggaggaaa ggcagtcctg acagaagac    5280 tgtcagcaga aggaaagtac tggactaccc gtgggtaagt cctgccattc aagactggag    5340
acacctggga aataaaaaga gcagggcact gctggtggga agaggcattt taccttccag    5400
tgcaaatcct gctcctttga tttaatgggg tgtactgggg ccaggggctg attcacttcc    5460
ttgggagatg gtggtgtttt catgaacatc tttgatcctt ccatttcatt tattcatcca    5520
tccattcaac aagtatttgc taaacactaa cttaagctaa tgctagggta gtgactgaga    5580
tgtaaaaata gattttagaa ttaaaacaaa atccaagtcc tcacacccct gtcatcccag    5640
gagatctttc cttgtggtgg tttctgtgag aattggccat cctgaggaca cagccaggac    5700
ggcagaggcc tcctggcctc agggcatgcc ctgcctacct tctgaaatgt ttaccccatt    5760
gaccaaactt ggctccagcc attgcggtgg tttctagata gccaggccca ccaagagata    5820
ttgccccttg atgagagtca aacaccctgc ctacaaggag atgttttgaa atggagagga    5880
aaattggcac ctcatctttt aaaggcagta atggaattga ttttcagtaa ctgaatttgt    5940
gcacaaaaca ttctaaacac tagtgaagcc tgtttcgttg aactaattct ggctctggaa    6000 atgttttgt tttatagtta tttacgattt cgtttgtttg gattcaagct tagtttgtta    6060
atatgtataa tttagcatct attacactca tgtaaatatg gagtaagtat tgtaaactat    6120
ttcattgcgg ggattgtggg tgttatacat acatttagga ctgcaatttt ttggtatttt    6180
ttgtattgta aaataacagc taatttaagc aggaacaaga gaactaaggg aggtctgtgc    6240 atttttaaaca caaatgtgaa gaacttgtat ataaacaaaa gtaaatacta taatacaaac    6300
ttccttctga aataaaagta gatctggtaa aaaaaaaaaa agaaaaaaaa aaaaaaaaa    6360 gggcggccgc                                                         6370
```

<210> SEQ ID NO 13
<211> LENGTH: 686
<212> TYPE: PRT
<213> ORGANISM: Homo sapiens

```
<220> FEATURE:
<221> NAME/KEY: SITE
<222> LOCATION: (111)...(111)
<223> OTHER INFORMATION: Xaa=unknown amino acid

<400> SEQUENCE: 13

Met Tyr Tyr Cys Asn Lys Lys Thr Ser Cys Arg Ser Cys Ala Leu Asp
 1               5                  10                  15

Gln Asn Cys Gln Trp Glu Pro Arg Asn Gln Glu Cys Ile Ala Leu Pro
             20                  25                  30

Glu Asn Ile Cys Gly Ile Gly Trp His Leu Val Gly Asn Ser Cys Leu
         35                  40                  45

Lys Ile Thr Thr Ala Lys Glu Asn Tyr Asp Asn Ala Lys Leu Phe Cys
 50                  55                  60

Arg Asn His Asn Ala Leu Leu Ala Ser Leu Thr Thr Gln Lys Lys Val
65                   70                  75                  80

Glu Phe Val Leu Lys Gln Leu Arg Ile Met Gln Ser Ser Gln Ser Met
                 85                  90                  95

Ser Lys Leu Thr Leu Thr Pro Trp Val Gly Pro Ser Gly Arg Xaa Asn
            100                 105                 110

Val Ser Tyr Xaa Val Leu Gly Lys Asp Met Xaa Pro Ile Leu Gln Ile
        115                 120                 125

Val Leu Leu Gln Trp Asp Xaa Arg Leu Glu Ala Gln Cys Cys Leu Xaa
    130                 135                 140

Phe Cys Gly Asn Phe Xaa Ser Gly Thr Gln Leu Leu Arg Gly Leu Lys
145                 150                 155                 160

Ala Ala Thr Cys Ile Gln Pro Thr Xaa Met Val Val Ser Val Lys Gly
                165                 170                 175

Leu Gln Thr Thr Val Leu Arg Gln Cys Arg Thr Pro Cys Ala Leu Arg
            180                 185                 190

Thr Ala Cys Gly Asp Cys Thr Ser Gly Ser Ser Glu Xaa His Val Val
        195                 200                 205

Gln Gln His Glu Xaa Ser Val Trp Thr Pro Met Pro Met Trp Pro Pro
    210                 215                 220

Ser Leu Leu Xaa Gln Cys Met Glu Trp Tyr Thr Met Ser Thr Cys Pro
225                 230                 235                 240

Pro Glu Asn Cys Ser Gly Tyr Cys Thr Cys Ser His Cys Leu Glu Gln
                245                 250                 255

Pro Gly Cys Gly Trp Cys Thr Asp Pro Ser Asn Thr Gly Lys Gly Lys
            260                 265                 270

Cys Ile Glu Gly Ser Tyr Lys Gly Pro Val Lys Met Pro Ser Gln Ala
        275                 280                 285

Pro Thr Gly Asn Phe Tyr Pro Gln Pro Leu Leu Asn Ser Ser Met Cys
    290                 295                 300

Leu Glu Asp Ser Arg Tyr Asn Trp Ser Phe Ile His Cys Pro Ala Cys
305                 310                 315                 320

Gln Cys Asn Gly His Ser Lys Cys Ile Asn Gln Ser Ile Cys Glu Lys
                325                 330                 335

Cys Glu Asn Leu Thr Thr Gly Lys His Cys Glu Thr Cys Ile Ser Gly
            340                 345                 350

Phe Tyr Gly Asp Pro Thr Asn Gly Gly Lys Cys Gln Pro Cys Lys Cys
        355                 360                 365

Asn Gly His Ala Ser Leu Cys Asn Thr Asn Thr Gly Lys Cys Phe Cys
    370                 375                 380
```

```
Thr Thr Lys Gly Val Lys Gly Asp Glu Cys Gln Leu Cys Glu Val Glu
385                 390                 395                 400
Asn Arg Tyr Gln Gly Asn Pro Leu Arg Gly Thr Cys Tyr Tyr Thr Leu
            405                 410                 415
Leu Ile Asp Tyr Gln Phe Thr Phe Ser Leu Ser Gln Glu Asp Asp Arg
        420                 425                 430
Tyr Tyr Thr Ala Ile Asn Phe Val Ala Thr Pro Asp Glu Gln Asn Arg
            435                 440                 445
Asp Leu Asp Met Phe Ile Asn Ala Ser Lys Asn Phe Asn Leu Asn Ile
        450                 455                 460
Thr Trp Ala Ala Ser Phe Ser Ala Gly Thr Gln Ala Gly Glu Glu Met
465                 470                 475                 480
Pro Val Val Ser Lys Thr Asn Ile Lys Glu Tyr Lys Asp Ser Phe Ser
            485                 490                 495
Asn Glu Lys Phe Asp Phe Arg Asn His Pro Asn Ile Thr Phe Phe Val
            500                 505                 510
Tyr Val Ser Asn Phe Thr Trp Pro Ile Lys Ile Gln Ile Ala Phe Ser
            515                 520                 525
Gln His Ser Asn Phe Met Asp Leu Val Gln Phe Val Thr Phe Phe
        530                 535                 540
Ser Cys Phe Leu Ser Leu Leu Val Ala Ala Val Val Trp Lys Ile
545                 550                 555                 560
Lys Gln Ser Cys Trp Ala Ser Arg Arg Glu Gln Leu Leu Arg Glu
                565                 570                 575
Met Gln Gln Met Ala Ser Arg Pro Phe Ala Ser Val Asn Val Ala Leu
            580                 585                 590
Glu Thr Asp Glu Glu Pro Pro Asp Leu Ile Gly Gly Ser Ile Lys Thr
        595                 600                 605
Val Pro Lys Pro Ile Ala Leu Glu Pro Cys Phe Gly Asn Lys Ala Ala
610                 615                 620
Val Leu Ser Val Phe Val Arg Leu Pro Arg Gly Leu Gly Ile Pro
625                 630                 635                 640
Pro Pro Gly Gln Ser Gly Leu Ala Val Ala Ser Ala Leu Val Asp Ile
            645                 650                 655
Ser Gln Gln Met Pro Ile Val Tyr Lys Glu Lys Ser Gly Ala Val Arg
            660                 665                 670
Asn Arg Lys Gln Gln Pro Pro Ala Gln Pro Gly Thr Cys Ile
            675                 680                 685

<210> SEQ ID NO 14
<211> LENGTH: 8589
<212> TYPE: DNA
<213> ORGANISM: Homo sapiens

<400> SEQUENCE: 14
atggtggcgg tggccgcagc ggcggcaact gaggcaaggc tgaggaggag gacggcggcg      60
acggcagcgc tcgcgggcag gagcggcggg ccgcaccgac cctgcaccgc gacaggggcc     120
tggaggccgg gaccgcgcgc ccggctgtgt ctcccgcggg tgctgtcgcg ggcgctgccc     180 cgccgccgc tgctgccgct gctctttcg ctgctgctgc tgccgctgcc ccggagggcc       240
gaggccgctg cggtggcggc ggcggtgtcc ggctcggccg cagccgaggc caaggaatgt     300
gaccggccgt gtgtcaacgg cggtcgctgc aaccctggca ccggccagtg cgtctgcccc     360
gccggctggg tgggcgagca atgccagcac tgcggggcc gcttcagact aactggatct     420
```

-continued

```
tctgggtttg tgacagatgg acctggaaat tataaataca aaacgaagtg cacgtggctc    480
attgaaggac agccaaatag aataatgaga cttcgtttca atcattttgc tacagagtgt    540
agttgggacc atttatatgt ttatgatggg gactcaattt atgcaccgct agttgctgca    600
tttagtggcc tcattgttcc tgagagagat ggcaatgaga ctgtccctga ggttgttgcc    660
acatcaggtt atgccttgct gcatttttt agtgatgctg cttataattt gactggattt    720
aatattactt acagttttga tatgtgtcca ataactgct caggccgagg agagtgtaag    780
atcagtaata gcagcgatac tgttgaatgt gaatgttctg aaaactggaa aggtgaagca    840
tgtgacattc ctcactgtac agacaactgt ggttttcctc atcgaggcat ctgcaattca    900
agtgatgtca gaggatgctc ctgcttctca gactggcagg gtcctggatg ttcagttcct    960
gtaccagcta accagtcatt tggactcga gaggaatatt ctaacttaaa gctccccaga    1020
gcatctcata aagctgtggt caatggaaac attatgtggg ttgttggagg atatatgttc    1080
aaccactcag attataacat ggttctagcg tatgaccttg cttctaggga gtggcttcca    1140
ctaaaccgtt ctgtgaacaa tgtggttgtt agatatggtc attctttggc attatacaag    1200
gataaaattt acatgtatgg aggaaaaatt gattcaactg ggaatgtgac caatgagttg    1260 agagttttc acattcataa tgagtcatgg gtgttgttga cccctaaggc aaaggagcag    1320
tatgcagtgg ttgggcactc tgcacacatt gttacactga agaatggccg agtggtcatg    1380
ctggtcatct ttggtcactg ccctctctat ggatatataa gcaatgtgca ggaatatgat    1440
ttggataaga acacatggag tatattcac acccagggtg cccttgtgca aggggttac    1500 ggccatagca gtgtttacga ccataggacc agggccctat acgttcatgg tggctacaag    1560
gctttcagtg ccaataagta ccggcttgca gatgatctct accgatatga tgtggatacc    1620
cagatgtgga ccattcttaa ggacagccga ttttccgtt acttgcacac agctgtgata    1680
gtgagtggaa ccatgctggt gtttggggga aacacacaca atgacacatc tatgagccat    1740
ggcgccaaat gcttctcttc agatttcatg gcctatgaca ttgcctgtga ccgctggtca    1800
gtgcttccca gacctgatct ccaccatgat gtcaacagat ttggccattc agcagtctta    1860
cacaacagca ccatgtatgt gttcggtggt ttcaatagtc tcctcctcag cgacatcctg    1920
gtattcacct cggaacagtg tgatgcgcat cggagtgaag ccgcttgttt agcagcagga    1980
cctggtattc ggtgtgtgtg aacacaggg tcgtctcagt gtatctcgtg ggcgctggca    2040
actgatgaac aagaagaaaa gttaaaatca gaatgttttt ccaaaagaac tcttgaccat    2100
gacagatgtg accagcacac agattgttac agctgcacag ccaacaccaa tgactgccac    2160
tggtgcaatg accattgtgt ccccaggaac cacagctgct cagaaggcca gatctccatt    2220
tttaggtatg agaattgccc caaggataac cctatgtact actgtaacaa gaagaccagc    2280
tgcaggagct gtgccctgga ccagaactgc cagtgggagc cccggaatca ggagtgcatt    2340
gccctgcccg aaaatatctg tggcattggc tggcatttgg ttggaaactc atgtttgaaa    2400
attactactg ccaaggagaa ttatgacaat gctaaattgt tctgtaggaa ccacaatgcc    2460
cttttggctt ctcttacaac ccagaagaag gtagaatttg tccttaagca gctgcgaata    2520
atgcagtcat ctcagagcat gtccaagctc accttaaccc catgggtcgg ccttcggaag    2580
atcaatgtgt cctactggtg ctgggaagat atgtccccat tacaaatag tttactacag    2640 tggatgccgt ctgagcccag tgatgctgga ttctgtggaa ttttatcaga acccagtact    2700
cggggactga aggctgcaac ctgcatcaac ccactcaatg gtagtgtctg tgaaaggcct    2760
gcaaaccaca gtgctaagca gtgccggaca ccatgtgcct tgaggacagc atgtggagat    2820
```

-continued

```
tgcaccagcg gcagctctga gtgcatgtgg tgcagcaaca tgaagcagtg tgtggactcc    2880
aatgcctatg tggcctcctt cccttttggc cagtgtatgg aatggtatac gatgagcacc    2940 tgccccctg aaaattgttc aggctactgt acctgtagtc attgcttgga gcaaccaggc     3000
tgtggctggt gtactgatcc cagcaatact ggcaaaggga aatgcataga gggttcctat    3060
aaaggaccag tgaagatgcc ttcgcaagcc ctacaggaa atttctatcc acagccctg      3120 ctcaattcca gcatgtgtct agaggacagc agatacaact ggtctttcat tcactgtcca    3180
gcttgccaat gcaacggcca cagtaaatgc atcaatcaga gcatctgtga gaagtgtgag    3240
aacctgacca caggcaagca ctgcgagacc tgcatatctg gcttctacgg tgatcccacc    3300
aatggaggga aatgtcagcc atgcaagtgc aatgggcacg cgtctctgtg caacaccaac    3360
acgggcaagt gcttctgcac caccaagggc gtcaaggggg acgagtgcca gctatgtgag    3420
gtagaaaatc gataccaagg aaaccctctc agaggaacat gttattatac tcttcttatt    3480
gactatcagt tcacctttag tctatcccag gaagatgatc gctattacac agctatcaat    3540
tttgtggcta ctcctgacga acaaaacagg gatttggaca tgttcatcaa tgcctccaag    3600
aatttcaacc tcaacatcac ctgggctgcc agtttctcag ctggaaccca ggctggagaa    3660
gagatgcctg ttgtttcaaa aaccaacatt aaggagtaca agatagtttt ctctaatgag    3720
aagtttgatt ttcgcaacca cccaaatatc actttctttg tttatgtcag taatttcacc    3780
tggcccatca aaattcagat tgccttctct cagcacagca attttatgga cctggtacag    3840
ttcttcgtga ctttcttcag ttgtttcctc tctttgctcc tggtggctgc tgtggtttgg    3900
aagatcaaac aaagttgttg ggcctccaga cgtagagagc aacttcttcg agagatgcaa    3960
cagatggcca gccgtccctt tgcctctgta aatgtcgcct tggaaacaga tgaggagcct    4020
cctgatctta ttgggggggag tataaagact gttcccaaac ccattgcact ggagccgtgt    4080
tttggcaaca agccgctgt cctctctgtg tttgtgaggc tccctcgagg cctgggtggc     4140
atccctcctc ctgggcagtc aggtcttgct gtggccagcg ccctggtgga catttctcag    4200
cagatgccga tagtgtacaa ggagaagtca ggagccgtga aaaccggaa gcagcagccc    4260 cctgcacagc ctgggacctg catctgatgc tggggccagg actctcccca cgcacgagct    4320
agtgagtggc acaccagagc catctgcagg gaagggcgtg gcggggaaat ggctgtgcgg    4380
tgcgggacgg aagactggaa accctcaaag catctgactc acctgcatga tcacaagctt    4440
tctttgacgt tttctcccat ccgtgttcca gcatctaacc tttacttttt gcataggaaa    4500
tacttgattt aattacaggt ccagggatga gctgatggtt gctggaggag gccagtgtag    4560
agccagtgag agaactagga atgacactca ggttcactgt ggaaaactgt tcttgggact    4620
gtctcaactg tgcaaaaaac aaaagatgga gtgtttacaa gtagacattc gtcatcagtt    4680
gttcttgaac atggtctttt aaaaactagt cagatgaatt aacttgtttt catctgaagc    4740
ctgctatctt tttaaaga tgtgctattt attcttgcac gatttaggca attatctctc     4800
ttccagggag tacttttttt tctagttgag aattaataat ggtccatctc ttttgatcat    4860
atcaagctag gatagaaggg gggctatttt aaatgtcaag gtcagcagtg ttactttgaa    4920
tgtaaactgg tataataggt agttttctat agtaacttga ttaatttagt cttaatccat    4980
ttgaaactct ctcttccttt ctctctgcct gtccctctcc ttctccatct caccctccct    5040
ctctcacaca tacacacaca aacacataca cacaacacta agtgcctaga cttttaaatag   5100 atctagcaat tggaaagtta gtaagcctaa gttttttacat aattgcattc ctacattctt   5160
gtaaaattta aatagctacc attggcaatc tgcttttttt ctaaaatctg atttgcagcc    5220
```

```
aggaaagaat tttctcaccc aaggaacatt tgatctagca gcagggatga gaggaaagca    5280
gaaatgaatg aactgtgaaa gctcctgttt ttattatcaa aaaggacact gtcaagaagg    5340 cgcccctgc ccccacccc gtgtcaccct aggcctgata agcgatcaga ggaaaggact      5400
cattcatgtc acgcttcctt gagcagaaaa gagcactgag agcacttggg acccctggat    5460
cagagagcat ctgtgtgtcc tgcagcctcc tctgaacttg tggttcattc tcaggctggg    5520
gtggactcag atgccaggaa agggacagcc tcccattgtc aggcagaagc tgcccaaagc    5580
ctggagaagg acttgtttgc cctctttccc ccaggagggg ctcgacccac ccaccctccc    5640
tctcagacca aggtggtggc tgtgaggagg gcagcaaatg ctgacaagga tgaaaagcac    5700
atggaaaaaa atggacgagg agggaaaact ctgccaaatg gaaatgacc aaatttaaga    5760 gggtgggaca gtcccctgct cctctcccag agggcactgc ttggaaattg tgttttcccc    5820
atttatggtg ctctgtattc tggcattatg cagcagcctc ccagaagctc tcttctgctt    5880
caaaacctgg gatctctggc attaccctat gggatggac cgctggacag caatgctcga    5940
gtttgtgaat ttggagagat actcaaaaga gctaaaactg cagcatttta cctttaaatg    6000
cagtgcctag agagagagta ttgtctcttc cccaacacta accccactcc catgaagaat    6060
tgcctggaaa gatgttttca aggaatttga accataaaac actatctgat gcacagaaca    6120
cctctacttt gagactcacc tctcataaag cttcttttc acattactgt taaagaccag    6180
acgttctaga aaagacccct cctctcatga gctcccccat ccctgctaca gaacacagca    6240
cccatggcgc ctgcagtgga ctggcccctt aattcccaca ggcccccca gcaaggccaa    6300 agggaggccc ctgggtattg tcctcctaca aggaagatcc tctttgtttg ttcaaaggac    6360
cagttttcct aggccaaaga agtctcttcc ccatgttagt cctatgcctt gaaatatcat    6420
gcaccatgac ccacagccat ctggttatgt cttattttt tcctaaaaga taatgtttat    6480
ttttaaaaag gaaggaagaa gcaagtgaag tttcattctg ctccagcggt ggggaagccg    6540
ctgaatccac ctgcttctcc tttgcaaccg acagcaaaca gctttctccg gcctcagggc    6600
agaaaaaggg aatggcaggg agtaagaggc gctgggctcg agcctgtttt ccaagaagga    6660
attggttgtc atctggcagt gttgcgcgtc acaagagagc ctgtatataa attaaaatag    6720
tcaagacaac actgaccttg cacttgtaca taactataca gtagtgtcca gaatgttcag    6780
acattcggag tgtacataaa acagaaaaaa tcttcatgta ttttttattaa atataacaat    6840 gtctgagttt cacctaagat gtttttgtgc catatgctgg atatccaggt tctcgccagg    6900
ccccgataca tgaataacaa acccaagaaa cgcatcccca ttgtgtgatg tgttcagatg    6960
catctggcac caattaggta tttcttaaaa caggactcat ctgtcagagt gcacatgaaa    7020
aatcaggcag ggaatcgaaa cgacagcgct ggaggagact caggaagcag aggcgtccct    7080
gccgctgccc ttggccctgc aagcacatca tgaccctttc tggcagcctc ttggtgctct    7140
gggtagtgag ggatgaccag tcttgtcctg agaaatgttt ctcttagtct ttaagttcaa    7200
agactaacct gtagcaatca gactttccaa aaggggttc tccattttt gtagttttgt     7260 ctaaattttt aatgaccatt tcctggaatc agtttattat actgaaaact gggggtggga    7320
gtagggagct agtttgttga taaatagttc ccatttcccc gtgagaatt tgacataccc     7380 tggactcctg tgtgcctcct gccatccctg cacacagcct ggggagaagc ctgtgcctcc    7440
ccgtgtggag agaaggcaac cccagatccc ctgagctaac ccggaggaaa ggcagtcctg    7500
gacagaagac tgtcagcaga aggaaagtac tggactaccc gtgggtaagt cctgccattc    7560
aagactggag acacctggga aataaaaaga gcagggcact gctggtggga agaggcattt    7620
```

```
tacctttccag tgcaaatcct gctcctttga tttaatgggg tgtactgggg ccagggctg    7680 attcacttcc ttgggagatg gtggtgtttt catgaacatc tttgatcctt ccatttcatt    7740
tattcatcca tccattcaac aagtatttgc taaacactaa cttaagctaa tgctagggta    7800
gtgactgaga tgtaaaaata gattttagaa ttaaaacaaa atccaagtcc tcacacccct    7860
gtcatcccag gagatctttc cttgtggtgg tttctgtgag aattggccat cctgaggaca    7920
cagccaggac ggcagaggcc tcctggcctc agggcatgcc ctgcctacct tctgaaatgt    7980
ttaccccatt gaccaaactt ggctccagcc attgcggtgg tttctagata gccaggccca    8040
ccaagagata ttgccccttg atgagagtca acaccctgc ctacaaggag atgttttgaa     8100
atggagagga aaattggcac ctcatctttt aaaggcagta atggaattga ttttcagtaa    8160
ctgaatttgt gcacaaaaca ttctaaacac tagtgaagcc tgtttcgttg aactaattct    8220
ggctctggaa atgtttttgt tttatagtta tttacgattt cgtttgtttg gattcaagct    8280
tagtttgtta atatgtataa tttagcatct attacactca tgtaaatatg gagtaagtat    8340
tgtaaactat ttcattgcgg ggattgtggg tgttatacat acatttagga ctgcaatttt    8400
ttggtatttt ttgtattgta aaataacagc taatttaagc aggaacaaga gaactaaggg    8460
aggtctgtgc atttttaaaca caaatgtgaa gaacttgtat ataaacaaaa gtaaatacta    8520
taatacaaac ttccttctga aataaaagta gatctggtaa aaaaaaaaaa agaaaaaaaa    8580
aaaaaaaaa                                                            8589

<210> SEQ ID NO 15
<211> LENGTH: 2787
<212> TYPE: PRT
<213> ORGANISM: Homo sapiens

<400> SEQUENCE: 15

Met Val Ala Val Ala Ala Ala Ala Thr Glu Ala Arg Leu Arg Arg
 1               5                  10                  15

Arg Thr Ala Ala Thr Ala Ala Leu Ala Gly Arg Ser Gly Pro His
                20                  25                  30

Arg Pro Cys Thr Ala Thr Gly Ala Trp Arg Pro Gly Pro Arg Ala Arg
             35                  40                  45

Leu Cys Leu Pro Arg Val Leu Ser Arg Ala Leu Pro Pro Pro Leu
 50                  55                  60

Leu Pro Leu Leu Phe Ser Leu Leu Leu Pro Leu Pro Arg Glu Ala
 65                  70                  75                  80

Glu Ala Ala Ala Val Ala Ala Val Ser Gly Ser Ala Ala Glu
                 85                  90                  95

Ala Lys Glu Cys Asp Arg Pro Cys Val Asn Gly Gly Arg Cys Asn Pro
            100                 105                 110

Gly Thr Gly Gln Cys Val Cys Pro Ala Gly Trp Val Gly Glu Gln Cys
        115                 120                 125

Gln His Cys Gly Gly Arg Phe Arg Leu Thr Gly Ser Ser Gly Phe Val
    130                 135                 140

Thr Asp Gly Pro Gly Asn Tyr Lys Tyr Lys Thr Lys Cys Thr Trp Leu
145                 150                 155                 160

Ile Glu Gly Gln Pro Asn Arg Ile Met Arg Leu Arg Phe Asn His Phe
                165                 170                 175

Ala Thr Glu Cys Ser Trp Asp His Leu Tyr Val Tyr Asp Gly Asp Ser
            180                 185                 190
```

```
Ile Tyr Ala Pro Leu Val Ala Ala Phe Ser Gly Leu Ile Val Pro Glu
            195                 200                 205

Arg Asp Gly Asn Glu Thr Val Pro Glu Val Val Ala Thr Ser Gly Tyr
    210                 215                 220

Ala Leu Leu His Phe Phe Ser Asp Ala Ala Tyr Asn Leu Thr Gly Phe
225                 230                 235                 240

Asn Ile Thr Tyr Ser Phe Asp Met Cys Pro Asn Asn Cys Ser Gly Arg
                245                 250                 255

Gly Glu Cys Lys Ile Ser Asn Ser Ser Asp Thr Val Glu Cys Glu Cys
            260                 265                 270

Ser Glu Asn Trp Lys Gly Glu Ala Cys Asp Ile Pro His Cys Thr Asp
    275                 280                 285

Asn Cys Gly Phe Pro His Arg Gly Ile Cys Asn Ser Ser Asp Val Arg
290                 295                 300

Gly Cys Ser Cys Phe Ser Asp Trp Gln Gly Pro Gly Cys Ser Val Pro
305                 310                 315                 320

Val Pro Ala Asn Gln Ser Phe Trp Thr Arg Glu Glu Tyr Ser Asn Leu
                325                 330                 335

Lys Leu Pro Arg Ala Ser His Lys Ala Val Val Asn Gly Asn Ile Met
            340                 345                 350

Trp Val Val Gly Gly Tyr Met Phe Asn His Ser Asp Tyr Asn Met Val
    355                 360                 365

Leu Ala Tyr Asp Leu Ala Ser Arg Glu Trp Leu Pro Leu Asn Arg Ser
370                 375                 380

Val Asn Asn Val Val Val Arg Tyr Gly His Ser Leu Ala Leu Tyr Lys
385                 390                 395                 400

Asp Lys Ile Tyr Met Tyr Gly Gly Lys Ile Asp Ser Thr Gly Asn Val
                405                 410                 415

Thr Asn Glu Leu Arg Val Phe His Ile His Asn Glu Ser Trp Val Leu
            420                 425                 430

Leu Thr Pro Lys Ala Lys Glu Gln Tyr Ala Val Val Gly His Ser Ala
    435                 440                 445

His Ile Val Thr Leu Lys Asn Gly Arg Val Val Met Leu Val Ile Phe
450                 455                 460

Gly His Cys Pro Leu Tyr Gly Tyr Ile Ser Asn Val Gln Glu Tyr Asp
465                 470                 475                 480

Leu Asp Lys Asn Thr Trp Ser Ile Leu His Thr Gln Gly Ala Leu Val
                485                 490                 495

Gln Gly Gly Tyr Gly His Ser Ser Val Tyr Asp His Arg Thr Arg Ala
            500                 505                 510

Leu Tyr Val His Gly Gly Tyr Lys Ala Phe Ser Ala Asn Lys Tyr Arg
    515                 520                 525

Leu Ala Asp Asp Leu Tyr Arg Tyr Asp Val Asp Thr Gln Met Trp Thr
530                 535                 540

Ile Leu Lys Asp Ser Arg Phe Phe Arg Tyr Leu His Thr Ala Val Ile
545                 550                 555                 560

Val Ser Gly Thr Met Leu Val Phe Gly Gly Asn Thr His Asn Asp Thr
                565                 570                 575

Ser Met Ser His Gly Ala Lys Cys Phe Ser Ser Asp Phe Met Ala Tyr
            580                 585                 590

Asp Ile Ala Cys Asp Arg Trp Ser Val Leu Pro Arg Pro Asp Leu His
    595                 600                 605
```

-continued

```
His Asp Val Asn Arg Phe Gly His Ser Ala Val Leu His Asn Ser Thr
    610                 615                 620
Met Tyr Val Phe Gly Gly Phe Asn Ser Leu Leu Leu Ser Asp Ile Leu
625                 630                 635                 640
Val Phe Thr Ser Glu Gln Cys Asp Ala His Arg Ser Glu Ala Ala Cys
                645                 650                 655
Leu Ala Ala Gly Pro Gly Ile Arg Cys Val Trp Asn Thr Gly Ser Ser
            660                 665                 670
Gln Cys Ile Ser Trp Ala Leu Ala Thr Asp Glu Gln Glu Glu Lys Leu
        675                 680                 685
Lys Ser Glu Cys Phe Ser Lys Arg Thr Leu Asp His Asp Arg Cys Asp
    690                 695                 700
Gln His Thr Asp Cys Tyr Ser Cys Thr Ala Asn Thr Asn Asp Cys His
705                 710                 715                 720
Trp Cys Asn Asp His Cys Val Pro Arg Asn His Ser Cys Ser Glu Gly
                725                 730                 735
Gln Ile Ser Ile Phe Arg Tyr Glu Asn Cys Pro Lys Asp Asn Pro Met
            740                 745                 750
Tyr Tyr Cys Asn Lys Lys Thr Ser Cys Arg Ser Cys Ala Leu Asp Gln
        755                 760                 765
Asn Cys Gln Trp Glu Pro Arg Asn Gln Glu Cys Ile Ala Leu Pro Glu
    770                 775                 780
Asn Ile Cys Gly Ile Gly Trp His Leu Val Gly Asn Ser Cys Leu Lys
785                 790                 795                 800
Ile Thr Thr Ala Lys Glu Asn Tyr Asp Asn Ala Lys Leu Phe Cys Arg
                805                 810                 815
Asn His Asn Ala Leu Leu Ala Ser Leu Thr Thr Gln Lys Lys Val Glu
            820                 825                 830
Phe Val Leu Lys Gln Leu Arg Ile Met Gln Ser Ser Gln Ser Met Ser
        835                 840                 845
Lys Leu Thr Leu Thr Pro Trp Val Gly Leu Arg Lys Ile Asn Val Ser
    850                 855                 860
Tyr Trp Cys Trp Glu Asp Met Ser Pro Phe Thr Asn Ser Leu Leu Gln
865                 870                 875                 880
Trp Met Pro Ser Glu Pro Ser Asp Ala Gly Phe Cys Gly Ile Leu Ser
                885                 890                 895
Glu Pro Ser Thr Arg Gly Leu Lys Ala Ala Thr Cys Ile Asn Pro Leu
            900                 905                 910
Asn Gly Ser Val Cys Glu Arg Pro Ala Asn His Ser Ala Lys Gln Cys
        915                 920                 925
Arg Thr Pro Cys Ala Leu Arg Thr Ala Cys Gly Asp Cys Thr Ser Gly
    930                 935                 940
Ser Ser Glu Cys Met Trp Cys Ser Asn Met Lys Gln Cys Val Asp Ser
945                 950                 955                 960
Asn Ala Tyr Val Ala Ser Phe Pro Phe Gly Gln Cys Met Glu Trp Tyr
                965                 970                 975
Thr Met Ser Thr Cys Pro Pro Glu Asn Cys Ser Gly Tyr Cys Thr Cys
            980                 985                 990
Ser His Cys Leu Glu Gln Pro Gly Cys Gly Trp Cys Thr Asp Pro Ser
        995                 1000                1005
Asn Thr Gly Lys Gly Lys Cys Ile Glu Gly Ser Tyr Lys Gly Pro Val
    1010                1015                1020
```

```
Lys Met Pro Ser Gln Ala Pro Thr Gly Asn Phe Tyr Pro Gln Pro Leu
1025                1030                1035                1040

Leu Asn Ser Ser Met Cys Leu Glu Asp Ser Arg Tyr Asn Trp Ser Phe
            1045                1050                1055

Ile His Cys Pro Ala Cys Gln Cys Asn Gly His Ser Lys Cys Ile Asn
        1060                1065                1070

Gln Ser Ile Cys Glu Lys Cys Gly Asn Leu Thr Thr Gly Lys His Cys
    1075                1080                1085

Glu Thr Cys Ile Ser Gly Phe Tyr Gly Asp Pro Thr Asn Gly Gly Lys
1090                1095                1100

Cys Gln Pro Cys Lys Cys Asn Gly His Ala Ser Leu Cys Asn Thr Asn
1105                1110                1115                1120

Thr Gly Lys Cys Phe Cys Thr Thr Lys Gly Val Lys Gly Asp Glu Cys
            1125                1130                1135

Gln Leu Cys Glu Val Glu Asn Arg Tyr Gln Gly Asn Pro Leu Arg Gly
        1140                1145                1150

Thr Cys Tyr Tyr Thr Leu Leu Ile Asp Tyr Gln Phe Thr Phe Ser Leu
    1155                1160                1165

Ser Gln Glu Asp Asp Arg Tyr Tyr Thr Ala Ile Asn Phe Val Ala Thr
1170                1175                1180

Pro Asp Glu Gln Asn Arg Asp Leu Asp Met Phe Ile Asn Ala Ser Lys
1185                1190                1195                1200

Asn Phe Asn Leu Asn Ile Thr Trp Ala Ala Ser Phe Ser Ala Gly Thr
            1205                1210                1215

Gln Ala Gly Glu Glu Met Pro Val Val Ser Lys Thr Asn Ile Lys Glu
        1220                1225                1230

Tyr Lys Asp Ser Phe Ser Asn Glu Lys Phe Asp Phe Arg Asn His Pro
    1235                1240                1245

Asn Ile Thr Phe Phe Val Tyr Val Ser Asn Phe Thr Trp Pro Ile Lys
1250                1255                1260

Ile Gln Ile Ala Phe Ser Gln His Ser Asn Phe Met Asp Leu Val Gln
1265                1270                1275                1280

Phe Phe Val Thr Phe Phe Ser Cys Phe Leu Ser Leu Leu Leu Val Ala
            1285                1290                1295

Ala Val Val Trp Lys Ile Lys Gln Ser Cys Trp Ala Ser Arg Arg Arg
        1300                1305                1310

Glu Gln Leu Leu Arg Glu Met Gln Gln Met Ala Ser Arg Pro Phe Ala
    1315                1320                1325

Ser Val Asn Val Ala Leu Glu Thr Asp Glu Glu Pro Pro Asp Leu Ile
    1330                1335                1340

Gly Gly Ser Ile Lys Thr Val Pro Lys Pro Ile Ala Leu Glu Pro Cys
1345                1350                1355                1360

Phe Gly Asn Lys Ala Ala Val Leu Ser Val Phe Val Arg Leu Pro Arg
            1365                1370                1375

Gly Leu Gly Gly Ile Pro Pro Gly Gln Ser Gly Leu Ala Val Ala
        1380                1385                1390

Ser Ala Leu Val Asp Ile Ser Gln Gln Met Pro Ile Val Tyr Lys Glu
    1395                1400                1405

Lys Ser Gly Ala Val Arg Asn Arg Lys Gln Gln Pro Pro Ala Gln Pro
    1410                1415                1420

Gly Thr Cys Ile Cys Trp Gly Gln Gly Leu Ser His Ala Arg Ala Ser
1425                1430                1435                1440
```

-continued

```
Glu Trp His Thr Arg Ala Ile Cys Arg Glu Gly Arg Gly Glu Met
                1445                1450                1455

Ala Val Arg Cys Gly Thr Glu Asp Trp Lys Pro Ser Lys His Leu Thr
            1460                1465                1470

His Leu His Asp His Lys Leu Ser Leu Thr Val Ser Pro Ile Arg Val
        1475                1480                1485

Pro Ala Ser Asn Leu Leu Leu His Arg Lys Tyr Leu Ile Leu Gln
    1490                1495                1500

Val Gln Gly Ala Asp Gly Cys Trp Arg Arg Pro Val Ser Gln Glu Asn
1505                1510                1515                1520

Glu His Ser Gly Ser Leu Trp Lys Thr Val Leu Gly Thr Val Ser Thr
            1525                1530                1535

Val Gln Lys Thr Lys Asp Gly Val Phe Thr Ser Arg His Ser Ser Ser
        1540                1545                1550

Val Val Leu Glu His Gly Leu Leu Lys Thr Ser Gln Met Asn Leu Val
    1555                1560                1565

Phe Ile Ser Leu Leu Ser Phe Leu Lys Asp Val Leu Phe Ile Leu Ala
    1570                1575                1580

Arg Phe Arg Gln Leu Ser Leu Phe Gln Gly Val Pro Phe Leu Val
1585                1590                1595                1600

Glu Asn Trp Ser Ile Ser Phe Asp His Ile Lys Leu Gly Lys Gly Gly
            1605                1610                1615

Tyr Phe Lys Cys Gln Gly Gln Gln Cys Tyr Phe Glu Cys Lys Leu Val
        1620                1625                1630

Val Val Phe Tyr Ser Asn Leu Ile Asn Leu Val Leu Ile His Leu Lys
    1635                1640                1645

Leu Ser Leu Pro Phe Ser Leu Pro Val Pro Leu Leu Leu His Leu Thr
    1650                1655                1660

Leu Pro Leu Ser His Ile His Thr Gln Thr His Thr His Asn Thr Lys
1665                1670                1675                1680

Cys Leu Asp Phe Lys Ile Gln Leu Glu Ser Ala Val Phe Thr Leu His
            1685                1690                1695

Ser Tyr Ile Leu Val Lys Phe Lys Pro Leu Ala Ile Cys Phe Phe
        1700                1705                1710

Ser Lys Ile Phe Ala Ala Arg Lys Glu Phe Ser His Pro Arg Asn Ile
    1715                1720                1725

Ser Ser Ser Arg Asp Glu Arg Lys Ala Glu Met Asn Glu Leu Lys Leu
    1730                1735                1740

Leu Phe Leu Leu Ser Lys Arg Thr Leu Ser Arg Arg Pro Leu Pro
1745                1750                1755                1760

Pro Pro Pro Cys His Pro Arg Pro Asp Lys Arg Ser Glu Arg Thr
            1765                1770                1775

His Ser Cys His Ala Ser Leu Ser Arg Lys Glu His Glu His Leu Gly
        1780                1785                1790

Pro Leu Asp Gln Arg Ala Ser Val Cys Pro Ala Ala Ser Ser Glu Leu
    1795                1800                1805

Val Val His Ser Gln Ala Gly Val Asp Ser Asp Ala Arg Lys Gly Thr
    1810                1815                1820

Ala Ser His Cys Gln Ala Glu Ala Gln Ser Leu Glu Lys Asp Leu
1825                1830                1835                1840

Phe Ala Leu Phe Pro Pro Gly Gly Ala Arg Pro Thr His Pro Pro Ser
            1845                1850                1855
```

-continued

```
Gln Thr Lys Val Val Ala Val Arg Arg Ala Ala Asn Ala Asp Lys Asp
            1860                1865                1870
Glu Lys His Met Glu Lys Asn Gly Arg Gly Gly Lys Thr Leu Pro Asn
            1875                1880                1885
Gly Lys Pro Asn Leu Arg Gly Trp Asp Ser Pro Leu Leu Leu Ser Gln
            1890                1895                1900
Arg Ala Leu Leu Gly Asn Cys Val Phe Pro Ile Tyr Gly Ala Leu Tyr
1905                1910                1915                1920
Ser Gly Ile Met Gln Gln Pro Pro Arg Ser Ser Leu Leu Leu Gln Asn
            1925                1930                1935
Leu Gly Ser Leu Ala Leu Pro Tyr Trp Asp Gly Pro Leu Asp Ser Asn
            1940                1945                1950
Ala Arg Val Cys Glu Phe Gly Glu Ile Leu Lys Arg Ala Lys Thr Ala
            1955                1960                1965
Ala Phe Tyr Leu Met Gln Cys Leu Glu Arg Glu Tyr Cys Leu Phe Pro
            1970                1975                1980
Asn Thr Asn Pro Thr Pro Met Lys Asn Cys Leu Glu Arg Cys Phe Gln
1985                1990                1995                2000
Gly Ile Thr Ile Lys His Tyr Leu Met His Arg Thr Pro Leu Leu Asp
            2005                2010                2015
Ser Pro Leu Ile Lys Leu Leu Phe His Ile Thr Val Lys Asp Gln Thr
            2020                2025                2030
Phe Lys Arg Pro Leu Leu Ser Ala Pro Pro Ser Leu Leu Gln Asn Thr
            2035                2040                2045
Ala Pro Met Ala Pro Ala Val Asp Trp Pro Leu Asn Ser His Arg Pro
            2050                2055                2060
Pro Gln Gln Gly Gln Arg Glu Ala Pro Gly Tyr Cys Pro Pro Thr Arg
2065                2070                2075                2080
Lys Ile Leu Phe Val Cys Ser Lys Asp Gln Phe Ser Ala Lys Glu Val
            2085                2090                2095
Ser Ser Pro Cys Ser Tyr Ala Leu Lys Tyr His Ala Pro Pro Thr Ala
            2100                2105                2110
Ile Trp Leu Cys Leu Ile Phe Phe Leu Lys Asp Asn Val Tyr Phe Lys
            2115                2120                2125
Gly Arg Lys Lys Gln Val Lys Phe His Ser Ala Pro Ala Val Gly Lys
            2130                2135                2140
Pro Leu Asn Pro Pro Ala Ser Pro Leu Gln Pro Thr Ala Asn Ser Phe
2145                2150                2155                2160
Leu Arg Pro Gln Gly Arg Lys Arg Glu Trp Gln Gly Val Arg Gly Ala
            2165                2170                2175
Gly Leu Gly Ala Cys Phe Gln Glu Gly Ile Gly Cys His Leu Ala Val
            2180                2185                2190
Leu Arg Val Thr Arg Glu Pro Val Tyr Lys Leu Lys Ser Arg Gln His
            2195                2200                2205
Pro Cys Thr Cys Thr Leu Tyr Ser Ser Val Gln Asn Val Gln Thr Phe
            2210                2215                2220
Gly Val Tyr Ile Lys Gln Lys Lys Ser Ser Cys Ile Phe Ile Lys Tyr
2225                2230                2235                2240
Asn Asn Val Val Ser Pro Lys Met Phe Leu Cys His Met Leu Asp Ile
            2245                2250                2255
Gln Val Leu Ala Arg Pro Arg Tyr Met Asn Asn Lys Pro Lys Lys Arg
            2260                2265                2270
```

-continued

```
Ile Pro Ile Val Cys Val Gln Met His Leu Ala Pro Ile Arg Tyr Phe
        2275                2280                2285

Leu Lys Gln Asp Ser Ser Val Arg Val His Met Lys Asn Gln Ala Gly
    2290                2295                2300

Asn Arg Asn Asp Ser Ala Gly Gly Asp Ser Gly Ser Arg Gly Val Pro
2305                2310                2315                2320

Ala Ala Ala Leu Gly Pro Ala Ser Thr Ser Pro Phe Leu Ala Ala Ser
            2325                2330                2335

Trp Cys Ser Gly Gly Met Thr Ser Leu Val Leu Arg Asn Val Ser Leu
                2340                2345                2350

Ser Leu Val Gln Arg Leu Thr Cys Ser Asn Gln Thr Phe Gln Lys Gly
            2355                2360                2365

Val Leu His Phe Leu Phe Cys Leu Asn Phe Pro Phe Pro Gly Ile Ser
        2370                2375                2380

Leu Leu Tyr Lys Leu Gly Val Gly Val Gly Ser Phe Val Asp Lys Phe
2385                2390                2395                2400

Pro Phe Pro Arg Gly Glu Phe Asp Ile Pro Trp Thr Pro Val Cys Leu
                2405                2410                2415

Leu Pro Ser Leu His Thr Ala Trp Gly Glu Ala Cys Ala Ser Pro Cys
            2420                2425                2430

Gly Glu Lys Ala Thr Pro Asp Pro Leu Ser Pro Gly Lys Ala Val
        2435                2440                2445

Leu Asp Arg Arg Leu Ser Ala Glu Gly Lys Tyr Trp Thr Thr Arg Gly
2450                2455                2460

Val Leu Pro Phe Lys Thr Gly Asp Thr Trp Glu Ile Lys Arg Ala Gly
2465                2470                2475                2480

His Cys Trp Trp Glu Glu Ala Phe Tyr Leu Pro Val Gln Ile Leu Leu
                2485                2490                2495

Leu Phe Asn Gly Val Tyr Trp Gly Gln Gly Leu Ile His Phe Leu Gly
                2500                2505                2510

Arg Trp Trp Cys Phe His Glu His Leu Ser Phe His Phe Ile Tyr Ser
            2515                2520                2525

Ser Ile His Ser Thr Ser Ile Cys Thr Leu Thr Ala Asn Ala Arg Val
        2530                2535                2540

Val Thr Glu Met Lys Ile Leu Glu Leu Lys Gln Asn Pro Ser Pro His
2545                2550                2555                2560

Thr Pro Val Ile Pro Gly Asp Leu Ser Leu Trp Trp Phe Leu Glu Leu
                2565                2570                2575

Ala Ile Leu Arg Thr Gln Pro Gly Arg Gln Arg Pro Gly Leu Arg
            2580                2585                2590

Ala Cys Pro Ala Tyr Leu Leu Lys Cys Leu Pro His Pro Asn Leu Ala
        2595                2600                2605

Pro Ala Ile Ala Val Val Ser Arg Pro Gly Pro Arg Asp Ile Ala
    2610                2615                2620

Pro Glu Ser Asn Thr Leu Pro Thr Arg Arg Cys Phe Glu Met Glu Arg
2625                2630                2635                2640

Lys Ile Gly Thr Ser Ser Phe Lys Gly Ser Asn Gly Ile Asp Phe Gln
                2645                2650                2655

Leu Asn Leu Cys Thr Lys His Ser Lys His Ser Leu Phe Arg Thr Asn
            2660                2665                2670

Ser Gly Ser Gly Asn Val Phe Val Leu Leu Phe Thr Ile Ser Phe Val
        2675                2680                2685
```

```
Trp Ile Gln Ala Phe Val Asn Met Tyr Asn Leu Ala Ser Ile Thr Leu
    2690                2695                2700

Met Ile Trp Ser Lys Tyr Cys Lys Leu Phe His Cys Gly Asp Cys Gly
2705            2710                2715                2720

Cys Tyr Thr Tyr Ile Asp Cys Asn Phe Leu Val Phe Phe Val Leu Asn
                2725                2730                2735

Asn Ser Phe Lys Gln Glu Gln Glu Asn Gly Arg Ser Val His Phe Lys
            2740                2745                2750

His Lys Cys Glu Glu Leu Val Tyr Lys Gln Lys Ile Leu Tyr Lys Leu
        2755                2760                2765

Pro Ser Glu Ile Lys Val Asp Leu Val Lys Lys Lys Glu Lys Lys
    2770                2775                2780

Lys Lys Lys
2785

<210> SEQ ID NO 16
<211> LENGTH: 4072
<212> TYPE: DNA
<213> ORGANISM: Homo sapiens

<400> SEQUENCE: 16
```

| | | | | | |
|---|---|---|---|---|---|
| atggtggcgg | tggccgcagc | ggcggcaact | gaggcaaggc | tgaggaggag | gacggcggcg | 60 |
| acggcagcgc | tcgcgggcag | gagcggcggg | ccgcaccgac | cctgcaccgc | gacaggggcc | 120 |
| tggaggccgg | gaccgcgcgc | ccggctgtgt | ctcccgcggg | tgctgtcgcg | ggcgctgccc | 180 |
| ccgccgccgc | tgctgccgct | gctcttttcg | ctgctgctgc | tgccgctgcc | ccgggaggcc | 240 |
| gaggccgctg | cggtggcggc | ggcggtgtcc | ggctcggccg | cagccgaggc | caaggaatgt | 300 |
| gaccggccgt | gtgtcaacgg | cggtcgctgc | aaccctggca | ccggccagtg | cgtctgcccc | 360 |
| gccggctggg | tgggcgagca | atgccagcac | tgcgggggcc | gcttcagact | aactggatct | 420 |
| tctgggtttg | tgacagatgg | aacctggaaa | tataaataca | aaacgaagtg | cacgtggctc | 480 |
| attgaaggac | agccaaatag | aataatgaga | cttcgtttca | atcattttgc | tacagagtgt | 540 |
| agttgggacc | atttatatgt | ttatgatggg | gactcaattt | atgcaccgct | agttgctgca | 600 |
| tttagtggcc | tcattgttcc | tgagagagat | ggcaatgaga | ctgtccctga | ggttgttgcc | 660 |
| acatcaggtt | atgccttgct | gcattttttt | agtgatgctg | cttataattt | gactggattt | 720 |
| aatattactt | acagttttga | tatgtgtcca | ataactgct | caggccgagg | agagtgtaag | 780 |
| atcagtaata | gcagcgatac | tgttgaatgt | gaatgttctg | aaaactggaa | aggtgaagca | 840 |
| tgtgacattc | tcactgtac | agacaactgt | ggttttcctc | atcgaggcat | ctgcaattca | 900 |
| agtgatgtca | gaggatgctc | ctgcttctca | gactggcagg | gtcctggatg | ttcagttcct | 960 |
| gtaccagcta | accagtcatt | ttggactcga | gaggaatatt | ctaacttaaa | gctccccaga | 1020 |
| gcatctcata | aagctgtggt | caatggaaac | attatgtggg | ttgttggagg | atatatgttc | 1080 |
| aaccactcag | attataacat | ggttctagcg | tatgaccttg | cttctaggga | gtggcttcca | 1140 |
| ctaaaccgtt | ctgtgaacaa | tgtggttgtt | agatatggtc | attctttggc | attatacaag | 1200 |
| gataaaattt | acatgtatgg | aggaaaaatt | gattcaactg | ggaatgtgac | caatgagttg | 1260 |
| agagtttttc | acattcataa | tgagtcatgg | gtgttgttga | ccctaaggc | aaaggagcag | 1320 |
| tatgcagtgg | ttgggcactc | tgcacacatt | gttacactga | gaatggccg | agtggtcatg | 1380 |
| ctggtcatct | ttggtcactg | ccctctctat | ggatatataa | gcaatgtgca | ggaatatgat | 1440 |
| ttggataaga | acacatggag | tatattacac | acccagggtg | cccttgtgca | aggggttac | 1500 |

-continued

| | | | |
|---|---|---|---|
| ggccatagca gtgtttacga ccataggacc agggccctat acgttcatgg tggctacaag | 1560 |
| gctttcagtg ccaataagta ccggcttgca gatgatctct accgatatga tgtggatacc | 1620 |
| cagatgtgga ccattcttaa ggacagccga ttttccgtt acttgcacac agctgtgata | 1680 |
| gtgagtggaa ccatgctggt gtttggggga acacacaca atgacacatc tatgagccat | 1740 |
| ggcgccaaat gcttctcttc agatttcatg gcctatgaca ttgcctgtga ccgctggtca | 1800 |
| gtgcttccca gacctgatct ccaccatgat gtcaacagat ttggccattc agcagtctta | 1860 |
| cacaacagca ccatgtatgt gttcggtggt ttcaatagtc tcctcctcag cgacatcctg | 1920 |
| gtattcacct cggaacagtg tgatgcgcat cggagtgaag ccgcttgttt agcagcagga | 1980 |
| cctggtattc ggtgtgtgtg gaacacaggg tcgtctcagt gtatctcgtg ggcgctggca | 2040 |
| actgatgaac aagaagaaaa gttaaaatca gaatgttttt ccaaaagaac tcttgaccat | 2100 |
| gacagatgtg accagcacac agattgttac agctgcacag ccaacaccaa tgactgccac | 2160 |
| tggtgcaatg accattgtgt ccccaggaac cacagctgct cagaaggcca gatctccatt | 2220 |
| tttaggtatg agaattgccc aaggataac cctatgtact actgtaacaa gaagaccagc | 2280 |
| tgcaggagct gtgccctgga ccagaactgc cagtgggagc cccggaatca ggagtgcatt | 2340 |
| gccctgcccg aaaatatctg tggcattggc tggcatttgg ttggaaactc atgtttgaaa | 2400 |
| attactactg ccaaggagaa ttatgacaat gctaaattgt tctgtaggaa ccacaatgcc | 2460 |
| cttttggctt ctcttacaac ccagaagaag gtagaatttg tccttaagca gctgcgaata | 2520 |
| atgcagtcat ctcagagcat gtccaagctc accttaaccc catgggtcgg ccttcggaag | 2580 |
| atcaatgtgt cctactggtg ctgggaagat atgtccccat ttacaaatag tttactacag | 2640 |
| tggatgccgt ctgagcccag tgatgctgga ttctgtggaa tttatcaga acccagtact | 2700 |
| cggggactga aggctgcaac ctgcatcaac ccactcaatg gtagtgtctg tgaaaggcct | 2760 |
| gcaaaccaca gtgctaagca gtgccggaca ccatgtgcct gaggacagc atgtggagat | 2820 |
| tgcaccagcg gcagctctga gtgcatgtgg tgcagcaaca tgaagcagtg tgtggactcc | 2880 |
| aatgcctatg tggcctcctt cccttttggc cagtgtatgg aatggtatac gatgagcacc | 2940 |
| tgccccctg aaaattgttc aggctactgt acctgtagtc attgcttgga gcaaccaggc | 3000 |
| tgtggctggt gtactgatcc cagcaatact ggcaaaggga aatgcataga gggttcctat | 3060 |
| aaaggaccag tgaagatgcc ttcgcaagcc cctacaggaa atttctatcc acagcccctg | 3120 |
| ctcaattcca gcatgtgtct agaggacagc agatacaact ggtctttcat tcactgtcca | 3180 |
| gcttgccaat gcaacggcca cagtaaatgc atcaatcaga gcatctgtga aagtgtgag | 3240 |
| aacctgacca caggcaagca ctgcgagacc tgcatatctg gcttctacgg tgatcccacc | 3300 |
| aatggaggga atgtcagcc atgcaagtgc aatgggcacg cgtctctgtg caacaccaac | 3360 |
| acgggcaagt gcttctgcac caccaagggc gtcaaggggg acgagtgcca gctatgtgag | 3420 |
| gtagaaaatc gataccaagg aaaccctctc agaggaacat gttattatac tcttcttatt | 3480 |
| gactatcagt tcacctttag tctatcccag gaagatgatc gctattacac agctatcaat | 3540 |
| tttgtggcta ctcctgacga acaaaacagg gatttggaca tgttcatcaa tgcctccaag | 3600 |
| aatttcaacc tcaacatcac ctgggctgcc agtttctcag ctggaaccca ggctggagaa | 3660 |
| gagatgcctg ttgtttcaaa aaccaacatt aaggagtaca agatagttt ctctaatgag | 3720 |
| aagtttgatt tcgcaacca cccaaatatc actttctttg tttatgtcag taatttcacc | 3780 |
| tggcccatca aaattcaggt gcaaactgaa caatgaggac gcatggacac aggaagggga | 3840 |
| acatcacaca ccagggcctg ttgtggggtg ggggaagggg gaagggatag cattagggga | 3900 |

```
tatacctaat gttaaatgac gagttaatgg gtgcagcaca ccaacatggc atatgtatac    3960
atatgtaaca aacctgcatg ttgtgcacat gtaccctaaa acttaaagta taattaaaaa    4020
aaaaaaaaga aaaaaaaaaa aaaaaaaaaa aaaaaaaaaa aaaaaaaaaa aa            4072
```

<210> SEQ ID NO 17
<211> LENGTH: 1350
<212> TYPE: PRT
<213> ORGANISM: Homo sapiens

<400> SEQUENCE: 17

```
Met Val Ala Ala Ala Ala Thr Glu Ala Arg Leu Arg Arg Arg Thr
 1               5                  10                  15

Ala Ala Thr Ala Ala Leu Ala Gly Arg Ser Gly Gly Pro His Trp Asp
            20                  25                  30

Trp Asp Val Thr Arg Ala Gly Arg Pro Gly Leu Gly Ala Gly Leu Arg
        35                  40                  45

Leu Pro Arg Leu Leu Ser Pro Pro Leu Arg Pro Arg Leu Leu Leu Leu
    50                  55                  60

Leu Leu Leu Leu Pro Pro Pro Leu Leu Leu Leu Leu Pro Cys Glu
65                  70                  75                  80

Ala Glu Ala Ala Ala Ala Ala Ala Val Ser Gly Ser Ala Ala Ala
                85                  90                  95

Glu Ala Lys Glu Cys Asp Arg Pro Cys Val Asn Gly Arg Cys Asn
            100                 105                 110

Pro Gly Thr Gly Gln Cys Val Cys Pro Ala Gly Trp Val Gly Glu Gln
            115                 120                 125

Cys Gln His Cys Gly Gly Arg Phe Arg Leu Thr Gly Ser Ser Gly Phe
        130                 135                 140

Val Thr Asp Gly Pro Gly Asn Tyr Lys Tyr Lys Thr Lys Cys Thr Trp
145                 150                 155                 160

Leu Ile Glu Gly Gln Pro Asn Arg Ile Met Arg Leu Arg Phe Asn His
                165                 170                 175

Phe Ala Thr Glu Cys Ser Trp Asp His Leu Tyr Val Tyr Asp Gly Asp
            180                 185                 190

Ser Ile Tyr Ala Pro Leu Val Ala Ala Phe Ser Gly Leu Ile Val Pro
        195                 200                 205

Glu Arg Asp Gly Asn Glu Thr Val Pro Glu Val Val Ala Thr Ser Gly
    210                 215                 220

Tyr Ala Leu Leu His Phe Phe Ser Asp Ala Ala Tyr Asn Leu Thr Gly
225                 230                 235                 240

Phe Asn Ile Thr Tyr Ser Phe Asp Met Cys Pro Asn Asn Cys Ser Gly
                245                 250                 255

Arg Gly Glu Cys Lys Ile Ser Asn Ser Ser Thr Val Glu Cys Glu Cys
            260                 265                 270

Ser Glu Asn Trp Lys Gly Glu Ala Cys Asp Ile Pro His Cys Thr Asp
        275                 280                 285

Asn Cys Gly Phe Pro His Arg Gly Ile Cys Asn Ser Ser Asp Val Arg
    290                 295                 300

Gly Cys Ser Cys Phe Ser Asp Trp Gln Gly Pro Gly Cys Ser Val Pro
305                 310                 315                 320

Val Pro Ala Asn Gln Ser Phe Trp Thr Arg Glu Glu Tyr Ser Asn Leu
                325                 330                 335

Lys Leu Pro Arg Ala Ser His Lys Ala Val Val Asn Gly Asn Ile Met
            340                 345                 350
```

-continued

```
Trp Val Val Gly Gly Tyr Met Phe Asn His Ser Asp Tyr Asn Met Val
        355                 360                 365
Leu Ala Tyr Asp Leu Ala Ser Arg Glu Trp Leu Pro Leu Asn Arg Ser
        370                 375                 380
Val Asn Asn Val Val Val Arg Tyr Gly His Ser Leu Ala Leu Tyr Lys
385                 390                 395                 400
Asp Lys Ile Tyr Met Tyr Gly Gly Lys Ile Asp Thr Gly Asn Val Thr
                405                 410                 415
Asn Glu Leu Arg Val Phe His Ile His Asn Glu Ser Trp Val Leu Leu
            420                 425                 430
Thr Pro Lys Ala Lys Glu Gln Tyr Ala Val Val Gly His Ser Ala His
        435                 440                 445
Ile Val Thr Leu Lys Asn Gly Arg Val Val Met Leu Val Ile Phe Gly
        450                 455                 460
His Cys Pro Leu Tyr Gly Tyr Ile Ser Asn Val Gln Glu Tyr Asp Leu
465                 470                 475                 480
Asp Lys Asn Thr Trp Ser Ile Leu His Thr Gln Gly Ala Leu Val Gln
                485                 490                 495
Gly Gly Tyr Gly His Ser Ser Val Tyr Asp His Arg Thr Arg Ala Leu
            500                 505                 510
Tyr Val His Gly Gly Tyr Lys Ala Phe Ser Ala Asn Lys Tyr Arg Leu
        515                 520                 525
Ala Asp Asp Leu Tyr Arg Tyr Asp Val Asp Thr Gln Met Trp Thr Ile
        530                 535                 540
Leu Lys Asp Ser Arg Phe Phe Arg Tyr Leu His Thr Ala Val Ile Val
545                 550                 555                 560
Ser Gly Thr Met Leu Val Phe Gly Gly Asn Thr His Asn Asp Thr Ser
                565                 570                 575
Met Ser His Gly Ala Lys Cys Phe Ser Ser Asp Phe Met Ala Tyr Asp
            580                 585                 590
Ile Ala Cys Asp Arg Trp Ser Val Leu Pro Arg Pro Asp Leu His His
        595                 600                 605
Asp Val Asn Arg Phe Gly His Ser Ala Val Leu His Asn Ser Thr Met
        610                 615                 620
Tyr Val Phe Gly Gly Phe Asn Ser Leu Leu Leu Ser Asp Ile Leu Val
625                 630                 635                 640
Phe Thr Ser Glu Gln Cys Asp Ala His Arg Ser Glu Ala Ala Cys Leu
                645                 650                 655
Ala Ala Gly Pro Gly Ile Arg Cys Val Trp Asn Thr Gly Ser Ser Gln
            660                 665                 670
Cys Ile Ser Trp Ala Leu Ala Thr Asp Glu Gln Glu Lys Leu Lys
        675                 680                 685
Ser Glu Cys Phe Ser Lys Arg Thr Leu Asp His Asp Arg Cys Asp Gln
        690                 695                 700
His Thr Asp Cys Tyr Ser Cys Thr Ala Asn Thr Asn Asp Cys His Trp
705                 710                 715                 720
Cys Asn Asp His Cys Val Pro Arg Asn His Ser Cys Ser Glu Gly Gln
                725                 730                 735
Ile Ser Ile Phe Arg Tyr Glu Asn Cys Pro Lys Asp Asn Pro Met Tyr
            740                 745                 750
Tyr Cys Asn Lys Lys Thr Ser Cys Arg Ser Cys Ala Leu Asp Gln Asn
        755                 760                 765
```

-continued

```
Cys Gln Trp Glu Pro Arg Asn Gln Cys Ile Ala Leu Pro Glu Asn
    770                 775                 780

Ile Cys Gly Ile Gly Trp His Leu Val Gly Asn Ser Cys Leu Lys Ile
785                 790                 795                 800

Thr Thr Ala Lys Glu Asn Tyr Asp Asn Ala Lys Leu Phe Cys Arg Asn
                805                 810                 815

His Asn Ala Leu Leu Ala Ser Leu Thr Thr Gln Lys Lys Val Glu Phe
            820                 825                 830

Val Leu Lys Gln Leu Arg Ile Met Gln Ser Ser Gln Ser Met Ser Lys
            835                 840                 845

Leu Thr Leu Thr Pro Trp Val Gly Leu Arg Lys Ile Asn Val Ser Tyr
    850                 855                 860

Trp Cys Trp Glu Asp Met Ser Pro Phe Thr Asn Ser Leu Leu Gln Trp
865                 870                 875                 880

Met Pro Ser Glu Pro Ser Asp Ala Gly Phe Cys Gly Ile Leu Ser Glu
                885                 890                 895

Pro Ser Thr Arg Gly Leu Lys Ala Ala Thr Cys Ile Asn Pro Leu Asn
                900                 905                 910

Gly Ser Val Cys Glu Arg Pro Ala Asn His Ser Ala Lys Gln Cys Arg
            915                 920                 925

Thr Pro Cys Ala Leu Arg Thr Ala Cys Gly Asp Cys Thr Ser Gly Ser
    930                 935                 940

Ser Glu Cys Met Trp Cys Ser Asn Met Lys Gln Cys Val Asp Ser Asn
945                 950                 955                 960

Ala Tyr Val Ala Ser Phe Pro Phe Gly Gln Cys Met Glu Trp Tyr Thr
                965                 970                 975

Met Ser Thr Cys Pro Pro Glu Asn Cys Ser Gly Tyr Cys Thr Cys Ser
                980                 985                 990

His Cys Leu Glu Gln Pro Gly Cys Gly Trp Cys Thr Asp Pro Ser Asn
            995                 1000                1005

Thr Gly Lys Gly Lys Cys Ile Glu Gly Ser Tyr Lys Gly Pro Val Lys
    1010                1015                1020

Met Pro Ser Gln Ala Pro Thr Gly Asn Phe Tyr Pro Gln Pro Leu Leu
1025                1030                1035                1040

Asn Ser Ser Met Cys Leu Glu Asp Ser Arg Tyr Asn Trp Ser Phe Ile
                1045                1050                1055

His Cys Pro Ala Cys Gln Cys Asn Gly His Ser Lys Cys Ile Asn Gln
                1060                1065                1070

Ser Ile Cys Glu Lys Cys Glu Asn Leu Thr Thr Gly Lys His Cys Glu
            1075                1080                1085

Thr Cys Ile Ser Gly Phe Tyr Gly Asp Pro Thr Asn Gly Gly Lys Cys
    1090                1095                1100

Gln Pro Cys Lys Cys Asn Gly His Ala Ser Leu Cys Asn Thr Asn Thr
1105                1110                1115                1120

Gly Lys Cys Phe Cys Thr Thr Lys Gly Val Lys Gly Asp Glu Cys Gln
                1125                1130                1135

Leu Cys Glu Val Glu Asn Arg Tyr Gln Gly Asn Pro Leu Arg Gly Thr
            1140                1145                1150

Cys Tyr Tyr Thr Leu Leu Ile Asp Tyr Gln Phe Thr Phe Ser Leu Ser
        1155                1160                1165

Gln Glu Asp Asp Arg Tyr Tyr Thr Ala Ile Asn Phe Val Ala Thr Pro
    1170                1175                1180
```

Asp Glu Gln Asn Arg Asp Leu Asp Met Phe Ile Asn Ala Ser Lys Asn
1185                1190                1195                1200

Phe Asn Leu Asn Ile Thr Trp Ala Ala Ser Phe Ser Ala Gly Thr Gln
        1205                1210                1215

Ala Gly Glu Glu Met Pro Val Val Ser Lys Thr Asn Ile Lys Glu Tyr
        1220                1225                1230

Lys Asp Ser Phe Ser Asn Glu Lys Phe Asp Phe Arg Asn His Pro Asn
        1235                1240                1245

Ile Thr Phe Phe Val Tyr Val Ser Asn Phe Thr Trp Pro Ile Lys Ile
        1250                1255                1260

Gln Val Gln Thr Glu Gln Gly Arg Met Asp Thr Gly Arg Gly Thr Ser
1265                1270                1275                1280

His Thr Arg Ala Cys Cys Gly Val Gly Gly Arg Gly Arg Asp Ser Ile
        1285                1290                1295

Arg Gly Tyr Thr Cys Met Thr Ser Trp Val Gln His Thr Asn Met Ala
        1300                1305                1310

Tyr Val Tyr Ile Cys Asn Lys Pro Ala Cys Cys Ala His Val Pro Asn
        1315                1320                1325

Leu Lys Tyr Asn Lys Lys Lys Lys Lys Lys Lys Lys Lys Lys Lys Lys
        1330                1335                1340

Lys Lys Lys Lys Lys Lys
1345                1350

<210> SEQ ID NO 18
<211> LENGTH: 2625
<212> TYPE: DNA
<213> ORGANISM: Homo sapiens

<400> SEQUENCE: 18

| | | | | |
|---|---|---|---|---|
| atggtggcgg | tggccgcagc | ggcggcaact | gaggcaaggc | tgaggaggag | gacggcggcg | 60 |
| acggcagcgc | tcgcgggcag | gagcggcggg | ccgcaccgac | cctgcaccgc | gacaggggcc | 120 |
| tggaggccgg | gaccgcgcgc | ccggctgtgt | ctcccgcggg | tgctgtcgcg | ggcgctgccc | 180 |
| ccgccgccgc | tgctgccgct | gctcttttcg | ctgctgctgc | tgccgctgcc | ccgggaggcc | 240 |
| gaggccgctg | cggtggcggc | ggcggtgtcc | ggctcggccg | cagccgaggc | caaggaatgt | 300 |
| gaccggccgt | gtgtcaacgg | cggtcgctgc | aaccctggca | ccggccagtg | cgtctgcccc | 360 |
| gccggctggg | tgggcgagca | atgccagcac | tgcgggggcc | gcttcagact | aactggatct | 420 |
| tctgggtttg | tgacagatgg | aacctggaaat | tataaataca | aaacgaagtg | cacgtggctc | 480 |
| attgaaggac | agccaaatag | aataatgaga | cttcgtttca | atcattttgc | tacagagtgt | 540 |
| agttgggacc | atttatatgt | ttatgatggg | gactcaattt | atgcaccgct | agttgctgca | 600 |
| tttagtggcc | tcattgttcc | tgagagagat | ggcaatgaga | ctgtccctga | ggttgttgcc | 660 |
| acatcaggtt | atgccttgct | gcattttttt | agtgatgctg | cttataattt | gactggattt | 720 |
| aatattactt | acagttttga | tatgtgtcca | ataactgct | caggccgagg | agagtgtaag | 780 |
| atcagtaata | gcagcgatac | tgttgaatgt | gaatgttctg | aaaactggaa | aggtgaagca | 840 |
| tgtgacattc | tcactgtac | agacaactgt | ggttttcctc | atcgaggcat | ctgcaattca | 900 |
| agtgatgtca | gaggatgctc | ctgcttctca | gactggcagg | gtcctggatg | ttcagttcct | 960 |
| gtaccagcta | accagtcatt | ttggactcga | gaggaatatt | ctaacttaaa | gctccccaga | 1020 |
| gcatctcata | aagctgtggt | caatggaaac | attatgtggg | ttgttggagg | atatatgttc | 1080 |
| aaccactcag | attataacat | ggttctagcg | tatgaccttg | cttctaggga | gtggcttcca | 1140 |

-continued

```
ctaaaccgtt ctgtgaacaa tgtggttgtt agatatggtc attctttggc attatacaag    1200
gataaaattt acatgtatgg aggaaaaatt gattcaactg ggaatgtgac caatgagttg    1260 agagttttc acattcataa tgagtcatgg gtgttgttga ccctaaggc aaaggagcag      1320 tatgcagtgg ttgggcactc tgcacacatt gttacactga agaatggccg agtggtcatg    1380
ctggtcatct ttggtcactg ccctctctat ggatatataa gcaatgtgca ggaatatgat    1440
ttggataaga acacatggag tatattacac acccagggtg cccttgtgca agggggttac    1500
ggccatagca gtgtttacga ccataggacc agggccctat acgttcatgg tggctacaag    1560
gctttcagtg ccaataagta ccggcttgca gatgatctct accgatatga tgtggatacc    1620
cagatgtgga ccattcttaa ggacagccga tttttccgtt acttgcacac agctgtgata    1680
gtgagtggaa ccatgctggt gtttggggga aacacacaca atgacacatc tatgagccat    1740
ggcgccaaat gcttctcttc agatttcatg gcctatgaca ttgcctgtga ccgctggtca    1800
gtgcttccca gacctgatct ccaccatgat gtcaacagat ttggccattc agcagtctta    1860
cacaacagca ccatgtatgt gttcggtggt ttcaatagtc tcctcctcag cgacatcctg    1920
gtattcacct cggaacagtg tgatgcgcat cggagtgaag ccgcttgttt agcagcagga    1980
cctggtattc ggtgtgtgtg gaacacaggg tcgtctcagt gtatctcgtg ggcgctggca    2040
actgatgaac aagaagaaaa gttaaaatca gaatgttttt ccaaaagaac tcttgaccat    2100
gacagatgtg accagcacac agattgttac agctgcacag ccaacaccaa tgactgccac    2160
tggtgcaatg accattgtgt ccccaggaac acacagctgct cagaaggcca gatctccatt    2220
tttaggtatg agaattgccc caaggataac cctatgtact actgtaacaa gaagaccagc    2280
tgcaggagct gtgccctgga ccagaactgc agtgggagc cccggaatca ggagtgcatt    2340
gccctgcccg gtaggccttg cagggtcatc ttggtgtgtg tgggtccatt acttcagcct    2400
gcttccccca acactgtgca gcctaagttg aacctagcag aggggaagag ctaattctgt    2460
ccattcatcc cccacacgag tattatgggc tttttttgttt ttaactaaaa tacagttctt    2520
aagtatttgt tcctactgtc ctttgaaata aagtgaaaca tcctttgctg ctctgtaaaa    2580
aaaaaaaaaa aaaaaaaaaa aaaaaaaaaa aaaaaaaaaa aaaaa                    2625
```

<210> SEQ ID NO 19
<211> LENGTH: 871
<212> TYPE: PRT
<213> ORGANISM: Homo sapiens

<400> SEQUENCE: 19

```
Met Val Ala Ala Ala Ala Thr Glu Ala Arg Leu Arg Arg Thr
 1               5                  10                  15

Ala Ala Thr Ala Ala Leu Ala Gly Arg Ser Gly Gly Pro His Trp Asp
                20                  25                  30

Trp Asp Val Thr Arg Ala Gly Arg Pro Gly Leu Gly Ala Gly Leu Arg
            35                  40                  45

Leu Pro Arg Leu Leu Ser Pro Pro Leu Arg Pro Arg Leu Leu Leu Leu
        50                  55                  60

Leu Leu Leu Leu Pro Pro Pro Leu Leu Leu Leu Leu Pro Cys Glu
    65                  70                  75                  80

Ala Glu Ala Ala Ala Ala Ala Ala Val Ser Gly Ser Ala Ala Ala
                85                  90                  95

Glu Ala Lys Glu Cys Asp Arg Pro Cys Val Asn Gly Gly Arg Cys Asn
               100                 105                 110
```

-continued

```
Pro Gly Thr Gly Gln Cys Val Cys Pro Ala Gly Trp Val Gly Glu Gln
        115                 120                 125

Cys Gln His Cys Gly Gly Arg Phe Arg Leu Thr Gly Ser Ser Gly Phe
130                 135                 140

Val Thr Asp Gly Pro Gly Asn Tyr Lys Tyr Lys Thr Lys Cys Thr Trp
145                 150                 155                 160

Leu Ile Glu Gly Gln Pro Asn Arg Ile Met Arg Leu Arg Phe Asn His
                165                 170                 175

Phe Ala Thr Glu Cys Ser Trp Asp His Leu Tyr Val Tyr Asp Gly Asp
                180                 185                 190

Ser Ile Tyr Ala Pro Leu Val Ala Ala Phe Ser Gly Leu Ile Val Pro
                195                 200                 205

Glu Arg Asp Gly Asn Glu Thr Val Pro Glu Val Val Ala Thr Ser Gly
210                 215                 220

Tyr Ala Leu Leu His Phe Phe Ser Asp Ala Ala Tyr Asn Leu Thr Gly
225                 230                 235                 240

Phe Asn Ile Thr Tyr Ser Phe Asp Met Cys Pro Asn Asn Cys Ser Gly
                245                 250                 255

Arg Gly Glu Cys Lys Ile Ser Asn Ser Ser Thr Val Glu Cys Glu Cys
                260                 265                 270

Ser Glu Asn Trp Lys Gly Glu Ala Cys Asp Ile Pro His Cys Thr Asp
                275                 280                 285

Asn Cys Gly Phe Pro His Arg Gly Ile Cys Asn Ser Ser Asp Val Arg
290                 295                 300

Gly Cys Ser Cys Phe Ser Asp Trp Gln Gly Pro Gly Cys Ser Val Pro
305                 310                 315                 320

Val Pro Ala Asn Gln Ser Phe Trp Thr Arg Glu Glu Tyr Ser Asn Leu
                325                 330                 335

Lys Leu Pro Arg Ala Ser His Lys Ala Val Val Asn Gly Asn Ile Met
                340                 345                 350

Trp Val Val Gly Gly Tyr Met Phe Asn His Ser Asp Tyr Asn Met Val
                355                 360                 365

Leu Ala Tyr Asp Leu Ala Ser Arg Glu Trp Leu Pro Leu Asn Arg Ser
                370                 375                 380

Val Asn Asn Val Val Arg Tyr Gly His Ser Leu Ala Leu Tyr Lys
385                 390                 395                 400

Asp Lys Ile Tyr Met Tyr Gly Gly Lys Ile Asp Thr Gly Asn Val Thr
                405                 410                 415

Asn Glu Leu Arg Val Phe His Ile His Asn Glu Ser Trp Val Leu Leu
                420                 425                 430

Thr Pro Lys Ala Lys Glu Gln Tyr Ala Val Val Gly His Ser Ala His
                435                 440                 445

Ile Val Thr Leu Lys Asn Gly Arg Val Val Met Leu Val Ile Phe Gly
            450                 455                 460

His Cys Pro Leu Tyr Gly Tyr Ile Ser Asn Val Gln Glu Tyr Asp Leu
465                 470                 475                 480

Asp Lys Asn Thr Trp Ser Ile Leu His Thr Gln Gly Ala Leu Val Gln
                485                 490                 495

Gly Gly Tyr Gly His Ser Ser Val Tyr Asp His Arg Thr Arg Ala Leu
                500                 505                 510

Tyr Val His Gly Gly Tyr Lys Ala Phe Ser Ala Asn Lys Tyr Arg Leu
            515                 520                 525
```

-continued

Ala Asp Asp Leu Tyr Arg Tyr Asp Val Asp Thr Gln Met Trp Thr Ile
530                 535                 540

Leu Lys Asp Ser Arg Phe Phe Arg Tyr Leu His Thr Ala Val Ile Val
545                 550                 555                 560

Ser Gly Thr Met Leu Val Phe Gly Gly Asn Thr His Asn Asp Thr Ser
            565                 570                 575

Met Ser His Gly Ala Lys Cys Phe Ser Ser Asp Phe Met Ala Tyr Asp
            580                 585                 590

Ile Ala Cys Asp Arg Trp Ser Val Leu Pro Arg Pro Asp Leu His His
        595                 600                 605

Asp Val Asn Arg Phe Gly His Ser Ala Val Leu His Asn Ser Thr Met
        610                 615                 620

Tyr Val Phe Gly Gly Phe Asn Ser Leu Leu Leu Ser Asp Ile Leu Val
625                 630                 635                 640

Phe Thr Ser Glu Gln Cys Asp Ala His Arg Ser Glu Ala Ala Cys Leu
                645                 650                 655

Ala Ala Gly Pro Gly Ile Arg Cys Val Trp Asn Thr Gly Ser Ser Gln
            660                 665                 670

Cys Ile Ser Trp Ala Leu Ala Thr Asp Glu Gln Glu Lys Leu Lys
        675                 680                 685

Ser Glu Cys Phe Ser Lys Arg Thr Leu Asp His Asp Arg Cys Asp Gln
690                 695                 700

His Thr Asp Cys Tyr Ser Cys Thr Ala Asn Thr Asn Asp Cys His Trp
705                 710                 715                 720

Cys Asn Asp His Cys Val Pro Arg Asn His Ser Cys Ser Glu Gly Gln
                725                 730                 735

Ile Ser Ile Phe Arg Tyr Glu Asn Cys Pro Lys Asp Asn Pro Met Tyr
            740                 745                 750

Tyr Cys Asn Lys Lys Thr Ser Cys Arg Ser Cys Ala Leu Asp Gln Asn
        755                 760                 765

Cys Gln Trp Glu Pro Arg Asn Gln Glu Cys Ile Ala Leu Pro Gly Arg
        770                 775                 780

Pro Cys Arg Val Ile Leu Val Cys Val Gly Pro Leu Leu Gln Pro Ala
785                 790                 795                 800

Ser Pro Asn Thr Val Gln Pro Lys Leu Asn Leu Ala Glu Gly Lys Ser
                805                 810                 815

Phe Cys Pro Phe Ile Pro His Thr Ser Ile Met Gly Phe Phe Val Phe
            820                 825                 830

Asn Asn Thr Val Leu Lys Tyr Leu Phe Leu Leu Ser Phe Glu Ile Lys
            835                 840                 845

Asn Ile Leu Cys Cys Ser Val Lys Lys Lys Lys Lys Lys Lys Lys Lys
850                 855                 860

Lys Lys Lys Lys Lys Lys Lys
865                 870

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
tctcctagtt gtagtacatg ctgttg                                    26

<210> SEQ ID NO 21
<211> LENGTH: 28
<212> TYPE: DNA
<213> ORGANISM: Artificial Sequence
<220> FEATURE:
<223> OTHER INFORMATION: Primer

<400> SEQUENCE: 21
aggtcctgtc tcaagaaata gcaataac                              28

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
tttgaaggcc cctgaagtca gag                                   23

<210> SEQ ID NO 23
<211> LENGTH: 29
<212> TYPE: DNA
<213> ORGANISM: Artificial Sequence
<220> FEATURE:
<223> OTHER INFORMATION: Primer

<400> SEQUENCE: 23
ttgagtcccc atcataaaca tataaatgg                             29

<210> SEQ ID NO 24
<211> LENGTH: 29
<212> TYPE: DNA
<213> ORGANISM: Artificial Sequence
<220> FEATURE:
<223> OTHER INFORMATION: Primer

<400> SEQUENCE: 24
ttctaggcca aatagaataa tgagacttc                             29

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25
agaactaatt ccatgagatg agtgtg                                26

<210> SEQ ID NO 26
<211> LENGTH: 25
<212> TYPE: DNA
<213> ORGANISM: Artificial Sequence
<220> FEATURE:
<223> OTHER INFORMATION: Primer

<400> SEQUENCE: 26
tgaagttgct gtaatctggt ctgtg                                 25

<210> SEQ ID NO 27
<211> LENGTH: 22
<212> TYPE: DNA
<213> ORGANISM: Artificial Sequence
<220> FEATURE:
<223> OTHER INFORMATION: Primer -continued

<400> SEQUENCE: 27
aaggagcctg actagaagcc tc    22

<210> SEQ ID NO 28
<211> LENGTH: 27
<212> TYPE: DNA
<213> ORGANISM: Artificial Sequence
<220> FEATURE:
<223> OTHER INFORMATION: Primer

<400> SEQUENCE: 28
taaactccct acagttcact aactcag    27

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
agcgctgttg agtgtgaatg ttctg    25

<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
aaagccacag ttgtctgtac agtgag    26

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31
aggtctgcat tagttgcaat gttgc    25

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
tatacacccc cttatataca ctcag    25

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
agagcctctc ataaagctgt ggtc    24

<210> SEQ ID NO 34
<211> LENGTH: 25

```
<212> TYPE: DNA
<213> ORGANISM: Artificial Sequence
<220> FEATURE:
<223> OTHER INFORMATION: Primer

<400> SEQUENCE: 34
ttgaacatat atccgccaac aaccc                                        25

<210> SEQ ID NO 35
<211> LENGTH: 28
<212> TYPE: DNA
<213> ORGANISM: Artificial Sequence
<220> FEATURE:
<223> OTHER INFORMATION: Primer

<400> SEQUENCE: 35
cttggaatac tataaacttt caggctgc                                     28

<210> SEQ ID NO 36
<211> LENGTH: 29
<212> TYPE: DNA
<213> ORGANISM: Artificial Sequence
<220> FEATURE:
<223> OTHER INFORMATION: Primer

<400> SEQUENCE: 36
taaagcaaca ggaagagttg aacttcttg                                    29

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
tgcaccctgt gtgcacatgg                                              20

<210> SEQ ID NO 38
<211> LENGTH: 26
<212> TYPE: DNA
<213> ORGANISM: Artificial Sequence
<220> FEATURE:
<223> OTHER INFORMATION: Primer

<400> SEQUENCE: 38
ttacggtgtc ctaataataa gggcag                                       26

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
aatcatgggt attgttaact ccgaaagc                                     28

<210> SEQ ID NO 40
<211> LENGTH: 24
<212> TYPE: DNA
<213> ORGANISM: Artificial Sequence
<220> FEATURE:
<223> OTHER INFORMATION: Primer
```

-continued

<400> SEQUENCE: 40
tgtaacaatg tgtgccgagt gtcc                                          24

<210> SEQ ID NO 41
<211> LENGTH: 22
<212> TYPE: DNA
<213> ORGANISM: Artificial Sequence
<220> FEATURE:
<223> OTHER INFORMATION: Primer

<400> SEQUENCE: 41
tctctctcca gccctagagt tg                                            22

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
agaagaggag cctgcaacat tgac                                          24

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
tttgttggcg ctgaaagcct tg                                            22

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
tggccacagt agtgtttatg atgac                                         25

<210> SEQ ID NO 45
<211> LENGTH: 27
<212> TYPE: DNA
<213> ORGANISM: Artificial Sequence
<220> FEATURE:
<223> OTHER INFORMATION: Primer

<400> SEQUENCE: 45
ttaatcaatt gcctctgcag attctag                                       27

<210> SEQ ID NO 46
<211> LENGTH: 26
<212> TYPE: DNA
<213> ORGANISM: Artificial Sequence
<220> FEATURE:
<223> OTHER INFORMATION: Primer

<400> SEQUENCE: 46
tggcttacgt ataggggaa atcaag                                         26

<210> SEQ ID NO 47
<211> LENGTH: 24

```
<212> TYPE: DNA
<213> ORGANISM: Artificial Sequence
<220> FEATURE:
<223> OTHER INFORMATION: Primer

<400> SEQUENCE: 47
ttgtgtgtgt tccctccaaa cacc                                          24

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
ggaccattct taaggacagc cgat                                          24

<210> SEQ ID NO 49
<211> LENGTH: 26
<212> TYPE: DNA
<213> ORGANISM: Artificial Sequence
<220> FEATURE:
<223> OTHER INFORMATION: Primer

<400> SEQUENCE: 49
acatagtgat ctttccatca gcaaag                                        26

<210> SEQ ID NO 50
<211> LENGTH: 22
<212> TYPE: DNA
<213> ORGANISM: Artificial Sequence
<220> FEATURE:
<223> OTHER INFORMATION: Primer

<400> SEQUENCE: 50
tgaatgcaca gagaccctcc tg                                            22

<210> SEQ ID NO 51
<211> LENGTH: 26
<212> TYPE: DNA
<213> ORGANISM: Artificial Sequence
<220> FEATURE:
<223> OTHER INFORMATION: Primer

<400> SEQUENCE: 51
cctcttacca ttcagatact gttagg                                        26

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52
agcaacaact caaaccagcc ctac                                          24

<210> SEQ ID NO 53
<211> LENGTH: 23
<212> TYPE: DNA
<213> ORGANISM: Artificial Sequence
<220> FEATURE:
<223> OTHER INFORMATION: Primer
```

```
<400> SEQUENCE: 53
ttcttcagtt gccaactccc agg                                              23

<210> SEQ ID NO 54
<211> LENGTH: 21
<212> TYPE: DNA
<213> ORGANISM: Artificial Sequence
<220> FEATURE:
<223> OTHER INFORMATION: Primer

<400> SEQUENCE: 54
aagctgcttg tgtggcagca g                                                21

<210> SEQ ID NO 55
<211> LENGTH: 26
<212> TYPE: DNA
<213> ORGANISM: Artificial Sequence
<220> FEATURE:
<223> OTHER INFORMATION: Primer

<400> SEQUENCE: 55
agtaaggtga acaggaaagt acagag                                           26

<210> SEQ ID NO 56
<211> LENGTH: 24
<212> TYPE: DNA
<213> ORGANISM: Artificial Sequence
<220> FEATURE:
<223> OTHER INFORMATION: Primer

<400> SEQUENCE: 56
tacataagag aggctgccgc atag                                             24

<210> SEQ ID NO 57
<211> LENGTH: 23
<212> TYPE: DNA
<213> ORGANISM: Artificial Sequence
<220> FEATURE:
<223> OTHER INFORMATION: Primer

<400> SEQUENCE: 57
ccctacactc acactcatct agc                                              23

<210> SEQ ID NO 58
<211> LENGTH: 23
<212> TYPE: DNA
<213> ORGANISM: Artificial Sequence
<220> FEATURE:
<223> OTHER INFORMATION: Primer

<400> SEQUENCE: 58
ccctgtgttc cagatctcca ttg                                              23

<210> SEQ ID NO 59
<211> LENGTH: 24
<212> TYPE: DNA
<213> ORGANISM: Artificial Sequence
<220> FEATURE:
<223> OTHER INFORMATION: Primer

<400> SEQUENCE: 59
ttcctaggtc caccttgatc tgag                                             24

<210> SEQ ID NO 60
<211> LENGTH: 26
```

```
<212> TYPE: DNA
<213> ORGANISM: Artificial Sequence
<220> FEATURE:
<223> OTHER INFORMATION: Primer

<400> SEQUENCE: 60
agcacctgaa ttcaaatcag gatgag                                  26

<210> SEQ ID NO 61
<211> LENGTH: 29
<212> TYPE: DNA
<213> ORGANISM: Artificial Sequence
<220> FEATURE:
<223> OTHER INFORMATION: Primer

<400> SEQUENCE: 61
aaaccaaagt tctgaacaca ttaactcac                               29

<210> SEQ ID NO 62
<211> LENGTH: 25
<212> TYPE: DNA
<213> ORGANISM: Artificial Sequence
<220> FEATURE:
<223> OTHER INFORMATION: Primer

<400> SEQUENCE: 62
ctggttgcat tcatagctgt gtttc                                   25

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
acagaagcca gcatcactgg g                                       21

<210> SEQ ID NO 64
<211> LENGTH: 24
<212> TYPE: DNA
<213> ORGANISM: Artificial Sequence
<220> FEATURE:
<223> OTHER INFORMATION: Primer

<400> SEQUENCE: 64
ttactggtgc tgggaggata tgtc                                    24

<210> SEQ ID NO 65
<211> LENGTH: 26
<212> TYPE: DNA
<213> ORGANISM: Artificial Sequence
<220> FEATURE:
<223> OTHER INFORMATION: Primer

<400> SEQUENCE: 65
ataagtactt catcacctca gcgctc                                  26

<210> SEQ ID NO 66
<211> LENGTH: 24
<212> TYPE: DNA
<213> ORGANISM: Artificial Sequence
<220> FEATURE:
<223> OTHER INFORMATION: Primer
```

```
<400> SEQUENCE: 66
ttgatcttag ctgaccagtg tctc                                           24

<210> SEQ ID NO 67
<211> LENGTH: 25
<212> TYPE: DNA
<213> ORGANISM: Artificial Sequence
<220> FEATURE:
<223> OTHER INFORMATION: Primer

<400> SEQUENCE: 67
tctgcatgga cttgagcaga aagtc                                          25

<210> SEQ ID NO 68
<211> LENGTH: 30
<212> TYPE: DNA
<213> ORGANISM: Artificial Sequence
<220> FEATURE:
<223> OTHER INFORMATION: Primer

<400> SEQUENCE: 68
caaatcttgt gatagtgaat tacaagttgg                                     30

<210> SEQ ID NO 69
<211> LENGTH: 27
<212> TYPE: DNA
<213> ORGANISM: Artificial Sequence
<220> FEATURE:
<223> OTHER INFORMATION: Primer

<400> SEQUENCE: 69
tttatagctg ccctcaatac attttcc                                        27

<210> SEQ ID NO 70
<211> LENGTH: 22
<212> TYPE: DNA
<213> ORGANISM: Artificial Sequence
<220> FEATURE:
<223> OTHER INFORMATION: Primer

<400> SEQUENCE: 70
tgtacctgca gccattgctt gg                                             22

<210> SEQ ID NO 71
<211> LENGTH: 25
<212> TYPE: DNA
<213> ORGANISM: Artificial Sequence
<220> FEATURE:
<223> OTHER INFORMATION: Primer

<400> SEQUENCE: 71
ggatctgggc tctagtttat gtacg                                          25

<210> SEQ ID NO 72
<211> LENGTH: 24
<212> TYPE: DNA
<213> ORGANISM: Artificial Sequence
<220> FEATURE:
<223> OTHER INFORMATION: Primer

<400> SEQUENCE: 72
ttgaactata ggcacagaca gctg                                           24

<210> SEQ ID NO 73
<211> LENGTH: 23
```

<212> TYPE: DNA
<213> ORGANISM: Artificial Sequence
<220> FEATURE:
<223> OTHER INFORMATION: Primer

<400> SEQUENCE: 73
aacttgacct gtgtgactta cgc                                        23

<210> SEQ ID NO 74
<211> LENGTH: 26
<212> TYPE: DNA
<213> ORGANISM: Artificial Sequence
<220> FEATURE:
<223> OTHER INFORMATION: Primer

<400> SEQUENCE: 74
tcacagtcta tggtaatctg tcaagc                                     26

<210> SEQ ID NO 75
<211> LENGTH: 22
<212> TYPE: DNA
<213> ORGANISM: Artificial Sequence
<220> FEATURE:
<223> OTHER INFORMATION: Primer

<400> SEQUENCE: 75
aagggcaaca atgccctggc aa                                         22

<210> SEQ ID NO 76
<211> LENGTH: 26
<212> TYPE: DNA
<213> ORGANISM: Artificial Sequence
<220> FEATURE:
<223> OTHER INFORMATION: Primer

<400> SEQUENCE: 76
ttcctgcaaa tgggatagtc tctctg                                     26

<210> SEQ ID NO 77
<211> LENGTH: 26
<212> TYPE: DNA
<213> ORGANISM: Artificial Sequence
<220> FEATURE:
<223> OTHER INFORMATION: Primer

<400> SEQUENCE: 77
atcccccaag catttatcat tctcag                                     26

<210> SEQ ID NO 78
<211> LENGTH: 28
<212> TYPE: DNA
<213> ORGANISM: Artificial Sequence
<220> FEATURE:
<223> OTHER INFORMATION: Primer

<400> SEQUENCE: 78
tgtgtttcca gaaacctgct ttagtttg                                   28

<210> SEQ ID NO 79
<211> LENGTH: 26
<212> TYPE: DNA
<213> ORGANISM: Artificial Sequence
<220> FEATURE:
<223> OTHER INFORMATION: Primer

<400> SEQUENCE: 79
tagtactttt gtccaggatg accaag                                      26

<210> SEQ ID NO 80
<211> LENGTH: 30
<212> TYPE: DNA
<213> ORGANISM: Artificial Sequence
<220> FEATURE:
<223> OTHER INFORMATION: Primer

<400> SEQUENCE: 80
tgacaagaaa tgtcatgtct taacataagc                                  30

<210> SEQ ID NO 81
<211> LENGTH: 22
<212> TYPE: DNA
<213> ORGANISM: Artificial Sequence
<220> FEATURE:
<223> OTHER INFORMATION: Primer

<400> SEQUENCE: 81
ttcagagcct ccttccccaa ct                                          22

<210> SEQ ID NO 82
<211> LENGTH: 25
<212> TYPE: DNA
<213> ORGANISM: Artificial Sequence
<220> FEATURE:
<223> OTHER INFORMATION: Primer

<400> SEQUENCE: 82
tagtctgtag ctgaggccat tttgc                                       25

<210> SEQ ID NO 83
<211> LENGTH: 25
<212> TYPE: DNA
<213> ORGANISM: Artificial Sequence
<220> FEATURE:
<223> OTHER INFORMATION: Primer

<400> SEQUENCE: 83
aagcaagctg cagttaaggg actgt                                       25

<210> SEQ ID NO 84
<211> LENGTH: 23
<212> TYPE: DNA
<213> ORGANISM: Artificial Sequence
<220> FEATURE:
<223> OTHER INFORMATION: Primer

<400> SEQUENCE: 84
ttgggacctt gaggattgtt ccc                                         23

<210> SEQ ID NO 85
<211> LENGTH: 26
<212> TYPE: DNA
<213> ORGANISM: Artificial Sequence
<220> FEATURE:
<223> OTHER INFORMATION: Primer

<400> SEQUENCE: 85
cactcaacag gtaaaagtga tctgcc                                      26

<210> SEQ ID NO 86
<211> LENGTH: 27

```
<212> TYPE: DNA
<213> ORGANISM: Artificial Sequence
<220> FEATURE:
<223> OTHER INFORMATION: Primer

<400> SEQUENCE: 86
tgcatctgat cagtttgaat cagagag                                    27

<210> SEQ ID NO 87
<211> LENGTH: 26
<212> TYPE: DNA
<213> ORGANISM: Artificial Sequence
<220> FEATURE:
<223> OTHER INFORMATION: Primer

<400> SEQUENCE: 87
aaactgaggc ctgagttctg aaaagc                                     26

<210> SEQ ID NO 88
<211> LENGTH: 24
<212> TYPE: DNA
<213> ORGANISM: Artificial Sequence
<220> FEATURE:
<223> OTHER INFORMATION: Primer

<400> SEQUENCE: 88
caccaaagct ctgtaccact aagc                                       24

<210> SEQ ID NO 89
<211> LENGTH: 21
<212> TYPE: DNA
<213> ORGANISM: Artificial Sequence
<220> FEATURE:
<223> OTHER INFORMATION: Primer

<400> SEQUENCE: 89
tgactgtgca gtgatgcagg g                                          21

<210> SEQ ID NO 90
<211> LENGTH: 27
<212> TYPE: DNA
<213> ORGANISM: Artificial Sequence
<220> FEATURE:
<223> OTHER INFORMATION: Primer

<400> SEQUENCE: 90
ttgaccttga catttagaat agccctc                                    27

<210> SEQ ID NO 91
<211> LENGTH: 30
<212> TYPE: DNA
<213> ORGANISM: Artificial Sequence
<220> FEATURE:
<223> OTHER INFORMATION: Primer

<400> SEQUENCE: 91
gctgagaatt aataatggtc tttctctttg                                 30

<210> SEQ ID NO 92
<211> LENGTH: 22
<212> TYPE: DNA
<213> ORGANISM: Artificial Sequence
<220> FEATURE:
<223> OTHER INFORMATION: Primer
```

```
<400> SEQUENCE: 92
tacacagtga gaccctgtct cc                                              22

<210> SEQ ID NO 93
<211> LENGTH: 22
<212> TYPE: DNA
<213> ORGANISM: Artificial Sequence
<220> FEATURE:
<223> OTHER INFORMATION: Primer

<400> SEQUENCE: 93
tagctgaggt cccttgtgga ag                                              22

<210> SEQ ID NO 94
<211> LENGTH: 21
<212> TYPE: DNA
<213> ORGANISM: Artificial Sequence
<220> FEATURE:
<223> OTHER INFORMATION: Primer

<400> SEQUENCE: 94
agtgtcagag gaccatgctg g                                               21

<210> SEQ ID NO 95
<211> LENGTH: 23
<212> TYPE: DNA
<213> ORGANISM: Artificial Sequence
<220> FEATURE:
<223> OTHER INFORMATION: Primer

<400> SEQUENCE: 95
cttgaagcgt ccaactcatg tgc                                             23

<210> SEQ ID NO 96
<211> LENGTH: 26
<212> TYPE: DNA
<213> ORGANISM: Artificial Sequence
<220> FEATURE:
<223> OTHER INFORMATION: Primer

<400> SEQUENCE: 96
aactcataca tttgagcact gttgcc                                          26

<210> SEQ ID NO 97
<211> LENGTH: 23
<212> TYPE: DNA
<213> ORGANISM: Artificial Sequence
<220> FEATURE:
<223> OTHER INFORMATION: Primer

<400> SEQUENCE: 97
tgaggaggtg gggaatgcta atg                                             23

<210> SEQ ID NO 98
<211> LENGTH: 21
<212> TYPE: DNA
<213> ORGANISM: Artificial Sequence
<220> FEATURE:
<223> OTHER INFORMATION: Primer

<400> SEQUENCE: 98
acatagcaga gggctgctca c                                               21

<210> SEQ ID NO 99
<211> LENGTH: 21
```

```
<212> TYPE: DNA
<213> ORGANISM: Artificial Sequence
<220> FEATURE:
<223> OTHER INFORMATION: Primer

<400> SEQUENCE: 99
actgacctgt gggaacctgt g                                              21

<210> SEQ ID NO 100
<211> LENGTH: 26
<212> TYPE: DNA
<213> ORGANISM: Artificial Sequence
<220> FEATURE:
<223> OTHER INFORMATION: Primer

<400> SEQUENCE: 100
aatgctaggc atcatccctc ttctag                                         26

<210> SEQ ID NO 101
<211> LENGTH: 26
<212> TYPE: DNA
<213> ORGANISM: Artificial Sequence
<220> FEATURE:
<223> OTHER INFORMATION: Primer

<400> SEQUENCE: 101
aacatctaat agggactgag tgaccc                                         26

<210> SEQ ID NO 102
<211> LENGTH: 22
<212> TYPE: DNA
<213> ORGANISM: Artificial Sequence
<220> FEATURE:
<223> OTHER INFORMATION: Primer

<400> SEQUENCE: 102
ttctgtggtg ccttggcaag ag                                             22

<210> SEQ ID NO 103
<211> LENGTH: 25
<212> TYPE: DNA
<213> ORGANISM: Artificial Sequence
<220> FEATURE:
<223> OTHER INFORMATION: Primer

<400> SEQUENCE: 103
cacacataca cacacactaa gtgcc                                          25

<210> SEQ ID NO 104
<211> LENGTH: 32
<212> TYPE: DNA
<213> ORGANISM: Artificial Sequence
<220> FEATURE:
<223> OTHER INFORMATION: Primer

<400> SEQUENCE: 104
tggtagttac ttaaagttta caagaatgta gg                                  32

<210> SEQ ID NO 105
<211> LENGTH: 28
<212> TYPE: DNA
<213> ORGANISM: Artificial Sequence
<220> FEATURE:
<223> OTHER INFORMATION: Primer
```

-continued

<400> SEQUENCE: 105
aaatgctggg ataaaaagca tgaaccac                                    28

<210> SEQ ID NO 106
<211> LENGTH: 25
<212> TYPE: DNA
<213> ORGANISM: Artificial Sequence
<220> FEATURE:
<223> OTHER INFORMATION: Primer

<400> SEQUENCE: 106
ttcagttacc taatgggcac aaggc                                       25

<210> SEQ ID NO 107
<211> LENGTH: 23
<212> TYPE: DNA
<213> ORGANISM: Artificial Sequence
<220> FEATURE:
<223> OTHER INFORMATION: Primer

<400> SEQUENCE: 107
acgacactga cctcttgcac ttg                                         23

<210> SEQ ID NO 108
<211> LENGTH: 26
<212> TYPE: DNA
<213> ORGANISM: Artificial Sequence
<220> FEATURE:
<223> OTHER INFORMATION: Primer

<400> SEQUENCE: 108
tgtacaccct gaatgtctga acattc                                      26

<210> SEQ ID NO 109
<211> LENGTH: 25
<212> TYPE: DNA
<213> ORGANISM: Artificial Sequence
<220> FEATURE:
<223> OTHER INFORMATION: Primer

<400> SEQUENCE: 109
gcgttcattt ctgctcctgt aatgg                                       25

<210> SEQ ID NO 110
<211> LENGTH: 24
<212> TYPE: DNA
<213> ORGANISM: Artificial Sequence
<220> FEATURE:
<223> OTHER INFORMATION: Primer

<400> SEQUENCE: 110
tgagctctta atccctgcca ttcc                                        24

<210> SEQ ID NO 111
<211> LENGTH: 22
<212> TYPE: DNA
<213> ORGANISM: Artificial Sequence
<220> FEATURE:
<223> OTHER INFORMATION: Primer

<400> SEQUENCE: 111
tagggcttgt ccgtccataa gg                                          22

<210> SEQ ID NO 112
<211> LENGTH: 25

<212> TYPE: DNA
<213> ORGANISM: Artificial Sequence
<220> FEATURE:
<223> OTHER INFORMATION: Primer

<400> SEQUENCE: 112
tgttacggag atgaaaggct agacc                                              25

<210> SEQ ID NO 113
<211> LENGTH: 22
<212> TYPE: DNA
<213> ORGANISM: Artificial Sequence
<220> FEATURE:
<223> OTHER INFORMATION: Primer

<400> SEQUENCE: 113
taagccctgc actaacccac tc                                                 22

<210> SEQ ID NO 114
<211> LENGTH: 25
<212> TYPE: DNA
<213> ORGANISM: Artificial Sequence
<220> FEATURE:
<223> OTHER INFORMATION: Primer

<400> SEQUENCE: 114
tgttttgaga ggtgagcctt ctagc                                              25

<210> SEQ ID NO 115
<211> LENGTH: 25
<212> TYPE: DNA
<213> ORGANISM: Artificial Sequence
<220> FEATURE:
<223> OTHER INFORMATION: Primer

<400> SEQUENCE: 115
catgtcctac agttctgcta tcacc                                              25

<210> SEQ ID NO 116
<211> LENGTH: 26
<212> TYPE: DNA
<213> ORGANISM: Artificial Sequence
<220> FEATURE:
<223> OTHER INFORMATION: Primer

<400> SEQUENCE: 116
cttttcttca tccaattccc cacgag                                             26

<210> SEQ ID NO 117
<211> LENGTH: 24
<212> TYPE: DNA
<213> ORGANISM: Artificial Sequence
<220> FEATURE:
<223> OTHER INFORMATION: Primer

<400> SEQUENCE: 117
tctctaagct gcactgttgt ggct                                               24

<210> SEQ ID NO 118
<211> LENGTH: 24
<212> TYPE: DNA
<213> ORGANISM: Artificial Sequence
<220> FEATURE:
<223> OTHER INFORMATION: Primer -continued

<400> SEQUENCE: 118
tggaagccaa gagtcttgag ttgc    24

<210> SEQ ID NO 119
<211> LENGTH: 28
<212> TYPE: DNA
<213> ORGANISM: Artificial Sequence
<220> FEATURE:
<223> OTHER INFORMATION: Primer

<400> SEQUENCE: 119
gtctgcattt taaatgcaga gtgaagc    28

<210> SEQ ID NO 120
<211> LENGTH: 25
<212> TYPE: DNA
<213> ORGANISM: Artificial Sequence
<220> FEATURE:
<223> OTHER INFORMATION: Primer

<400> SEQUENCE: 120
cgaaacgcac gcacattttt accag    25

<210> SEQ ID NO 121
<211> LENGTH: 26
<212> TYPE: DNA
<213> ORGANISM: Artificial Sequence
<220> FEATURE:
<223> OTHER INFORMATION: Primer

<400> SEQUENCE: 121
gtgtgattta gcatctgtcg cacttg    26

<210> SEQ ID NO 122
<211> LENGTH: 26
<212> TYPE: DNA
<213> ORGANISM: Artificial Sequence
<220> FEATURE:
<223> OTHER INFORMATION: Primer

<400> SEQUENCE: 122
tgtatgtata acccaacaat cgctgc    26

<210> SEQ ID NO 123
<211> LENGTH: 26
<212> TYPE: DNA
<213> ORGANISM: Artificial Sequence
<220> FEATURE:
<223> OTHER INFORMATION: Primer

<400> SEQUENCE: 123
tccagagtac agggagaaac taaagg    26

<210> SEQ ID NO 124
<211> LENGTH: 94
<212> TYPE: PRT
<213> ORGANISM: Homo sapiens

<400> SEQUENCE: 124

Phe Arg Asn His Pro Asn Ile Thr Phe Phe Val Tyr Val Ser Asn Phe
 1               5                  10                  15

Thr Trp Pro Ile Lys Ile Gln Ile Ala Phe Ser Gln His Ser Asn Phe
            20                  25                  30

```
Met Asp Leu Val Gln Phe Phe Val Thr Phe Phe Ser Cys Phe Leu Ser
        35                  40                  45

Leu Leu Leu Val Ala Ala Val Val Trp Lys Ile Lys Gln Ser Cys Trp
50                  55                  60

Ala Ser Arg Arg Arg Glu Gln Leu Leu Arg Glu Met Gln Gln Met Ala
65                  70                  75                  80

Ser Arg Pro Phe Ala Ser Val Glu Thr Leu Pro Trp Asn Arg
                85                  90
```

<210> SEQ ID NO 125
<211> LENGTH: 113
<212> TYPE: PRT
<213> ORGANISM: Homo sapiens

<400> SEQUENCE: 125

```
Phe Arg Ser Asn Pro Asn Ile Thr Phe Tyr Val Tyr Val Ser Asn Phe
1               5                   10                  15

Ser Trp Pro Ile Lys Ile Gln Ile Ala Phe Ser Gln His Asn Thr Ile
                20                  25                  30

Met Asp Leu Val Gln Phe Val Thr Phe Phe Ser Cys Phe Leu Ser
        35                  40                  45

Leu Leu Leu Val Ala Ala Val Val Trp Lys Ile Lys Gln Thr Cys Trp
50                  55                  60

Ala Ser Arg Arg Arg Glu Gln Leu Leu Arg Glu Arg Gln Gln Met Ala
65                  70                  75                  80

Ser Arg Pro Phe Ala Ser Val Asp Val Ala Leu Glu Val Gly Ala Glu
                85                  90                  95

Gln Thr Glu Phe Leu Arg Gly Pro Leu Glu Gly Ala Pro Lys Pro Ile
            100                 105                 110

Ala
```

<210> SEQ ID NO 126
<211> LENGTH: 100
<212> TYPE: PRT
<213> ORGANISM: Homo sapiens

<400> SEQUENCE: 126

```
Phe Gly Pro Asp Ser Asn Thr Thr Phe Phe Val Arg Val Tyr Asn Phe
1               5                   10                  15

Asn Thr Pro Val Gln Ile Val Val Ser Phe Ala Gln Ser Pro Pro Ile
                20                  25                  30

Asn Trp Val Leu Phe Phe Val Ile Phe Ala Ala Cys Phe Ile Val Leu
        35                  40                  45

Leu Val Val Ala Gly Leu Leu Trp Met Ile Lys Val Arg Ile Glu Ala
50                  55                  60

Tyr Arg Arg Asn Gln Arg Arg Ile Asp Glu Ile Glu His Met Ala Ser
65                  70                  75                  80

Arg Pro Phe Ala Ser Thr Lys Met Glu Leu Ser Met Leu Ser Gln Phe
                85                  90                  95

Ser Ser Ala Gly
            100
```

<210> SEQ ID NO 127
<211> LENGTH: 118
<212> TYPE: PRT
<213> ORGANISM: Homo sapiens -continued

```
<400> SEQUENCE: 127

Leu Lys Ser Ser Arg Phe Tyr Leu Leu Leu Gly Val Gly Asp Pro
1               5                   10                  15

Ser Gly Pro Gly Ala Asn Gly Ser Ala Asp Ser Gln Gly Leu Leu Phe
            20                  25                  30

Phe Arg Gln Asp Gln Ala His Ile Asp Leu Phe Val Phe Phe Ser Val
        35                  40                  45

Phe Phe Ser Cys Phe Phe Leu Phe Leu Ser Leu Cys Val Leu Leu Trp
    50                  55                  60

Lys Ala Lys Gln Ala Leu Asp Gln Arg Gln Glu Gln Arg Arg His Leu
65                  70                  75                  80

Gln Glu Met Thr Lys Met Ala Ser Arg Pro Phe Ala Lys Val Thr Val
                85                  90                  95

Cys Phe Pro Pro Asp Pro Thr Ala Pro Ala Ser Ala Trp Lys Pro Ala
            100                 105                 110

Gly Leu Pro Pro Pro Ala
            115

<210> SEQ ID NO 128
<211> LENGTH: 11
<212> TYPE: DNA
<213> ORGANISM: Artificial Sequence
<220> FEATURE:
<223> OTHER INFORMATION: Primer

<400> SEQUENCE: 128
ttcctcactg g                                                          11

<210> SEQ ID NO 129
<211> LENGTH: 10
<212> TYPE: DNA
<213> ORGANISM: Artificial Sequence
<220> FEATURE:
<223> OTHER INFORMATION: Primer

<400> SEQUENCE: 129
ggacacacag                                                            10
```

COMPOSITIONS AND METHODS FOR THE DIAGNOSIS AND TREATMENT OF BODY WEIGHT DISORDERS, INCLUDING OBESITY

This application is a divisional of U.S. application Ser. No. 09/245,041, filed Feb. 5, 1999, now U.S. Pat. No. 6,274,339 which claims benefit to Provisional Application No. 60/093,630, filed on Jul. 21, 1998 and of Provisional Application No. 60/104,978, filed Oct. 20, 1998, the contents of each of which are incorporated by reference in their entirety.

1. INTRODUCTION

The present invention relates to mammalian mahogany genes, including the human mahogany gene, which are novel genes involved in the control of mammalian body weight. The invention encompasses nucleotide sequences of the mahogany gene, host cell expression systems of the mahogany gene, and hosts which have been transformed by these expression systems, including transgenic animals. The invention also encompasses novel mahogany gene products, including mahogany proteins, polypeptides and peptides containing amino acid sequences mahogany proteins, fusion proteins of mahogany proteins polypeptides and peptides, and antibodies directed against such mahogany gene products.

The present invention also relates to methods and compositions for the diagnosis and treatment of mammalian body weight disorders, including obesity, cachexia, and anorexia, and for the identification of subjects susceptible to such disorders. Further, the invention relates to methods of using the mahogany gene and gene products of the invention for the identification of compounds which modulate the expression of the mahogany gene and/or the activity of the mahogany gene product. Such compounds can be useful as therapeutic agents in the treatment of mammalian body weight disorders, including obesity, cachexia, and anorexia.

2. BACKGROUND OF THE INVENTION

Obesity represents the most prevalent of body weight disorders, and it is the most important nutritional disorder in the western world, with estimates of its prevalence ranging from 30% to 50% within the middle-aged population. Other body weight disorders, such as anorexia nervosa and bulimia nervosa, which together affect approximately 0.2% of the female population of the western world, also pose serious health threats. Further, such disorders as anorexia and cachexia (wasting) are also prominent features of other diseases such as cancer, cystic fibrosis, and AIDS.

Obesity, defined as an excess of body fat relative to lean body mass, also contributes to other diseases. For example, this disorder is responsible for increased incidence of diseases such as coronary artery disease, hypertension, stroke, diabetes, hyperlipidemia, and some cancers (See, e.g., Nishina, P. M. et al., 1994, Metab. 43: 554–558; Grundy, S. M. & Barnett, J. P., 1990, Dis. Mon. 36: 641–731). Obesity is not merely a behavioral problem, i.e., the result of voluntary hyperphagia. Rather, the differential body composition observed between obese and normal subjects results from differences in both metabolism and neurologic/metabolic interactions. These differences seem to be, to some extent, due to differences in gene expression, and/or level of gene products or activity (Friedman, J. M. et al., 1991, Mammalian Gene 1: 130–144).

The epidemiology of obesity strongly shows that the disorder exhibits inherited characteristics (Stunkard, 1990, N. Eng. J. Med. 322: 1438). Moll et al. have reported that, in many populations, obesity seems to be controlled by a few genetic loci (Moll et al., 1991, Am. J. Hum. Gen. 49: 1243). In addition, human twin studies strongly suggest a substantial genetic basis in the control of body weight, with estimates of heritability of 80–90% (Simopoulos, A. P. & Childs, B., eds., 1989, in "Genetic Variation and Nutrition in Obesity", World Review of Nutrition and Diabetes 63, S. Karger, Basel, Switzerland; Borjeson, M., 1976, Acta. Paediatr. Scand. 65: 279–287).

In other studies, non-obese persons who deliberately attempted to gain weight by systematically over-eating were found to be more resistant to such weight gain and able to maintain an elevated weight only by very high caloric intake. In contrast, spontaneously obese individuals are able to maintain their status with normal or only moderately elevated caloric intake. In addition, it is a commonplace experience in animal husbandry that different strains of swine, cattle, etc., have different predispositions to obesity. Studies of the genetics of human obesity, and of animal models of obesity demonstrate that obesity results from complex defective regulation of both food intake, food induced energy expenditure, and of the balance between lipid and lean body anabolism.

There are a number of genetic diseases in man and other species which feature obesity among their more prominent symptoms, along with, frequently, dysmorphic features and mental retardation. For example, Prader-Willi syndrome (PWS; reviewed in Knoll, J. H. et al., 1993, Am. J. Med. Genet. 46: 2–6) affects approximately 1 in 20,000 live births, and involves poor neonatal muscle tone, facial and genital deformities, and generally obesity.

In addition to PWS, many other pleiotropic syndromes have been characterized which include obesity as a symptom. These syndromes are genetically straightforward, and appear to involve autosomal recessive alleles. Such diseases include, among others, Ahlstroem, Carpenter, Bardet-Biedl, Cohen, and Morgagni-Stewart-Monel Syndromes.

A number of models exists for the study of obesity (see, e.g., Bray, G. A., 1992, Prog. Brain Res. 93: 333–341; and Bray, G. A., 1989, Amer. J. Clin. Nutr. 5: 891–902). For example, animals having mutations which lead to syndromes that include obesity symptoms have also been identified. Attempts have been made to utilize such animals as models for the study of obesity, and the best studied animal models to date for genetic obesity are mice. For reviews, see, e.g., Friedman, J. M. et al., 1991, Mamm. Gen. 1: 130–144; Friedman, J. M. and Liebel, R. L., 1992, Cell 69: 217–220.

Studies utilizing mice have confirmed that obesity is a very complex trait with a high degree of heritability. Mutations at a number of loci have been identified which lead to obese phenotypes. These include the autosomal recessive mutations obese (ob), diabetes (db), fat (fat), and tubby (tub).

The dominant Yellow mutation (Ay) at the agouti locus causes a pleiotropic syndrome which causes moderate adult onset obesity, a yellow coat color, and a high incidence of tumor formation (Herberg, L. and Coleman, D. L., 1977, Metabolism 26:59), and an abnormal anatomic distribution of body fat (Coleman, D. L., 1978, Diabetologia 14:141–148). The mutation causes the widespread expression of a protein which is normally seen only in neonatal skin (Michaud, E. J. et al., 1994, Genes Devel. 8:1463–1472). The agouti protein has been reported to be a competitive antagonist of α-MSH binding to the melanocortin receptors MC1-R and MC4-R in vitro (Lu et al., 1996, Nature 371:799–802), and the authors speculated that de-regulated ubiquitous expression of agouti may lead to obesity by antagonism of melanocortin receptors expressed outside the hair follicles.

Mahogany (mg) and mahoganoid (md) are mutations that suppress the phenotypic effects of agouti protein in vivo (Lane and Green, 1960, J. Hered. 51: 228–230). The mahogany and mahoganoid mutation have been mapped to mouse chromosomes 2 and 16, respectively (Green, 1989, "Catalog of mutant genes and polymorphic loci", pp. 12–403 in *Genetic Variants and Strains of the Laboratory Mouse*, Lyon, M. F. and Searle, A. G., eds., Oxford University Press, Oxford). Mutations of both mg and md have been shown to suppress the effects of agouti on obesity as well as on coat color (Miller et al., 1997, Genetics 146: 1407–1415).

In summary, therefore, obesity, which poses a major, worldwide health problem, represents a complex, highly heritable trait. Given the severity, prevalence, and potential heterogeneity of such disorders, there exists a great need for the identification of those genes that participate in the control of body weight.

3. SUMMARY OF THE INVENTION

The present invention relates to the identification of novel nucleic acid molecules and proteins encoded by such nucleic acid molecules that are involved in the control of mammalian body weight, and which, further, are associated with mammalian body weight disorders such as obesity, cachexia, and anorexia. The nucleic acid molecules of the present invention represent the genes corresponding to the mammalian mahogany gene, including the human mahogany gene.

In particular, the compositions of the present invention include nucleic acid molecules which comprise the following sequences: (a) nucleotide sequences of the murine mahogany gene (SEQ ID NO.: 1) shown in FIG. 2A, as well as allelic variants and homologs thereof, as shown, e.g., in FIGS. 8A-C and 9A; (b) nucleotide sequences that encode the mahogany gene product amino acid sequence (SEQ ID NO.: 2) shown in FIG. 2B; (c) nucleotide sequences that encode portions of the mahogany gene product corresponding to its functional domains and individual exons; (d) nucleotide sequences comprising the novel mahogany gene sequences disclosed herein that encode mutants of the mahogany gene product in which all or a part of one or more of the domains is deleted or altered, as shown, e.g., in FIG. 6; (e) nucleotide sequences that encode fusion proteins comprising the mahogany gene product (SEQ ID NO.: 2), or one or more of its domains fused to a heterologous polypeptide; (f) nucleotide sequences within the mahogany gene, as well as chromosome sequences flanking the mahogany gene, see, e.g., FIG. 3, which can be utilized as part of the methods of the present invention for the diagnosis of mammalian body weight disorders, including obesity, cachexia, and anorexia, which are mediated by the mahogany gene, as well as for the identification of subjects susceptible to such disorders; (g) nucleic acid sequences that hybridize to the above described sequences under stringent or moderately stringent conditions, particularly human mg homologues, as shown, e.g., FIG. 10. The nucleic acid molecules of the invention include, but are not limited to, cDNA and genomic DNA sequences of the mahogany gene.

The present invention also encompasses expression products of the nucleic acid molecules listed above; i.e., proteins and/or polypeptides that are encoded by the above mahogany nucleic acid molecules.

Agonists and antagonists of the mahogany gene and/or gene product are also included in the present invention. Such agonists and antagonists will include, for example, small molecules, large molecules, and antibodies directed against the mahogany gene product. Agonists and antagonists of the invention also include nucleotide sequences, such as antisense and ribozyme molecules, and gene or regulatory sequence replacement constructs, that can be used to inhibit or enhance expression of the mahogany gene.

The present invention further encompasses cloning vectors, including expression vectors, that contain the nucleic acid molecules of the invention and can be used to express those nucleic acid molecules in host organisms. Further, host organisms which have been transformed with these nucleic acid molecules are also encompassed in the present invention. Host organisms of the invention include organisms transformed with the cloning vectors described above, e.g., transgenic animals, particularly non-human transgenic animals, and particularly transgenic non-human mammals.

The transgenic animals of the invention include animals that express a mutant variant or polymorphism of a mahogany gene, particularly a mutant variant or polymorphism of a mahogany gene that is associated with a weight disorder such as obesity, cachexia, or anorexia. The transgenic animals of the invention further include those that express a mahogany transgene at higher or lower levels than normal. The transgenic animals of the invention further include those which express the mahogany gene in all their cells, "mosaic" animals which express the mahogany gene in only some of their cells, and those in which the mahogany gene is selectively introduced into and expressed in a specific cell type(s). The transgenic animals of the invention also include "knock-out" animals. Knock-out animals comprise animals which have been engineered to no longer express the mahogany gene.

The present invention also relates to methods and compositions for the diagnosis of mammalian body weight disorders, including obesity, cachexia, and anorexia, as well as for the identification of subjects susceptible to such disorders. Such methods comprise, for example, measuring expression of the mahogany gene in a patient sample, or detecting a mutation in the mahogany gene in the genome of a mammal, including a human, suspected of exhibiting such a weight disorder. The nucleic acid molecules of the invention can also be used as diagnostic hybridization probes, or as primers for diagnostic PCR analysis to identify of mahogany gene mutations, allelic variations, or regulatory defects, such as defects in the expression of the mahogany gene. Such diagnostic PCR analyses can be used to diagnose individuals with a body weight disorder associated with a particular mahogany gene mutation, allelic variation, or regulatory defect. Such diagnostic PCR analyses can also be used to identify individuals susceptible to such body weight disorders and hyperphagia.

Methods and compositions, including pharmaceutical compositions, for the treatment of body weight disorders such as obesity, cachexia, and anorexia are also included in the invention. Such methods and compositions are capable of modulating the level of mahogany gene expression and/or the level of activity of the mahogany gene product. Such methods include, for example, modulating the expression of the mahogany gene and/or the activity of the mahogany gene product for the treatment of a body weight disorder which is mediated by some other gene, for example by the agouti gene.

The invention still further relates to methods for identifying compounds which modulate the expression of the mammalian mahogany gene and/or the synthesis or activity of mammalian mahogany gene products. Such compounds include therapeutic compounds which can be used as pharmaceutical compositions to reduce or eliminate the symptoms of mammalian body weight disorders such as obesity, cachexia, and anorexia. Cellular and non-cellular assays are described that can be used to identify compounds that interact with the mahogany gene and/or gene product, e.g., modulate the activity of the mahogany gene and/or bind to the mahogany gene product. Such cell-based assays of the invention utilize cells, cell lines, or engineered cells or cell lines that express the mahogany gene product.

In one embodiment, such methods comprise contacting a compound to a cell that expresses a mahogany gene, measuring the level of mahogany gene expression, gene product expression, or gene product activity, and comparing this level to the level of mahogany gene expression, gene product expression, or gene product activity produced by the cell in the absence of the compound, such that if the level obtained in the presence of the compound differs from that obtained in its absence, a compound that modulates the expression of the mammalian mahogany gene and/or the synthesis or activity of mammalian mahogany gene products has been identified.

In an alternative embodiment, such methods comprise administering a compound to a host, e.g., a transgenic animal that expresses a mahogany transgene or a mutant mahogany transgene, and measuring the level of mahogany gene expression, gene product expression, or gene product activity. The measured level is compared to the level of mahogany gene expression, gene product expression, or gene product activity in a host that is not exposed to the compound, such that if the level obtained when the host is exposed to the compound differs from that obtained when the host is not exposed to the compound, a compound that modulates the expression of the mammalian mahogany gene and/or the synthesis or activity of mammalian mahogany gene products, and/or the symptoms of a mammalian body weight disorder, such as obesity, cachexia, or anorexia, has been identified.

The Example presented in Section 6, below, describes the genetic and physical mapping of the mahogany gene to a specific 700 kb interval of mouse chromosome 2. The example presented in Section 7, below, describes the identification of a transcription unit within this chromosome interval, referred to herein as the MG gene, which represents the mahogany gene. The expression and sequence analysis of this candidate mahogany gene is described in the example presented in Section 8, below. These experiments prove that the candidate gene MG is indeed the mahogany gene.

DEFINITIONS

As used herein, the following terms shall have the abbreviations indicated.
BAC, bacterial artificial chromosomes
bp, base pair(s)
EST, expressed sequence tag
mg, mahogany gene
RFLP, restriction fragment length polymorphism
RT-PCR, reverse transcriptase PCR
SSCP, single-stranded conformational polymorphism
SSLP, simple sequence length polymorphisms
STS, short tag sequence
YAC, yeast artificial chromosome

4. BRIEF DESCRIPTION OF THE FIGURES

FIG. 1. Physical map of the mahogany interval of mouse chromosome 2.

FIG. 2. Panel A(1)–A(9): cDNA nucleotide sequence of the wild-type (C57BL/6J) murine mahogany gene (SEQ ID NO: 1), including the 5' and 3' untranslated regions, and Panel B: the derived amino acid sequence (SEQ ID NO: 2) of the mahogany gene product.

Figure 3A:
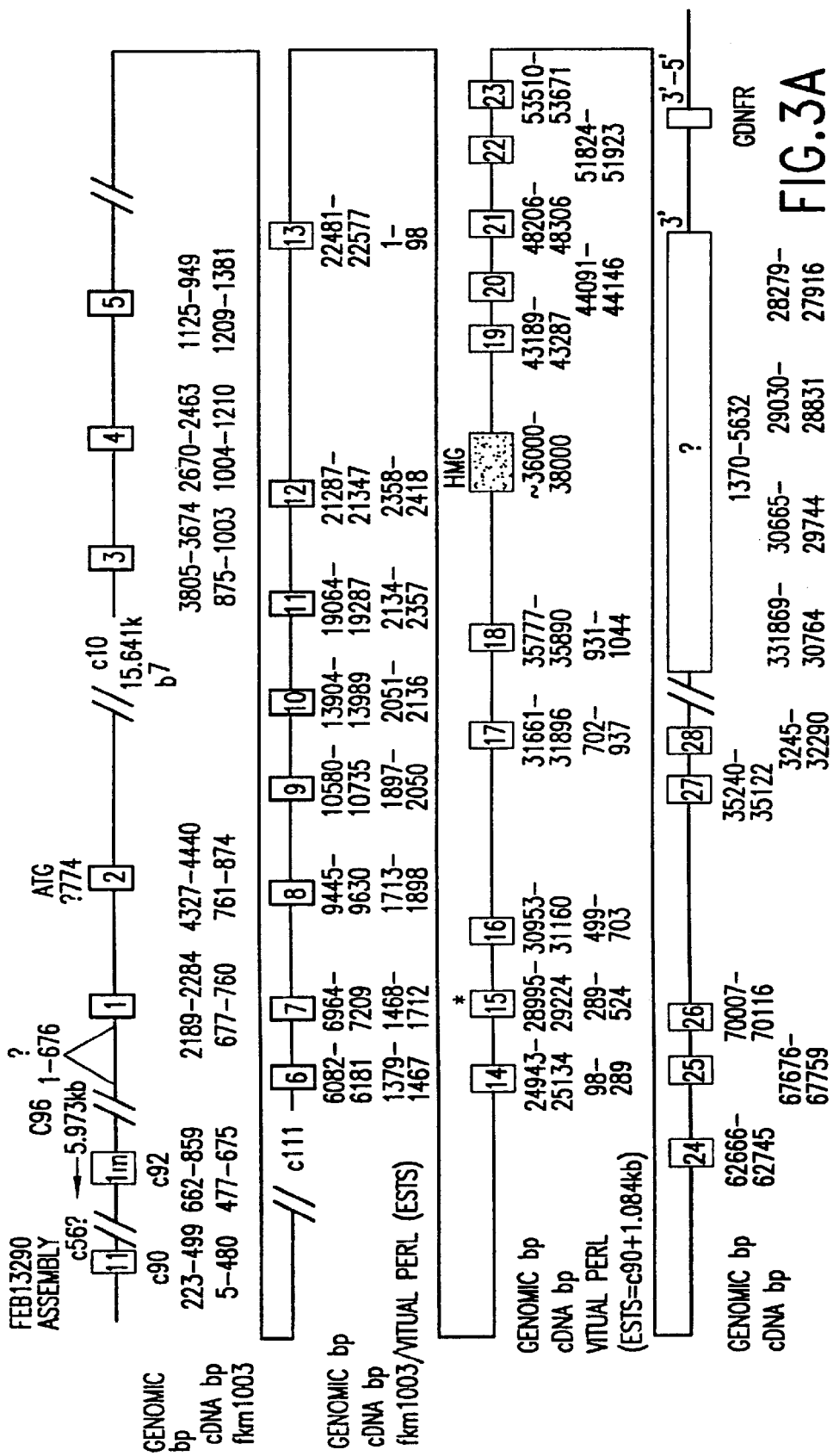

FIG. 3. Genomic structure and nucleotide sequences derived from the wild-type (C57BL/6J) mouse genomic regions containing the mg gene. Panel A, genomic structure; Panel B(1)–B(17), genomic sequence c56 (SEQ ID NO: 3); Panel C(1)–C(6), genomic sequence c96 (SEQ ID NO: 4); Panel D(1)–D(86), genomic sequence of c110/111 (SEQ ID NO: 5).

FIG. 4. Structural depiction of MG cDNA without introns. CUB=CUB domain, metal=metallothionin domain; T-transmembrane domain.

FIGS. 5(1)–5(4). Nucleotide sequence of primers used to amplify each of the exons in the mg gene.

FIG. 6. Nucleotide sequence of the wild-type (SEQ ID NO: 6) and mahogany mutant (SEQ ID NO: 7) sequences in exon 15 of the MG gene. Bases shown in bold are deleted in Mg3J mutant mg.

Figure 7:
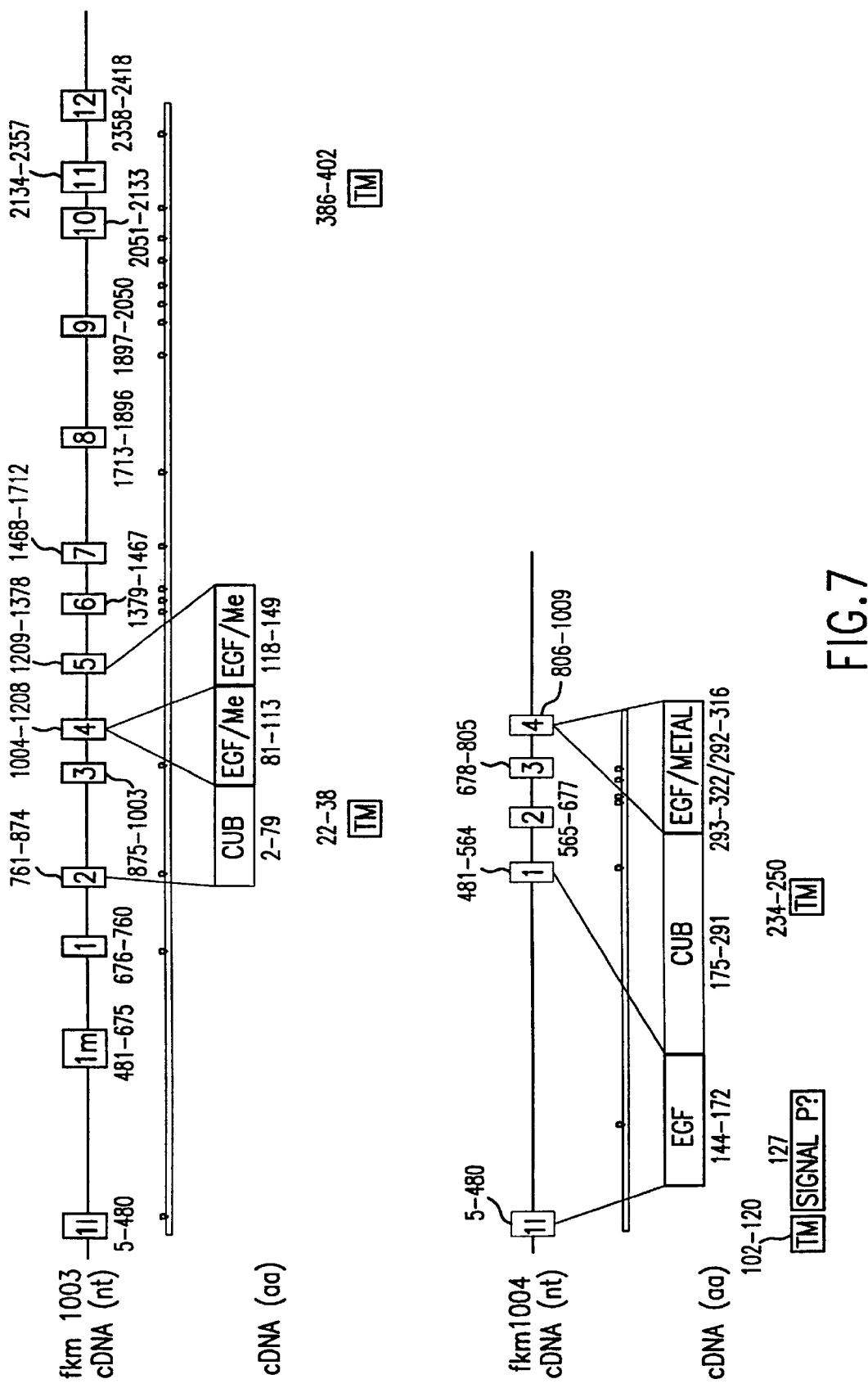

FIG. 7. Differential 5' start sequences in the murine mahogany gene showing splice forms akm1003 and akm1004.

Figure 8E:
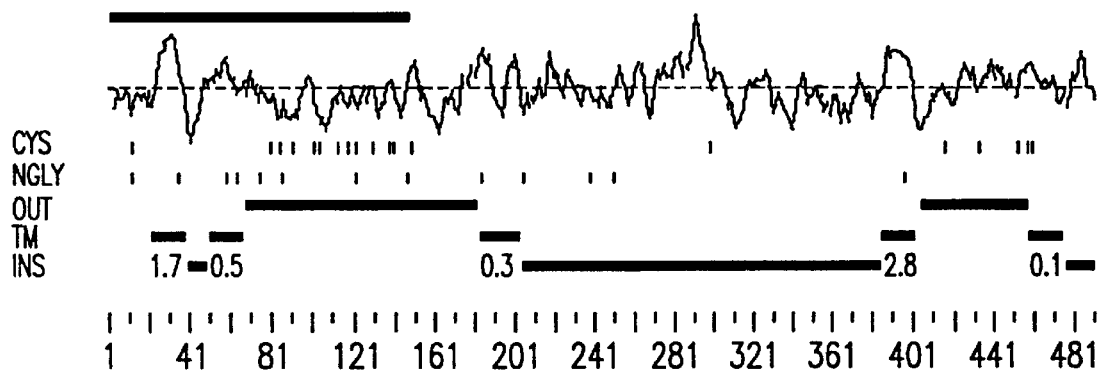

FIG. 8. Panel A-C, cDNA sequence (SEQ ID NO: 8) from one form of the differential 5' start site found in the murine (akm1003), Panel D, amino acid sequence (SEQ ID NO: 9) encoded by the cDNA of Panel A-C; Panel E, hydropathy plot of the akm1003 amino acid sequence.

Figure 9C:
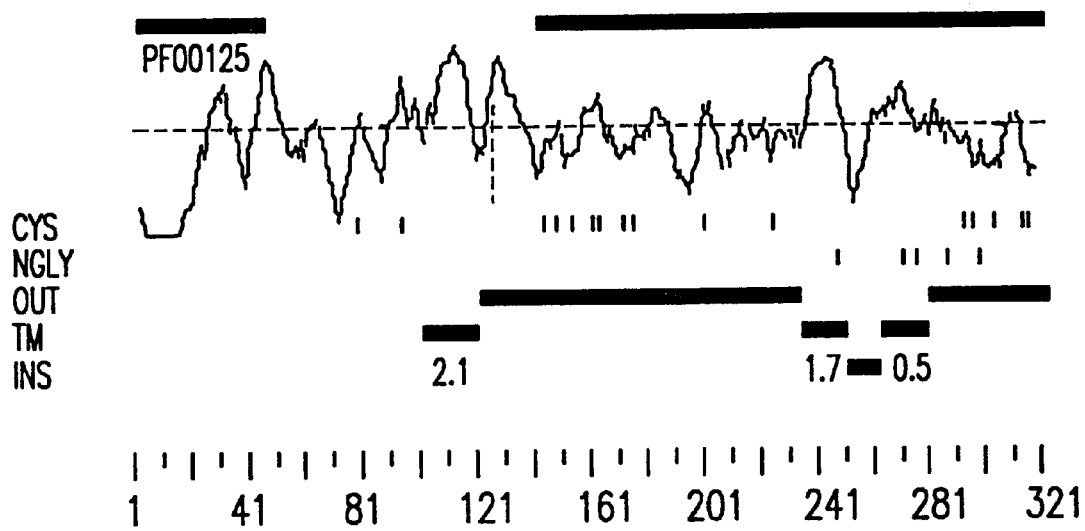

FIG. 9. Panel A, cDNA sequence (SEQ ID NO: 10) from one form of the differential 5' start site found in the murine (akm1004); Panel B, amino acid sequence (SEQ ID NO: 11) encoded by the cDNA of Panel A; Panel C, hydropathy plot of the akm1004 amino acid sequence.

FIG. 10. Nucleotide sequence (SEQ ID NO: 12) of a contig containing a portion of the human MG cDNA, panel A(1)–A(7) and the translated amino acid sequence (SEQ ID NO: 13), panel B.

Figure 11A:
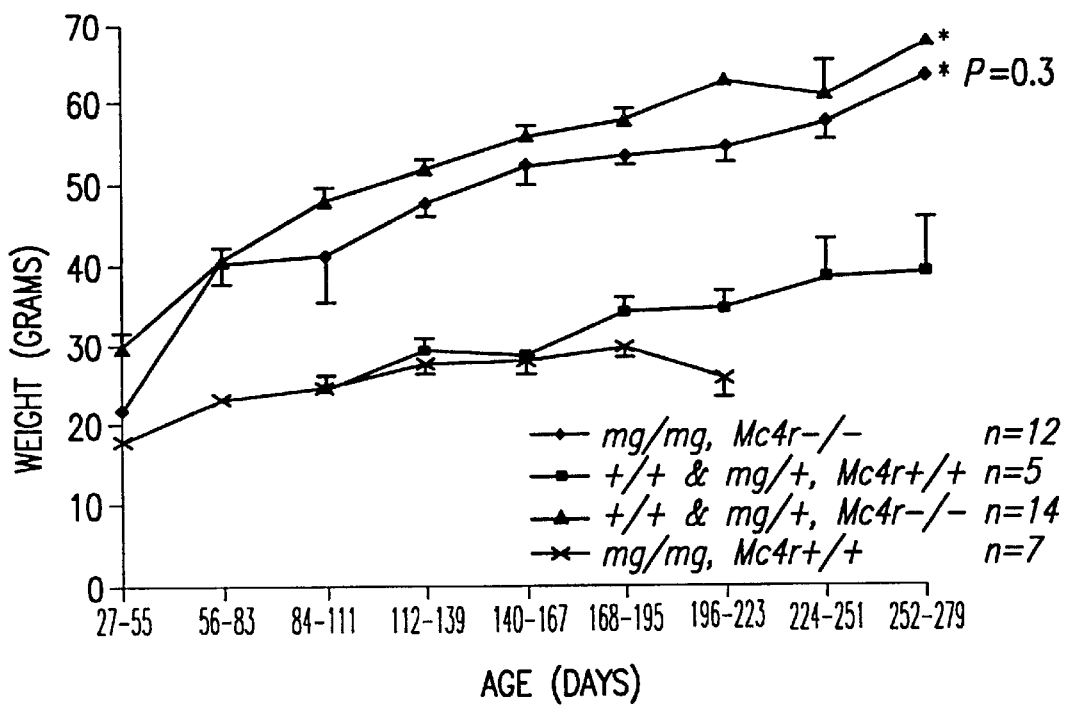
Figure 11B:
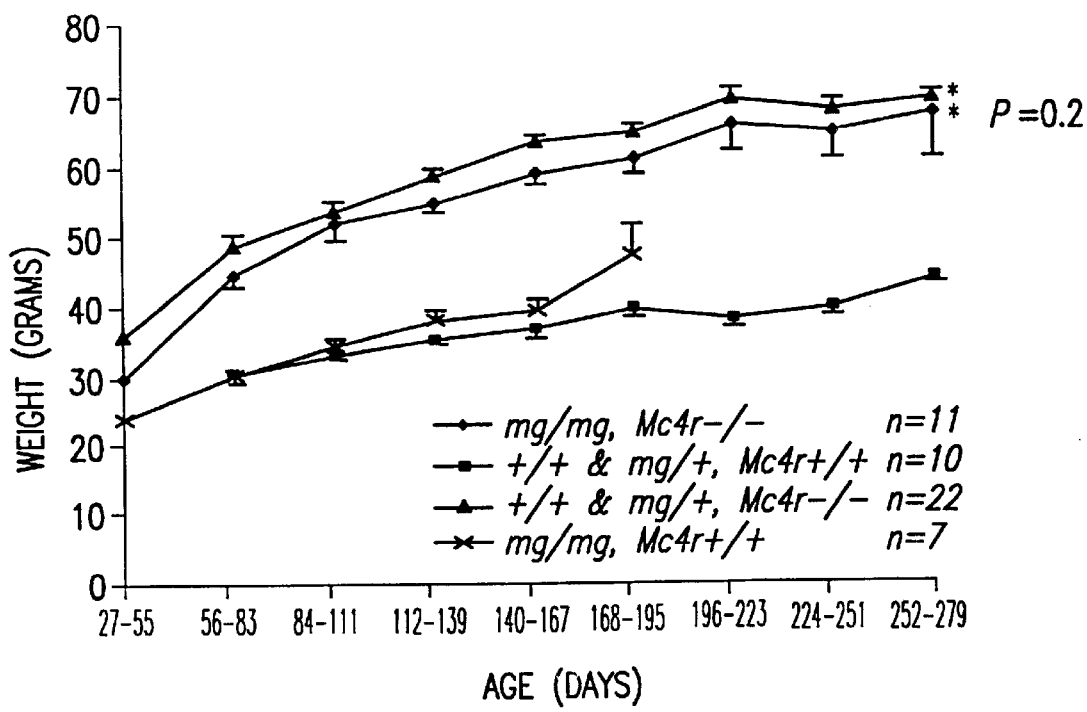

FIG. 11. Effect of mg on MC4r−/− induced weight gain in females (FIG. 11A) and males (FIG. 11B); values depicted are the mean+/−SD within a designated time interval.

FIG. 12. Effect of mg on monogenic obese mutants $Lepr^{db}$ (FIG. 12A), tub (FIG. 12B), $Cpe^{fat}$ (FIG. 12C), and on high fat diet induced obesity (FIG. 12D); the values indicated are the mean+/−SD of the weight length ratio for each animal.

Figure 13:
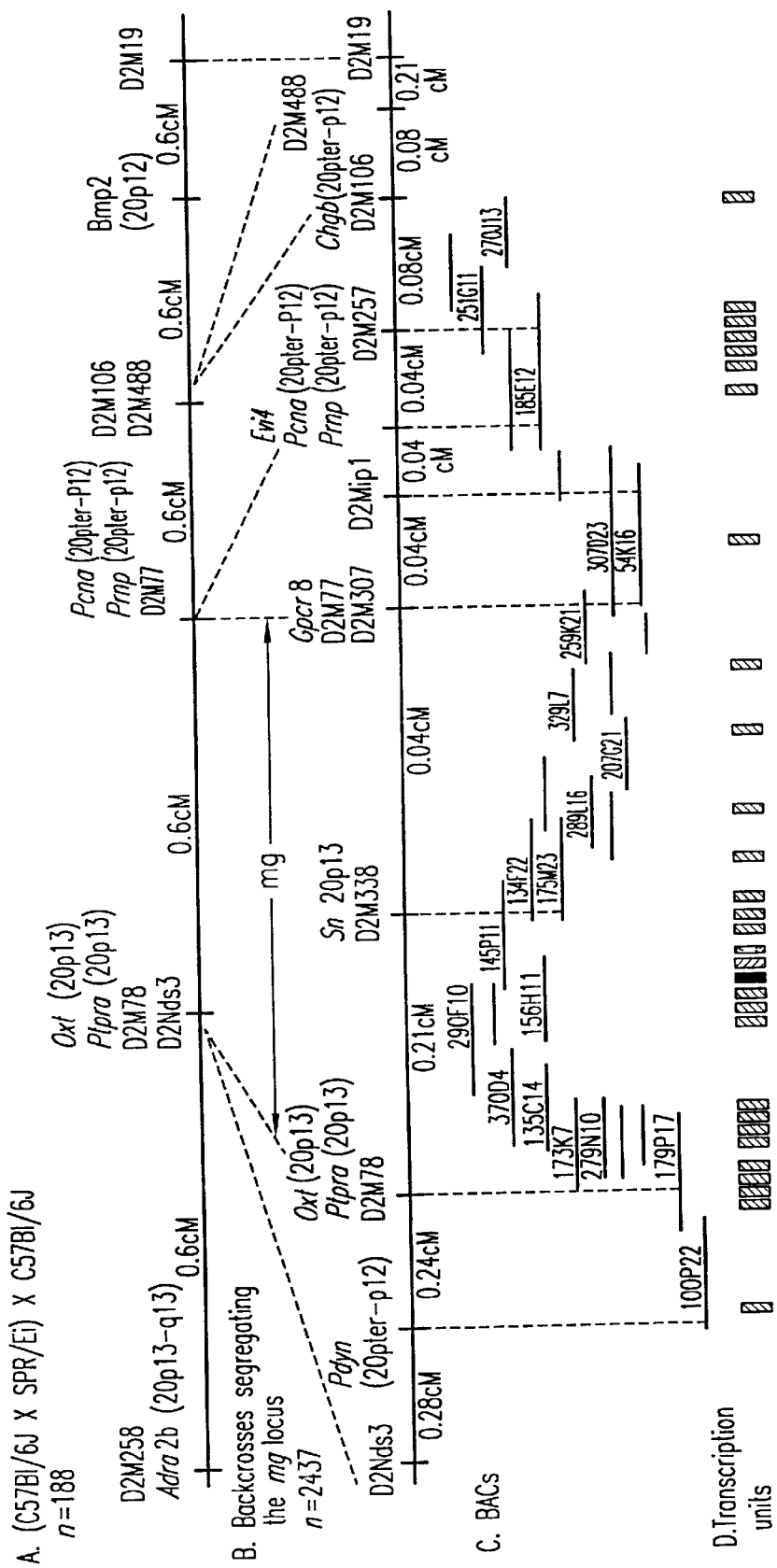

FIG. 13. Genetic and physical map of the region surrounding the mg locus; all MIT markers are presented with shortened names, e.g., D2MIT77 is indicated as D2M77; locations of loci which also mapped on the human cytogenetic map are indicated in parentheses after the gene symbol.

FIG. 13A. The genetic map of the mg gene region on the Millennium BSB mapping panel (Misumi, D. J. et al., 1997, *Science* 278:135–138);

FIG. 13B. The genetic map obtained from crosses segregating mg mutant alleles;

FIG. 13C. The ~1 Mb BAC contig across the mg gene region of mouse Chromosome 2;

FIG. 13D. The transcriptional units identified in the mg region; the filled box indicates the mg gene, whereas the hatched box is a member of the High Mobility Group (HMG) gene family which sits between coding exons 21 and 22 of the mg gene.

Figure 14:
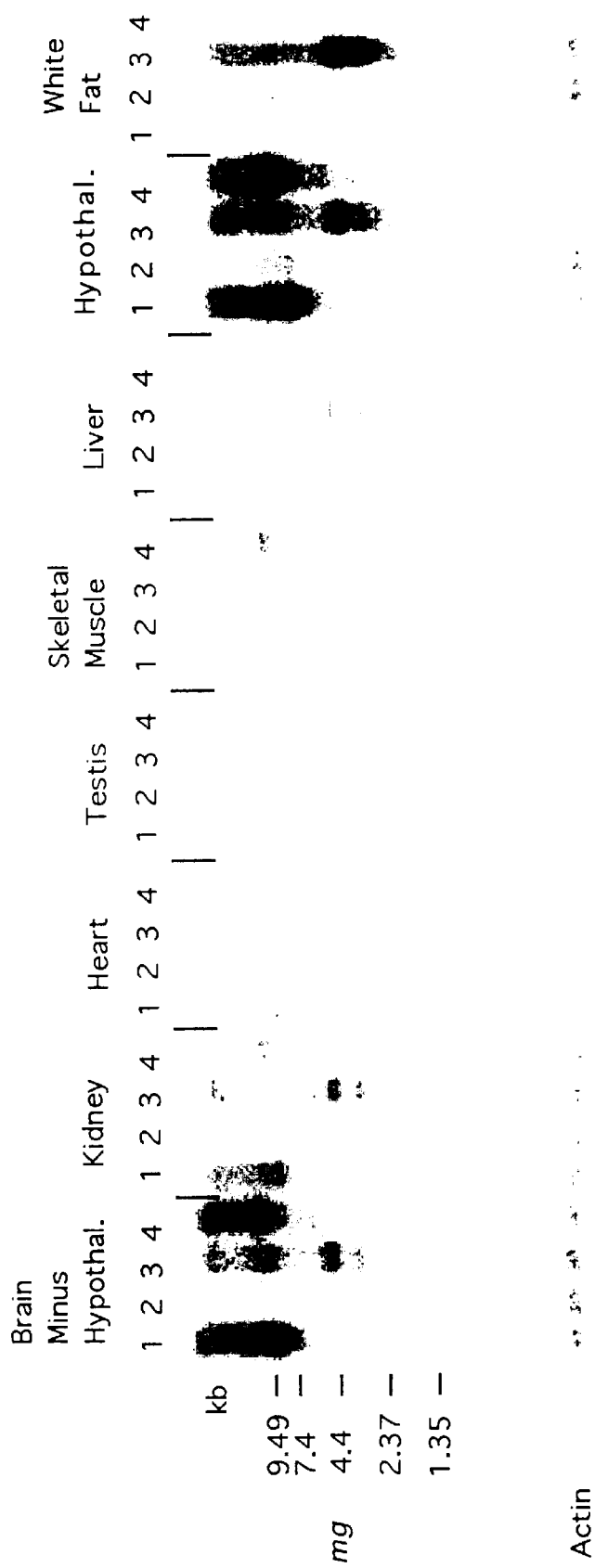
Figure 15B:
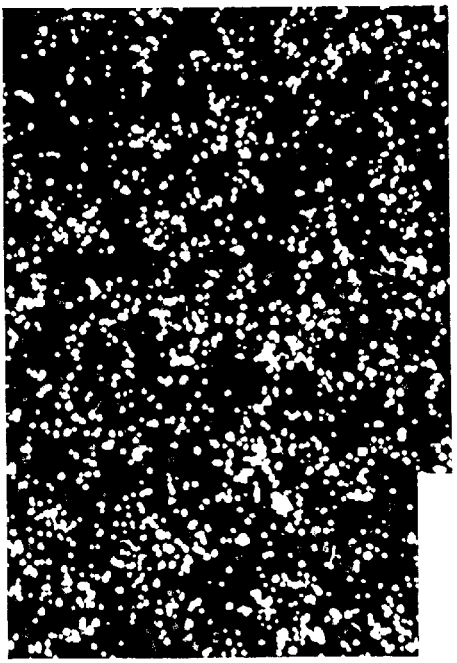
Figure 15D:
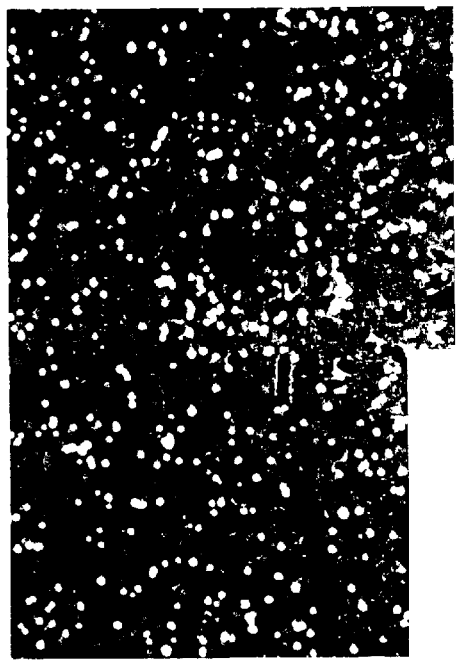
Figure 15A:
Figure 15C:
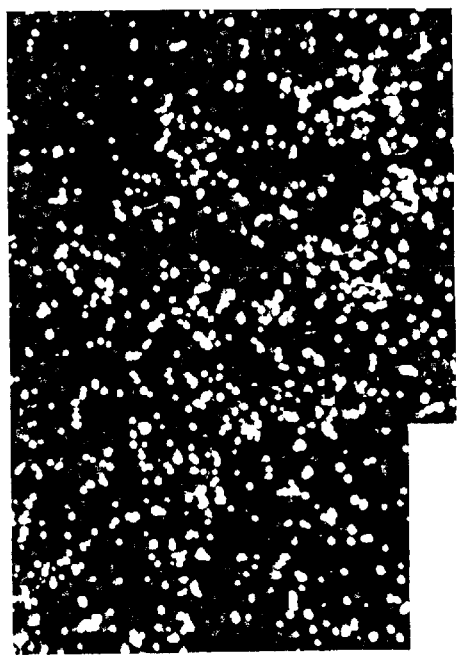

FIG. 14. Northern blot analysis with C3H/HeJ (lane 1), and three mutant alleles of mg: C3HeB/FeJ-$mg^{3J}$ (Lane 2), LDJ/Le-mg (Lane 3), and C3H/HeJ-mg$^J$ (Lane 4); the size marker is shown on the left, and hybridization with actin is shown below for loading comparisons.

FIG. 15. In situ hybridization data: FIG. 15A demonstrates widespread expression of mg throughout the mouse brain is seen in an antisense autoradiographic image of a C3H/HeJ brain at the level of the 3rd ventricle; decreased expression in mg mutants is documented in selected antisense darkfield images of 10 µm whole mount cross sections of the ventromedial hypothalamic nucleic (VMH) of C3H/HeJ (FIG. 15B), LDJ/Le-mg (FIG. 15C), and C3HeB/FeJ-mg$^{3J}$ (FIG. 15D).

Figure 16B:
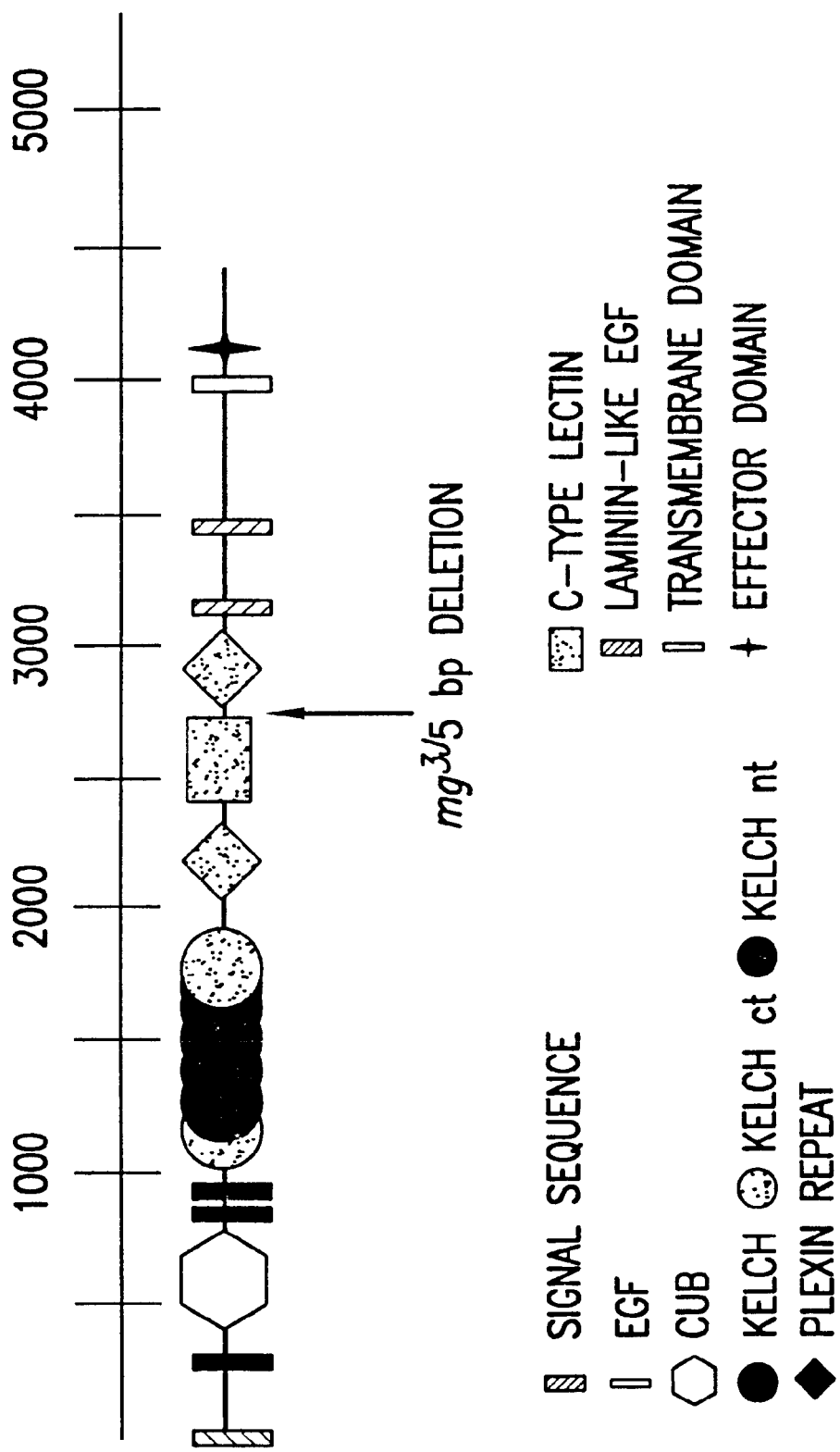

FIG. 16. Alignment of the MG protein sequence with its family members showing the transmembrane region (indicated in brackets) and cytoplasmic tail (FIG. 16A); and a schematic of the molecular modular architecture of MG (FIG. 16B).

FIGS. 17A–D. Sequence alignment of the predicted MG protein sequence (top) with the Attractin protein sequence. Characteristic MG domains are as indicated. See Section 10.2 for details.

FIGS. 18A–D. Panel A1–A8: cDNA nucleotide sequence (SEQ ID NO: 14) of the long splice variant of the human ortholog of the mahogany gene, and Panel B-D: the derived amino acid sequence (SEQ ID NO: 15) of the mahogany gene product which it encodes.

FIGS. 19A–D. Panel A-C: cDNA nucleotide sequence (SEQ ID NO: 16) of a shorter splice variant of the human ortholog of the mahogany gene, and Panel D: the derived amino acid sequence (SEQ ID NO: 17) of the mahogany gene product which it encodes.

FIGS. 20A–C. Panel A-B: cDNA nucleotide sequence (SEQ ID NO: 18) of a second shorter splice variant of the human ortholog of the mahogany gene, and Panel C: the derived amino acid sequence (SEQ ID NO: 19) of the mahogany gene product which it encodes.

5. DETAILED DESCRIPTION OF THE INVENTION

Described herein is the identification of the novel mammalian mahogany (mg) gene, including the human mahogany gene, which is involved in the control of mammalian body weight. Also described are recombinant mammalian, including human mahogany DNA molecules, cloned genes, and degenerate variants thereof. The compositions of the present invention further include mg gene products (e.g., proteins) that are encoded by the mg DNA molecules of the invention, and the modulation of mg gene expression and/or mg gene product activity in the treatment of mammalian body weight disorders, including obesity, cachexia, and anorexia. Also described herein are antibodies against mg gene products (e.g., proteins), or conserved variants or fragments thereof, and nucleic acid probes useful for the identification of mg gene mutations, and the use of such nucleic acid probes in diagnosing mammalian body weight disorders, including obesity, cachexia, and anorexia. Further described are methods for the use of the mg gene and/or mg gene products in the identification of compounds which modulate the activity of the mg gene product.

5.1. The Mahogany Gene

The mahogany genes are novel mammalian genes involved in the control of body weight. The nucleic acid sequences of the mahogany genes, including the murine mahogany gene (SEQ ID NO: 1) shown in FIG. 2A, (with splice variants shown in FIGS. 8A-C and 9A) are described herein. The genomic sequence and structure, i.e., the intron/exon structure, of the mahogany genes have also been elucidated, FIG. 3.

The mahogany gene nucleic acid molecules of the present invention comprise: (a) the DNA sequence shown in FIG. 2 (SEQ ID NO: 1), or any DNA sequence that encodes the amino acid sequence of the mahogany gene product shown in FIG. 2, (SEQ ID NO: 2); (b) nucleotide sequences comprising the novel mahogany sequences disclosed herein that encode mutants of the mahogany gene product in which all or a part of one or more of the domains is deleted or altered, FIG. 6; (c) nucleotide sequences that encode fusion proteins comprising a mahogany gene product, or one of its domains fused to a heterologous polypeptide; and (d) nucleotide sequences within a mahogany gene, nucleotide sequences on the chromosome flanking the mahogany gene, FIG. 3, which can be utilized as part of the methods of the invention for identifying and diagnosing individuals who exhibit or are susceptible to weight disorders, including obesity, cachexia, and anorexia.

The mahogany nucleotide sequences of the invention further comprise: (a) any nucleotide sequence that hybridizes to the complement of a nucleic acid molecule that encodes a mahogany gene product under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., New York, at p. 2.10.3) particularly human mg sequences, FIG. 10; and (b) any nucleotide sequence that hybridizes to the complement of a nucleic acid molecule that encodes a mahogany gene product under less stringent conditions, such as moderately stringent conditions, e.g., washing in 0.2×SSC/0.1% SDS at 42° C. (Ausubel et al., 1989, supra), yet which still encodes a functionally equivalent mahogany gene product.

"Functionally equivalent", as utilized herein, refers to a gene product (e.g., a protein) capable of exhibiting a substantially similar in vivo activity as the endogenous mg gene products encoded by the mg gene sequences described above. The in vivo activity of the mg gene product, as used herein, refers to the ability of the mg gene product, when present in an appropriate cell type, to ameliorate, prevent, or delay the appearance of the mahogany phenotype relative to its appearance when that cell type lacks a functional mahogany gene product.

The invention also includes nucleic acid molecules, preferably DNA molecules, that are the complements of the nucleotide sequences described above. Among the nucleic acid molecules of the invention are deoxyoligonucleotides ("oligos") which hybridize under highly stringent or moderately stringent conditions to the mahogany nucleic acid molecules described above. Exemplary highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as antisense molecules, useful, for example, in mahogany gene regulation, and/or as antisense primers in amplification reactions of mahogany gene nucleic acid sequences. With respect to mahogany gene regulation, such techniques can be used to regulate, for example, weight disorders such as obesity, cachexia, or anorexia. Such sequences may also be used as part of ribozyme and/or triple helix sequences, which are also useful for mahogany gene regulation. Still further, such molecules may be used as components of diagnostic methods whereby, for example, the presence of a particular mahogany allele associated with a weight disorder, such as obesity, cachexia, or anorexia, may be detected. Among the molecules which can be used for diagnostic methods, such as those which involve amplification of genomic mahogany sequences, are primers or probes that can routinely be obtained using the genomic and cDNA sequences disclosed herein.

The nucleotide sequences of the present invention also include (a) DNA vectors that contain any of the foregoing mahogany coding sequences and/or their complements; (b) DNA expression vectors that contain any of the foregoing mahogany coding sequences operatively associated with a regulatory element that directs the expression of the coding sequences; and (c) genetically engineered host cells and organisms that contain any of the foregoing mahogany coding sequences operatively associated with a regulatory element that directs the expression of the coding sequence in the host cell. As used herein, regulatory elements include, but are not limited to inducible and non-inducible promoters, enhancers, operators, and other elements known to those skilled in the art that drive and regulate gene expression. Such regulatory elements include, but are not limited to, the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3'-phosphoglycerate kinase, the promoters of acid phosphatase, and the promoters of the yeast alpha-mating factors.

In addition to the mahogany gene sequences described above, homologs of such sequences, exhibiting extensive homology to one or more domains of the mahogany gene product can be present in other species. In a preferred embodiment, the mahogany gene homologue maps to a chromosomal region that is syntenic to the chromosomal region of the mahogany gene. In a particularly preferred embodiment, a human mahogany gene homologue sequence maps to a human chromosome region that is syntenic to the region of mouse chromosome 2 to which the murine mahogany gene maps, namely 20p15, and comprises the contiged human MG cDNA provided herein. Further, there can also exist homologue genes at other genetic loci within the genome of the same species which encode proteins having extensive homology to one or more domains of the mahogany gene product. Such mahogany homologs can include, for example, secreted forms of the mahogany sequences, see, e.g., Duke-Cohan, J. S. et al. (1998, *Proc. Natl. Acad. Sci. U.S.A.* 95:11336–11341). Such sequences, can be used, for example, in the screening assays, described in Section 5.4.2 below, for compounds that interact with the mahogany gene and/or its gene product and that may therefore be useful in treating and ameliorating body weight disorders.

Other mahogany homologs can be identified and readily isolated, without undue experimentation, by molecular biological techniques well known in the art, and are therefore within the scope of the present invention. As an example, in order to clone a human mahogany gene homologue using isolated murine mahogany gene sequences, such murine mahogany gene sequences may be labeled and used to screen a cDNA library constructed from mRNA obtained from appropriate cells or tissues derived from the organism (in this case, human) of interest. With respect to the cloning of such a human mahogany homologue, a human cDNA library may, for example be used for screening, such as a cDNA library obtained from mRNA isolated from brain tissues, particularly containing hypothalamic regions.

The hybridization washing conditions used should be of a lower stringency when the cDNA library is derived from an organism different from the type of organism from which the labeled sequence was derived. With respect to the cloning of a human mahogany homologue, for example, hybridization can be performed for 4 hours at 65° C. using Amersham Rapid Hyb™ buffer (Cat. #RPN1639) according to manufacturer's protocol, followed by washing, with a final washing stringency of 1.0×SSC/0.1% SDS at 50° C. for 20 minutes being preferred.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, the labeled fragment may be used to screen a genomic library derived from the organism of interest, again, using appropriately stringent conditions.

Further, a mahogany gene homologue may be isolated from nucleic acid of the organism of interest by performing PCR using two degenerate oligonucleotide primer pools designed on the basis of amino acid sequences within the mahogany gene product disclosed herein. The template for the reaction may be cDNA obtained by reverse transcription of mRNA prepared from, for example, human or non-human cell lines or tissue known or suspected to express a mahogany gene allele.

The PCR product may be subcloned and sequenced to ensure that the amplified sequences represent the sequences of a mahogany gene nucleic acid sequence. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library. This method has been used to isolate sequences encoding each of the murine MG gene exons as well as to isolate contigs containing the human MG sequences provided herein, FIG. 10.

PCR technology may also be utilized to isolate full length cDNA sequences. For example, RNA may be isolated, following standard procedures, from an appropriate cellular or tissue source (i.e., one known, or suspected, to express the mahogany gene). A reverse transcription reaction may be performed on the RNA using an oligonucleotide primer specific for the most 5' end of the amplified fragment for the priming of the first strand synthesis. The resulting RNA/DNA hybrid may then be "tailed" with guanines using a standard terminal transferase reaction, they hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989 supra.

Mahogany gene sequences may additionally be used to isolate mutant mahogany alleles. Such mutant alleles may be isolated from individuals either known or proposed to have a phenotype which contributes to the symptoms of body weight disorders such as obesity, cachexia, or anorexia or disorders associated with hyperphagia. Mutant alleles and mutant allele products may then be utilized in the therapeutic and diagnostic systems described below. Additionally, such mahogany gene sequences can be used to detect mahogany gene regulatory (e.g. promoter) defects which can affect body weight.

A cDNA of a mutant mahogany gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant mahogany allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant mahogany allele to that of the normal mahogany allele, the mutation(s) responsible for the loss of alteration of activity of the mutant mahogany gene product can be ascertained.

Alternatively, a genomic library can be constructed using DNA obtained from an individual suspected of or known to carry the mutant mahogany allele, or a cDNA library can be constructed using RNA from a tissue known, or suspected to express the mutant mahogany allele. The normal mahogany gene or any suitable fragment thereof may then be labeled and used as a probe to identify the corresponding mutant mahogany allele is such libraries. Clones containing the mutant mahogany gene sequences may then be purified and subjected to sequence analysis according to methods well known to those of skill in the art.

Additionally, an expression library can be constructed utilizing cDNA synthesized from, for example, RNA isolated from a tissue known, or suspected to express a mutant mahogany allele in an individual suspected of or known to carry such a mutant allele. In this manner, gene products made by the putatively mutant tissue may be expressed and screened using standard antibody screening techniques in conjunction with antibodies raised against the normal mahogany gene product as described, below, in Section 5.3. For screening techniques, see, for example, Harlow, E. and Lane, eds., 1988, "Antibodies: A Laboratory Manual", Cold Spring Harbor Press, Cold Spring Harbor. In cases where a mahogany mutation results in an expressed gene product with altered function (e.g., as a result of a missense or a frameshift mutation) a polyclonal set of anti-mahogany gene product antibodies are likely to cross-react with the mutant mahogany gene product. Library clones detected via their reaction with such labeled antibodies can be purified and subjected to sequence analysis according to methods well known to those of skill in the art.

5.2. Protein Products of the Mahogany Gene

Mahogany gene products (e.g., proteins), polypeptides and peptide fragments, mutant, truncated, or deleted forms of the mahogany gene product, and/or fusion proteins of the mahogany gene product can be prepared for a variety of uses. For example, such gene products, or peptide fragments thereof, can be used for the generation of antibodies in diagnostic assays, or for the identification of other cellular or extracellular products involved in the regulation of mammalian body weight.

FIG. 2 shows the amino acid sequence (SEQ ID NO: 2) of the murine form of a mahogany gene product. Mahogany gene products, also referred to herein as mahogany proteins, of the present invention additionally include those gene products encoded by the mahogany gene sequences described in Section 5.1, above, particularly the human homologue of the murine mg gene, a fragment of which is shown in FIG. 10.

In addition, mahogany gene products may include proteins that represent functionally equivalent gene products. Such an equivalent mahogany gene product may contain deletions, including internal deletions, additions, including additions yielding fusion proteins, or substitutions of amino acid residues within and/or adjacent to the amino acid sequence encoded by the mahogany gene sequences described, in Section 5.1, above, but that result in a "silent" change, in that the change produces a functionally equivalent mahogany gene product. Such amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Functionally equivalent", as utilized herein, refers to a gene product (e.g., a protein) capable of exhibiting a substantially similar in vivo activity as the endogenous mg gene products encoded by the mg gene sequences described in Section 5.1, above. The in vivo activity of the mg gene product, as used herein, refers to the ability of the mg gene product, when present in an appropriate cell type, to ameliorate, prevent, or delay the appearance of the mahogany phenotype relative to its appearance when that cell type lacks a functional mahogany gene product.

Alternatively, where alteration of function is desired, deletion or non-conservative alterations can produce altered, including reduced-activity, mahogany gene products. Such alterations can, for example, alter one or more of the biological functions of the mahogany gene product. Further, such alterations can be selected so as to generate mahogany gene products that are better suited for expression, scale up, etc. in the host cells chosen. For example, cysteine residues can be deleted or substituted with another amino acid residue in order to eliminate disulfide bridges.

As another example, altered mahogany gene products can be engineered that correspond to mutants or variants of the mahogany gene product associated with mammalian weight disorders, such as obesity, cachexia, or anorexia. Altered mahogany gene products can also be engineered that correspond to mutants or variants of the mahogany gene product known to neutralize or ameliorate the symptoms of body weight disorders, such as obesity, cachexia, or anorexia, which are mediated by some other gene, including, but not limited to, body weight disorders mediated by the agouti gene.

Also within the scope of the present invention are peptides and/or proteins corresponding to one or more domains of the mahogany protein or any one of the individual exon encoded regions of the MG protein, as well as fusion proteins in which the full length mahogany protein, a mahogany peptide, or a truncated mahogany protein or peptide is fused to an unrelated heterologous protein. Such proteins and peptides can be designed on the basis of the mahogany nucleotide sequence disclosed in Section 5.1, above, and/or on the basis of the mahogany amino acid sequence disclosed in the Section.

Fusion proteins of the invention include, but are not limited to, IgFc fusions which stabilize the mahogany protein or peptide and prolong half life in vivo; or fusions to any amino acid sequence that allows the fusion protein to be anchored to the cell membrane; or fusions to an enzyme, fluorescent protein, or luminescent protein which provides a marker function.

The mahogany gene products, peptide fragments thereof and fusion proteins thereof, may be produced by recombinant DNA technology using techniques well known in the art. Thus, methods for preparing the mahogany gene products, polypeptides, peptides, fusion peptide and fusion polypeptides of the invention by expressing nucleic acid containing mahogany gene sequences are described herein. Methods that are well known to those skilled in the art can be used to construct expression vectors containing mahogany gene product coding sequences and appropriate transcriptional and translational control signals. These methods include, for example, in vitro recombinant DNA techniques, synthetic techniques, and in vivo genetic recombination. See, for example, the techniques described in Sambrook, et al., 1989, supra, and Ausubel, et al., 1989, supra. Alternatively, RNA capable of encoding mahogany gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the mahogany gene product coding sequences of the invention. Such host-expression systems represent vehicles by which the coding sequences of interest may be produced and subsequently purified, but also represent cells that may, when transformed or transfected with the appropriate nucleotide coding sequences, exhibit the mahogany gene product of the invention in situ. These include but are not limited to microorganisms such as bacteria (e.g., *E. coli, B. subtilis*) transformed with recombinant bacteriophage DNA, plasmid DNA or cosmid DNA expression vectors containing mahogany gene product coding sequences; yeast (e.g., Saccharomyces, Pichia) transformed with recombinant yeast expression vectors containing the mahogany gene product coding sequences; insect cell systems infected with recombinant virus expression vectors (e.g., baculovirus) containing the mahogany gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing mahogany gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the mahogany gene product being expressed. For example, when a large quantity of such a protein is to be produced, for the generation of pharmaceutical compositions of mahogany gene product or for raising antibodies to mahogany gene product, for example, vectors that direct the expression of high levels of fusion protein products that are readily purified may be desirable. Such vectors include, but are not limited, to the *E. coli* expression vector pUR278 (Ruther et al., 1983, EMBO J. 2, 1791), in which the mahogany gene product coding sequence may be ligated individually into the vector in frame with the lac Z coding region so that a fusion protein is produced; pIN vectors (Inouye and Inouye, 1985, Nucleic Acids Res. 13, 3101–3109; Van Heeke and Schuster, 1989, J. Biol. Chem. 264, 5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica*, nuclear polyhidrosis virus (AcNPV) is used as a vector to express foreign genes. The virus grows in *Spodoptera frugiperda* cells. The mahogany gene product coding sequence may be cloned individually into non-essential regions (for example the polyhedrin gene) of the virus and placed under control of an AcNPV promoter (for example the polyhedrin promoter). Successful insertion of mahogany gene product coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith, et al., 1983, J. Virol. 46, 584; Smith, U.S. Pat. No. 4,215,051).

In mammalian host cells, a number of viral-based expression systems may be utilized. In cases where an adenovirus is used as an expression vector, the mahogany gene product coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing mahogany gene product in infected hosts. (e.g., See Logan and Shenk, 1984, Proc. Natl. Acad. Sci. USA 81, 3655–3659). Specific initiation signals may also be required for efficient translation of inserted mahogany gene product coding sequences. These signals include the ATG initiation codon and adjacent sequences. In cases where an entire mahogany gene, including its own initiation codon and adjacent sequences, is inserted into the appropriate expression vector, no additional translational control signals may be needed. However, in cases where only a portion of the mahogany gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153, 516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and WI38.

For long-term, high-yield production of recombinant proteins, stable expression is preferred. For example, cell lines that stably express the mahogany gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the mahogany gene product. Such engineered cell lines may be particularly useful in screening and evaluation of compounds that affect the endogenous activity of the mahogany gene product.

A number of selection systems may be used, including but not limited to the herpes simplex virus thymidine kinase (Wigler, et al., 1977, Cell 11, 223), hypoxanthine-guanine phosphoribosyltransferase (Szybalska and Szybalski, 1962, Proc. Natl. Acad. Sci. USA 48, 2026), and adenine phosphoribosyltransferase (Lowy, et al., 1980, Cell 22, 817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77, 3567; O'Hare, et al., 1981, Proc. Natl. Acad. Sci. USA 78, 1527); gpt, which confers resistance to mycophenolic acid (Mulligan and Berg, 1981, Proc. Natl. Acad. Sci. USA 78, 2072); neo, which confers resistance to the aminoglycoside G-418 (Colberre-Garapin, et al., 1981, J. Mol. Biol. 150, 1); and hygro, which confers resistance to hygromycin (Santerre, et al., 1984, Gene 30, 147).

Alternatively, the expression characteristic of an endogenous mahogany gene within a cell line or microorganism my be modified by inserting a heterologous DNA regulatory element into the genome of a stable cell line or cloned microorganism such that the inserted regulatory element is operatively linked with the endogenous mahogany gene. For example, an endogenous mahogany gene which is normally "transcriptionally silent", i.e., a mahogany gene which is normally not expressed, or is expressed only a very low levels in a cell line or microorganism, may be activated by inserting a regulatory element which is capable of promoting the expression of a normally expressed gene product in that cell line or microorganism. Alternatively, a transcriptionally silent, endogenous mahogany bene may be activated by insertion of a promiscuous regulatory element that works across cell types.

A heterologous regulatory element may be inserted into a stable cell line or cloned microorganism, such it is operatively linked with an endogenous mahogany gene, using techniques, such as targeted homologous recombination, which are well known to those of skill in the art, and described e.g., in Chappel, U.S. Pat. Nos. 4,215,051; 5,578, 461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al., 1991, Proc. Natl. Acad. Sci. USA 88, 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$.nitriloacetic acid-agarose columns and histidine-tagged proteins are selectively eluted with imidazole-containing buffers.

The mahogany gene products can also be expressed in transgenic animals. Animals of any species, including, but not limited to, mice, rats, rabbits, guinea pigs, pigs, micropigs, goats, sheep, and non-human primates, e.g., baboons, monkeys, and chimpanzees may be used to generate mahogany transgenic animals. The term "transgenic," as used herein, refers to animals expressing mahogany gene sequences from a different species (e.g., mice expressing human mahogany gene sequences), as well as animals that have been genetically engineered to over express endogenous (i.e., same species) mahogany sequences or animals that have been genetically engineered to no longer express endogenous mahogany gene sequences (i.e., "knock-out" animals), and their progeny.

Any technique known in the art may be used to introduce a mahogany gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, Proc. Natl. Acad. Sci., USA 82, 6148–6152); gene targeting in embryonic stem cells (Thompson, et al., 1989, Cell 56, 313–321); electroporation of embryos (Lo, 1983, Mol. Cell. Biol. 3, 1803–1814); and sperm-mediated gene transfer (Lavitrano et al., 1989, Cell 57, 717–723) (For a review of such techniques, see Gordon, 1989, Transgenic Animals, Intl. Rev. Cytol. 115, 171–229).

Any technique known in the art may be used to produce transgenic animal clones containing a mahogany transgene, for example, nuclear transfer into enucleated oocytes of nuclei from cultured embryonic, fetal or adult cells induced to quiescence (Campbell, et al., 1996, Nature 380, 64–66; Wilmut, et al., Nature 385, 810–813).

The present invention provides for transgenic animals that carry a mahogany transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. USA 89, 6232–6236). The regulatory sequences required for such a cell-type specific activation will depend upon the particular cell type of interest, and will be apparent to those of skill in the art. When it is desired that the mahogany transgene be integrated into the chromosomal site of the endogenous mahogany gene, gene targeting is preferred. Briefly, when such a technique is to be utilized, vectors containing some nucleotide sequences homologous to the endogenous mahogany gene are designed for the purpose of integrating, via homologous recombination with chromosomal sequences, into and disrupting the function of the nucleotide sequence of the endogenous mahogany gene. The transgene may also be selectively introduced into a particular cell type, thus inactivating the endogenous mahogany gene in only that cell type, by following, for example, the teaching of Gu, et al. (Gu, et al., 1994, Science 265, 103–106). The regulatory sequences required for such a cell-type specific inactivation will depend upon the particular cell type of interest, and will be apparent to those of skill in the art.

Once transgenic animals have been generated, the expression of the recombinant mahogany gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of mahogany gene-expressing tissue, may also be evaluated immunocytochemically using antibodies specific for the mahogany transgene product.

5.3. Antibodies to Mahogany Gene Products

Described herein are methods for the production of antibodies capable of specifically recognizing one or more mg gene product epitopes, or epitopes of conserved variants, or peptide fragments of the mg gene products. Further, antibodies that specifically recognize mutant forms of mg gene products, are encompassed by the invention.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a mg gene product in an biological sample and may, therefore, be utilized as part of a diagnostic or prognostic technique whereby patients may be tested for abnormal levels of mg gene products, and/or for the presence of abnormal forms of such gene products. Such antibodies may also be utilized in conjunction with, for example, compound screening schemes, as described, below, in Section 5.4.2, for the evaluation of the effect of test compounds on mg gene product levels and/or activity. Additionally, such antibodies can be used in conjunction with the gene therapy techniques described, below, in Section 5.4.3.2, to, for example, evaluate the normal and/or engineered mahogany-expressing cells prior to their introduction into the patient.

Anti-mg gene product antibodies may additionally be used in methods for inhibiting abnormal mg gene product activity. Thus, such antibodies may, therefore, be utilized as part of weight disorder treatment methods.

For the production of antibodies against a mg gene product, various host animals may be immunized by injection with a mg gene product, or a portion thereof. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as a mg gene product, or an antigenic functional derivative thereof. For the production of polyclonal antibodies, host animals such as those described above, may be immunized by injection with mg gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256, 495–497; and U.S. Pat. No. 4,376,110), the human B-cell hybridoma technique (Kosbor et al., 1983, Immunology Today 4, 72; Cole et al., 1983, Proc. Natl. Acad. Sci. USA 80, 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, Proc. Natl. Acad. Sci., 81, 6851–6855; Neuberger, et al., 1984, Nature 312, 604–608; Takeda, et al., 1985, Nature, 314, 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.)

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242, 423–426; Huston, et al., 1988, Proc. Natl. Acad. Sci. USA 85, 5879–5883; and Ward, et al., 1989, Nature 334, 544–546) can be adapted to produce single chain antibodies against mahogany gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments, which can be produced by pepsin digestion of the antibody molecule and the Fab fragments, which can be generated by reducing the disulfide bridges of the F(ab')$_2$ fragments. Alternatively, Fab expression libraries may be constructed (Huse, et al., 1989, Science, 246, 1275–1281) to allow rapid and easy identification of monoclonal Fab fragments with the desired specificity.

5.4. Uses of the Mahogany Genes, Gene Products, and Antibodies

Described herein are various applications of the mahogany genes, of the mahogany gene products, including peptide fragments thereof, and of antibodies directed against mahogany gene products and peptide fragments thereof. Such applications include, for example, prognostic and diagnostic evaluation of body weight disorders and the identification of subjects with a predisposition to such disorders, as described below, in Section 5.4.1. Additionally, such applications include methods for the treatment of body weight and body weight disorders, as described, below, in Section 5.4.2, and for the identification of compounds which modulate the expression of the mahogany gene and/or the activity of the mahogany gene product, as described in Section 5.4.3, below. Such compounds can include, for example, other cellular products which are involved in body weight regulation. These compounds can be used, for example, in the amelioration of body weight disorders, including obesity, cachexia, and anorexia.

While, for clarity, the uses described in this section are primarily uses related to body weight disorder abnormalities, it is to be noted that each of the diagnostic and therapeutic treatments described herein can additionally be utilized in connection with other defects associated with the mahogany gene, such as hyperpigmentation, hyperphagia and other disorders resulting in increased metabolic rates.

5.4.1. Diagnosis of Body Weight Disorder Abnormalities

A variety of methods can be employed for the diagnostic and prognostic evaluation of body weight disorders, including obesity, cachexia, and anorexia, and for the identification of subjects having a predisposition to such disorders.

Such methods may, for example, utilize reagents such as the mahogany gene nucleotide sequences described in Section 5.1, and antibodies directed against mahogany gene products, including peptide fragments thereof, as described, above, in Section 5.3. Specifically, such reagents may be used, for example, for:

(1) the detection of the presence of mahogany gene mutations, or the detection of either over- or under-expression of mahogany gene relative to levels of mahogany expression in a wild-type, non-body weight disorder state which correlates with certain body weight disorders or susceptibility toward such body weight disorders;

(2) the detection of over- or under-abundance of mahogany gene product relative to the abundance of mahogany gene product in a wild-type non-body weight disorder state which correlates with certain body weight disorders or susceptibility toward such body weight disorders; and (3) the detection of an aberrant level of mahogany gene product activity relative to mahogany gene product activity levels in a wild-type, non-body weight disorder state which correlates with certain body weight disorders or susceptibility toward such body weight disorders.

Mahogany gene nucleotide sequences can, for example, be used to diagnose a body weight disorder using, for example, the techniques for detecting mutations in the mahogany gene described above in Section 5.1, above.

The methods described herein may be performed, for example, by utilizing pre-packaged diagnostic kits comprising at least one specific mahogany gene nucleic acid or anti-mahogany gene product antibody reagent described herein, which may be conveniently used, e.g., in clinical settings, to screen and diagnose patients exhibiting body weight disorder abnormalities, and to screen those individuals exhibiting a predisposition to developing a body weight disorder abnormality.

For the detection of mahogany gene mutations, any nucleated cell can be used as a starting source for genomic nucleic acid. For the detection of mahogany gene expression or mahogany gene products, any cell type or tissue in which the mahogany gene is expressed may be utilized, such as, for example, tissues or cells shown herein to express the MG gene.

Nucleic acid-based detection techniques are described, below, in Section 5.4.1.1. Peptide detection techniques are described, below, in Section 5.4.1.2.

5.4.1.1. Detection of Mahogany Gene Nucleic Acid Molecules

Mutations or polymorphisms within the mahogany gene can be detected by utilizing a number of techniques. Nucleic acid from any nucleated cell can be used as the starting point for such assay techniques, and may be isolated according to standard nucleic acid preparation procedures which are well known to those of skill in the art.

Genomic DNA may be used in hybridization or amplification assays of biological samples to detect abnormalities involving mahogany gene structure, including point mutations, insertions, deletions and chromosomal rearrangements. Such assays may include, but are not limited to, Southern analyses, single stranded conformation polymorphism analyses (SSCP), and PCR analyses.

Diagnostic methods for the detection of mahogany gene-specific mutations can involve for example, contacting and incubating nucleic acids obtained from a sample, e.g., derived from a patient sample or other appropriate cellular source with one or more labeled nucleic acid reagents including recombinant DNA molecules, cloned genes or degenerate variants thereof, such as described in Section 5.1, above, under conditions favorable for the specific annealing of these reagents to their complementary sequences within or flanking the mahogany gene. Preferably, the lengths of these nucleic acid reagents are at least 15 to 30 nucleotides.

After incubation, all non-annealed nucleic acids are removed from the nucleic acid:mahogany molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled mahogany nucleic acid reagents is accomplished using standard techniques well-known to those in the art. The mahogany gene sequences to which the nucleic acid reagents have annealed can be compared to the annealing pattern expected from a normal mahogany gene sequence in order to determine whether a mahogany gene mutation is present.

In a preferred embodiment, mahogany gene mutations or polymorphisms can be detected by using a microassay of mahogany nucleic acid sequences immobilized to a substrate or "gene chip" (see, e.g. Cronin, et al., 1996, Human Mutation 7:244–255).

Alternative diagnostic methods for the detection of mahogany gene specific nucleic acid molecules, in patient samples or other appropriate cell sources, may involve their amplification, e.g., by PCR (the experimental embodiment set forth in Mullis, 1987, U.S. Pat. No. 4,683,202), followed by the analysis of the amplified molecules using techniques well known to those of skill in the art, such as, for example, those listed above. The resulting amplified sequences can be compared to those that would be expected if the nucleic acid being amplified contained only normal copies of the mahogany gene in order to determine whether a mahogany gene mutation exists.

Among those mahogany nucleic acid sequences which are preferred for such amplification-related diagnostic screening analyses are oligonucleotide primers which amplify mahogany exon sequences. The sequences of such oligonucleotide primers are, therefore, preferably derived from mahogany intron sequences so that the entire exon, or coding region, can be analyzed as discussed below. Primer pairs useful for amplification of mahogany exons are preferably derived from adjacent introns. Appropriate primer pairs can be chosen such that each of the 25 mahogany exons are amplified. Primers for the amplification of mahogany exons can be routinely designed by one of ordinary skill in the art by utilizing the exon and intron sequences of mahogany shown in Figures, particularly FIGS. 3 and 5(1)–5(4).

Additional mahogany nucleic acid sequences which are preferred for such amplification-related analyses are those which will detect the presence of a mahogany polymorphism which doffers from the consensus mahogany sequence depicted in Figures, particularly those that detect the polymorphism identified in exon 15 (FIG. 7). Such polymorphisms include ones which represent mutations associated with body weight disorders such as obesity, cachexia, or anorexia.

Further, well-known genotyping techniques can be performed to type polymorphisms that are in close proximity to mutations in the mahogany gene itself, including mutations associated with weight disorders such as obesity, cachexia, or anorexia. Such polymorphisms can be used to identify individuals in families likely to carry mutations in the mahogany gene. If a polymorphism exhibits linkage disequilibrium with mutations in the mahogany gene, the polymorphism can also be used to identify individuals in the general population who are likely to carry such mutations. Polymorphisms that can be used in this way include restriction fragment length polymorphisms (RFLPs), which involve sequence variations in restriction enzyme target sequences, single-base polymorphisms, and simple sequence length polymorphisms (SSLPs).

For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the mahogany gene, and the diagnosis of diseases and disorders related to mutations in the mahogany gene.

Also, Caskey et al. (U.S. Pat. No. 5,364,759) describe a DNA profiling assay for detecting short tri and tetra nucleotide repeat sequences. The process includes extracting the DNA of interest, such as the mahogany gene, amplifying the extracted DNA, and labelling the repeat sequences to form a genotypic map of the individual's DNA.

A mahogany probe could additionally be used to directly identify RFLPs. Further, a mahogany probe or primers derived from the mahogany sequence could be used to isolate genomic clones such as YACs, BACs, PACs, cosmids, phage, or plasmids. The DNA contained in these clones can be screened for single-base polymorphisms or SSLPs using standard hybridization or sequencing procedures.

The level of mahogany gene expression can also be assayed. For example, RNA from a cell type or tissue known, or suspected, to express the mahogany gene, such as muscle, brain, kidney, testes, heart, liver, lung, skin, hypothalamus, spleen, and adipose tissue may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the mahogany gene. Such analyses may reveal both quantitative and qualitative aspects of the expression pattern of the mahogany gene, including activation or inactivation of mahogany gene expression.

In one embodiment of such a detection scheme, a cDNA molecule is synthesized from an RNA molecule of interest (e.g., by reverse transcription of the RNA molecule into cDNA). All or part of the resulting cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the mahogany gene nucleic acid reagents described in Section 5.1. The preferred lengths of such nucleic acid reagents are at least 9–30 nucleotides.

For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

As an alternative to amplification techniques, standard Northern analyses can be performed to determine the level of mRNA expression of the mahogany gene, if a sufficient quantity of the appropriate cells can be obtained.

Additionally, it is possible to perform such mahogany gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

5.4.1.2. Detection of Mahogany Gene Products

Mahogany gene products, including both wild-type and mutant mahogany gene products, conserved variants, and polypeptide fragments thereof, which are discussed, above, in Section 5.2, may be detected using antibodies which are directed against such mahogany gene products. Such antibodies, which are discussed in Section 5.3, below, may thereby be used as diagnostics and prognostics for a body eight disorder. Such methods may be used to detect abnormalities in the level of mahogany gene expression or of mahogany gene product synthesis, or abnormalities in the structure, temporal expression, and/or physical location of mahogany gene product. The antibodies and immunoassay methods described herein have, for example, important in vitro applications in assessing the efficacy of treatments for body weight disorders such as obesity, cachexia, and anorexia. Antibodies, or fragments of antibodies, such as those described below, may be used to screen potentially therapeutic compounds in vitro to determine their effects on mahogany gene expression and mahogany gene product production. The compounds that have beneficial effects on body weight disorders, such as obesity, cachexia, and anorexia, can thereby be identified, and a therapeutically effective dose determined.

In vitro immunoassays may also be used, for example, to assess the efficacy of cell-based gene therapy for a body weight disorders, including obesity, cachexia, and anorexia. Antibodies directed against mahogany gene products may be used in vitro to determine, for example, the level of mahogany gene expression achieved in cells genetically engineered to produce mahogany gene product. In the case of intracellular mahogany gene products, such an assessment is done, preferably, using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those that are known, or suspected, to express the mahogany gene. The protein isolation methods employed herein may, for example, be such as those described in Harlow and Lane (1988, "Antibodies: A Laboratory Manual", Cold Spring Harbor Laboratory Press, Cold Spring Harbor, N.Y.). The isolated cells can be derived from cell culture or from a patient. The analysis of cells taken from culture may be a necessary step in the assessment of cells to be used as part of a cell-based gene therapy technique or, alternatively, to test the effect of compounds on the expression of the mahogany gene.

Preferred diagnostic methods for the detection of mahogany gene products, conserved variants or peptide fragments thereof, may involve, for example, immunoassays wherein the mahogany gene products or conserved variants or peptide fragments are detected by their interaction with an anti-mahogany gene product-specific antibody.

For example, antibodies, or fragments of antibodies, such as those described, above, in Section 5.3, may be used to quantitatively or qualitatively detect the presence of mahogany gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred for mahogany gene products that are expressed on the cell surface.

The antibodies (or fragments thereof) useful in the present invention may, additionally, be employed histologically, as in immunofluorescence or immunoelectron microscopy, for in situ detection of mahogany gene products, conserved variants or peptide fragments thereof. In situ detection may be accomplished by removing a histological specimen from a patient, and applying thereto a labeled antibody that binds to a mahogany polypeptide. The antibody (or fragment) is preferably applied by overlaying the labeled antibody (or fragment) onto a biological sample. Through the use of such a procedure, it is possible to determine not only the presence of the mahogany gene product, conserved variants or peptide fragments, but also its distribution in the examined tissue. Using the present invention, those of ordinary skill will readily recognize that any of a wide variety of histological methods (such as staining procedures) can be modified in order to achieve in situ detection of a mahogany gene product.

Immunoassays for mahogany gene products, conserved variants, or peptide fragments thereof will typically comprise: (1) incubating a sample, such as a biological fluid, a tissue extract, freshly harvested cells, or lysates of cells in the presence of a detectably labeled antibody capable of identifying mahogany gene products, conserved variants or peptide fragments thereof; and (2) detecting the bound antibody by any of a number of techniques well-known in the art.

The biological sample may be brought in contact with and immobilized onto a solid phase support or carrier, such as nitrocellulose, that is capable of immobilizing cells, cell particles or soluble proteins. The support may then be washed with suitable buffers followed by treatment with the detectably labeled mahogany gene product specific antibody. The solid phase support may then be washed with the buffer a second time to remove unbound antibody. The amount of bound label on the solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which the mahogany gene product-specific antibody can be detectably labeled is by linking the same to an enzyme, such as for use in an enzyme immunoassay (EIA) (Voller, A., "The Enzyme Linked Immunosorbent Assay (ELISA)", 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, α-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect mahogany gene products through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.4.2. Screening Assays for Compounds that Interact with the Mahogany Gene or Gene Product The following assays are designed to identify compounds that bind to a mahogany gene product, compounds that bind to proteins, or portions of proteins that interact with a mahogany gene product, compounds that interfere with the interaction of a mahogany gene product with proteins and compounds that modulate the activity of the mahogany gene (i.e., modulate the level of mahogany gene expression and/or modulate the level of mahogany gene product activity). Assays may additionally be utilized that identify compounds that bind to mahogany gene regulatory sequences (e.g., promoter sequences; see e.g., Platt, 1994, J. Biol. Chem. 269, 28558–28562), which is incorporated herein by reference in its entirety, and that can modulate the level of mahogany gene expression. Such compounds may include, but are not limited to, small organic molecules, such as ones that are able to cross the blood-brain barrier, gain to and/or entry into an appropriate cell and affect expression of the mahogany gene or some other gene involved in the body weight regulatory pathway, or intracellular proteins.

Methods for the identification of such proteins are described, below, in Section 5.4.2.2. Such proteins may be involved in the control and/or regulation of body weight. Further, among these compounds are compounds that affect the level of mahogany gene expression and/or mahogany gene product activity and that can be used in the therapeutic treatment of body weight disorders, including obesity, cachexia, and anorexia, as described, below, in Section 5.9.

Compounds may include, but are not limited to, peptides such as, for example, soluble peptides, including but not limited to, Ig-tailed fusion peptides, and members of random peptide libraries; (see, e.g., Lam, et al., 1991, Nature 354, 82–84; Houghten, et al., 1991, Nature 354, 84–86), and combinatorial chemistry-derived molecular library made of D- and/or L-configuration amino acids, phosphopeptides (including, but not limited to members of random or partially degenerate, directed phosphopeptide libraries; see, e.g., Songyang, et al., 1993, Cell 72, 767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Compounds identified via assays such as those described herein may be useful, for example, in elaborating the biological function of the mahogany gene product and for ameliorating body weight disorders, such as obesity, cachexia, or anorexia. Assays for testing the effectiveness of compounds identified by, for example, techniques such as those described in Sections 5.4.2.1–5.4.2.3, are discussed, below, in Section 5.4.2.4.

5.4.2.1. In Vitro Screening Assays for Compounds that Bind to the Mahogany Gene Product In vitro systems may be designed to identify compounds capable of binding the mahogany gene products of the invention. Compounds identified may be useful, for example, in modulating the activity of unimpaired and/or mutant mahogany gene products, may be useful in elaborating the biological function of the mahogany gene product, may be utilized in screens for identifying compounds that disrupt normal mahogany gene product interactions, or may in themselves disrupt such interactions.

The principle of the assays used to identify compounds that bind to the mahogany gene product involves preparing a reaction mixture of the mahogany gene product and the test compound under conditions and for a time sufficient to allow the two components to interact and bind, thus forming a complex that can be removed and/or detected in the reaction mixture. These assays can be conducted in a variety of ways. For example, one method to conduct such an assay involves anchoring a mahogany gene product or a test substance onto a solid support and detecting mahogany gene product/test compound complexes formed on the solid support at the end of the reaction. In one embodiment of such a method, the mahogany gene product may be anchored onto a solid support, and the test compound, which is not anchored, may be labeled, either directly or indirectly.

In practice, microtiter plates are conveniently utilized as the solid support. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for mahogany gene product or the test compound to anchor any complexes formed in solution, and a labeled antibody specific for the other component of the possible complex to detect anchored complexes.

5.4.2.2. Assays for Proteins that Interact with the Mahogany Gene Product

Any method suitable for detecting protein-protein interactions may be employed for identifying mahogany gene product-protein interactions.

Among the traditional methods that may be employed are co-immunoprecipitation, cross-linking and co-purification through gradients or chromatographic columns. Utilizing procedures such as these allows for the identification of proteins that interact with mahogany gene products. Such proteins can include, but are not limited, the mahoganoid gene product.

Once isolated, such a protein can be identified and can be used in conjunction with standard techniques, to identify proteins it interacts with. For example, at least a portion of the amino acid sequence of a protein that interacts with the mahogany gene product can be ascertained using techniques well known to those of skill in the art, such as via the Edman degradation technique (see, e.g., Creighton, 1983, "Proteins: Structures and Molecular Principles," W. H. Freeman & Co., N.Y., pp. 34–49). The amino acid sequence obtained may be used as a guide for the generation of oligonucleotide mixtures that can be used to screen for gene sequences encoding such proteins. Screening may be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Additionally, methods may be employed that result in the simultaneous identification of genes that encode a protein which interacts with a mahogany gene product. These methods include, for example, probing expression libraries with labeled mahogany gene product, using mahogany gene product in a manner similar to the well known technique of antibody probing of λgt11 libraries.

One method that detects protein interactions in vivo, the two-hybrid system, is described in detail for illustration only and not by way of limitation. One version of this system has been described (Chien, et al., 1991, Proc. Natl. Acad. Sci. USA, 88, 9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the mahogany gene product and the other consists of the transcription activator protein's activation domain fused to an unknown protein that is encoded by a cDNA that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodologies may be used to screen activation domain libraries for proteins that interact with the "bait" gene product. By way of example, and not by way of limitation, mahogany gene products may be used as the bait gene product. Total genomic or cDNA sequences are fused to the DNA encoding an activation domain. This library and a plasmid encoding a hybrid of a bait mahogany gene product fused to the DNA-binding domain are co-transformed into a yeast reporter strain, and the resulting transformants are screened for those that express the reporter gene. For example, a bait mahogany gene sequence, such as the open reading frame of the mahogany gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait mahogany gene product are to be detected can be made using methods routinely practiced in the art. According to the particular system described herein, for example, the cDNA fragments can be inserted into a vector such that they are translationally fused to the transcriptional activation domain of GAL4. Such a library can be co-transformed along with the bait mahogany gene-GAL4 fusion plasmid into a yeast strain that contains a lacZ gene driven by a promoter that contains GAL4 activation sequence. A cDNA encoded protein, fused to a GAL4 transcriptional activation domain that interacts with bait mahogany gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait mahogany gene product-interacting protein using techniques routinely practiced in the art.

5.4.2.3. Assays for Compounds that Interfere with Mahogany Gene Product Macromolecule Interaction The mahogany gene products may, in vivo, interact with one or more macromolecules, such as proteins. For example, the mahogany gene products may, in vivo, interact with the mahoganoid gene products. Other macromolecules which interact with the mahogany gene products may include, but are not limited to, nucleic acid molecules and those proteins identified via methods such as those described, above, in Sections 5.4.2.1–5.4.2.2. For purposes of this discussion, the macromolecules are referred to herein as "binding partners". Compounds that disrupt mahogany gene product binding to a binding partner may be useful in regulating the activity of the mahogany gene product, especially mutant mahogany gene products. Such compounds may include, but are not limited to molecules such as peptides, and the like, as described, for example, in Section 5.4.2.1 above.

The basic principle of an assay system used to identify compounds that interfere with the interaction between the mahogany gene product and a binding partner or partners involves preparing a reaction mixture containing the mahogany gene product and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of mahogany gene product and its binding partner. Control reaction mixtures are incubated without the test compound or with a compound which is known not to block complex formation. The formation of any complexes between the mahogany gene product and the binding partner is then detected. The formation of a complex in the control reaction, but not in the reaction mixture containing the test compound, indicates that the compound interferes with the interaction of the mahogany gene product and the binding partner. Additionally, complex formation within reaction mixtures containing the test compound and normal mahogany gene product may also be compared to complex formation within reaction mixtures containing the test compound and a mutant mahogany gene product. This comparison may be important in those cases wherein it is desirable to identify compounds that disrupt interactions of mutant but not normal mahogany gene product.

The assay for compounds that interfere with the interaction of the mahogany gene products and binding partners can be conducted in a heterogeneous or homogeneous format. Heterogeneous assays involve anchoring either the mahogany gene product or the binding partner onto a solid support and detecting complexes formed on the solid support at the end of the reaction. In homogeneous assays, the entire reaction is carried out in a liquid phase. In either approach, the order of addition of reactants can be varied to obtain different information about the compounds being tested. For example, test compounds that interfere with the interaction between the mahogany gene products and the binding partners, e.g., by competition, can be identified by conducting the reaction in the presence of the test substance; i.e., by adding the test substance to the reaction mixture prior to or simultaneously with the mahogany gene product and interactive intracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the mahogany gene product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the mahogany gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex formation or that disrupt preformed complexes can be identified.

In an alternate embodiment of the invention, a homogeneous assay can be used. In this approach, a preformed complex of the mahogany gene product and the interactive binding partner is prepared in which either the mahogany gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt mahogany gene product/binding partner interaction can be identified.

In another embodiment of the invention, these same techniques can be employed using peptide fragments that correspond to the binding domains of the mahogany gene product and/or the binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments is engineered to express peptide fragments of the protein, it can then be tested for binding activity and purified or synthesized.

For example, and not by way of limitation, a mahogany gene product can be anchored to a solid material as described, above, in this Section by making a GST-1 fusion protein and allowing it to bind to glutathione agarose beads. The binding partner can be labeled with a radioactive isotope, such as $^{35}S$, and cleaved with a proteolytic enzyme such as trypsin. Cleavage products can then be added to the anchored GST-1 fusion protein and allowed to bind. After washing away unbound peptides, labeled bound material, representing the binding partner binding domain, can be eluted, purified, and analyzed for amino acid sequence by well-known methods. Peptides so identified can be produced synthetically or produced using recombinant DNA technology.

5.4.2.4. Assays for the Identification of Compounds that Ameliorate Body Weight Disorders Compounds, including but not limited to binding compounds identified via assay techniques such as those described, above, in Sections 5.4.2.1–5.4.2.3, can be tested for the ability to ameliorate body weight disorder symptoms, including obesity, cachexia, and anorexia. It should be noted that the assays described herein can identify compounds that affect mahogany activity by either affecting mahogany gene expression or by affecting the level of mahogany gene product activity. For example, compounds may be identified that are involved in another step in the pathway in which the mahogany gene and/or mahogany gene product is involved, such as, for example, a step which is either "upfield" or "downfield" of the step in the pathway mediated by the mahogany gene. Such compounds may, by affecting this same pathway, modulate the effect of mahogany on the development of body weight disorders. Such compounds can be used as part of a therapeutic method for the treatment of the disorder.

Described below are cell-based and animal model-based assays for the identification of compounds exhibiting such an ability to ameliorate body weight disorder symptoms.

First, cell-based systems can be used to identify compounds that may act to ameliorate body weight disorder symptoms. Such cell systems can include, for example, recombinant or non-recombinant cell, such as cell lines, that express the mahogany gene.

In utilizing such cell systems, cells that express mahogany may be exposed to a compound suspected of exhibiting an ability to ameliorate body weight disorder symptoms, at a sufficient concentration and for a sufficient time to elicit such an amelioration of such symptoms in the exposed cells. After exposure, the cells can be assayed to measure alterations in the expression of the mahogany gene, e.g., by assaying cell lysates for mahogany mRNA transcripts (e.g., by Northern analysis) or for mahogany gene products expressed by the cell; compounds that modulate expression of the mahogany gene are good candidates as therapeutics.

In addition, animal-based systems or models for a mammalian body weight disorder, for example, transgenic mice containing a human or altered form of mahogany gene, may be used to identify compounds capable of ameliorating symptoms of the disorder. Such animal models may be used as test substrates for the identification of drugs, pharmaceuticals, therapies and interventions. For example, animal models may be exposed to a compound suspected of exhibiting an ability to ameliorate symptoms, at a sufficient concentration and for a sufficient time to elicit such an amelioration of body weight disorder symptoms. The response of the animals to the exposure may be monitored by assessing the reversal of the symptoms of the disorder.

With regard to intervention, any treatments that reverse any aspect of body weight disorder-like symptoms should be considered as candidates for human therapeutic intervention in such a disorder. Dosages of test agents may be determined by deriving dose-response curves, as discussed in Section 5.5.1, below.

5.4.3. Compounds and Methods for the Treatment of Body Weight Disorders

Described below are methods and compositions whereby body weight disorders, including obesity, cachexia, and anorexia, may be treated. Such methods can comprise, for example administering compounds which modulate the expression of a mammalian mahogany gene and/or the synthesis or activity of a mammalian mahogany gene product, so that symptoms of the body weight disorder are ameliorated. Alternatively, in those instances whereby the mammalian body weight disorder results from mahogany gene mutations, such methods can comprise supplying the mammal with a nucleic acid molecule encoding an unimpaired mahogany gene product such that an unimpaired mahogany gene product is expressed and symptoms of the disorder are ameliorated.

In another embodiment of methods for the treatment of mammalian body weight disorders resulting from mahogany gene mutations, such methods can comprise supplying the mammal with a cell comprising a nucleic acid molecule that encodes an unimpaired mahogany gene product such that the cell expresses the unimpaired mahogany gene product, and symptoms of the disorder are ameliorated.

Because a loss of normal mahogany gene function results in the restoration of a non-obese phenotype in individuals exhibiting an agouti mutation (e.g. individuals that ectopically express the agouti gene in all tissues) a decrease or elimination of normal mahogany gene product would facilitate progress towards a normal body weight state in such individuals. Methods for inhibiting or reducing the level of mahogany gene product synthesis or expression can include, for example, methods such as those described in Section 5.4.3.1.

Alternatively, symptoms of certain body weight disorders such as, for example, cachexia and anorexia, which involve a lower than normal body weight phenotype, may be ameliorated by increasing the level of mahogany gene expression and/or mahogany gene product activity. Methods for enhancing the expression or synthesis of mahogany can include, for example, methods such as those described below, in Section 5.4.3.2.

5.4.3.1. Inhibitory Antisense, Ribozyme and Triple Helix Approaches

In another embodiment, symptoms of body weight disorders may be ameliorated by decreasing the level of mahogany gene expression and/or mahogany gene product activity by using mahogany gene sequences in conjunction with well-known antisense, gene "knock-out," ribozyme and/or triple helix methods to decrease the level of mahogany gene expression. Among the compounds that may exhibit the ability to modulate the activity, expression or synthesis of the mahogany gene, including the ability to ameliorate the symptoms of a mammalian body weight disorder, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarily, although preferred, is not required.

A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the mahogany gene could be used in an antisense approach to inhibit translation of endogenous mahogany mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86, 6553–6556; Lemaitre, et al., 1987, Proc. Natl. Acad. Sci. U.S.A. 84, 648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6, 958–976) or intercalating agents (see, e.g., Zon, 1988, Pharm. Res. 5, 539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15, 6625–6641). The oligonucleotide is a 2'-0-methylribonucleotide (Inoue, et al., 1987, Nucl. Acids Res. 15, 6131–6148), or a chimeric RNA-DNA analogue (Inoue, et al., 1987, FEBS Lett. 215, 327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16, 3209), methylphosphonate oligonucleotides can be prepared by use of controlled pore glass polymer supports (Sarin, et al., 1988, Proc. Natl. Acad. Sci. U.S.A. 85, 7448–7451), etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290, 304–310), the promoter contained in the 3' long terminal repeat of Rous sarcoma virus (Yamamoto, et al., 1980, Cell 22, 787–797), the herpes thymidine kinase promoter (Wagner, et al., 1981, Proc. Natl. Acad. Sci. U.S.A. 78, 1441–1445), the regulatory sequences of the metallothionein gene (Brinster, et al., 1982, Nature 296, 39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, Science 247, 1222–1225).

Ribozymes are enzymatic RNA molecules capable of catalyzing the specific cleavage of RNA. (For a review, see Rossi, 1994, Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference*, VCH Publishers, New York, (see especially FIG. 4, page 833) and in Haseloff and Gerlach, 1988, Nature, 334, 585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al., 1984, Science, 224, 574–578; Zaug and Cech, 1986, Science, 231, 470–475; Zaug, et al., 1986, Nature, 324, 429–433; published International patent application No. WO 88/04300 by University Patents Inc.; Been and Cech, 1986, Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317, 230–234; Thomas and Capecchi, 1987, Cell 51, 503–512; Thompson, et al., 1989, Cell 5, 313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.9.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.4.3.2. Gene Replacement Therapy

Mahogany gene nucleic acid sequences, described above in Section 5.1, can be utilized for the treatment of a mammalian body weight disorders, including obesity, cachexia, and anorexia. Such treatment can be in the form of gene replacement therapy. Specifically, one or more copies of a normal mahogany gene or a portion of the mahogany gene that directs the production of a mahogany gene product exhibiting normal mahogany gene function, may be inserted into the appropriate cells within a patient, using vectors that include, but are not limited to adenovirus, adeno-associated virus, and retrovirus vectors, in addition to other particles that introduce DNA into cells, such as liposomes.

Because the mahogany gene is expressed in the brain, such gene replacement therapy techniques should be capable delivering mahogany gene sequences to these cell types within patients. Thus, in one embodiment, techniques that are well known to those of skill in the art (see, e.g., PCT Publication No. WO89/10134, published Apr. 25, 1988) can be used to enable mahogany gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration of such mahogany gene sequences to the site of the cells in which the mahogany gene sequences are to be expressed.

Additional methods that may be utilized to increase the overall level of mahogany gene expression and/or mahogany gene product activity include using target homologous recombination methods, discussed in Section 5.2, above, to modify the expression characteristic of an endogenous mahogany gene in a cell or microorganism by inserting a heterologous DNA regulatory element such that the inserted regulatory element is operatively linked with the endogenous mahogany gene in question. Targeted homologous recombination can be thus used to activated transcription of an endogenous mahogany gene that is "transcriptionally silent", i.e., is not normally expressed, or to enhance the expression of an endogenous mahogany gene that is normally expressed.

Further, the overall level of mahogany gene expression and/or mahogany gene product activity may be increased by the introduction of appropriate mahogany-expressing cells, preferably autologous cells, into a patient at positions and in numbers that are sufficient to ameliorate body weight disorder symptoms. Such cells may be either recombinant or non-recombinant.

Among the cells that can be administered to increase the overall level of mahogany gene expression in a patient are normal cells, preferably brain cells, that express the mahogany gene. Alternatively, cells, preferably autologous cells, can be engineered to express mahogany gene sequences, and may then be introduced into a patient in positions appropriate for the amelioration of the body weight disorder symptoms. Alternately, cells that express an unimpaired mahogany gene and that are from a MHC matched individual can be utilized, and may include, for example, brain cells. The expression of the mahogany gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, in Section 5.4.2, that are capable of modulating mahogany gene product activity can be administered using standard techniques that are well known to those of skill in the art. In instances in which the compounds to be administered are to involve an interaction with brain cells, the administration techniques should include well known ones that allow for a crossing of the blood-brain barrier.

5.5. Pharmaceutical Preparations and Methods of Administration

The compounds that are determined to affect mahogany gene expression or gene product activity can be administered to a patient at therapeutically effective doses to treat or ameliorate body weight disorders, such as obesity, anorexia, or cachexia. A therapeutically effective dose refers to that amount of the compound sufficient to result in amelioration of symptoms of such a disorder.

5.5.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.5.2. Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLE

Genetic and Physical Mapping of the Mahogany Locus

In the Example presented herein, studies are described which, first, define the genetic interval on mouse chromosome 2 within which the mahogany gene lies, and second, successfully narrow the interval to approximately 0.29 cM. Further, the physical mapping of this interval is described.

Mouse crosses were performed to obtain homozygous mg/mg mice. First, LDJ-Le-mg mice were crossed with CAST/Ei mice. The F1s were back-crossed with LDJ-Le-mg mice and the resulting litters scored for coat color. Mice showing coat color of mg/mg homozygotes were genotyped to using D2/NDS3 and D2/MIT19 markers to identify meiotic events. Mice showing recombinant events were fine structure mapped using various markers shown in FIG. 1. All genotyping was performed using PCR-SSLP and then analyzed using PAGE.

After 2300 meiosesis, the mahogany gene was mapped to a 0.99 cM interval FIG. 1. This corresponded to an interval width of 700 kb.

Physical Mapping of the Genetic Interval: The 700 kb mahogany region on mouse chromosome 2 is shown in FIG. 1. Genetic markers, clones spanning the region and open reading frames in the interval are shown in the figure.

7. EXAMPLE

Identification of a Candidate Mahogany Gene

In the Example presented herein, a gene is identified within the cloned DNA described in the Example in Section 6, above, which corresponds to a candidate mahogany gene.

Clones spanning the 700 kb region were sequenced and open reading frames were identified and analyzed through this interval. Nucleic acid sequencing was performed using ABI sequencers and the manufactures recommended procedures. Many novel sequences encoding proteins are located in this integral, see the bottom of FIG. 1. With each open reading frame identified, mutational analysis, primarily via SSCP analysis, was used with the three alleles of the mahogany phenotype mice to identify which of the open reading frames within this interval contain a mutation in an mg mouse.

A mutation was found in one of the genomic/cDNA sequences found in the integral in mg3J mice. FIGS. 3 and 2 provide the genomic and cDNA sequences surrounding the mutation, FIG. 6 shows the mutation in mg3J, and FIGS. 8 and 9 show splice variants in the 5' end of the murine mg gene. The mutation in mg3J mice is a deletion of a GCTGC sequence which results in the creation of a frameshift. Based on the chromosomal location and mutation identification, the cDNA provided in FIG. 2 and the corresponding genomic DNA which contains the contigs provided in FIG. 3 represent the mg gene/locus.

Further analysis of cDNA clones identified two distinct splice variants in the 5' end of the mg gene. FIG. 7 provides an analysis of the structure of the two splice variants, denoted akm1003 and akm1004. FIGS. 8 and 9 provide the nucleic acid and amino acid sequence of the 5' ends of these splice variants and structural analysis of the protein encoded by the 5' regions.

Analysis of libraries of human cDNA sequences led to the identification of three forms of the human ortholog of the mg gene: a long form (FIGS. 18A-D) and two shorter splice forms, each of which is shown in FIGS. 19A-D and 20A-C.

8. EXAMPLE

Characterization of the Mahogany Gene

In the example presented herein, the nucleic acid sequence of the mahogany gene transcript identified in the example presented in Section 7, above, is used to generate Northern analysis data which characterize the expression of the mahogany transcript in a number of tissues both of wild type mice, and of mice exhibiting the mahogany phenotype. The results presented in this example are consistent with the mg gene being the mahogany gene.

For Northern analysis, polyA RNA was isolated from wild-type and the original mg mutant, mg3J and mg-Lester mice and utilized from the Northern analysis following standard protocols. Northern blots prepared from this mRNA was hybridized with a probe obtained from sequences common to the akm1003 and akm1004 sequences. Specifically PCR primers TTCCTCACTGG and GGACACACAG were used to amplify cDNA from the akm1003 sequence which had been radiolabelled by random priming using a Gibco-BRL kit according to the manufacturer's recommended protocol.

An mg transcript was found in all mice examined in mRNA isolated from brain (minus the hypothalamus), kidney, heart, testes, liver, skin, and hypothalamus. No expression was seen in muscle.

In a Northern blot run on RNA samples from mahogany mice, the mg transcript was found to be expressed at a reduced level in all tissues in mRNA isolated from mg3J mice, as a varied size fragment in mg-Lester derived mRNA, and at different levels and sizes in original mg mutant mice derived mRNA.

These results are consistent with the mg gene disclosed herein as being the mahogany gene.

9. EXAMPLE

Effects of the Mahogany Gene on Genetic and Dietary Obesity

This section describes experiments which examine whether the mg gene acts specifically within the agouti pathway. Specifically, these experiments test whether mg can suppress the obesity of other monogenic obese mutants as well as whether it can suppress diet-induced obesity. The results show that mg does not suppress obesity in any of the monogenic obese mutants. However, mg can suppress diet-induced obesity. Thus, the mg gene and its corresponding gene product and compounds that modulate mg expression and/or activity have implications in the treatment of diet-induced obesity disorders, as well as in the treatment of disorders related directly to the mg or agouti gene.

9.1. Materials and Methods

Genetic crosses: The crosses, and the number of animals for each (n) were (LDJ/Le-mg/mg×CAST/Ei)×LDJ/Le-mg/mg (n=1588), (C3HeB/FeJ-mg$^{3J}$/mg$^{3J}$×CAST/Ei)×C3HeB/FeJ-mg$^{3J}$/mg$^{3J}$ (n=324), (C3HeB/FeJ-mg$^{3J}$/mg$^{3J}$×MOLF/Ei)×C3HeB/FeJ-mg$^{3J}$/mg$^{3J}$ (n=216) and (C3HeB/FeJ-mg$^{3J}$/mg$^{3J}$×C57BL6/J)×C3HeB/FeJ-mg$^{3J}$/mg$^{3J}$ (n=309). The 2437 $N_2$ mice were analysed by coat colour to determine their genotype at the mg locus. As mice change color slightly at each hair molt and because the phenotype of mg/mg vs. mg/+ can be subtle, all mice were phenotyped at the same age by a single person. Genomic DNA was made from a tail biopsy of each mouse and analysed for multiple simple sequence length repeat polymorphism (SSLP) markers. The first ~100 mice were typed for a series of polymorphic Mit genetic markers (Deitrich, W. F. et al., 1996, *Nature* 380:149–152) from distal mouse chromosome 2 in order to accurately delimit the position of mg. With the first ~100 mice it was determined that mg mapped approximately 15 cM proximal of Agouti between markers D2Mit19 and D2Nds3 (FIG. 13). All remaining animals were genotyped for D2Mit19 and D2Nds3. Animals recombinant in that interval were typed with all available Mit markers between and for the ever growing number of markers developed during the project which, finally totaled 265 markers.

9.2. Result

The murine mahogany (mg) gene is known to act in a dosage dependent manner within the agouti pathway, to compensate for the agouti overexpression and for lack of signaling from the nul allele McIr (Miller, K. A. et al., 1997, *Genetics* 146:1407–1415; Dinulescu, D. M. et al., *Proc. Natl. Acad. Sci.*, in press; Robbins, L. S. et al., 1993, *Cell* 72:827–834). The phenotype of mice homozygous for both mg and a null allele of Mc1r (recessive yellow, Mc1r$^e$) is yellow, the same as the phenotype of Mc1r$^e$/Mc1r$^e$ mice, indicating that mg is not acting downstream of Mc1r. A similar experiment was performed with obese Mcr4 knock out mice (FIG. 11). For both sexes, all the animals homozygous for Mc4r−/− were approximately equally obese and were heavier than the mice wild-type at Mc4r independent of the genotype for mg. This data strengthens and confirms the Mc1r data previously published, strongly suggesting that mg acts at or upstream of both melanocortin receptors.

Figure 12A:
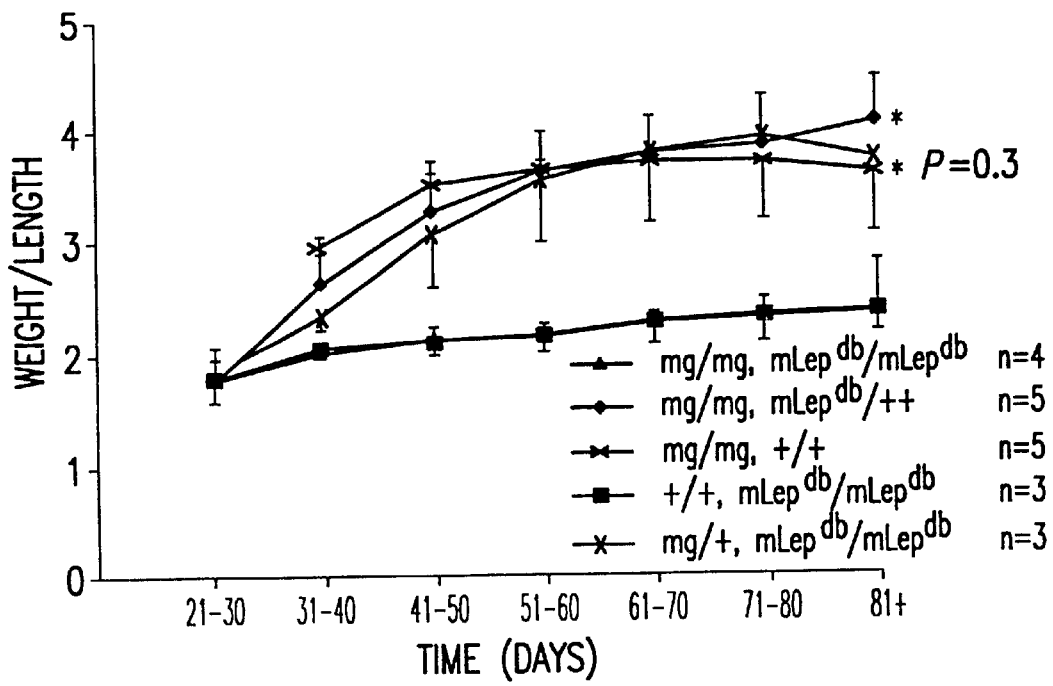
Figure 12B:
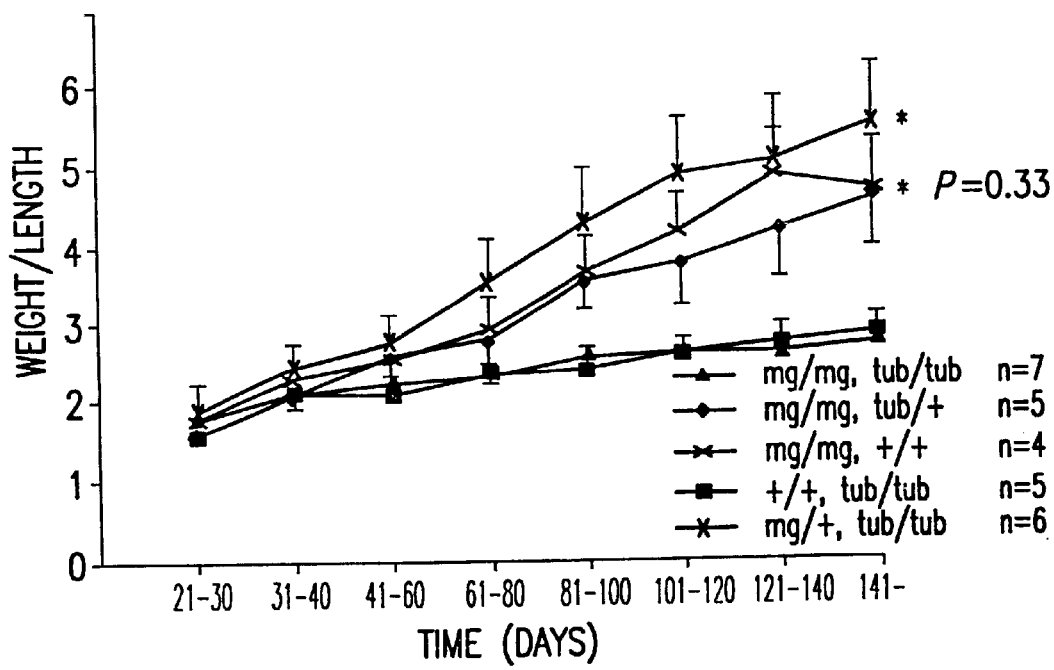
Figure 12C:
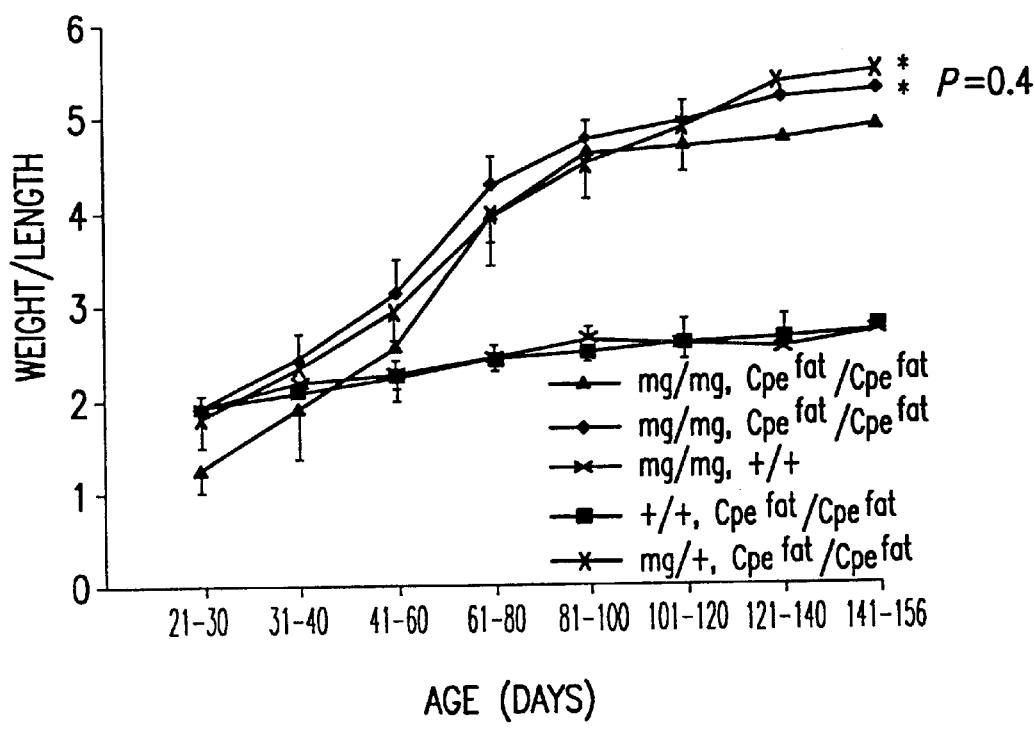
Figure 12D:
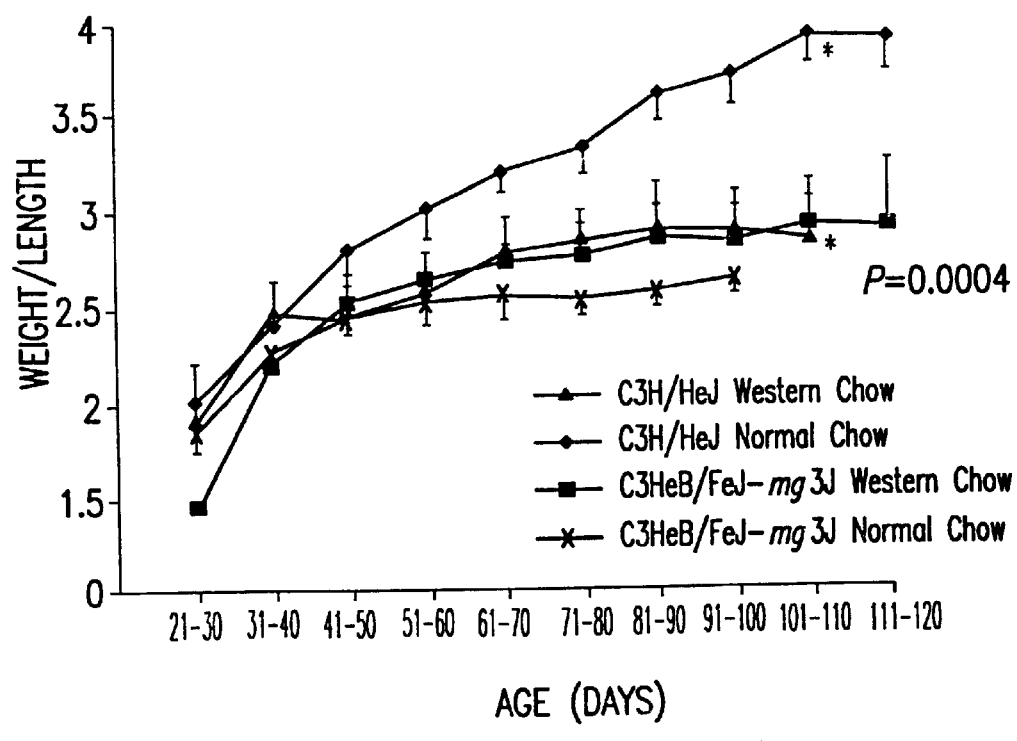

To test whether mg acts specifically within the agouti pathway, experiments were performed to determine whether mg can suppress the obesity of other monogenic obese mutants of the mouse and whether it could suppress diet-induced obesity. Appropriate genetic crosses were set up to product mice segregating mg and one of the mouse obesity mutations Cpe$^{fat}$, tub, or Lepr$^{db}$ such that all combinations of homozygous and heterozygous animals were on the same mix of genetic background. No suppression of obesity was seen for any of the monogenic obese mutants (FIG. 12) lending credence to the assumed specificity of action within the agouti pathway. To ask whether mg can suppress diet induced obesity C3HeB/FeJ-mg$^{3J}$ and C3H/HeJ mice were placed, at weaning, either on normal chow having a physiological fuel value (PFV) of 3.63 kcal/gm with 9% fat, or onto a high fat diet having a PFV of 4.53 kcal/gm with 42.2% fat. Food consumption and body weight were measured weekly. Converting the grams of food consumed to calories indicated that C3H/HeJ mice on normal chow and high fat diet consumed ~97 kCal/week and ~96 kCal/week, respectively. C3HeB/FeJ-mg$^{3J}$ mice on normal chow and high fat diet consumed ~83 kCal/week and ~81 kCal/week, respectively. Despite the equal calorie intake, the C3H/HeJ mice on the high fat diet readily gained more weight than the C3H/HeJ mice on normal chow (p=0.0004). In stark contrast, the C3HeB/FeJ-mg$^{3J}$ mice on either diet showed no statistically significant difference in weight (FIG. 12D). Female data showed the same trends, although there was no statistical significance between any of the mice on either diet.

10. Experiment: Mapping and Sequencing of the Mahogany Gene

This section describes experiments wherein the murine mahogany gene was genetically and physically mapped to an approximately 0.6 cM interval, and then sequenced. The murine mg sequence obtained was then used to isolate and sequence the human mg gene. Northern and in situ analyses of mg expression in mouse tissue are also described, and sequence motifs of the predicted MG polypeptide are discussed.

10.1. Materials and Methods

Physical Mapping: More than 36,000 individual sequences from the region were compared by BLAST (Altschul, S. F. et al., 1990, *J. Mol. Biol.* 215:403–410) to publicly available sequence databases and analyzed using GRAIL (Guan, X. et al., 1992, *Proc. Eighth IEEE Conference on AI Applications*:9–13) to identify potential coding sequence. In addition, sequences from overlapping BACs were assembled using phrap (Sing, C. F. et al., 1998, *Genome Res.* 8:175–185; Ewing B. and Green, P., 1998, *Genome Res.* 8:186–194; Gordon, D. et al., 1998, *Genome Res.* 8:195–202), and the resulting contigs were also analyzed using BLAST and GRAIL to aid in gene prediction. This data was displayed in ACEdb (Durbin, Richard and Mieg, Jean Thierry, 1991, A *C. elegans* Database, Documentation, code, and data available from anonymous FTP servers at lirmm.lirmm.fr, cele, mrc-lmb.cam.ac.uk, and ncbi.nlm.nih.gov) to further visualize predicted exons and their relationships to each other.

Northern Blot Analysis: PolyA+ RNA was extracted from the tissues indicated from wild-type, C3H/HeJ and the three mutant alleles of mg, C3HeB/FeJ-mg$^{3J}$, LDJ/Le-mg, and C3H/HeJ-mg$^L$, according to the manufacturer's instructions. RNA STAT-60 (Tel-Test, Inc., 1511 Sounty Rd. 129, Friendswood, Tex. 77546) was used to isolate total RNA. PolyA+ was isolated using Poly(A)Pure™ mRNA purification kit (Ambion, Inc., 2130 Woodward St. #200, Austin, Tex. 78744). 2 μg of each mRNA was separated on a 1% agarose-formaldehyde gel, transferred to nylon, and hybridized with a probe for mg corresponding to nt 990–1406 of the murine cDNA sequence with Rapid-hyb Buffer (Amersham LIFE SCIENCE, Gaithersberg, Md.). Filters were washed with 0.11×SSC, 0.1% SDS and exposed to KODAK X-omat film overnight.

10.2. Results

A positional cloning strategy was undertaken to identify the mg gene. Multiple genetic crosses were set up to produce second generation mice (n-2437) segregating mg which were used to genetically localise the mg locus (FIG. 13B). When the genetic map critical interval for mg was resolved to ~0.6 cM physical mapping was initiated. Approximately 1 Mb was contiged with 30 BACs (FIG. 13C), most of which were made into random sheared libraries for shot gun sequencing. At completion of the project it was estimated that 85% sequence coverage across the interval had been achieved and that all genes within the region had been found. Twenty-nine genes were identified, 15 of which are novel genes. Within the final minimal interval for mg, indicated by the arrows in FIG. 13, there were eleven genes of which nine were unknown. All of these genes were tested as candidates for mg by examining the three mutant alleles of the mahogany locus, the original allele, mg, that arose in a stock of Swiss×C3H mice, and two alleles that have independently arisen on the C3H background, C3HeB/FeJ-mg$^{3J}$/mg$^{3J}$ and C3H/He-mg$^L$/mg$^L$. Each gene was examined by Northern blot analysis and RT-PCR analysis of RNA from tissues from wild-type and mg mutant mice, by Southern blot analysis of DNA from wild-type and mg mutant mice, and by SSCP analysis of genomic PCR products designed to cover the intron-exon boundaries of much of each of the genes. In all, 20 genes were analyzed in this manner, one of which showed a northern blot difference between the wild type and mutant alleles (FIG. 14).

The wild type expression pattern of this gene gives three bands of size ~9 kb, 4.5 kb, and 3.8 kb, of which the larges message is the most prominent (FIG. 14). The smaller two bands can be seen in all tissues but, depending upon tissue, may require extended exposure. Each of the different mg alleles gave a different expression pattern. C3HeB/FeJ-mg$^{3J}$/mg$^{3J}$ has extremely low expression, the 9 kb message only being very faint in brain, hypothalamus, and fat on northerns. C3H/He-mg$^L$/mg$^L$ expresses a single aberrant band of approximately 9.5–10 kb in kidney, heart, muscle, fat, and, most prominently, brain and hypothalamus. The LDJ/Le-mg/mg shows an altered ratio of the three wild type messages: the 9 kb message is reduced, while the two smaller messages are more highly expressed, in particular being very abundant in fat and hypothalamus. In situ analysis was used to look more closely at mg expression in the brain and specifically the hypothalamus. Overall hybridization in LDJ/Le-mg/mg looks equivalent to that of wild type, and the C3HeB/FeJ-mg$^{3J}$/mg$^{3J}$ shows an overall reduction of expression. Close examination of the hypothalamic region in both wild type and mutant alleles revealed differences in the ventromedial hypothalamic nucleus (VMH). Both C3HeB/FeJ-mg$^{3J}$/mg$^{3J}$ and the LDJ/Le-mg/mg have reduced VMH expression (FIG. 15) which is particularly interesting as many neuropeptides and receptors known to be involved in body weight regulation are expressed in the VMH, including Mc4r.

Initially, two overlapping mouse cDNAs of 1051 bps and 2419 bps were identified. Using these cDNAs as a starting point it was possible to build over 7990 bps of human sequences, using both the public EST database and an in house database, as well as identifying one cDNA clone from a human liver library. The 23 ESTs used in the contiging are listed in Table I below. Using the derived human sequence, it was then possible to estimate the intron-exon boundaries within the mouse genomic sequence. These were verified by PCR amplification and sequencing. In total, 4079 bps of mouse sequence was obtained, of which 4011 bp are coding sequence. The mouse genomic locus spans over 160 kb, and has 31 identified exons, at least one of which is differentially spliced.

TABLE I

| Gene Bank Accession # | Clone ID # | Clone Source |
| --- | --- | --- |
| NA | NA | Human Endothelial Cell (MPI) |
| AA062169 | 482948 | Soares mouse P3NMF19.5 |
| NA | NA | Human Liver (MPI) |
| AA350292 | 151062 | Infant Brain |
| R87660 | 194640 | Soares Fetal Liver Spleen 1 NFLS |
| T69367 | 82898 | Stratagene Liver |
| T92696 | 118881 | Stratagene Lung |
| H11351 | 47626 | Soares Infant Brain 1 NIB |
| AA350293 | 151062 | Infant Brain |
| AA297697 | 149184 | Fetal Heart II |
| AB011120 | NA | Human Male Brain |
| AA297214 | 129808 | Embryo, 12 week I |
| AA298732 | 184690 | T-Lymphocyte |
| AI076479 | 1676623 | Soares Total Fetus Nb2HF8 9W |
| AA771958 | 1359202 | Soares parathyroid tumor NbHPA |
| R84298 | 194640 | Soares Fetal Liver Spleen 1NFLS |
| D81046 | 1178923 | Human Fetal Brain (Tfujiwara) |
| AA378603 | 183010 | Synovial Sarcoma |
| D60710 | 962349 | Clontech Human Fetal Brain (#6535) |
| D20236 | pm1235 | Human Promyelocyte |
| AA345684 | 147210 | Gall Bladder I |
| H45413 | 182870 | Soares Breast 3NbHBst |
| AA044305 | 486349 | Soares Pregnant Uterus NbHPu |

The mutant mahogany alleles were also sequenced, checking all intron-exon boundaries. A 5 bp deletion at 2809 nt was found in the coding sequence of the mg gene from C3HeB/FeJ-mg$^{3J}$/mg$^{3J}$ which introduces a stop codon a position 937, two codons 3' of the deletion. This mutation will result in a seriously truncated protein lacking many interesting domains, as discussed below. The mg$^{3J}$ allele is the same allele that showed extremely low expression levels. The combined Northern blot analysis, in situ hybridization analysis, and sequence analysis of the mutant mg$^{3J}$ allele strongly suggest that this gene is the mouse mahogany gene.

The 4011 bp of open reading frame (ORF) of mouse MG predicts a 1336 amino acid polypeptide with molecular mass of 148,706 D (FIG. 17, top sequence). BLAST searches of the NCBI and SwissProt protein databases identified two human paralogues with a similar modular architecture (KIAA0534, Genbank accession no. 3043592; and MEGF8, Genbank accession no. AB011541), as well as a C. elegans homologue (YC81_CAEEL, Genbank accession no. Q19981).

Another human protein, Attractin or DPPT-L (Duke-Cohen, J. S. et al., 1998, Proc. Natl. Acad. Sci. U.S.A. 95:11336–11341), appears to be a 1198 amino acid residue, approximately 134,000 D, secreted splice variant of the MG polypeptide. An alignment of the predicted MG (top) and Attractin (bottom) amino acid sequences is shown in FIG. 17. Attractin has not identified as being involved in the regulation of body weight. Rather, the protein is reported to mediate an interaction between T lymphocytes and monocytes that leads to the adherence and spreading of monocytes that become foci for T lymphocyte clustering (see Duke-Cohen et al., supra).

Searching the MG polypeptide with the SMART domain tool (Schultz, J. et al., 1998, Proc. Natl. Acad. Sci. U.S.A. 95:5857–5864) revealed sequence motifs that may provide further clues to its biological function (FIG. 16B, FIG. 17). The single transmembrane spanning MG protein has a large extracellular sequence of 1289 amino acids containing three EGF domains (Nakayama, M. et al., 1998, Genomics 51:27–34), two laminin-like EGF repeats, a CUB domain (Bork, P. and Beckmann, G., 1993, Mol. Biol. 231:539–545), a C-type lectin domain (Drickamer, K., 1995, Nat. Struct. Biol. 6:437–439; Weis W. I., and Drickamer, K., 1996, Ann. Rev. Biochem. 65:441–473), two plexin-like repeats (Maestrini, E. et al., 1996, Proc. Natl. Acad. Sci. U.S.A. 93:674–678), and six consecutive kelch repeats (Bork, P. and Doolittle, R. F., 1994, J. Mol. Biol. 236:1277–1282). Multiple EGF domains are commonly found in Type-1 membrane proteins involved in cell adhesion and receptor-ligand interactions (Schultz, J. et al, 1998, Proc. Natl. Acad. Sci. USA 95:5857–5864). Laminin-EGF-like modules are found in a variety of proteoglycans such as perlecan and heparin sulphate proteoglycan. As CUB domains also frequently occur in glycosylated proteins and c-type lectins are known to be carbohydrate binders, it is likely that MG is heavily glycosylated and that carbohydrate interactions are essential for its function. Many kelch motif containing proteins have been found that, like MG, have multiple consecutive domains. Such consecutive four-stranded β-sheet Kelch motifs form a bladed beta "propeller fold" that is common in many sialidases and other enzymes (Maestrini, E. et al., supra). Unlike the other well recognized domains, the "plexin" repeat is less well defined. It was first recognized as a triple repeat in the Xenopus gene plexin that has similarity to MET (Bork, P. and Beckmann, G., 1993, Mol. Biol. 231:539–545). Since then, this cysteine rich repeat has been found in 6 MET gene family members, three of which signal via tyrosine kinase and three of which are hypothesized to have putative signaling function via a novel conserved cytoplasmic domain. However, it is fascinating that there is an eight amino acid stretch that is 100% conserved in the four proteins shown in FIG. 16A from human, mouse, and C. elegans. The conservation of sequence across such widely evolutionary divergent species strongly indicates a functional domain, possible a putative signaling motif.

The multi-domain structure of MG is complex, but draws many similarities from receptor and receptor-like proteins. The full-length MG polypeptide is predicted to be a large membrane-spanning protein with multiple extracellular domains that may have a binding or gathering function as well as a highly conserved putative signaling motif in the cytoplasmic tail.

11. References Cited

The present invention is not to be limited in scope by the specific embodiments described herein, which are intended as single illustrations of individual aspects of the invention. Functionally equivalent methods and components are within the scope of the present invention. Indeed, various modifications of the invention, in addition to those shown and described herein, will become apparent to those skilled in the art from the foregoing description and accompanying drawings.

All publications and patent applications mentioned in the specification are herein incorporated by reference to the same extent as if each individual publication or patent application was specifically and individually indicated to be incorporated by reference.

What is claimed is:

1. An isolated polypeptide comprising the amino acid sequence of SEQ ID NO: 2, SEQ ID NO: 9, SEQ ID NO: 11, SEQ ID NO: 13, SEQ ID NO: 15, SEQ ID NO: 17, or SEQ ID NO: 19.

2. The isolated polypeptide of claim 1, wherein the polypeptide comprises the amino acid sequence of SEQ ID NO: 2.

3. The isolated polypeptide of claim 1 wherein the polypeptide comprises the amino acid sequence of SEQ ID NO: 9.

4. The isolated polypeptide of claim 1, wherein the polypeptide comprises the amino acid sequence of SEQ ID NO: 11.

5. The isolated polypeptide of claim 1, wherein the polypeptide comprises the amino acid sequence of SEQ ID NO: 13.

6. The isolated polypeptide of claim 1, wherein the polypeptide comprises the amino acid sequence of SEQ ID NO: 15.

7. The isolated polypeptide of claim 1, wherein the polypeptide comprises the amino acid sequence of SEQ ID NO: 17.

8. The isolated polypeptide of claim 1, wherein the polypeptide comprises the amino acid sequence of SEQ ID NO: 19.

9. An isolated polypeptide encoded by the open reading frame of SEQ ID NO:1, SEQ ID NO: 8; SEQ ID NO: 10; SEQ ID NO: 12; SEQ ID NO: 14; SEQ ID NO: 16; or SEQ ID NO: 18.

10. The isolated polypeptide of claim 9, wherein the polypeptide is encoded by a nucleic acid molecule which hybridizes under said stringent hybridization and wash conditions to a complement of the open reading frame of SEQ ID NO: 14.

11. The isolated polypeptide of claim 9, wherein the polypeptide is encoded by a nucleic acid molecule which hybridizes under said stringent hybridization and wash conditions to a complement of the open reading frame of SEQ ID NO: 16.

12. The isolated polypeptide of claim 9, wherein the polypeptide is encoded by a nucleic acid molecule which hybridizes under said stringent hybridization and wash conditions to a complement of the open reading frame of SEQ ID NO: 18.

13. An isolated polypeptide encoded by a nucleic acid molecule which hybridizes under stringent conditions to a complement of the open reading frame of SEQ ID NO:1, SEQ ID NO: 8; SEQ ID NO: 10; SEQ ID NO: 12; SEQ ID NO: 14; SEQ ID NO: 16; or SEQ ID NO: 18, wherein said hybridization occurs across the full length of said nucleic acid molecule and across the full length of said complement, wherein said stringent hybridization conditions comprise hybridizing in 0.5 M NaHPO$_4$, 7% SDS, 1 mM EDTA at 68° C. and washing in 0.1%×SSC/0/1% at 68° C., and wherein said polypeptide modulates the melanocortin signal transduction pathway.

14. The isolated polypeptide of claim 13, wherein the polypeptide is encoded by a nucleic acid molecule which hybridizes under said stringent hybridization and wash conditions to a complement of the open reading frame of SEQ ID NO: 14.

15. The isolated polypeptide of claim 13, wherein the polypeptide is encoded by a nucleic acid molecule which hybridizes under said stringent hybridization and wash conditions to a complement of the open reading frame of SEQ ID NO: 16.

16. The isolated polypeptide of claim 13, wherein the polypeptide is encoded by a nucleic acid molecule which hybridizes under said stringent hybridization and wash conditions to a complement of the open reading frame of SEQ ID NO: 18.

17. A fusion polypeptide comprising the amino acid sequence of SEQ ID NO: 2, SEQ ID NO: 9, SEQ ID NO: 11, SEQ ID NO: 13, SEQ ID NO: 15, SEQ ID NO: 17, or SEQ ID NO: 19 and a heterologous amino acid sequence.

* * * * *